(12) United States Patent
Albrecht et al.

(10) Patent No.: US 10,906,978 B2
(45) Date of Patent: Feb. 2, 2021

(54) ANTI-CD3 ANTIBODIES, ANTI-CD123 ANTIBODIES AND BISPECIFIC ANTIBODIES SPECIFICALLY BINDING TO CD3 AND/OR CD123

(71) Applicant: SANOFI, Paris (FR)

(72) Inventors: Jana Albrecht, Frankfurt (DE); Cédric Barriere, Paris (FR); Christian Beil, Frankfurt (DE); Jochen Beninga, Eltville (DE); Chantal Carrez, Thiais (FR); Stéphane Guerif, Paris (FR); Katja Kroll, Frankfurt (DE); Christian Lange, Holler (DE); Cendrine Lemoine, Massy (FR); Wulf-Dirk Leuschner, Niedernhausen (DE); Ercole Rao, Moerfelden-Walldorf (DE); Marion Schneider, Hofheim (DE); Marie-Cécile Wetzel, Paris (FR); Peter Wonerow, Frankfurt (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/943,685

(22) Filed: Apr. 2, 2018

(65) Prior Publication Data

US 2018/0222987 A1 Aug. 9, 2018

Related U.S. Application Data

(63) Continuation of application No. 15/654,857, filed on Jul. 20, 2017, now abandoned, which is a continuation of application No. PCT/EP2016/051386, filed on Jan. 22, 2016.

(30) Foreign Application Priority Data

Jan. 23, 2015 (EP) .................................. 15305077

(51) Int. Cl.
| | |
|---|---|
| *C07K 16/28* | (2006.01) |
| *C07K 16/30* | (2006.01) |
| *G01N 33/574* | (2006.01) |
| *A61K 39/00* | (2006.01) |

(52) U.S. Cl.
CPC ...... *C07K 16/2866* (2013.01); *C07K 16/2809* (2013.01); *C07K 16/30* (2013.01); *G01N 33/57492* (2013.01); *A61K 2039/505* (2013.01); *C07K 2317/21* (2013.01); *C07K 2317/24* (2013.01); *C07K 2317/31* (2013.01); *C07K 2317/33* (2013.01); *C07K 2317/52* (2013.01); *C07K 2317/55* (2013.01); *C07K 2317/56* (2013.01); *C07K 2317/565* (2013.01); *C07K 2317/92* (2013.01); *C07K 2318/00* (2013.01); *G01N 2333/7155* (2013.01)

(58) Field of Classification Search
None
See application file for complete search history.

(56) References Cited

U.S. PATENT DOCUMENTS

| | | | |
|---|---|---|---|
| 4,179,337 | A | 12/1979 | Davis |
| 4,301,144 | A | 11/1981 | Iwashita |
| 4,361,549 | A | 11/1982 | Kung |
| 4,496,689 | A | 1/1985 | Mitra |
| 4,640,835 | A | 2/1987 | Shimizu |
| 4,670,417 | A | 6/1987 | Iwasaki |
| 4,791,192 | A | 12/1988 | Nakagawa |
| 4,816,567 | A | 3/1989 | Cabilly |
| 4,861,719 | A | 3/1989 | Miller |
| 5,202,238 | A | 4/1993 | Fell |
| 5,204,244 | A | 4/1993 | Fell |
| 5,225,539 | A | 7/1993 | Winter |
| 5,278,056 | A | 1/1994 | Bank |
| 5,500,362 | A | 3/1996 | Robinson |
| 5,530,101 | A | 6/1996 | Queen |
| 5,565,332 | A | 10/1996 | Hoogenboom |
| 5,585,089 | A | 12/1996 | Queen |

(Continued)

FOREIGN PATENT DOCUMENTS

| | | |
|---|---|---|
| CN | 1984931 B | 11/2012 |
| CN | CA 102796198 | 11/2012 |

(Continued)

OTHER PUBLICATIONS

Angelot-Delettre et al. (Haematologica. Feb. 2015;100(2):223-30, epub Nov. 7, 2014). (Year: 2014).*

(Continued)

*Primary Examiner* — Zachary S Skelding
(74) *Attorney, Agent, or Firm* — McDonnell Boehnen Hulbert & Berghoff LLP

(57) ABSTRACT

The present invention concerns antibody-like binding protein specifically binding to CD3 and binding specifically to at least one further antigen, for example CD123. The present invention also concerns antibody-like binding protein specifically binding to CD123 and binding specifically to at least one further antigen. The invention further concerns anti-CD3 antibodies and anti-CD123 antibodies. The invention also relates to pharmaceutical compositions comprising the antibody-like binding protein, anti-CD3 antibodies or anti-CD123 antibodies of the invention, and their use to treat cancer. The invention further relates to isolated nucleic acids, vectors and host cells comprising a sequence encoding said antibody-like binding protein, anti-CD3 or anti-CD123 antibody and the use of said anti-CD123 antibody as a diagnostic tool.

Figure 5:
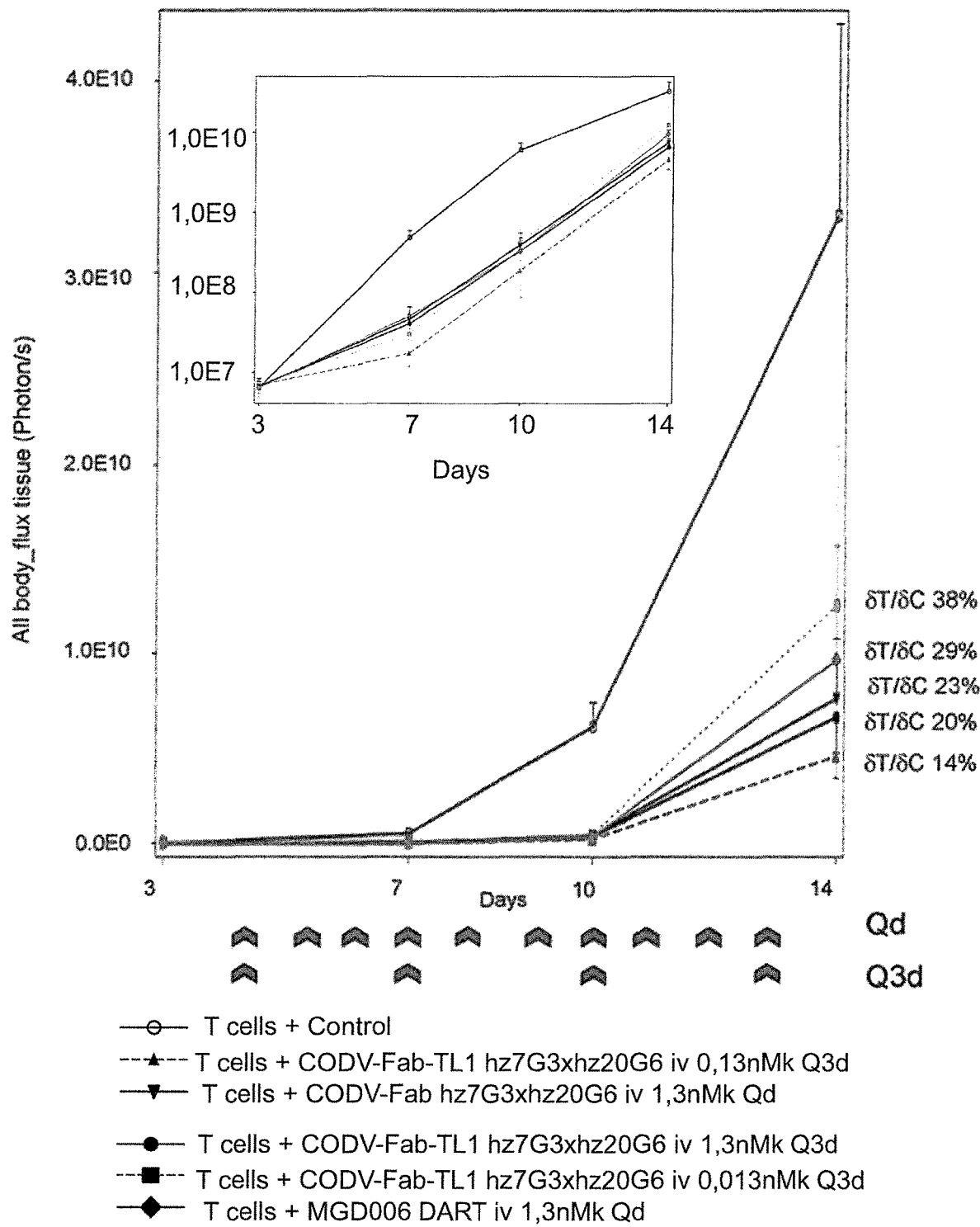

22 Claims, 19 Drawing Sheets
Specification includes a Sequence Listing.

(56) References Cited

U.S. PATENT DOCUMENTS

| | | | |
|---|---|---|---|
| 5,731,168 | A | 3/1998 | Carter |
| 5,821,337 | A | 10/1998 | Carter |
| 5,859,205 | A | 1/1999 | Adair |
| 5,882,877 | A | 3/1999 | Gregory |
| 5,885,573 | A | 7/1999 | Bluestone |
| 5,929,212 | A | 7/1999 | Jolliffe |
| 5,955,358 | A | 9/1999 | Huse |
| 6,013,516 | A | 1/2000 | Verma |
| 6,113,901 | A | 9/2000 | Bluestone |
| 6,143,297 | A | 11/2000 | Bluestone |
| 6,177,078 | B1 | 1/2001 | Lopez |
| 6,352,694 | B1 | 3/2002 | June |
| 6,406,696 | B1 | 6/2002 | Bluestone |
| 6,733,743 | B2 | 5/2004 | Jordan |
| 8,216,805 | B2 | 7/2012 | Carter |
| 2005/0003403 | A1 | 1/2005 | Rossi |
| 2006/0177896 | A1 | 8/2006 | Mach et al. |
| 2010/0150918 | A1 | 6/2010 | Kufer et al. |
| 2011/0027266 | A1 | 2/2011 | Lee |
| 2011/0293619 | A1 | 12/2011 | Kufer et al. |
| 2015/0232557 | A1 | 8/2015 | Tan et al. |
| 2016/0068605 | A1 | 3/2016 | Nemeth et al. |
| 2016/0176973 | A1 | 6/2016 | Kufer et al. |
| 2018/0057597 | A1 | 3/2018 | Albrecht et al. |
| 2019/0241657 | A1 | 8/2019 | Albrecht et al. |

FOREIGN PATENT DOCUMENTS

| | | |
|---|---|---|
| CN | N 102796199 | 11/2012 |
| EP | 0173494 A2 | 3/1986 |
| EP | 125023 B1 | 6/1991 |
| EP | 0239400 B1 | 8/1994 |
| EP | 1 394 253 | 3/2004 |
| EP | 0592106 B1 | 11/2004 |
| EP | 0519596 B1 | 2/2005 |
| EP | 2050764 A1 | 4/2009 |
| EP | 2 714 733 | 4/2014 |
| EP | 2789630 A1 | 10/2014 |
| EP | 2 809 682 | 12/2014 |
| EP | 2839842 A1 | 2/2015 |
| EP | 2 958 942 | 12/2015 |
| EP | 2 968 415 | 1/2016 |
| WO | 87/02671 A1 | 5/1987 |
| WO | 87/05330 A1 | 9/1987 |
| WO | 91/09967 A1 | 7/1991 |
| WO | 94/19478 A1 | 9/1994 |
| WO | 95/14785 A1 | 6/1995 |
| WO | 96/02576 A1 | 2/1996 |
| WO | 96/22378 A1 | 7/1996 |
| WO | 97/10354 A1 | 3/1997 |
| WO | 98/45322 A2 | 10/1998 |
| WO | 98/52975 A1 | 11/1998 |
| WO | 99/54440 A1 | 10/1999 |
| WO | 2008/119567 A2 | 10/2008 |
| WO | 2009/032661 A1 | 3/2009 |
| WO | WO 2010/126066 | 11/2010 |
| WO | WO 2011/100786 | 8/2011 |
| WO | 2011/109588 A1 | 9/2011 |
| WO | 2011/156860 A1 | 12/2011 |
| WO | 2012/021934 A1 | 2/2012 |
| WO | 2012/135345 A1 | 10/2012 |
| WO | 2013/173820 A2 | 11/2013 |
| WO | WO 2014/106015 A2 | 7/2014 |
| WO | 2014/129270 A1 | 8/2014 |
| WO | 2014/138805 A1 | 9/2014 |
| WO | WO 2014/138819 | 9/2014 |
| WO | WO 2014/151910 A1 | 9/2014 |
| WO | WO 2014/191113 | 12/2014 |
| WO | 2015/026892 A1 | 2/2015 |
| WO | WO 2016/036937 | 3/2016 |
| WO | WO 2016/182751 | 11/2016 |

OTHER PUBLICATIONS

Testa et al. (Biomarker Research 2014, 2:4). (Year: 2014).*
Munoz et al. (Haematologica 2001; 86:1261-1269). (Year: 2001).*
Alibaud L. et al. "A new monoclonal anti-CD3epsilon antibody reactive on paraffin sections." Journal of Histochemistry and Cytochemistry 2000, 48(12): 1609-1616.
Brady G. et al. "New cosmid vectors developed for eukaryotic DNA cloning." Gene 1984, 27(2): 223-232.
Edge A. et al. "Deglycosylation of glycoproteins by trifluoromethanesulfonic acid." Analytical Biochemistry 1981, 118(1): 131-137.
Gazzano-Santoro H. et al. "A non-radioactive complement-dependent cytotoxicity assay for anti-CD20 monoclonal antibody." Journal of Immunological Methods 1997, 202(2): 163-171.
Gillies S. et al. "A tissue-specific transcription enhancer element is located in the major intron of a rearranged immunoglobulin heavy chain gene." Cell 1983, 33(3): 717-728.
International Search Report and Written Opinion, dated Jun. 13, 2016, European Patent Office, issued in international application No. PCT/EP2016/051386.
Kastrup J et al. "In vitro production and characterization of partly assembled human CD3 complexes." Scandanavian Journal of Immunolology 2002, 56(5): 436-442.
Marrella et al. "Anti-CD3 mAb improves thymic architecture and prevents autoimmune manifestations in a mouse model of Omenn syndrome: therapeutic implications." Blood 2012, 120(5): 1005-1014.
Mason J. et al. "Transcription cell type specificity is conferred by an immunoglobulin VH gene promoter that includes a functional consensus sequence." Cell 1985, 41(2): 479-487.
Miyaji, H. et al. "Expression of human beta-interferon in Namalwa KJM-1 which was adapted to serum-free medium." Cytotechnology 1990, 3(2): 133-140.
Neuberger M. "Making novel antibodies by expressing transfected immunoglobulin genes." Trends in Biochemical Sciences 1985, 10(9): 347-349.
Padlan E. "A possible procedure for reducing the immunogenicity of antibody variable domains while preserving their ligand-binding properties." Molecular Immunology 1991, 28(4-5): 489-498.
Rader C. "DARTs take aim at BiTEs." Blood 2011, 117(17): 4403-4404.
Remington's Pharmaceutical Sciences, Fifteenth Edition (1975), Mack Publishing Co., Easton, PA, 1975: "Analgesics and Antipyretics", pp. 1035-1038, and "Tablets, Capsules, and Pills", pp. 1570-1580.
Salmeron A et al. "A conformational epitope expressed upon association of CD3-epsilon with either CD3-delta or CD3-gamma is the main target for recognition by anti-CD3 monoclonal antibodies." J Immunol. 1991, 147(9): 3047-3052.
Shopes B. "A genetically engineered human IgG mutant with enhanced cytolytic activity." The Journal of Immunology 1992, 148(9): 2918-2922.
Kuo et al. "Engineering a CD123xCD3 bispecific scFvimmunofusion for the treatment of leukemia and elimination of leukemia stem cells." Protein Engineering, Design and Selection 2012, 25(10): 561-569.
Stein C. et al. "Novel conjugates of single-chain Fv antibody fragments specific for stem cell antigen CD123 mediate potent death of acute myeloid leukaemia cells." Bristish J Hematology 2010, 148(6): 879-889.
Studnicka G. et al. "Human-engineered monoclonal antibodies retain full specific binding activity by preserving non-CDR complementarity-modulating residues." Protein Engineering, Design and Selection 1994, 7(6): 805-814.
Thotakura et al. "Enzymatic deglycosylation of glycoproteins." Methods in Enzymology 1987, 138: 350-359.
O'Hare K. et al. "Transformation of mouse fibroblasts to methotrexate resistance by a recombinant plasmid expressing a prokaryotic dihydrofolate reductase." Proceedings of the National Academy of Sciences 1981, 78.3: 1527-1531.
Caron P. et al. "Engineered humanized dimeric forms of IgG are more effective antibodies." Journal of Experimental Medicine 1992, 176.4: 1191-1195.

(56) References Cited

OTHER PUBLICATIONS

Riechmann L. et al. "Reshaping human antibodies for therapy." Nature 1988, 332: 323-327.
Roguska M. et al. "Humanization of murine monoclonal antibodies through variable domain resurfacing." Proceedings of the National Academy of Sciences 1994, 91.3: 969-973.
Urlaub G. et al. "Isolation of Chinese hamster cell mutants deficient in dihydrofolate reductase activity." Proceedings of the National Academy of Sciences 1980, 77.7: 4216-4220.
Kuwana et al. "Production of the constant domain of murine T-cell receptor β-chain in *Escherichia coli*." FEBS letters 1987, 219.2: 360-364.
Mizukami, et al. "A new SV40-based vector developed for cDNA expression in animal cells." The Journal of Biochemistry 1987, 101.5: 1307-1310.
Morrison et al. "Chimeric human antibody molecules: mouse antigen-binding domains with human constant region domains." Proceedings of the National Academy of Sciences 1984, 81.21: 6851-6855.
Almagro & Fransson "Humanization of Antibodies." Front Biosci; . 2008:13: 1619-1633, Frontiers in Bioscience.
Berman et al., "The Protein Data Bank." Nucleic Acids Research, 2000, 28:235-242, Oxford University Press.
Choi, "Recombinant chimeric OKT3 scFv IgM antibodies mediate immune suppression while reducing T cell activation in vitro" Eur. J. Immunol. 2001,31(1), 94-106, Wiley-VCH.
Harmsen and De Haard HJ, "Properties, production, and applications of camelid single-domain antibody fagments." Appl. Microbiol. Biotechnol. Nov. 2007;77(1):13-22, Springer, Berlin, Germany.
Hezareh, M. et al., "Effector Function Activities of a Panel of Mutants of a Broadly Neutralizing Antibody against Human Immunodeficiency Virus Type 1." J Virol. Dec. 2001; 75(24): 12161-12168, Elsevier.
Jendeberg, L. et al., "Engineering of Fc1 and Fc3 from human immunoglobulin G to analyse subclass specificity for staphylococcal protein A." J. Immunological Meth. 1997 201: 25-34, Elsevier Science B.V.
Jespers et al., "Guiding the selection of human antibodies from phage display repertoires to a single epitope of an antigen." Biotechnology 1994 12, 899, Nature Publishing Group.
Kjer-Nielsen et al., "Crystal structure of the human T cell receptor CD3 heterodimer complexed to the therapeutic mAb OKT3." PNAS 2004, 101(20):7675-7680, The National Academy of Sciences of the USA.
International Preliminary Report on Patentability, dated Apr. 25, 2017, European Patent Office, issued in international patent application No. PCT/EP2015/074550.
International Search Report and Written Opinion, dated Jan. 29, 2016, European Patent Office, issued in international patent application No. PCT/EP2015/074550.
Lefranc et al. "IMGT unique numbering for immunoglobulin and T cell receptor variable domains and Ig superfamily V-like domains." Dev. Comp. Immunol., 2003, 27(1):55-77, Elsevier Science Ltd.
Needleman and Wunsch, "General Method Applicable to the Search for Similarities in the Amino Acid Sequence of Two Proteins." J. Mol. Biol. 1970, 48:443-453, Elsevier.
Nitta, "Preliminary Trial of Specific Targeting Therapy Against Malignant Glioma." Lancet 1990, 335: 368-376, Elsevier.
Sanna et al., "Rapid Assay of phage-derived recombinant human Fabs as bispecific antibodies." Bio/Technology 1995, 13:1221-1224, Nature Publishing Group.
Shitara K et al. "A new vector for the high level expression of chimeric antibodies in myeloma cells." J Immunol Methods. Jan. 3, 1994;167(1-2):271-8, Elsevier.
Thistlethwaite et al., "Evolving use of OKT3 monoclonal antibody for treatment of renal allograft rejection." Transplantation 198438, 695-701, Williams & Wilkins Co.
Woodle et al., "OKT3 therapy for hepatic allograft rejection." Transplantation 1991, 51, 1207-1212, Williams & Wilkins Co.
Yannelly, et al., "Use of anti-CD3 monoclonal antibody in the generation of effector cells from human solid tumors for use in cancer biotherapy." J. Immunol. Meth. 1990, 1, 91-100, Elsevier.
Bedouelle et al., "Diversity and junction residues as hotspots of binding energy in an antibody neutralizing the dengue virus." FEBS J. 273(1):34-46 (Jan. 2006).
Brown et al., "Tolerance of single, but not multiple, amino acid replacements in antibody VH CDR 2: a means of minimizing B cell wastage from somatic hypermutation?" J. Immunol. 156(9):3285-91 (May 1996).
Colman, "Effects of amino acid sequence changes on antibody-antigen interactions." Research in Immunology 145(1):33-36 (Jan. 1994).
North et al., "A new clustering of antibody CDR loop conformations." J. Mol. Biol. 406(2):228-56 (Feb. 2011; Epub Oct. 28, 2010).
Rudikoff et al., "Single amino acid substitution altering antigen-binding specificity." PNAS 79:1979-83 (Mar. 1982).
Vajdos et al., "Comprehensive functional maps of the antigen-binding site of an anti-ErbB2 antibody obtained with shotgun scanning mutagenesis." J. Mol. Biol. 320(2):415-28 (Jul. 2002).
Zhang et al., "Molecular cloning and characterization of CD3[epsilon] in Chinese domestic goose (*Anser cygnoides*)." Gene 2015, 564(2): 160-167.
Chichili et al., "A CD3×CD123 bispecific DART for redirecting host T cells to myelogenous leukemia: Preclinical activity and safety in nonhuman primates" Sci Trans Med 7(289):289ra82 pp. 1-14 (May 2015).
Chu et al., "Immunotherapy with Long-Lived Anti-CD123 + Anti-CD3 Bispecific Antibodies Stimulates Potent T Cell-Mediated Killing of Human AML Cell Lines and of CD123+ Cells in Monkeys: A Potential Therapy for Acute Myelogenous Leukemia" Blood 124 (21): 2316 (Dec. 2014). Abstract of Poster.

* cited by examiner

| | | |
|---|---|---|
| 11D7-C3VL | SGISDRFSGSGSGTDFTLKISRVEPEDLGVYYCGQGTHYPFTFGSGTKLEIK | 112 |
| 1B6-C9VL | SGISDRFSGSSASGTDFTLKISRVEPDDLGVYYCGQGTHYPFTFGSGTKLEIK | 112 |
| 20B5-P10VL | SGISDRFSGSGSGTDFTLKISRVEPDDLGVYYCGQGTHYPFTFGSGTKLEIK | 112 |
| 4B4-D7VL | SGTSDRPFTGSGSGTDFTLKISRVEPDDLGVYYCGQGTEYPFTFGSGTKLEIK | 112 |
| 11H3-E5VL | SGISDRPFTGSGSGTDFTLKISRVEPEDLGVYYCGQGTQYPFTFGSGTKLEIK | 112 |
| 11F9-F8VL | SGISDRFSGSGSGTDFTLKISRVEPDDLGVYYCGQGAHYPFTFGSGTKLEIK | 112 |
| 20G6-F3VL | SGFSDRFSGSGSGTDFTLKISRVDPDDLGVYYCGQGTQYPFTFGSGTKLEIK | 112 |
| 20B5-P10VL | SGISDRFSGSGSSGTDFILKISRVEPDDLGVYYCGQGTQYPFTFGSGTKLEIK | 112 |
| 13H2-C2VL | SGISDRFSGSGSGTDFILKISRVEPDDLGVFYCGQGTQYPFTFGAGTKLELK | 113 |
| 3H6-D2 | SGISDRFSGSGSGTDFTLKISRVEPDDLGVYYCGQGTQYPFTFGAGTKLELK | 112 |
| 18G9-H11VL | SGISDRFSGSGSGTDFTLKISRVAFTDLGVYYCGQGSQYPFTFGAGTKLELK | 112 |
| 10F4-C10VL | SGFSDRFSGSGSGSGTDFTLKISRVEPDDLGVYYCGQGTQYPFTFGAGTKLELK | 112 |
| 11F3-B9VL | SGFSDRFSGSGSGSGTDFTLKISRVEPDDLGVYYCGQGTQYPFTFGAGTKLELK | 112 |
| 16F8-A7VL | SGFSDRFSGSGSGSGTDFTLKISRVEPDDLGVYYCGQGTQYPFTFGAGTKLELK | 112 |
| 18F5-H10VL | SGISDRFSGSGSGSGTDFTLKISRVEPEDLGVYYCGQGTQYPFTFGAGTKLELK | 113 |
| 12G3-H8VL | SGISDRFSGSGSGTDFTLKISRVEPDDLGVYYCGQGTQYPFTFGPGTKLEIK | 113 |
| 4B7-C9VL | SGISDRFSGSGSGTDFTLKISRLEPDDLGVYYCGQGTQYPFTFGSGTKLEIK | 112 |
| 5B1-G2VL | SGISDRFSGSGSGSGTDFTLKISRIBPDDLGIYYCGQGSQYPFTFGSGTKLEIK | 112 |
| 13C1-P6VL | SGISDRFSGSGSGTDFTLKISRIEPDDLGVYYCGQGTQYPFTFGSGTKLEIK | 112 |
| 10E6-G6VL | SGISDRFSGSGSGTDFTLKISRIEPDDLGVYYCGQGTHYPFTFGSGTKLEIK | 112 |
| | ** *;*;:*****,*,******;,****;*** | |

FIG. 2 (cont.)

```
1E1-G5VH     QVQLQESGPTLVKPGDSVKMSCKAFGYTFTDHIIHWVKQSHGKSLEWIGYINPYSGGTNY  60
9F6-G3VH     QVQLQESGPTLVKPGDSVKMSCKASGYTFTDYIIHWVKQSHGKSLEWIGYINPYSDGTNY  60
8B11-B7VH    QVQLQESGPTLVNPGDSVKMSCKASGYTFTDHIIHWVKQSHGKSLEWIGYINPYSGGANY  60
6D6-B8VH     QVQLQESGPTLVKPGDSVKMSCKASAYTFTDNIIHWVKQSHGKSLDWIGYINPYSGGTNY  60
             ************ *********** . ******* ********** ********* .**
             ***********:************:.********:**********:************

1E1-G5VH     NEKFKSKATLTVDKSSSTAYMEFSRLTSEDSAICYCALNYGSYYAMDAWGQGTSVTVSS  119
9F6-G3VH     NEKFKSKATLTVDKSSSTAYMEFSRLTSEDSAIYFCALNYGSYYAMDAWGQGTSVTVSS  119
8B11-B7VH    NGKFKSKATLTIDKSSSTAYMEFSRLTSGDSAIYYCALNYGSYYAMDAWGQGTSVTVSS  119
6D6-B8VH     NGWFRSKATLTVDKSSSTAYMEFSRLTSDDSAIYYCALNYGSYYAMDAWGQGTSVTVS-  118
             *  *:******::*************** ****  ***********************

6D6-B8VL     DIQMTQSPASLSASLGETVTIIDCRPSEDIFNNLAWYQQKPGNSPQLLIYDANSLADGVPS  60
9F6-G3VL     DIQMTQSPASLSASLGETVTIECRPSEDIHSNVAWYQQKPGNSPQLLIYDASNLADGVPS  60
1E1-G5VL     DIQMTQSPASLSASLGQTVTIECRPSEDIYSNLAWFQQKPGSSPQLLIYDANNLADGVPS  60
8B11-B7VL    DIQMTQSPASLSASLGETVTIECRTSKDIYSNLAWFQQEPGNSPQLLIYDASNLADGVPS  60
             ****************:**** ** *:**  *:**:**:**.*********:.******

6D6-B8VL     RFSGSGSGTQYSLMIIRLQSEDVASYFCHQYNIYPYTFGAGTKLELK  107
9F6-G3VL     RFSGSGSGTQYSLKINSLQSEDVASYFCHQYNIYPYTFGSGTKLELK  107
1E1-G5VL     RFSGSGSGTQYSLKINSLQSEDVASYFCQQYNKYPYTFGTGTKLELK  107
8B11-B7VL    RFSGSGSGTQYSLQINNLQSEDVASYFCHQYNNYPYTFGTGTKLELK  107
             *************  * :**********:***  *****:******
```

FIG.3

| | | |
|---|---|---|
| 9B8-G6VH | EVKLQESGPSLVQSSQTLSLTCTVSGFSLTSYHIHWVRQPPGKGLEWMGVMWSDGDTSYS | 60 |
| 9D7-C8VH | EVKLQESGPSLVQSSQTLSLTCTVSGFSLTSYHIHWVRQTPGKGLEWMGVMWSDGDTSYN | 60 |
| 6C10-C4VH | EVKLQESGPSLVQPSETLSLTCTVSGFSLTSYSVHWVRQHSGKSLEWMGRMWNDGDTSYN | 60 |
| | ************ ****:.*: *:*. * *.:********** | |
| 9B8-G6VH | SALKSRLSISRDTSQSQVFLKMNSLQTEDTATYYCARGDYSSYIYLWFAYWGQGTLVTVS | 121 |
| 9D7-C8VH | SALKSRLSISRDTSQSQVFLKMNSLQTEDTATYYCARGYYSSYLYLWFAYWGQGTLVTVS | 121 |
| 6C10-C4VH | SAFTSRLSISRDTSKGQVFLKMNSLQTEDTGTYYCARGHRTP-----FDYWGQVMVTVS | 116 |
| | :.:****:.********.*.****: .* *. *.* **** | |
| 6C10-C4VL | DIVMTQSPSSLAVSAGETVTINCKSSQSFLSSGDERNYVAWYQHKPGQSPKLLIYWASTR | 60 |
| 9B8-G6VL | DIVMTQSPSSLAVSAGETVTINCKSSQSFLSSGDERNYVAWYQHKPGQSPKLLIYWASTR | 60 |
| 9D7-C8VL | DIVMTQSPSSLAVSEGETVTINCKSSQSFLSSGDKNYVAWYQYKPGQSPKLLIYWASTR | 60 |
| | ************ *************:.*.:************* | |
| 6C10-C4VL | HSGVPDRFIGSGSGTDFTLTISSVQAEDLAIYYCQQYDTPLTFGSTKLEIK | 113 |
| 9B8-G6VL | HSGVPDRFIGSGSGTDFTLTISSVQAEDLAIYYCQQYDTPLTFGSTKLEIK | 113 |
| 9D7-C8VL | QSGVPDRFIGSGSGTDFTLTISTVQAEDLAIYYCQQYDTPLTFGSTKLEIK | 113 |
| | :******************:**************************** | |

FIG.4

ANTI-CD3 ANTIBODIES, ANTI-CD123 ANTIBODIES AND BISPECIFIC ANTIBODIES SPECIFICALLY BINDING TO CD3 AND/OR CD123

This application is a continuation of U.S. application Ser. No. 15/654,857, filed Jul. 20, 2017 (now abandoned), which is a national stage application under 35 U.S.C. § 371 of International Application No. PCT/EP2016/051386, filed Jan. 22, 2016, which claims the benefit of European Application No. 15305077.8, filed Jan. 23, 2015, the disclosures of each of which are explicitly incorporated by reference herein in their entirety.

The present invention concerns antibody-like binding protein specifically binding to CD3 and binding specifically to at least one further antigen, for example CD123. The invention further concerns anti-CD3 antibodies and anti-CD123 antibodies. The present invention also concerns antibody-like binding protein specifically binding to CD123 and binding specifically to at least one further antigen. The invention also relates to pharmaceutical compositions comprising the antibody-like binding protein, anti-CD3 antibodies or anti-CD123 antibodies of the invention, and their use to treat cancer. The invention further relates to isolated nucleic acids, vectors and host cells comprising a sequence encoding said antibody-like binding protein, anti-CD3 or anti-CD123 antibody and the use of said anti-CD123 antibody as a diagnostic tool.

The first generation of bispecific antibodies was developed over 20 years ago. Since then a number of clinical studies have tested bispecific antibodies engineered to target cancer cell surface antigens. This group of anti-cancer fusion proteins contains two or more functional domains that localize immunological effector cells in the proximity of targeted cancer cells to achieve anti-cancer activity.

As bispecific antibody technology developed, a different group of fusion proteins named bispecific T-cell engagers (BiTE) were generated by connecting two antibody single chain variable regions (scFv) only (no Fc amino acid segments were included) with a flexible linker, one scFv binds targeted cells and the other binds CD3 on T cell surface. One BiTE, blinatumomab, with CD19×CD3 bi-specific binding activities showed promising results in Phase II clinical trials for patients with minimal residual disease in B-lineage acute lymphoblastic.

CD123 (the interleukin-3 receptor alpha chain IL-3Rα) is a tumor antigen over-expressed in a variety of hematological neoplasms. The majority of AML blasts express surface CD123 and this expression does not vary by subtype of AML. Higher expression of CD123 on AML at diagnosis has been reported to be associated with poorer prognosis. It has been reported that CD123 is expressed on leukemic stem cells (LSCs). There is growing evidence to suggest that AML arises from these leukemic stem cells (LSCs) which have been shown to be quiescent and relatively resistant to DNA damaging chemotherapy.

The increased expression of CD123 on LSCs compared with hematopoietic stem cells (HSCs) presents thus an opportunity for therapeutic targeting of AML-LSCs.

The monoclonal antibody (MAb) 7G3, raised against CD123, has previously been shown to inhibit IL-3 mediated proliferation and activation of both leukemic cell lines and primary cells (U.S. Pat. No. 6,177,078). However, it has remained unclear whether targeting CD123 can functionally impair AML-LSCs.

The use of CD123×CD3 antibody-like binding protein leads to tumor cell killing, as herein shown by the inventors.

The idea of producing a bispecific antibody-like binding protein with CD123×CD3 bi-specific binding activities has already been proposed and described in the international patent application WO2013/173820.

Furthermore, a CD123×CD3 Dual Affinity Re-Targeting (DART) Bi-Specific Antibody Based Molecule from MacroGenics entered phase I clinical trials in 2014.

However, as shown by the inventors, the CD123×CD3 Dual Affinity Re-Targeting (DART) Bi-Specific Antibody Based Molecule from MacroGenics, for example, has an activation of 82% of CD4+ expressing T-cells and 83% of CD8+ expressing T-cells in the absence of target cells. The inappropriate activation of T-cells may lead to severe side effects, such as the cytokine release syndrome. The cytokine release syndrome refers to the release of cytokines by the activated T cells producing a type of systemic inflammatory response similar to that found in severe infections and characterized by hypotension, pyrexia and rigors. Deaths due to cytokine release syndrome have been reported for example for OKT3.

Therefore, in spite of these advancements in bispecific antibody technology, there remains a need for additional cancer therapeutics, particularly those that efficiently target and kill cancer cells, either directly or indirectly.

The inventors have succeeded in generating, screening and selecting specific rat anti-CD3 antibodies displaying high affinity for both human and *Macaca fascicularis* CD3 protein.

The inventors developed antibody-like binding proteins having biological and immunological specificity to the antigen CD3 and at least one further target antigen. In one example, to demonstrate the use of these anti-CD3 antibodies in the generation of bispecific antibody-like binding proteins the inventors generated anti-CD3/anti-CD123 antibody-like binding proteins and demonstrated the therapeutic use thereof. Those bispecific anti-CD3/anti-CD123 antibody-like binding proteins have a low T-cell activation, as it has been observed for the anti-CD3 antibody alone. However, once the CD123 expressing target cells, such as THP-1 cells, are present the bispecific anti-CD3/anti-CD123 antibody-like binding protein shows a high activation of T-cells. Accordingly, the anti-CD3 antibody of the invention defined above is particularly useful for the preparation of antibody-like binding proteins of the invention.

Definitions

Throughout the instant application, the term "and/or" is a grammatical conjunction that is to be interpreted as encompassing that one or more of the cases it connects may occur. For example, the wording "such native sequence proteins can be prepared using standard recombinant and/or synthetic methods" indicates that native sequence proteins can be prepared using standard recombinant and synthetic methods or native sequence proteins can be prepared using standard recombinant methods or native sequence proteins can be prepared using synthetic methods.

Furthermore, throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of"). Furthermore the indefinite article "a" or "an" does not exclude a plurality. The mere fact that certain measures are recited in mutually different dependent claims does not indicate that a combination of these measures cannot be used to advantage.

The term "gene" means a DNA sequence that codes for, or corresponds to, a particular sequence of amino acids which comprises all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

A sequence "at least 85% identical to a reference sequence" is a sequence having, on its entire length, 85%, or more, in particular 90%, 91%, 92%, 93%, 94%, 95%, 96%, 97%, 98% or 99% sequence identity with the entire length of the reference sequence.

In the context of the present application, the "percentage of identity" is calculated using a global pairwise alignment (i.e. the two sequences are compared over their entire length). Methods for comparing the identity of two or more sequences are well known in the art. The «needle» program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk World Wide Web site. The percentage of identity between two polypeptides, in accordance with the invention, is calculated using the EMBOSS: needle (global) program with a "Gap Open" parameter equal to 10.0, a "Gap Extend" parameter equal to 0.5, and a Blosum62 matrix.

Proteins consisting of an amino acid sequence "at least 80%, 85%, 90%, 95%, 96%, 97%, 98% or 99% identical" to a reference sequence may comprise mutations such as deletions, insertions and/or substitutions compared to the reference sequence. In case of substitutions, the protein consisting of an amino acid sequence at least 80%, 85%, 90%, 95%, 96%, 97%, 98% or 99% identical to a reference sequence may correspond to a homologous sequence derived from another species than the reference sequence.

"Amino acid substitutions" may be conservative or non-conservative. Preferably, substitutions are conservative substitutions, in which one amino acid is substituted for another amino acid with similar structural and/or chemical properties. The substitution preferably corresponds to a conservative substitution as indicated in the table below.

| Conservative substitutions | Type of Amino Acid |
| --- | --- |
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

An "antibody" also called "immunoglobulin" may be a natural or conventional antibody in which two heavy chains are linked to each other by disulfide bonds and each heavy chain is linked to a light chain by a disulfide bond. There are two types of light chain, lambda (l) and kappa (κ). There are five main heavy chain classes (or isotypes) which determine the functional activity of an antibody molecule: IgM, IgD, IgG, IgA and IgE. Each chain contains distinct sequence domains. The light chain includes two domains or regions, a variable domain (VL) and a constant domain (CL). The heavy chain includes four domains, a variable domain (VH) and three constant domains ($C_{H1}$, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences that together define the binding affinity and specificity of the natural Fv region of a native immunoglobulin binding site. The light and heavy chains of an immunoglobulin each have three CDRs, designated CDR1-L, CDR2-L, CDR3-L and CDR1-H, CDR2-H, CDR3-H, respectively. A conventional antibody antigen-binding site, therefore, includes six CDRs, comprising the CDR set from each of a heavy and a light chain V region.

In context of the invention, the antibody or immunoglobulin is an IgM, IgD, IgG, IgA and IgE.

"Framework Regions" (FRs) refer to amino acid sequences interposed between CDRs, i.e. to those portions of immunoglobulin light and heavy chain variable regions that are relatively conserved among different immunoglobulins in a single species. The light and heavy chains of an immunoglobulin each have four FRs, designated FR1-L, FR2-L, FR3-L, FR4-L, and FR1-H, FR2-H, FR3-H, FR4-H, respectively. Accordingly, the light chain variable domain may thus be designated as (FR1-L)-(CDR1-L)-(FR2-L)-(CDR2-L)-(FR3-L)-(CDR3-L)-(FR4-L) and the heavy chain variable domain may thus be designated as (FR1-H)-(CDR1-H)-(FR2-H)-(CDR2-H)-(FR3-H)-(CDR3-H)-(FR4-H).

Knowing the amino acid sequence of the CDRs one skilled in the art can easily determine the framework regions FR1-L, FR2-L, FR3-L, FR4-L and/or FR1-H, FR2-H, FR3-H, FR4-H.

As used herein, a "human framework region" is a framework region that is substantially identical (about 85%, or more, in particular 90%, 95%, 97%, 99% or 100%) to the framework region of a naturally occurring human antibody.

In the context of the invention, CDR/FR definition in an immunoglobulin light or heavy chain is to be determined based on IMGT definition (Lefranc et al. Dev. Comp. Immunol., 2003, 27(1):55-77; www.imgt.org).

As used herein, the term "antibody" denotes conventional antibodies and fragments thereof, as well as single domain antibodies and fragments thereof, in particular variable heavy chain of single domain antibodies, and chimeric, humanized, bispecific or multispecific antibodies.

As used herein, antibody or immunoglobulin also includes "single domain antibodies" which have been more recently described and which are antibodies whose complementary determining regions are part of a single domain polypeptide. Examples of single domain antibodies include heavy chain antibodies, antibodies naturally devoid of light chains, single domain antibodies derived from conventional four-chain antibodies, engineered single domain antibodies. Single domain antibodies may be derived from any species including, but not limited to mouse, human, camel, llama, goat, rabbit, bovine. Single domain antibodies may be naturally occurring single domain antibodies known as heavy chain antibody devoid of light chains. In particular, Camelidae species, for example camel, dromedary, llama, alpaca and guanaco, produce heavy chain antibodies naturally devoid of light chain. Camelid heavy chain antibodies also lack the CH1 domain.

The variable heavy chain of these single domain antibodies devoid of light chains are known in the art as "VHH" or "nanobody". Similar to conventional VH domains, VHHs contain four FRs and three CDRs. Nanobodies have advantages over conventional antibodies: they are about ten times smaller than IgG molecules, and as a consequence properly folded functional nanobodies can be produced by in vitro expression while achieving high yield. Furthermore, nanobodies are very stable, and resistant to the action of proteases. The properties and production of nanobodies have been reviewed by Harmsen and De Haard H J (Appl. Microbiol. Biotechnol. 2007 November; 77(1):13-22).

The term "monoclonal antibody" or "mAb" as used herein refers to an antibody molecule of a single amino acid composition that is directed against a specific antigen, and is not to be construed as requiring production of the antibody by any particular method. A monoclonal antibody may be produced by a single clone of B cells or hybridoma, but may also be recombinant, i.e. produced by protein engineering.

The term "chimeric antibody" refers to an engineered antibody which in its broadest sense contains one or more regions from one antibody and one or more regions from on or more other antibody(ies). In particular a chimeric antibody comprises a VH domain and a VL domain of an antibody derived from a non-human animal, in association with a CH domain and a CL domain of another antibody, in particular a human antibody. As the non-human animal, any animal such as mouse, rat, hamster, rabbit or the like can be used. A chimeric antibody may also denote a multispecific antibody having specificity for at least two different antigens.

The term "humanized antibody" refers to an antibody which is wholly or partially of non-human origin and which has been modified to replace certain amino acids, in particular in the framework regions of the heavy and light chains, in order to avoid or minimize an immune response in humans. The constant domains of a humanized antibody are most of the time human CH and CL domains.

Numerous methods for humanization of an antibody sequence are known in the art; see e.g. the review by Almagro & Fransson (2008) Front Biosci. 13: 1619-1633. One commonly used method is CDR grafting, or antibody reshaping, which involves grafting of the CDR sequences of a donor antibody, generally a mouse antibody, into the framework scaffold of a human antibody of different specificity. Since CDR grafting may reduce the binding specificity and affinity, and thus the biological activity, of a CDR grafted non-human antibody, back mutations may be introduced at selected positions of the CDR grafted antibody in order to retain the binding specificity and affinity of the parent antibody. Identification of positions for possible back mutations can be performed using information available in the literature and in antibody databases. Amino acid residues that are candidates for back mutations are typically those that are located at the surface of an antibody molecule, while residues that are buried or that have a low degree of surface exposure will not normally be altered. An alternative humanization technique to CDR grafting and back mutation is resurfacing, in which non-surface exposed residues of non-human origin are retained, while surface residues are altered to human residues. Another alternative technique is known as "guided selection" (Jespers et al. (1994) Biotechnology 12, 899) and can be used to derive from for example a murine or rat antibody a fully human antibody conserving the epitope and binding characteristics of the parental antibody. A further method of humanization is the so-called 4D humanization. The 4D humanization protocol is described in the patent application US20110027266 A1 (WO2009032661A1) and is exemplified in the following applying the 4D humanization to humanize the rat antibody variable light (VL) and heavy (VH) domains. In one example, a rat antibody homology model was done with typically MOE software (v. 2011.10—Chemical Computing Group, Quebec, Canada) using PDB structures (Berman et al., Nucleic Acids Research, 2000, 28:235-242) as templates and was subsequently energy minimized using the standard procedures implemented in MOE. A molecular dynamics (MD) simulation was then performed on the minimized 3D homology model (done with MOE software) of rat antibody and compared to the, for example, 49 human models derived from the seven representative light chains (vk1, vk2, vk3, vk4, vlambda1, vlambda2, vlambda3) and the seven representative heavy chains (vh1a, vh1b, vh2, vh3, vh4, vh5, vh6) designed by LGCR/SDI and available within MOE. For instance, one model of chains couple (Vkx-Vhx) with the best both hydrophobic, electrostatic components and sequence identity outside CDR has been selected for the "4D humanization". For the pairwise association between the rat antibody variable domain and the selected model, the sequences were aligned based typically on the optimal 3D superposition of the alpha carbons of the corresponding homology models. The unwanted motifs were then considered and mutated. Finally, the resulting humanized sequences were blasted for sequence similarity against, for instance, the IEDB database (http://www.immuneepitope-.org; version 2012/01/30 accessible locally) to ensure that none of the sequences contain any known B- or T-cell epitope listed in.

For chimeric antibodies, humanization typically involves modification of the framework regions of the variable region sequences.

Amino acid residues that are part of a CDR will typically not be altered in connection with humanization, although in certain cases it may be desirable to alter individual CDR amino acid residues, for example to remove a glycosylation site, a deamidation site or an undesired cysteine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, in particular by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues. Substitution in a CDR sequence to remove one of the implicated residues is also intended to be encompassed by the present invention.

"Fragments" of (conventional) antibodies comprise a portion of an intact antibody, in particular the antigen binding region or variable region of the intact antibody. Examples of antibody fragments include Fv, Fab, F(ab')2, Fab', dsFv, (dsFv)2, scFv, sc(Fv)2, diabodies, bispecific and multispecific antibodies formed from antibody fragments. A fragment of a conventional antibody may also be a single domain antibody, such as a heavy chain antibody or VHH.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, in particular by using gene recombination techniques. Divalent and multivalent antibody fragments can form either spontaneously by association of monovalent scFvs, or can be generated by coupling monovalent scFvs by a peptide linker, such as divalent sc(Fv)$_2$. "dsFv" is a VH::VL heterodimer stabilised by a disulphide bond. "(dsFv)2" denotes two dsFv coupled by a peptide linker.

The term "bispecific antibody" or "BsAb" typically denotes an antibody, which combines the antigen-binding sites of two antibodies within a single molecule. Thus, BsAbs are able to bind two different antigens simultaneously. Genetic engineering has been used with increasing frequency to design, modify, and produce antibodies or antibody derivatives with a desired set of binding properties and effector functions as described for instance in EP 2 050 764 A1.

The term "multispecific antibody" denotes an antibody that combines the antigen-binding sites of two or more antibodies within a single molecule.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

The term "hybridoma" denotes a cell, which is obtained by subjecting a B cell prepared by immunizing a non-human mammal with an antigen to cell fusion with a myeloma cell derived from a mouse or the like which produces a desired monoclonal antibody having an antigen specificity.

By "purified" and "isolated" it is meant, when referring to a polypeptide (i.e. the antibody of the invention) or a nucleotide sequence, that the indicated molecule is present in the substantial absence of other biological macromolecules of the same type. The term "purified" as used herein in particular means at least 75%, 85%, 95%, or 98% by weight, of biological macromolecules of the same type are present. An "isolated" nucleic acid molecule that encodes a particular polypeptide refers to a nucleic acid molecule that is substantially free of other nucleic acid molecules that do not encode the subject polypeptide; however, the molecule may include some additional bases or moieties, which do not deleteriously affect the basic characteristics of the composition.

The term "antigen" or "target antigen" as used herein refers to a molecule or a portion of a molecule that is capable of being bound by an antibody or an antibody-like binding protein. The term further refers to a molecule or a portion of a molecule that is capable of being used in an animal to produce antibodies that are capable of binding to an epitope of that antigen. A target antigen may have one or more epitopes. With respect to each target antigen recognized by an antibody or by an antibody-like binding protein, the antibody-like binding protein is capable of competing with an intact antibody that recognizes the target antigen.

"Affinity" is defined, in theory, by the equilibrium association between the whole antibody and the antigen. Affinity may be expressed for example in half-maximal effective concentration ($EC_{50}$) or the equilibrium dissociation constant (KD).

"Half maximal effective concentration" also called "$EC_{50}$" refers to the concentration of a drug, antibody or toxicant which induces a response halfway between the baseline and maximum after a specified exposure time. $EC_{50}$ and affinity are inversely related, the lower the $EC_{50}$ value the higher the affinity of the antibody.

"$K_D$" is the equilibrium dissociation constant, a ratio of $k_{off}/k_{on}$, between the antibody and its antigen. $K_D$ and affinity are inversely related. The $K_D$ value relates to the concentration of antibody and the lower the $K_D$ value and the higher the affinity of the antibody. Affinity can be experimentally assessed by a variety of known methods, such as measuring association and dissociation rates with surface Plasmon resonance or measuring the $EC_{50}$ in an immunochemical assay (ELISA, FACS). Enzyme-linked immunosorbent assay (ELISA) is a biochemistry assay that uses a solid-phase enzyme immunoassay to detect the presence of a substance, usually an antigen, in a liquid sample or wet sample. Antigens from the sample are attached to a surface. Then, a further specific antibody is applied over the surface so it can bind to the antigen. This antibody is linked to an enzyme, and, in the final step, a substance containing the enzyme's substrate is added. The subsequent reaction produces a detectable signal, most commonly a color change in the substrate. Fluorescence-activated cell sorting (FACS) provides a method for sorting a heterogeneous mixture of biological cells into two or more containers, one cell at a time, based upon the specific light scattering and fluorescent characteristics of each cell. In these assays, the $EC_{50}$ is the concentration of the antibody which induces a response halfway between the baseline and maximum after some specified exposure time on a defined concentration of antigen by ELISA (enzyme-linked immuno-sorbent assay) or cell expressing the antigen by FACS (Fluorescence Activated Cell Sorting). Surface plasmon resonance is a label free method wherein the binding of a molecule in the soluble phase (the "analyte") is directly measured to a "ligand" molecule immobilized on a sensor surface. In the sensor device the binding of the ligand is monitored by an optical phenomenon termed surface plasmon. In particular, when the "analyte" molecule dissociates from the "ligand" molecule, a decrease in SPR signal (expressed in resonance units, RU) is observed. Association ('on rate', $k_a$) and Dissociation rates ('off rate', $k_d$) are obtained from the signal obtained during the association and dissociation and the equilibrium dissociation constant ('binding constant', $K_D$) can be calculated therefrom. The signal given in resonance units (RU) depends on the size of the ligand present in the analyte, however in case the experimental conditions are the same, i.e. the ligand is the same molecule at the same condition the obtained RU can indicate affinity, wherein the higher the obtained signal in RU the higher the binding.

A monoclonal antibody binding to antigen 1 (Ag1) is "cross-reactive" to antigen 2 (Ag2) when the $EC_{50}$s are in a similar range for both antigens. In the present application, a monoclonal antibody binding to Ag1 is cross-reactive to Ag2 when the ratio of affinity of Ag2 to affinity of Ag1 is equal or less than 10 (in particular 5, 2, 1 or 0.5), affinities being measured with the same method for both antigens.

A monoclonal antibody binding to Ag1 is "not significantly cross-reactive" to Ag2 when the affinities are very different for the two antigens. Affinity for Ag2 may not be measurable if the binding response is too low. In the present application, a monoclonal antibody binding to Ag1 is not significantly cross-reactive to Ag2, when the binding response of the monoclonal antibody to Ag2 is less than 5% of the binding response of the same monoclonal antibody to Ag1 in the same experimental setting and at the same antibody concentration. In practice, the antibody concentration used can be the $EC_{50}$ or the concentration required to reach the saturation plateau obtained with Ag1.

As used herein "specificity" denotes the capacity of an antibody to discriminate the target peptide sequence to which its binds ("epitope") from closely related, highly homologous, peptide sequences.

A monoclonal antibody "binds specifically" to Ag1 when it is not significantly cross-reactive to Ag2.

A "domain" may be any region of a protein, generally defined on the basis of sequence homologies and often related to a specific structural or functional entity.

A "recombinant" molecule is one that has been prepared, expressed, created, or isolated by recombinant means.

As used herein, the term "subject" denotes a mammal, such as a rodent, a feline, a canine, and a primate. In particular, a subject according to the invention is a human.

Anti CD3 Antibodies

"CD3" denotes an antigen that is expressed on T-cells as part of the multimolecular T-cell receptor complex and that consists of at least three different chains CD3ε, CD3δ and CD3γ. CD3δ and CD3γ have a low sequence identity and/or similarity to human CD3ε (similarity and identity is less than 20%). CD3ε and CDR3δ can form together a complex, herein called "CD3ε/δ-complex". CD3ε also forms a complex with CDR3γ, the so-called "CD3ε/γ-complex" Clustering of CD3 on T-cells, e.g., by immobilized anti-CD3-antibodies, leads to T-cell activation similar to the engagement of the T-cell receptor but independent from its clone typical specificity. "CD3ε" comprises three domains, an intracellular domain, a transmembrane domain and an extracellular domain.

Most prior art anti-CD3-antibodies recognize the CD3ε-chain. One of such prior art anti-CD3-antibodies is OKT3. Prior art has exemplified T cell activation events employing antibody molecules for example by employing the antibody molecule OKT3. The anti-CD3 antibody and variant thereof have been described in the prior art (U.S. Pat. Nos. 4,361, 549; 4,361,549; 5,885,573; 5,929,212; and WO 98/52975 or U.S. Pat. No. 5,955,358). OKT3 has been further used as potent immunosuppressive agent in clinical transplantation to treat allograft rejection (Thistlethwaite 1984, Transplantation 38, 695-701; Woodle 1991, Transplantation 51, 1207-1212; Choi 2001, Eur. J. Immunol. 31(1), 94-106).

Major drawbacks of this therapy are T cell activation manifested in cytokine release due to cross-linking between T cells and FcγR-bearing cells and the human anti-mouse antibody (HAMA) response. Several publications have described alterations such as humanization of OKT3 to reduce these side effects: U.S. Pat. Nos. 5,929,212; 5,885, 573 and others. On the other hand, OKT3 or other anti-CD3-antibodies can be used as immunopotentiating agents to stimulate T cell activation and proliferation (U.S. Pat. No. 6,406,696 Bluestone; U.S. Pat. No. 6,143,297 Bluestone; U.S. Pat. No. 6,113,901 Bluestone; Yannelly 1990, J. Immunol. Meth. 1, 91-100). Anti-CD3-anti bodies have also been described as agents used in combination with anti-CD28-antibodies to induce T cell proliferation (U.S. Pat. No. 6,352,694). OKT3 has further been used by itself or as a component of a bispecific antibody to target cytotoxic T cells to tumor cells or virus infected cells (Nitta 1990, Lancet 335, 368-376; Sanna 1995, Bio/Technology 13, 1221-1224; WO 99/54440).

Approaches up to now using antibodies as agents for recruiting T-cells have been hampered by several findings. First, natural or engineered antibodies having a high binding affinity to T-cells often do not activate the T-cells to which they are bound. Second, natural or engineered antibodies having a low binding affinity to T-cells are also often ineffective with respect to their ability to trigger T-cell mediated cell lysis.

A reference sequence of full-length human CD3ε protein, including the signal peptide, is available from the Uniprot database under accession number P07766 and herein enclosed under SEQ ID NO: 1 (as available on Dec. 12, 2014).

A reference sequence of full-length *Macaca fascicularis* CD3ε protein, including the signal peptide, is available from the Uniprot database under accession number Q95LI5 and herein enclosed under SEQ ID NO: 2 (as available on Dec. 12, 2014).

A sequence of mature human CD3ε His-tagged Fc-fusion proteins, cloned by the inventors from genomic DNA, is disclosed under SEQ ID NO: 3. Said mature human CD3ε His-tagged Fc-fusion protein comprises amino acids 23 to 126 of the full-length human CD3ε protein and thus comprises the extracellular domain of human CD3ε.

A sequence of mature *Macaca fascicularis* CD3ε Fc-fusion protein, cloned by the inventors from genomic DNA, is disclosed under SEQ ID NO: 4. Said mature *Macaca fascicularis* CD3ε Fc-fusion protein comprises amino acids 23 to 117 of the full-length *Macaca fascicularis* CD3ε protein and thus comprises the extracellular domain of human or *Macaca fascicularis* CD3ε, containing one Alanine to Valine exchange at the amino acid position 35 in comparison to amino acid position 57 of the wild-type sequence.

Domain organization of human and *Macaca fascicularis* CD3ε is as it follows (based on Uniprot P07766 sequence (human) and Uniprot Q95LI5 sequence (*Macaca fascicularis*)):

| CD3ε domains | Positions on SEQ ID NO: 1 (human) | Positions on SEQ ID NO: 2 (*Macaca fascicularis*) |
|---|---|---|
| Extracellular | 23-126 | 22-117 |
| Transmembrane domain | 127-152 | 118-138 |
| Cytoplasmic | 153-207 | 139-198 |

Accordingly, the extracellular domain of human CD3ε consists of amino acids at positions 23-126 of SEQ ID NO: 1 and the extracellular domain of *Macaca fascicularis* CD3ε consists of amino acids at positions 22-117 of SEQ ID NO: 2.

The inventors have succeeded in generating, screening and selecting specific mouse and rat anti-CD3 antibodies. These anti-CD3 antibodies display high affinity for both human and *Macaca fascicularis* CD3 protein, and have however a low T-cell activation in the absence of target cells.

The inventors have determined the sequence of variable heavy and light chains of such monoclonal antibodies, the so-called anti-CD3 antibodies "20G6-F3", "4B4-D7", "4E7-C9", "18F5-H10", "12D2-E5", "11D7-C3", "11H3-E5", "13H2-C2", "13C1-F6", "18H11-F10", "1E6-C9", "10F4-C10", "10E6-G6", "18G9-H11", "11F3-B9", "12G3-E8", "5B1-G2", "16F8-A7", "11F9-F8", "3G5-E10", "9D7-F3", "8C2-F7", "20E5-F10", "20B5-F10", "6C9-C9", "3E8-G1", "3H6-D2" and "8H2".

The so-called "20G6-F3" anti-CD3 antibody comprises:
a heavy chain variable domain of consisting of sequence (SEQ ID NO: 5)
EVQLVETGGSLVQPGKSLKLTCATSGFTFTKAWMHWVRQSPEKQLEWVAQ

IKDKSNSYATYYAESVKGRFTISRDDSKSTIYLQMNSLKEEDTAIYYCRG

VYYALSPFDYWGQGVMVTVSS, with CDRs shown in bold characters and underlined) comprising CDR1-H of sequence SEQ ID NO: 6, a CDR2-H of sequence SEQ ID NO: 7, and a CDR3-H of sequence SEQ ID NO: 8, and
a light chain variable domain consisting of sequence (SEQ ID NO: 9)
DVVMTQTPVSLSVSLGGQVSISCRSSQSLVHNNGNTYLSWYLQKPGQSPQ

SLIYKVSNRFSGFSDRFSGSGSGTDFTLKISRVDPDDLGVYYCGQGTQYP

FTFGSGTKLEIK, with CDRs shown in bold characters and underlined) comprising CDR1-L of sequence SEQ ID NO: 10, a CDR2-L consisting of sequence 'KVS', and a CDR3-L of sequence SEQ ID NO: 11.

The so-called "4B4-D7" anti-CD3 antibody comprises:
a heavy chain variable domain consisting of sequence (SEQ ID NO: 12)
EVQLVETGGRLVQPGRSLKLTCATSGFTFSNAWMHWVRQSPEKQLEWVAQ

IKARSNNYATYYAESVKGRFTISRDDSKSTIYLQMNSLKEEDTAIYYCRG

TYYASKPFDYWGQGVMVTVSS, with CDRs shown in bold characters and underlined) comprising CDR1-H of sequence SEQ ID NO: 13, a CDR2-H of sequence SEQ ID NO: 14, and a CDR3-H of sequence SEQ ID NO: 15, and
a light chain variable domain consisting of sequence (SEQ ID NO: 16)
DVVMTQTPVSLSVSLGGQVSISCRSSQSLVHDNGNTYLSWSLQRPGQSPQ

VLIYKVSNRFSGTSDRFTGSGSGTDFTLKISRVEPDDLGVYYCGQGTQYP

FTFGSGTKLEIK, with CDRs shown in bold characters and underlined) comprising CDR1-L of sequence SEQ ID NO: 17, a CDR2-L consisting of sequence 'KVS', and a CDR3-L of sequence SEQ ID NO: 11.

The so-called "4E7-C9" anti-CD3 antibody comprises:
A heavy chain variable domain consisting of sequence (SEQ ID NO: 18)
EVQVVETGGSLVQPGKSLKLTCATSGFTFSNAWMHWVRQSPEKQLEWVAQ

IKDKSNNNYATYYAESLKGRFTISRDDPKRSIYLQMNSLREEDTAIYYCRY

VHYGIGYAMDAWGQGTSVTVSS, with CDRs shown in bold characters and underlined) comprising CDR1-H of sequence SEQ ID NO: 13, a CDR2-H of sequence SEQ ID NO: 19, and a CDR3-H of sequence SEQ ID NO: 20, and
a light chain variable domain consisting of sequence (SEQ ID NO: 21)
DVVMTQTPVSLSVSLGGQVSISCRSSQSLEHNNGNTYLSWYLQKPGQSPQ

PLIYKVSNRFSGISDRFSGSGSGTDFTLKISRVEPDDLGVYYCGQGTQYP

FTFGPGTKLELK, with CDRs shown in bold characters and underlined) comprising CDR1-L of sequence SEQ ID NO: 22, a CDR2-L consisting of sequence 'KVS', and a CDR3-L of sequence SEQ ID NO: 11.

The so-called "18F5-H10" anti-CD3 antibody comprises:
a heavy chain variable domain consisting of sequence (SEQ ID NO: 23)
EVQVVETGGSLVQPGKSLKLTCATSGFTFTNAWMHWVRRSPEKQLEWVAQ

IKDKSNNYATYYAESVKGRFTISRDDSKSSIYLQMNSLKEEDTAIYYCRY

VHYRFAYALDAWGRGTSVSVSS, with CDRs shown in bold characters and underlined) comprising CDR1-H of sequence SEQ ID NO: 24, a CDR2-H of sequence SEQ ID NO: 19, and a CDR3-H of sequence SEQ ID NO: 25, and
a light chain variable domain consisting of sequence (SEQ ID NO: 26)
DVLMTQTPVSLSVSLGGQVSISCRSSQSLVHTNGNTYLSWYLQKPGQSPQ

LLIYKVSNRLSGISDRFSGSGSGTDFTLKISRVEPDDLGVYYCGQGTHYP

FTFGAGTKLELK, with CDRs shown in bold characters and underlined) comprising CDR1-L of sequence SEQ ID NO: 27, a CDR2-L consisting of sequence 'KVS', and a CDR3-L of sequence SEQ ID NO:28.

The so-called "12D2-E5" anti-CD3 antibody comprises:
a heavy chain variable domain consisting of sequence (SEQ ID NO: 29)
EVKLVESGGGLVQPGRSLRLSCAASGFNFYAYWMGWVRQAPGKGLEWIGE

IKKDGTTINYTPSLKDRFTISRDNAQNTLYLQMTKLGSEDTALYYCAREE

RDGYFDYWGQGVMVTVSS, with CDRs shown in bold characters and underlined) comprising CDR1-H of sequence SEQ ID NO: 30, a CDR2-H of sequence SEQ ID NO: 31, and a CDR3-H of sequence SEQ ID NO: 32, and
a light chain variable domain consisting of sequence (SEQ ID NO: 33)
QFVLTQPNSVSTNLGSTVKLSCKRSTGNIGSNYVNWYQQHEGRSPTTMIY

RDDKRPDGVPDRFSGSIDRSSNSALLTINNVQTEDEADYFCQSYSSGIVF

GGGTKLTVL, with CDRs shown in bold characters and underlined) comprising CDR1-L of sequence SEQ ID NO: 34, a CDR2-L consisting of sequence 'RDD', and a CDR3-L of sequence SEQ ID NO: 35.

The so-called "11D7-C3" anti-CD3 antibody comprises:
a heavy chain variable domain consisting of sequence (SEQ ID NO: 36)
EVQFVETGGSLVQPGKSLKLTCATSGFTFSNAWMHWVRQSPEKQLEWVAQ

IKAKSNNYATYYAESVKGRFTISRDDSKSSVYLQMNSLKEEDTATYYCRG

LYYGLSPSDYWGQGVMVTVSS, with CDRs shown in bold characters and underlined) comprising CDR1-H of sequence SEQ ID NO: 13, a CDR2-H of sequence SEQ ID NO: 37, and a CDR3-H of sequence SEQ ID NO: 38, and
a light chain variable domain consisting of sequence (SEQ ID NO: 39)
DVVMTQTPVSLSVSLGGQVSISCRSSQSLVHNNGNTYLSWYLQKPGQSPQ

LLIYKVSNRFSGISDRFSGSGSGTDFTLKISRVEPDDLGVYYCGQGTHYP

FTFGSGTKLEIK, with CDRs shown in bold characters and underlined) comprising CDR1-L of sequence SEQ ID NO: 10, a CDR2-L consisting of sequence 'KVS', and a CDR3-L of sequence SEQ ID NO: 28.

The so-called "11H3-E5" anti-CD3 antibody comprises:
a heavy chain variable domain consisting of sequence (SEQ ID NO: 40)
EVQLVETGGSLVQPGKSLKLTCATSGFTFSNAWMHWVRQSPEKQLEWVAQ

IKAKSNNYATYYAESVKGRFTISRDDSKSSVYLQMNSLKEEDTAIYYCRG

TYYAYKPFDYWGQGVMVTVSS, with CDRs shown in bold characters and underlined) comprising CDR1-H of sequence SEQ ID NO: 13, a CDR2-H of sequence SEQ ID NO: 37, and a CDR3-H of sequence SEQ ID NO: 41, and
a light chain variable domain consisting of sequence (SEQ ID NO: 42)
DVVMTQTPVSLSVSLGGQVSISCRSSQSLVHDNGNTYLSWSLQKPGQSPQ

VLIYKVSNRFSGTSDRFTGSGSGTDFTLKISRVEPDDLGVYYCGQGTQYP

FTFGSGTKLEIK, with CDRs shown in bold characters and underlined) comprising CDR1-L of sequence SEQ ID NO: 17, a CDR2-L consisting of sequence 'KVS', and a CDR3-L of sequence SEQ ID NO: 11.

The so-called "13H2-C2" anti-CD3 antibody comprises:
a heavy chain variable domain consisting of sequence (SEQ ID NO: 43)
EEELVETGGSLVQFGKSLKLTCATSGFTFSNAWMHWVRQSFDKQLEWVAQ

IKAKSNNYATYYAESVKGRFTISRDDSKSSVYLQMNNLKEEDTAIYYCRY

VHYGLAPMDAWGQGTSVTVSS, with CDRs shown in bold characters and underlined) comprising CDR1-H of sequence SEQ ID NO: 13, a CDR2-H of sequence SEQ ID NO: 37, and a CDR3-H of sequence SEQ ID NO: 44, and
a light chain variable domain consisting of sequence (SEQ ID NO: 45)
DVVMTQTPVSLSVSLGGQVSISCRSSQSLVHNNGNTYLSWYLQKAGQSPQ

LLIYKVSNRFSGISDRFSGSGSGTDFILKISRVEPDDLGVFYCGQGTQYP

FTFGAGTKLELK, with CDRs shown in bold characters and underlined) comprising CDR1-L of sequence SEQ ID NO: 10, a CDR2-L consisting of sequence 'KVS', and a CDR3-L of sequence SEQ ID NO: 11.

The so-called "13C1-F6" anti-CD3 antibody comprises:
a heavy chain variable domain consisting of sequence (SEQ ID NO: 46)
EVQLVETGGTLVQPGKSLKLTCATSGFTFSNAWMHWVRQSPEKQLEWVAQ

IKAKSNNYATYYAESVKGRFTISRDDSKTSVYLQLNSLREEDTAIYYCRG

TQYGYNPFDYWGQGVMVTVSS, with CDRs shown in bold characters and underlined) comprising CDR1-H of sequence SEQ ID NO: 13, a CDR2-H of sequence SEQ ID NO: 37, and a CDR3-H of sequence SEQ ID NO: 47, and
a light chain variable domain consisting of sequence (SEQ ID NO: 48)
DVVMTQSPVSLSVSLGGQVSISCRSSQSLVHNNGNTYLSWYLQRSGQSPQ

LLIYKVSNRLSGISDRFSGSGSGTDFTLKISRIEPDDLGVYYCGQGTQYP

FTFGSGTRLEIK, with CDRs shown in bold characters and underlined) comprising CDR1-L of sequence SEQ ID NO: 10, a CDR2-L consisting of sequence 'KVS', and a CDR3-L of sequence SEQ ID NO: 11.

The so-called "18H11-F10" anti-CD3 antibody comprises:
a heavy chain variable domain consisting of sequence (SEQ ID NO: 49)
EVQLVESGGGLVQPGRSLKLSCAASGFIFSDYYMAWVRQAPKKGLEWVAT

ISISGSRTYYPDSVKGRFTVSRDNAKSSLYLQMNSLKSEDTATYYCATNN

PGGWFVYWGQGTLVTVSS, with CDRs shown in bold characters and underlined) comprising CDR1-H of sequence SEQ ID NO: 50, a CDR2-H of sequence SEQ ID NO: 51, and a CDR3-H of sequence SEQ ID NO: 52, and
a light chain variable domain consisting of sequence (SEQ ID NO: 53)
NIQMTQSPSLLSASVGDRVTLSCKAGQNINNDLAWYQQKLGEAPRLLIYN

ANSLQTGIPSRFSGSGSGADFTLTISSLQPEDVATYFCQQYSSGDTFGAG

TKLELK, with CDRs shown in bold characters and underlined) comprising CDR1-L of sequence SEQ ID NO: 54, a CDR2-L consisting of sequence 'NAN', and a CDR3-L of sequence SEQ ID NO: 55.

The so-called "1E6-C9" anti-CD3 antibody comprises:
a heavy chain variable domain consisting of sequence (SEQ ID NO: 56)
EVQLVETGGSLVQPGKSLKLTCATSGFTFSYAWMHWVRQSPDKQLQWVAQ

IKAKSNNYATYYAESVEGRFTISRDDSKSSVYLQMNSLKEEDTAIYYCRG

VYYGLLGLDAWGQGTSVTVSS, with CDRs shown in bold characters and underlined) comprising CDR1-H of sequence SEQ ID NO: 57, a CDR2-H of sequence SEQ ID NO: 37, and a CDR3-H of sequence SEQ ID NO: 58, and
a light chain variable domain consisting of sequence (SEQ ID NO: 59)
DVVMTQTPVSLSVRLGGQVSISCRSSQSLVHNNGNTYLSWFLQKPGQSPQ

LLIYKVSNRFSGISDRFSGSASGTDFTLKISRVEPDDLGVYYCGQGTHYP

FTFGSGTKLEIK, with CDRs shown in bold characters and underlined) comprising CDR1-L of sequence SEQ ID NO: 10, a CDR2-L consisting of sequence 'KVS', and a CDR3-L of sequence SEQ ID NO: 28.

The so-called "10F4-C10" anti-CD3 antibody comprises:
a heavy chain variable domain consisting of sequence (SEQ ID NO: 60)
EVQLVETGGSLVQFGKSLKITCATSGFTFSNAWMHWVRQSFEKQLEWVAQ

IKAKSNNYATYYAESVKGRFTISRDDSKSSIYLQMNSLKEEDTAIYYCRA

VNYGNYPLDYWGQGVMVTVSS, with CDRs shown in bold characters and underlined) comprising CDR1-H of sequence SEQ ID NO: 13, a CDR2-H of sequence SEQ ID NO: 37, and a CDR3-H of sequence SEQ ID NO: 61, and
a light chain variable domain consisting of sequence (SEQ ID NO: 62)
DVVMTQTPVSLSVSLGGQVSISCRSSQSLVHNNGNTYLSWCLQKPGQSPQ

LLIYKVSNRFSGISDRFSGSGSGTDFTLKISRVEPDDLGVYYCGQGTQYP

FTFGAGTKLELK, with CDRs shown in bold characters and underlined) comprising CDR1-L of sequence SEQ ID NO: 10, a CDR2-L consisting of sequence 'KVS', and a CDR3-L of sequence SEQ ID NO: 11.

The so-called "10E6-G6" anti-CD3 antibody comprises:
a heavy chain variable domain consisting of sequence (SEQ ID NO: 63)
EVQLVETGGGLVQSGKSLKLTCATSGFTVTNAWMHWVRQSPEQLEWVAQI

KAKSNNYETYYAESVKGRFTISRDDSKSSVYLQMNSLKEEDTAIYYCRGT

QYGYNPFDYWGQGVMVTVSS, with CDRs shown in bold characters and underlined) comprising CDR1-H of sequence SEQ ID NO: 64, a CDR2-H of sequence SEQ ID NO: 65, and a CDR3-L of sequence SEQ ID NO: 47, and
a light chain variable domain consisting of sequence (SEQ ID NO: 66)
DVVMTQSPVSLSVSLGGQVSISCRSSQSLVHNNGYTYLSWYLQKPGQSPQ

VFIYKVSNRFSGISDRFSGSGSGTDFTLKISRIEPDDLGVYYCGQGTHYP

FTFGSGTKLEIK, with CDRs shown in bold characters and underlined) comprising CDR1-L of sequence SEQ ID NO: 67, a CDR2-L consisting of sequence 'KVS', and a CDR3-L of sequence SEQ ID NO: 28.

The so-called "18G9-H11" anti-CD3 antibody comprises:
a heavy chain variable domain consisting of sequence (SEQ ID NO: 68)
EVQLVETGGSLVQPGKSLKLTCATSGFTFSNAWIQWVRQSPEKQLEWVAQ

IKAKSNNYATYYAESVKGRFTISRDDSKSSVYLQMNSLKEEDTALYYCTW

RHYYSSHTMDAWGQGTLVTVSS, with CDRs shown in bold characters and underlined) comprising CDR1-H of sequence SEQ ID NO: 13, a CDR2-H of sequence SEQ ID NO: 37, and a CDR3-H of sequence SEQ ID NO: 69, and
a light chain variable domain consisting of sequence (SEQ ID NO: 70)
DVVMTQTPVSLSVSLGGQVSISCRSSQSLVHNNGNTYLSWYLQKPGQSPQ

LLIYKVSNRFSGISDRFSGSGSGTDFTLKISRVAPTDLGVYYCGQGSQYP

FTFGAGTKLELK, with CDRs shown in bold characters and underlined) comprising CDR1-L of sequence SEQ ID NO: 10, a CDR2-L consisting of sequence 'KVS', and a CDR3-L of sequence SEQ ID NO: 71.

The so-called "11F3-B9" anti-CD3 antibody comprises:
a heavy chain variable domain consisting of sequence (SEQ ID NO: 72)
EVQLVETGGSLVQFGKSLTLTCATSGFTFSNAWMHWVRQSFEKQLEWVAQIKAKSNNYATYYAESVKGRFTISRDDSKRSVYLQMNSLKEEDTAIYYCRYVNYGLAPMDVWGQGTSVTVSS, with CDRs shown in bold characters and underlined) comprising CDR1-H of sequence SEQ ID NO: 13, a CDR2-H of sequence SEQ ID NO: 37, and a CDR3-H of sequence SEQ ID NO: 84, and
a light chain variable domain consisting of sequence (SEQ ID NO: 73)
DVVMTQTPVSLSVSLGGQVSISCRSSQSLVHDNGNTYLSWYLQKPGQSPQLLIYKVSNRFSGFSDRFSGSGSGTDFTLKISRVEPDDLGVYYCGQGTQYPFTFGAGTKLELK, with CDRs shown in bold characters and underlined) comprising CDR1-L of sequence SEQ ID NO: 17, a CDR2-L consisting of sequence 'KVS', and a CDR3-L of sequence SEQ ID NO: 11.

The so-called "12G3-E8" anti-CD3 antibody comprises:
a heavy chain variable domain consisting of sequence (SEQ ID NO: 74)
EVRVVETGGSLVQPGKSLKLTCATSGFTFSLAWMHWVRQSPEKKLEWVAQIKDKANNYATYYAESVKGRFTISRDDSKRSVYLQMNRLKEEDTAIYYCRGVYYGFSMTPFDYWGQGVMVTVSS, with CDRs shown in bold characters and underlined) comprising CDR1-H of sequence SEQ ID NO: 75, a CDR2-H of sequence SEQ ID NO: 76, and a CDR3-H of sequence SEQ ID NO: 77, and
a light chain variable domain consisting of sequence (SEQ ID NO: 78)
DVAMTQTPVSLSVSLGGQVSISCRSSQSLVHNNGNTYLSWYLQKPGQSPQVLIYKVSNRFSGISDRFSGSGSGADFTLKISRVEPDDLGVYYCGQGTQYPFTFGAGTKLELK, with CDRs shown in bold characters and underlined) comprising CDR1-L of sequence SEQ ID NO: 10, a CDR2-L consisting of sequence 'KVS', and a CDR3-L of sequence SEQ ID NO: 11.

The so-called "5B1-G2" anti-CD3 antibody comprises:
a heavy chain variable domain consisting of sequence (SEQ ID NO: 79)
EVQVVETGGSLVQPGKSLKLTCATSGFSFSNAWMHWVRQSPEKQLEWVAQIKDKANNYATYYAESVKGRFTISRDDSKGSIYLQMNSLKEEDTAVYYCRGGLYYGLFPSDYWGQGVMVTVSS, with CDRs shown in bold characters and underlined) comprising CDR1-H of sequence SEQ ID NO: 80, a CDR2-H of sequence SEQ ID NO: 76, and a CDR3-H of sequence SEQ ID NO: 81, and
a light chain variable domain consisting of sequence (SEQ ID NO: 82)
DVVMTQTPVSLSVSLGGQVSISCRSSQSLVHNNGNTYLSWYLLKPGQSPQLLIYKVSNRFSGISDRFSGGGSGTDFTLKISRLEPDDLGIYYCGQGTQYPFTFGSGTKLEIK, with CDRs shown in bold characters and underlined) comprising CDR1-L of sequence SEQ ID NO: 10, a CDR2-L consisting of sequence 'KVS', and a CDR3-L of sequence SEQ ID NO: 11.

The so-called "16F8-A7" anti-CD3 antibody comprises:
a heavy chain variable domain comprising the sequence (SEQ ID NO: 83)
VETGGNLVQPGKSLKLTCATSGFTFSNAWMHWVRQSPEKQLEWVAQIKAKSNNYATYYAESVKGRFTISRDDSKSSVYLQMNSLKEEDTAIYYCRYVNGYGLAPMDVWGQGTSVTVSS, with CDRs shown in bold characters and underlined) comprising CDR1-H of sequence SEQ ID NO: 13, a CDR2-H of sequence SEQ ID NO: 37, and a CDR3-H of sequence SEQ ID NO: 84, and
a light chain variable domain consisting of sequence (SEQ ID NO: 85)
DVVMTQTPVSLSVSLGGQVSISCRSSQSLVHNNGNTYLSWYLQKPGQSPQLLIYKVSNRFSGFSDRFSGSGSGTDFTLKISRVEPDDLGVYYCGQGTQYPFTFGAGTKLELK, with CDRs shown in bold characters and underlined) comprising CDR1-L of sequence SEQ ID NO: 10, a CDR2-L consisting of sequence 'KVS', and a CDR3-L of sequence SEQ ID NO: 11.

The so-called "11F9-F8" anti-CD3 antibody comprises:
a heavy chain variable domain consisting of sequence (SEQ ID NO: 46)
EVQLVETGGTLVQPGKSLKLTCATSGFTFSNAWMHWVRQSPEKQLEWVAQIKAKSNNYATYYAESVKGRFTISRDDSKTSVYLQLNSLREEDTAIYYCRGTQYGYNPFDYWGQGVMVTVSS, with CDRs shown in bold characters and underlined) comprising CDR1-H of sequence SEQ ID NO: 13, a CDR2-H of sequence SEQ ID NO: 37, and a CDR3-H of sequence SEQ ID NO: 47, and
a light chain variable domain consisting of sequence (SEQ ID NO: 87)
DVVLTQTPVSLSVSLGGQVSISCRSSQSLVHNNGNTYLSWSLQKPGQSPQVLIYKVSNRFSGISNRFSGSGSGTDFTLKISRVEPDDLGVYYCGQGAHYPFTFGSGTKLEIK, with CDRs shown in bold characters and underlined) comprising CDR1-L of sequence SEQ ID NO: 10, a CDR2-L consisting of sequence 'KVS', and a CDR3-L of sequence SEQ ID NO: 88.

The so-called "3G5-E10" anti-CD3 antibody comprises:
a heavy chain variable domain consisting of sequence (SEQ ID NO: 89)
EVKLVESGGGLVQPGRSLKLSCAASGFNFNVYWMGWVRQAPGKGLEWIGEIKKDSNSINYTPSLKEKFTISRDNAQNTLYLQVNKLGSEDTAIYYCAREERDGYFDYWGQGVMVTVSS, with CDRs shown in bold characters and underlined) comprising CDR1-H of sequence SEQ ID NO: 90, a CDR2-H of sequence SEQ ID NO: 91, and a CDR3-H of sequence SEQ ID NO: 32, and
a light chain variable domain consisting of sequence (SEQ ID NO: 92)
NIVMTQSPKSMSMSVGERVTLTCKASENVVTYVSWYQQKPEQSPKLLIYGASNRYTGVPDRFTGSGSATDFTLTISSVQAEDLADYHCGQGYSYPYTFGGGTKLEIK, with CDRs shown in bold characters and underlined) comprising CDR1-L of sequence SEQ ID NO: 93, a CDR2-L consisting of sequence 'GAS', and a CDR3-L of sequence SEQ ID NO: 94.

The so-called "9D7-F3" anti-CD3 antibody comprises:
a heavy chain variable domain consisting of sequence (SEQ ID NO: 95)
AVQLVESGGGLVQPKESLKISCAASGFTFSNAAMYWVRQAPGKGLEWVARIRTKPNNYATYYADSVTGRFIISRDDSRSMVYLQMDNLQTEDTAMYYCTALISTAMAAWGQGTSVTVSS, with CDRs shown in bold characters and underlined) comprising CDR1-H of sequence SEQ ID NO: 96, a CDR2-H of sequence SEQ ID NO: 97, and a CDR3-H of sequence SEQ ID NO: 98, and
a light chain variable domain consisting of sequence (SEQ ID NO: 99)
DIQMTQSPSFLSASVGDRVTINCKASQNINKYLNWYHQMLGEAPKLVISNTNNLQAGIPSRFSGSGSGTDFTLTISSLQPEDVATYFCLQHRSGYTFGLGTKLELK, with CDRs shown in bold characters and underlined) comprising CDR1-L of sequence SEQ ID NO: 100, a CDR2-L consisting of sequence 'NTN', and a CDR3-L of sequence SEQ ID NO: 101.

The so-called "8C2-F7" anti-CD3 antibody comprises:
a heavy chain variable domain consisting of sequence (SEQ ID NO: 102)
QIQLVQSGPELKKPGESVKISCKASGYTFTDFAMNWVKQAPGNGLKWMGWINTQTGKPTYADGFKQRFVFSLETSASTIYLQINNLNIEDTATYFCTRGALASVGQGVLVTVSS, with CDRs shown in bold characters and underlined) comprising CDR1-H of sequence SEQ ID NO: 103, a CDR2-H of sequence SEQ ID NO: 104, and a CDR3-H of sequence SEQ ID NO: 105, and
a light chain variable domain consisting of sequence (SEQ ID NO: 106)
DVVMTQTPVSLSVSLGSHVSISCRSSQSLVHNNGNTYLSWYLQKPGQSPQPLIYKVSNRFSGISDRFSGSGSGTDFTLEINRVEPDDLGVYYCGQGAQYPFTFGSGTKLEIK, with CDRs shown in bold characters and underlined) comprising CDR1-L of sequence SEQ ID NO: 10, a CDR2-L consisting of sequence 'KVS', and a CDR3-L of sequence SEQ ID NO: 11.

The so-called "20E5-F10" anti-CD3 antibody comprises:
a heavy chain variable domain consisting of sequence (SEQ ID NO: 107)
EVQLVETGENLVQPGKSLRLTCATSGFSFSNAWMHWIRQSPEKQLEWVAQIKDKSNNYATYYAESVNGRFTISRDDSKSSIYLHMDNLKEEDSAIYYCRYVHYGVRFFYTMDVWGQGTSVTVSS, with CDRs shown in bold characters and underlined) comprising CDR1-H of sequence SEQ ID NO: 80, a CDR2-H of sequence SEQ ID NO: 19, and a CDR3-H of sequence SEQ ID NO: 108, and
a light chain variable domain consisting of sequence (SEQ ID NO: 109)
DVVMTQTPVSLSVSLGDQVSISCRPSQSLVHNNGNTYLSWYLQKPGQSPHPLIYKVSNRFSGISDRFSGSGSGTDFTLKISRVEPDDLGVYYCGQGTQYPFTFGSGTKLEIK, with CDRs shown in bold characters and underlined) comprising CDR1-L of sequence SEQ ID NO: 10, a CDR2-L consisting of sequence 'KVS', and a CDR3-L of sequence SEQ ID NO: 11.

The so-called "20B5-F10" anti-CD3 antibody comprises:
a heavy chain variable domain consisting of sequence (SEQ ID NO: 110)
EVQLVETGGSLVQPGKSLKLTCATSGFTFSNAWMHWVRQSPEKQLEWVAQIKAKSNNYATYYAESVKGRFTISRDDSISSVYLQMNNLKEEDTAIYYCRGVYYGFLGMDAWGQGTSVTVSS, with CDRs shown in bold characters and underlined) comprising CDR1-H of sequence SEQ ID NO: 13, a CDR2-H of sequence SEQ ID NO: 37, and a CDR3-H of sequence SEQ ID NO: 111, and
a light chain variable domain consisting of sequence (SEQ ID NO: 112)
DVVMTQTPVSLSVSLGGQVSISCRSSQRLVHNNGNTYLSWYLQKPGQSPQLLVYKVSNRFSGISDRFSGSGSGTDFTLKISRVEPDDLGVYYCGQGTEYPFTFGSGTKLEIK, with CDRs shown in bold characters and underlined) comprising CDR1-L of sequence SEQ ID NO: 113, a CDR2-L consisting of sequence 'KVS', and a CDR3-L of sequence SEQ ID NO: 114.

The so-called "6C9-C9" anti-CD3 antibody comprises:
a heavy chain variable domain consisting of sequence (SEQ ID NO: 115)
AVQLVESGGGLVRPKESLKISCAASGFTFRNAAMYWVRQAPGKGLEWVARIRTQPNNYAKYYADSVKDRFTISRDDSKSMVYLQMDNLKTEDTAMYYCTGLVVTAMDAWGQGTSVTVSS, with CDRs shown in bold characters and underlined) comprising CDR1-H of sequence SEQ ID NO: 116, a CDR2-H of sequence SEQ ID NO: 117, and a CDR3-H of sequence SEQ ID NO: 118, and
a light chain variable domain consisting of sequence (SEQ ID NO: 119)
DIQMTQSPSFLSASVGDRVTINCKASQNINKYLNWYQQKLGEAPKLLIYVTNNLQTGIPSRFSGSGSGTDYTLTISSLQPEDVATYFCLQHRSMYTFGTGTKLELK, with CDRs shown in bold characters and underlined) comprising CDR1-L of sequence SEQ ID NO: 100, a CDR2-L consisting of sequence A/TN', and a CDR3-L of sequence SEQ ID NO: 120.

The so-called "3E8-G1" anti-CD3 antibody comprises:
a heavy chain variable domain consisting of sequence (SEQ ID NO: 121)
EVQVVESGGGLVQPGRSLKLSCAASGFTFSNYYMDWVRQAPKKGLEWVATITASGSRIYYPDSVKGRFTISRDNAKSSLYLLMNSLKSEDTATYYCARERTDAYFDYWGQGVMVTVSS, with CDRs shown in bold characters and underlined) comprising CDR1-H of sequence SEQ ID NO: 122, a CDR2-H of sequence SEQ ID NO: 123, and a CDR3-H of sequence SEQ ID NO: 124, and
a light chain variable domain consisting of sequence (SEQ ID NO: 125)
QFILTQPNSVSTILGSTVKLSCKRSTGNIGTNYVSWYQHHEGRSPTTMIYRDDKRPDGVPDRFSGSIDRSSNSALLTINNVQTEDEADYFCQSYISGLNPVFGGGSKLTVL, with CDRs shown in bold characters and underlined) comprising CDR1-L of sequence SEQ ID NO: 126, a CDR2-L consisting of sequence 'RDD', and a CDR3-L of sequence SEQ ID NO: 127.

The so-called "3H6-D2" anti-CD3 antibody comprises:
a heavy chain variable domain consisting of sequence (SEQ ID NO: 128)
EVQLVETGGRLVQPGKSLKLTCATSGFTFSNAWMHWVRQSPEKQLEWVAQIKDKSNNYATYYAESVKGRFTISRDDSKSIIYLQMNSLKEEDTAIYYCRALTYYGYKRDAMDGWGHGTSVTVSS, with CDRs shown in bold characters and underlined) comprising CDR1-H of sequence SEQ ID NO: 13, a CDR2-H of sequence SEQ ID NO: 19, and a CDR3-H of sequence SEQ ID NO: 129, and a light chain variable domain consisting of sequence (SEQ ID NO: 130)
DVVMTQTPVSLSVSLGGQVSISCRSSQSLVHNNGNTYLSWYLQKPGQSPQLLIYKVSNRFSGISDRFSGSGSGTDFTLKISRVEPDDLGVYYCGQGTQYPFTFGAGTKLELK, with CDRs shown in bold characters and underlined) comprising CDR1-L of sequence SEQ ID NO: 10, a CDR2-L consisting of sequence 'KVS', and a CDR3-L of sequence SEQ ID NO: 11.

The so-called "8H2" anti-CD3 antibody comprises:
a heavy chain variable domain consisting of sequence (SEQ ID NO: 131)
QIQLVQSGPELKKPGESVKISCKASGYTFTDFAMNWVKQAPGNGLKWMGWINTQTGKPTYADGFKQRFVFSLETSASTIYLQINNLNIEDTATYFCTRGALASVGQGVMVTVSS, with CDRs shown in bold characters and underlined) comprising CDR1-H of sequence SEQ ID NO: 103, a CDR2-H of sequence SEQ ID NO: 104, and a CDR3-H of sequence SEQ ID NO: 105, and
a light chain variable domain consisting of sequence (SEQ ID NO: 132)
DVVMTQTPVSLSVAIGQPASISCKSSQSLVGTSGKTYLNWLLQRPGQSPKRLIYLVSKLDSGIPDRFSGSGSETDFTLKISRVETDDLGVYYCLQGSHFPLTFGSGTKLEIK, with CDRs shown in bold characters and underlined) comprising CDR1-L of sequence SEQ ID NO: 133, a CDR2-L consisting of sequence 'LVS', and a CDR3-L of sequence SEQ ID NO: 134.

In an embodiment, the anti-CD3 antibody of the invention binds to human CD3. In another embodiment, the anti-CD3 antibody of the invention further binds to *Macaca fascicularis* CD3. In particular, the anti-CD3 antibody of the invention binds to the extracellular domain of human CD3, or of both human and *Macaca fascicularis* CD3. More specifically, the antibody binds to CD3ε. More specifically, the anti-CD3 antibody binds to the human and *Macaca fascicularis* extracellular domain of CD3ε. The anti-CD3 antibody binds to CD3ε when present in the form of a complex, such as a CD3ε/δ complex, or when present as single protein, indifferently whether expressed in isolated form, or present in a soluble extracellular domain or full-length membrane-anchored CD3ε as present in for example in T-cells.

The anti-CD3 antibody according to the invention is specific for the surface human CD3 protein, or of both human and *Macaca fascicularis* CD3 proteins, in particular to CD3ε.

In an embodiment, the anti-CD3 antibody according to the invention has a ratio of affinity for *Macaca fascicularis* CD3 on affinity for human CD3 (KD(*Macaca fascicularis*)/KD(human)) which is ≤10, in particular ≤6, ≤5, ≤4, ≤3, for example or ≤2, ≤1 or ≤0.5. Such a polypeptide according to the invention may be used in toxicological studies performed in monkeys the toxicity profile observed in monkeys relevant to anticipate potential adverse effects in humans In particular, the anti-CD3 antibody of the invention does not bind to, or does not significantly cross-react with CD3γ and/or CD3δ protein(s).

In particular, the antibody does not bind to, or does not significantly cross-react with the extracellular domain of the aforementioned human and *Macaca fascicularis* CD3γ and/or CD3δ protein(s).

The sequence of full-length human CD3δ protein is available in Uniprot database under accession number P04234 (SEQ ID NO: 86, as available on Dec. 14, 2014). The extracellular domain of human CD3δ consists of amino acids at positions 22-105 of SEQ ID NO: 86.

The sequence of full-length human CD3γ protein is available in Uniprot database under accession number P09693 (SEQ ID NO: 185, as available on Dec. 14, 2014). The extracellular domain of human CD3γ consists of amino acids at positions 23-116 of SEQ ID NO: 185.

Furthermore, the anti-CD3 antibody according to the invention has an affinity (KD) for human CD3 or *Macaca fascicularis* CD3, or both, which is ≤90 nM, ≤50 nM, or ≤30 nM, for instance ≤20 nM, ≤10 nM, ≤8 nM, ≤6 nM, ≤4 nM or ≤2 nM, for instance an affinity of 0.1 nM to 10 nM, in particular of 0.1 nM to 8 nM, or of 0.1 nM to 4 nM.

Affinity for human CD3 or for *Macaca fascicularis* CD3 is determined as the KD value with surface plasmon resonance using soluble recombinant CD3ε/δ complex from human and *Macaca fascicularis* as capture antigen.

In one example, binding affinities of an anti-CD3 antibody is measured by surface plasmon resonance (SPR) using for instance a Biacore3000 instrument (GE Healthcare). Assay buffer is for example HBS-EP (BR-1001-88, GE Healthcare). As antigen may be used, for example, the human CD3ε and human CD3δ subunit extracellular domain constructs, including the signal peptide, in form of Fc-fusion proteins as described in the examples. Alternatively, use may be made, as antigen, of the *Macaca fascicularis* CD3ε and *Macaca fascicularis* CD3δ subunit extracellular domain constructs, including the signal peptide, in form of Fc-fusion proteins as described in the examples. Capture of human or *Macaca fascicularis* CD3ε/δ-Fc fusion proteins is achieved using, for example, the human antibody capture kit (GE Healthcare). For example, the capture antibody may be coupled to CM5 chips (BR-1001-88, GE Healthcare) to for instance approx. 12.000 RU using for example the amine coupling kit (BR-100-50, GE Healthcare). The CD3ε/δ-Fc fusions proteins are captured at 10 μl/min to approx. 70 RU to yield Rmax values of 30 RU. Binding kinetics for an anti-CD3 antibody may be measured at, for example, 30 μl/min for 240 s and 600 s. for association and dissociation phase, respectively. For example, two fold dilutions of an anti-CD3 antibody from 3 to 400 nM in assay buffer may be used. Regeneration of the capture surface may be performed with for example a 1 min injection of for instance 3M MgCl$_2$ solution at 30 μl/min. For data analysis for example the BIAevaluation software v.4.1 (GE Healthcare) may be used. Data may be fit globally using a 1:1 Langmuir model with mass transfer.

In an embodiment, the anti-CD3 antibody of the invention also has an apparent EC50 as, for example, determined by FACS analysis on human T-cells, which is ≤60 nM, for instance ≤50 nM, ≤30 nM, ≤20 nM or ≤15 nM. Typically, the apparent EC50 is within the range 1 to 60 nM, in particular 1 to 30 nM, for example 1 to 20 nM.

In one embodiment, the anti-CD3 antibody of the invention has a T-cell activation that is less than 10%, less than 8%, less than 6%, less than 4%, less than 2%, less than 1%, for example less than 0.5% in the absence of target cells.

The term "activation of T-cells" herein refers to triggering CD3 signaling involving cytotoxic granule fusion, transient cytokine release, and proliferation. The antibody-like binding protein and the anti-CD3 antibody of the invention target CD3ε and activate T-cells in the presence of target cells; this activity is also referred to as a "T-cell engaging effect". The T-cell engaging effect induces cytotoxicity in the target cell.

As known by the skilled in the art, activation of T-cells induces the expression of surface marker such as CD69 and CD25. The activation of T-cells can thus be measured by detecting and measuring the expression of CD4+/CD25+, CD4+/CD69+, CD8+/CD25+, or CD8+/CD69+ T cells. Methods to measure T-cell activation are known to the skilled in the art.

A method to measure T-cell activation is further disclosed in the example section (Example 3.3). Accordingly, in context of the invention T-cell activation is measured either as the percentage of cells expressing CD69 in % of the total number of cells, or as the percentage of cells expressing CD4 and CD69 in % of total number of cells, or as the percentage of cells expressing CD8 and CD69 in % of the total number of cells.

"Low T-cell activation" in context with the anti-CD3 antibody of the invention refers to less than 10%, less than 8%, less than 6%, less than 4%, less than 2%, less than 1%, for example less than 0.5% T-cell activation in the absence of target cells.

Alignments of the sequences of the VH and VL regions of the "20G6-F3", "4B4-D7", "4E7-C9", "18F5-H10", "12D2-E5", "11D7-C3", "11H3-E5", "13H2-C2", "13C1-F6", "18H11-F10", "1E6-C9", "10F4-C10", "10E6-G6", "18G9-H11", "11F3-B9", "12G3-E8", "5B1-G2", "16F8-A7", "11F9-F8", "3G5-E10", "9D7-F3", "8C2-F7", "20E5-F10", "20B5-F10", "6C9-C9", "3E8-G1", "3H6-D2" and "8H2" anti-CD3 antibodies were performed. The comparison of the CDR-H and CDR-L sequences tends to indicate that, structurally, "20G6-F3", "4B4-D7", "4E7-C9", "18F5-H10", "11D7-C3", "11H3-E5", "13H2-C2", "13C1-F6", "1E6-C9", "10F4-C10", "10E6-G6", "18G9-H11", "11F3-B9", "12G3-E8", "5B1-G2", "16F8-A7", "11F9-F8", "20E5-F10", "20B5-F10" and "3H6-D2" are closely related, said antibodies probably binding to the same epitope. The comparison of the CDR-H and CDR-L sequences of said related antibodies is presented in FIGS. 1 and 2, respectively. CDR positions were identified that are strictly conserved between the antibodies and which are thus assumed to be important for specificity, whereas other positions could support substitution.

Accordingly, the antibody according to the invention comprises:

a heavy chain variable domain comprising a CDR1-H consisting of sequence GFX$_1$X$_2$X$_3$X$_4$AW (SEQ ID NO: 331) wherein X$_1$ is T or S, X$_2$ is F or V, X$_3$ is S or T and X$_4$ is N, K, L or Y, or any combination thereof; and a CDR2-H consisting of sequence IKX$_1$X$_2$X$_3$NX$_4$YX$_5$T (SEQ ID NO: 332) wherein X$_1$ is A or D, X$_2$ is K or R, X$_3$ is S or A, X$_4$ is N or S and X$_5$ is A or E, or any combination thereof; and a CDR3-H consisting of sequence TWRHYYSSHTMDA (SEQ ID NO: 69) or RALTYYGYKRDAMDG (SEQ ID NO: 129) or RX$_1$X$_2$X$_3$YX$_4$X$_5$X$_6$X$_7$X$_8$X$_9$X$_{10}$X$_{11}$DX$_{12}$ (SEQ ID NO: 333) wherein X$_1$ is Y, G or A, X$_2$ is V, T or L, X$_3$ is H, N, Y or Q, X$_4$ is G, R or A, X$_5$ is F or V or no amino acid, X$_6$ is R or no amino acid, X$_7$ is F, S or I or no amino acid, X$_8$ is F, L, N, M, Y, S, A or G, X$_9$ is Y, A, K, S, N, T, F or L, X$_{10}$ is A, P, G or T, X$_{11}$ is M, L, F or S and X$_{12}$ is A, V or Y, or any combination thereof; and a light chain variable domain comprising a CDR1-L consisting of sequence QX$_1$LX$_2$HX$_3$NGX$_4$TY (SEQ ID NO: 334) wherein X$_1$ is R or S, X$_2$ is V or E, X$_3$ is N, D or T, and X$_4$ is N or Y, or any combination thereof; and a CDR2-L consisting of sequence 'KVS'; and a CDR3-L consisting of sequence GQGX$_1$X$_2$YPFT (SEQ ID NO: 335) wherein X$_1$ is T, A or S and X$_2$ is H, E or Q, or any combination thereof.

According to an embodiment, the anti-CD3 antibody according to the invention comprises the CDR sequences of the heavy and/or light chains of one of 28 so-called "20G6-F3", "4B4-D7", "4E7-C9", "18F5-H10", "12D2-E5", "11D7-C3", "11H3-E5", "13H2-C2", "13C1-F6", "18H11-F10", "1E6-C9", "10F4-C10", "10E6-G6", "18G9-H11", "11F3-B9", "12G3-E8", "5B1-G2", "16F8-A7", "11F9-F8", "3G5-E10", "9D7-F3", "8C2-F7", "20E5-F10", "20B5-F10", "6C9-C9", "3E8-G1", "3H6-D2" and "8H2" anti-CD3 antibodies listed above.

Therefore, the invention relates to an anti-CD3 antibody, which comprises:

a) a heavy chain variable domain comprising CDR1-H of sequence SEQ ID NO: 6 or a sequence differing from SEQ ID NO: 6 by one amino acid substitution; CDR2-H of sequence SEQ ID NO: 7 or a sequence differing from SEQ ID NO: 7 by one or more amino acid substitution; CDR3-H of sequence SEQ ID NO: 8 or a sequence differing from SEQ ID NO: 8 by one amino acid substitution; and a light chain variable domain comprising CDR1-L of sequence SEQ ID NO: 10 or SEQ ID NO: 142 or a sequence differing from SEQ ID NO: 10 or SEQ ID NO: 142 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or b) a heavy chain variable domain comprising CDR1-H of sequence SEQ ID NO: 13 or a sequence differing from SEQ ID NO: 13 by one amino acid substitution; CDR2-H of sequence SEQ ID NO: 14 or a sequence differing from SEQ ID NO: 14 by one or more amino acid substitutions; CDR3-H of sequence SEQ ID NO: 15 or a sequence differing from SEQ ID NO: 15 by one amino acid substitution; and a light chain variable domain comprising CDR1-L of sequence SEQ ID NO: 17 or SEQ ID NO: 184 or a sequence differing from SEQ ID NO: 17 or SEQ ID NO: 184 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or c) a heavy chain variable domain comprising CDR1-H of sequence SEQ ID NO: 13 or a sequence differing from SEQ ID NO: 13 by one amino acid substitution; CDR2-H of sequence SEQ ID NO: 19 or a sequence differing from SEQ ID NO: 19 by one or more amino acid substitutions; CDR3-H of sequence SEQ ID NO: 20 or a sequence differing from SEQ ID NO: 20 by one amino acid substitution; and a light chain variable domain comprising CDR1-L of sequence SEQ ID NO: 22 or a sequence differing from SEQ ID NO: 22 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or d) a heavy chain variable domain comprising CDR1-H of sequence SEQ ID NO: 24 or a sequence differing from SEQ ID NO: 24 by one amino acid substitution; CDR2-H of sequence SEQ ID NO: 19 or a sequence differing from SEQ ID NO: 19 by one or more amino acid substitutions; CDR3-H of sequence SEQ ID NO: 25 or a sequence differing from SEQ ID NO: 25 by one amino acid substitution; and a light chain variable domain comprising CDR1-L of sequence SEQ ID NO: 27 or a sequence differing from SEQ ID NO: 27 by one amino acid substitution; CDR2-L of sequence 'KVS' or a sequence differing from the sequence 'KVS' by one amino acid substitution and CDR3-L of sequence SEQ ID NO: 28 or a sequence differing from SEQ ID NO: 28 by one amino acid substitution; or e) a heavy chain variable domain comprising CDR1-H of sequence SEQ ID NO: 30 or a sequence differing from SEQ ID NO: 30 by one amino acid substitution; CDR2-H of sequence SEQ ID NO: 31 or a sequence differing from SEQ ID NO: 31 by one or more amino acid substitutions; CDR3-H of sequence SEQ ID NO: 32 or a sequence differing from SEQ ID NO: 32 by one amino acid substitution; and a light chain variable domain comprising CDR1-L of sequence SEQ ID NO: 34 or a sequence differing from SEQ ID NO: 34 by one amino acid substitution; CDR2-L of sequence 'RDD' or a sequence differing from the sequence 'RDD' by one amino acid substitution and CDR3-L of sequence SEQ ID NO: 35 or a sequence differing from SEQ ID NO: 35 by one amino acid substitution; or f) a heavy chain variable domain comprising CDR1-H of sequence SEQ ID NO: 13 or a sequence differing from SEQ ID NO: 13 by one amino acid substitution; CDR2-H of sequence SEQ ID NO: 37 or a sequence differing from SEQ ID NO: 37 by one or more amino acid substitutions; CDR3-H of sequence SEQ ID NO: 38 or a sequence differing from SEQ ID NO: 38 by one amino acid substitution; and a light chain variable domain comprising CDR1-L of sequence SEQ ID NO: 10 or a sequence differing from SEQ ID NO: 10 by one amino acid substitution; CDR2-L of sequence 'KVS' or a sequence differing from the sequence 'KVS' by one amino acid substitution and CDR3-L of sequence SEQ ID NO: 28 or a sequence differing from SEQ ID NO: 28 by one amino acid substitution; or g) a heavy chain variable domain comprising CDR1-H of sequence SEQ ID NO: 13 or a sequence differing from SEQ ID NO: 13 by one amino acid substitution; CDR2-H of sequence SEQ ID NO: 37 or a sequence differing from SEQ ID NO: 37 by one or more amino acid substitutions; CDR3-H of sequence SEQ ID NO: 41 or a sequence differing from SEQ ID NO: 41 by one amino acid substitution; and a light chain variable domain comprising CDR1-L of sequence SEQ ID NO: 17 or a sequence differing from SEQ ID NO: 17 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or h) a heavy chain variable domain comprising CDR1-H of sequence SEQ ID NO: 13 or a sequence differing from SEQ ID NO: 13 by one amino acid substitution; CDR2-H of sequence SEQ ID NO: 37 or a sequence differing from SEQ ID NO: 37 by one or more amino acid substitutions; CDR3-H of sequence SEQ ID NO: 44 or a sequence differing from SEQ ID NO: 44 by one amino acid substitution; and
a light chain variable domain comprising CDR1-L of sequence SEQ ID NO: 10 or a sequence differing from SEQ ID NO: 10 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or i) a heavy chain variable domain comprising CDR1-H of sequence SEQ ID NO: 13 or a sequence differing from SEQ ID NO: 13 by one amino acid substitution; CDR2-H of sequence SEQ ID NO: 37 or a sequence differing from SEQ ID NO: 37 by one or more amino acid substitutions; CDR3-H of sequence SEQ ID NO: 47 or a sequence differing from SEQ ID NO: 47 by one amino acid substitution; and
a light chain variable domain comprising CDR1-L of sequence SEQ ID NO: 10 or a sequence differing from SEQ ID NO: 10 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or j) a heavy chain variable domain comprising CDR1-H of sequence SEQ ID NO: 50 or a sequence differing from SEQ ID NO: 50 by one amino acid substitution; CDR2-H of sequence SEQ ID NO: 51 or a sequence differing from SEQ ID NO: 51 by one or more amino acid substitutions; CDR3-H of sequence SEQ ID NO: 52 or a sequence differing from SEQ ID NO: 52 by one amino acid substitution; and
a light chain variable domain comprising CDR1-L of sequence SEQ ID NO: 54 or a sequence differing from SEQ ID NO: 54 by one amino acid substitution; CDR2-L of sequence 'NAN' or a sequence differing from the sequence 'NAN' by one amino acid substitution and CDR3-L of sequence SEQ ID NO: 55 or a sequence differing from SEQ ID NO: 55 by one amino acid substitution; or k) a heavy chain variable domain comprising CDR1-H of sequence SEQ ID NO: 57 or a sequence differing from SEQ ID NO: 57 by one amino acid substitution; CDR2-H of sequence SEQ ID NO: 37 or a sequence differing from SEQ ID NO: 37 by one or more amino acid substitutions; CDR3-H of sequence SEQ ID NO: 58 or a sequence differing from SEQ ID NO: 58 by one amino acid substitution; and
a light chain variable domain comprising CDR1-L of sequence SEQ ID NO: 10 or a sequence differing from SEQ ID NO: 10 by one amino acid substitution; CDR2-L of sequence 'KVS' or a sequence differing from the sequence 'KVS' by one amino acid substitution and CDR3-L of sequence SEQ ID NO: 28 or a sequence differing from SEQ ID NO: 28 by one amino acid substitution; or l) a heavy chain variable domain comprising CDR1-H of sequence SEQ ID NO: 13 or a sequence differing from SEQ ID NO: 13 by one amino acid substitution; CDR2-H of sequence SEQ ID NO: 37 or a sequence differing from SEQ ID NO: 37 by one or more amino acid substitutions; CDR3-H of sequence SEQ ID NO: 61 or a sequence differing from SEQ ID NO: 61 by one amino acid substitution; and
a light chain variable domain comprising CDR1-L of sequence SEQ ID NO: 10 or a sequence differing from SEQ ID NO: 10 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or m) a heavy chain variable domain comprising CDR1-H of sequence SEQ ID NO: 64 or a sequence differing from SEQ ID NO: 64 by one amino acid substitution; CDR2-H of sequence SEQ ID NO: 65 or a sequence differing from SEQ ID NO: 65 by one or more amino acid substitutions; CDR3-H of sequence SEQ ID NO: 47 or a sequence differing from SEQ ID NO: 47 by one amino acid substitution; and
a light chain variable domain comprising CDR1-L of sequence SEQ ID NO: 67 or a sequence differing from SEQ ID NO: 67 by one amino acid substitution; CDR2-L of sequence 'KVS' or a sequence differing from the sequence 'KVS' by one amino acid substitution and CDR3-L of sequence SEQ ID NO: 28 or a sequence differing from SEQ ID NO: 28 by one amino acid substitution; or n) a heavy chain variable domain comprising CDR1-H of sequence SEQ ID NO: 13 or a sequence differing from SEQ ID NO: 13 by one amino acid substitution; CDR2-H of sequence SEQ ID NO: 37 or a sequence differing from SEQ ID NO: 37 by one or more amino acid substitutions; CDR3-H of sequence SEQ ID NO: 69 or a sequence differing from SEQ ID NO: 69 by one amino acid substitution; and
a light chain variable domain comprising CDR1-L of sequence SEQ ID NO: 10 or a sequence differing from SEQ ID NO: 10 by one amino acid substitution; CDR2-L of sequence 'KVS' or a sequence differing from the sequence 'KVS' by one amino acid substitution and CDR3-L of sequence SEQ ID NO: 71 or a sequence differing from SEQ ID NO: 71 by one amino acid substitution; or o) a heavy chain variable domain comprising CDR1-H of sequence SEQ ID NO: 13 or a sequence differing from SEQ ID NO: 13 by one amino acid substitution; CDR2-H of sequence SEQ ID NO: 37 or a sequence differing from SEQ ID NO: 37 by one or more amino acid substitutions; CDR3-H of sequence SEQ ID NO: 84 or a sequence differing from SEQ ID NO: 84 by one amino acid substitution; and
a light chain variable domain comprising CDR1-L of sequence SEQ ID NO: 17 or a sequence differing from SEQ ID NO: 17 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or p) a heavy chain variable domain comprising CDR1-H of sequence SEQ ID NO: 75 or a sequence differing from SEQ ID NO: 75 by one amino acid substitution;

CDR2-H of sequence SEQ ID NO: 76 or a sequence differing from SEQ ID NO: 76 by one or more amino acid substitutions; CDR3-H of sequence SEQ ID NO: 77 or a sequence differing from SEQ ID NO: 77 by one amino acid substitution; and a light chain variable domain comprising CDR1-L of sequence SEQ ID NO: 10 or a sequence differing from SEQ ID NO: 10 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or q) a heavy chain variable domain comprising CDR1-H of sequence SEQ ID NO: 80 or a sequence differing from SEQ ID NO: 80 by one amino acid substitution; CDR2-H of sequence SEQ ID NO: 76 or a sequence differing from SEQ ID NO: 76 by one or more amino acid substitutions; CDR3-H of sequence SEQ ID NO: 81 or a sequence differing from SEQ ID NO: 81 by one amino acid substitution; and a light chain variable domain comprising CDR1-L of sequence SEQ ID NO: 10 or a sequence differing from SEQ ID NO: 10 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or r) a heavy chain variable domain comprising CDR1-H of sequence SEQ ID NO: 13 or a sequence differing from SEQ ID NO: 13 by one amino acid substitution; CDR2-H of sequence SEQ ID NO: 37 or a sequence differing from SEQ ID NO: 37 by one or more amino acid substitutions; CDR3-H of sequence SEQ ID NO: 84 or a sequence differing from SEQ ID NO: 84 by one amino acid substitution; and a light chain variable domain comprising CDR1-L of sequence SEQ ID NO: 10 or a sequence differing from SEQ ID NO: 10 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or s) a heavy chain variable domain comprising CDR1-H of sequence SEQ ID NO: 13 or a sequence differing from SEQ ID NO: 13 by one amino acid substitution; CDR2-H of sequence SEQ ID NO: 37 or a sequence differing from SEQ ID NO: 37 by one or more amino acid substitutions; CDR3-H of sequence SEQ ID NO: 47 or a sequence differing from SEQ ID NO: 47 by one amino acid substitution; and a light chain variable domain comprising CDR1-L of sequence SEQ ID NO: 10 or a sequence differing from SEQ ID NO: 10 by one amino acid substitution; CDR2-L of sequence 'KVS' or a sequence differing from the sequence 'KVS' by one amino acid substitution and CDR3-L of sequence SEQ ID NO: 88 or a sequence differing from SEQ ID NO: 88 by one amino acid substitution; or t) a heavy chain variable domain comprising CDR1-H of sequence SEQ ID NO: 90 or a sequence differing from SEQ ID NO: 90 by one amino acid substitution; CDR2-H of sequence SEQ ID NO: 91 or a sequence differing from SEQ ID NO: 91 by one or more amino acid substitutions; CDR3-H of sequence SEQ ID NO: 32 or a sequence differing from SEQ ID NO: 32 by one amino acid substitution; and a light chain variable domain comprising CDR1-L of sequence SEQ ID NO: 93 or a sequence differing from SEQ ID NO: 93 by one amino acid substitution; CDR2-L of sequence 'GAS' or a sequence differing from the sequence 'GAS' by one amino acid substitution and CDR3-L of sequence SEQ ID NO: 94 or a sequence differing from SEQ ID NO: 94 by one amino acid substitution; or u) a heavy chain variable domain comprising CDR1-H of sequence SEQ ID NO: 96 or a sequence differing from SEQ ID NO: 96 by one amino acid substitution; CDR2-H of sequence SEQ ID NO: 97 or a sequence differing from SEQ ID NO: 97 by one or more amino acid substitutions; CDR3-H of sequence SEQ ID NO: 98 or a sequence differing from SEQ ID NO: 98 by one amino acid substitution; and a light chain variable domain comprising CDR1-L of sequence SEQ ID NO: 100 or a sequence differing from SEQ ID NO: 100 by one amino acid substitution; CDR2-L of sequence 'NTN' or a sequence differing from the sequence 'NTN' by one amino acid substitution and CDR3-L of sequence SEQ ID NO: 101 or a sequence differing from SEQ ID NO: 101 by one amino acid substitution; or v) a heavy chain variable domain comprising CDR1-H of sequence SEQ ID NO: 103 or a sequence differing from SEQ ID NO: 103 by one amino acid substitution; CDR2-H of sequence SEQ ID NO: 104 or a sequence differing from SEQ ID NO: 104 by one or more amino acid substitutions; CDR3-H of sequence SEQ ID NO: 105 or a sequence differing from SEQ ID NO: 105 by one amino acid substitution; and a light chain variable domain comprising CDR1-L of sequence SEQ ID NO: 10 or a sequence differing from SEQ ID NO: 10 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or w) a heavy chain variable domain comprising CDR1-H of sequence SEQ ID NO: 80 or a sequence differing from SEQ ID NO: 80 by one amino acid substitution; CDR2-H of sequence SEQ ID NO: 19 or a sequence differing from SEQ ID NO: 19 by one or more amino acid substitutions; CDR3-H of sequence SEQ ID NO: 108 or a sequence differing from SEQ ID NO: 108 by one amino acid substitution; and a light chain variable domain comprising CDR1-L of sequence SEQ ID NO: 10 or a sequence differing from SEQ ID NO: 10 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or x) a heavy chain variable domain comprising CDR1-H of sequence SEQ ID NO: 13 or a sequence differing from SEQ ID NO: 13 by one amino acid substitution; CDR2-H of sequence SEQ ID NO: 37 or a sequence differing from SEQ ID NO: 37 by one or more amino acid substitutions; CDR3-H of sequence SEQ ID NO: 111 or a sequence differing from SEQ ID NO: 111 by one amino acid substitution; and a light chain variable domain comprising CDR1-L of sequence SEQ ID NO: 113 or a sequence differing from SEQ ID NO: 113 by one amino acid substitution; CDR2-L of sequence 'KVS' or a sequence differing from the sequence 'KVS' by one amino acid substitution and CDR3-L of sequence SEQ ID NO: 114 or a sequence differing from SEQ ID NO: 114 by one amino acid substitution; or y) a heavy chain variable domain comprising CDR1-H of sequence SEQ ID NO: 116 or a sequence differing from SEQ ID NO: 116 by one amino acid substitution; CDR2-H of sequence SEQ ID NO: 117 or a sequence differing from SEQ ID NO: 117 by one or more amino acid substitutions; CDR3-H of sequence SEQ ID NO: 118 or a sequence differing from SEQ ID NO: 118 by one amino acid substitution; and a light chain variable domain comprising CDR1-L of sequence SEQ ID NO: 100 or a sequence differing from SEQ ID NO: 100 by one amino acid substitution; CDR2-L of sequence A/TN' or a sequence differing from the sequence 'VTN' by one amino acid substitution and CDR3-L of sequence SEQ ID NO: 120 or a sequence differing from SEQ ID NO: 120 by one amino acid substitution; or z) a heavy chain variable domain comprising CDR1-H of sequence SEQ ID NO: 122 or a sequence differing from SEQ ID NO: 122 by one amino acid substitution; CDR2-H of sequence SEQ ID NO: 123 or a sequence differing from SEQ ID NO: 123 by one or more amino acid substitutions; CDR3-H of sequence SEQ ID NO: 124 or a sequence differing from SEQ ID NO: 124 by one amino acid substitution; and a light chain variable domain comprising CDR1-L of sequence SEQ ID NO: 126 or a sequence differing from SEQ ID NO: 126 by one amino acid substitution; CDR2-L of sequence 'RDD' or a sequence differing from the sequence 'RDD' by one amino acid substitution and CDR3-L of sequence SEQ ID NO: 127 or a sequence differing from SEQ ID NO: 127 by one amino acid substitution; or aa) a heavy chain variable domain comprising CDR1-H of sequence SEQ ID NO: 13 or a sequence differing from SEQ ID NO: 13 by one amino acid substitution; CDR2-H of sequence SEQ ID NO: 19 or a sequence differing from SEQ ID NO: 19 by one or more amino acid substitutions; CDR3-H of sequence SEQ ID NO: 129 or a sequence differing from SEQ ID NO: 129 by one amino acid substitution; and a light chain variable domain comprising CDR1-L of sequence SEQ ID NO: 10 or a sequence differing from SEQ ID NO: 10 by one amino acid substitution; CDR2-L of sequence 'KVS' or a sequence differing from the sequence 'KVS' by one amino acid substitution and CDR3-L of sequence SEQ ID NO: 11 or a sequence differing from SEQ ID NO: 11 by one amino acid substitution; or bb) a heavy chain variable domain comprising CDR1-H of sequence SEQ ID NO: 103 or a sequence differing from SEQ ID NO: 103 by one amino acid substitution; CDR2-H of sequence SEQ ID NO: 104 or a sequence differing from SEQ ID NO: 104 by one or more amino acid substitutions; CDR3-H of sequence SEQ ID NO: 105 or a sequence differing from SEQ ID NO: 105 by one amino acid substitution; and a light chain variable domain comprising CDR1-L of sequence SEQ ID NO: 133 or a sequence differing from SEQ ID NO: 133 by one amino acid substitution; CDR2-L of sequence 'LVS' or a sequence differing from the sequence 'LVS' by one amino acid substitution and CDR3-L of sequence SEQ ID NO: 134 or a sequence differing from SEQ ID NO: 134 by one amino acid substitution.

One or more individual amino acids may be altered by substitution, in particular by conservative substitution, in one or more of the above CDR sequences. Such an alteration may be intended for example to remove a glycosylation site or a deamidation site, in connection with humanization of the antibody.

Based on the alignments of the sequences of the VH and VL regions of the "20G6-F3", "4B4-D7", "4E7-C9", "18F5-H10", "11D7-C3", "11H3-E5", "13H2-C2", "13C1-F6", "1E6-C9", "10F4-C10", "10E6-G6", "18G9-H11", "11F3-B9", "12G3-E8", "5B1-G2", "16F8-A7", "11F9-F8", "20E5-F10", "20B5-F10" and "3H6-D2" different amino acid substitutions were identified. Therefore, in one embodiment, an amino acid is substituted:

in CDR1-H at one or more of positions 3 to 6, for instance at position 3, 5 or 6 of CDR1-H of sequence GFTFSNAW (SEQ ID NO: 13) or for instance at position 4 and 5 of CDR1-H of sequence GFTFSNAW (SEQ ID NO: 13); and/or in CDR2-H, at one or more of positions 3 to 5, 7 and 9, for instance at positions 3, 4, 5, 7 or 9 of CDR2-H of sequence IKAKSNNYAT (SEQ ID NO: 37), or for instance at positions 3 and 5 or 3 and 7 of CDR2-H of sequence IKAKSNNYAT (SEQ ID NO: 37); and/or in CDR3-H, at one or more of positions 2 to 4, 7 to 10 and 12, for instance at positions 2, 3, 4, 6, 7, 8, 9 and 10 or at positions 2, 4, 6, 8, 10 and 12 or at positions 2, 3, 7 and 8 of CDR3-H of sequence RGVYYALSPFDY (SEQ ID NO:8), or at position 7 and 8 of CDR3-H of sequence RGLYYGLSPSDY (SEQ ID NO: 38), or at position at positions 2, 3, 4, 6, 7, 8, 9 and 10 of CDR3-H of sequence RGLYYGLSPSDY (SEQ ID NO: 38); and/or in CDR1-L, at one or more of positions 2, 4, 6, and 9, for example at position 6 of CDR1-L of sequence QSLVHDNGNTY (SEQ ID NO: 17) or QSLVHTNG-NTY (SEQ ID NO: 27) or at position 2 of CDR1-L of sequence QSLVHNNGNTY (SEQ ID NO: 10) or QRLVHNNGNTY (SEQ ID NO: 113) or at position 4, 6 and 9 of CDR1-L of sequence QSLVHNNGNTY (SEQ ID NO: 10); and/or in CDR3-L, at one or more of positions 4 and 5, for instance at position 4 of CDR3-L of sequence GQGSQYPFT (SEQ ID NO: 71) or GQGTQYPFT (SEQ ID NO: 11), or at position 4 and 5 of CDR3-L of sequence GQGAHYPFT (SEQ ID NO: 88) or position 5 of CDR3-L of sequence GQGTHYPFT (SEQ ID NO: 28) or GQGTEYPFT (SEQ ID NO: 114).

The anti-CD3 antibody according to the invention is in particular a conventional antibody, in particular a conventional monoclonal antibody, or an antibody fragment, a bispecific or multispecific antibody.

The anti-CD3 antibody according to the invention in particular comprises or consists of an IgG, or a fragment thereof.

According to a further embodiment, the invention relates to an anti-CD3 antibody, which comprises:

a) a heavy chain variable domain comprising CDR1-H of sequence SEQ ID NO: 6, CDR2-H of sequence SEQ ID NO: 7, CDR3-H of sequence SEQ ID NO: 8 and a light chain variable domain comprising CDR1-L of sequence SEQ ID NO: 10 or SEQ ID NO: 142, CDR2-L of sequence 'KVS' and CDR3-L of sequence SEQ ID NO: 11; or
b) a heavy chain variable domain comprising CDR1-H of sequence SEQ ID NO: 13, CDR2-H of sequence SEQ ID NO: 14, CDR3-H of sequence SEQ ID NO: 15 and a light chain variable domain comprising CDR1-L of sequence SEQ ID NO: 17 or SEQ ID NO: 184, CDR2-L of sequence 'KVS' and CDR3-L of sequence SEQ ID NO: 11; or
c) a heavy chain variable domain comprising CDR1-H of sequence SEQ ID NO: 13, CDR2-H of sequence SEQ ID NO: 19, CDR3-H of sequence SEQ ID NO: 20 and a light chain variable domain comprising CDR1-L of sequence SEQ ID NO: 22, CDR2-L of sequence 'KVS' and CDR3-L of sequence SEQ ID NO: 11; or
d) a heavy chain variable domain comprising CDR1-H of sequence SEQ ID NO: 24, CDR2-H of sequence SEQ ID NO: 19, CDR3-H of sequence SEQ ID NO: 25 and a light chain variable domain comprising CDR1-L of sequence SEQ ID NO: 27, CDR2-L of sequence 'KVS' and CDR3-L of sequence SEQ ID NO: 28; or
e) a heavy chain variable domain comprising CDR1-H of sequence SEQ ID NO: 30, CDR2-H of sequence SEQ ID NO: 31, CDR3-H of sequence SEQ ID NO: 32 and a light chain variable domain comprising CDR1-L of sequence SEQ ID NO: 34, CDR2-L of sequence 'RDD' and CDR3-L of sequence SEQ ID NO: 35; or
f) a heavy chain variable domain comprising CDR1-H of sequence SEQ ID NO: 13, CDR2-H of sequence SEQ ID NO: 37, CDR3-H of sequence SEQ ID NO: 38 and a light chain variable domain comprising CDR1-L of sequence SEQ ID NO: 10, CDR2-L of sequence 'KVS' and CDR3-L of sequence SEQ ID NO: 28; or
g) a heavy chain variable domain comprising CDR1-H of sequence SEQ ID NO: 13, CDR2-H of sequence SEQ ID NO: 37, CDR3-H of sequence SEQ ID NO: 41 and a light chain variable domain comprising CDR1-L of sequence SEQ ID NO: 17, CDR2-L of sequence 'KVS' and CDR3-L of sequence SEQ ID NO: 11; or
h) a heavy chain variable domain comprising CDR1-H of sequence SEQ ID NO: 13, CDR2-H of sequence SEQ ID NO: 37, CDR3-H of sequence SEQ ID NO: 44 and a light chain variable domain comprising CDR1-L of sequence SEQ ID NO: 10, CDR2-L of sequence 'KVS' and CDR3-L of sequence SEQ ID NO: 11; or
i) a heavy chain variable domain comprising CDR1-H of sequence SEQ ID NO: 13, CDR2-H of sequence SEQ ID NO: 37, CDR3-H of sequence SEQ ID NO: 47 and a light chain variable domain comprising CDR1-L of sequence SEQ ID NO: 10, CDR2-L of sequence 'KVS' and CDR3-L of sequence SEQ ID NO: 11; or
j) a heavy chain variable domain comprising CDR1-H of sequence SEQ ID NO: 50, CDR2-H of sequence SEQ ID NO: 51, CDR3-H of sequence SEQ ID NO: 52 and a light chain variable domain comprising CDR1-L of sequence SEQ ID NO: 54, CDR2-L of sequence 'NAN' and CDR3-L of sequence SEQ ID NO: 55; or
k) a heavy chain variable domain comprising CDR1-H of sequence SEQ ID NO: 57, CDR2-H of sequence SEQ ID NO: 37, CDR3-H of sequence SEQ ID NO: 58 and a light chain variable domain comprising CDR1-L of sequence SEQ ID NO: 10, CDR2-L of sequence 'KVS' and CDR3-L of sequence SEQ ID NO: 28; or
l) a heavy chain variable domain comprising CDR1-H of sequence SEQ ID NO: 13, CDR2-H of sequence SEQ ID NO: 37, CDR3-H of sequence SEQ ID NO: 61 and a light chain variable domain comprising CDR1-L of sequence SEQ ID NO: 10, CDR2-L of sequence 'KVS' and CDR3-L of sequence SEQ ID NO: 11; or
m) a heavy chain variable domain comprising CDR1-H of sequence SEQ ID NO: 64, CDR2-H of sequence SEQ ID NO: 65, CDR3-H of sequence SEQ ID NO: 47 and a light chain variable domain comprising CDR1-L of sequence SEQ ID NO: 67, CDR2-L of sequence 'KVS' and CDR3-L of sequence SEQ ID NO: 28; or
n) a heavy chain variable domain comprising CDR1-H of sequence SEQ ID NO: 13, CDR2-H of sequence SEQ ID NO: 37, CDR3-H of sequence SEQ ID NO: 69 and a light chain variable domain comprising CDR1-L of sequence SEQ ID NO: 10, CDR2-L of sequence 'KVS' and CDR3-L of sequence SEQ ID NO: 71; or
o) a heavy chain variable domain comprising CDR1-H of sequence SEQ ID NO: 13, CDR2-H of sequence SEQ ID NO: 37, CDR3-H of sequence SEQ ID NO: 84 and a light chain variable domain comprising CDR1-L of sequence SEQ ID NO: 17, CDR2-L of sequence 'KVS' and CDR3-L of sequence SEQ ID NO: 11; or
p) a heavy chain variable domain comprising CDR1-H of sequence SEQ ID NO: 75, CDR2-H of sequence SEQ ID NO: 76, CDR3-H of sequence SEQ ID NO: 77 and a light chain variable domain comprising CDR1-L of sequence SEQ ID NO: 10, CDR2-L of sequence 'KVS' and CDR3-L of sequence SEQ ID NO: 11; or
q) a heavy chain variable domain comprising CDR1-H of sequence SEQ ID NO: 80, CDR2-H of sequence SEQ ID NO: 76, CDR3-H of sequence SEQ ID NO: 81 and a light chain variable domain comprising CDR1-L of sequence SEQ ID NO: 10, CDR2-L of sequence 'KVS' and CDR3-L of sequence SEQ ID NO: 11; or
r) a heavy chain variable domain comprising CDR1-H of sequence SEQ ID NO: 13, CDR2-H of sequence SEQ ID NO: 37, CDR3-H of sequence SEQ ID NO: 84 and a light chain variable domain comprising CDR1-L of sequence SEQ ID NO: 10, CDR2-L of sequence 'KVS' and CDR3-L of sequence SEQ ID NO: 11; or
s) a heavy chain variable domain comprising CDR1-H of sequence SEQ ID NO: 13, CDR2-H of sequence SEQ ID NO: 37, CDR3-H of sequence SEQ ID NO: 47 and a light chain variable domain comprising CDR1-L of sequence SEQ ID NO: 10, CDR2-L of sequence 'KVS' and CDR3-L of sequence SEQ ID NO: 88; or
t) a heavy chain variable domain comprising CDR1-H of sequence SEQ ID NO: 90, CDR2-H of sequence SEQ ID NO: 91, CDR3-H of sequence SEQ ID NO: 32 and a light chain variable domain comprising CDR1-L of sequence SEQ ID NO: 93, CDR2-L of sequence 'GAS' and CDR3-L of sequence SEQ ID NO: 94; or
u) a heavy chain variable domain comprising CDR1-H of sequence SEQ ID NO: 96, CDR2-H of sequence SEQ ID NO: 97, CDR3-H of sequence SEQ ID NO: 98 and a light chain variable domain comprising CDR1-L of sequence SEQ ID NO: 100, CDR2-L of sequence 'NTN' and CDR3-L of sequence SEQ ID NO: 101; or
v) a heavy chain variable domain comprising CDR1-H of sequence SEQ ID NO: 103, CDR2-H of sequence SEQ ID NO: 104, CDR3-H of sequence SEQ ID NO: 105 and a light chain variable domain comprising CDR1-L of sequence SEQ ID NO: 10, CDR2-L of sequence 'KVS' and CDR3-L of sequence SEQ ID NO: 11; or
w) a heavy chain variable domain comprising CDR1-H of sequence SEQ ID NO: 80, CDR2-H of sequence SEQ ID NO: 19, CDR3-H of sequence SEQ ID NO: 108 and a light chain variable domain comprising CDR1-L of sequence SEQ ID NO: 10, CDR2-L of sequence 'KVS' and CDR3-L of sequence SEQ ID NO: 11; or
x) a heavy chain variable domain comprising CDR1-H of sequence SEQ ID NO: 13, CDR2-H of sequence SEQ ID NO: 37, CDR3-H of sequence SEQ ID NO: 111 and a light chain variable domain comprising CDR1-L of sequence SEQ ID NO: 113, CDR2-L of sequence 'KVS' and CDR3-L of sequence SEQ ID NO: 114; or
y) a heavy chain variable domain comprising CDR1-H of sequence SEQ ID NO: 116, CDR2-H of sequence SEQ ID NO: 117, CDR3-H of sequence SEQ ID NO: 118 and a light chain variable domain comprising CDR1-L of sequence SEQ ID NO: 100, CDR2-L of sequence VTN' and CDR3-L of sequence SEQ ID NO: 120; or
z) a heavy chain variable domain comprising CDR1-H of sequence SEQ ID NO: 122, CDR2-H of sequence SEQ ID NO: 123, CDR3-H of sequence SEQ ID NO: 124 and a light chain variable domain comprising CDR1-L of sequence SEQ ID NO: 126, CDR2-L of sequence 'RDD' and CDR3-L of sequence SEQ ID NO: 127; or
aa) a heavy chain variable domain comprising CDR1-H of sequence SEQ ID NO: 13, CDR2-H of sequence SEQ ID NO: 19, CDR3-H of sequence SEQ ID NO: 129 and a light chain variable domain comprising CDR1-L of sequence SEQ ID NO: 10, CDR2-L of sequence 'KVS' and CDR3-L of sequence SEQ ID NO: 11; or
bb) a heavy chain variable domain comprising CDR1-H of sequence SEQ ID NO: 103, CDR2-H of sequence SEQ ID NO: 104, CDR3-H of sequence SEQ ID NO: 105; and
a light chain variable domain comprising CDR1-L of sequence SEQ ID NO: 133, CDR2-L of sequence 'LVS' and CDR3-L of sequence SEQ ID NO: 134.

The invention also provides an anti-CD3 antibody comprising at least the heavy chain variable domain and/or the light chain variable domain of one of the so-called anti-CD3 antibodies listed above.

Thus, the invention relates in particular to an anti-CD3 antibody, which comprises:
a) a heavy chain variable domain of sequence SEQ ID NO: 5 or a sequence at least 85% identical thereto, and/or a light chain variable domain of sequence SEQ ID NO: 9, or a sequence at least 85% identical thereto; or
b) a heavy chain variable domain of sequence SEQ ID NO: 12 or a sequence at least 85% identical thereto, and/or a light chain variable domain of sequence SEQ ID NO: 16, or a sequence at least 85% identical thereto; or
c) a heavy chain variable domain of sequence SEQ ID NO: 18 or a sequence at least 85% identical thereto, and/or a light chain variable domain of sequence SEQ ID NO: 21, or a sequence at least 85% identical thereto; or
d) a heavy chain variable domain of sequence SEQ ID NO: 23 or a sequence at least 85% identical thereto, and/or a light chain variable domain of sequence SEQ ID NO: 26, or a sequence at least 85% identical thereto; or
e) a heavy chain variable domain of sequence SEQ ID NO: 29 or a sequence at least 85% identical thereto, and/or a light chain variable domain of sequence SEQ ID NO: 33, or a sequence at least 85% identical thereto; or
f) a heavy chain variable domain of sequence SEQ ID NO: 36 or a sequence at least 85% identical thereto, and/or a light chain variable domain of sequence SEQ ID NO: 39, or a sequence at least 85% identical thereto; or
g) a heavy chain variable domain of sequence SEQ ID NO: 40 or a sequence at least 85% identical thereto, and/or a light chain variable domain of sequence SEQ ID NO: 42, or a sequence at least 85% identical thereto; or
h) a heavy chain variable domain of sequence SEQ ID NO: 43 or a sequence at least 85% identical thereto, and/or a light chain variable domain of sequence SEQ ID NO: 45, or a sequence at least 85% identical thereto; or
i) a heavy chain variable domain of sequence SEQ ID NO: 46 or a sequence at least 85% identical thereto, and/or a light chain variable domain of sequence SEQ ID NO: 48, or a sequence at least 85% identical thereto; or
j) a heavy chain variable domain of sequence SEQ ID NO: 49 or a sequence at least 85% identical thereto, and/or a light chain variable domain of sequence SEQ ID NO: 53, or a sequence at least 85% identical thereto; or
k) a heavy chain variable domain of sequence SEQ ID NO: 56 or a sequence at least 85% identical thereto, and/or a light chain variable domain of sequence SEQ ID NO: 59, or a sequence at least 85% identical thereto; or
l) a heavy chain variable domain of sequence SEQ ID NO: 60 or a sequence at least 85% identical thereto, and/or a light chain variable domain of sequence SEQ ID NO: 62, or a sequence at least 85% identical thereto; or
m) a heavy chain variable domain of sequence SEQ ID NO: 63 or a sequence at least 85% identical thereto, and/or a light chain variable domain of sequence SEQ ID NO: 66, or a sequence at least 85% identical thereto; or
n) a heavy chain variable domain of sequence SEQ ID NO: 68 or a sequence at least 85% identical thereto, and/or a light chain variable domain of sequence SEQ ID NO: 70, or a sequence at least 85% identical thereto; or
o) a heavy chain variable domain of sequence SEQ ID NO: 72 or a sequence at least 85% identical thereto, and/or a light chain variable domain of sequence SEQ ID NO: 73, or a sequence at least 85% identical thereto; or
p) a heavy chain variable domain of sequence SEQ ID NO: 74 or a sequence at least 85% identical thereto, and/or a light chain variable domain of sequence SEQ ID NO: 78, or a sequence at least 85% identical thereto; or
q) a heavy chain variable domain of sequence SEQ ID NO: 79 or a sequence at least 85% identical thereto, and/or a light chain variable domain of sequence SEQ ID NO: 82, or a sequence at least 85% identical thereto; or
r) a heavy chain variable domain comprising sequence SEQ ID NO: 83 or a sequence at least 85% identical thereto, and/or a light chain variable domain of sequence SEQ ID NO: 85, or a sequence at least 85% identical thereto; or
s) a heavy chain variable domain of sequence SEQ ID NO: 46 or a sequence at least 85% identical thereto, and/or a light chain variable domain of sequence SEQ ID NO: 87, or a sequence at least 85% identical thereto; or
t) a heavy chain variable domain of sequence SEQ ID NO: 89 or a sequence at least 85% identical thereto, and/or a light chain variable domain of sequence SEQ ID NO: 92, or a sequence at least 85% identical thereto; or u) a heavy chain variable domain of sequence SEQ ID NO: 95 or a sequence at least 85% identical thereto, and/or a light chain variable domain of sequence SEQ ID NO: 99, or a sequence at least 85% identical thereto; or v) a heavy chain variable domain of sequence SEQ ID NO: 102 or a sequence at least 85% identical thereto, and/or a light chain variable domain of sequence SEQ ID NO: 106, or a sequence at least 85% identical thereto; or w) a heavy chain variable domain of sequence SEQ ID NO: 107 or a sequence at least 85% identical thereto, and/or a light chain variable domain of sequence SEQ ID NO: 109, or a sequence at least 85% identical thereto; or x) a heavy chain variable domain of sequence SEQ ID NO: 110 or a sequence at least 85% identical thereto, and/or a light chain variable domain of sequence SEQ ID NO: 112, or a sequence at least 85% identical thereto; or y) a heavy chain variable domain of sequence SEQ ID NO: 115 or a sequence at least 85% identical thereto, and/or a light chain variable domain of sequence SEQ ID NO: 119, or a sequence at least 85% identical thereto; or z) a heavy chain variable domain of sequence SEQ ID NO: 121 or a sequence at least 85% identical thereto, and/or a light chain variable domain of sequence SEQ ID NO: 125, or a sequence at least 85% identical thereto; or aa) a heavy chain variable domain of sequence SEQ ID NO: 128 or a sequence at least 85% identical thereto, and/or a light chain variable domain of sequence SEQ ID NO: 130, or a sequence at least 85% identical thereto; or bb) a heavy chain variable domain of sequence SEQ ID NO: 131 or a sequence at least 85% identical thereto, and/or a light chain variable domain of sequence SEQ ID NO: 132, or a sequence at least 85% identical thereto.

For instance, the sequence of the variable domain of heavy or light chain may differ from the reference sequence SEQ ID NO: 5, 9, 12, 16, 18, 21, 23, 26, 29, 33, 36, 39, 40, 42, 43, 45, 46, 48, 49, 53, 56, 59, 60, 62, 63, 66, 68, 70, 72, 73, 74, 78, 79, 82, 83, 85, 87, 89, 92, 95, 99, 102, 106, 107, 109, 110, 112, 115, 119, 121, 125, 128, 130, 131, 132, as appropriate, by one or more amino acid substitution(s), in particular by one or more conservative amino acid substitution(s) and/or substitution(s) with canonical residues. In particular, the sequence of the variable domain of heavy or light chain may differ from the reference sequence SEQ ID NO: 5, 9, 12, 16, 18, 21, 23, 26, 29, 33, 36, 39, 40, 42, 43, 45, 46, 48, 49, 53, 56, 59, 60, 62, 63, 66, 68, 70, 72, 73, 74, 78, 79, 82, 83, 85, 87, 89, 92, 95, 99, 102, 106, 107, 109, 110, 112, 115, 119, 121, 125, 128, 130, 131, 132, by conservative amino acid substitution(s), only.

The sequence alterations as compared with sequence SEQ ID NO: 5, 9, 12, 16, 18, 21, 23, 26, 29, 33, 36, 39, 40, 42, 43, 45, 46, 48, 49, 53, 56, 59, 60, 62, 63, 66, 68, 70, 72, 73, 74, 78, 79, 82, 83, 85, 87, 89, 92, 95, 99, 102, 106, 107, 109, 110, 112, 115, 119, 121, 125, 128, 130, 131, 132 will in particular be present essentially in one or more of the framework regions, FR1-L, FR2-L, FR3-L, FR4-L and/or FR1-H, FR2-H, FR3-H, FR4-H.

However, amino acid substitutions in one or more CDRs are also possible. In particular, the sequence of the light chain variable domain may differ from sequence SEQ ID NO: 9 at least by a S to R substitution at position 28 of SEQ ID NO: 9 (in CDR1-L), and/or at least by a V to E substitution at position 30 of SEQ ID NO: 9 (in CDR1-L), and/or at least by a N to D or T substitution at position 33 of SEQ ID NO: 9 (in CDR1-L), and/or at least by a N to Y substitution at position 35 of SEQ ID NO: 9 (in CDR1-L) and/or the sequence of the light chain variable domain may differ from sequence SEQ ID NO: 9 at least by a T to S or A substitution at position 97 of SEQ ID NO: 9 (in CDR3-L), and/or at least by a Q to H or E substitution at position 98 of SEQ ID NO: 9 (in CDR3-L) and/or the heavy chain variable domain may differ from sequence SEQ ID NO: 5 at least by a T to N or S substitution at position 28 of SEQ ID NO: 5 (in CDR1-H), and/or at least by a F to V substitution at position 29 of SEQ ID NO: 5 (in CDR1-H), or at least by a T to N or Y substitution at position 30 of SEQ ID NO: 5 (in CDR1-H), or at least by a K to L or Y substitution at position 31 of SEQ ID NO: 5 (in CDR1-H) and/or the heavy chain variable domain may differ from sequence SEQ ID NO: 5 at least by a D to A substitution at position 53 of SEQ ID NO: 5 (in CDR2-H), or at least by a K to R substitution at position 54 of SEQ ID NO: 5 (in CDR2-H), or at least by a S to A substitution at position 55 of SEQ ID NO: 5 (in CDR2-H), or at least by a S to N substitution at position 57 of SEQ ID NO: 5 (in CDR2-H), or at least by a A to E substitution at position 59 of SEQ ID NO: 5 (in CDR2-H) and/or the heavy chain variable domain may differ from sequence SEQ ID NO: 5 at least by a G to A substitution at position 100 of SEQ ID NO: 5 (in CDR3-H) and/or at least by a T to V substitution at position 101 of SEQ ID NO: 5 (in CDR3-H) at least by a Q to Y substitution at position 102 of SEQ ID NO: 5 (in CDR3-H).

In one embodiment, the anti-CD3 antibody of the invention and a fragment thereof is, respectively, a rat antibody and a fragment of a rat antibody.

In one aspect of the invention, the anti-CD3 antibody of the invention may also be a chimeric antibody, and in particular a rat/human antibody, e.g. an antibody comprising rat variable domains of heavy and light chains and a CH domain and a CL domain from a human antibody.

In a further aspect of the invention, the anti-CD3 antibody may also be a humanized antibody or a fragment of a humanized antibody obtained, for example, by CDR-grafting or by the 4D method (US20110027266).

Accordingly, in one embodiment, the anti-CD3 antibody of the invention is a humanized antibody comprising
a) a heavy chain variable domain comprising of an amino acid sequence selected from the group consisting of SEQ ID NO: 135, SEQ ID NO: 136, SEQ ID NO: 137, SEQ ID NO: 138, SEQ ID NO: 144, SEQ ID NO: 145, SEQ ID NO: 146, SEQ ID NO: 147, SEQ ID NO: 152, SEQ ID NO: 153, and
a light chain variable domain comprising of an amino acid sequence selected from the group consisting of SEQ ID NO: 139, SEQ ID NO: 140, SEQ ID NO: 141, SEQ ID NO: 143, SEQ ID NO: 148, SEQ ID NO: 149, SEQ ID NO: 150, SEQ ID NO: 151, SEQ ID NO: 154, SEQ ID NO: 155, SEQ ID NO: 156, SEQ ID NO: 157, or
b) a heavy chain variable domain comprising of an amino acid sequence selected from the group consisting of SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 183, and a light chain variable domain comprising of an amino acid sequence selected from the group consisting of SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 182.

According to a further embodiment, the anti-CD3 antibody of the invention is a humanized antibody comprising:
a) a heavy chain variable domain of sequence SEQ ID NO: 138 and/or a light chain variable domain of sequence SEQ ID NO: 143; or
b) a heavy chain variable domain of sequence SEQ ID NO: 171 and/or a light chain variable domain of sequence SEQ ID NO: 158; or
c) a heavy chain variable domain of sequence SEQ ID NO: 176 and/or a light chain variable domain of sequence SEQ ID NO: 164.

In one embodiment, the anti-CD3 antibody according to the invention comprises the three CDR sequences or the variable domain of the heavy chain, or the six CDR sequences or variable domains of the heavy and light chains of one of so-called anti-CD3 antibodies listed above.

The invention further refers to a fragment of the humanized anti-CD3 antibody as defined above. In one embodiment, the humanized anti-CD3 antibody described above is a chimeric antibody.

The anti-CD3 antibody according to the invention may also be a single domain antibody or a fragment thereof. In particular, a single domain antibody fragment may consist of a variable heavy chain (VHH) which comprises the CDR1-H, CDR2-H and CDR3-H of one of the antibodies described above. The anti-CD3 antibody may also be a heavy chain antibody, i.e. an antibody devoid of light chain, which may or may not contain a CH1 domain.

The single domain antibody or a fragment thereof may also comprise the framework regions of a camelid single domain antibody, and optionally the constant domain of a camelid single domain antibody.

The anti-CD3 antibody according to the invention may also be an antibody fragment, in particular a humanized antibody fragment, selected from the group consisting of Fv, Fab, F(ab')2, Fab', dsFv, (dsFv)2, scFv, sc(Fv)2, and diabodies.

Accordingly, the anti-CD3 antibody of the invention is a Fab comprising, or consisting of
a) the heavy chain amino acid sequence SEQ ID NO: 186 and/or the light chain amino acid sequence SEQ ID NO: 187; or
b) the heavy chain amino acid sequence SEQ ID NO: 188 and/or the light chain amino acid sequence SEQ ID NO: 189; or
c) the heavy chain amino acid sequence SEQ ID NO: 190 and/or the light chain amino acid sequence SEQ ID NO: 191; or
d) the heavy chain amino acid sequence SEQ ID NO: 192 and/or the light chain amino acid sequence SEQ ID NO: 193.

In an embodiment, the CD3-antibody is a bispecific or multispecific antibody formed from at least one antibody fragment or at least one variable domain of the anti-CD3 antibodies of the invention. Multispecific antibodies are polyvalent protein complexes as described for instance in EP 2 050 764 A1 or US 2005/0003403 A1.

The bispecific or multispecific CD3-antibodies according to the invention can have specificity for (a) extracellular domain of human or human and *Macaca fascicularis* CD3, targeted by one of the above described anti-CD3 antibodies and (b) at least one other antigen.

In one embodiment, the other antigen is CD123 and accordingly the resulting bispecific antibody is a CD3/CD123 bispecific antibody. Conventional bi-specific antibodies can be produced by techniques that are known to the skilled in the art.

Antibodies and fragments of anti-CD3 antibodies according to the invention can be used in an isolated (e.g., purified) from or contained in a vector, such as a membrane or lipid vesicle (e.g. a liposome).

In one further embodiment, the anti-CD3 antibody of the invention is for use for the preparation of antibody-like binding protein of the invention further defined in the section "antibody-like binding protein".

Any combination of the above embodiments makes part of the invention.

Anti CD123 Antibodies

"CD123" (Cluster of Differentiation 123) is also known as "Interleukin 3 receptor, alpha (IL3RA)" or "IL3R", "IL3RX", "IL3RY", "IL3RAY", "hIL-3Ra" and denotes an interleukin 3 specific subunit of a heterodimeric cytokine receptor. The functional interleukin 3 receptor is a heterodimer that comprises a specific alpha chain (IL-3A; CD123) and the IL-3 receptor beta chain ($\beta_0$; CD 131) that is shared with the receptors for granulocyte macrophage colony stimulating factor (GM-CSF) and interleukin 5 (IL-5). CD123 is a type I integral transmembrane protein with a deduced Molecular Weight of about 43 kDa containing an extracellular domain involved in IL-3 binding, a transmembrane domain and a short cytoplasmic tail of about 50 amino acids. The extracellular domain is composed of two regions: an N-terminal region of about 100 amino acids, the sequence of which exhibits similarity to equivalent regions of the GM-CSF and IL-5 receptor alpha-chains; and a region proximal to the transmembrane domain that contains four conserved cysteine residues and a WSXWS motif, common to other members of this cytokine receptor family. The IL-3 binding domain comprises about 200 amino acid residue cytokine receptor motifs (CRMs) made up of two Ig-like folding domains. The extracellular domain of CD123 is highly glycosylated, with N-glycosylation necessary for both ligand binding and receptor signaling. The protein family gathers three members: IL3RA (CD123A), CSF2RA and IL5RA. The overall structure is well conserved between the three members but sequence homologies are very low. One 300 amino-acid long isoform of CD123 has been discovered so far, but only on the RNA level which is accessible on the Getentry database under the accession number ACM24116.1.

U.S. Pat. No. 6,177,078 discloses the anti-IL-3Receptor alpha chain (IL-3Ra, CD123) monoclonal antibody 7G3, and the ability of 7G3 to bind to the N-terminal domain, specifically amino acid residues 19-49, of IL-3Ra. U.S. Pat. No. 6,733,743 discloses a method of impairing a hematologic cancer progenitor cell that expresses CD123 but does not significantly express CD131, by contacting the cell with a composition of an antibody and a cytotoxic agent (selected from a chemotherapeutic agent, a toxin or an alpha-emitting radioisotope) whereby the composition binds selectively to CD123 in an amount effective to cause cell death. However, it has remained unclear whether targeting CD123 can functionally impair AML-LSCs.

A reference sequence of full-length human CD123 protein, including signal peptide, is available from the NCBI database under the accession number NP_002174.1 and under the Uniprot accession number P26951 and is herein disclosed under SEQ ID NO: 194 (as available on Dec. 14, 2014). A reference sequence of full-length Macaca fascicularis CD123 protein, including signal peptide, is available from GenBank database under the accession number EHH61867.1 and under the Uniprot accession number G8F3K3 and is herein disclosed under SEQ ID NO: 195 (as available on Dec. 14, 2014).

A sequence of a mature human CD123 Strep-II tagged Fc-fusion protein, cloned by the inventors from genomic DNA, is disclosed under SEQ ID NO: 196. Said mature human CD123 Fc-fusion protein comprises amino acids 19 to 305 of the full-length human CD123 protein and thus comprises the extracellular domain of human CD123. A sequence of a mature Macaca fascicularis CD123 Strep-II tagged Fc-fusion protein, cloned by the inventors from cDNA, is disclosed under SEQ ID NO: 197. Said mature Macaca fascicularis CD123 Fc-fusion protein comprises amino acids 19 to 305 of the full-length Macaca fascicularis CD123 protein and thus comprises the extracellular domain of Macaca fascicularis CD123.

Domain organization of human and Macaca fascicularis CD123 is as follows (based on the human CD123 sequence accessible in the NCBI database under accession NP_002174.1 (SEQ ID NO: 194) and based on the Macaca fascicularis CD123 sequence accessible in the Uniprot database under accession number G8F3K3, SEQ ID NO: 195):

| Human CD123 domains | Positions on SEQ ID NO: 194 (human) | Positions on SEQ ID NO: 195 (Macaca fascicularis) |
| --- | --- | --- |
| Extracellular | 19-305 | 19-305 |
| Transmembrane domain | 306-325 | 306-325 |
| Cytoplasmic | 326-378 | 326-378 |

Accordingly, the extracellular domain of human CD123 consists of amino acids at positions 19-305 of SEQ ID NO: 194.

CD123 (the interleukin-3 receptor alpha chain IL-3Ra) is a tumor antigen over-expressed in a variety of hematological neoplasms. The majority of AML blasts express surface CD123 and this expression does not vary by subtype of AML. Higher expression of CD123 on AML at diagnosis has been reported to be associated with poorer prognosis. CD123 expression has been reported in other hematological malignancies including myelodysplasia, systemic mastocytosis, blastic plasmacytoid dendritic cell neoplasm (BPDCN), ALL and hairy cell leukemia.

CD123 is expressed on AML leukemic stem cells and growing evidences suggest that AML arises from these LSCs, which have been shown to be quiescent and relatively resistant to DNA damaging chemotherapy. It is hypothesized that the persistence of LSCs underpins relapse after initial remission and thus the eradication of LSCs can be considered a requirement for cure, and an important therapeutic goal.

"Leukemic stem cells (LSCs)" are cancer cells that possess characteristics associated with normal stem cells, that is, the property of self renewal and the capability to develop multiple lineages. Such cells are proposed to persist in hematological cancers such as AML as distinct populations. The LCS present in AML patients are so called "AML-LCSs".

"Acute myelogenous leukemia (AML)" is a clonal disorder clinically presenting as increased proliferation of heterogeneous and undifferentiated myeloid blasts. The leukemic hierarchy is maintained by a small population of LSCs (AML-LCSs), which have the distinct ability for self-renewal, and are able to differentiate into leukemic progenitors. These progenitors generate the large numbers of leukemic blasts readily detectable in patients at diagnosis and relapse, leading ultimately to mortality. AML-LSC have been commonly reported as quiescent cells, in contrast to rapidly dividing clonogenic progenitors. This property of AML-LSCs renders conventional chemotherapeutics that target proliferating cells less effective, potentially explaining the current experience in which a high proportion of AML patients enter complete remission, but almost invariably relapse, with <30% of adults surviving for more than 4 years. In addition, minimal residual disease occurrence and poor survival has been attributed to high LSC frequency at diagnosis in AML patients. Consequently, it is imperative for the long-term management of AML (and similarly other above mentioned hematological cancer conditions) that new treatments are developed to specifically eliminate LSCs.

Over-expression of CD123 has been reported on AML blasts and on $CD34^+$/CD38 AML-LSCs relative to normal hematopoietic cells.

CD123 thus provides an important therapeutic target for cancer therapy, in particular for cancer therapy in patients having poor prognosis.

The inventors have succeeded in generating, screening and selecting specific mouse and rat anti-CD123 antibodies displaying high affinity for both human and Macaca fascicularis CD123 protein, and which do not significantly cross-react with human CSF2RA and IL5RA proteins, and with Macaca fascicularis CD3 proteins.

The inventors have determined the sequence of variable heavy and light chains of such monoclonal antibodies, the so-called "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", and "9F6-G3" anti-CD123 antibodies.

The so-called "3E3-D3" anti-CD123 antibody comprises:
a heavy chain variable domain consisting of sequence (SEQ ID NO: 226
QVQLQESGPGLVQPSQTLSLTCTVSGFSLTTYDVHWVRQPPGKGLEWMGR

IQNGGITDYNSALKSRLIISRDTSKSQVFLKMNSVQTEDTAMYFCAKTGS

YFYAFDHWGQGTLVTVSS, with CDRs shown in bold characters) comprising CDR1-H of sequence SEQ ID NO: 227, a CDR2-H of sequence SEQ ID NO: 228, and a CDR3-H of sequence SEQ ID NO: 229, or
a heavy chain variable domain consisting of sequence (SEQ ID NO: 277
QVQLQESGPGLVQPSQTLSLTCTVSGFSLTTYDVHWVRQPPGKGLEWMGR

IQNAGITDYNSALKSRLIISRDTSKSQVFLKMNSVQTEDTAMYFCAKTGS

YFYAFDHWGQGTLVTVSS, with CDRs shown in bold characters) comprising CDR1-H of sequence SEQ ID NO: 227, a CDR2-H of sequence SEQ ID NO:353, and a CDR3-H of sequence SEQ ID NO: 229, or a heavy chain variable domain consisting of sequence (SEQ ID NO: 278)
QVQLQESGPGLVQPSQTLSLTCTVSGFSLTTYDVHWVRQPPGKGLEWMGR IQDGGITDYNSALKSRLIISRDTSKSQVFLKMNSVQTEDTAMYFCAKTGS YFYAFDHWGQGTLVTVSS, with CDRs shown in bold characters) comprising CDR1-H of sequence SEQ ID NO: 227, a CDR2-H of sequence SEQ ID NO: 279, and a CDR3-H of sequence SEQ ID NO: 229, and —a light chain variable domain consisting of sequence (SEQ ID NO: 230)
QFVLTQPNSVSTNLGSTVKLSCKRNTGNIGSNYVNWYQQHEGRSPTTMIY RDDKRPDGVPDRFSGSIDRSSNSALLTINNVQTEDEADYFCQSYSSGINI IFGGGTKLTVL, with CDRs shown in bold characters) comprising CDR1-L of sequence SEQ ID NO: 231, a CDR2-L consisting of sequence 'RDD', and a CDR3-L of sequence SEQ ID NO: 232.

The so-called "1E1-G5" anti-CD123 antibody comprises:
a heavy chain variable domain consisting of sequence (SEQ ID NO: 198)
QVQLQESGPTLVKPGDSVKMSCKAFGYTFTDHIIHWVKQSHGKSLEWIGY INPYSGGTNYNEKFKSKATLTVDKSSTAYMEFSRLTSEDSAICYCALNY GSYYAMDAWGQGTSVTVSS, with CDRs shown in bold characters) comprising CDR1-H of sequence SEQ ID NO: 199, a CDR2-H of sequence SEQ ID NO: 200, and a CDR3-H of sequence SEQ ID NO: 201 and a light chain variable domain consisting of sequence (SEQ ID NO: 202)
DIQMTQSPASLSASLGQTVTIECRPSEDIYSNLAWFQQKPGSSPQLLIYD ANNLADGVPSRFSGSGSGTQYSLKINSLQSEDVASYFCQQYNKYPYTFGT GTKLELK, with CDRs shown in bold characters) comprising CDR1-L of sequence SEQ ID NO: 203, a CDR2-L consisting of sequence DAN', and a CDR3-L of sequence SEQ ID NO: 204.

The so-called "2B8-F3" anti-CD123 antibody comprises:
a heavy chain variable domain consisting of sequence (SEQ ID NO: 205)
EVQLVESGGGLVQPGRSLKLSCAASGFTFSDYNMAWVRQAPKKGLEWVAT ILYDGGRTYYRGSVKGRFTISRDNAKSTLYLRMDSLRSEDTATYYCATHS RGTDYFDYWGQGVMVTVSS, with CDRs shown in bold characters) comprising CDR1-H of sequence SEQ ID NO: 206, a CDR2-H of sequence SEQ ID NO: 207, and a CDR3-H of sequence SEQ ID NO: 208 and a light chain variable domain consisting of sequence (SEQ ID NO: 209)
EIVLTQSPTSMTASPGEQVTITCRASSSINYMHWYQQKPGASPRPWIYET SKLASGVPDRFSGSASGTSYSLTINNMEAEDAATYYCQQWNYPSWTFGGG TKLELK, with CDRs shown in bold characters) comprising CDR1-L of sequence SEQ ID NO: 210, a CDR2-L consisting of sequence 'ETS', and a CDR3-L of sequence SEQ ID NO: 211.

The so-called "2F8-D6" anti-CD123 antibody comprises:
a heavy chain variable domain consisting of sequence (SEQ ID NO: 212)
QVQLKESGPGLVQPSQTLSLTCTVSGFSLTSYGVSWVRQPPGKGLEWIAT ISSAGSTYYDLVLKSRLSITRDTSKSQVFLKVHSLQTEDTAIYLCARDAP VFNYGSYNAMDSWGQGTSVTVSS, with CDRs shown in bold characters) comprising CDR1-H of sequence SEQ ID NO: 213, a CDR2-H of sequence SEQ ID NO: 214, and a CDR3-H of sequence SEQ ID NO: 215 and a light chain variable domain consisting of sequence (SEQ ID NO: 216)
DIQMTQSPSFLSATVGDRVTINCKASQNINKYLNWYQQKLGEAPKRLIYN TNSLQTGIPSRFSGSGSGTDYTLTISSLQPEDVATYFCLQHKSGLTFGSG TKLEIK, with CDRs shown in bold characters) comprising CDR1-L of sequence SEQ ID NO: 217, a CDR2-L consisting of sequence 'NTN', and a CDR3-L of sequence SEQ ID NO: 218.

The so-called "3B10-E6" anti-CD123 antibody comprises:
a heavy chain variable domain consisting of sequence (SEQ ID NO: 219)
QVQLQQSGPELRRPGSSVRLSCKASGYRIKDFLIHWIKNRPEHGLEWIGW IDPEDGETKYAQKFQTKATLTADTSSNTAYMQLSSLTSEDTATYFCARWG DVYYGLMRGHVMDAWGQGTSVTVSS, with CDRs shown in bold characters) comprising CDR1-H of sequence SEQ ID NO: 220, a CDR2-H of sequence SEQ ID NO: 221, and a CDR3-H of sequence SEQ ID NO: 222 and a light chain variable domain consisting of sequence (SEQ ID NO: 223)
DVLMTQTPVSLPVSLGGQVSISCRSSQSLVHSDGDTYLHWYLQKPGQSPQ LLIYRVSNRFSGVPDRFSGSGSGTDFTLKISRVEPEDLGLYYCLQTTHFP PWTFGGGTKLEMK, with CDRs shown in bold characters) comprising CDR1-L of sequence SEQ ID NO: 224, a CDR2-L consisting of sequence 'RVS', and a CDR3-L of sequence SEQ ID NO: 225.

The so-called "5A5-B4" anti-CD123 antibody comprises:
a heavy chain variable domain consisting of sequence (SEQ ID NO: 233)
QIQIVQSGSDVTSTCNGCGTCYFSGFSLSTTGICVSWIRQPSGKGQEWLA

DFCWDDGKGYNPSLKNRLSISKDTSNNQVFLKITSVDTADTATYYCARRR

VYYGIYFDYWGQGVMVTVSS, with CDRs shown in bold characters) comprising CDR1-H of sequence SEQ ID NO: 234, a CDR2-H of sequence SEQ ID NO: 235, and a CDR3-H of sequence SEQ ID NO: 236 and
a light chain variable domain consisting of sequence (SEQ ID NO: 237)
DIVMTQSPALAVSPGERVSISCRASNSVSTRMHWYQQKPGQQPKLLIYGA

SNLESGVPARFSGSGSGTDFTLTIDPVEADDIATYFCQQSWNDPLTFGSG

TKLEIK, with CDRs shown in bold characters) comprising CDR1-L of sequence SEQ ID NO: 238, a CDR2-L consisting of sequence 'GAS', and a CDR3-L of sequence SEQ ID NO: 239.

The so-called "6B10-E4" anti-CD123 antibody comprises:
a heavy chain variable domain consisting of sequence (SEQ ID NO: 240)
EVQLVESGGGLVQPGRSLKLSCAASGFTFSHYNMAWVRQAPKKGLEWVAT

ITYDDHSTYYRDSVKGRFTISRDTAKSTLYLQMDSLRSEDTATYYCARLV

NYAFAYWGQGTLVTVSS, with CDRs shown in bold characters) comprising CDR1-H of sequence SEQ ID NO: 241, a CDR2-H of sequence SEQ ID NO: 242, and a CDR3-H of sequence SEQ ID NO: 243 and
a light chain variable domain consisting of sequence (SEQ ID NO: 244)
NIVMTQSPKSMSISVGDRVTMNCKASQTVGNNIAWYQQKPGLSPQLLIDY

ASNRYTGVPNRFTGGGYGTDFILTINSVQAEDAAFYYCQRMYNSPTFGGG

TKLELK, with CDRs shown in bold characters) comprising CDR1-L of sequence SEQ ID NO: 245, a CDR2-L consisting of sequence 'YAS', and a CDR3-L of sequence SEQ ID NO: 246.

The so-called "6C10-C4" anti-CD123 antibody comprises:
a heavy chain variable domain consisting of sequence (SEQ ID NO: 247)
EVKLQESGPSLVQPSETLSLTCTVSGFSLTSYSVHWVRQHSGKSLEWMGR

MWNDGDTSYNSAFTSRLSISRDTSKGQVFLKMNSLQTEDTGTYYCARGHR

TPFDYWGQGVMVTVSS, with CDRs shown in bold characters) comprising CDR1-H of sequence SEQ ID NO: 248, a CDR2-H of sequence SEQ ID NO: 249, and a CDR3-H of sequence SEQ ID NO: 250 and
a light chain variable domain consisting of sequence (SEQ ID NO: 251)
DIVMTQSPSSLAVSAGETVTINCKSSQSFLSSGDERNYVAWYQHKPGQSP

KLLIYWASTRHSGVPDRFIGSGSGTDFTLTISSVQAEDLAIYYCQQYYDT

PLTFGSGTKLEIK, with CDRs shown in bold characters) comprising CDR1-L of sequence SEQ ID NO: 252, a CDR2-L consisting of sequence WAS', and a CDR3-L of sequence SEQ ID NO: 253.

The so-called "6D6-B8" anti-CD123 antibody comprises:
a heavy chain variable domain consisting of sequence (SEQ ID NO: 254)
QVQLQESGPTLVKPGDSVKMSCKASAYTFTDNIIHWVKQSHGKSLDWIGY

INPYSGGTNYNGWFRSKATLTVDKSSSTAYMEFSRLTSDDSAIYYCALNY

GSYYAMDAWGQGTSVTVSS, with CDRs shown in bold characters) comprising CDR1-H of sequence SEQ ID NO: 255, a CDR2-H of sequence SEQ ID NO: 200, and a CDR3-H of sequence SEQ ID NO: 201 and
a light chain variable domain consisting of sequence (SEQ ID NO: 256)
DIQMTQSPASLSASLGETVTIDCRPSEDIFNNLAWYQQKPGNSPQLLIYD

ANSLADGVPSRFSGSGSGTQYSLMIIRLQSEDVASYFCHQYNIYPYTFGA

GTKLELK, with CDRs shown in bold characters) comprising CDR1-L of sequence SEQ ID NO: 257, a CDR2-L consisting of sequence DAN', and a CDR3-L of sequence SEQ ID NO: 258.

The so-called "8611-137" anti-CD123 antibody comprises:
a heavy chain variable domain consisting of sequence (SEQ ID NO: 259)
QVQLQESGPTLVNPGDSVKMSCKASGYTFTDHIIHWVKQSHGKSLEWIGY

INPYSGGANYNGKFKSKATLTIDKSSSTAYMEFSRLTSGDSAIYYCALNY

GSYYAMDAWGQGTSVTVSS, with CDRs shown in bold characters) comprising CDR1-H of sequence SEQ ID NO: 199, a CDR2-H of sequence SEQ ID NO: 260, and a CDR3-H of sequence SEQ ID NO: 201 and
a light chain variable domain consisting of sequence (SEQ ID NO: 261)
DIQMTQSPASLSASLGETVTIECRTSKDIYSNLAWFQQEPGNSPQLLIYD

ASNLADGVPSRFSGSGSGTQYSLQINNLQSEDVASYFCHQYNNYPYTFGT

GTKLELK, with CDRs shown in bold characters) comprising CDR1-L of sequence SEQ ID NO: 262, a CDR2-L consisting of sequence 'DAS', and a CDR3-L of sequence SEQ ID NO: 263.

The so-called "9B8-G6" anti-CD123 antibody comprises:
a heavy chain variable domain consisting of sequence (SEQ ID NO: 264)
EVKLQESGPSLVQSSQTLSLTCTVSGFSLTSYHIHWVRQPPGKGLEWMGV

MWSDGDTSYSSALKSRLSISRDTSQSQVFLKMNSLQTEDTATYYCARGDY

SSYIYLWFAYWGQGTLVTVSS, with CDRs shown in bold characters) comprising CDR1-H of sequence SEQ ID NO: 265, a CDR2-H of sequence SEQ ID NO: 266, and a CDR3-H of sequence SEQ ID NO: 267 and
a light chain variable domain consisting of sequence (SEQ ID NO: 251)
DIVMTQSPSSLAVSAGETVTINCKSSQSFLSSGDERNYVAWYQHKPGQSP

KLLIYWASTRHSGVPDRFIGSGSGTDFTLTISSVQAEDLAIYYCQQYYDT

PLTFGSGTKLEIK, with CDRs shown in bold characters) comprising CDR1-L of sequence SEQ ID NO: 252, a CDR2-L consisting of sequence WAS', and a CDR3-L of sequence SEQ ID NO: 253.

The so-called "9D7-C8" anti-CD123 antibody comprises:
a heavy chain variable domain consisting of sequence (SEQ ID NO: 268)
EVKLQESGPSLVQSSQTLSLTCTVSGFSLTSYHIHWVRQTPGKGLEWMGV

MWSDGDTSYNSALKSRLSISRDTSQSQVFLKMNSLQTEDTATYYCARGYY

SSYLYLWFAYWGQGTLVTVSS, with CDRs shown in bold characters) comprising CDR1-H of sequence SEQ ID NO: 265, a CDR2-H of sequence SEQ ID NO: 266, and a CDR3-H of sequence SEQ ID NO: 269 and
a light chain variable domain consisting of sequence (SEQ ID NO: 270)
DIVMTQSPSSLAVSEGETVTINCKSSQSFLSSGDGKNYVAWYQYKPGQSP

KLLIYWASTRQSGVPDRFIGSGSGTDFTLTISTVQAEDLAIYYCQQYYDT

PLTFGSGTKLEIK, with CDRs shown in bold characters) comprising CDR1-L of sequence SEQ ID NO: 271, a CDR2-L consisting of sequence WAS', and a CDR3-L of sequence SEQ ID NO: 253.

The so-called "9F6-G3" anti-CD123 antibody comprises:
a heavy chain variable domain consisting of sequence (SEQ ID NO: 272)
QVQLQESGPTLVKPGDSVKMSCKASGYTFTDYIIHWVKQSHGKSLEWIGY

INPYSDGTNYNEKFKSKATLTVDKSTSTAYMEFSRLTSEDSAIYFCALNY

GSYYAMDAWGQGTSVTVSS, with CDRs shown in bold characters) comprising CDR1-H of sequence SEQ ID NO: 273, a CDR2-H of sequence SEQ ID NO: 274, and a CDR3-H of sequence SEQ ID NO: 201 and a light chain variable domain consisting of sequence (SEQ ID NO: 275)
DIQMTQSPASLSASLGETVTIECRPSEDIHSNVAWYQQKPGNSPQLLIYD

ASNLADGVPSRFSGSGSGTQYSLKINSLQSEDVASYFCHQYNIYPYTFGS

GTKLELK, with CDRs shown in bold characters) comprising CDR1-L of sequence SEQ ID NO: 276, a CDR2-L consisting of sequence DAS', and a CDR3-L of sequence SEQ ID NO: 258.

In one aspect of the invention, the anti-CD123 antibody binds to human CD123. In another embodiment, the anti-CD123 antibody further binds to Macaca fascicularis CD123. In particular, the anti-CD123 antibody of the invention binds to the extracellular domain of human CD123, or of both, human and Macaca fascicularis CD123. More specifically, the anti-CD123 antibody binds to the distal moiety of CD123, for example, to the amino acids at position 19 to 49 of human CD123 of the amino acid sequence SEQ ID NO: 194. The anti-CD123 antibody binds to CD123, indifferently whether expressed in isolated form, or present in a soluble extracellular domain or full-length membrane-anchored CD123 as present in CD123 expressing cells such as AML cells or CD123 transfected cells. The anti-CD123 antibody according to the invention is specific to cells that express human and Macaca fascicularis CD123 proteins on their surface, for example CD123 expressing cancer cells.

The anti-CD123 antibody according to the invention has a ratio of affinity for Macaca fascicularis CD123 on affinity for human CD123 (KD (Macaca fascicularis)/KD (human) which is ≤10, in particular or ≤6, ≤5, ≤4, ≤2, ≤1 or ≤0.5. Thus, the polypeptide according to the invention may be used in toxicological studies performed in monkeys the toxicity profile observed in monkeys relevant to anticipate potential adverse effects in humans.

In particular, the anti-CD123 antibody of the invention does not bind to, or does not significantly cross-react with CSF2RA and IL5RA proteins.

In particular, the antibody does not bind to, or does not significantly cross-react with the extracellular domain of the aforementioned human and Macaca fascicularis CSF2RA and IL5RA proteins.

Furthermore, the anti-CD123 antibody according to the invention has an affinity (KD) for human CD123 or Macaca fascicularis CD123, or both, of ≤50 nM, ≤40 nM, ≤30 nM for instance ≤20 nM, ≤15 nM, ≤10 nM, ≤8 nM, ≤6 nM, ≤4 nM, ≤2 nM, ≤1 nM or ≤0.5 nM, for instance an affinity of 0.1 nM to 20 nM, for example 0.1 nM to 10 nM, in particular of 0.1 nM to 2 nM, or of 0.1 nM to 1 nM.

In one example, affinity for human CD3 or for Macaca fascicularis CD3 is determined as the KD value with surface plasmon resonance using recombinant CD123 protein from human and Macaca fascicularis as capture antigen, for example with human and Macaca fascicularis CD123-Fc fusion protein.

As antigen may be used for example the human or Macaca fascicularis CD123 extracellular domain including the signal sequence corresponding to the amino acid sequence from position M1 to R305 of the wild type protein (SEQ ID NO: 194 (human), SEQ ID NO: 195 (Macaca fascicularis)). The resulting amino acid sequence for human or Macaca fascicularis CD123 mature protein is listed as SEQ ID NO: 196 and SEQ ID NO: 197, respectively. Biacore measurements are known to the skilled in the art. In the present example the Biacore measurement may be performed as described in the section "anti CD3 antibodies" above.

The anti-CD123 antibody of the invention may also have an apparent affinity constant (apparent KD), as, for example, determined by FACS analysis on CD123 expressing cells such as CD123 transfected HEK293 cells using non purified anti-CD123 antibody in hybridoma supernatant, which is 20 nM, for instance ≤15 nM, ≤10 nM, ≤6 nM, ≤5 nM, ≤3 nM, ≤2 nM or ≤1 nM. Typically, the apparent KD is within the range 0.1 to 20 nM, in particular 0.1 to 10 nM, for example 0.1 to 5 nM.

Alignments of the sequences of the VH and VL regions of the so-called "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", "9F6-G3" anti-CD123 antibodies. The comparison of the CDR-H and CDR-L sequences tends to indicate that, structurally, "1E1-G5", "6D6-B8", "8B11-B7" and "9F6-G3" anti-CD123 antibodies, on one hand, and "6C10-C4", 9B8-G6", "9D7-C8" anti-CD123 antibodies, on the other hand, are closely related, said antibodies probably binding to the same epitope. The alignment of the so-called "1E1-G5", "6D6-B8", "8B11-B7" and "9F6-G3" anti-CD123 antibodies and "6C10-C4", 9B8-G6", "9D7-C8" anti-CD123 antibodies are shown in FIGS. 3 and 4, respectively. The comparison of the CDR-H and CDR-L sequences further identifies CDR positions that are strictly conserved between the two groups of antibodies and which are thus assumed to be important for specificity, whereas other positions could support substitution.

Accordingly, the antibody according to the invention comprises:

a) a heavy chain variable domain comprising a CDR1-H consisting of sequence $X_1$YTFTDX$_2$I (SEQ ID NO: 336) wherein $X_1$ is G or A and $X_2$ is H, Y or N, or any combination thereof; and
a CDR2-H consisting of sequence INPYSX$_1$GX$_2$ (SEQ ID NO: 337) wherein $X_1$ is G or D and $X_2$ is T or A, or any combination thereof; and
a CDR3-H consisting of sequence ALNYGSYYAMDA (SEQ ID NO 201), and
a light chain variable domain comprising a CDR1-L consisting of sequence $X_1$DIX$_2$X$_3$N (SEQ ID NO: 338) wherein $X_1$ is E or K, $X_2$ is F, H or Y and $X_3$ is N or S, or any combination thereof; and
a CDR2-L consisting of sequence 'DAN' or 'DAS'; and
a CDR3-L consisting of sequence $X_1$QYNX$_2$YPYT (SEQ ID NO: 339) wherein $X_1$ is H or Q and $X_2$ is I, K or N, or any combination thereof; or b) a heavy chain variable domain comprising a CDR1-H consisting of sequence GFSLTSYX$_1$ (SEQ ID NO: 340) wherein $X_1$ is H or S; and
a CDR2-H consisting of sequence MWX$_1$DGDT (SEQ ID NO: 341) wherein $X_1$ is S or N; and
a CDR3-H consisting of sequence ARGX$_1$X$_2$X$_3$X$_4$X$_5$X$_6$X$_7$X$_8$X$_9$FX$_{10}$Y (SEQ ID NO: 342) wherein $X_1$ is D, Y or H, $X_2$ is Y or R, $X_3$ is S or T, $X_4$ is S or P, $X_5$ is Y or no amino acid, $X_6$ is L, I or no amino acid, $X_7$ is Y or no amino acid, $X_8$ is L or no amino acid, $X_9$ is W or no amino acid, $X_{10}$ is A or D, or any combination thereof, and
a light chain variable domain comprising a CDR1-L consisting of sequence QSFLSSGDX$_1$X$_2$NY (SEQ ID NO: 343) wherein $X_1$ is E or G and $X_2$ is R or K, or any combination thereof; and a CDR2-L consisting of sequence 'WAS'; and
a CDR3-L consisting of sequence QQYYDTPLT (SEQ ID NO: 253).

According to an embodiment, the anti-CD123 antibody according to the invention comprises the CDR sequences of the heavy and/or light chains of one of 13 so-called "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", and "9F6-G3" anti-CD123 antibodies listed above.

Therefore, the invention relates to an anti-CD123 antibody, which comprises:

a) a heavy chain variable domain comprising CDR1-H of sequence SEQ ID NO: 227 or a sequence differing from SEQ ID NO: 227 by one amino acid substitution; CDR2-H of sequence SEQ ID NO: 228 or SEQ ID NO: 353 or SEQ ID NO: 279 or a sequence differing from SEQ ID NO: 228 or SEQ ID NO: 353 or SEQ ID NO: 279 by one or more amino acid substitutions; CDR3-H of sequence SEQ ID NO: 229 or a sequence differing from SEQ ID NO: 229 by one amino acid substitution; and
a light chain variable domain comprising CDR1-L of sequence SEQ ID NO: 231 or a sequence differing from SEQ ID NO: 231 by one amino acid substitution; CDR2-L of sequence 'RDD' or a sequence differing from 'RDD' by one amino acid substitution and CDR3-L of sequence SEQ ID NO: 232 or a sequence differing from SEQ ID NO: 232 by one amino acid substitution; or b) a heavy chain variable domain comprising CDR1-H of sequence SEQ ID NO: 199 or a sequence differing from SEQ ID NO: 199 by one amino acid substitution; CDR2-H of sequence SEQ ID NO: 200 or a sequence differing from SEQ ID NO: 200 by one or more amino acid substitutions; CDR3-H of sequence SEQ ID NO: 201 or a sequence differing from SEQ ID NO: 201 by one amino acid substitution; and
a light chain variable domain comprising CDR1-L of sequence SEQ ID NO: 203 or a sequence differing from SEQ ID NO: 203 by one amino acid substitution; CDR2-L of sequence 'DAN' or a sequence differing from DAN' by one amino acid substitution and CDR3-L of sequence SEQ ID NO: 204 or a sequence differing from SEQ ID NO: 204 by one amino acid substitution; or c) a heavy chain variable domain comprising CDR1-H of sequence SEQ ID NO: 206 or a sequence differing from SEQ ID NO: 206 by one amino acid substitution; CDR2-H of sequence SEQ ID NO: 207 or a sequence differing from SEQ ID NO: 207 by one or more amino acid substitutions; CDR3-H of sequence SEQ ID NO: 208 or a sequence differing from SEQ ID NO: 208 by one amino acid substitution; and
a light chain variable domain comprising CDR1-L of sequence SEQ ID NO: 210 or a sequence differing from SEQ ID NO: 210 by one amino acid substitution; CDR2-L of sequence 'ETS' or a sequence differing from 'ETS' by one amino acid substitution and CDR3-L of sequence SEQ ID NO: 211 or a sequence differing from SEQ ID NO: 211 by one amino acid substitution; or d) a heavy chain variable domain comprising CDR1-H of sequence SEQ ID NO: 213 or a sequence differing from SEQ ID NO: 213 by one amino acid substitution; CDR2-H of sequence SEQ ID NO: 214 or a sequence differing from SEQ ID NO: 214 by one or more amino acid substitutions; CDR3-H of sequence SEQ ID NO: 215 or a sequence differing from SEQ ID NO: 215 by one amino acid substitution; and a light chain variable domain comprising CDR1-L of sequence SEQ ID NO: 217 or a sequence differing from SEQ ID NO: 217 by one amino acid substitution; CDR2-L of sequence 'NTN' or a sequence differing from 'NTN' by one amino acid substitution and CDR3-L of sequence SEQ ID NO: 218 or a sequence differing from SEQ ID NO: 218 by one amino acid substitution; or e) a heavy chain variable domain comprising CDR1-H of sequence SEQ ID NO: 220 or a sequence differing from SEQ ID NO: 220 by one amino acid substitution; CDR2-H of sequence SEQ ID NO: 221 or a sequence differing from SEQ ID NO: 221 by one or more amino acid substitutions; CDR3-H of sequence SEQ ID NO: 222 or a sequence differing from SEQ ID NO: 222 by one amino acid substitution; and a light chain variable domain comprising CDR1-L of sequence SEQ ID NO: 224 or a sequence differing from SEQ ID NO: 224 by one amino acid substitution; CDR2-L of sequence 'RVS' or a sequence differing from 'RVS' by one amino acid substitution and CDR3-L of sequence SEQ ID NO: 225 or a sequence differing from SEQ ID NO: 225 by one amino acid substitution; or f) a heavy chain variable domain comprising CDR1-H of sequence SEQ ID NO: 234 or a sequence differing from SEQ ID NO: 234 by one amino acid substitution; CDR2-H of sequence SEQ ID NO: 235 or a sequence differing from SEQ ID NO: 235 by one or more amino acid substitutions; CDR3-H of sequence SEQ ID NO: 236 or a sequence differing from SEQ ID NO: 236 by one amino acid substitution; and a light chain variable domain comprising CDR1-L of sequence SEQ ID NO: 238 or a sequence differing from SEQ ID NO: 238 by one amino acid substitution; CDR2-L of sequence 'GAS' or a sequence differing from 'GAS' by one amino acid substitution and CDR3-L of sequence SEQ ID NO: 239 or a sequence differing from SEQ ID NO: 239 by one amino acid substitution; or g) a heavy chain variable domain comprising CDR1-H of sequence SEQ ID NO: 241 or a sequence differing from SEQ ID NO: 241 by one amino acid substitution; CDR2-H of sequence SEQ ID NO: 242 or a sequence differing from SEQ ID NO: 242 by one or more amino acid substitutions; CDR3-H of sequence SEQ ID NO: 243 or a sequence differing from SEQ ID NO: 243 by one amino acid substitution; and a light chain variable domain comprising CDR1-L of sequence SEQ ID NO: 245 or a sequence differing from SEQ ID NO: 245 by one amino acid substitution; CDR2-L of sequence 'YAS' or a sequence differing from 'YAS' by one amino acid substitution and CDR3-L of sequence SEQ ID NO: 246 or a sequence differing from SEQ ID NO: 246 by one amino acid substitution; or h) a heavy chain variable domain comprising CDR1-H of sequence SEQ ID NO: 248 or a sequence differing from SEQ ID NO: 248 by one amino acid substitution; CDR2-H of sequence SEQ ID NO: 249 or a sequence differing from SEQ ID NO: 249 by one or more amino acid substitutions; CDR3-H of sequence SEQ ID NO: 250 or a sequence differing from SEQ ID NO: 250 by one amino acid substitution; and a light chain variable domain comprising CDR1-L of sequence SEQ ID NO: 252 or a sequence differing from SEQ ID NO: 252 by one amino acid substitution; CDR2-L of sequence WAS' or a sequence differing from WAS' by one amino acid substitution and CDR3-L of sequence SEQ ID NO: 253 or a sequence differing from SEQ ID NO: 253 by one amino acid substitution; or i) a heavy chain variable domain comprising CDR1-H of sequence SEQ ID NO: 255 or a sequence differing from SEQ ID NO: 255 by one amino acid substitution; CDR2-H of sequence SEQ ID NO: 200 or a sequence differing from SEQ ID NO: 200 by one or more amino acid substitutions; CDR3-H of sequence SEQ ID NO: 201 or a sequence differing from SEQ ID NO: 201 by one amino acid substitution; and a light chain variable domain comprising CDR1-L of sequence SEQ ID NO: 257 or a sequence differing from SEQ ID NO: 257 by one amino acid substitution; CDR2-L of sequence 'DAN' or a sequence differing from DAN' by one amino acid substitution and CDR3-L of sequence SEQ ID NO: 258 or a sequence differing from SEQ ID NO: 258 by one amino acid substitution; or j) a heavy chain variable domain comprising CDR1-H of sequence SEQ ID NO: 199 or a sequence differing from SEQ ID NO: 199 by one amino acid substitution; CDR2-H of sequence SEQ ID NO: 260 or a sequence differing from SEQ ID NO: 260 by one or more amino acid substitutions; CDR3-H of sequence SEQ ID NO: 201 or a sequence differing from SEQ ID NO: 201 by one amino acid substitution; and a light chain variable domain comprising CDR1-L of sequence SEQ ID NO: 262 or a sequence differing from SEQ ID NO: 262 by one amino acid substitution; CDR2-L of sequence 'DAS' or a sequence differing from 'DAS' by one amino acid substitution and CDR3-L of sequence SEQ ID NO: 263 or a sequence differing from SEQ ID NO: 263 by one amino acid substitution; or k) a heavy chain variable domain comprising CDR1-H of sequence SEQ ID NO: 265 or a sequence differing from SEQ ID NO: 265 by one amino acid substitution; CDR2-H of sequence SEQ ID NO: 266 or a sequence differing from SEQ ID NO: 266 by one or more amino acid substitutions; CDR3-H of sequence SEQ ID NO: 267 or a sequence differing from SEQ ID NO: 267 by one amino acid substitution; and a light chain variable domain comprising CDR1-L of sequence SEQ ID NO: 252 or a sequence differing from SEQ ID NO: 252 by one amino acid substitution; CDR2-L of sequence WAS' or a sequence differing from WAS' by one amino acid substitution and CDR3-L of sequence SEQ ID NO: 253 or a sequence differing from SEQ ID NO: 253 by one amino acid substitution; or l) a heavy chain variable domain comprising CDR1-H of sequence SEQ ID NO: 265 or a sequence differing from SEQ ID NO: 265 by one amino acid substitution; CDR2-H of sequence SEQ ID NO: 266 or a sequence differing from SEQ ID NO: 266 by one or more amino acid substitutions; CDR3-H of sequence SEQ ID NO: 269 or a sequence differing from SEQ ID NO: 269 by one amino acid substitution; and a light chain variable domain comprising CDR1-L of sequence SEQ ID NO: 271 or a sequence differing from SEQ ID NO: 271 by one amino acid substitution; CDR2-L of sequence WAS' or a sequence differing from WAS' by one amino acid substitution and CDR3-L of sequence SEQ ID NO: 253 or a sequence differing from SEQ ID NO: 253 by one amino acid substitution; or m) a heavy chain variable domain comprising CDR1-H of sequence SEQ ID NO: 273 or a sequence differing from SEQ ID NO: 273 by one amino acid substitution; CDR2-H of sequence SEQ ID NO: 274 or a sequence differing from SEQ ID NO: 274 by one or more amino acid substitutions; CDR3-H of sequence SEQ ID NO: 201 or a sequence differing from SEQ ID NO: 201 by one amino acid substitution; and a light chain variable domain comprising CDR1-L of sequence SEQ ID NO: 276 or a sequence differing from SEQ ID NO: 276 by one amino acid substitution; CDR2-L of sequence 'DAS' or a sequence differing from 'DAS' by one amino acid substitution and CDR3-L of sequence SEQ ID NO: 258 or a sequence differing from SEQ ID NO: 258 by one amino acid substitution.

One or more individual amino acids may be altered by substitution, in particular by conservative substitution, in one or more of the above CDR sequences. Such an alteration may be intended for example to remove a glycosylation site or a deamidation site, in connection with humanization of the antibody.

Based on the alignments of the sequences of the VH and VL regions of "1E1-G5", "6D6-B8", "8B11-B7", "9F6-G3" anti-CD123 antibodies different amino acid substitutions were identified. Therefore, in one embodiment, an amino acid may be substituted:

in CDR1-H at one or more of positions 1 and 7, for instance at position 7 of CDR1-H of sequence GYTFT-DHI (SEQ ID NO:199) or GYTFTDYI (SEQ ID NO:273) for instance at position 1 and 5 of CDR1-H of sequence AYTFTDNI (SEQ ID NO: 255); and/or in CDR2-H, at one or more of positions 6 and 8, for instance at positions 6 and/or 8 of CDR2-H of sequence INPYSGGT (SEQ ID NO: 200) or INPYSDGT (SEQ ID NO: 274) or INPYSGGA (SEQ ID NO: 260); and/or in CDR1-L, at one or more of positions 1, 4 and 5, for example at position 1 or 1, 4 and 5 of CDR1-L of sequence KDIYSN (SEQ ID NO: 262) or EDIFNN (SEQ ID NO: 257); and/or in CDR2-L, at positions 3 of sequence 'DAN' or 'DAS'; and/or in CDR3-L, at one or more of positions 1 and 5, for instance at position 1 and/or 5 of CDR3-L of sequence HQYNIYPYT (SEQ ID NO: 258) or QQYNKYPYT (SEQ ID NO: 204) or HQYNNYPYT (SEQ ID NO: 263).

In a further embodiment, an amino acid is substituted:

in CDR1-H at position 8, for instance at position 8 of CDR1-H of sequence GFSLTSYH (SEQ ID NO:265) or GFSLTSYS (SEQ ID NO: 248); and/or in CDR2-H at positions 3, for instance at positions 3 of CDR2-H of sequence MWSDGD (SEQ ID NO: 265) or MWNDGD (SEQ ID NO: 248); and/or in CDR3-H at positions 4 and 9, for instance at positions 4 and 9 of CDR3-H of sequence ARGDYSSYIYLW-FAY (SEQ ID NO: 267) or ARGYYSSYLYLWFAY (SEQ ID NO: 269); and/or in CDR1-L, at one or more of positions 9 and 10, for example at position 9 and 10 of CDR1-L of sequence QSFLSSGDERNY (SEQ ID NO: 252) or QSFLSSGDGKNY (SEQ ID NO: 271).

According to an embodiment, the antibody comprises a) a heavy chain variable domain comprising CDR1-H of sequence SEQ ID NO: 227, CDR2-H of sequence SEQ ID NO: 228, SEQ ID NO:353, SEQ ID NO:279, CDR3-H of sequence SEQ ID NO: 229, and
a light chain variable domain comprising CDR1-L of sequence SEQ ID NO: 231, CDR2-L of sequence 'RDD' and CDR3-L of sequence SEQ ID NO: 232; or n) a heavy chain variable domain comprising CDR1-H of sequence SEQ ID NO: 199, CDR2-H of sequence SEQ ID NO: 200, CDR3-H of sequence SEQ ID NO: 201, and
a light chain variable domain comprising CDR1-L of sequence SEQ ID NO: 203, CDR2-L of sequence 'DAN' and CDR3-L of sequence SEQ ID NO: 204; or o) a heavy chain variable domain comprising CDR1-H of sequence SEQ ID NO: 206, CDR2-H of sequence SEQ ID NO: 207, CDR3-H of sequence SEQ ID NO: 208, and
a light chain variable domain comprising CDR1-L of sequence SEQ ID NO: 210, CDR2-L of sequence 'ETS' and CDR3-L of sequence SEQ ID NO: 211; or p) a heavy chain variable domain comprising CDR1-H of sequence SEQ ID NO: 213, CDR2-H of sequence SEQ ID NO: 214, CDR3-H of sequence SEQ ID NO: 215, and
a light chain variable domain comprising CDR1-L of sequence SEQ ID NO: 217, CDR2-L of sequence 'NTN' and CDR3-L of sequence SEQ ID NO: 218; or q) a heavy chain variable domain comprising CDR1-H of sequence SEQ ID NO: 220, CDR2-H of sequence SEQ ID NO: 221, CDR3-H of sequence SEQ ID NO: 222, and
a light chain variable domain comprising CDR1-L of sequence SEQ ID NO: 224, CDR2-L of sequence 'RVS' and CDR3-L of sequence SEQ ID NO: 225; or r) a heavy chain variable domain comprising CDR1-H of sequence SEQ ID NO: 234, CDR2-H of sequence SEQ ID NO: 235, CDR3-H of sequence SEQ ID NO: 236, and
a light chain variable domain comprising CDR1-L of sequence SEQ ID NO: 238, CDR2-L of sequence 'GAS' and CDR3-L of sequence SEQ ID NO: 239; or s) a heavy chain variable domain comprising CDR1-H of sequence SEQ ID NO: 241, CDR2-H of sequence SEQ ID NO: 242, CDR3-H of sequence SEQ ID NO: 243, and
a light chain variable domain comprising CDR1-L of sequence SEQ ID NO: 245, CDR2-L of sequence 'YAS' and CDR3-L of sequence SEQ ID NO: 246; or t) a heavy chain variable domain comprising CDR1-H of sequence SEQ ID NO: 248, CDR2-H of sequence SEQ ID NO: 249, CDR3-H of sequence SEQ ID NO: 250, and
a light chain variable domain comprising CDR1-L of sequence SEQ ID NO: 252, CDR2-L of sequence WAS' and CDR3-L of sequence SEQ ID NO: 253; or u) a heavy chain variable domain comprising CDR1-H of sequence SEQ ID NO: 255, CDR2-H of sequence SEQ ID NO: 200, CDR3-H of sequence SEQ ID NO: 201, and a light chain variable domain comprising CDR1-L of sequence SEQ ID NO: 257, CDR2-L of sequence 'DAN' and CDR3-L of sequence SEQ ID NO: 258; or v) a heavy chain variable domain comprising CDR1-H of sequence SEQ ID NO: 199, CDR2-H of sequence SEQ ID NO: 260, CDR3-H of sequence SEQ ID NO: 201, and
a light chain variable domain comprising CDR1-L of sequence SEQ ID NO: 262, CDR2-L of sequence 'DAS' and CDR3-L of sequence SEQ ID NO: 263; or w) a heavy chain variable domain comprising CDR1-H of sequence SEQ ID NO: 265, CDR2-H of sequence SEQ ID NO: 266, CDR3-H of sequence SEQ ID NO: 267, and
a light chain variable domain comprising CDR1-L of sequence SEQ ID NO: 252, CDR2-L of sequence WAS' and CDR3-L of sequence SEQ ID NO: 253; or x) a heavy chain variable domain comprising CDR1-H of sequence SEQ ID NO: 265, CDR2-H of sequence SEQ ID NO: 266, CDR3-H of sequence SEQ ID NO: 269, and
a light chain variable domain comprising CDR1-L of sequence SEQ ID NO: 271, CDR2-L of sequence WAS' and CDR3-L of sequence SEQ ID NO: 253; or y) a heavy chain variable domain comprising CDR1-H of sequence SEQ ID NO: 273, CDR2-H of sequence SEQ ID NO: 274, CDR3-H of sequence SEQ ID NO: 201, and
a light chain variable domain comprising CDR1-L of sequence SEQ ID NO: 276, CDR2-L of sequence 'DAS' and CDR3-L of sequence SEQ ID NO: 258.

The anti-CD123 antibody according to the invention is in particular a conventional antibody, in particular a conventional monoclonal antibody, or an antibody fragment, a bispecific or multispecific antibody.

The anti-CD123 antibody according to the invention in particular comprises or consists of an IgG, or a fragment thereof.

The invention also provides an anti-CD123 antibody as defined above further comprising at least the heavy chain variable domain and/or the light chain variable domain of one of the so-called anti-CD123 antibodies listed above.

Thus, the invention relates in particular to an anti-CD123 antibody, which comprises:

a) a heavy chain variable domain of sequence SEQ ID NO: 226 or SEQ ID NO: 277 or SEQ ID NO: 278 or a sequence at least 85% identical thereto, and/or a light chain variable domain of sequence SEQ ID NO: 230, or a sequence at least 85% identical thereto; or b) a heavy chain variable domain of sequence SEQ ID NO: 198 or a sequence at least 85% identical thereto, and/or a light chain variable domain of sequence SEQ ID NO: 202, or a sequence at least 85% identical thereto; or c) a heavy chain variable domain of sequence SEQ ID NO: 205 or a sequence at least 85% identical thereto, and/or a light chain variable domain of sequence SEQ ID NO: 209, or a sequence at least 85% identical thereto; or d) a heavy chain variable domain of sequence SEQ ID NO: 212 or a sequence at least 85% identical thereto, and/or a light chain variable domain of sequence SEQ ID NO: 216, or a sequence at least 85% identical thereto; or e) a heavy chain variable domain of sequence SEQ ID NO: 219 or a sequence at least 85% identical thereto, and/or a light chain variable domain of sequence SEQ ID NO: 223, or a sequence at least 85% identical thereto; or f) a heavy chain variable domain of sequence SEQ ID NO: 233 or a sequence at least 85% identical thereto, and/or a light chain variable domain of sequence SEQ ID NO: 237, or a sequence at least 85% identical thereto; or g) a heavy chain variable domain of sequence SEQ ID NO: 240 or a sequence at least 85% identical thereto, and/or a light chain variable domain of sequence SEQ ID NO: 244, or a sequence at least 85% identical thereto; or h) a heavy chain variable domain of sequence SEQ ID NO: 247 or a sequence at least 85% identical thereto, and/or a light chain variable domain of sequence SEQ ID NO: 251, or a sequence at least 85% identical thereto; or i) a heavy chain variable domain of sequence SEQ ID NO: 254 or a sequence at least 85% identical thereto, and/or a light chain variable domain of sequence SEQ ID NO: 256, or a sequence at least 85% identical thereto; or j) a heavy chain variable domain of sequence SEQ ID NO: 259 or a sequence at least 85% identical thereto, and/or a light chain variable domain of sequence SEQ ID NO: 261, or a sequence at least 85% identical thereto; or k) a heavy chain variable domain of sequence SEQ ID NO: 264 or a sequence at least 85% identical thereto, and/or a light chain variable domain of sequence SEQ ID NO: 251, or a sequence at least 85% identical thereto; or l) a heavy chain variable domain of sequence SEQ ID NO: 268 or a sequence at least 85% identical thereto, and/or a light chain variable domain of sequence SEQ ID NO: 270, or a sequence at least 85% identical thereto; or m) a heavy chain variable domain of sequence SEQ ID NO: 272 or a sequence at least 85% identical thereto, and/or a light chain variable domain of sequence SEQ ID NO: 275, or a sequence at least 85% identical thereto.

For instance, the sequence of the variable domain of heavy or light chain may differ from the reference sequence SEQ ID NO: 226, 277, 278, 230, 198, 202, 205, 209, 212, 216, 219, 223, 233, 237, 240, 244, 247, 251, 254, 256, 259, 261, 264, 251, 268, 270, 272 or 275, as appropriate, by one or more amino acid substitution(s), in particular by one or more conservative amino acid substitution(s) and/or substitution(s) with canonical residues. In particular, the sequence of the variable domain of heavy or light chain may differ from the reference sequence SEQ ID NO: 226, 277, 278, 230, 198, 202, 205, 209, 212, 216, 219, 223, 233, 237, 240, 244, 247, 251, 254, 256, 259, 261, 264, 251, 268, 270, 272 or 275 by conservative amino acid substitution(s), only.

The sequence alterations as compared with sequence SEQ ID NO: 226, 277, 278, 230, 198, 202, 205, 209, 212, 216, 219, 223, 233, 237, 240, 244, 247, 251, 254, 256, 259, 261, 264, 251, 268, 270, 272 or 275 will in particular be present essentially in one or more of the framework regions, FR1-L, FR2-L, FR3-L, FR4-L and/or FR1-H, FR2-H, FR3-H, FR4-H.

In one embodiment, the anti-CD123 antibody of the invention and a fragment thereof is, respectively, a rat antibody and a fragment of a rat antibody.

The anti-CD123 antibody of the invention may also be a chimeric antibody, and in particular a rat/human antibody, e.g. an antibody comprising rat variable domains of heavy and light chains and a CH domain and a CL domain from a human antibody. The polypeptide may be a fragment of such an antibody. The anti-CD123 antibody may also be a humanized antibody or a fragment of a humanized antibody obtained by CDR-grafting or by the 4D method (US20110027266).

Accordingly, in one embodiment, the anti-CD123 antibody of the invention is a humanized antibody comprising:
a) a heavy chain variable domain comprising of an amino acid sequence selected from the group consisting of SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 301 and SEQ ID NO: 302; and
b) a light chain variable domain comprising of an amino acid sequence selected from the group consisting of SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 303, SEQ ID NO: 304 and SEQ ID NO: 305.

In one embodiment, the anti-CD123 antibody according to the invention comprises the three CDR sequences or the variable domain of the heavy chain, or the six CDR sequences or variable domains of the heavy and light chains of one of so-called anti-CD123 antibodies listed above.

The invention further refers to a fragment of the humanized anti-CD123 antibody as defined above. In one embodiment, the humanized anti-CD123 antibody described above is a chimeric antibody.

The anti-CD123 antibody according to the invention may also be a single domain antibody or a fragment thereof. In particular, a single domain antibody fragment may consist of a variable heavy chain (VHH) which comprises the CDR1-H, CDR2-H and CDR3-H of one of the antibodies described above. The CD123-antibody may also be a heavy chain antibody, i.e. an antibody devoid of light chain, which may or may not contain a CH1 domain.

The single domain antibody or a fragment thereof may also comprise the framework regions of a camelid single domain antibody, and optionally the constant domain of a camelid single domain antibody.

The anti-CD123 antibody according to the invention may also be an antibody fragment, in particular a humanized antibody fragment, selected from the group consisting of Fv, Fab, F(ab')2, Fab', dsFv, (dsFv)2, scFv, sc(Fv)2, and diabodies.

The CD123-antibody may also be a bispecific or multispecific antibody formed from at least one antibody fragment or at least one variable domains of the anti-CD123 antibody of the invention. Multispecific antibodies are polyvalent protein complexes as described for instance in EP 2 050 764 A1 or US 2005/0003403 A1.

The bispecific or multispecific CD123-antibodies according to the invention can have specificity for (a) extracellular domain of human or human and *Macaca fascicularis* CD123 targeted by one of the above described anti-CD123 antibodies and (b) at least one other antigen.

In a particular embodiment, the other antigen is CD3 and accordingly the resulting bispecific antibody is a CD3/CD123 bispecific antibody. Conventional bi-specific antibodies can be produced by techniques that are known to the skilled in the art.

Antibodies and fragments thereof according to the invention can be used in an isolated (e.g., purified) from or contained in a vector, such as a membrane or lipid vesicle (e.g. a liposome).

In one further embodiment, the anti-CD123 antibody of the invention is used for the preparation of antibody-like binding protein of the invention further defined in the section "antibody-like binding protein".

Any combination of the above embodiments makes part of the invention.

Antibody-Like Binding Proteins

The inventors have generated several antibody-like binding proteins the so called "7G3×20G6", "7G3×4E7", "7G3×4B4", "7G3×18F5", "hz20G6×7G3", "7G3×hz4B4", "hz4B4×3E3" "hz20G6×7G3-TL4" and "hz20G6×hz7G3" antibody-like binding proteins, wherein the term "hz" denotes humanized antibodies. These antibody-like binding proteins have a CODV design, in particular a CODV-Fab or CODV-Ig design.

The "CODV format" in context of the present invention refers to the cross-over dual variable (CODV) configuration of bispecific antibodies or multispecific antibodies. The CODV format allows a interchangeability of variable domains with retention of folding and ultimate binding affinity.

The CODV format has been previously described in the international patent application WO2012/135345. Accordingly, in one embodiment, the antibody-like binding protein of the invention is in the CODV format as previously described in the international patent application WO2012/135345, which is incorporated herein by reference.

In one embodiment, the invention refers to an antibody-like binding protein in the CODV-Fab format. Accordingly, in one embodiment, the invention refers to an antibody-like binding protein comprising two polypeptide chains that form two antigen-binding sites, wherein a first polypeptide has a structure represented by the formula [I]:

$$V_{D1}\text{-}L_1\text{-}V_{D2}\text{-}L_2\text{-}C_L \qquad [\text{I}]$$

and a second polypeptide has a structure represented by the formula [II]:

$$V_{D3}\text{-}L_3\text{-}V_{D4}\text{-}L_4\text{-}C_{H1} \qquad [\text{II}]$$

wherein:
$V_{D1}$ is a variable domain of heavy or light chain of a first immunoglobulin;
$V_{D2}$ is a variable domain of heavy or light chain of a second immunoglobulin;
$V_{D3}$ is a variable domain of heavy or light chain of said second immunoglobulin;
$V_{D4}$ is a variable domain of heavy or light chain of said first immunoglobulin;
$C_L$ is a light chain constant domain of an immunoglobulin;
$C_{H1}$ is a $C_{H1}$ heavy chain constant domain of an immunoglobulin;
$L_1$, $L_2$, $L_3$, and $L_4$ are amino acid linkers;
and wherein the first and the second polypeptide form a cross-over light chain-heavy chain pair, and
wherein $V_{D1}$ and $V_{D2}$ are both either variable domains of light chains, or variable domains of heavy chains, and $V_{D3}$ and $V_{D4}$ are both variable domains of heavy chains if $V_{D1}$ and $V_{D2}$ are variable domains of light chains, or $V_{D3}$ and $V_{D4}$ are both variable domains of light chains if $V_{D1}$ and $V_{D2}$ are variable domains of heavy chains.

Adding a Fc domain to the antibody-like binding protein in the CODV-Fab further stabilizes the antibody-like binding protein. More precisely, adding a Fc domain to the polypeptide of formula (II) of antibody-like binding protein in the CODV-Fab increases the half-life of the antibody-like binding protein and thus improves the pharmacokinetic profile of the antibody-like binding protein. Adding one Fc region to the CODV-Fab results in dimerization of polypeptides containing the Fc domain and the resulting antibody-like binding protein is an antibody-like binding protein in the CODV-Ig format. The invention therefore further refers to an antibody like binding protein in the CODV-Ig format.

Therefore, the invention further refers to an antibody-like binding protein comprising four polypeptide chains that form four antigen-binding sites, wherein two polypeptide chains have a structure represented by the formula [I]:

$$V_{D1}\text{-}L_1\text{-}V_{D2}\text{-}L_2\text{-}C_L \qquad [I]$$

and two polypeptide chains have a structure represented by the formula [III]:

$$V_{D3}\text{-}L_3\text{-}V_{D4}\text{-}L_4\text{-}C_{H1}\text{-}F_c \qquad [III]$$

wherein:
$V_{D1}$ is a variable domain of heavy or light chain of a first immunoglobulin;
$V_{D2}$ is a variable domain of heavy or light chain of a second immunoglobulin;
$V_{D3}$ is a variable domain of heavy or light chain of said second immunoglobulin;
$V_{D4}$ is a variable domain of heavy or light chain of said first immunoglobulin;
$C_L$ is a light chain constant domain of an immunoglobulin;
$C_{H1}$ is a $C_{H1}$ heavy chain constant domain of an immunoglobulin;
$F_c$ is the immunoglobulin hinge region and $CH_2$, $CH_3$ immunoglobulin heavy chain constant domains of an immunoglobulin;
$L_1$, $L_2$, $L_3$, and $L_4$ are amino acid linkers;
and wherein the polypeptides of formula I and the polypeptides of formula III form a cross-over light chain-heavy chain pair, and
wherein $V_{D1}$ and $V_{D2}$ are both either variable domains of light chains, or variable domains of heavy chains, and $V_{D3}$ and $V_{D4}$ are both variable domains of heavy chains if $V_{D1}$ and $V_{D2}$ are variable domains of light chains, or $V_{D3}$ and $V_{D4}$ are both variable domains of light chains if $V_{D1}$ and $V_{D2}$ are variable domains of heavy chains.

In said CODV-Ig format, the two polypeptide chains having a structure represented by the formula [III] dimerize through their $F_c$ domains.

In a further embodiment, a first $F_c$ domain is added to the polypeptide of formula [II] of antibody-like binding protein CODV-Fab, and a second $F_c$ domain (called $F_a$) is added to the polypeptide of formula [I] of the antibody-like binding protein CODV-Fab. Furthermore, in the same embodiment a linker $L_5$ is present between $C_L$ and the $F_a$ domain of the polypeptide chains of formula [I] resulting in the polypeptide chains of formula [IV].

Accordingly, the invention further refers to an antibody-like binding protein comprising two polypeptide chains that form two antigen-binding sites, wherein one polypeptide chain has a structure represented by the formula [IV]:

$$V_{D1}\text{-}L_1\text{-}V_{D2}\text{-}L_2\text{-}C_L\text{-}L_5\text{-}F_{c2} \qquad [IV]$$

and one polypeptide chain has a structure represented by the formula [III]:

$$V_{D3}\text{-}L_3\text{-}V_{D4}\text{-}L_4\text{-}C_{H1}\text{-}F_c \qquad [III]$$

wherein:
$V_{D1}$ is a variable domain of heavy or light chain of a first immunoglobulin;
$V_{D2}$ is a variable domain of heavy or light chain of a second immunoglobulin;
$V_{D3}$ is a variable domain of heavy or light chain of said second immunoglobulin;
$V_{D4}$ is a variable domain of heavy or light chain of said first immunoglobulin;
$C_L$ is a light chain constant domain of an immunoglobulin;
$C_{H1}$ is a $C_{H1}$ heavy chain constant domain of an immunoglobulin;
$F_c$ is the immunoglobulin hinge region and $CH_2$, $CH_3$ immunoglobulin heavy chain constant domains of an immunoglobulin;
$F_{c2}$ is the immunoglobulin hinge region and $CH_2$, $CH_3$ immunoglobulin heavy chain constant domains of an immunoglobulin;
$L_1$, $L_2$, $L_3$, $L_4$ and $L_5$ are amino acid linkers;
and wherein the polypeptide of formula [IV] and the polypeptide of formula [III] form a cross-over light chain-heavy chain pair, and
wherein $V_{D1}$ and $V_{D2}$ are both either variable domains of light chains, or variable domains of heavy chains, and $V_{D3}$ and $V_{D4}$ are both variable domains of heavy chains if $V_{D1}$ and $V_{D2}$ are variable domains of light chains, or $V_{D3}$ and $V_{D4}$ are both variable domains of light chains if $V_{D1}$ and $V_{D2}$ are variable domains of heavy chains.

This CODV format, in which the polypeptide chains represented by the formulae [III] and [IV] dimerize through their respective $F_{c2}$ and $F_c$ regions, is herein called CODV-Fab-TL.

In another embodiment of the CODV-Fab, a first $F_c$ domain is added to the polypeptide chain represented by formula [II] (resulting in formula and the antibody-like binding protein comprise a third polypeptide chain comprising, or consisting of a second $F_c$ domain (called $F_{c3}$).

The invention further refers to an antibody-like binding protein which comprises three polypeptide chains that form two antigen-binding sites, wherein
a first polypeptide has a structure represented by the formula [I]:

$$V_{D1}\text{-}L_1\text{-}V_{D2}\text{-}L_2\text{-}C_L \qquad [I]$$

a second polypeptide has a structure represented by the formula [III]:

$$V_{D3}\text{-}L_3\text{-}V_{D4}\text{-}L_4\text{-}C_{H1}\text{-}F_c \qquad [III]$$

a third polypeptide $F_3$ (also called Fc stump") which is the immunoglobulin hinge region and $CH_2$, $CH_3$ immunoglobulin heavy chain constant domains of an immunoglobulin;
wherein
$V_{D1}$ is a variable domain of heavy or light chain of a first immunoglobulin;
$V_{D2}$ is a variable domain of heavy or light chain of a second immunoglobulin;
$V_{D3}$ is a variable domain of heavy or light chain of said second immunoglobulin;
$V_{D4}$ is a variable domain of heavy or light chain of said first immunoglobulin;
$C_L$ is a light chain constant domain of an immunoglobulin;
$C_{H1}$ is a $C_{H1}$ heavy chain constant domain of an immunoglobulin;

$F_c$ is the immunoglobulin hinge region and $CH_2$, $CH_3$ immunoglobulin heavy chain constant domains of an immunoglobulin;

$L_1$, $L_2$, $L_3$, and $L_4$ are amino acid linkers;

and wherein the polypeptide of formula [I] and the polypeptide of formula [III] form a cross-over light chain-heavy chain pair, and wherein $V_{D1}$ and $V_{D2}$ are both either variable domains of light chains, or variable domains of heavy chains, and $V_{D3}$ and $V_{D4}$ are both variable domains of heavy chains if $V_{D1}$ and $V_{D2}$ are variable domains of light chains, or $V_{D3}$ and $V_{D4}$ are both variable domains of light chains if $V_{D1}$ and $V_{D2}$ are variable domains of heavy chains;

and wherein the polypeptide of formula [III] heterodimerizes with the third polypeptide through its $F_c$ domain.

Accordingly, in said embodiment, the so-called "Fc stump" ($F_{c3}$) heterodimerizes with the Fc region of the polypeptide according to formula III. This CODV format is herein called CODV-Fab-OL. This construct avoids that the CODV-Fab form aggregates.

In one embodiment of the CODV-Fab-OL, both $F_c$ and $F_{c3}$ are immunoglobulin variants in which the CH3 domain has been modified: each of $F_c$ and $F_{c3}$ has been genetically engineered at the CH3-CH3 interface to promote heteromultimer formation according to the so-called "Knob-into-Hole" technology which has been described in U.S. Pat. Nos. 5,731,168 and 8,216,805, notably, and which are herein incorporated by reference.

Accordingly, in an embodiment the CH3 domain of one of $F_c$ and $F_{c3}$ contains the mutations Y349C, T366S, L368A, and Y407V, while the CH3 domain of the other of $F_c$ and $F_{c3}$ contains the mutations S354C and T366W (amino acid position being indicated by reference to an IgG1 sequence).

Examples of suitable $F_c$ and $F_{c3}$ pairs include the pair SEQ ID NO: 396 ($F_c$) and SEQ ID NO: 397 ($F_{c3}$), and the pair SEQ ID NO: 394 ($F_c$) and SEQ ID NO: 398 ($F_{c3}$).

In one embodiment of the invention, the first immunoglobulin or the second immunoglobulin is one anti-CD3 antibody as defined in the section «anti-CD3 antibodies» above.

In another embodiment of the invention, the first immunoglobulin or the second immunoglobulin is one anti-CD123 antibody as defined in the section «anti-CD123 antibodies» above.

According to one embodiment of the invention, $V_{D1}$ and $V_{D2}$ of polypeptide of formula I or formula [IV] are both either variable domains of light chains, or variable domains of heavy chains, and $V_{D3}$ and $V_{D4}$ of polypeptide II or III are both variable domains of heavy chains or of light chains. This interchangeability is also referred to as "swapability" and thus determines the cross-over dual variable (CODV) configuration of the antibody-like binding proteins of the invention.

According to the above definition, $V_{D1}$ and $V_{D4}$ are variable domains of heavy or light chain of a first immunoglobulin and $V_{D2}$ and $V_{D3}$ are variable domains of heavy or light chain of a second immunoglobulin, $V_{D1}$ and $V_{D4}$ are therefore to be considered as cognate domains as well as $V_{D2}$ and $V_{D3}$.

Accordingly, the term "cross-over" refers to the swapped alignment of $V_{D1}$ or $V_{D2}$ of polypeptide of formula [I] or formula [IV] with respect to its cognate variable domain $V_{D4}$ or $V_{D3}$ of polypeptide of formula [II] or formula [III].

In one particular embodiment, $V_{D1}$ and $V_{D2}$ are light chain variable domains and $V_{D3}$ and $V_{D4}$ are heavy chain variable domains.

The antibody-like binding proteins of the invention may be prepared using domains or sequences obtained or derived from any human or non-human antibody, including, for example, human, rat, or humanized antibodies.

In one embodiment, the immunoglobulin is an IgG immunoglobulin.

Accordingly, in one embodiment, $C_L$ is a light chain constant domain of an IgG immunoglobulin. In a further embodiment, $C_{H1}$ is a $C_{H1}$ heavy chain constant domain of an IgG immunoglobulin.

In one embodiment, the antibody-like binding protein of the invention may be prepared using domains or sequences of the anti-CD3 antibody and anti-CD123 antibody herein described.

The term "linker" as used herein refers to one or more amino acid residues inserted between immunoglobulin domains to provide sufficient mobility for the domains of the light and heavy chains to fold into cross over dual variable region immunoglobulins. In some embodiments, a linker consists of 0 amino acid meaning that the linker is absent. A linker is inserted at the transition between variable domains or between variable and constant domains, respectively, at the sequence level. The transition between domains can be identified because the approximate size of the immunoglobulin domains is well understood. The precise location of a domain transition can be determined by locating peptide stretches that do not form secondary structural elements such as beta-sheets or alpha-helices as demonstrated by experimental data or as can be assumed by techniques of modeling or secondary structure prediction. The linkers described in context of the invention are the linkers $L_1$, $L_2$, $L_3$, $L_4$ and $L_5$. $L_1$ is located between the N-terminal $V_{D1}$ domain and the $V_{D2}$ domain; $L_2$ is located between the $V_{D2}$ and the C-terminal $C_L$ domain. The linkers $L_3$ and $L_4$ are located on polypeptide as defined according to formula II or III of the antibody-like-proteins. More precisely, $L_3$ is located between the N-terminal $V_{D3}$ and the $V_{D4}$ domains and $L_4$ is located between the $V_{D4}$ and the C-terminal $C_{H1}$-Fc domains. $L_5$ is located between $C_L$ and the N-terminal $F_{c2}$. The linkers $L_1$, $L_2$, $L_3$, $L_4$ and $L_5$ are independent, but in some embodiments, they have the same sequence and/or length.

In some antibody-like binding proteins of the invention, the length of $L_3$ is at least twice the length of L. In other antibody-like binding proteins of the invention, the length of $L_4$ is at least twice the length of $L_2$. In some antibody-like binding proteins of the invention, the length of $L_1$ is at least twice the length of $L_3$. In other antibody-like binding proteins of the invention, the length of $L_2$ is at least twice the length of $L_4$.

In one embodiment, the linker $L_1$, $L_2$, $L_3$ and $L_4$ comprise 0 to 20 amino acids. In one embodiment, $L_5$ comprises 0 to 10 amino acids.

In some antibody-like binding proteins of the invention, $L_1$ is 3 to 12 amino acid residues in length, $L_2$ is 3 to 14 amino acid residues in length, $L_3$ is 1 to 8 amino acid residues in length, and $L_4$ is 1 to 3 amino acid residues in length. In other antibody-like binding proteins, $L_1$ is 5 to 10 amino acid residues in length, $L_2$ is 5 to 8 amino acid residues in length, $L_3$ is 1 to 5 amino acid residues in length, and $L_4$ is 1 to 2 amino acid residues in length. In a preferred antibody-like binding protein, $L_1$ is 7 amino acid residues in length, $L_2$ is 5 amino acid residues in length, $L_3$ is 1 amino acid residues in length, and $L_4$ is 2 amino acid residues in length.

In some antibody-like binding proteins of the invention, $L_1$ is 1 to 3 amino acid residues in length, $L_2$ is 1 to 4 amino acid residues in length, $L_3$ is 2 to 15 amino acid residues in length, and $L_4$ is 2 to 15 amino acid residues in length. In other antibody-like binding proteins, Li is 1 to 2 amino acid residues in length, $L_2$ is 1 to 2 amino acid residues in length, $L_3$ is 4 to 12 amino acid residues in length, and $L_4$ is 2 to 12 amino acid residues in length. In a preferred antibody-like binding protein, $L_1$ is 1 amino acid residue in length, $L_2$ is 2 amino acid residues in length, $L_3$ is 7 amino acid residues in length, and $L_4$ is 5 amino acid residues in length.

In some antibody-like binding proteins of the invention, $L_1$, $L_3$, or $L_4$ may be equal to zero. However, in antibody-like binding proteins wherein $L_3$, or $L_4$ is equal to zero, the corresponding transition linker between the variable region and constant region or between the dual variable domains on the other chain cannot be zero. In some embodiments, $L_1$ is equal to zero and $L_3$ is 2 or more amino acid residues, $L_3$ is equal to zero and $L_1$ is equal to 1 or more amino acid residues, or $L_4$ is equal to 0 and $L_2$ is 3 or more amino acid residues.

In some antibody-like binding proteins of the invention, at least one of the linkers selected from the group consisting of $L_2$, $L_3$, and $L_4$ contains at least one cysteine residue.

Examples of suitable linkers include a single glycine, threonine or serine residue; a dipeptide such as a diglycine peptide, histidine-threonine peptide or glycine-serine dipeptide; a tripeptide with three glycines, the tripeptide Thr-His-Thr, the tripeptide Gly-Gly-Ser; a peptide with four glycine residues; a peptide with five glycine residues; a peptide with six glycine residues; a peptide with seven glycine residues; a peptide with eight glycine residues. Other combinations of amino acid residues may be used such as the peptide Gly-Gly-Gly-Ser (SEQ ID NO: 354), the peptide Gly-Gly-Gly-Gly-Ser (SEQ ID NO: 344), the peptide Ser-Gly-Gly-Gly-Gly-Ser (SEQ ID NO: 355), the peptide Gly-Ser-Gly-Gly-Gly-Gly-Ser (SEQ ID NO: 356), the peptide Gly-Gly-Ser-Gly-Gly-Gly-Gly-Ser (SEQ ID NO: 357), the peptide Gly-Gly-Gly-Ser-Gly-Gly-Gly-Gly-Ser (SEQ ID NO: 358), and the peptide Gly-Gly-Gly-Gly-Ser-Gly-Gly-Gly-Gly-Ser (SEQ ID NO: 345). Other suitable linkers include a single Ser, and Val residue; the dipeptide Arg-Thr, Gln-Pro, Ser-Ser, Thr-Lys, and Ser-Leu; Lys-Thr-His-Thr (SEQ ID NO: 359); Lys-Thr-His-Thr-Ser (SEQ ID NO: 360); Asp-Lys-Thr-His-Thr-Ser (SEQ ID NO: 361); Asp-Lys-Thr-His-Thr-Ser-Pro (SEQ ID NO: 362); Ser-Asp-Lys-Thr-His-Thr-Ser-Pro (SEQ ID NO: 363); Ser-Asp-Lys-Thr-His-Thr-Ser-Pro-Pro (SEQ ID NO: 364); Lys-Ser-Asp-Lys-Thr-His-Thr-Ser-Pro-Pro-Ser (SEQ ID NO: 365); Pro-Lys-Ser-Asp-Lys-Thr-His-Thr-Ser-Pro-Pro-Ser (SEQ ID NO: 366); Pro-Lys-Ser-Asp-Lys-Thr-His-Thr-Ser-Pro-Pro-Ser-Pro (SEQ ID NO: 367); Glu-Pro-Lys-Ser-Asp-Lys-Thr-His-Thr-Ser-Pro-Pro-Ser-Pro (SEQ ID NO: 368); Glu-Pro-Lys-Ser-Asp-Lys-Thr-His-Thr-Ser-Pro-Pro-Ser-Pro-Gly (SEQ ID NO: 369); Gly-Glu-Pro-Lys-Ser-Asp-Lys-Thr-His-Thr-Ser-Pro-Pro-Ser-Pro-Gly (SEQ ID NO: 370); Gly-Glu-Pro-Lys-Ser-Asp-Lys-Thr-His-Thr-Ser-Pro-Pro-Ser-Pro-Gly-Gly (SEQ ID NO: 371); Gly-Gly-Glu-Pro-Lys-Ser-Asp-Lys-Thr-His-Thr-Ser-Pro-Pro-Ser-Pro-Gly-Gly (SEQ ID NO: 372); Gly-Gly-Gly-Glu-Pro-Lys-Ser-Asp-Lys-Thr-His-Thr-Ser-Pro-Pro-Ser-Pro-Gly-Gly (SEQ ID NO: 373); Gly-Gly-Gly-Glu-Pro-Lys-Ser-Asp-Lys-Thr-His-Thr-Ser-Pro-Pro-Ser-Pro-Gly-Gly-Gly (SEQ ID NO: 374); Thr-Val-Ala-Ala-Pro (SEQ ID NO: 346), Gln-Pro-Lys-Ala-Ala (SEQ ID NO: 347), Gln-Arg-Ile-Glu-Gly (SEQ ID NO: 348); Ala-Ser-Thr-Lys-Gly-Pro-Ser (SEQ ID NO: 349), Arg-Thr-Val-Ala-Ala-Pro-Ser (SEQ ID NO: 350), Gly-Gln-Pro-Lys-Ala-Ala-Pro (SEQ ID NO: 307), Thr-Lys-Gly-Pro-Ser (SEQ ID NO: 309), His-Ile-Asp-Ser-Pro-Asn-Lys (SEQ ID NO: 351), and Gly-Gly-Ser-Gly-Ser-Ser-Gly-Ser-Gly-Gly (SEQ ID NO: 389). The examples listed above are not intended to limit the scope of the invention in any way, and linkers comprising randomly selected amino acids selected from the group consisting of valine, leucine, isoleucine, serine, threonine, lysine, arginine, histidine, aspartate, glutamate, asparagine, glutamine, glycine, and proline have been shown to be suitable in the antibody-like binding proteins of the invention.

The identity and sequence of amino acid residues in the linker may vary depending on the type of secondary structural element necessary to achieve in the linker. For example, glycine, serine, and alanine are best for linkers having maximum flexibility. Some combination of glycine, proline, threonine, and serine are useful if a more rigid and extended linker is necessary. Any amino acid residue may be considered as a linker in combination with other amino acid residues to construct larger peptide linkers as necessary depending on the desired properties.

In one embodiment, the linker $L_1$ is of sequence Gly-Gln-Pro-Lys-Ala-Ala-Pro (SEQ ID NO: 307), the linker $L_2$ is of sequence Thr-Lys-Gly-Pro-Ser (SEQ ID NO: 309), the linker $L_3$ is of sequence 'S' and the linker $L_4$ is of sequence 'RT'.

In a further embodiment, the sequences of linkers $L_1$, $L_2$, $L_3$, and $L_4$ are selected from the group consisting of threonine; a dipeptide such as a histidine-threonine peptide; the tripeptide Thr-His-Thr, Lys-Thr-His-Thr (SEQ ID NO: 359); Lys-Thr-His-Thr-Ser (SEQ ID NO: 360); Asp-Lys-Thr-His-Thr-Ser (SEQ ID NO: 361); Asp-Lys-Thr-His-Thr-Ser-Pro (SEQ ID NO: 362); Ser-Asp-Lys-Thr-His-Thr-Ser-Pro (SEQ ID NO: 363); Ser-Asp-Lys-Thr-His-Thr-Ser-Pro-Pro (SEQ ID NO: 364); Lys-Ser-Asp-Lys-Thr-His-Thr-Ser-Pro-Pro-Ser (SEQ ID NO: 365); Pro-Lys-Ser-Asp-Lys-Thr-His-Thr-Ser-Pro-Pro-Ser (SEQ ID NO: 366); Pro-Lys-Ser-Asp-Lys-Thr-His-Thr-Ser-Pro-Pro-Ser-Pro (SEQ ID NO: 367); Glu-Pro-Lys-Ser-Asp-Lys-Thr-His-Thr-Ser-Pro-Pro-Ser-Pro (SEQ ID NO: 368); Glu-Pro-Lys-Ser-Asp-Lys-Thr-His-Thr-Ser-Pro-Pro-Ser-Pro-Gly (SEQ ID NO: 369); Gly-Glu-Pro-Lys-Ser-Asp-Lys-Thr-His-Thr-Ser-Pro-Pro-Ser-Pro-Gly (SEQ ID NO: 370); Gly-Glu-Pro-Lys-Ser-Asp-Lys-Thr-His-Thr-Ser-Pro-Pro-Ser-Pro-Gly-Gly (SEQ ID NO: 371); Gly-Gly-Glu-Pro-Lys-Ser-Asp-Lys-Thr-His-Thr-Ser-Pro-Pro-Ser-Pro-Gly-Gly (SEQ ID NO: 372); Gly-Gly-Glu-Pro-Lys-Ser-Asp-Lys-Thr-His-Thr-Ser-Pro-Pro-Ser-Pro-Gly-Gly (SEQ ID NO: 373) and Gly-Gly-Gly-Glu-Pro-Lys-Ser-Asp-Lys-Thr-His-Thr-Ser-Pro-Pro-Ser-Pro-Gly-Gly-Gly (SEQ ID NO: 374), In one embodiment the sequence of linker $L_5$ is selected from the group consisting of a single serine residue, a dipeptide such as a glycine-serine dipeptide; a tripeptide Gly-Gly-Ser, the peptide Gly-Gly-Gly-Ser (SEQ ID NO: 354), the peptide Gly-Gly-Gly-Gly-Ser (SEQ ID NO: 344), the peptide Ser-Gly-Gly-Gly-Gly-Ser (SEQ ID NO: 355), the peptide Gly-Ser-Gly-Gly-Gly-Gly-Ser (SEQ ID NO: 356), the peptide Gly-Gly-Ser-Gly-Gly-Gly-Gly-Ser (SEQ ID NO: 357), the peptide Gly-Gly-Gly-Ser-Gly-Gly-Gly-Gly-Ser (SEQ ID NO: 358), the peptide Gly-Gly-Gly-Gly-Ser-Gly-Gly-Gly-Gly-Ser (SEQ ID NO: 345), and the peptide Gly-Gly-Ser-Gly-Ser-Ser-Gly-Ser-Gly-Gly (SEQ ID NO: 389).

The term "Fc domain" as used herein encompasses native Fc and Fc variants and sequences as defined above. As with Fc variants and native Fc molecules, the term "Fc domain" includes molecules in monomeric or multimeric form, whether digested from whole antibody or produced by other means.

The term "native Fc" as used herein refers to a molecule comprising the sequence of a non-antigen-binding fragment resulting from digestion of an antibody or produced by other means, whether in monomeric or multimeric form, and can contain the hinge region. The original immunoglobulin source of the native Fc is, in particular, of human origin and can be any of the immunoglobulins, although IgGl and IgG2 are preferred. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgGl, IgG2, IgG3, IgAl, and IgA2). One example of a native Fc is a disulfide-bonded dimer resulting from papain digestion of an IgG. The term "native Fc" as used herein is generic to the monomeric, dimeric, and multimeric forms.

The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc. Furthermore, a native Fc comprises regions that can be removed because they provide structural features or biological activity that are not required for the antibody-like binding proteins of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

In some embodiments, when the antibody like binding protein contains two $F_c$ domains, i.e. in the CODV-Ig ($F_c$ and $F_{c2}$), CODV-Fab-TL (two $F_c$ domains), and CODV-Fab-OL ($F_c$ and $F_{c3}$), the two $F_c$ domains are of the same immunoglobulin isotype or isotype subclass. Accordingly, in some embodiments both $F_c$ and $F_{c2}$ of CODV-Ig, or both $F_c$ domains of CODV-Fab-TL, or both $F_c$ and $F_3$ of CODV-Fab-OL are of the IgG1 subclass, or of the IgG2 subclass, or of the IgG3 subclass, or of the IgG4 subclass.

All antibody like binding proteins as described herein have no effector function. This means that when the antibody like binding protein contains one or more $F_c$ domain(s) (i.e. $F_c$ in formula [III], $F_{c2}$ in formula [IV][and/or $F_{c3}$) of the IgG1 subclass, said on or more $F_c$ domain(s) of IgG1 backbone contain(s) a double mutation L234A and L235A (so-called "LALA mutation") which abolishes Fc effector function. The Fc double mutant L234A and L235A does not bind FcγR or C1q, and both ADCC and CDC functions of the Fc domain of IgG1 subclass are abolished (Hezareh, M. et al., J Virol. 2001 December; 75(24): 12161-12168).

In one example, the $F_c$ region comprises the amino acid sequence SEQ ID NO: 330, SEQ ID NO: 394, or SEQ ID NO: 396. In one embodiment, the $F_{c2}$ region comprises two amino acid exchanges within the CH3 domain H435R and Y436F, as described in Jendeberg, L. et al. (1997, J. Immunological Meth. 201: 25-34). Accordingly, in one embodiment the $F_{c2}$ region comprises the amino acid sequence SEQ ID NO: 327. In another embodiment, the $F_{c2}$ region comprises the amino acid sequence SEQ ID NO: 392.

The so-called CODV-Fab "7G3×20G6" antibody-like binding protein comprises:

one polypeptide according to formula I of the amino acid sequence DVVMTQTPVSLSVSLGGQVSIS-CRSSQSLVHNNGN-TYLSWYLQKPGQSPQSLIYKVSN RFSGFS-DRFSGSGSGTDFTLKISRVDPDDLGVYY CGQGTQYPFTFGSGTKLEIK GQPKAAPDFVMTQSPSSLTVTAGEKVTM SCK-SSQSLLNSGNQKNYLTWYLQKPGQPPKLLIY WASTRESGVPDRFTGSGSGTDFTLTISSVQAED-LAVYYCQNDYSYPYTFGGGTKLEIK TKGPSRTVAAPSVFIFPPSDEQLKSGTASVVCL LNNFYPREAKVQWKVDNALQSGNS QESVTE-QDSKDSTYSLSSTLTLSKADYEKHKVYACE-VTHQGLSSPVTKSFNRGEC (SEQ ID NO: 306, linkers are indicated in bold and underlined) comprising $V_{D1}$ of sequence SEQ ID NO: 9, $L_1$ of sequence SEQ ID NO: 307, $V_{D2}$ of sequence SEQ ID NO: 308, $L_2$ of sequence SEQ ID NO: 309 and $C_L$ of sequence SEQ ID NO: 310, and one polypeptide according to formula II of the amino acid sequence EVQLQQSGPELVKPGASVKMSCK-ASGYTFTDYYMKWVKQSHGKSLEWIG-DIIPSNGA TFYNQKFKGKATLTVDRSSSTAYMHLNSLTSED-SAVYYCTRSHLLRASWFAYWGQGT LVTVSA SEVQLVETGGSLVQPGKSLKLTCATSGFTFTK AWMHWVRQSPEKQLEWVAQ IKDKSNSYATYY-AESVKGRFTISRDDSKSTIYLQMNSLKEED-TAIYYCRGVYYYALSPFDY WGQGVMVTVSS RTASTKGPSVFPLAPSSKSTSGGTAALGCLV KDYFPEPVTVSWNSG ALTSGVHTFPAVLQSSG-LYS-LSSVVTVPSSSLGTQTYICNVNHKPSNTKVDKKV (SEQ ID NO: 311, linkers are indicated in bold and underlined) comprising $V_{D3}$ of sequence SEQ ID NO: 312, $L_3$ of the amino acid sequence 'S', $V_{D4}$ of sequence SEQ ID NO: 5, $L_4$ of the amino acid sequence 'RT' and $C_{H1}$ of sequence SEQ ID NO: 313.

The so-called CODV-Fab "7G3×4E7" antibody-like binding protein comprises:

one polypeptide according to formula I of the amino acid sequence DVVMTQTPVSLSVSLGGQVSIS-CRSSQSLEHNNGN-TYLSWYLQKPGQSPQPLIYKVSN RFSGIS-DRFSGSGSGTDFTLKISRVEPDDLGVYYCG QGTQYPFTFGPGTKLELK GQPKAAPDFVMTQSPSSLTVTAGEKVTMSC KSSQSLLNSGNQKNYLTWYLQKPGQPPKLLIY WASTRESGVPDRFTGSGSGTDFTLTISSVQAED-LAVYYCQNDYSYPYTFGGGTKLEIK TKGPSRTVAAPSVFIFPPSDEQLKSGTASVVC LLNNFYPREAKVQWKVDNALQSGNS QESVTE-QDSKDSTYSLSSTLTLSKADYEKHKVYACE-VTHQGLSSPVTKSFNRGEC (SEQ ID NO: 314, linkers are indicated in bold and underlined) comprising $V_{D1}$ of sequence SEQ ID NO: 21, $L_1$ of sequence SEQ ID NO: 307, $V_{D2}$ of sequence SEQ ID NO: 308, $L_2$ of sequence SEQ ID NO: 309 and $C_L$ of sequence SEQ ID NO: 310, and one polypeptide according to formula II of the amino acid sequence EVQLQQSGPELVKPGASVKMSCK-ASGYTFTDYYMKWVKQSHGKSLEWIG-DIIPSNGA TFYNQKFKGKATLTVDRSSSTAYMHLNSLTSED-SAVYYCTRSHLLRASWFAYWGQGT LVTVSA SEVQVVETGGSLVQPGKSLKLTCATSGFTFSN AWMHWVRQSPEKQLEWVA QIKDKSNNYATYY- AESLKGRFTISRDDPKRSIYLQMNSLREED-
TAIYYCRYVHYGIGYA MDAWGQGTSVTVSS
RTASTKGPSVFPLAPSSKSTSGGTAALGCLVK
DYFPEPVTVSW NSGALTSGVHTFPAVLQSSG-
LYS-
LSSVVTVPSSSLGTQTYICNVNHKPSNTKVDKKV
(SEQ ID NO: 315, linkers are indicated in bold and underlined) comprising $V_{D3}$ of sequence SEQ ID NO: 312, $L_3$ of the amino acid sequence 'S', $V_{D4}$ of sequence SEQ ID NO: 18, $L_4$ of the amino acid sequence 'RT' and $C_{H1}$ of sequence SEQ ID NO: 313.

The so-called CODV-Fab "7G3×4B4" antibody-like binding protein comprises:

one polypeptide according to formula I of the amino acid sequence DVVMTQTPVSLSVSLGGQVSIS-
CRSSQSLVHDNGN-
TYLSWSLQRPGQSPQVLIYKVS NRFSGTS-
DRFTGSGSGTDFTLKISRVEPDDLGVYYCGQ
GTQYPFTFGSGTKLEIK
GQPKAAPDFVMTQSPSSLTVTAGEKVTMSC
KSSQSLLNSGNQKNYLTWYLQKPGQPPKLL
IYWASTRESGVPDRFTGSGSGTDFTLTISSVQAE-
DLAVYYCQNDYSYPYTFGGGTKLEI K
TKGPSRTVAAPSVFIFPPSDEQLKSGTASVV
CLLNNFYPREAKVQWKVDNALQSGNS
QESVTEQDSKDSTYSLSSTLTLSKADYEKHKVY-
ACEVTHQGLSSPVTKSFNRGEC (SEQ ID NO: 316, linkers are indicated in bold and underlined) comprising $V_{D1}$ of sequence SEQ ID NO: 16, $L_1$ of sequence SEQ ID NO: 307, $V_{D2}$ of sequence SEQ ID NO: 308, $L_2$ of sequence SEQ ID NO: 309 and $C_L$ of sequence SEQ ID NO: 310, and one polypeptide according to formula II of the amino acid sequence EVQLQQSGPELVKPGASVKMSCK-
ASGYTFTDYYMKWVKQSHGKSLEWIG-
DIIPSNGA
TFYNQKFKGKATLTVDRSSSTAYMHLNSLTSED-
SAVYYCTRSHLLRASWFAYWGQGT LVTVSA
SEVQLVETGGRLVQPGRSLKLTCATSGFTF
SNAWMHVVRQSPEKQLEWVA QIKARSN-
NYATYYAESVKGRFTISRDDSKSTIYLQMNSL-
KEEDTAIYYCRGTYYASKPF
DYWGQGVMVTVSS
RTASTKGPSVFPLAPSSKSTSGGTAALGCLV
KDYFPEPVTVSWN SGALTSGVHTFPAVLQSSG-
LYS-
LSSVVTVPSSSLGTQTYICNVNHKPSNTKVDKKV
(SEQ ID NO: 317, linkers are indicated in bold and underlined) comprising $V_{D3}$ of sequence SEQ ID NO: 312, $L_3$ of the amino acid sequence 'S', $V_{D4}$ of sequence SEQ ID NO: 12, $L_4$ of the amino acid sequence 'RT' and $C_{H1}$ of sequence SEQ ID NO: 313.

The so-called CODV-Fab "7G3×18F5" antibody-like binding protein comprises:

one polypeptide according to formula I of the amino acid sequence DVLMTQTPVSLSVSLGGQVSIS-
CRSSQSLVHTNGN-
TYLSWYLQKPGQSPQLLIYKVSN RLSGIS-
DRFSGSGSGTDFTLKISRVEPDDLGVYYC
GQGTHYPFTFGAGTKLELKGQPK
AAPDFVMTQSPSSLTVTAGEKVTMSCKSSQS
LLNSGNQKNYLTWYLQKPGQPPKLLIY WAST-
RESGVPDRFTGSGSGTDFTLTISSVQAED-
LAVYYCQNDYSYPYTFGGGTKLEIK
TKGPSRTVAAPSVFIFPPSDEQLKSGTASV
VCLLNNFYPREAKVQWKVDNALQSGNS
QESVTEQDSKDSTYSLSSTLTLSKADYEKHKVY-
ACEVTHQGLSSPVTKSFNRGEC (SEQ ID NO: 318, linkers are indicated in bold and underlined) comprising $V_{D1}$ of sequence SEQ ID NO: 26, $L_1$ of sequence SEQ ID NO: 307, $V_{D2}$ of sequence SEQ ID NO: 308, $L_2$ of sequence SEQ ID NO: 309 and $C_L$ of sequence SEQ ID NO: 310, and one polypeptide according to formula II of the amino acid sequence EVQLQQSGPELVKPGASVKMSCK-
ASGYTFTDYYMKWVKQSHGKSLEWIG-
DIIPSNGA
TFYNQKFKGKATLTVDRSSSTAYMHLNSLTSED-
SAVYYCTRSHLLRASWFAYWGQGT LVTVSA
SEVQVVETGGSLVQPGKSLKLTCATSGFTF
TNAWMHVVVRRSPEKQLEWVA QIKDKSN-
NYATYYAESVKGRFTISRDDSKSSIYLQMNSL-
KEEDTAIYYCRYVHYRFAYAL
DAWGRGTSVSVSS
RTASTKGPSVFPLAPSSKSTSGGTAALGCL
VKDYFPEPVTVSWN SGALTSGVHTFPAVLQSSG-
LYS-
LSSVVTVPSSSLGTQTYICNVNHKPSNTKVDKKV
(SEQ ID NO: 319, linkers are indicated in bold and underlined) comprising $V_{D3}$ of sequence SEQ ID NO: 312, $L_3$ of the amino acid sequence 'S', $V_{D4}$ of sequence SEQ ID NO: 23, $L_4$ of the amino acid sequence 'RT' and $C_{H1}$ of sequence SEQ ID NO: 313.

The so-called CODV-Fab "hz20G6×7G3" antibody-like binding protein comprises:

one polypeptide according to formula I of the amino acid sequence DFVMTQSPSSLTVTAGEKVTMSCK-
SSQSLLNSGNQKNYLTWYLQKPGQPPKLLIYWA
STRESGVPDRFTGSGSGTDFTLTISSVQAED-
LAVYYCQNDYSYPYTFGGGTKLEIK
GQPKAAPDIVMTQTPLSLSVTPGQPASIS
CKSSQSLVHNNGNTYLSWYLQKPGQSPQSLI
YKVSNRFSGVPDRFSGSGSGTDFTLKISRVEAE-
DVGVYYCGQGTQYPFTFGSGTKVEI K
TKGPSRTVAAPSVFIFPPSDEQLKSGTAS
VVCLLNNFYPREAKVQWKVDNALQSGNS
QESVTEQDSKDSTYSLSSTLTLSKADYEKHKVY-
ACEVTHQGLSSPVTKSFNRGEC (SEQ ID NO: 320, linkers are indicated in bold and underlined) comprising $V_{D1}$ of sequence SEQ ID NO: 308, $L_1$ of sequence SEQ ID NO: 307, $V_{D2}$ of sequence SEQ ID NO: 143, $L_2$ of sequence SEQ ID NO: 309 and $C_L$ of sequence SEQ ID NO: 310, and one polypeptide according to formula II of the amino acid sequence QVQLVESGGGVVQPGRSLRLS-
CAASGFTFTKAWMHWVRQAPGKQLEW
VAQIKDKSN SYATYYADSVKGRFTISRDDSKNT-
LYLQMNSLRAEDTAVYYCRGVYYAL-
SPFDYWGQ GTLVTVSS
SEVQLQQSGPELVKPGASVKMSCKASGY
TFTDYYMKWVKQSHGKSLEWI GDIIPSNGAT-
FYNQKFKGKATLTVDRSSSTAYMHLNSLTSED-
SAVYYCTRSHLLRASWF AYWGQGTLVTVSA
RTASTKGPSVFPLAPSSKSTSGGTAALGCLV
KDYFPEPVTVSWN SGALTSGVHTFPAVLQSSG-
LYS-
LSSVVTVPSSSLGTQTYICNVNHKPSNTKVDKKV
(SEQ ID NO: 321, linkers are indicated in bold and underlined) comprising $V_{D3}$ of sequence SEQ ID NO: 138, $L_3$ of the amino acid sequence 'S', $V_{D4}$ of sequence SEQ ID NO: 312, $L_4$ of the amino acid sequence 'RT' and $C_{H1}$ of sequence SEQ ID NO: 313.

The so-called CODV-Fab "7G3×hz4B4" antibody-like binding protein comprises:

one polypeptide according to formula I of the amino acid sequence DVVMTQTPVSLSVSVGGRVSIS-CRSSQSLVHDNGNTYLSWSLQKPGK-SPKVLIYKVSN RFSGVSSRFTGSGSGTDFTLKISSVQPD-DLGVYYCGQGTQYPFTFGSGTKLEIK GQPKAAPDFVMTQSPSSLTVTAGEKVT MSCK-SSQSLLNSGNQKNYLTWYLQKPGQPPKLLIY WASTRESGVPDRFTGSGSGTDFTLTISSVQAED-LAVYYCQNDYSYPYTFGGGTKLEIK TKGPSRTVAAPSVFIFPPSDEQLKSGTASVV CLLNNFYPREAKVQWKVDNALQSGNS QESVTEQDSKDSTYSLSSTLTLSKADYEKHKVY-ACEVTHQGLSSPVTKSFNRGEC (SEQ ID NO: 322, linkers are indicated in bold and underlined) comprising $V_{D1}$ of sequence SEQ ID NO: 158, $L_1$ of sequence SEQ ID NO: 307, $V_{D2}$ of sequence SEQ ID NO: 308, $L_2$ of sequence SEQ ID NO: 309 and $C_L$ of sequence SEQ ID NO: 310, and one polypeptide according to formula II of the amino acid sequence EVQLQQSGPELVKPGASVKMSCK-ASGYTFTDYYMKWVKQSHGKSLEWIG-DIIPSNGA TFYNQKFKGKATLTVDRSSSTAYMHLNSLTSED-SAVYYCTRSHLLRASWFAYWGQGT LVTVSA SQVQLVETGGGLVKPGQSLKLTCATSGFTF SNAWMHWVRQSPEKGLEWVA QIKARSN-NYATYYAESVKGRFTISRDDSKSTIYLQMNSLT-PEDTAIYYCRGTYYASKPFD YWGQGVMVTVSS RTASTKGPSVFPLAPSSKSTSGGTAALGCL VKDYFPEPVTVSWNS GALTSGVHTFPAVLQSSG-LYS-LSSVVTVPSSSLGTQTYICNVNHKPSNTKVDKKV (SEQ ID NO: 323, linkers are indicated in bold and underlined) comprising $V_{D3}$ of sequence SEQ ID NO: 312, $L_3$ of the amino acid sequence 'S', $V_{D4}$ of sequence SEQ ID NO: 171, $L_4$ of the amino acid sequence 'RT' and $C_{H1}$ of sequence SEQ ID NO: 313.

The so-called CODV-Fab "hz4B4×3E3" antibody-like binding protein comprises:

one polypeptide according to formula I of the amino acid sequence QFVLTQPNSVSTNLGSTVKLSCKRN-TGNIGSNYVNWYQQHEGRSPTTMIYRDDKRPD GVPDRFSGSIDRSSNSALLTINNVQTEDEAD-YFCQSYSSGINIIFGGGTKLTVL GQPKAAPDVVMTQTPVSLSVSVGGRVSIS-CRSSQSLVHDNGNTYLSWSLQKPGK-SPKVLIYKV SNRFSGVSSRFTGSGSGTDFTLKISSVQPD-DLGVYYCGQGTQYPFTFGSGTKLEIK TKGPSRTVAAPSVFIFPPSDEQLKSGTASV VCLLNNFYPREAKVQWKVDNALQSGNSQE SVTEQDSKDSTYSLSSTLTLSKADYEKHKVY-ACEVTHQGLSSPVTKSFNRGEC (SEQ ID NO: 324, linkers are indicated in bold and underlined) comprising $V_{D1}$ of sequence SEQ ID NO: 230, $L_1$ of sequence SEQ ID NO: 307, $V_{D2}$ of sequence SEQ ID NO: 158, $L_2$ of sequence SEQ ID NO: 309 and $C_L$ of sequence SEQ ID NO: 310, and one polypeptide according to formula II of the amino acid sequence QVQLVETGGGLVKPGQSLKLT-CATSGFTFSNAWMHWVRQSPEKGLEWVAQIK-ARSN NYATYYAESVKGRFTISRDDSK-STIYLQMNSLTPEDTAIYYCRGTYYASKP FDYWGQG VMVTVSS SQVQLQESGPGLVQPSQTLSLTCTVSGFSL TTY-DVHWVRQPPGKGLEWM GRIQNGGITDYN-SALKSRLIISRDTSKSQVFLKMNSVQTED-TAMYFCAKTGSYFYAFDH WGQGTLVTVSS RTASTKGPSVFPLAPSSKSTSGGTAALGCL VKDYFPEPVTVSWNSG ALTSGVHTFPAVLQSSG-LYS-LSSVVTVPSSSLGTQTYICNVNHKPSNTKVDKKV (SEQ ID NO: 325, linkers are indicated in bold and underlined) comprising $V_{D3}$ of sequence SEQ ID NO: 171, $L_3$ of the amino acid sequence 'S', $V_{D4}$ of sequence SEQ ID NO: 226, $L_4$ of the amino acid sequence 'RT' and $C_{H1}$ of sequence SEQ ID NO: 313.

The so-called CODV-Fab "hz20G6×hz7G3" antibody-like binding protein comprises:

one polypeptide according to formula [I] consisting essentially of the amino acid sequence:

```
                                    (SEQ ID NO: 388
DIVMTQSPDSLAVSLGERATINCESSQSLLNSGNQKNYLTWYQQKPGQPP

KPLIYWASTRESGVPDRFSGSGSGTDFTLTISSLQAEDVAVYYCQNDYSY

PYTFGQGTKLEIKGGSGSGSGGDIVMTQTPLSLSVTPGQPASISCKSSQ

SLVHNNANTYLSWYLQKPGQSPQSLIYKVSNRFSGVPDRFSGSGSGTDFT

LKISRVEAEDVGVYYCGQGTQYPFTFGSGTKVEIKGGSGSGSGGRTVAA

PSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRG

EC,
``` linkers are indicated in bold and underlined) comprising $V_{D1}$ of sequence SEQ ID NO: 385, $L_1$ of sequence SEQ ID NO: 389, $V_{D2}$ of sequence SEQ ID NO: 141, $L_2$ of sequence SEQ ID NO: 389 and $C_L$ of sequence SEQ ID NO: 310, and one polypeptide according to formula [III] consisting essentially of the amino acid sequence QVQLVES-GGGVVQPGRSLRLS-CAASGFTFTKAWMHWVRQAPGKQLE WVAQIKDKSN SYATYYADSVKGRFTISRDD-SKNTLYLQMNSLRAEDTAVYYCRGVYYAL-SPFDYWGQ GTLVTVSS EVQLVQSGAEVKKPGESLKISCKGSGYSFT DYYMKWARQMPGKGLEWMGDIIPSSGAT-FYNQKFKGQVTISADKSISTTYLQWSSLKASD-TAMYYCARSHLLRASWFAYWGQGTMVTVS-SASTKGPSVFPLAPSSKSTSGGTAALGCLVK DYFPEPVTVSWNSG ALTSGVHTFPAVLQSSG-LYS-LSSVVTVPSSSLGTQTYICNVNHKPSNTKVDKKV (SEQ ID NO: 390) comprising $V_{D3}$ of sequence SEQ ID NO: 138, $L_3$ is 0 amino acid, $V_{D4}$ of sequence SEQ ID NO: 383 (in italic and underlined), $L_4$ is 0 amino acid and $C_{H1}$ of sequence SEQ ID NO: 313.

In one example, the polypeptides according to formula II of the so-called CODV-Fab "7G3×20G6", "7G3×4E7", "7G3×4B4", "7G3×18F5", "hz20G6×7G3", "7G3×hz4B4", "hz4B4×3E3" and "hz20G6×hz7G3" antibody-like binding proteins further comprise the sequence EPKSCDKTH-THHHHHH (SEQ ID NO: 352) corresponding to a hinge sequence and a Histag used, for example, for purification.

The so-called CODV-Fab "hz20G6×7G3-TL4" (also called CODV-Fab-TL4 "hz20G6×7G3") antibody-like binding protein comprises:

one polypeptide according to formula [IV] consisting essentially of the amino acid sequence DFVMTQSPSSLTVTAGEKVTMSCK- SSQSLLNSGNQKNYLTWYLQKPGQPPKLLIYWASTRESGVPDRFTGSGSGTDFTLTISSVQAEDLAVYYCQNDYSYPYTFGGGTKLEIKGQPKAAPDIVMTQTPLSLSVTPGQPASISCKSSQSLVHNNGNTYLSWYLQKPGQSPQSLIYKVSNRFSGVPDRFSGSGSGTDFTLKISRVEAEDVGVYYCGQGTQYPFTFGSGTKVEI K TKGPSRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC ESKYGPPCPPCPAPEFEGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNRFTQKSLSLSLG (SEQ ID NO: 326, linkers are indicated in bold and underlined) comprising $V_{D1}$ of sequence SEQ ID NO: 308, $L_1$ of sequence SEQ ID NO: 307, $V_{D2}$ of sequence SEQ ID NO: 143, $L_2$ of sequence SEQ ID NO: 309, $C_L$ of sequence SEQ ID NO: 310 and $F_{c2}$ (underlined) of sequence SEQ ID NO: 327, and one polypeptide according to formula [III] of the amino acid sequence QVQLVESGGGVVQPGRSLRLSCAASGFTFTKAWMHWVRQAPGKQLEWVAQIKDKSN SYATYYADSVKGRFTISRDDSKNTLYLQMNSLRAEDTAVYYCRGVYYALSPFDYWGQ GTLVTVSS SEVQLQQSGPELVKPGASVKMSCKASGYTFTDYYMKWVKQSHGKSLEWI GDIIPSNGATFYNQKFKGKATLTVDRSSSTAYMHLNSLTSEDSAVYYCTRSHLLRASWF AYWGQGTLVTVSA RTASTKGPSVFPLAPCSRSTSESTAALGCLVKDYFPEPVTVSWN SGALTSGVHTFPAVLQSSGLYSLSSWTVPSSSLGTKTYTCNVDHKPSNTKVDKRVES KYGPPCPPCPAPEFEGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKT ISKAKGQPREPQVYTLPPSQEEMTKNQVSLTCLVKGFYPSDIAVEWESNGQPENNYKT TPPVLDSDGSFFLYSRLTVDKSRWQEGNVFSCSVMHEALHNHYTQKSLSLSLG (SEQ ID NO: 328, linkers are indicated in bold and underlined) comprising $V_{D3}$ of sequence SEQ ID NO: 138, $L_3$ of the amino acid sequence 'S', $V_{D4}$ of sequence SEQ ID NO: 312, $L_4$ of the amino acid sequence 'RT', and $C_{H1}$ of sequence SEQ ID NO: 329, and $F_c$ of sequence SEQ ID NO: 330.

In the above CODV-Fab-TL4 "hz20G6×7G3" antibody-like binding protein, the Fc of sequence SEQ ID NO: 330 and $F_{c2}$ of sequence SEQ ID NO: 327 are from an IgG4 backbone. Said antibody-like binding protein is in a CODV-Fab-TL format and contains or consists of one polypeptide of formula III and one polypeptide of formula IV.

The so-called CODV-Fab-TL1 "hz20G6×hz7G3" antibody-like binding protein comprises:

one polypeptide according to formula IV of the amino acid sequence (SEQ ID NO: 391
DIVMTQSPDSLAVSLGERATINCESSQSLLNSGNQKNYLTWYQQKPGQPP

KPLIYWASTRESGVPDRFSGSGSGTDFTLTISSLQAEDVAVYYCQNDYSY

PYTFGQGTKLEIKGGSGSSGSGGDIVMTQTPLSLSVTPGQPASISCKSSQ

SLVHNNANTYLSWYLQKPGQSPQSLIYKVSNRFSGVPDRFSGSGSGTDFT

LKISRVEAEDVGVYYCGQGTQYPFTFGSGTKVEIKGGSGSSGSGGRTVAA

PSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRG

EC<u>DKTHTCPPCPAPEAAGGPSVFLFPPKPKDTLMISRTPEVTCVVVDVSH</u>

<u>EDPEVKFNWYVDGVEVHNAKTKPREEQYNSTYRVVSVLTVLHQDWLNGKE</u>

<u>YKCKVSNKALPAPIEKTISKAKGQPREPQVYTLPPSRDELTKNQVSLTCL</u>

<u>VKGFYPSDIAVEWESNGQPENNYKTTPPVLDSDGSFFLYSKLTVDKSRWQ</u>

<u>QGNVFSCSVMHEALHNRFTQKSLSLSPG</u>, linkers are indicated in bold and underlined) comprising $V_{D1}$ of sequence SEQ ID NO: 385, $L_1$ of sequence SEQ ID NO: 389, $V_{D2}$ of sequence SEQ ID NO: 141, $L_2$ of sequence SEQ ID NO: 389, $C_L$ of sequence SEQ ID NO: 310, $L_5$ which contains 0 amino acid, and $F_{c2}$ (underlined) of sequence SEQ ID NO: 392; and one polypeptide according to formula III of the amino acid sequence QVQLVESGGGVVQPGRSLRLSCAASGFTFTKAWMHVVVRQAPGKQLE WVAQIKDKSN SYATYYADSVKGRFTISRDDSKNTLYLQMNSLRAEDTAVYYCRGVYYALSPFDYWGQ GTLVTVSSEVQLVQSGAEVKKPGESLKISCKGSGYSFTDYYM KWARQMPGKGLEWM GDIIPSSGATFYNQKFKGQVTISADKSISTTYLQWSSLKASDTAMYYCARSHLLRASWF AYWGQGTMVTVSSASTKGPSVFPLAPSSKSTSGGTAALGCLV KDYFPEPVTVSWNSG ALTSGVHTFPAVLQSSGLYSLSSVVTVPSSSLGTQTYICNVNHKPSNTKVDKKV <u>EPKSCDKTHTCPPCPAPEAAGGPSVFLFPPKPK</u> <u>DTLMISRTPEVTCVWDVSHEDPEVKFNWYVDG</u> <u>VEVHNAKTKPREEQYNSTYRVVSVLTVLHQD</u> <u>WLNGKEYKCKVSNKALPAPIEKTISKAKGQPR</u> <u>EPQVYTLPPSRDELTKNQVSLTCLVKGFYPS</u> <u>DIAVEWESNGQPENNYKTTPPVLDSDGSFFLY</u> <u>SKLTVDKSRWQQGNVFSCSVMHEALHNHYTQ</u> <u>KSLSLSPG</u> (SEQ ID NO: 393) comprising $V_{D3}$ of sequence SEQ ID NO: 138, $L_3$ is 0 amino acid, $V_{D4}$ of sequence SEQ ID NO: 383 (in italic), $L_4$ is 0 amino acid, $C_{H1}$ of sequence SEQ ID NO: 313, and $F_c$ (underlined) of sequence SEQ ID NO: 394.

In the CODV-Fab-TL1 "hz20G6×7G3" antibody-like binding protein, the Fc of sequence SEQ ID NO: 394 and $F_{c2}$ of sequence SEQ ID NO: 392 are from an IgG1 backbone. Said antibody-like binding protein is in a CODV-Fab-TL format. It contains or consists of one polypeptide of formula IV and one polypeptide of formula III.

The so-called CODV-Fab-OL1 "hz20G6×hz7G3" antibody-like binding protein comprises:

one polypeptide according to formula I of the amino acid sequence (SEQ ID NO: 388)
DIVMTQSPDSLAVSLGERATINCESSQSLLNSGNQKNYLTWYQQKPGQPP

KPLIYWASTRESGVPDRFSGSGSGTDFTLTISSLQAEDVAVYYCQNDYSY

PYTFGQGTKLEIKGGSGSSGSGGDIVMTQTPLSLSVTPGQPASISCKSSQ

SLVHNNANTYLSWYLQKPGQSPQSLIYKVSNRFSGVPDRFSGSGSGTDFT

LKISRVEAEDVGVYYCGQGTQYPFTFGSGTKVEIKGGSGSSGSGGRTVAA

PSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRG

EC, linkers are indicated in bold and underlined) comprising $V_{D1}$ of sequence SEQ ID NO: 385, $L_1$ of sequence SEQ ID NO: 389, $V_{D2}$ of sequence SEQ ID NO: 141, $L_2$ of sequence SEQ ID NO: 389, and $C_L$ of sequence SEQ ID NO: 310; and one polypeptide according to formula III of the amino acid sequence QVQLVESGGGVVQPGRSLRLS-CAASGFTFTKAWMHWVRQAPGKQLE WVAQIKDKSN SYATYYADSVKGRFTISRDD-SKNTLYLQMNSLRAEDTAVYYCRGVYYAL-SPFDYWGQ GTLVTVSS EVQLVQSGAEVKKPGESLKISCKGSGYSFT DYYMKWARQMPGKGLEWMGDIIPSSGAT FYNQKFKGQVTISADKSISTTYLQWSSLKASD TAMYYCARSHLLRASWFAYWGQGTMVTVS SASTKGPSVFPLAPSSKSTSGGTAALGCLVKDY FPEPVTVSWNSGALTSGVHTFPAVLQSSGLYS LSSWTVPSSSLGTQTYICNVNHKPSNTKVDKKV EPKSCDKTHTCPPCPAPEAAGGPSVFLFPPKPK DTLMISRTPEVTCVWDVSHEDPE-VKFNWYVDGVEVHNAKTKPREEQYN-STYRVVSVLTVLHQDWLNGKEYKCKVSNKAL-PAPIEKTISKAKGQPREPQVYTLPPCRDEL TKNQVSLWCLVKGFYPSDIAVEWESNGQPEN-NYKTTPPVLDSDGSFFLYSK-LTVDKSRWQQGNVFSCSVMHEALHNRF TQKSLSLSPG (SEQ ID NO: 395) comprising $V_{D3}$ of sequence SEQ ID NO: 138, $L_3$ is 0 amino acid, $V_{D4}$ of sequence SEQ ID NO: 383 (in italic and underlined), $L_4$ is 0 amino acid, $C_{H1}$ of sequence SEQ ID NO: 313, and $F_c$ (underlined) of sequence SEQ ID NO: 396;

and wherein the so-called CODV-Fab-OL1 "hz20G6×hz7G3" antibody-like binding protein further comprises a Fc stump ($F_{c3}$) of the amino acid sequence: GSDKTH-TCPPCPAPEAAGGPSVFLFPPKPKDTLMISRTPE-VTCVVVDVSHEDPEVKFN WYVDGVEVHNAKTKPREEQYN-STYRVVSVLTVLHQDWLNGKEYKCKVSNKALPAPIE KTISKAKGQPREPQVCTLPPSRDELTKNQVSLSCAV-KGFYPSDIAVEWESNGQPENNY KTTPPVLDSDGSF-FLVSKLTVDKSRWQQGNVFSCSVMHEALHN-HYTQKSLSLSPG (SEQ ID NO: 397) and which heterodimerises with the Fc region of the polypeptide according to formula III.

Said antibody-like binding protein is in a CODV-Fab-OL format, i.e. it contains or consists of one polypeptide of formula I, one polypeptide of formula III, and one Fc stump. Its $F_c$ and $F_{c3}$ sequences have been engineered according to the "Knob-into-Hole" technology and further contain the double mutation L234A and L235A.

The $F_c$ sequence of sequence SEQ ID NO: 396 has been designed to contain RF residues at positions 200-221 (in bold above), instead of HY residues which would have otherwise been present at these positions of the Fc region. The HY>RF mutation (i.e. H435R and Y436F in CH3 domain as described by Jendeberg, L. et al. 1997, J. Immunological Meth., 201: 25-34) is advantageous for purification purposes as it abolishes binding to protein A. In the case of CODV-Fab-OL1 "hz20G6×hz7G3", the $F_c$ stump of sequence SEQ ID NO: 397 comprises HY residues at positions 217-218 (in bold above).

The so-called CODV-Fab-OL1a "hz20G6×hz7G3" antibody-like binding protein comprise:

one polypeptide according to formula I of the amino acid sequence DIVMTQSPDSLAVSLGERATIN-CESSQSLLNSGNQKNYLTWYQQKPGQPPKPLIY-WAS TRESGVPDRFSGSGSGTDFTLTISSLQAE-DVAVYYCQNDYSYPYTFGQGTKLEIKGGS GSSGSGGDIVMTQTPLSLSVTPGQPASISCK-SSQSLVHNNANTYLSWYLQKPGQSPQ SLIYKVSNRFSGVPDRFSGSGSGTDFTLKISRVE-AEDVGVYYCGQGTQYPFTFGSGTK VEIKGGSGSSGSGGRTVAAPSVFIFPPSD-EQLKSGTASVVCLLNNFYPREAKVQWKVD NALQSGNSQESVTEQDSKDSTYSLSSTLTL-SKADYEKHKVYACEVTHQGLSSPVTKSF NRGEC (SEQ ID NO: 388) which comprises $V_{D1}$ of sequence SEQ ID NO: 385, $L_1$ of sequence SEQ ID NO: 389, $V_{D2}$ of sequence SEQ ID NO: 141, $L_2$ of sequence SEQ ID NO: 389, and $C_L$ of sequence SEQ ID NO: 310;

one polypeptide according to formula III of the amino acid sequence: QVQLVESGGGVVQPGRSLRLS-CAASGFTFTKAWMHWVRQAPGKQLEWV AQIKDKSN SYATYYADSVKGRFTISRDDSKNT-LYLQMNSLRAEDTAVYYCRGVYYAL-SPFDYWGQ GTLVTVSS EVQLVQSGAEVKKPGESLKISCKGSGYSFT DYYMKWARQMPGKGLEWMGDIIPSSGAT FYNQKFKGQVTISADKSISTTYLQWSSLKASD TAMYYCARSHLLRASWFAYWGQGTMVTVS SASTKGPSVFPLAPSSKSTSGGTAALGCLVKDYF-PEPVTVSWNSG ALTSGVHTFPAVLQSSGLYS-LSSVVTVPSSSLGTQTYICNVNHKPSNTKVDKKV EPKSCDKTHTCPPCPAPEAAGGPSVFLFPPKPK DTLMISRTPEVTCVWDVSHEDPE VKFNWYVDGVEVHNAKTKPREEQYN STYRVVSVLTVLHQDWLNGKEYKCKVSNKAL PAPIEKTISKAKGQPREPQVYTLPPCRDELT KNQVSLWCLVKGFYPSDIAVEWESNGQPEN NYKTTPPVLDSDGSFFLYSK LTVDKSRWQQGNVFSCSVMHEALHN HYTQKSLSLSPG (SEQ ID NO: 399) comprising $V_{D3}$ of sequence SEQ ID NO: 138, $L_3$ is 0 amino acid, $V_{D4}$ of sequence SEQ ID NO: 383 (in italic and underlined), $L_4$ is 0 amino acid, $C_{H1}$ of sequence SEQ ID NO: 313, and $F_c$ (underlined) of sequence SEQ ID NO: 400;

and wherein the so-called CODV-Fab-OL1a "hz20G6×hz7G3" antibody-like binding protein further comprises a Fc stump ($F_{c3}$) of the amino acid sequence: GSDKTHTCPPCPA-PEAAGGPSVFLFPPKPKDTLMISRTPE-VTCVVVDVSHEDPEVKFN WYVDGVEVHNAKTKPREEQYN-STYRVVSVLTVLHQDWLNGKEYKCKVSNKAL-PAPIE KTISKAKGQPREPQVCTLPPSRDELT-KNQVSLSCAVKGFYPSDIAVEWESNGQPENNY KTTPPVLDSDGSFFLVSK-LTVDKSRWQQGNVFSCSVMHEALHNRFTQ KSLSLSPG (SEQ ID NO: 398) which heterodimerises with the Fc region of the polypeptide according to formula III.

The $F_c$ of sequence SEQ ID NO: 400 comprises HY residues at positions 200-221 (in bold above) while the $F_c$ stump of sequence SEQ ID NO: 398 comprises RF residues at positions 217-218 (in bold above).

Said antibody-like binding protein is in a CODV-Fab-OL format, i.e. it contains or consists of one polypeptide of formula I, one polypeptide of formula III and one Fc stump. Its $F_c$ and $F_{c3}$ sequences have been engineered according to the "Knob-into-Hole" technology and contain the double mutation L234A and L235A.

In one embodiment, the first immunoglobulin or the second immunoglobulin is one anti-CD123 antibody selected from the so-called "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", and "9F6-G3" anti-CD123 antibodies, or a humanized form thereof, or the anti-CD123 antibody "7G3" described herein below, for example the anti-CD123 antibodies "3E3-D3" or "7G3", or a humanized form thereof.

In one embodiment, the first immunoglobulin or the second immunoglobulin is one anti-CD3 antibody selected from the so-called "20G6-F3", "4B4-D7", "4E7-C9", "18F5-H10", "12D2-E5", "11D7-C3", "11H3-E5", "13H2-C2", "13C1-F6", "18H11-F10", "1E6-C9", "10F4-C10", "10E6-G6", "18G9-H11", "11F3-B9", "12G3-E8", "5B1-G2", "16F8-A7", "11F9-F8", "3G5-E10", "9D7-F3", "8C2-F7", "20E5-F10", "20B5-F10", "6C9-C9", "3E8-G1", "3H6-D2", and "8H2" anti-CD3 antibodies, or a humanized form thereof, for example the so-called "20G6-F3", "4B4-D7", "4E7-C9", "18F5-H10", and "hz20G6" anti-CD3 antibodies, for instance the so-called so-called "20G6-F3", "4B4-D7" anti-CD3 antibodies.

Accordingly, $V_{D1}$ and $V_{D4}$, or $V_{D2}$ and $V_{D3}$ are the variable domains of a heavy or light chain of an anti-CD3 antibody, wherein said anti-CD3 antibody comprises:
a) a heavy chain variable domain comprising CDR1-H of sequence SEQ ID NO: 6, CDR2-H of sequence SEQ ID NO: 7, CDR3-H of sequence SEQ ID NO: 8 and a light chain variable domain comprising CDR1-L of sequence SEQ ID NO: 10 or SEQ ID NO: 142, CDR2-L of sequence 'KVS' and CDR3-L of sequence SEQ ID NO: 11; or
b) a heavy chain variable domain comprising CDR1-H of sequence SEQ ID NO: 13, CDR2-H of sequence SEQ ID NO: 14, CDR3-H of sequence SEQ ID NO: 15 and a light chain variable domain comprising CDR1-L of sequence SEQ ID NO: 17 or SEQ ID NO: 184, CDR2-L of sequence 'KVS' and CDR3-L of sequence SEQ ID NO: 11; or
c) a heavy chain variable domain comprising CDR1-H of sequence SEQ ID NO: 13, CDR2-H of sequence SEQ ID NO: 19, CDR3-H of sequence SEQ ID NO: 20 and a light chain variable domain comprising CDR1-L of sequence SEQ ID NO: 22, CDR2-L of sequence 'KVS' and CDR3-L of sequence SEQ ID NO: 11, or
d) a heavy chain variable domain comprising CDR1-H of sequence SEQ ID NO: 24, CDR2-H of sequence SEQ ID NO: 19, CDR3-H of sequence SEQ ID NO: 25 and a light chain variable domain comprising CDR1-L of sequence SEQ ID NO: 27, CDR2-L of sequence 'KVS' and CDR3-L of sequence SEQ ID NO: 28, and
wherein $V_{D1}$ is the variable domain of heavy chain as defined above if $V_{D4}$ is the variable domain of light chain or $V_{D1}$ is the variable domain of the light chain as defined above if $V_{D4}$ is the variable domain of the heavy chain, or $V_{D2}$ is the variable domain of heavy chain as defined above if $V_{D3}$ is the variable domain of light chain or $V_{D2}$ is the variable domain of the light chain as defined above if $V_{D3}$ is the variable domain of the heavy chain.

In a further embodiment, $V_{D1}$ and $V_{D4}$ or $V_{D2}$ and $V_{D3}$ are the variable domains of a heavy or light chain of an anti-CD3 antibody, wherein said anti-CD3 antibody is a humanized antibody and comprises:
a) a heavy chain variable domain of sequence SEQ ID NO: 138, or a sequence at least 85% identical thereto and/or a light chain variable domain of sequence SEQ ID NO: 143, or a sequence at least 85% identical thereto; or
b) a heavy chain variable domain of sequence SEQ ID NO: 171, or a sequence at least 85% identical thereto and/or a light chain variable domain of sequence SEQ ID NO: 158, or a sequence at least 85% identical thereto; or
c) a heavy chain variable domain of sequence SEQ ID NO: 176, or a sequence at least 85% identical thereto and/or a light chain variable domain of sequence SEQ ID NO: 164, or a sequence at least 85% identical thereto; or
wherein $V_{D1}$ is the variable domain of heavy chain as defined above if $V_{D4}$ is the variable domain of light chain or $V_{D1}$ is the variable domain of the light chain as defined above if $V_{D4}$ is the variable domain of the heavy chain, or $V_{D2}$ is the variable domain of heavy chain as defined above if $V_{D3}$ is the variable domain of light chain or $V_{D2}$ is the variable domain of the light chain as defined above if $V_{D3}$ is the variable domain of the heavy chain.

In said sequence at least 85% identical to SEQ ID NO: 138, SEQ ID NO: 143, SEQ ID NO: 171, SEQ ID NO: 158, SEQ ID NO: 176, or SEQ ID NO: 164, the sequences of the 6 CDRs are unchanged compared to the 6 CDRs present in the reference sequence SEQ ID NO: 138, SEQ ID NO: 143, SEQ ID NO: 171, SEQ ID NO: 158, SEQ ID NO: 176, or SEQ ID NO: 164.

In an embodiment, the antibody-like binding protein of the invention binds to human CD3. In another embodiment, the antibody-like binding protein of the invention further binds to *Macaca fascicularis* CD3. In particular, the antibody-like binding protein of the invention binds to the extracellular domain of human CD3, or of both human and *Macaca fascicularis* CD3. More specifically, the antibody binds to CD3ε. More specifically, the antibody-like binding protein binds to the human or human and *Macaca fascicularis* extracellular domain of CD3ε. The antibody-like binding protein binds to CD3ε when present in the form of a complex, such as a CD3ε/δ complex, or when present as single protein, indifferently whether expressed in isolated form, or present in a soluble extracellular domain or full-length membrane-anchored CD3ε as present in for example in T-cells. The antibody-like binding protein according to the invention is specific for the surface human CD3 protein, or of both human and *Macaca fascicularis* CD3 proteins, in particular to CD3ε.

The antibody-like binding according to the invention has a ratio of affinity for *Macaca fascicularis* CD3 on affinity for human CD3 (KD(*Macaca fascicularis*)/KD(human) which is ≤10, in particular ≤6, ≤5, ≤4, ≤3, ≤2, ≤1 or ≤0.5. Thus, the antibody-like binding protein according to the invention may be used in toxicological studies performed in monkeys the toxicity profile observed in monkeys relevant to anticipate potential adverse effects in humans.

Furthermore, the antibody-like binding protein according to the invention has an affinity (KD) for human CD3 or *Macaca fascicularis* CD3, or both, which is ≤50 nM, ≤40 nM, or ≤30 nM, for instance ≤20 nM, for example an affinity of 0.1 nM to 30 nM, in particular of 0.4 nM to 20 nM, or of 0.4 nM to 15 nM.

In one embodiment, the antibody-like binding protein of the invention has a T-cell activation that is lower than less than 20%, less than 18%, less than 16%, less than 14%, less than 12%, less than 10% in the absence of target cells.

In one embodiment, the antibody-like binding protein of the invention has a T-cell activation that is higher than 55%, higher than 60%, higher than 62%, higher than 64%, higher than 66%, higher than 68%, higher than 70% in the presence of target cells.

"Low T-cell activation" in the context of the antibody-like binding proteins of the invention refers to a T-cell activation less than 20%, less than 18%, less than 16%, less than 14%, less than 12%, less than 10%.

"Target cells" herein refer to cells that express the second antigen, in one example target cells herein refer to CD123 expressing cells such as THP-1 cells.

"High T-cell activation" herein refers to a T-cell activation higher than 50%, higher than 55%, higher than 60%, higher than 62%, higher than 64%, higher than 66%, higher than 68%, higher than 70%.

In a further embodiment, the invention relates to an antibody-like binding protein having biological and immunological specificity to at least one further target antigen.

Therefore, in one aspect of the invention, the antibody-like binding protein of the invention binds further to at least one other target antigen. Accordingly, in one embodiment, the antibody-like binding protein of the invention is bispecific and capable of binding two different antigen targets or epitopes.

Accordingly, in one embodiment the first immunoglobulin is an immunoglobulin directed against at least one further target if the second immunoglobulin is one anti-CD123 antibody as defined in the section «anti-CD123 antibodies» above, or the second immunoglobulin is an immunoglobulin directed against at least one further target if the first immunoglobulin is one anti-CD123 antibody as defined in the section «anti-CD123 antibodies» above.

In one further embodiment the first immunoglobulin is an immunoglobulin directed against at least one further target if the second immunoglobulin is one anti-CD3 antibody as defined in the section «anti-CD3 antibodies» above, or the second immunoglobulin is an immunoglobulin directed against at least one further target if the first immunoglobulin is one anti-CD3 antibody as defined in the section «anti-CD3 antibodies» above.

The antibody-like binding protein of the invention has a T-cell engaging effect. This T-cell engaging effect induces cytotoxicity in the target cell. In one embodiment, the target cell is a CD123 expressing cell, such as a CD123 expressing cancer cell, for example THP-1 or TF-1.

Accordingly, in one embodiment the antibody-like binding protein according to the invention is able to engage primary T-cells and to lyse target cells in vitro wherein the ($EC_{50}$) is ≤40 pM, ≤35 pM, for instance ≤30 pM.

"Cytotoxicity" herein refers to the quality of a compound, such as the antibody-like binding protein or an anti-CD123 antibody of the invention, to be toxic to cells. Cytotoxicity may be induced by different mechanisms of action and can thus be divided into cell-mediated cytotoxicity, apoptosis, antibody-dependent cell-mediated cytotoxicity (ADCC) or complement-dependent cytotoxicity (CDC).

"Antibody-dependent cell-mediated cytotoxicity" or "ADCC" refers to a mechanism of cell-mediated immune defense whereby an effector cell of the immune system actively lyses a target cell, whose membrane-surface antigens have been bound by specific antibodies.

"Complement-dependent cytotoxicity" or "CDC", in the context of the invention, refers to lysis of a target cell in the presence of complement system proteins.

"Cell-mediated cytotoxicity" refers to cytolysis of a target cell by effector lymphocytes, such as cytotoxic T lymphocytes or natural killer cells and can thus be distinguished into T-cell-mediated cytotoxicity and NK-cell cytotoxicity.

In one embodiment, cytotoxicity herein refers to Cell-mediated cytotoxicity for example T-cell-mediated cytotoxicity.

Furthermore, in one embodiment the cell-mediated cytotoxicity refers to cell-mediated cytotoxicity by T-cells.

Accordingly, the antibody-like binding protein of the invention induces cell-mediated cytotoxicity in the target cell mediated by T-cells.

Methods to measure cytotoxicity are known to the skilled in the art and include using 51-Chromium (Cr) release assay, live/dead cell staining of target cells including propidium iodide, 7-AAD, and other stains that are known to the skilled in the art, detection of lytic molecules released by T cells including granzyme and perforin by flow cytometry or ELISA, detection of lactate dehydrogenase (LDH) released into the media from damaged cells as a biomarker for cellular cytotoxicity and cytolysis, detection of cell surface mobilization of CD107a, Annexin V (calcium-dependent phospholipid-binding proteins) staining of apoptotic target cells and for example detection of activated Caspase-3 (CASP3). Furthermore, the skilled in the art can distinguish between the different mechanisms of cytotoxicity based on the test selected and based on the experimental set up.

In one example, cell-mediated cytotoxicity may be for example measured using CFSE to label target cells and 7-AAD to label dead cells as described, for instance, in example 3.2.

In a further embodiment, the antibody-like binding protein is capable of binding to CD3 and at least one further antigen target, for example CD123.

In one embodiment, the antibody-like binding protein is capable of inhibiting the function of this further antigen target, for example CD123.

In one aspect of the invention, the antibody-like binding protein binds to human CD123. In another embodiment, the antibody-like binding protein further binds to *Macaca fascicularis* CD123. In particular, the antibody-like binding protein of the invention binds to the extracellular domain of human CD123, or of both, human and *Macaca fascicularis* CD123. More specifically, the antibody-like binding protein binds to the distal moiety of CD123, for example, to the amino acids starting from position 19 to 49 of human CD123 of the amino acid sequence SEQ ID NO: 104. The antibody-like binding protein binds to CD123, indifferently whether expressed in isolated form, or present in a soluble extracellular domain or full-length membrane-anchored CD123 as present in CD123 expressing cells such as AML cells or CD123 transfected cells. The antibody-like binding protein according to the invention is specific to cells that express human or human and *Macaca fascicularis* CD123 proteins on their surface, for example CD123 expressing cancer cells.

Accordingly, the antibody-like binding protein according to the invention has an affinity (KD) for human CD123 or

*Macaca fascicularis* CD123, or both, which is ≤20 nM, ≤15 nM, or ≤10 nM, for instance ≤5 nM, for example an affinity of 0.01 nM to 5 nM, in particular of 0.1 nM to 5 nM.

Accordingly, in one embodiment, the first immunoglobulin is one anti-CD3 antibody selected from the so-called "20G6-F3", "4B4-D7", "4E7-C9", "18F5-H10", "12D2-E5", "11D7-C3", "11H3-E5", "13H2-C2", "13C1-F6", "18H11-F10", "1E6-C9", "10F4-C10", "10E6-G6", "18G9-H11", "11F3-B9", "12G3-E8", "5B1-G2", "16F8-A7", "11F9-F8", "3G5-E10", "9D7-F3", "8C2-F7", "20E5-F10", "20B5-F10", "6C9-C9", "3E8-G1", "3H6-D2", and "8H2" anti-CD3 antibodies, or a humanized form thereof, for example the so-called "20G6-F3", "4B4-D7", "4E7-C9", "18F5-H10", "hz4B4" and "hz20G6" anti-CD3 antibodies, and the second immunoglobulin is one anti-CD123 antibody selected from the so-called "3E3-D3", "1E1-G5", "2B8-F3", "2F8-D6", "3B10-E6", "5A5-B4", "6B10-E4", "6C10-C4", "6 D6-B8", "8B11-B7", "9B8-G6", "9D7-C8", and "9F6-G3" anti-CD123 antibodies.

Accordingly, in a further embodiment, the second immunoglobulin is one anti-CD3 antibody selected from the so-called "20G6-F3", "4B4-D7", "4E7-C9", "18F5-H10", "12D2-E5", "11D7-C3", "11H3-E5", "13H2-C2", "13C1-F6", "18H11-F10", "1E6-C9", "10F4-C10", "10E6-G6", "18G9-H11", "11F3-B9", "12G3-E8", "5B1-G2", "16F8-A7", "11F9-F8", "3G5-E10", "9D7-F3", "8C2-F7", "20E5-F10", "20B5-F10", "6C9-C9", "3E8-G1", "3H6-D2", and "8H2" anti-CD3 antibodies, or a humanized form thereof, for example the so-called "20G6-F3", "4B4-D7", "4E7-C9", "18F5-H10", "hz4B4" and "hz20G6" anti-CD3 antibodies, and the first immunoglobulin is one anti-CD123 antibody selected from the so-called "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", and "9F6-G3" anti-CD123 antibodies.

Accordingly, in one embodiment, the $V_{D1}$ and $V_{D4}$ or $V_{D2}$ and $V_{D3}$ comprise a heavy chain variable domain and a light chain variable domain, each of them either defined by three CDR sequences or by heavy and light chain variable domain sequences of one the 13 so-called "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", and "9F6-G3" anti-CD123 antibodies as defined above, wherein $V_{D1}$ and $V_{D4}$, both comprise the three CDR sequences of the heavy and light chain variable domain sequences of one anti-CD123 antibody as defined above, if $V_{D2}$ and $V_{D3}$, both comprise three CDR sequences of heavy and light chain variable domain sequences of one of the anti-CD3 antibodies as defined above, or wherein $V_{D2}$ and $V_{D3}$, both comprise the three CDRs of the heavy and light chain variable domain sequences of one anti-CD123 antibody as defined above, if $V_{D1}$ and $V_{D4}$ comprise CDR sequences of heavy and light chain variable domain sequences of one of the anti-CD3 antibodies as defined above.

Accordingly, in one embodiment $V_{D1}$ and $V_{D4}$ are the variable domain of heavy or light chain of an anti-CD3 antibody, wherein said anti-CD3 antibody comprises a heavy chain variable domain comprising CDR1-H of sequence SEQ ID NO: 6, CDR2-H of sequence SEQ ID NO: 7, CDR3-H of sequence SEQ ID NO: 8 and a light chain variable domain comprising CDR1-L of sequence SEQ ID NO: 10 or SEQ ID NO: 142, CDR2-L of sequence 'KVS' and CDR3-L of sequence SEQ ID NO: 11 and $V_{D2}$ and $V_{D3}$ are the variable domain of heavy or light chain of an anti-CD123 antibody selected from the group consisting of "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", "9F6-G3" anti-CD123 antibodies as described above under the section "anti-CD123 antibodies", wherein $V_{D1}$ and $V_{D2}$ are both variable domains of light chains if $V_{D3}$ and $V_{D4}$ are both variable domains of heavy chains or $V_{D1}$ and $V_{D2}$ are both variable domains of heavy chains if $V_{D3}$ and $V_{D4}$ are both variable domains of light chains.

Accordingly, in a further embodiment $V_{D2}$ and $V_{D3}$ are the variable domain of heavy or light chain of an anti-CD3 antibody, wherein said anti-CD3 antibody comprises a heavy chain variable domain comprising CDR1-H of sequence SEQ ID NO: 6, CDR2-H of sequence SEQ ID NO: 7, CDR3-H of sequence SEQ ID NO: 8 and a light chain variable domain comprising CDR1-L of sequence SEQ ID NO: 10 or SEQ ID NO: 142, CDR2-L of sequence 'KVS' and CDR3-L of sequence SEQ ID NO: 11 and $V_{D1}$ and $V_{D4}$ are the variable domain of heavy or light chain of an anti-CD123 antibody selected from the group consisting of "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", "9F6-G3" anti-CD123 antibodies as described above under the section "anti-CD123 antibodies", wherein $V_{D1}$ and $V_{D2}$ are both variable domains of light chains if $V_{D3}$ and $V_{D4}$ are both variable domains of heavy chains or $V_{D1}$ and $V_{D2}$ are both variable domains of heavy chains if $V_{D3}$ and $V_{D4}$ are both variable domains of light chains.

Accordingly, in a further embodiment $V_{D1}$ and $V_{D4}$ are the variable domain of heavy or light chain of an anti-CD3 antibody, wherein said anti-CD3 antibody comprises a heavy chain variable domain comprising CDR1-H of sequence SEQ ID NO: 13, CDR2-H of sequence SEQ ID NO: 14, CDR3-H of sequence SEQ ID NO: 15 and a light chain variable domain comprising CDR1-L of sequence SEQ ID NO: 17 or SEQ ID NO: 184, CDR2-L of sequence 'KVS' and CDR3-L of sequence SEQ ID NO: 11 and $V_{D2}$ and $V_{D3}$ are the variable domain of heavy or light chain of an anti-CD123 antibody selected from the group consisting of "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", "9F6-G3" anti-CD123 antibodies as described above under the section "anti-CD123 antibodies", wherein $V_{D1}$ and $V_{D2}$ are both variable domains of light chains if $V_{D3}$ and $V_{D4}$ are both variable domains of heavy chains or $V_{D1}$ and $V_{D2}$ are both variable domains of heavy chains if $V_{D3}$ and $V_{D4}$ are both variable domains of light chains.

Accordingly, in a further embodiment $V_{D1}$ and $V_{D4}$ are the variable domain of heavy or light chain of an anti-CD3 antibody, wherein said anti-CD3 antibody comprises a heavy chain variable domain comprising CDR1-H of sequence SEQ ID NO: 13, CDR2-H of sequence SEQ ID NO: 14, CDR3-H of sequence SEQ ID NO: 15 and a light chain variable domain comprising CDR1-L of sequence SEQ ID NO: 17 or SEQ ID NO: 184, CDR2-L of sequence 'KVS' and CDR3-L of sequence SEQ ID NO: 11 and $V_{D2}$ and $V_{D3}$ are the variable domain of heavy or light chain of an anti-CD123 antibody selected from the group consisting of "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", "9F6-G3" anti-CD123 antibodies as described above under the section "anti-CD123 antibodies", wherein $V_{D1}$ and $V_{D2}$ are both variable domains of light chains if $V_{D3}$ and $V_{D4}$ are both variable domains of heavy chains or V$_{D1}$ and V$_{D2}$ are both variable domains of heavy chains if V$_{D3}$ and V$_{D4}$ are both variable domains of light chains.

In a further embodiment V$_{D1}$ and V$_{D4}$ are the variable domain of heavy or light chain of a humanized anti-CD3 antibody, wherein said anti-CD3 antibody comprises a heavy chain variable a heavy chain variable domain of sequence SEQ ID NO: 138 and/or a light chain variable domain of sequence SEQ ID NO: 143 and V$_{D2}$ and V$_{D3}$ are the variable domain of heavy or light chain of an anti-CD123 antibody selected from the group consisting of "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", "9F6-G3" anti-CD123 antibodies as described above under the section "anti-CD123 antibodies", wherein V$_{D1}$ and V$_{D2}$ are both variable domains of light chains if V$_{D3}$ and V$_{D4}$ are both variable domains of heavy chains or V$_{D1}$ and V$_{D2}$ are both variable domains of heavy chains if V$_{D3}$ and V$_{D4}$ are both variable domains of light chains.

In a further embodiment V$_{D2}$ and V$_{D3}$ are the variable domain of heavy or light chain of a humanized anti-CD3 antibody, wherein said anti-CD3 antibody comprises a heavy chain variable a heavy chain variable domain of sequence SEQ ID NO: 138 and/or a light chain variable domain of sequence SEQ ID NO: 143 and V$_{D1}$ and V$_{D4}$ are the variable domain of heavy or light chain of an anti-CD123 antibody selected from the group consisting of "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", "9F6-G3" anti-CD123 antibodies as described above under the section "anti-CD123 antibodies", wherein V$_{D1}$ and V$_{D2}$ are both variable domains of light chains if V$_{D3}$ and V$_{D4}$ are both variable domains of heavy chains or V$_{D1}$ and V$_{D2}$ are both variable domains of heavy chains if V$_{D3}$ and V$_{D4}$ are both variable domains of light chains.

In a further embodiment V$_{D1}$ and V$_{D4}$ are the variable domain of heavy or light chain of a humanized anti-CD3 antibody, wherein said anti-CD3 antibody comprises a heavy chain a heavy chain variable domain of sequence SEQ ID NO: 171 and/or a light chain variable domain of sequence SEQ ID NO: 158 and V$_{D2}$ and V$_{D3}$ are the variable domain of heavy or light chain of an anti-CD123 antibody selected from the group consisting of "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", "9F6-G3" anti-CD123 antibodies as described above under the section "anti-CD123 antibodies", wherein V$_{D1}$ and V$_{D2}$ are both variable domains of light chains if V$_{D3}$ and V$_{D4}$ are both variable domains of heavy chains or V$_{D1}$ and V$_{D2}$ are both variable domains of heavy chains if V$_{D3}$ and V$_{D4}$ are both variable domains of light chains.

In a further embodiment V$_{D2}$ and V$_{D3}$ are the variable domain of heavy or light chain of a humanized anti-CD3 antibody, wherein said anti-CD3 antibody comprises a heavy chain a heavy chain variable domain of sequence SEQ ID NO: 171 and/or a light chain variable domain of sequence SEQ ID NO: 158 and V$_{D1}$ and V$_{D4}$ are the variable domain of heavy or light chain of an anti-CD123 antibody selected from the group consisting of "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", "9F6-G3" anti-CD123 antibodies as described above under the section "anti-CD123 antibodies", wherein V$_{D1}$ and V$_{D2}$ are both variable domains of light chains if V$_{D3}$ and V$_{D4}$ are both variable domains of heavy chains or V$_{D1}$ and V$_{D2}$ are both variable domains of heavy chains if V$_{D3}$ and V$_{D4}$ are both variable domains of light chains.

In a further embodiment V$_{D1}$ and V$_{D4}$ are the variable domain of heavy or light chain of a humanized anti-CD3 antibody, wherein said anti-CD3 antibody comprises a heavy chain a heavy chain variable domain of sequence SEQ ID NO: 176 and/or a light chain variable domain of sequence SEQ ID NO: 164 and V$_{D2}$ and V$_{D3}$ are the variable domain of heavy or light chain of an anti-CD123 antibody selected from the group consisting of "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", "9F6-G3" anti-CD123 antibodies as described above under the section "anti-CD123 antibodies", wherein V$_{D1}$ and V$_{D2}$ are both variable domains of light chains if V$_{D3}$ and V$_{D4}$ are both variable domains of heavy chains or V$_{D1}$ and V$_{D2}$ are both variable domains of heavy chains if V$_{D3}$ and V$_{D4}$ are both variable domains of light chains.

In a further embodiment V$_{D2}$ and V$_{D3}$ are the variable domain of heavy or light chain of a humanized anti-CD3 antibody, wherein said anti-CD3 antibody comprises a heavy chain a heavy chain variable domain of sequence SEQ ID NO: 176 and/or a light chain variable domain of sequence SEQ ID NO: 164 and V$_{D1}$ and V$_{D4}$ are the variable domain of heavy or light chain of an anti-CD123 antibody selected from the group consisting of "3E3-D3", "1E1-G5", "2B8-F3", "2F8-D6", "3B10-E6", "5A5-B4", "6B10-E4", "6C10-C4", "6D6-B8", "8B11-B7", "9B8-G6", "9D7-C8", "9F6-G3" anti-CD123 antibodies as described above under the section "anti-CD123 antibodies", wherein V$_{D1}$ and V$_{D2}$ are both variable domains of light chains if V$_{D3}$ and V$_{D4}$ are both variable domains of heavy chains or V$_{D1}$ and V$_{D2}$ are both variable domains of heavy chains if V$_{D3}$ and V$_{D4}$ are both variable domains of light chains.

According to a further aspect of the invention, the first or second immunoglobulin is the anti-CD123 antibody 7G3. Therefore, in one embodiment V$_{D1}$ and V$_{D4}$ or V$_{D2}$ and V$_{D3}$ comprise a heavy chain variable domain and a light chain variable domain as defined by CDR sequences of heavy and light chain variable domain sequences of the antibody 7G3 as defined herein below. In one embodiment V$_{D1}$ and V$_{D4}$, or V$_{D2}$ and V$_{D3}$ comprise a heavy chain variable domain and a light chain variable domain of the antibody 7G3 as described in the patent application WO2013/173820, which is incorporated herein by reference.

Accordingly, the so-called "7G3" anti-CD123 antibody as herein used comprises:
a heavy chain variable domain consisting of sequence EVQLQQSGPELVKPGASVKMSCK-ASGYTFTDYYMKWVKQSHGKSLEWIG-DIIPSNGA TFYNQKFKGKATLTVDRSSSTAYMHLNSLTSED-SAVYYCTRSHLLRASWFAYWGQGT LVTVSA (SEQ ID NO: 312, with CDRs shown in bold characters) comprising CDR1-H of sequence SEQ ID NO: 375, a CDR2-H of sequence SEQ ID NO: 376, and a CDR3-H of sequence SEQ ID NO: 377 and
a light chain variable domain consisting of sequence DFVMTQSPSSLTVTAGEKVTMSCK-SSQSLLNSGNQKNYLTWYLQKPGQPPKLLIYWA STRESGVPDRFTGSGSGTDFTLTISSVQAED-LAVYYCQNDYSYPYTFGGGTKLEIK (SEQ ID NO: 308, with CDRs shown in bold characters) comprising CDR1-L of sequence SEQ ID NO: 378, a CDR2-L of sequence WAS', and a CDR3-L of sequence SEQ ID NO: 379.

In a further aspect of the invention, the antibody 7G3 may also be a humanized antibody or a fragment of a humanized antibody. Accordingly, in one embodiment, the antibody 7G3 of the invention is a humanized antibody comprising a heavy chain variable domain consisting of sequence EVQLVQSGAEVKKPGESLKIS-CKGSGYSFTDYYMKWARQMPGKGLEWMG-DIIPSNGA TFYNQKFKGQVTISADKSIST-TYLQWSSLKASDTAMYYCARSHLLRASWFAY WGQGT MVTVSS (SEQ ID NO: 380, with CDRs shown in bold characters) comprising CDR1-H of sequence SEQ ID NO: 381, a CDR2-H of sequence SEQ ID NO: 377, and a CDR3-H of sequence SEQ ID NO: 382, or a heavy chain variable domain consisting of sequence EVQLVQSGAEVKKPGESLKISCKGSGYSFTDYYMK-WARQMPGKGLEWMGDIIPSSGA TFYNQKFKGQVTI-SADKSISTTYLQWSSLKASDTAMYYCARSHLLRAS-WFAYWGQGT MVTVSS (SEQ ID NO: 383, with CDRs shown in bold characters) comprising CDR1-H of sequence SEQ ID NO: 381, a CDR2-H of sequence SEQ ID NO: 384, and a CDR3-H of sequence SEQ ID NO: 382, or a light chain variable domain consisting of sequence DIVMTQSPDSLAVSLGERATIN-CESSQSLLNSGNQKNYLTWYQQKPGQPPKPLIY-WAS TRESGVPDRFSGSGSGTDFTLTISSLQAE-DVAVYYCQNDYSYPYTFGQGTKLEIK (SEQ ID NO: 385, with CDRs shown in bold characters) comprising CDR1-L of sequence SEQ ID NO: 378, a CDR2-L of sequence WAS', and a CDR3-L of sequence SEQ ID NO: 379.

In one embodiment, the antibody-like binding protein that binds specifically to human CD3ε and human CD123 comprises a) a light chain variable domain of a first immunoglobulin ($V_{D1}$) consisting of the amino acid sequence SEQ ID NO: 9 or a sequence at least 85% identical thereto, a light chain variable domain of a second immunoglobulin ($V_{D2}$) consisting of the amino acid sequence SEQ ID NO: 308 or a sequence at least 85% identical thereto, a heavy chain variable domain of the second immunoglobulin ($V_{D3}$) consisting of the amino acid sequence SEQ ID NO: 312 or a sequence at least 85% identical thereto and a heavy chain variable domain of the first immunoglobulin ($V_{D4}$) consisting of the amino acid sequence SEQ ID NO: 5 or a sequence at least 85% identical thereto, or b) a light chain variable domain of a first immunoglobulin (VA consisting of the amino acid sequence SEQ ID NO: 21 or a sequence at least 85% identical thereto, a light chain variable domain of a second immunoglobulin ($V_{D2}$) consisting of the amino acid sequence SEQ ID NO: 308 or a sequence at least 85% identical thereto, a heavy chain variable domain of the second immunoglobulin ($V_{D3}$) consisting of the amino acid sequence SEQ ID NO: 312 or a sequence at least 85% identical thereto and a heavy chain variable domain of the first immunoglobulin ($V_{D4}$) consisting of the amino acid sequence SEQ ID NO: 18 or a sequence at least 85% identical thereto, or c) a light chain variable domain of a first immunoglobulin (VA consisting of the amino acid sequence SEQ ID NO: 16 or a sequence at least 85% identical thereto, a light chain variable domain of a second immunoglobulin ($V_{D2}$) consisting of the amino acid sequence SEQ ID NO: 308 or a sequence at least 85% identical thereto, a heavy chain variable domain of the second immunoglobulin ($V_{D3}$) consisting of the amino acid sequence SEQ ID NO: 312 or a sequence at least 85% identical thereto and a heavy chain variable domain of the first immunoglobulin ($V_{D4}$) consisting of the amino acid sequence SEQ ID NO 12 or a sequence at least 85% identical thereto, or d) a light chain variable domain of a first immunoglobulin (VA consisting of the amino acid sequence SEQ ID NO: 26 or a sequence at least 85% identical thereto, a light chain variable domain of a second immunoglobulin ($V_{D2}$) consisting of the amino acid sequence SEQ ID NO: 308 or a sequence at least 85% identical thereto, a heavy chain variable domain the second immunoglobulin ($V_{D3}$) consisting of the amino acid sequence SEQ ID NO: 312 or a sequence at least 85% identical thereto and a heavy chain variable domain of the first immunoglobulin ($V_{D4}$) consisting of the amino acid sequence SEQ ID NO: 23 or a sequence at least 85% identical thereto, or e) a light chain variable domain of a first immunoglobulin (VA consisting of the amino acid sequence SEQ ID NO: 308 or a sequence at least 85% identical thereto, a light chain variable domain of a second immunoglobulin ($V_{D2}$) consisting of the amino acid sequence SEQ ID NO: 143 or a sequence at least 85% identical thereto, a heavy chain variable domain of the second immunoglobulin ($V_{D3}$) consisting of the amino acid sequence SEQ ID NO: 138 or a sequence at least 85% identical thereto and a heavy chain variable domain of the first immunoglobulin ($V_{D4}$) consisting of the amino acid sequence SEQ ID NO: 312 or a sequence at least 85% identical thereto, or f) a light chain variable domain of a first immunoglobulin (VA consisting of the amino acid sequence SEQ ID NO: 158 or a sequence at least 85% identical thereto, a light chain variable domain of a second immunoglobulin ($V_{D2}$) consisting of the amino acid sequence SEQ ID NO: 308 or a sequence at least 85% identical thereto, a heavy chain variable domain of the second immunoglobulin ($V_{D3}$) consisting of the amino acid sequence SEQ ID NO: 312 or a sequence at least 85% identical thereto and a heavy chain variable domain of a first immunoglobulin ($V_{D4}$) consisting of the amino acid sequence SEQ ID NO: 171 or a sequence at least 85% identical thereto, g) a light chain variable domain of a first immunoglobulin (VA consisting of the amino acid sequence SEQ ID NO: 230 or a sequence at least 85% identical thereto, a light chain variable domain of a second immunoglobulin ($V_{D2}$) consisting of the amino acid sequence SEQ ID NO: 158 or a sequence at least 85% identical thereto, a heavy chain variable domain of the second immunoglobulin ($V_{D3}$) consisting of the amino acid sequence SEQ ID NO: 171 or a sequence at least 85% identical thereto and a heavy chain variable domain of the first immunoglobulin ($V_{D4}$) consisting of the amino acid sequence SEQ ID NO: 226 or a sequence at least 85% identical thereto, h) a light chain variable domain of a first immunoglobulin ($V_{D1}$) consisting of the amino acid sequence SEQ ID NO: 385 or a sequence at least 85% identical thereto, a light chain variable domain of a second immunoglobulin ($V_{D2}$) consisting of the amino acid sequence SEQ ID NO: 141 or a sequence at least 85% identical thereto, a heavy chain variable domain of the second immunoglobulin ($V_{D3}$) consisting of the amino acid sequence SEQ ID NO: 138 or a sequence at least 85% identical thereto and a heavy chain variable domain of the first immunoglobulin ($V_{D4}$) consisting of the amino acid sequence SEQ ID NO: 383 or a sequence at least 85% identical thereto.

In said above sequence at least 85% identical to a reference sequence (e.g. a sequence at least 85% identical to SEQ ID NO: 383 or SEQ ID NO: 385), the sequences of the 6 CDRs are unchanged compared to the 6 CDRs present in the reference sequence.

In one embodiment the antibody binding protein according to any of the definitions a) to g) further comprises the linker $L_1$ of sequence SEQ ID NO: 307, $L_2$ of sequence SEQ ID NO: 309, $L_3$ of the amino acid sequence 'S', $L_4$ of the amino acid sequence 'RT' and $C_{H1}$ of sequence SEQ ID NO: 313.

In one embodiment, the antibody binding protein according to any of the definitions a) to g) further comprises $F_{c2}$ of sequence SEQ ID NO: 327.

In one embodiment, the antibody binding protein according to definition h) further comprises the linker $L_1$ of sequence SEQ ID NO: 389, $L_2$ of sequence SEQ ID NO: 389, $L_3$ and $L_4$ consisting of 0 amino acid, and $C_{H1}$ of sequence SEQ ID NO: 313.

In one embodiment, the antibody binding protein according to definition h) further comprises $F_{c2}$ of sequence SEQ ID NO: 392.

In one embodiment, $L_5$ of the antibody binding protein according to any of the definitions a) to h) contains 0 amino acids.

In a further embodiment the antibody binding protein according to any of the definitions a) to g) further comprises the linker $L_1$ of sequence SEQ ID NO: 307, $L_2$ of sequence SEQ ID NO: 309, $L_3$ of the amino acid sequence 'S', $L_4$ of the amino acid sequence 'RT', $C_{H1}$ of sequence SEQ ID NO: 329 and $F_c$ of sequence SEQ ID NO: 330.

In a further embodiment, the antibody binding protein according to definition h) further comprises the linker $L_1$ of sequence SEQ ID NO: 389, $L_2$ of sequence SEQ ID NO: 389, $L_3$ and $L_4$ consisting of 0 amino acid, $C_{H1}$ of sequence SEQ ID NO: 313 and $F_c$ of sequence SEQ ID NO: 394.

In a further embodiment, the antibody binding protein according to definition h) further comprises a Fc stump of sequence SEQ ID NO: 397 or SEQ ID NO: 398, or a sequence at least 85% identical to SEQ ID NO: 397 or SEQ ID NO: 398.

In an embodiment, the antibody binding protein that binds specifically to human CD3ε and human CD123 comprises, or essentially consists of:
a) one polypeptide of formula [I] consisting of sequence SEQ ID NO: 388 ($V_{D1}$ of sequence SEQ ID NO: 385, $L_1$ of sequence SEQ ID NO: 389, $V_{D2}$ of sequence SEQ ID NO: 141, $L_2$ of sequence SEQ ID NO: 389 and $C_L$ of sequence SEQ ID NO: 310),
or a sequence at least 85% identical to SEQ ID NO: 388 in which the 3 CDRs of sequences SEQ ID NO: 378, WAS' and SEQ ID NO: 379 of hz7G3 light chain variable domain ($V_{D1}$ of sequence SEQ ID NO: 385), and the 3 CDRs of sequences. SEQ ID NO:142, 'KVS' and SEQ ID NO:11 of hz20G6 light chain variable domain ($V_{D2}$ of sequence SEQ ID NO: 141) are unaltered; and
b) one polypeptide of formula [II] consisting of sequence SEQ ID NO: 390 ($V_{D3}$ of sequence SEQ ID NO: 138, $L_3$ is 0 amino acid, $V_{D4}$ of sequence SEQ ID NO: 383, $L_4$ is 0 amino acid and $C_{H1}$ of sequence SEQ ID NO: 313), or
a sequence at least 85% identical to SEQ ID NO: 390 in which the 3 CDRs of sequences SEQ ID NO:381, SEQ ID NO:384, and SEQ ID NO: 382 of the hz7G3 heavy chain variable domain ($V_{D4}$ of sequence SEQ ID NO: 383), and the 3 CDRs of sequences SEQ ID NO: 6, SEQ ID NO: 7, SEQ ID NO: 8 of hz20G6 heavy chain variable domain ($V_{D3}$ of sequence SEQ ID NO: 138) are unaltered;

and wherein the polypeptide of formula [I] and the polypeptide of formula [II] form a cross-over light chain-heavy chain pair.

In an embodiment, the antibody binding protein that binds specifically to human CD3ε and human CD123 comprises, or essentially consists of:
a) one polypeptide according to formula [IV] of the amino acid sequence SEQ ID NO: 391 ($V_{D1}$ of sequence SEQ ID NO: 385, $L_1$ of sequence SEQ ID NO: 389, $V_{D2}$ of sequence SEQ ID NO: 141, $L_2$ of sequence SEQ ID NO: 389, $C_L$ of sequence SEQ ID NO: 310, $L_5$ which contains 0 amino acid, and $F_{c2}$ of sequence SEQ ID NO: 392), or
a sequence at least 85% identical to SEQ ID NO: 391 in which the 3 CDRs of sequences SEQ ID NO: 378, WAS' and SEQ ID NO: 379 of hz7G3 light chain variable domain ($V_{D1}$ of sequence SEQ ID NO: 385), and the 3 CDRs of sequences. SEQ ID NO:142, 'KVS' and SEQ ID NO:11 of hz20G6 light chain variable domain ($V_{D2}$ of sequence SEQ ID NO: 141) are unaltered; and
b) one polypeptide according to formula [III] of the amino acid sequence SEQ ID NO: 393 ($V_{D3}$ of sequence SEQ ID NO: 138, $L_3$ is 0 amino acid, $V_{D4}$ of sequence SEQ ID NO: 383, $L_4$ is 0 amino acid, $C_{H1}$ of sequence SEQ ID NO: 313, and $F_c$ of sequence SEQ ID NO: 394), or
a sequence at least 85% identical to SEQ ID NO: 393 in which the 3 CDRs of sequences SEQ ID NO:381, SEQ ID NO:384, and SEQ ID NO: 382 of the hz7G3 heavy chain variable domain ($V_{D4}$ of sequence SEQ ID NO: 383), and the 3 CDRs of sequences SEQ ID NO: 6, SEQ ID NO: 7, SEQ ID NO: 8 of hz20G6 heavy chain variable domain ($V_{D3}$ of sequence SEQ ID NO: 138) are unaltered;

and wherein the polypeptide of formula [IV] and the polypeptide of formula [III] form a cross-over light chain-heavy chain pair.

In said antibody like binding protein, the polypeptide chains represented by the formulae [III] and [IV] dimerize through their respective $F_{c2}$ and $F_c$ regions.

In an embodiment, the antibody binding protein that binds specifically to human CD3ε and human CD123 comprises, or essentially consists of:
a) one polypeptide according to formula [I] consisting of the amino acid sequence SEQ ID NO: 388 ($V_{D1}$ of sequence SEQ ID NO: 385, $L_1$ of sequence SEQ ID NO: 389, $V_{D2}$ of sequence SEQ ID NO: 141, $L_2$ of sequence SEQ ID NO: 389 and $C_L$ of sequence SEQ ID NO: 310) or
a sequence at least 85% identical to SEQ ID NO: 388 in which the 3 CDRs of sequences SEQ ID NO: 378, WAS' and SEQ ID NO: 379 of hz7G3 light chain variable domain ($V_{D1}$ of sequence SEQ ID NO: 385), and the 3 CDRs of sequences. SEQ ID NO:142, 'KVS' and SEQ ID NO:11 of hz20G6 light chain variable domain ($V_{D2}$ of sequence SEQ ID NO: 141) are unaltered; and
b) one polypeptide according to formula [III] of the amino acid sequence SEQ ID NO: 395 ($V_{D3}$ of sequence SEQ ID NO: 138, $L_3$ is 0 amino acid, $V_{D4}$ of sequence SEQ ID NO: 383, $L_4$ is 0 amino acid, $C_{H1}$ of sequence SEQ ID NO: 313, and $F_c$ of sequence SEQ ID NO: 396), or
a sequence at least 85% identical to SEQ ID NO: 395 in which the 3 CDRs of sequences SEQ ID NO:381, SEQ ID NO:384, and SEQ ID NO: 382 of the hz7G3 heavy chain variable domain ($V_{D4}$ of sequence SEQ ID NO: 383), and the 3 CDRs of sequences SEQ ID NO: 6, SEQ ID NO: 7, SEQ ID NO: 8 of hz20G6 heavy chain variable domain ($V_{D3}$ of sequence SEQ ID NO: 138) are unaltered; and
c) one Fc stump (polypeptide $F_{c3}$) of the amino acid sequence SEQ ID NO: 397, or a sequence at least 85% identical thereto, wherein said $F_3$ stump or the sequence at least 85% identical thereto heterodimerises with the $F_c$ region of the polypeptide according to formula [III]; and wherein the polypeptide of formula [I] and the polypeptide of formula [III] form a cross-over light chain-heavy chain pair.

In an embodiment, the antibody binding protein that binds specifically to human CD3ε and human CD123 comprises, or essentially consists of:
a) one polypeptide according to formula [I] consisting of the amino acid sequence SEQ ID NO: 388 ($V_{D1}$ of sequence SEQ ID NO: 385, $L_1$ of sequence SEQ ID NO: 389, $V_{D2}$ of sequence SEQ ID NO: 141, $L_2$ of sequence SEQ ID NO: 389 and $C_L$ of sequence SEQ ID NO: 310) or
a sequence at least 85% identical to SEQ ID NO: 388 in which the 3 CDRs of sequences SEQ ID NO: 378, WAS' and SEQ ID NO: 379 of hz7G3 light chain variable domain ($V_{D1}$ of sequence SEQ ID NO: 385), and the 3 CDRs of sequences. SEQ ID NO:142, 'KVS' and SEQ ID NO:11 of hz20G6 light chain variable domain ($V_{D2}$ of sequence SEQ ID NO: 141) are unaltered;
b) a polypeptide according to formula III of the amino acid sequence SEQ ID NO: 399 ($V_{D3}$ of sequence SEQ ID NO: 138, $L_3$ is 0 amino acid, $V_{D4}$ of sequence SEQ ID NO: 383, $L_4$ is 0 amino acid, $C_{H1}$ of sequence SEQ ID NO: 313, and $F_c$ of sequence SEQ ID NO: 400), or
a sequence at least 85% identical thereto in which the 3 CDRs of sequences SEQ ID NO:381, SEQ ID NO:384, and SEQ ID NO: 382 of the hz7G3 heavy chain variable domain ($V_{D4}$ of sequence SEQ ID NO: 383), and the 3 CDRs of sequences SEQ ID NO: 6, SEQ ID NO: 7, SEQ ID NO: 8 of hz20G6 heavy chain variable domain ($V_{D3}$ of sequence SEQ ID NO: 138) are unaltered; and
c) one Fc stump (polypeptide $F_{c3}$) of the amino acid sequence SEQ ID NO: 398, or a sequence at least 85% identical thereto, wherein said $F_3$ stump or the sequence at least 85% identical thereto heterodimerises with the Fc region of the polypeptide according to formula [III]; and wherein the polypeptide of formula [I] and the polypeptide of formula [III] form a cross-over light chain-heavy chain pair.

Immunoconjugates

In one embodiment, the anti-CD123 antibody of the invention is conjugated or linked to a growth inhibitory agent, cytotoxic agent, or a prodrug-activating enzyme. In particular, anti-CD123 antibodies of the invention are indeed useful for targeting said growth inhibitory agent, cytotoxic agent, or a prodrug to the cancerous cells expressing or over-expressing CD123 on their surface.

Nucleic Acids, Vectors and Recombinant Host Cells

A further object of the invention relates to a nucleic acid sequence comprising or consisting of a sequence encoding an anti-CD3 antibody, anti-CD123 antibody or an antibody-like binding protein as defined above.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a cell which has been transfected, infected or transformed by a nucleic acid and/or a vector according to the invention.

The term "transformation" means the introduction of a "foreign" (i.e. extrinsic) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce a recombinant antibody of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. The YB2/0 cell is preferred, since ADCC activity of chimeric or humanized antibodies is enhanced when expressed in this cell.

In particular, for expression of humanized antibody or antibody-like binding protein, the expression vector may be either of a type in which a gene encoding an antibody heavy chain and a gene encoding an antibody light chain exists on separate vectors or of a type in which both genes exist on the same vector (tandem type). In respect of easiness of construction of a humanized antibody and antibody-like binding protein expression vector, easiness of introduction into animal cells, and balance between the expression levels of antibody H and L chains in animal cells, humanized antibody expression vector of the tandem type is preferred (Shitara K et al. J Immunol Methods. 1994 Jan. 3; 167(1-2):271-8). Examples of tandem type humanized antibody expression vector include pKANTEX93 (WO 97/10354), pEE18 and the like.

The present invention also relates to a method of producing a recombinant host cell expressing an anti-CD3 antibody, anti-CD123 antibody or an antibody-like binding protein according to the invention, said method comprising the steps consisting of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody.

Such recombinant host cells can be used for the production of anti-CD3 antibody, at least one anti-CD123 antibody or at least one antibody-like binding protein of the invention. Methods of Producing Antibodies Antibody-Like Binding Protein of the Invention One embodiment of the invention provides a method for making an antibody-like binding protein comprising two polypeptide chains that form two antigen-binding sites, wherein a first polypeptide has a structure represented by the formula [I]:

$$V_{D1}\text{-}L_1\text{-}V_{D2}\text{-}L_2\text{-}C_L \qquad [I]$$

and a second polypeptide has a structure represented by the formula [II]:

$$V_{D3}\text{-}L_3\text{-}V_{D4}\text{-}L_4\text{-}C_{H1} \qquad [II]$$

wherein:
$V_{D1}$ is a variable domain of heavy or light chain of a first immunoglobulin;
$V_{D2}$ is a variable domain of heavy or light chain of a second immunoglobulin;
$V_{D3}$ is a variable domain of heavy or light chain of said second immunoglobulin;
$V_{D4}$ is a variable domain of heavy or light chain of said first immunoglobulin;
$C_L$ is a light chain constant domain of an immunoglobulin;
$C_{H1}$ is a $C_{H1}$ heavy chain constant domain of an immunoglobulin;
$L_1$, $L_2$, $L_3$, and $L_4$ are amino acid linkers;
and wherein the first and the second polypeptide form a cross-over light chain-heavy chain pair, and
wherein $V_{D1}$ and $V_{D2}$ are both either variable domains of light chains, or variable domains of heavy chains, and $V_{D3}$ and $V_{D4}$ are both variable domains of heavy chains if $V_{D1}$ and $V_{D2}$ are variable domains of light chains, or $V_{D3}$ and $V_{D4}$ are both variable domains of light chains if $V_{D1}$ and $V_{D2}$ are variable domains of heavy chains.

In a further embodiment, the invention provides a method for making an antibody-like binding protein comprising four polypeptide chains that form four antigen-binding sites, wherein two polypeptide chains have a structure represented by the formula [I]:

$$V_{D1}\text{-}L_1\text{-}V_{D2}\text{-}L_2\text{-}C_L \qquad [I]$$

and two polypeptide chains have a structure represented by the formula (III):

$$V_{D3}\text{-}L_3\text{-}V_{D4}\text{-}L_4\text{-}C_{H1}\text{-}F_c \qquad [III]$$

wherein:
$V_{D1}$ is a variable domain of heavy or light chain of a first immunoglobulin;
$V_{D2}$ is a variable domain of heavy or light chain of a second immunoglobulin;
$V_{D3}$ is a variable domain of heavy or light chain of said second immunoglobulin;
$V_{D4}$ is a variable domain of heavy or light chain of said first immunoglobulin;
$C_L$ is a light chain constant domain of an immunoglobulin;
$C_{H1}$ is a $C_{H1}$ heavy chain constant domain of an immunoglobulin;
$F_c$ is the immunoglobulin hinge region and $CH_2$, $CH_3$ immunoglobulin heavy chain constant domains of an immunoglobulin;
$L_1$, $L_2$, $L_3$, and $L_4$ are amino acid linkers;
and wherein the polypeptides of formula I and the polypeptides of formula III form a cross-over light chain-heavy chain pair, and
wherein $V_{D1}$ and $V_{D2}$ are both either variable domains of light chains, or variable domains of heavy chains, and $V_{D3}$ and $V_{D4}$ are both variable domains of heavy chains if $V_{D1}$ and $V_{D2}$ are variable domains of light chains, or $V_{D3}$ and $V_{D4}$ are both variable domains of light chains if $V_{D1}$ and $V_{D2}$ are variable domains of heavy chains.

In a further embodiment, the invention provides a method for making an antibody-like binding protein comprising four polypeptide chains that form four antigen-binding sites, wherein two polypeptide chains have a structure represented by the formula [IV]:

$$V_{D1}\text{-}L_1\text{-}V_{D2}\text{-}L_2\text{-}C_L\text{-}L_5\text{-}F_{c2} \qquad [IV]$$

and two polypeptide chains have a structure represented by the formula [III]:

$$V_{D3}\text{-}L_3\text{-}V_{D4}\text{-}L_4\text{-}C_{H1}\text{-}F_c \qquad [III]$$

wherein:
$V_{D1}$ is a variable domain of heavy or light chain of a first immunoglobulin;

$V_{D2}$ is a variable domain of heavy or light chain of a second immunoglobulin;

$V_{D3}$ is a variable domain of heavy or light chain of said second immunoglobulin;

$V_{D4}$ is a variable domain of heavy or light chain of said first immunoglobulin;

$C_L$ is a light chain constant domain of an immunoglobulin;

$C_{H1}$ is a $C_{H1}$ heavy chain constant domain of an immunoglobulin;

$F_c$ is the immunoglobulin hinge region and $CH_2$, $CH_3$ immunoglobulin heavy chain constant domains of an immunoglobulin;

$F_{c2}$ is the immunoglobulin hinge region and $CH_2$, $CH_3$ immunoglobulin heavy chain constant domains of an immunoglobulin;

$L_1$, $L_2$, $L_3$, $L_4$ and $L_5$ are amino acid linkers;

and wherein the polypeptides of formula I and the polypeptides of formula III form a cross-over light chain-heavy chain pair, and wherein $V_{D1}$ and $V_{D2}$ are both either variable domains of light chains, or variable domains of heavy chains, and $V_{D3}$ and $V_{D4}$ are both variable domains of heavy chains if $V_{D1}$ and $V_{D2}$ are variable domains of light chains, or $V_{D3}$ and $V_{D4}$ are both variable domains of light chains if $V_{D1}$ and $V_{D2}$ are variable domains of heavy chains.

In one embodiment of the invention, the first immunoglobulin or the second immunoglobulin is one anti-CD3 antibody as defined in the section «anti-CD3 antibodies» above.

In another embodiment of the invention, the first immunoglobulin or the second immunoglobulin is one anti-CD123 antibody as defined in the section «anti-CD123 antibodies» above.

An Anti-CD3 antibody, anti-CD123 antibody and/or antibody-like binding proteins of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies or immunoglobulin chains, by standard techniques for production of polypeptides. For instance, they can be synthesized using well-known solid phase method, in particular using a commercially available peptide synthesis apparatus (such as that made by Applied Biosystems, Foster City, Calif.) and following the manufacturer's instructions. Alternatively, antibodies, immunoglobulin chains and antibody-like binding proteins of the invention can be synthesized by recombinant DNA techniques as is well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

In particular, the invention further relates to a method of producing anti-CD3 antibodies, anti-CD123 antibodies and/or antibody-like binding proteins of the invention, which method comprises the steps consisting of: (i) culturing a transformed host cell according to the invention; (ii) expressing said antibody or polypeptide; and (iii) recovering the expressed antibody or polypeptide.

Anti-CD3 antibodies, anti-CD123 antibodies and/or antibody-like binding proteins of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, a humanized chimeric anti-CD3 antibodies and/or anti-CD123 of the present invention can be produced by obtaining nucleic sequences encoding humanized VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. In analogy thereto, a humanized antibody-like binding protein can be obtained by using for the variable domain of heavy or light chain of a first humanized immunoglobulin ($V_{D1}$), for the variable domain of heavy or light chain of a second humanized immunoglobulin ($V_{D2}$), for the variable domain of heavy or light chain of said second immunoglobulin ($V_{D3}$), and for the variable domain of heavy or light chain of said first immunoglobulin the variable domains of the heavy and light chains of two humanized antibodies.

As the CH domain of a human chimeric antibody or the CH domain of antibody-like binding protein of the invention, it may be any region which belongs to human immunoglobulin heavy chains, but those of IgG class are suitable and any one of subclasses belonging to IgG class, such as IgG1, IgG2, IgG3 and IgG4, can also be used. Also, as the CL of a human chimeric antibody or the CL of an antibody-like binding protein of the invention, it may be any region which belongs to human immunoglobulin light chains, and those of kappa class or lambda class can be used.

Methods for producing humanized or chimeric antibodies involve conventional recombinant DNA and gene transfection techniques are well known in the art (See Morrison S L. et al. (1984) and patent documents U.S. Pat. Nos. 5,202,238; and 5,204,244).

Methods for producing humanized antibodies based on conventional recombinant DNA and gene transfection techniques are well known in the art (See, e. g., Riechmann L. et al. 1988; Neuberger M S. et al. 1985). Antibodies can be humanized using a variety of techniques known in the art including, for example, the technique disclosed in the application WO2009/032661, CDR-grafting (EP 239,400; PCT publication WO91/09967; U.S. Pat. Nos. 5,225,539; 5,530, 101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with CD3 or CD123 with a protease, such as papaine. Also, the Fab can be produced by inserting DNA sequences encoding both chains of the Fab of the antibody into a vector for prokaryotic expression, or for eukaryotic expression, and introducing the vector into procaryotic or eukaryotic cells (as appropriate) to express the Fab.

The F(ab')2 of the present invention can be obtained treating an antibody which specifically reacts with CD3 or CD123 with a protease, pepsin. Also, the F(ab')2 can be produced by binding Fab' described below via a thioether bond or a disulfide bond.

The Fab' of the present invention can be obtained treating F(ab')2 which specifically reacts with CD3 or CD123 with a reducing agent, such as dithiothreitol. Also, the Fab' can be produced by inserting DNA sequences encoding Fab' chains of the antibody into a vector for prokaryotic expression, or a vector for eukaryotic expression, and introducing the vector into prokaryotic or eukaryotic cells (as appropriate) to perform its expression.

The scFv of the present invention can be produced by taking sequences of the CDRs or VH and VL domains as previously described, constructing a DNA encoding an scFv fragment, inserting the DNA into a prokaryotic or eukaryotic expression vector, and then introducing the expression vector into prokaryotic or eukaryotic cells (as appropriate) to express the scFv. To generate a humanized scFv fragment, a well known technology called CDR grafting may be used, which involves selecting the complementary determining regions (CDRs) according to the invention, and grafting them onto a human scFv fragment framework of known three dimensional structure (see, e. g., WO98/45322; WO 87/02671; U.S. Pat. Nos. 5,859,205; 5,585,089; 4,816,567; EP0173494).

Modification of the Antibodies of the Invention

Amino acid sequence modification(s) of the antibodies or antibody-like binding proteins as described herein are contemplated. For example, it may be desirable to improve the binding affinity and/or other biological properties of the antibody nor or antibody-like binding protein. For instance, it is known that when a humanized antibody is produced by simply grafting only CDRs in VH and VL of an antibody derived from a non-human animal in FRs of the VH and VL of a human antibody, the antigen binding activity may be reduced in comparison with that of the original antibody derived from a non-human animal. It is considered that several amino acid residues of the VH and VL of the non-human antibody, not only in CDRs but also in FRs, may be directly or indirectly associated with the antigen binding activity. Hence, substitution of these amino acid residues with different amino acid residues derived from FRs of the VH and VL of the human antibody would reduce the binding activity. In order to solve the problem, in human antibodies grafted with non-human CDRs, attempts have to be made to identify, among amino acid sequences of the FR of the VH and VL of human antibodies, an amino acid residue which is directly associated with binding of the antibody, or which interacts with an amino acid residue of a CDR, or which maintains the three-dimensional structure of the antibody and which is directly associated with binding to the antigen. The reduced antigen binding activity could be increased by replacing the identified amino acids with amino acid residues of the original antibody derived from a non-human animal. An antibody-like binding protein of the invention may comprise the variable regions of a humanized antibody and therefore herein mentioned considerations apply equally to antibody-like binding proteins of the invention.

Modifications and changes may be made in the structure of the antibodies of the present invention, and in the DNA sequences encoding them, and still result in a functional antibody, antibody-like binding protein or polypeptide with desirable characteristics.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate −3.5); asparagine (−3.5); lysine (−3.9); and arginine (−4.5).

A further object of the present invention also encompasses function-conservative variants of the polypeptides of the anti-CD3 antibodies, anti-CD123 antibodies and antibody-like binding proteins of the present invention.

For example, certain amino acids may be substituted by other amino acids in a protein structure without appreciable loss of activity. Since the interactive capacity and nature of a protein define its biological functional activity, certain amino acid substitutions can be made in a protein sequence, and of course in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

It is known in the art that certain amino acids may be substituted by other amino acids having a similar hydropathic index or score and still result in a protein with similar biological activity, i.e. still obtain a biological functionally equivalent protein. It is also possible to use well-established technologies, such as alanine-scanning approaches, to identify, in an antibody or polypeptide of the invention, all the amino acids that can be substituted without significant loss of binding to the antigen. Such residues can be qualified as neutral, since they are not involved in antigen binding or in maintaining the structure of the antibody. One or more of these neutral positions can be substituted by alanine or by another amino acid can without changing the main characteristics of the antibody or polypeptide of the invention.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

It may be also desirable to modify the anti-CD3 antibody, anti-CD123 antibody and antibody-like binding protein of the present invention with respect to effector function, e.g. so as to enhance or reduce antigen-dependent cell-mediated cytotoxicity (ADCC) and/or complement dependent cytotoxicity (CDC) of the antibody. This may be achieved by introducing one or more amino acid substitutions in an Fc region of the antibody, herein also called Fc-variants in context with the antibody-like binding proteins of the present invention. Alternatively or additionally, cysteine residue(s) may be introduced in the Fc region, thereby allowing inter-chain disulfide bond formation in this region. The homodimeric antibody thus generated may have improved or reduced internalization capability and/or increased complement-mediated cell killing and/or antibody-dependent cellular cytotoxicity (ADCC) (Caron P C. et al. 1992; and Shopes B. 1992).

Another type of amino acid modification of the anti-CD3 antibody, anti-CD123 antibody and antibody-like binding protein of the invention may be useful for altering the original glycosylation pattern of the anti-CD3 antibody, anti-CD123 antibody and antibody-like binding protein, i.e. by deleting one or more carbohydrate moieties found in the anti-CD3 antibody, anti-CD123 antibody and antibody-like binding protein, and/or adding one or more glycosylation sites that are not present in the anti-CD3 antibody, anti-CD123 antibody and antibody-like binding protein. The presence of either of the tripeptide sequences asparagine-X-serine, and asparagine-X-threonine, where X is any amino acid except proline, creates a potential glycosylation site. Addition or deletion of glycosylation sites to the anti-CD3 antibody, anti-CD123 antibody and antibody-like binding protein is conveniently accomplished by altering the amino acid sequence such that it contains one or more of the above-described tripeptide sequences (for N-linked glycosylation sites).

Another type of modification involves the removal of sequences identified, either in silico or experimentally, as potentially resulting in degradation products or heterogeneity of anti-CD3 antibody, anti-CD123 antibody and antibody-like binding protein preparations. As examples, deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in an anti-CD3 antibody, anti-CD123 antibody and antibody-like binding protein or polypeptide of the invention, it may therefore be desirable to remove the site, typically by conservative substitution to remove one of the implicated residues. Such substitutions in a sequence to remove one or more of the implicated residues are also intended to be encompassed by the present invention.

Another type of covalent modification involves chemically or enzymatically coupling glycosides to the anti-CD3 antibody, anti-CD123 antibody and antibody-like binding protein. These procedures are advantageous in that they do not require production of anti-CD3 antibody, anti-CD123 antibody or antibody-like binding protein in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Removal of any carbohydrate moieties present on the anti-CD3 antibody, anti-CD123 antibody or antibody-like binding protein may be accomplished chemically or enzymatically. Chemical deglycosylation requires exposure of the anti-CD3 antibody, anti-CD123 antibody or antibody-like binding protein to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Another type of covalent modification of the anti-CD3 antibody, anti-CD123 antibody or antibody-like binding protein comprises linking the antibody to one of a variety of non proteinaceous polymers, eg., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Pharmaceutical Compositions

The anti-CD3 antibody, anti-CD123 antibody and/or antibody-like binding protein of the invention may be combined with pharmaceutically acceptable excipients, and optionally sustained-release matrices, such as biodegradable polymers, to form therapeutic compositions.

Thus, another object of the invention relates to a pharmaceutical composition comprising an anti-CD3 antibody, an anti-CD123 antibody or antibody-like binding protein of the invention and a pharmaceutically acceptable carrier.

The invention also relates to an anti-CD3 antibody, an anti-CD123 antibody or antibody-like binding protein according to the invention, for use as a medicament. The invention also relates to a pharmaceutical composition of the invention for use as a medicament.

The terms "pharmaceutical composition" or "therapeutic composition" as used herein refer to a compound or composition capable of inducing a desired therapeutic effect when properly administered to a patient.

Such therapeutic or pharmaceutical compositions may comprise a therapeutically effective amount of an anti-CD3 antibody, an anti-CD123 antibody or antibody-like binding protein or drug conjugates thereof, in admixture with a pharmaceutically or physiologically acceptable formulation agent selected for suitability with the mode of administration.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

As used herein, "pharmaceutically-acceptable carriers" includes any and all solvents, dispersion media, coatings, antibacterial and antifungal agents, and the like that are physiologically compatible. Examples of suitable carriers, diluents and/or excipients include one or more of water, amino acids, saline, phosphate buffered saline, dextrose, glycerol, ethanol, and the like, as well as combination thereof. In many cases, it will be preferable to include isotonic agents, such as sugars, polyalcohols, or sodium chloride in the composition and formulation may also contain an antioxidant such as tryptamine and a stabilizing agent such as Tween 20.

The form of the pharmaceutical compositions, the route of administration, the dosage and the regimen naturally depend upon the condition to be treated, the severity of the illness, the age, weight, and gender of the patient, etc.

The pharmaceutical compositions of the invention can be formulated for a topical, oral, parenteral, intranasal, intravenous, intramuscular, subcutaneous or intraocular administration and the like.

In particular, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody or immunoconjugate of the invention may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

A anti-CD3 antibody, anti-CD123 antibody or antibody-like binding of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, glycine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In one embodiment, an anti-CD3 antibody, anti-CD123 antibody or antibody-like binding protein of the invention is formulated within a therapeutic mixture to comprise about 0.01 to 100 milligrams, per dose or so.

In addition to the anti-CD3 antibody, anti-CD123 antibody or antibody-like binding protein formulated for parenteral administration, such as intravenous or intramuscular injection, other pharmaceutically acceptable forms include, e.g. tablets or other solids for oral administration; time-release capsules; and any other form currently used.

In certain embodiments, the use of liposomes and/or nanoparticles is contemplated for the introduction of polypeptides such as anti-CD3 antibody, anti-CD123 antibody or antibody-like binding protein into host cells. The formation and use of liposomes and/or nanoparticles are known to those of skill in the art. Nanocapsules can generally entrap compounds in a stable and reproducible way.

To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

Therapeutic Methods and Uses

The inventors have shown for several bi-specific compounds of the invention, such as "hz20G6×7G3", "7G3×hz4B4", "hz4B4×3E3" and "hz20G6×7G3-TL4" T-cell mediated cytotoxicity on a CD123 positive tumor cell line model. Furthermore, the inventors demonstrated the capacity of for several bi-specific compounds of the invention to activate T-cells in presence of target cells leading to cytotoxicity of the tumor cells. The inventors further demonstrated the low activation of T-cells in the absence of T-cell activation in absence of target cells.

It is well known that therapeutic anti-CD123 monoclonal antibodies can lead to the depletion of cells bearing the antigen specifically recognized by the antibody. This depletion can be mediated through at least three mechanisms: antibody mediated cellular cytotoxicity (ADCC), complement dependent cytotoxicity (CDC) and direct anti-tumour inhibition of tumour growth through signals given via the antigen targeted by the antibody. In one embodiment, the anti-CD123 antibodies of the invention induce cytotoxicity in a CD123 expressing cell by antibody mediated cellular cytotoxicity (ADCC), complement dependent cytotoxicity (CDC).

"Complement dependent cytotoxicity" or "CDC" refers to the lysis of a target cell in the presence of complement. Activation of the classical complement pathway is initiated by the binding of the first component of the complement system to antibodies which are bound to their cognate antigen. To assess complement activation, a CDC assay, e.g. as described in Gazzano-Santoro et al. (1997) may be performed.

"Antibody-dependent cell-mediated cytotoxicity" or "ADCC" refers to a form of cytotoxicity in which secreted antibodies bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell. To assess ADCC activity of a molecule of interest, an in vitro ADCC assay, such as that described in U.S. Pat. No. 5,500,362 or 5,821,337 may be performed.

As described above in the section "anti-CD3 antibodies" the anti-CD3 antibodies of the invention have a low T-cell activation they thus have a therapeutic potential in a subject for use as an immunosuppressive agent.

Furthermore, an antibody-like binding protein as defined above aims at enhancing the patient's immune response to tumors by targeting T-cells to tumor cells. In one embodiment, the antibody-like binding protein as defined above targets CD3ε subunit of the T-cell Receptor (TCR) at the surface of the T-cell and the other arm targets a CD123 expressing cancer cell, wherein the co-engagement of T-cell and tumor cell by the bispecific construct leads to the formation of a cytolytic synapse which induces T-cell activation and results in tumor cell killing. The tumor cell killing may be mediated through at least two mechanisms: Perforin/Granzyme Killing and FasL/Fas Killing, for example Perforin/Granzyme Killing.

Therefore, in one embodiment the invention provides a method of treating or preventing a disease or disorder comprising administering to a subject in need thereof a therapeutically effective amount of an anti-CD3 antibody, an anti-CD123 antibody, antibody-like binding protein or a pharmaceutical composition of the invention as defined above in the section "Pharmaceutical composition".

The invention further refers to the use of anti-CD3 antibody, an anti-CD123 antibody, antibody-like binding protein or a pharmaceutical composition of the invention for the preparation of a medicament for treating or preventing a disease or disorder in a subject. In one embodiment, the invention refers to the use of an of anti-CD3 antibody, anti-CD123 antibody, antibody-like binding protein or a pharmaceutical composition for treating or preventing a disease or disorder in a subject.

The term "subject" or "individual" are used interchangeably and may be, for example, a human or a non-human mammal. For example, the subject is a bat; a ferret; a rabbit; a feline (cat); a canine (dog); a primate (monkey), an equine (horse); a human, including man, woman and child. In one embodiment a "subject" refers to a human.

In the context of the invention, the term "treating" or "treatment", refers to a therapeutic use (i.e. on a subject having a given disease) and means reversing, alleviating, inhibiting the progress of one or more symptoms of such disorder or condition. Therefore, treatment does not only refer to a treatment that leads to a complete cure of the disease, but also to treatments that slow down the progression of the disease and/or prolong the survival of the subject.

By "preventing" is meant a prophylactic use (i.e. on a subject susceptible of developing a given disease).

In one embodiment, a "disease" or "disorder" is any condition that would benefit from treatment with the anti-CD123 antibody or antibody-like binding protein of the invention. In one embodiment, this includes chronic and acute disorders or diseases including those pathological conditions which predisposes the subject to the disorder in question. The term "in need of treatment" refers to a subject having already the disorder as well as those in which the disorder is to be prevented.

In one embodiment, a "disease" or "disorder" is any condition that would benefit from treatment with the anti-CD3 antibody of the invention. Therefore, in one embodiment, this includes diseases or disorders characterized by pathological immune responses.

A "pathological immune response" in the context of the invention is an inflammatory immune response.

In one embodiment, the disease, characterized by a pathological immune response, is an autoimmune diseases, a transplantation-related diseases, or an inflammation-associated disease.

The auto-immune disease is, for example, Crohn's disease, ulcerative colitis and type 1 diabetes or a transplantation-related disease such as graft-versus-host disease (GVHD).

Therefore, in one embodiment, the subject has been diagnosed to suffer from a disease or disorder characterized by a pathological immune response.

In one embodiment, the subject has been diagnosed to suffer from an auto-immune disease.

In another embodiment, the disorder refers to cancer.

In a further embodiment, cancer relates to hematological cancer, in particular to hematological cancer associated with CD123 expression.

In one embodiment, expression of CD123 by cancer cells is readily assayed for instance by using an anti-CD123 antibody according to the invention, as described in the following section "Diagnostic uses".

"Hematological cancers associated with CD123 expression" include leukemias (such as acute myelogenous leukemia, chronic myelogenous leukemia, acute lymphoid leukemia, chronic lymphoid leukemia, hairy cell leukemia and myelodysplasia syndrome) and malignant lymphoproliferative conditions, blastic plasmacytoid dendritic cell neoplasm (BPDCN), systemic mastocytosis, including lymphomas (such as multiple myeloma, non-Hodgkin's lymphoma, Burkitt's lymphoma, and small cell- and large cell-follicular lymphoma).

As described above in the section 'anti-CD123 antibodies" LSCs express CD123.

Thus, in a related embodiment cancer refers to hematological cancer associated associated with leukemic stem cells.

The hematologic cancer conditions associated with leukemic stem cells (LSCs) which are to be treated in accordance with the present invention include leukemias (such as acute myelogenous leukemia, chronic myelogenous leukemia, acute lymphoid leukemia, chronic lymphoid leukemia, and myelodysplasia syndrome) and malignant lymphoproliferative conditions, including lymphomas (such as multiple myeloma, non-Hodgkin's lymphoma, Burkitt's lymphoma, and small cell- and large cell-follicular lymphoma).

In one aspect of the invention, the hematologic cancer is acute myelogenous leukemia (AML).

In one embodiment, the subject has been diagnosed to suffer from AML.

In a further embodiment, the subject has already been treated with chemotherapy until complete remission but relapsed.

The "relapse" is defined as the reoccurrence of AML after complete remission.

"Complete remission" or "CR" is defined as follows: normal values for neutrophil ($>1.0*10^9$/L), haemoglobin level of 10 g/dL and platelet count ($>100*10^9$/L) and independence from red cell transfusion; blast cells less than 5%, no clusters or collections of blasts, and absence of Auer rods on bone marrow examination; and normal maturation of blood cells (morphology; myelogramme) and absence of extramedullary leukemia.

In one embodiment, the anti-CD3 antibody, anti-CD123 antibody or antibody-like binding protein of the invention is used alone or in combination with any suitable growth-inhibitory agent.

By a "therapeutically effective amount" of the polypeptide of the invention is meant a sufficient amount of the polypeptide to treat said cancer disease, at a reasonable benefit/risk ratio applicable to any medical treatment. It will be understood, however, that the total daily usage of the polypeptides and compositions of the present invention will be decided by the attending physician within the scope of sound medical judgment. The specific therapeutically effective dose level for any particular patient will depend upon a variety of factors including the disorder being treated and the severity of the disorder; activity of the specific polypeptide employed; the specific composition employed, the age, body weight, general health, sex and diet of the patient; the time of administration, route of administration, and rate of excretion of the specific polypeptide employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved.

In one embodiment, efficacy of the treatment with an anti-CD3 antibody, an anti-CD123 antibody or antibody-like binding protein of the invention or immunoconjugate according to the invention is readily assayed in vivo, for instance in a mouse model of cancer and by measuring, for example, changes in tumor volume between treated and control groups.

Diagnostic Uses

CD123 has been reported to be over-expressed on the surface of a variety of hematological neoplasms.

Therefore, CD123 constitutes a cancer marker and, therefore, has the potential to be used to indicate the effectiveness of an anti-cancer therapy or detecting recurrence of the disease.

In an embodiment, the anti-CD123 antibody of the invention is used as component of an assay in the context of a therapy targeting CD123 expressing tumours, in order to determine susceptibility of the patient to the therapeutic agent, monitor the effectiveness of the anti-cancer therapy or detect recurrence of the disease after treatment. In particular, the same anti-CD123 antibody of the invention is used both as component of the therapeutic agent and as component of the diagnostic assay.

Thus, a further object of the invention relates to an anti-CD123 antibody according to the invention for use for in vivo detecting CD123 expression in a subject, or for use for ex vivo detecting CD123 expression in biological sample of a subject. In one embodiment, said detection is intended, in particular for:

a) diagnosing the presence of a cancer in a subject, or b) determining susceptibility of a patient having cancer to a therapeutic agent targeting CD123, in particular an anti-CD123 antibody or antibody-like binding protein according to the invention, or c) monitoring effectiveness of anti-CD123 cancer therapy or detecting cancer relapse after anti-CD123 cancer therapy, in particular for therapy with an anti-CD123 antibody or antibody-like binding protein according to the invention; by detecting expression of the surface protein CD123 on tumor cells.

In an embodiment, the antibody is intended for an in vitro or ex vivo use. For example, CD123 is detected in vitro or ex vivo in a biological sample obtained from a subject, using an anti-CD123 antibody of the invention. The use according to the invention may also be an in vivo use. For example, an anti-CD123 antibody or antibody-like binding protein according to the invention is administered to the subject and antibody-cells complexes are detected and/or quantified, whereby the detection of said complexes is indicative of a cancer.

The invention further relates to an in vitro or ex vivo method of detecting the presence of a cancer in a subject, comprising the steps consisting of:

(a) contacting a biological sample of a subject with an anti-CD123 antibody according to the invention, in particular in conditions sufficient for the antibody to form complexes with said biological sample;

(b) measuring the level of antibody bound to said biological sample, (c) detecting the presence of a cancer by comparing the measured level of bound antibody with a control, an increased level of bound antibody compared to control being indicative of a cancer.

The invention also relates to an in vitro or ex vivo method of determining susceptibility of a patient having cancer to a therapeutic agent targeting CD123, in particular to an anti-CD123 antibody or antibody-like binding protein according to the invention, which method comprises the steps consisting of:

(a) contacting a biological sample of a patient having cancer with an anti-CD123 antibody according to the invention, in particular in conditions sufficient for the antibody to form complexes with said biological sample;
(b) measuring the level of antibody bound to said biological sample sample,
(c) comparing the measured level of bound antibody to said biological sample with the level of antibody bound to a control;
wherein an increased level of bound antibody to said biological sample compared to control is indicative of a patient susceptible to a therapeutic agent targeting at least CD123.

In the above methods, said control can be a normal, non cancerous, biological sample of the same type, or a reference value determined a representative of the antibody binding level in normal biological sample of the same type.

In an embodiment, the anti-CD123 antibody of the invention are useful for diagnosing hematological cancers associated with CD123 expression including leukemias (such as acute myelogenous leukemia, chronic myelogenous leukemia, acute lymphoid leukemia, chronic lymphoid leukemia, hairy cell leukemia and myelodysplasia syndrome) and malignant lymphoproliferative conditions, blastic plasmacytoid dendritic cell neoplasm (BPDCN), systemic mastocytosis, including lymphomas (such as multiple myeloma, non-Hodgkin's lymphoma, Burkitt's lymphoma, and small cell- and large cell-follicular lymphoma).

The invention further relates to an in vitro or ex vivo method of monitoring effectiveness of anti-CD123 cancer therapy, comprising the steps consisting of:
(a) contacting a biological sample of a subject undergoing anti-CD123 cancer therapy, with an anti-CD123 antibody or antibody-like binding protein according to the invention, in particular in conditions sufficient for the antibody to form complexes with said biological sample;
(b) measuring the level of antibody bound to said biological sample,
(c) comparing the measured level of bound antibody with the level of antibody bound to a control;
wherein a decreased level of bound antibody to said biological sample compared to control is indicative of effectiveness of said anti-CD123 cancer therapy.

In said method, an increased level of bound antibody to said biological sample compared to control is indicative of ineffectiveness of said anti-CD123 cancer therapy.

Said control is in particular a biological sample of the same type as the biological sample submitted to analysis, but which was obtained from the subject previously in time, during the course of the anti-CD123 cancer therapy.

The invention further relates to an in vitro or ex vivo method of detecting cancer relapse after anti-CD123 cancer therapy, comprising the steps consisting of:
(a) contacting a biological sample of a subject having completed anti-CD123 cancer therapy, with an anti-CD123 antibody or antibody-like binding protein according to the invention, in particular in conditions sufficient for the antibody to form complexes with said biological sample;
(b) measuring the level of antibody bound to said biological sample,
(c) comparing the measured level of bound antibody with the level of antibody bound to a control;
wherein an increased level of bound antibody to said biological sample compared to control is indicative of cancer relapse after anti-CD123 cancer therapy.

Said control is in particular a biological sample of the same type as the biological sample submitted to analysis, but which was obtained from the subject previously in time, upon or after completion of the anti-CD123 cancer therapy. Said anti-CD123 cancer therapy is in particular a therapy using an anti-CD123 antibody or antibody-like binding protein or immunoconjugate according to the invention. Said anti-CD123 cancer therapy targets a CD123 expressing cancer, in particular a hematological cancers associated with CD123 expression including leukemias (such as acute myelogenous leukemia, chronic myelogenous leukemia, acute lymphoid leukemia, chronic lymphoid leukemia, hairy cell leukemia and myelodysplasia syndrome) and malignant lymphoproliferative conditions, blastic plasmacytoid dendritic cell neoplasm (BPDCN), systemic mastocytosis, including lymphomas (such as multiple myeloma, non-Hodgkin's lymphoma, Burkitt's lymphoma, and small cell- and large cell-follicular lymphoma).

In an embodiment, anti-CD123 of the invention is labelled with a detectable molecule or substance, such as a fluorescent molecule, a radioactive molecule or any other labels known in the that provide (either directly or indirectly) a signal.

As used herein, the term "labeled", with regard to the anti-CD123 antibody according to the invention, is intended to encompass direct labeling of the anti-CD123 antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the polypeptide, as well as indirect labeling of the polypeptide by reactivity with a detectable substance.

In a further embodiment, an anti-CD123 antibody of the invention is labelled with a radioactive molecule by any method known to the art. For example radioactive molecules include but are not limited radioactive atom for scintigraphic studies such as $I^{123}$, $I^{124}$, $In^{111}$, $Re^{186}$, $Re^{188}$, $Tc^{99}$. In one example, polypeptides of the invention are also labelled with a spin label for nuclear magnetic resonance (NMR) imaging (also known as magnetic resonance imaging, MRI), such as iodine-123, indium-111, fluorine-19, carbon-13, nitrogen-15, oxygen-17, gadolinium, manganese or iron.

A "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. Therefore, biological samples encompass clinical samples, cells in culture, cell supernatants, cell lysates, serum, plasma, biological fluid, and tissue samples, in particular tumor sample.

The invention also relates to an in vivo method of detecting the presence of a cancer in a subject, comprising the steps consisting of:
a) administering an antibody according to the invention detectably labelled to a patient;
b) detecting localization of said detectably labelled antibody in the patient by imaging.

In one embodiment, antibodies of the invention are useful for staging of cancer (e.g., in radioimaging). They are used, for example, alone or in combination with other cancer markers.

The terms "detection" or "detected" as used herein includes qualitative and/or quantitative detection (measuring levels) with or without reference to a control.

In the content of the invention, the term "diagnosing", as used herein, means the determination of the nature of a medical condition intended to identify a pathology which affects the subject from a number of collected data.

In said method, the cancer is a CD123 expressing cancer as defined above.

Kits

Finally, the invention also provides kits comprising at least one anti-CD3 antibody, at least one anti-CD123 antibody or at least one antibody-like binding protein of the invention. Kits containing anti-CD123 or anti-CD3 antibodies of the invention find use in detecting the surface protein CD123 or CD3, or in therapeutic or diagnostic assays. Kits of the invention can contain a polypeptide or anti-CD3 antibody, at least one anti-CD123 antibody or at least one antibody-like binding protein coupled to a solid support, e.g., a tissue culture plate or beads (e.g., sepharose beads). Kits can be provided which contain antibodies for detection and quantification of the surface protein CD123 or CD3 in vitro, e.g. in an ELISA or a Western blot. In one embodiment, said antibody is useful for detection and is provided with a label such as a fluorescent or radiolabel.

In one embodiment, the invention encompasses kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and lyosyringes).

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of"). Furthermore the indefinite article "a" or "an" does not exclude a plurality. The mere fact that certain measures are recited in mutually different dependent claims does not indicate that a combination of these measures cannot be used to advantage.

The invention will now be described in more details with reference to the following figures and examples. All literature and patent documents cited herein are hereby incorporated by reference. While the invention has been illustrated and described in detail in the foregoing description, the examples are to be considered illustrative or exemplary and not restrictive.

BRIEF DESCRIPTION OF THE SEQUENCES

SEQ ID NO: 1 shows the amino acid sequence of full-length human CD3ε protein, including the signal peptide, as available from the Uniprot database under accession number P07766.

SEQ ID NO: 2 shows the amino acid sequence of full-length *Macaca fascicularis* CD3ε protein, including the signal peptide, as available from the Uniprot database under accession number Q95LI5.

SEQ ID NO: 3 shows the amino acid sequence of mature human CD3ε His-tagged Fc-fusion comprising amino acids 23 to 126 of the full-length wild-type human CD3ε protein.

SEQ ID NO: 4 shows the amino acid sequence of mature *Macaca fascicularis* CD3ε Fc-fusion comprising amino acids 23 to 117 of the full-length wild-type *Macaca fascicularis* CD3ε protein (SEQ ID NO:2) containing one Ala to Val exchange at amino acid position 35 in comparison to amino acid position 57 of the wild-type sequence.

SEQ ID NO: 5 shows the amino acid sequence of the heavy chain variable domain of the so-called "20G6-F3" antibody.

SEQ ID NO: 6, 7 and 8 show the amino acid sequences of CDR1-H, CDR2-H and CDR3-H of the so-called "20G6-F3" antibody.

SEQ ID NO: 9 shows the amino acid sequence of the light chain variable domain of the so-called "20G6-F3" antibody.

SEQ ID NO: 10 shows the amino acid sequence of CDR1-L of the so-called "20G6-F3", "11D7-C3", "13H2-C2", "13C1-F6", "1E6-C9, "10F4-C10", "18G9-H11", "12G3-E8", "5B1-G2", "16F8-A7", "11F9-F8", "8C2-F7", "20E5-F10" and "3H6-D2" antibodies.

SEQ ID NO: 11 shows the amino acid sequence of CDR3-L of the so-called "20G6-F3", "4B4-D7", "11H3-E5", "13H2-C2", "13C1-F6", "10F4-C10", "4E7-C9", "11F3-B9", "12G3-E8", "5B1-G2", "16F8-A7", "20E5-F10" and "3H6-D2" antibodies.

SEQ ID NO: 12 shows the amino acid sequence of the heavy chain variable domain of the so-called "4B4-D7" antibody.

SEQ ID NO: 13 shows the amino acid sequence of CDR1-H of the so-called "4B4-D7", "11D7-C3", "11H3-E5", "13H2-C2", "13C1-F6", "10F4-C10", "18G9-H11", "4E7-C9", "11F3-B9", "16F8-A7", "11F9-F8", "20B5-F10" and "3H6-D2" antibodies.

SEQ ID NO: 14 and 15 show the amino acid sequences of CDR2-H and CDR3-H of the so-called "4B4-D7" antibody.

SEQ ID NO: 16 shows the amino acid sequence of the light chain variable domain of the so-called "4B4-D7" antibody.

SEQ ID NO: 17 shows the amino acid sequence of CDR1-L of the so-called "4B4-D7", "11H3-E5" and "11F3-B9" antibodies.

SEQ ID NO: 18 shows the amino acid sequence of the heavy chain variable domain of the so-called "4E7-C9" antibody.

SEQ ID NO: 19 shows the amino acid sequence of CDR2-H of the so-called "4E7-C9", "18F5-H10", "20E5-F10" and "3H6-D2" antibodies.

SEQ ID NO: 20 shows the amino acid sequence of CDR3-H of the so-called "4E7-C9" antibody.

SEQ ID NO: 21 shows the amino acid sequence of the light chain variable domain of the so-called "4E7-C9" antibody.

SEQ ID NO: 22 shows the amino acid sequence of CDR1-H of the so-called "4E7-C9" antibody.

SEQ ID NO: 23 shows the amino acid sequence of the heavy chain variable domain of the so-called "18F5-H10" antibody.

SEQ ID NO: 24 shows the amino acid sequence of CDR1-H of the so-called "18F5-H10" antibody.

SEQ ID NO: 25 shows the amino acid sequence of CDR3-H of the so-called "18F5-H10" antibody.

SEQ ID NO: 26 shows the amino acid sequence of the light chain variable domain of the so-called "18F5-H10" antibody.

SEQ ID NO: 27 shows the amino acid sequence of CDR1-L of the so-called "18F5-H10" anti-CD3 antibody.

SEQ ID NO: 28 shows the amino acid sequence of CDR3-L of the so-called "18F5-H10", "11D7-C3", "1E6-C9" and "10E6-G6" anti-CD3 antibodies.

SEQ ID NO: 29 shows the amino acid sequence of the heavy chain variable domain of the so-called "12D2-E5" anti-CD3 antibody.

SEQ ID NO: 30 and 31 show the amino acid sequences of CDR1-H and CDR2-H of the so-called "12D2-E5" anti-CD3 antibody.

SEQ ID NO: 32 shows the amino acid sequence of CDR3-H of the so-called "12D2-E5" and "3G5-E10" anti-CD3 antibodies.

SEQ ID NO: 33 shows the amino acid sequence of the light chain variable domain of the so-called "12D2-E5" anti-CD3 antibody.

SEQ ID NO: 34 and 35 show the amino acid sequences of CDR1-H and CDR3-H of the so-called "12D2-E5" anti-CD3 antibody.

SEQ ID NO: 36 shows the amino acid sequence of the heavy chain variable domain of the so-called "11D7-C3" anti-CD3 antibody.

SEQ ID NO: 37 shows the amino acid sequence of CDR2-H of the so-called "11D7-C3", "11H3-E5", "13H2-C2", "13C1-F6", "1E6-C9", "10F4-C10", "18G9-H11", "11F3-B9", "16F8-A7", "11F9-F8" and "20B5-F10" anti-CD3 antibodies.

SEQ ID NO: 38 shows the amino acid sequence of CDR3-H of the so-called "11D7-C3" anti-CD3 antibody.

SEQ ID NO: 39 shows the amino acid sequence of the light chain variable domain of the so-called "11D7-C3" anti-CD3 antibody.

SEQ ID NO: 40 shows the amino acid sequence of the heavy chain variable domain of the so-called "11H3-E5" anti-CD3 antibody.

SEQ ID NO: 41 shows the amino acid sequence of CDR3-H of the so-called called "11H3-E5" anti-CD3 antibody.

SEQ ID NO: 42 shows the amino acid sequence of the light chain variable domain of the so-called "11H3-E5" anti-CD3 antibody.

SEQ ID NO: 43 shows the amino acid sequence of the heavy chain variable domain of the so-called "13H2-C2" anti-CD3 antibody.

SEQ ID NO: 44 shows the amino acid sequence of CDR3-H of the so-called "13H2-C2" anti-CD3 antibody.

SEQ ID NO: 45 shows the amino acid sequence of the light chain variable domain of the so-called "13H2-C2" anti-CD3 antibody.

SEQ ID NO: 46 shows the amino acid sequence of the heavy chain variable domain of the so-called "13C1-F6" and "11F9-F8" anti-CD3 antibodies.

SEQ ID NO: 47 shows the amino acid sequence of CDR3-H of so-called "13C1-F6", "10E6-G6" and "11F9-F8" anti-CD3 antibodies.

SEQ ID NO: 48 shows the amino acid sequence of the light chain variable domain of the so-called "13H2-C2" anti-CD3 antibody.

SEQ ID NO: 49 shows the amino acid sequence of the heavy chain variable domain of the so-called "18H11-F10" anti-CD3 antibody.

SEQ ID NO: 50, 51 and 52 show the amino acid sequences of CDR1-H, CDR2-H and CDR3-H of the so-called "18H11-F10" anti-CD3 antibody.

SEQ ID NO: 53 shows the amino acid sequence of the light chain variable domain of the so-called "18H11-F10" anti-CD3 antibody.

SEQ ID NO: 54 and 55 show the amino acid sequences of CDR1-L and CDR3-L of the so-called "18H11-F10" anti-CD3 antibody.

SEQ ID NO: 56 shows the amino acid sequence of the heavy chain variable domain of the so-called "1E6-C9" anti-CD3 antibody.

SEQ ID NO: 57 and 58 show the amino acid sequences of CDR1-H and CDR3-H of the so-called "1E6-C9" anti-CD3 antibody.

SEQ ID NO: 59 shows the amino acid sequence of the light chain variable domain of the so-called "1E6-C9" anti-CD3 antibody.

SEQ ID NO: 60 shows the amino acid sequence of the heavy chain variable domain of the so-called "10F4-C10" anti-CD3 antibody.

SEQ ID NO: 61 shows the amino acid sequence of CDR3-H of the so-called "10F4-C10" anti-CD3 antibody.

SEQ ID NO: 62 shows the amino acid sequence of the light chain variable domain of the so-called "10F4-C10" anti-CD3 antibody.

SEQ ID NO: 63 shows the amino acid sequence of the heavy chain variable domain of the so-called "10E6-G6" anti-CD3 antibody.

SEQ ID NO: 64 and 65 show the amino acid sequences of CDR1-H and CDR2-H of the so-called "10E6-G6" anti-CD3 antibody.

SEQ ID NO: 66 shows the amino acid sequence of the light chain variable domain of the so-called "10E6-G6" anti-CD3 antibody.

SEQ ID NO: 67 shows the amino acid sequence of CDR1-L of the so-called "10E6-G6" anti-CD3 antibody.

SEQ ID NO: 68 shows the amino acid sequence of the heavy chain variable domain of the so-called "18G9-H11" anti-CD3 antibody.

SEQ ID NO: 69 shows the amino acid sequence of CDR3-H of the so-called "18G9-H11" anti-CD3 antibody.

SEQ ID NO: 70 shows the amino acid sequence of the light chain variable domain of the so-called "18G9-H11" anti-CD3 antibody.

SEQ ID NO: 71 shows the amino acid sequence of CDR3-L of the so-called "18G9-H11" anti-CD3 antibody.

SEQ ID NO: 72 shows the amino acid sequence of the heavy chain variable domain of the so-called "11F3-B9" anti-CD3 antibody.

SEQ ID NO: 73 shows the amino acid sequence of the light chain variable domain of the so-called "11F3-B9" anti-CD3 antibody.

SEQ ID NO: 74 shows the amino acid sequence of the heavy chain variable domain of the so-called "12G3-E8" anti-CD3 antibody.

SEQ ID NO: 75, 76 and 77 show the amino acid sequences of CDR1-H, CDR2-H and CDR3-H of the so-called "12G3-E8" anti-CD3 antibody.

SEQ ID NO: 78 shows the amino acid sequence of the light chain variable domain of the so-called "12G3-E8" anti-CD3 antibody.

SEQ ID NO: 79 shows the amino acid sequence of the heavy chain variable domain of the so-called "5B1-G2" anti-CD3 antibody.

SEQ ID NO: 80 and 81 show the amino acid sequences of CDR1-H and CDR3-H of the so-called "5B1-G2" anti-CD3 antibody.

SEQ ID NO: 82 shows the amino acid sequence of the light chain variable domain of the so-called "5B1-G2" anti-CD3 antibody.

SEQ ID NO: 83 shows the amino acid sequence of a part of the variable domain of the heavy chain of the so-called "16F8-A7" anti-CD3 antibody.

SEQ ID NO: 84 shows the amino acid sequence of CDR3-H of the so-called "16F8-A7" and "11F3-B9" anti-CD3 antibodies.

SEQ ID NO: 85 shows the amino acid sequence of the light chain variable domain of the so-called "16F8-A7" anti-CD3 antibody.

SEQ ID NO: 86 shows the amino acid sequence of full-length human CD3δ protein, including the signal peptide, as available from the Uniprot database under accession number P04234.

SEQ ID NO: 87 shows the amino acid sequence of the light chain variable domain of the so-called "11F9-F8" anti-CD3 antibody.

SEQ ID NO: 88 shows the amino acid sequence of CDR3-L of the so-called "11F9-F8" anti-CD3 antibody.

SEQ ID NO: 89 shows the amino acid sequence of the heavy chain variable domain of the so-called "3G5-E10" anti-CD3 antibody.

SEQ ID NO: 90 and 91 show the amino acid sequences of CDR1-H and CDR2-H of the so-called "3G5-E10" anti-CD3 antibody.

SEQ ID NO: 92 shows the amino acid sequence of the light chain variable domain of the so-called "3G5-E10" anti-CD3 antibody.

SEQ ID NO: 93 and 94 show the sequences of CDR1-L and CDR3-L of the so-called "3G5-E10" anti-CD3 antibody.

SEQ ID NO: 95 shows the amino acid sequence of the heavy chain variable domain of the so-called "9D7-F3" anti-CD3 antibody.

SEQ ID NO: 96, 97 and 98 show the amino acid sequences of CDR1-H, CDR2-H and CDR3-H of the so-called "9D7-F3" anti-CD3 antibody.

SEQ ID NO: 99 shows the amino acid sequence of the light chain variable domain of the so-called "9D7-F3" anti-CD3 antibody.

SEQ ID NO: 100 and 101 show the amino acid sequences of CDR1-L and CDR3-L of the so-called "9D7-F3" and "6C9-C9" anti-CD3 antibody.

SEQ ID NO: 102 shows the amino acid sequence of the heavy chain variable domain of the so-called "8C2-F7" anti-CD3 antibody.

SEQ ID NO: 103, 104 and 105 show the amino acid sequences of CDR1-H, CDR2-H and CDR3-H of the so-called "8C2-F7" anti-CD3 antibody.

SEQ ID NO: 106 shows the amino acid sequence of the light chain variable domain of the so-called "8C2-F7" anti-CD3 antibody.

SEQ ID NO: 107 shows the amino acid sequence of the heavy chain variable domain of the so-called "20E5-F10" anti-CD3 antibody.

SEQ ID NO: 108 shows the amino acid sequences of CDR3-H of the so-called "20E5-F10" anti-CD3 antibody.

SEQ ID NO: 109 shows the amino acid sequence of the light chain variable domain of the so-called "20E5-F10" anti-CD3 antibody.

SEQ ID NO: 110 shows the amino acid sequence of the heavy chain variable domain of the so-called "20B5-F10" anti-CD3 antibody.

SEQ ID NO: 111 shows the amino acid sequence of CDR3-H of the so-called "20B5-F10" anti-CD3 antibody.

SEQ ID NO: 112 shows the amino acid sequence of the light chain variable domain of the so-called "20B5-F10" anti-CD3 antibody.

SEQ ID NO: 113 and 114 show the amino acid sequences of CDR1-L and CDR3-L of the so-called "20B5-F10" anti-CD3 antibody.

SEQ ID NO: 115 shows the amino acid sequence of the heavy chain variable domain of the so-called "6C9-C9" anti-CD3 antibody.

SEQ ID NO: 116, 117 and 118 show the amino acid sequences of CDR1-H, CDR2-H and CDR3-H of the so-called "6C9-C9" anti-CD3 antibody.

SEQ ID NO: 119 shows the amino acid sequence of the light chain variable domain of the so-called "6C9-C9" anti-CD3 antibody.

SEQ ID NO: 120 shows the amino acid sequence of CDR3-L of the so-called "6C9-C9" anti-CD3 antibody.

SEQ ID NO: 121 shows the amino acid sequence of the heavy chain variable domain of the so-called "3E8-G1" anti-CD3 antibody.

SEQ ID NO: 122, 123 and 124 show the amino acid sequences of CDR1-H, CDR2-H and CDR3-H of the so-called "3E8-G1" anti-CD3 antibody SEQ ID NO: 125 shows the amino acid sequence of the light chain variable domain of the so-called "3E8-G1" anti-CD3 antibody.

SEQ ID NO: 126 and 127 show the amino acid sequences of CDR1-L and CDR3-L of the so-called "3E8-G1" anti-CD3 antibody.

SEQ ID NO: 128 shows the amino acid sequence of the heavy chain variable domain of the so-called "3H6-D2" anti-CD3 antibody.

SEQ ID NO: 129 show the amino acid sequence of CDR3-H of the so-called "3H6-D2" anti-CD3 antibody.

SEQ ID NO: 130 shows the amino acid sequence of the light chain variable domain of the so-called "3H6-D2" anti-CD3 antibody.

SEQ ID NO: 131 shows the amino acid sequence of the heavy chain variable domain of the so-called "8H2" anti-CD3 antibody.

SEQ ID NO: 132 shows the amino acid sequence of the light chain variable domain of the so-called "8H2" anti-CD3 antibody.

SEQ ID NO: 133 and 134 show the amino acid sequences of CDR1-L and CDR3-L of the so-called "8H2" anti-CD3 antibody.

SEQ ID NO: 135 shows the VH variant amino acid sequence VH1a of humanized "20G6" anti-CD3 antibody.

SEQ ID NO: 136 shows the VH variant amino acid sequence VH1b of humanized "20G6" anti-CD3 antibody.

SEQ ID NO: 137 shows the VH variant amino acid sequence VH1c of humanized "20G6" anti-CD3 antibody.

SEQ ID NO: 138 shows the VH variant amino acid sequence VH1d of humanized "20G6" anti-CD3 antibody.

SEQ ID NO: 139 shows the VL variant amino acid sequence VL1a of humanized "20G6" anti-CD3 antibody.

SEQ ID NO: 140 shows the VL variant amino acid sequence VL1b of humanized "20G6" anti-CD3 antibody.

SEQ ID NO: 141 shows the VL variant amino acid sequence VL1c of humanized "20G6" anti-CD3 antibody.

SEQ ID NO: 142 shows the amino acid sequence of the CDR1-L of the VL1c variant of the humanized "20G6" anti-CD3 antibody.

SEQ ID NO: 143 shows the VL variant amino acid sequence VL1d of humanized "20G6" anti-CD3 antibody.

SEQ ID NO: 144 shows the VH variant amino acid sequence VH2a of humanized "20G6" anti-CD3 antibody.

SEQ ID NO: 145 shows the VH variant amino acid sequence VH2b of humanized "20G6" anti-CD3 antibody.

SEQ ID NO: 146 shows the VH variant amino acid sequence VH2c of humanized "20G6" anti-CD3 antibody.

SEQ ID NO: 147 shows the VH variant amino acid sequence VH2d of humanized "20G6" anti-CD3 antibody.

SEQ ID NO: 148 shows the VL variant amino acid sequence VL2a of humanized "20G6" anti-CD3 antibody.

SEQ ID NO: 149 shows the VL variant amino acid sequence VL2b of humanized "20G6" anti-CD3 antibody.

SEQ ID NO: 150 shows the VL variant amino acid sequence VL2c of humanized "20G6" anti-CD3 antibody.

SEQ ID NO: 151 shows the VL variant amino acid sequence VL2d of humanized "20G6" anti-CD3 antibody.

SEQ ID NO: 152 shows the VH variant amino acid sequence VH3a of humanized "20G6" anti-CD3 antibody.

SEQ ID NO: 153 shows the VH variant amino acid sequence VH3b of humanized "20G6" anti-CD3 antibody.

SEQ ID NO: 154 shows the VL variant amino acid sequence VL3a of humanized "20G6" anti-CD3 antibody.

SEQ ID NO: 155 shows the VL variant amino acid sequence VL3b of humanized "20G6" anti-CD3 antibody.

SEQ ID NO: 156 shows the VL variant amino acid sequence VL3c of humanized "20G6" anti-CD3 antibody.

SEQ ID NO: 157 shows the VL variant amino acid sequence VL3d of humanized "20G6" anti-CD3 antibody.

SEQ ID NO: 158 shows the VL variant amino acid sequence VL1A of humanized "4B4" anti-CD3 antibody.

SEQ ID NO: 159 shows the VL variant amino acid sequence VL1B of humanized "4B4" anti-CD3 antibody.

SEQ ID NO: 160 shows the VL variant amino acid sequence VL2A of humanized "4B4" anti-CD3 antibody.

SEQ ID NO: 161 shows the VL variant amino acid sequence VL2B of humanized "4B4" anti-CD3 antibody.

SEQ ID NO: 162 shows the VL variant amino acid sequence VL1Cmodif1 of humanized "4B4" anti-CD3 antibody.

SEQ ID NO: 163 shows the VL variant amino acid sequence VL1Cmodif2 of humanized "4B4" anti-CD3 antibody.

SEQ ID NO: 164 shows the VL variant amino acid sequence VL1Cmodif3 of humanized "4B4" anti-CD3 antibody.

SEQ ID NO: 165 shows the VL variant amino acid sequence VL1Amodif1 of humanized "4B4" anti-CD3 antibody.

SEQ ID NO: 166 shows the VL variant amino acid sequence VL1Amodif2 of humanized "4B4" anti-CD3 antibody.

SEQ ID NO: 167 shows the VL variant amino acid sequence VL1Amodif3 of humanized "4B4" anti-CD3 antibody.

SEQ ID NO: 168 shows the VL variant amino acid sequence VL2C of humanized "4B4" anti-CD3 antibody.

SEQ ID NO: 169 shows the VL variant amino acid sequence VL2D of humanized "4B4" anti-CD3 antibody.

SEQ ID NO: 170 shows the VL variant amino acid sequence VL2F of humanized "4B4" anti-CD3 antibody.

SEQ ID NO: 171 shows the VH variant amino acid sequence VH1A of humanized "4B4" anti-CD3 antibody.

SEQ ID NO: 172 shows the VH variant amino acid sequence VH1B of humanized "4B4" anti-CD3 antibody.

SEQ ID NO: 173 shows the VH variant amino acid sequence VH2A of humanized "4B4" anti-CD3 antibody.

SEQ ID NO: 174 shows the VH variant amino acid sequence VH2B of humanized "4B4" anti-CD3 antibody.

SEQ ID NO: 175 shows the VH variant amino acid sequence VH6Bmodif1 of humanized "4B4" anti-CD3 antibody.

SEQ ID NO: 176 shows the VH variant amino acid sequence VH6Bmodif2 of humanized "4B4" anti-CD3 antibody.

SEQ ID NO: 177 shows the VH variant amino acid sequence VH6Amodif1 of humanized "4B4" anti-CD3 antibody.

SEQ ID NO: 178 shows the VH variant amino acid sequence VH6Amodif2 of humanized "4B4" anti-CD3 antibody.

SEQ ID NO: 179 shows the VH variant amino acid sequence VH6Amodif3 of humanized "4B4" anti-CD3 antibody.

SEQ ID NO: 180 shows the VH variant amino acid sequence VH6C of humanized "4B4" anti-CD3 antibody.

SEQ ID NO: 181 shows the VH variant amino acid sequence VH6D of humanized "4B4" anti-CD3 antibody.

SEQ ID NO: 182 shows the VL variant amino acid sequence D7-VK3mut of humanized "4B4" anti-CD3 antibody.

SEQ ID NO: 183 shows the VH variant amino acid sequence D7-VH1mut of humanized "4B4" anti-CD3 antibody.

SEQ ID NO: 184 shows the amino acid sequence of the CDR1-L of the VL1B, VL2B, VL1Cmodif3 and VL2F variants of the humanized "4B4" anti-CD3 antibody.

SEQ ID NO: 185 shows the amino acid sequence of full-length human CD3γ protein, including the signal peptide, as available from the Uniprot database under accession number P09693.

SEQ ID NO: 186 shows the amino acid sequence of the heavy chain of the Fab of so-called "20G6-F3" anti-CD3 antibody.

SEQ ID NO: 187 shows the amino acid sequence of the light chain of the Fab of so-called "20G6-F3" anti-CD3 antibody.

SEQ ID NO: 188 shows the amino acid sequence of the heavy chain of the Fab of so-called "4E7-C9" anti-CD3 antibody.

SEQ ID NO: 189 shows the amino acid sequence of the light chain of the Fab of so-called "4E7-C9" anti-CD3 antibody.

SEQ ID NO: 190 shows the amino acid sequence of the heavy chain of the Fab of so-called "4B4-D7" anti-CD3 antibody.

SEQ ID NO: 191 shows the amino acid sequence of the light chain of the Fab of so-called "4B4-D7" anti-CD3 antibody.

SEQ ID NO: 192 shows the amino acid sequence of the heavy chain of the Fab of so-called "18F5-H10" anti-CD3 antibody.

SEQ ID NO: 193 shows the amino acid sequence of the light chain of the Fab of so-called "18F5-H10" anti-CD3 antibody.

SEQ ID NO: 194 shows the amino acid sequence of full-length human CD123 protein, including the signal peptide, as available from the NCBI database under NP_002174.1 and from the Uniprot database under P26951.

SEQ ID NO: 195 shows the amino acid sequence of full-length *Macaca fascicularis* CD123 protein, including the signal peptide, as available from the GenBank database under EHH61867.1 and Uniprot database under G8F3K3.

SEQ ID NO: 196 shows the amino acid sequence of mature human CD123 Strep-II tagged Fc-fusion comprising amino acids 22 to 305 of the full-length human CD123 protein (SEQ ID NO: 194).

SEQ ID NO: 197 shows the amino acid sequence of mature *Macaca fascicularis* CD123 Strep-II tagged Fc-fusion comprising amino acids 22 to 305 of the full-length *Macaca fascicularis* CD123 protein (SEQ ID NO: 195).

SEQ ID NO: 198 shows the amino acid sequence of the heavy chain variable domain of the so-called "1E1-G5" anti-CD123 antibody.

SEQ ID NO: 199 shows the amino acid sequences of CDR1-H of the so-called "1E1-G5" and "8B11-B7" anti-CD123 antibody.

SEQ ID NO: 200 shows the amino acid sequences of CDR2-H of the so-called "1E1-G5" and "6D6-B8" anti-CD123 antibody.

SEQ ID NO: 201 show the amino acid sequences of CDR3-H of the so-called "1E1-G5", "6D6-B8", "8B11-B7" and "9F6-G3" anti-CD123 antibody.

SEQ ID NO: 202 shows the amino acid sequence of the light chain variable domain of the so-called "1E1-G5" anti-CD123 antibody.

SEQ ID NO: 203 and 204 show the amino acid sequences of CDR1-L and CDR3-L of the so-called "1E1-G5" anti-CD123 antibody.

SEQ ID NO: 205 shows the amino acid sequence of the heavy chain variable domain of the so-called "2B8-F3" anti-CD123 antibody.

SEQ ID NO: 206, 207 and 208 show the amino acid sequences of CDR1-H, CDR2-H and CDR3-H of the so-called "2B8-F3" anti-CD123 antibody.

SEQ ID NO: 209 shows the amino acid sequence of the light chain variable domain of the so-called "2B8-F3" anti-CD123 antibody.

SEQ ID NO: 210 and 211 show the amino acid sequences of CDR1-L and CDR3-L of the so-called "2B8-F3" anti-CD123 antibody.

SEQ ID NO: 212 shows the amino acid sequence of the heavy chain variable domain of the so-called "2F8-D6" anti-CD123 antibody.

SEQ ID NO: 213, 214 and 215 show the amino acid sequences of CDR1-H, CDR2-H and CDR3-H of the so-called "2F8-D6" anti-CD123 antibody.

SEQ ID NO: 216 shows the amino acid sequence of the light chain variable domain of the so-called "2F8-D6" anti-CD123 antibody.

SEQ ID NO: 217 and 218 show the amino acid sequences of CDR1-L and CDR3-L of the so-called "2F8-D6" anti-CD123 antibody.

SEQ ID NO: 219 shows the amino acid sequence of the heavy chain variable domain of the so-called "3B10-E6" anti-CD123 antibody.

SEQ ID NO: 220, 221 and 222 show the amino acid sequences of CDR1-H, CDR2-H and CDR3-H of the so-called "3B10-E6" anti-CD123 antibody. SEQ ID NO: 223 shows the amino acid sequence of the light chain variable domain of the so-called "3B10-E6" anti-CD123 antibody.

SEQ ID NO: 224 and 225 show the amino acid sequences of CDR1-L and CDR3-L of the so-called "3B10-E6" anti-CD123 antibody.

SEQ ID NO: 226 shows the amino acid sequence of the heavy chain variable domain of the so-called "3E3-D3" anti-CD123 antibody.

SEQ ID NO: 227, 228 and 229 show the amino acid sequences of CDR1-H, CDR2-H and CDR3-H of the so-called "3E3-D3" anti-CD123 antibody.

SEQ ID NO: 230 shows the amino acid sequence of the light chain variable domain of the so-called "3E3-D3" anti-CD123 antibody.

SEQ ID NO: 231 and 232 show the amino acid sequences of CDR1-L and CDR3-L of the so-called "3E3-D3" anti-CD123 antibody.

SEQ ID NO: 233 shows the amino acid sequence of the heavy chain variable domain of the so-called "5A5-B4" anti-CD123 antibody.

SEQ ID NO: 234, 235 and 236 show the amino acid sequences of CDR1-H, CDR2-H and CDR3-H of the so-called "5A5-B4" anti-CD123 antibody.

SEQ ID NO: 237 shows the amino acid sequence of the light chain variable domain of the so-called "5A5-B4" anti-CD123 antibody.

SEQ ID NO: 238 and 239 show the amino acid sequences of CDR1-L and CDR3-L of the so-called "5A5-B4" anti-CD123 antibody.

SEQ ID NO: 240 shows the amino acid sequence of the heavy chain variable domain of the so-called "6B10-E4" anti-CD123 antibody.

SEQ ID NO: 241, 242 and 243 show the amino acid sequences of CDR1-H, CDR2-H and CDR3-H of the so-called "6B10-E4" anti-CD123 antibody. SEQ ID NO: 244 shows the amino acid sequence of the light chain variable domain of the so-called "6B10-E4" anti-CD123 antibody.

SEQ ID NO: 245 and 246 show the amino acid sequences of CDR1-L and CDR3-L of the so-called "6B10-E4" anti-CD123 antibody.

SEQ ID NO: 247 shows the amino acid sequence of the heavy chain variable domain of the so-called "6C10-C4" anti-CD123 antibody.

SEQ ID NO: 248, 249 and 250 show the amino acid sequences of CDR1-H, CDR2-H and CDR3-H of the so-called "6C10-C4" anti-CD123 antibody.

SEQ ID NO: 251 shows the amino acid sequence of the light chain variable domain of the so-called "6C10-C4" and "9B8-G6" anti-CD123 antibody. SEQ ID NO: 252 shows the amino acid sequence of CDR1-L of the so-called "6C10-C4" and "9B8-G6" anti-CD123 antibody.

SEQ ID NO: 253 shows the amino acid sequence of CDR3-L of the so-called "6C10-C4", "9B8-G6" and "9D7-G3" anti-CD123 antibodies.

SEQ ID NO: 254 shows the amino acid sequence of the heavy chain variable domain of the so-called "6D6-B8" anti-CD123 antibody.

SEQ ID NO: 255 shows the amino acid sequence of CDR1-H of the so-called "6D6-B8" anti-CD123 antibody.

SEQ ID NO: 256 shows the amino acid sequence of the light chain variable domain of the so-called "6D6-B8" anti-CD123 antibody.

SEQ ID NO: 257 and 258 show the amino acid sequences of CDR1-L and CDR3-L of the so-called "6D6-B8" anti-CD123 antibody.

SEQ ID NO: 259 shows the amino acid sequence of the heavy chain variable domain of the so-called "8B11-B7" anti-CD123 antibody.

SEQ ID NO: 260 shows the amino acid sequence of CDR2-H of the so-called "8B11-B7" anti-CD123 antibody.

SEQ ID NO: 261 shows the amino acid sequence of the light chain variable domain of the so-called "8B11-B7" anti-CD123 antibody.

SEQ ID NO: 262 and 263 show the amino acid sequences of CDR1-L and CDR3-L of the so-called "8B11-B7" anti-CD123 antibody.

SEQ ID NO: 264 shows the amino acid sequence of the heavy chain variable domain of the so-called "9B8-G6" anti-CD123 antibody.

SEQ ID NO: 265 and 266 show the amino acid sequences of CDR1-H and CDR2-H of the so-called "9B8-G6" and "9D7-C8" anti-CD123 antibodies. SEQ ID NO: 267 shows the amino acid sequences of CDR3-H of the so-called "9B8-G6" anti-CD123 antibody.

SEQ ID NO: 268 shows the amino acid sequence of the heavy chain variable domain of the so-called "9D7-C8" anti-CD123 antibody.

SEQ ID NO: 269 shows the amino acid sequences of CDR3-H of the so-called "9D7-C8" anti-CD123 antibody.

SEQ ID NO: 270 shows the amino acid sequence of the light chain variable domain of the so-called "9D7-C8" anti-CD123 antibody.

SEQ ID NO: 271 shows the amino acid sequences of CDR1-L of the so-called "9D7-C8" anti-CD123 antibody.

SEQ ID NO: 272 shows the amino acid sequence of the heavy chain variable domain of the so-called "9F6-G3" anti-CD123 antibody.

SEQ ID NO: 273 and 274 show the amino acid sequences of CDR1-H and CDR2-H of the so-called "9F6-G3" anti-CD123 antibody.

SEQ ID NO: 275 shows the amino acid sequence of the light chain variable domain of the so-called "9F6-G3" anti-CD123 antibody.

SEQ ID NO: 276 shows the amino acid sequence of CDR1-L of the so-called "9F6-G3" anti-CD123 antibody.

SEQ ID NO: 277 shows the VH variant amino acid sequence VH_G45A of "3E3" anti-CD123 antibody.

SEQ ID NO: 278 shows the VH variant amino acid sequence VHmDG of "3E3" anti-CD123 antibody.

SEQ ID NO: 279 shows the amino acid sequence of CDR2-H of the variant VHmDG of "3E3" anti-CD123 antibody and CDR2-H of variant VH1Fm2DG of humanized "3E3" anti-CD123 antibody.

SEQ ID NO: 280 shows the VH variant amino acid sequence VH1A of humanized "3E3" anti-CD123 antibody.

SEQ ID NO: 281 shows the VH variant amino acid sequence VH1B of humanized "3E3" anti-CD123 antibody.

SEQ ID NO: 282 shows the VH variant amino acid sequence VH1C of humanized "3E3" anti-CD123 antibody.

SEQ ID NO: 283 shows the VH variant amino acid sequence VH1D of humanized "3E3" anti-CD123 antibody.

SEQ ID NO: 284 shows the VH variant amino acid sequence VH1E of humanized "3E3" anti-CD123 antibody.

SEQ ID NO: 285 shows the VH variant amino acid sequence VH1F of humanized "3E3" anti-CD123 antibody.

SEQ ID NO: 286 shows the VH variant amino acid sequence VH1G of humanized "3E3" anti-CD123 antibody SEQ ID NO: 287 shows the VH variant amino acid sequence VH1Fm1 of humanized "3E3" anti-CD123 antibody SEQ ID NO: 288 shows the VH variant amino acid sequence VH1Fm2 of humanized "3E3" anti-CD123 antibody SEQ ID NO: 289 shows the VH variant amino acid sequence VH1Fm2DG of humanized "3E3" anti-CD123 antibody SEQ ID NO: 290 shows the VH variant amino acid sequence VH1Dm1 of humanized "3E3" anti-CD123 antibody SEQ ID NO: 291 shows the VH variant amino acid sequence VH1Em1 of humanized "3E3" anti-CD123 antibody SEQ ID NO: 292 shows the VL variant amino acid sequence VL1A of humanized "3E3" anti-CD123 antibody.

SEQ ID NO: 293 shows the VL variant amino acid sequence VL1B of humanized "3E3" anti-CD123 antibody.

SEQ ID NO: 294 shows the VL variant amino acid sequence VL1C of humanized "3E3" anti-CD123 antibody.

SEQ ID NO: 295 shows the VL variant amino acid sequence VL1D of humanized "3E3" anti-CD123 antibody.

SEQ ID NO: 296 shows the VL variant amino acid sequence VL1E of humanized "3E3" anti-CD123 antibody.

SEQ ID NO: 297 shows the VL variant amino acid sequence VL1F of humanized "3E3" anti-CD123 antibody.

SEQ ID NO: 298 shows the VL variant amino acid sequence VL1G of humanized "3E3" anti-CD123 antibody.

SEQ ID NO: 299 shows the VL variant amino acid sequence VL1Fm1 of humanized "3E3" anti-CD123 antibody.

SEQ ID NO: 300 shows the VL variant amino acid sequence VL1Fm2 of humanized "3E3" anti-CD123 antibody.

SEQ ID NO: 301 shows the VH variant amino acid sequence VH2A of humanized "3E3" anti-CD123 antibody.

SEQ ID NO: 302 shows the VH variant amino acid sequence VH3A of humanized "3E3" anti-CD123 antibody.

SEQ ID NO: 303 shows the VL variant amino acid sequence VL2A of humanized "3E3" anti-CD123 antibody.

SEQ ID NO: 304 shows the VL variant amino acid sequence VL2Am1 of humanized "3E3" anti-CD123 antibody.

SEQ ID NO: 305 shows the VL variant amino acid sequence VL2Am2 of humanized "3E3" anti-CD123 antibody.

SEQ ID NO: 306 shows the amino acid sequence of polypeptide according to formula I of the so-called CODV-Fab "7G3×20G6" antibody-like binding protein.

SEQ ID NO: 307 shows the amino acid sequence of the linker L1 of the so-called CODV-Fab "7G3×20G6", "7G3×4E7", "7G3×4B4", "7G3×18F5", "hz20G6×7G3", "7G3×hz4B4", "hz4B4×3E3" and CODV-Fab "hz20G6×7G3-TL4" antibody-like binding proteins SEQ ID NO: 308 shows the amino acid sequence of the variable light chain domain of 7G3 representing the $V_{D1}$ or $V_{D2}$ domain of the so-called CODV-Fab "7G3×20G6", "7G3×4E7", "7G3×4B4", "7G3×18F5", "hz20G6×7G3", "7G3×hz4B4" and CODV-Fab "hz20G6×7G3-TL4" antibody-like binding proteins.

SEQ ID NO: 309 shows the amino acid sequence of the linker L2 of the so-called CODV-Fab "7G3×20G6", "7G3×4E7", "7G3×4B4", "7G3×18F5", "hz20G6×7G3", "7G3×hz4B4", "hz4B4×3E3" and CODV-Fab "hz20G6×7G3-TL4" antibody-like binding proteins.

SEQ ID NO: 310 shows the amino acid sequence CL of the so-called CODV-Fab "7G3×20G6", "7G3×4E7", "7G3×4B4", "7G3×18F5", "hz20G6×7G3", "7G3×hz4B4" and "hz4B4×3E3" antibody-like binding proteins.

SEQ ID NO: 311 shows the amino acid sequence of the polypeptide according to formula II of the so-called CODV-Fab "7G3×20G6" antibody-like binding protein.

SEQ ID NO: 312 shows the amino acid sequence of the variable heavy chain domain of 7G3 representing herein the $V_{H1}$ or $V_{H2}$ domain of the so-called CODV-Fab "7G3×20G6", "7G3×4E7", "7G3×4B4", "7G3×18F5", "hz20G6×7G3", "7G3×hz4B4" and CODV-Fab "hz20G6×7G3-TL4" antibody-like binding proteins.

SEQ ID NO: 313 shows the amino acid sequence $C_{H1}$ of the so-called CODV-Fab "7G3×20G6", "7G3×4E7", "7G3×4B4", "7G3×18F5", "hz20G6×7G3", "7G3×hz4B4", "hz4B4×3E3" antibody-like binding proteins.

SEQ ID NO: 314 shows the amino acid sequence of polypeptide according to formula I of the so-called CODV-Fab "7G3×4E7" antibody-like binding protein.

SEQ ID NO: 315 shows the amino acid sequence of the polypeptide according to formula II of the so-called CODV-Fab "7G3×4E7" antibody-like binding protein.

SEQ ID NO: 316 shows the amino acid sequence of polypeptide according to formula I of the so-called CODV-Fab "7G3×4B4" antibody-like binding protein.

SEQ ID NO: 317 shows the amino acid sequence of the polypeptide according to formula II of the so-called CODV-Fab "7G3×4B4" antibody-like binding protein.

SEQ ID NO: 318 shows the amino acid sequence of polypeptide according to formula I of the so-called CODV-Fab "7G3×18F5" antibody-like binding protein.

SEQ ID NO: 319 shows the amino acid sequence of the polypeptide according to formula II of the so-called CODV-Fab "7G3×18F5" antibody-like binding protein.

SEQ ID NO: 320 shows the amino acid sequence of polypeptide according to formula I of the so-called CODV-Fab "hz20G6×7G3" antibody-like binding protein.

SEQ ID NO: 321 shows the amino acid sequence of the polypeptide according to formula II of the so-called CODV-Fab "hz20G6×7G3" antibody-like binding protein.

SEQ ID NO: 322 shows the amino acid sequence of polypeptide according to formula I of the so-called CODV-Fab 7G3×hz4B4" antibody-like binding protein.

SEQ ID NO: 323 shows the amino acid sequence of the polypeptide according to formula II of the so-called CODV-Fab "7G3×hz4B4" antibody-like binding protein.

SEQ ID NO: 324 shows the amino acid sequence of polypeptide according to formula I of the so-called CODV-Fab "hz4B4×3E3" antibody-like binding protein. SEQ ID NO: 325 shows the amino acid sequence of the polypeptide according to formula II of the so-called CODV-Fab "hz4B4×3E3" antibody-like binding protein.

SEQ ID NO: 326 shows the amino acid sequence of polypeptide according to formula I of the so-called CODV-Fab "hz20G6×7G3 TL4" antibody-like binding protein.

SEQ ID NO: 327 shows the amino acid sequence $F_{c2}$ of the so-called CODV-Fab "hz20G6×7G3-TL4" antibody-like binding protein.

SEQ ID NO: 328 shows the amino acid sequence of the polypeptide according to formula III of the so-called CODV-Fab "hz20G6×7G3-TL4" antibody-like binding protein.

SEQ ID NO: 329 shows the amino acid sequence $C_{H1}$ of the so-called CODV-Fab "hz20G6×7G3-TL4" antibody-like binding protein.

SEQ ID NO: 330 shows the amino acid sequence $F_c$ of the so-called CODV-Fab "hz20G6×7G3-TL4" antibody-like binding protein.

SEQ ID NO: 331 shows a consensus sequence for CDR1-H of the so-called "20G6-F3", "4B4-D7", "4E7-C9", "18F5-H10", "11D7-C3", "11H3-E5", "13H2-C2", "13C1-F6", "1E6-C9", "10F4-C10", "10E6-G6", "18G9-H11", "11F3-B9", "12G3-E8", "5B1-G2", "16F8-A7", "11F9-F8", "20E5-F10", "20B5-F10", "3H6-D2" anti-CD3 antibodies based on sequence alignment.

SEQ ID NO: 332 shows a consensus sequence for CDR2-H of the so-called "20G6-F3", "4B4-D7", "4E7-C9", "18F5-H10", "11D7-C3", "11H3-E5", "13H2-C2", "13C1-F6", "1E6-C9", "10F4-C10", "10E6-G6", "18G9-H11", "11F3-B9", "12G3-E8", "5B1-G2", "16F8-A7", "11F9-F8", "20E5-F10", "20B5-F10", "3H6-D2" anti-CD3 antibodies based on sequence alignment.

SEQ ID NO:333 shows a consensus sequence for CDR3-H of the so-called "20G6-F3", "4B4-D7", "4E7-C9", "18F5-H10", "11D7-C3", "11H3-E5", "13H2-C2", "13C1-F6", "1E6-C9", "10F4-C10", "10E6-G6", "18G9-H11", "11F3-B9", "12G3-E8", "5B1-G2", "16F8-A7", "11F9-F8", "20E5-F10", "20B5-F10", "3H6-D2" anti-CD3 antibodies based on sequence alignment.

SEQ ID NO: 334 shows a consensus sequence for CDR1-L of the so-called "20G6-F3", "4B4-D7", "4E7-C9", "18F5-H10", "11D7-C3", "11H3-E5", "13H2-C2", "13C1-F6", "1E6-C9", "10F4-C10", "10E6-G6", "18G9-H11", "11F3-B9", "12G3-E8", "5B1-G2", "16F8-A7", "11F9-F8", "20E5-F10", "20B5-F10", "3H6-D2" anti-CD3 antibodies based on sequence alignment.

SEQ ID NO:335 shows a consensus sequence for CDR3-L of the so-called "20G6-F3", "4B4-D7", "4E7-C9", "18F5-H10", "11D7-C3", "11H3-E5", "13H2-C2", "13C1-F6", "1E6-C9", "10F4-C10", "10E6-G6", "18G9-H11", "11F3-B9", "12G3-E8", "5B1-G2", "16F8-A7", "11F9-F8", "20E5-F10", "20B5-F10", "3H6-D2" anti-CD3 antibodies based on sequence alignment.

SEQ ID NO: 336 shows a consensus sequence for CDR1-H of the so-called "1E1-G5", "6D6-B8", "8B11-B7", ", "9F6-G3" anti-CD123 antibodies based on sequence alignment.

SEQ ID NO:337 shows a consensus sequence for CDR2-H of the so-called "1E1-G5", "6D6-B8", "8B11-B7", "9F6-G3" anti-CD123 antibodies based on sequence alignment.

SEQ ID NO: 338 shows a consensus sequence for CDR1-L of the so-called "1E1-G5", "6D6-B8", "8B11-B7", "9F6-G3" anti-CD123 antibodies based on sequence alignment.

SEQ ID NO: 339 shows a consensus sequence for CDR3-L of the so-called "1E1-G5", "6D6-B8", "8B11-B7", "9F6-G3" anti-CD123 antibodies based on sequence alignment.

SEQ ID NO: 340 shows a consensus sequence for CDR1-H of the so-called "6C10-C4", 9B8-G6", "9D7-C8" anti-CD123 antibodies based on sequence alignment.

SEQ ID NO: 341 shows a consensus sequence for CDR2-H of the so-called "1E1-G5", "6D6-B8", "8B11-B7", "9F6-G3" anti-CD123 antibodies based on sequence alignment.

SEQ ID NO:342 shows a consensus sequence for CDR3-H of the so-called "1E1-G5", "6D6-B8", "8B11-B7", "9F6-G3" anti-CD123 antibodies based on sequence alignment.

SEQ ID NO: 343 shows a consensus sequence for CDR1-L of "1E1-G5", "6D6-B8", "8B11-B7", "9F6-G3" anti-CD123 antibodies based on sequence alignment.

SEQ ID NO: 344 shows the amino acid sequence of a linker sequence (Gly-Gly-Gly-Gly-Ser).

SEQ ID NO: 345 shows the amino acid sequence of a linker sequence (Gly-Gly-Gly-Gly-Ser-Gly-Gly-Gly-Gly-Ser).

SEQ ID NO: 346 shows the amino acid sequence of a linker sequence (Thr-Val-Ala-Ala-Pro).

SEQ ID NO: 347 shows the amino acid sequence of a linker sequence (Gln-Pro-Lys-Ala-Ala).

SEQ ID NO: 348 shows the amino acid sequence of a linker sequence (Gln-Arg-Ile-Glu-Gly).

SEQ ID NO: 349 shows the amino acid sequence of a linker sequence (Ala-Ser-Thr-Lys-Gly-Pro-Ser).

SEQ ID NO: 350 shows the amino acid sequence of a linker sequence (Ala-Ser-Thr-Lys-Gly-Pro-Ser).

SEQ ID NO: 351 shows the amino acid sequence of a linker sequence (His-Ile-Asp-Ser-Pro-Asn-Lys).

SEQ ID NO: 352 shows the amino acid sequence of a linker and His-tag sequence added C-terminally to polypeptide according to formula II of the so-called CODV-Fab "7G3×20G6", "7G3×4E7", "7G3×4B4", "7G3×18F5", "hz20G6×7G3", "7G3×hz4B4" and "hz4B4×3E3" antibody-like binding proteins corresponding to a hinge sequence and a His-tag used for example for purification.

SEQ ID NO: 353 shows the amino acid sequence of CDR2-H of a variant of the so-called "3E3" anti-CD123 antibody.

SEQ ID NO: 354 shows the amino acid sequence of a linker sequence (Gly-Gly-Gly-Ser).

SEQ ID NO: 355 shows the amino acid sequence of a linker sequence (Ser-Gly-Gly-Gly-Ser).

SEQ ID NO: 356 shows the amino acid sequence of a linker sequence (Gly-Ser-Gly-Gly-Gly-Gly-Ser).

SEQ ID NO: 357 shows the amino acid sequence of a linker sequence (Gly-Gly-Ser-Gly-Gly-Gly-Gly-Ser).

SEQ ID NO: 358 shows the amino acid sequence of a linker sequence (Gly-Gly-Gly-Ser-Gly-Gly-Gly-Gly-Ser).

SEQ ID NO: 359 shows the amino acid sequence of a linker sequence (Lys-Thr-His-Thr).

SEQ ID NO: 360 shows the amino acid sequence of a linker sequence (Lys-Thr-His-Thr-Ser).

SEQ ID NO: 361 shows the amino acid sequence of a linker sequence (Asp-Lys-Thr-His-Thr-Ser).

SEQ ID NO: 362 shows the amino acid sequence of a linker sequence (Asp-Lys-Thr-His-Thr-Ser-Pro).

SEQ ID NO: 363 shows the amino acid sequence of a linker sequence (Ser-Asp-Lys-Thr-His-Thr-Ser-Pro).

SEQ ID NO: 364 shows the amino acid sequence of a linker sequence (Ser-Asp-Lys-Thr-His-Thr-Ser-Pro-Pro).

SEQ ID NO: 365 shows the amino acid sequence of a linker sequence (Lys-Ser-Asp-Lys-Thr-His-Thr-Ser-Pro-Pro-Ser)

SEQ ID NO: 366 shows the amino acid sequence of a linker sequence (Pro-Lys-Ser-Asp-Lys-Thr-His-Thr-Ser-Pro-Pro-Ser).

SEQ ID NO: 367 shows the amino acid sequence of a linker sequence (Pro-Lys-Ser-Asp-Lys-Thr-His-Thr-Ser-Pro-Pro-Ser-Pro) SEQ ID NO: 368 shows the amino acid sequence of a linker sequence (Glu-Pro-Lys-Ser-Asp-Lys-Thr-His-Thr-Ser-Pro-Pro-Ser-Pro)

SEQ ID NO: 369 shows the amino acid sequence of a linker sequence (Glu-Pro-Lys-Ser-Asp-Lys-Thr-His-Thr-Ser-Pro-Pro-Ser-Pro-Gly).

SEQ ID NO: 370 shows the amino acid sequence of a linker sequence (Gly-Glu-Pro-Lys-Ser-Asp-Lys-Thr-His-Thr-Ser-Pro-Pro-Ser-Pro-Gly).

SEQ ID NO: 371 shows the amino acid sequence of a linker sequence (Gly-Glu-Pro-Lys-Ser-Asp-Lys-Thr-His-Thr-Ser-Pro-Pro-Ser-Pro-Gly-Gly).

SEQ ID NO: 372 shows the amino acid sequence of a linker sequence (Gly-Gly-Glu-Pro-Lys-Ser-Asp-Lys-Thr-His-Thr-Ser-Pro-Pro-Ser-Pro-Gly-Gly)

SEQ ID NO: 373 shows the amino acid sequence of a linker sequence (Gly-Gly-Glu-Pro-Lys-Ser-Asp-Lys-Thr-His-Thr-Ser-Pro-Pro-Ser-Pro-Gly-Gly-Gly).

SEQ ID NO: 374 shows the amino acid sequence of a linker sequence (Gly-Gly-Gly-Glu-Pro-Lys-Ser-Asp-Lys-Thr-His-Thr-Ser-Pro-Pro-Ser-Pro-Gly-Gly-Gly)

SEQ ID NO: 375, 376 and 377 show the amino acid sequences of CDR1-H, CDR2-H and CDR3-H of the so-called "7G3" antibody.

SEQ ID NO: 378 and 379 show the amino acid sequence of CDR1-L and CDR3-L of the so-called "7G3" antibody.

SEQ ID NO: 380 shows the amino acid sequence of a variant of the heavy chain variable domain of the so-called humanized "7G3" antibody.

SEQ ID NO: 381 and 382 show the amino acid sequences of CDR1-H and CDR3-H of the so-called humanized "7G3" antibody.

SEQ ID NO: 383 shows the amino acid sequence of a further variant of the heavy chain variable domain of the so-called humanized "7G3" antibody.

SEQ ID NO: 384 shows the amino acid sequences of CDR2-H of one of the so-called humanized "7G3" antibody.

SEQ ID NO: 385 shows the amino acid sequence of the light chain variable domain of the so-called humanized "7G3" antibody.

SEQ ID NO:386 shows the amino acid sequence SEQ ID NO:1 as shown in WO2015026892.

SEQ ID NO: 387 shows the amino acid sequence SEQ ID NO:3 as shown in WO2015026892.

SEQ ID NO: 388 shows the amino acid sequence of the polypeptide according to formula I of the so-called CODV-Fab "hz20G6×hz7G3", CODV-Fab-OL1 "hz20G6×hz7G3" and CODV-Fab-OL1a "hz20G6×hz7G3" antibody-like binding proteins.

SEQ ID NO: 389 shows the amino acid sequence of a linker sequence (Gly-Gly-Ser-Gly-Ser-Ser-Gly-Ser-Gly-Gly).

SEQ ID NO: 390 shows the amino acid sequence of the polypeptide according to formula II of the so-called CODV-Fab "hz20G6×hz7G3" antibody-like binding protein.

SEQ ID NO: 391 shows the amino acid sequence of the polypeptide according to formula IV of the so-called CODV-Fab-TL1 "hz20G6×hz7G3" antibody-like binding protein.

SEQ ID NO: 392 shows the amino acid sequence of the $F_{c2}$ region of the so-called CODV-Fab-TL1 "hz20G6×hz7G3" antibody-like binding protein.

SEQ ID NO: 393 shows the amino acid sequence of the polypeptide according to formula III of the so-called CODV-Fab-TL1 "hz20G6×hz7G3" antibody-like binding protein.

SEQ ID NO: 394 shows the amino acid sequence of the $F_c$ region of the so-called CODV-Fab-TL1 "hz20G6×hz7G3". SEQ ID NO: 395 shows the amino acid sequence of the polypeptide according to formula II of the so-called CODV-Fab-OL1 "hz20G6×hz7G3" antibody-like binding protein.

SEQ ID NO: 396 shows the amino acid sequence of the $F_c$ region of the so-called CODV-Fab-OL1 "hz20G6×hz7G3" antibody-like binding protein.

SEQ ID NO: 397 shows the amino acid sequence of the Fc stump ($Fc_3$) of the so-called CODV-Fab-OL1 "hz20G6×hz7G3" antibody-like binding protein.

SEQ ID NO: 398 shows the amino acid sequence of the Fc stump ($Fc_3$) of the so-called CODV-Fab-OL1a "hz20G6×hz7G3" antibody-like binding protein.

SEQ ID NO: 399 shows the amino acid sequence of the polypeptide according to formula II of the so-called CODV-Fab-OL1a "hz20G6×hz7G3" antibody-like binding protein.

SEQ ID NO: 400 shows the amino acid sequence of the Fc stump ($Fc_3$) of the so-called CODV-Fab-OL1a "hz20G6×hz7G3" antibody-like binding protein.

FIGURES

FIG. 1: Sequence alignments of the VH regions of the so-called "20G6-F3" (SEQ ID NO. 5), "4B4-D7" (SEQ ID NO. 12), "4E7-C9" (SEQ ID NO. 18), "18F5-H10" (SEQ ID NO. 23), "11D7-C3" (SEQ ID NO. 36), "11H3-E5" (SEQ ID NO. 40), "13H2-C2" (SEQ ID NO. 43), "13C1-F6" (SEQ ID NO. 46), "1E6-C9" (SEQ ID NO. 56), "10F4-C10" (SEQ ID NO. 60), "10E6-G6" (SEQ ID NO. 63), "18G9-H11" (SEQ ID NO. 68), "11F3-B9" (SEQ ID NO. 72), "12G3-E8" (SEQ ID NO. 74), "5B1-G2" (SEQ ID NO. 79), "16F8-A7" (SEQ ID NO. 83), "11F9-F8" (SEQ ID NO. 46), "20E5-F10" (SEQ ID NO. 107), "20B5-F10" (SEQ ID NO. 110), and "3H6-D2" (SEQ ID NO. 128) anti-CD3 antibodies.

Figure 2:
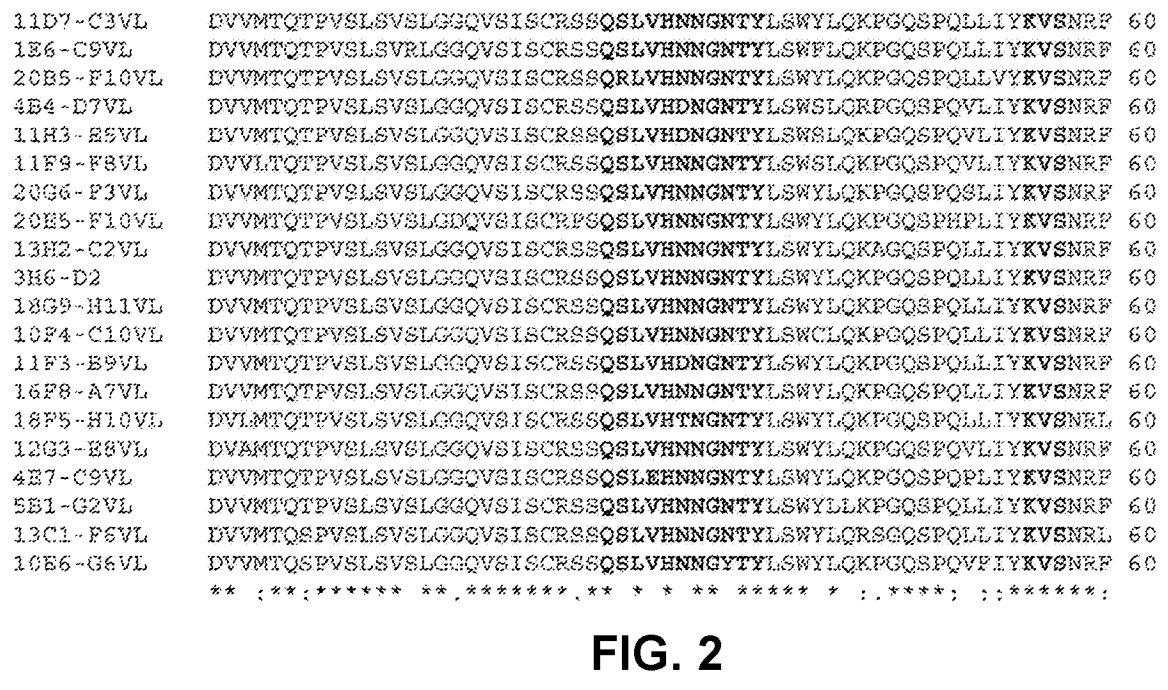

FIG. 2: Sequence alignments of the VL regions of so-called "20G6-F3" (SEQ ID NO. 9), "4B4-D7" (SEQ ID NO. 16), "4E7-C9" (SEQ ID NO. 21), "18F5-H10" (SEQ ID NO. 26), "11D7-C3" (SEQ ID NO. 39), "11H3-E5"(SEQ ID NO.

42), "13H2-C2"(SEQ ID NO. 45), "13C1-F6" (SEQ ID NO. 48), "1E6-C9" (SEQ ID NO. 59), "10F4-C10"(SEQ ID NO. 62), "10E6-G6" (SEQ ID NO. 66), "18G9-H11"(SEQ ID NO. 70), "11F3-B9"(SEQ ID NO. 73), "12G3-E8" (SEQ ID NO. 78), "5B1-G2" (SEQ ID NO. 82), "16F8-A7"(SEQ ID NO. 85), "11F9-F8" (SEQ ID NO. 87), "20E5-F10" (SEQ ID NO. 109), "20B5-F10" (SEQ ID NO. 112), and "3H6-D2" (SEQ ID NO. 130) anti-CD3 antibodies.

FIG. 3: Sequence alignments of the VH and VL regions of the so-called "1E1-G5", (SEQ ID NO. 198 and SEQ ID NO. 202, respectively), "6D6-B8" (SEQ ID NO. 254 and SEQ ID NO. 256, respectively), "8B11-B7" (SEQ ID NO. 259 and SEQ ID NO. 261, respectively), and "9F6-G3" (SEQ ID NO. 272 and SEQ ID NO. 275, respectively) anti-CD123 antibodies.

FIG. 4: Sequence alignments of the VH and VL regions of so-called "6C10-C4"(SEQ ID NO. 247 and SEQ ID NO. 251, respectively), "9B8-G6" (SEQ ID NO. 264 and SEQ ID NO. 251, respectively), and "9D7-C8" (SEQ ID NO. 268 and SEQ ID NO. 270, respectively) anti-CD123 antibodies.

Figure 7:
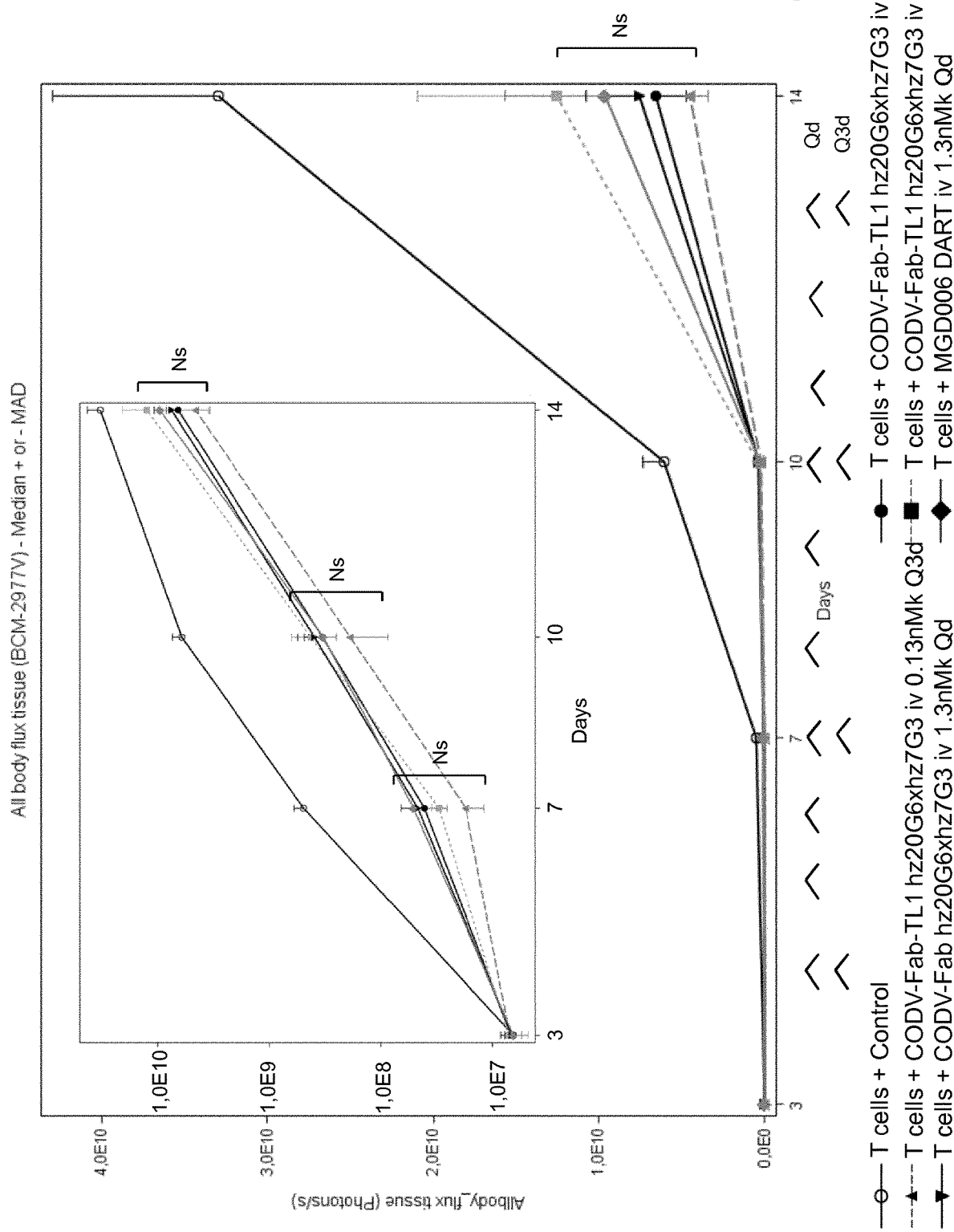

FIGS. 5 and 7: Fully human CODV-Fab-TL1 "hz20G6× hz7G3" IV Q3d in presence of human T cells inhibits Molm13 tumor growth in whole body at all tested doses.

Figure 6:
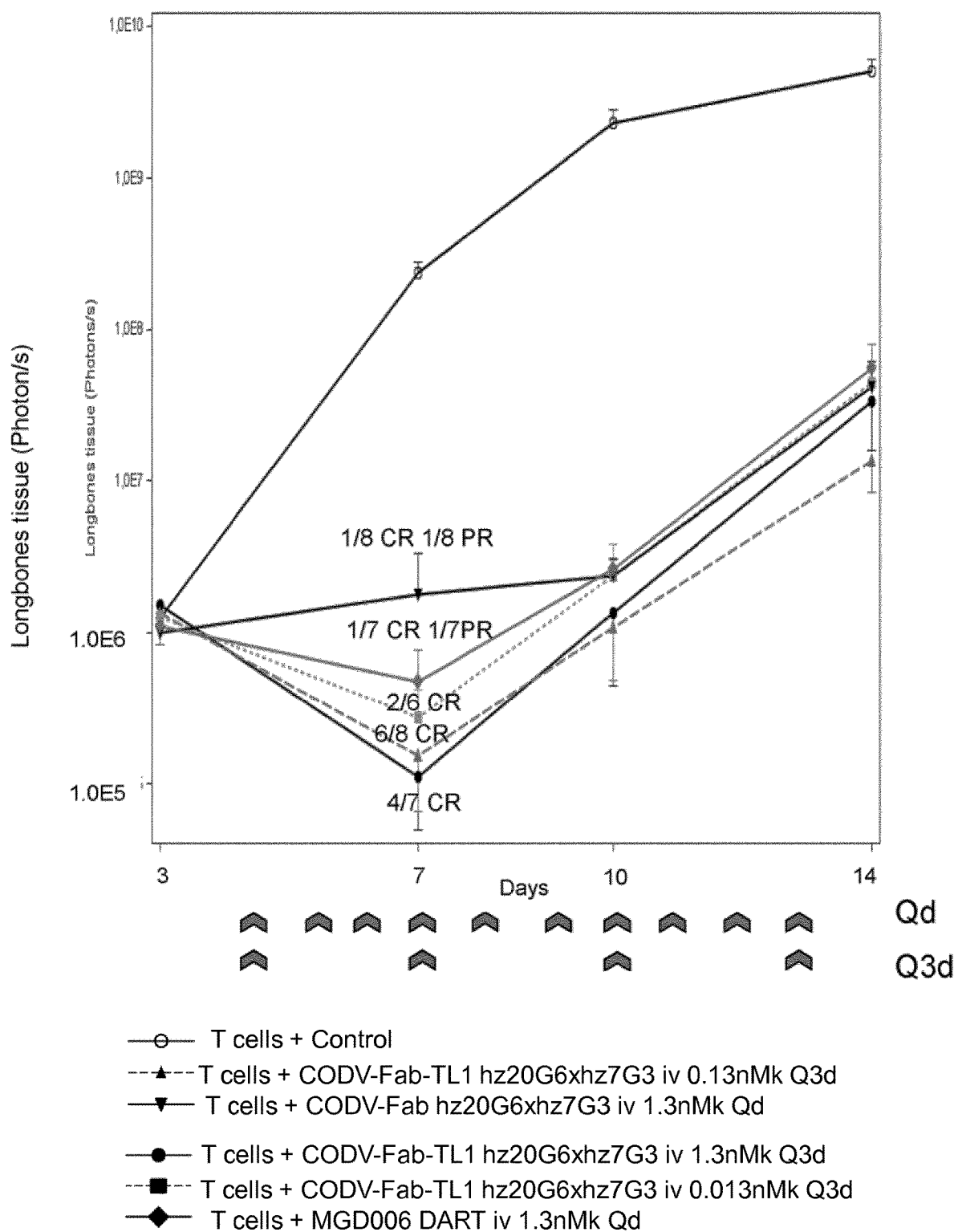
Figure 8:
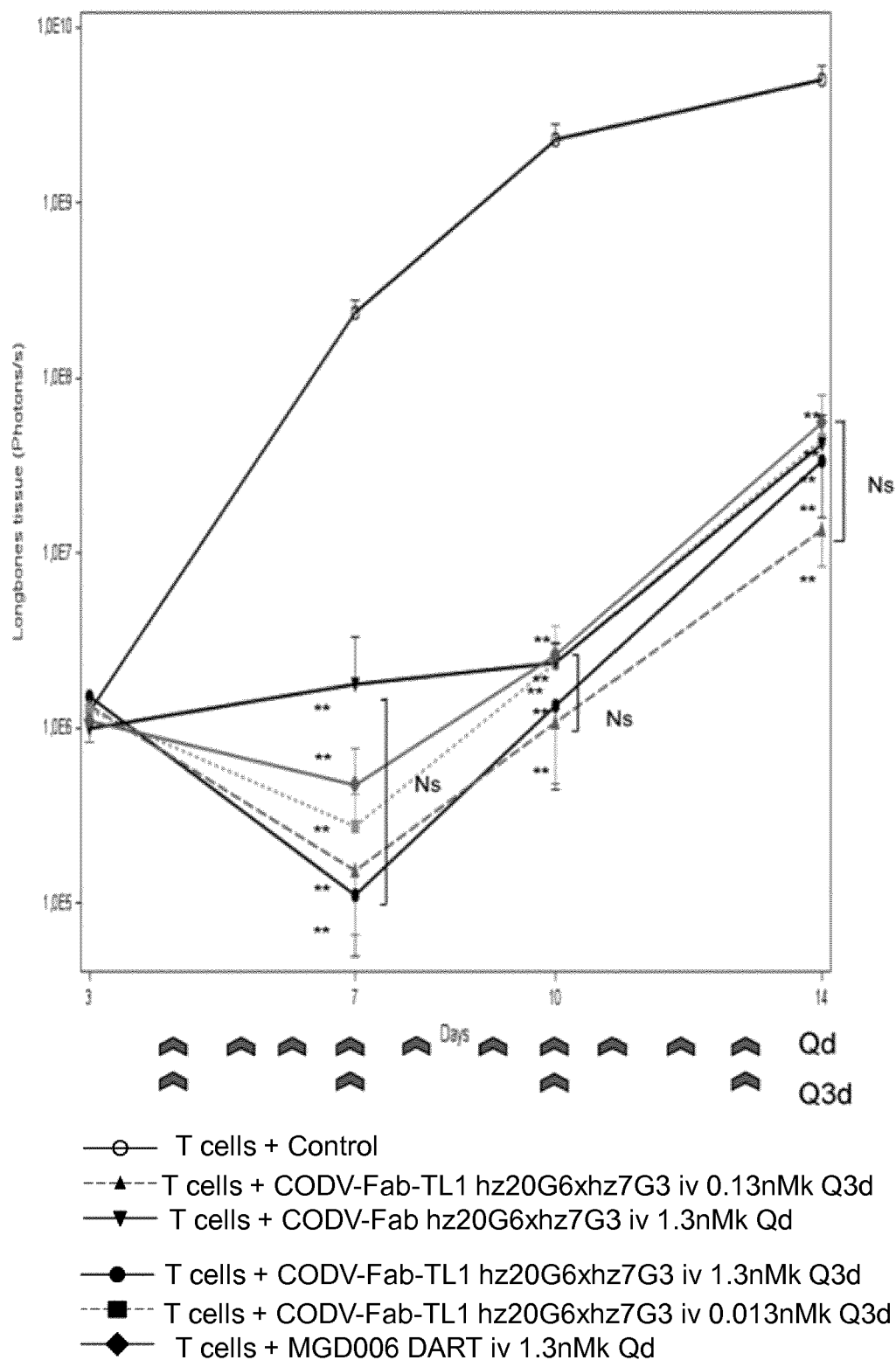

FIGS. 6 and 8: Fully human CODV-Fab-TL1 "hz20G6× hz7G3" IV Q3d in presence of human T cells is associated with tumor regression in long bones at all tested doses.

Figure 9:
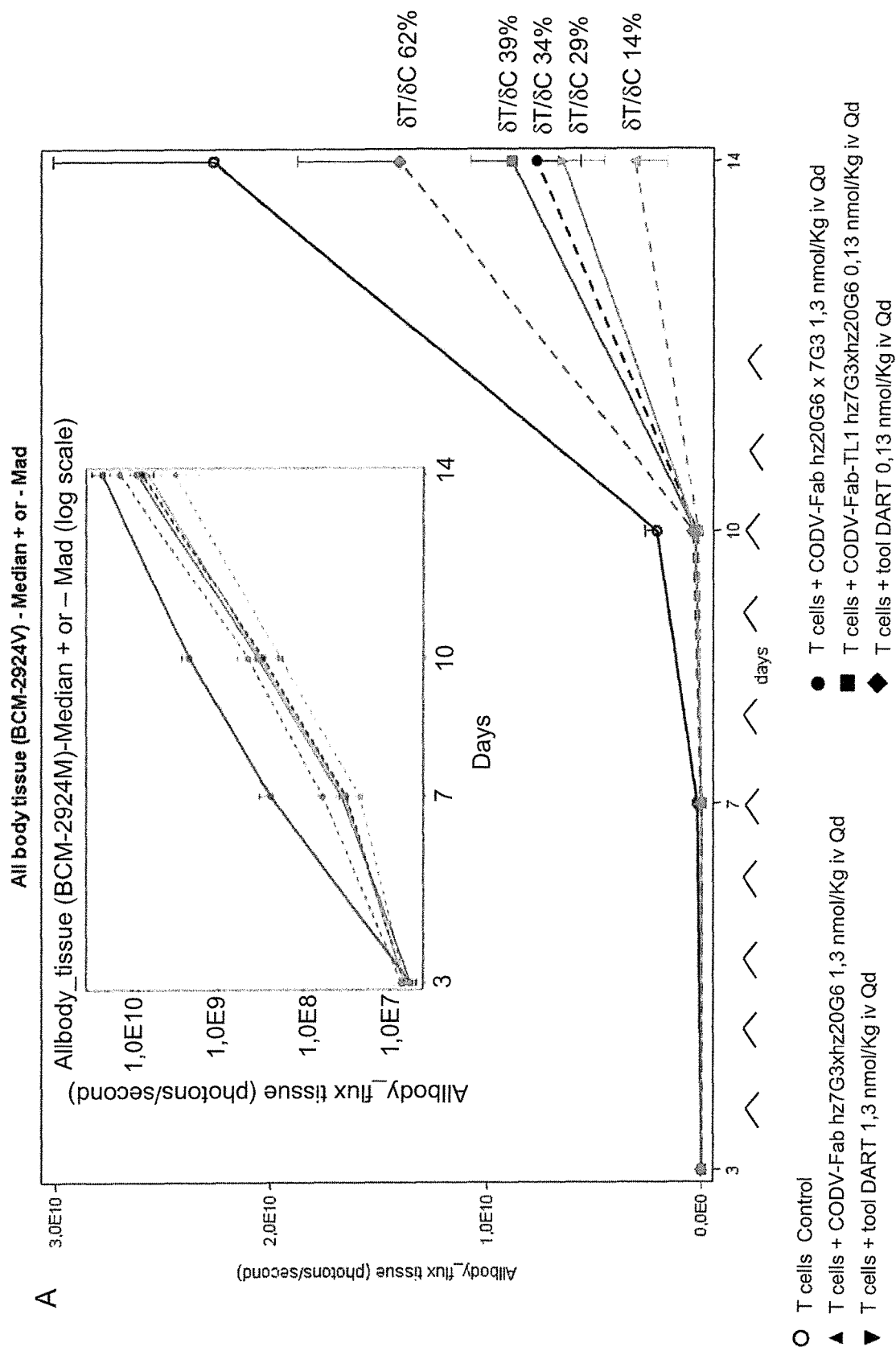
Figure 11:
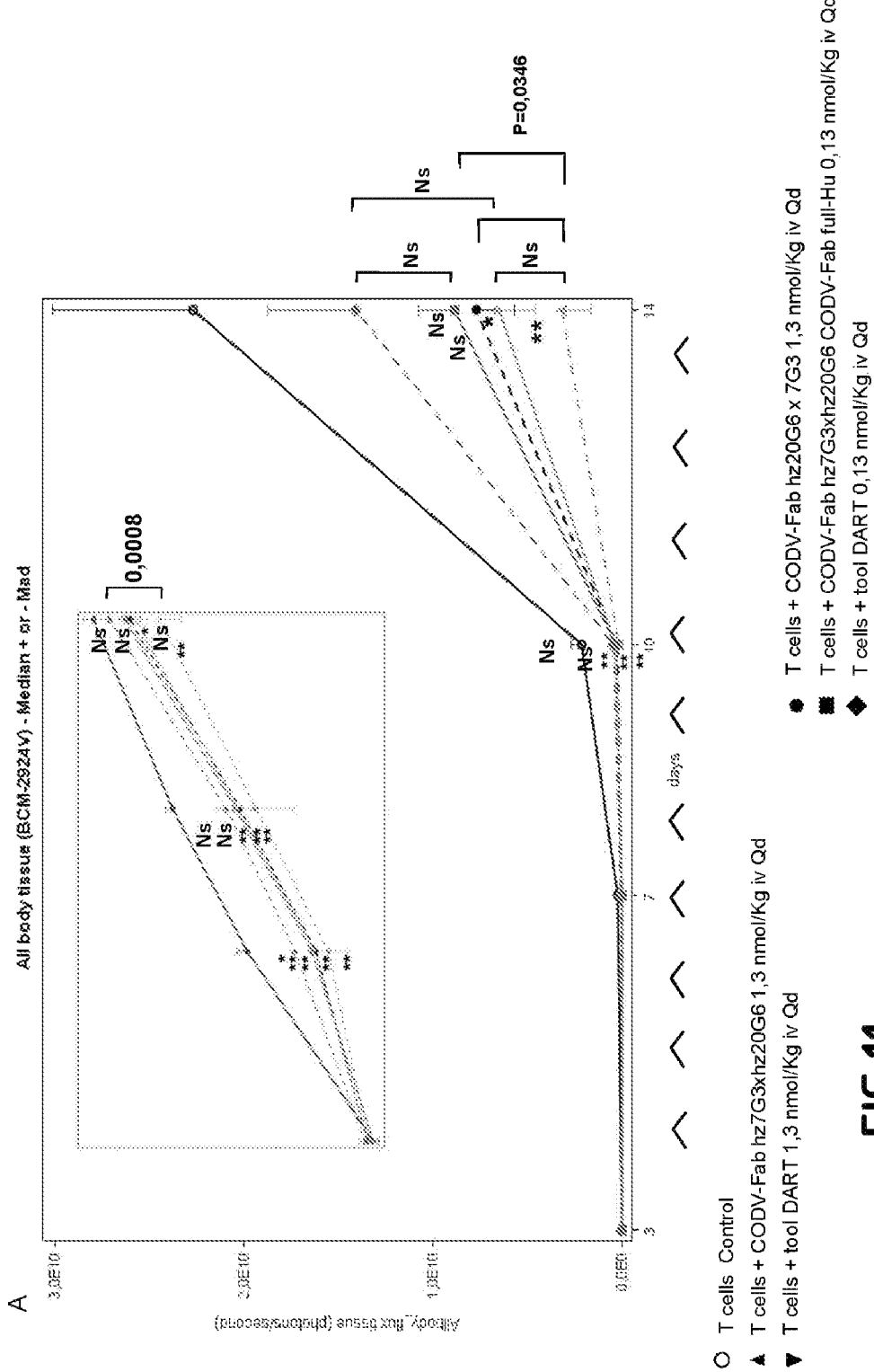

FIGS. 9 and 11: Fully human CODV-Fab "hz20G6× hz7G3" IV in presence of human T cells inhibited tumor growth.

Figure 10:
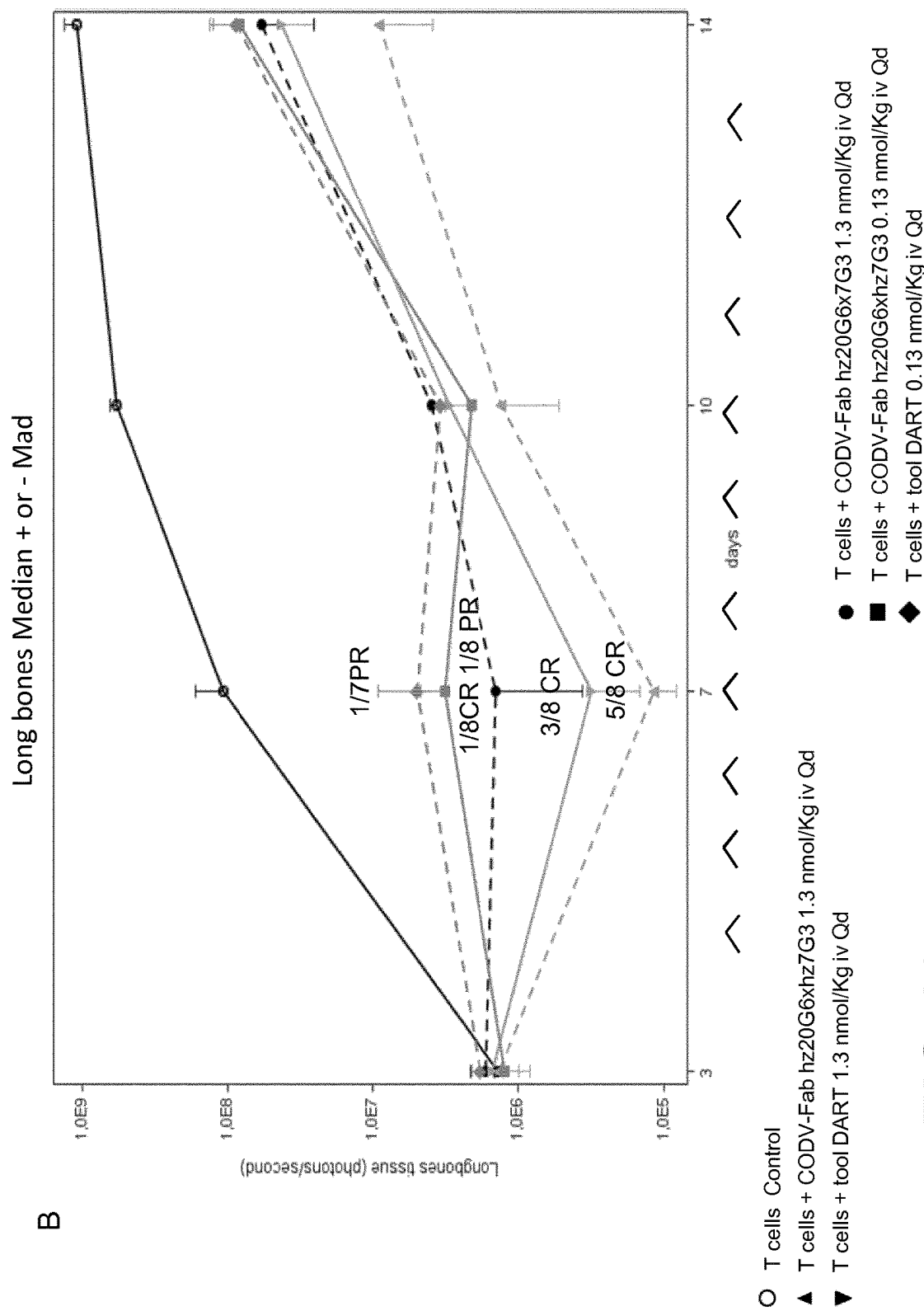
Figure 12:
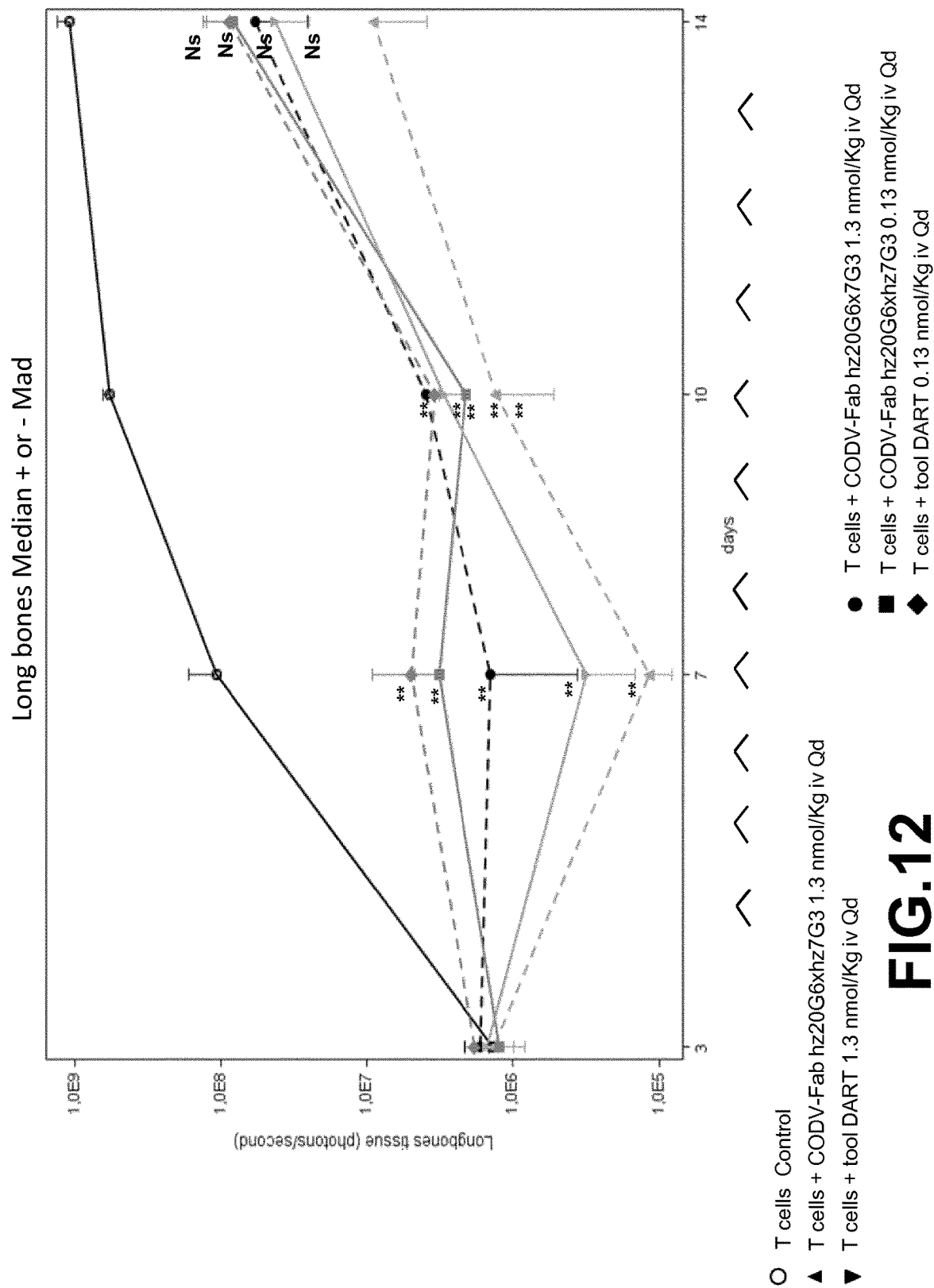

FIGS. 10 and 12: Fully human CODV-Fab "hz20G6× hz7G3" IV in presence of human T cells was associated with tumor regression in long bones.

Figure 13:
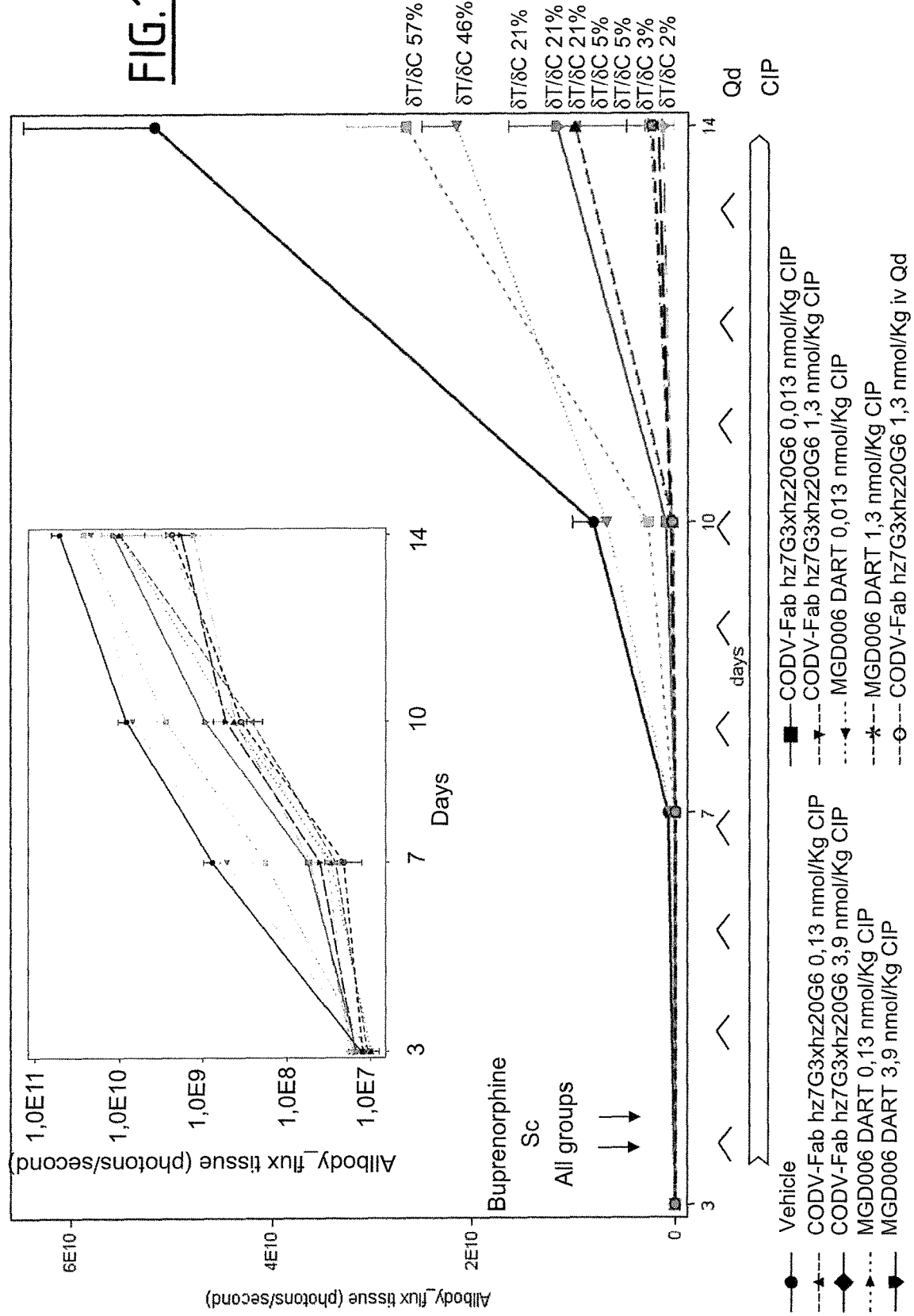
Figure 15:
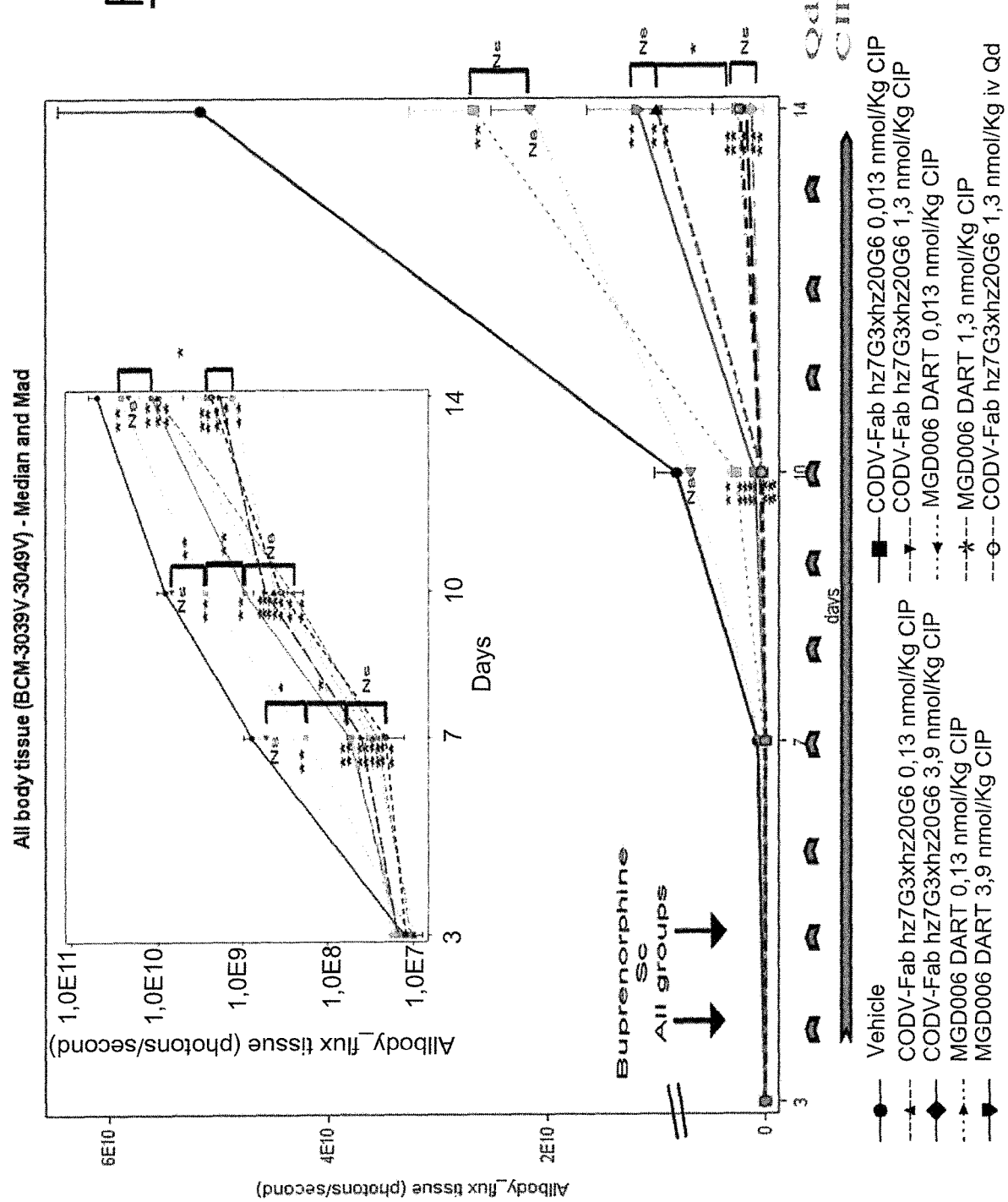

FIGS. 13 and 15: Fully human CODV-Fab "hz20G6× hz7G3" CIP in presence of human T cells inhibited whole body tumor growth at dosage of 0.13 nmol/Kg/day or above.

Figure 14:
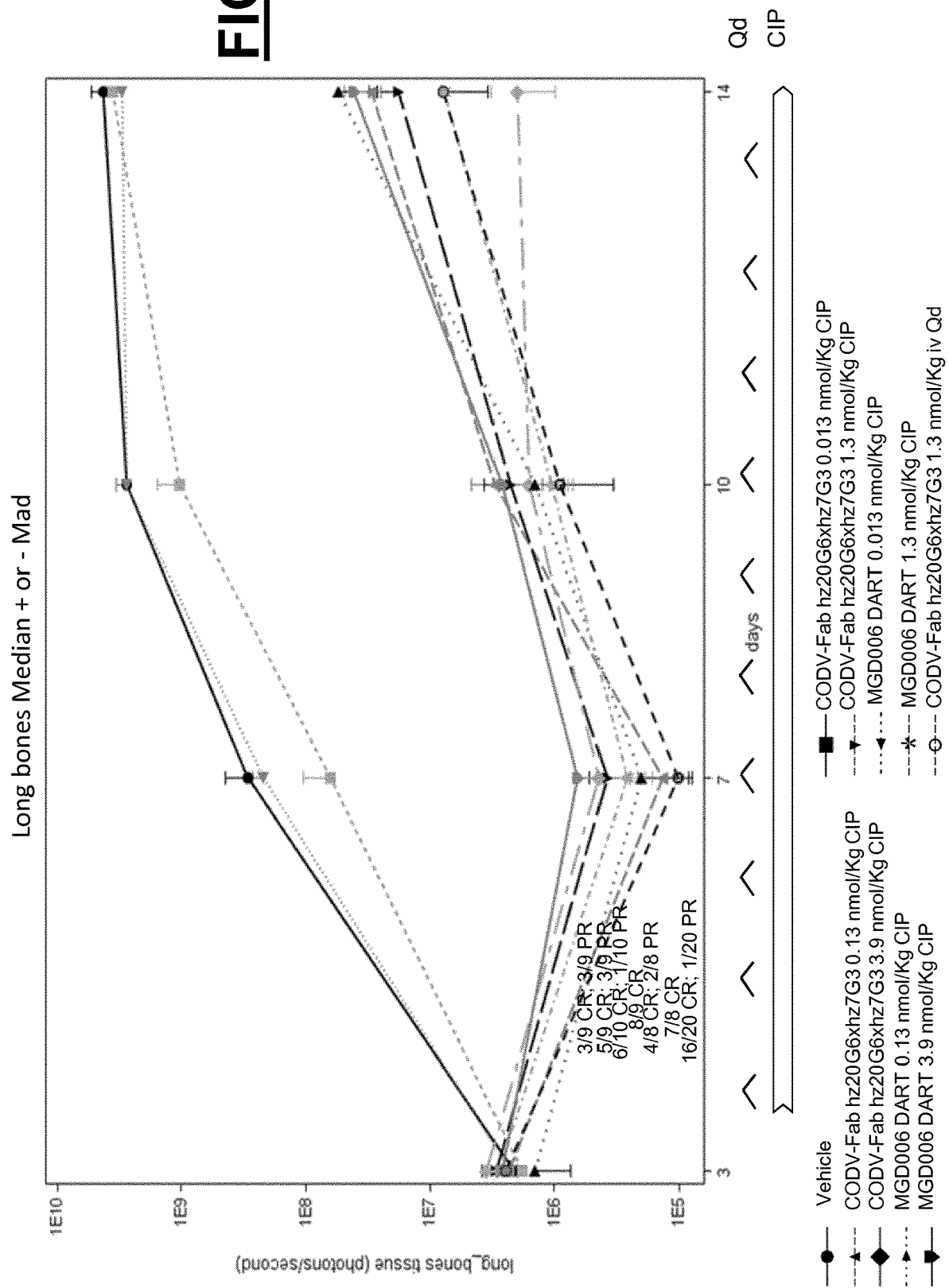
Figure 16:
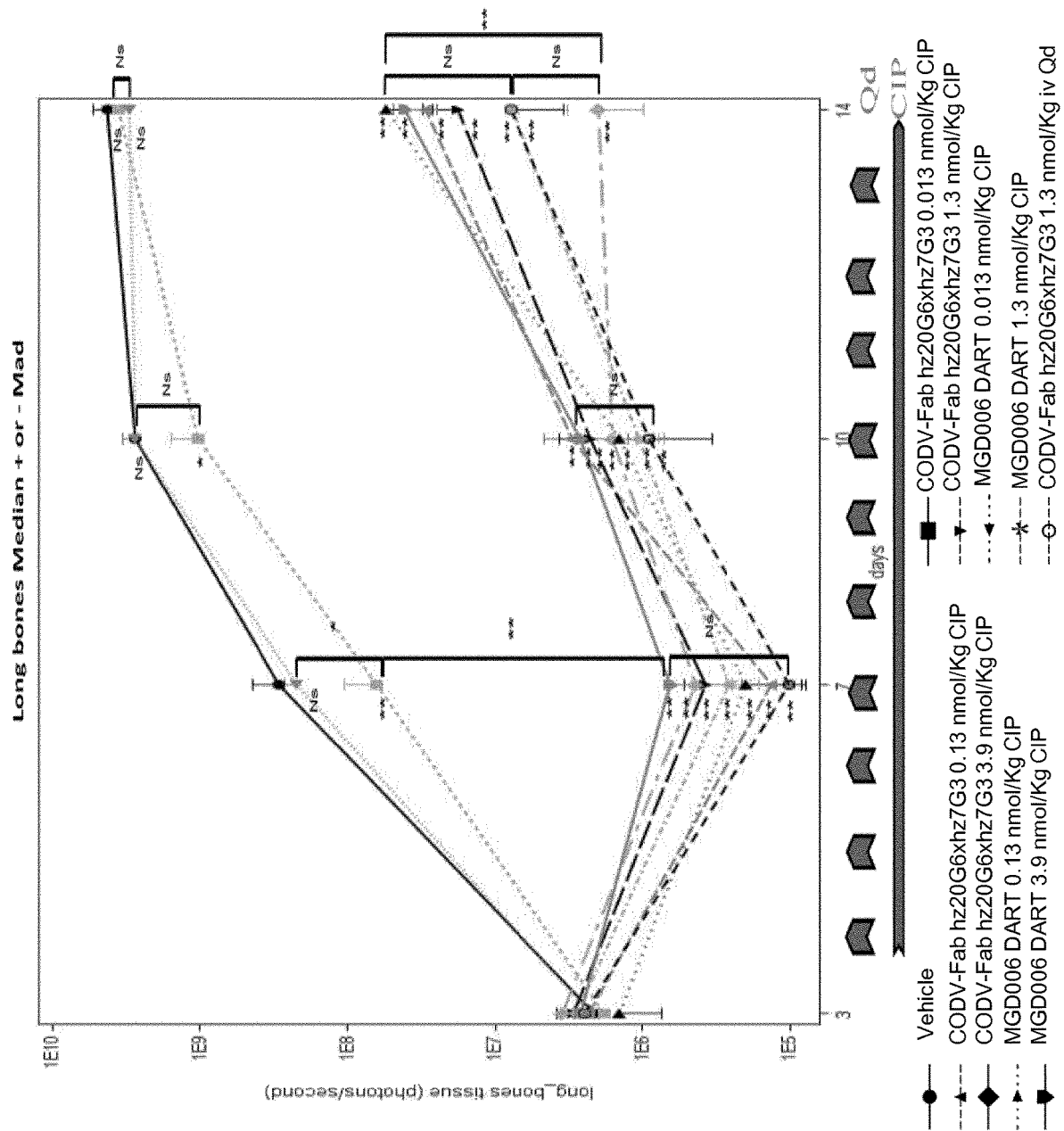

FIGS. 14 and 16: Fully human CODV-Fab "hz20G6× hz7G3" CIP in presence of human T cells inhibited tumor growth in long bones at dosage of 0.13 nmol/Kg/day or above.

Figure 17:
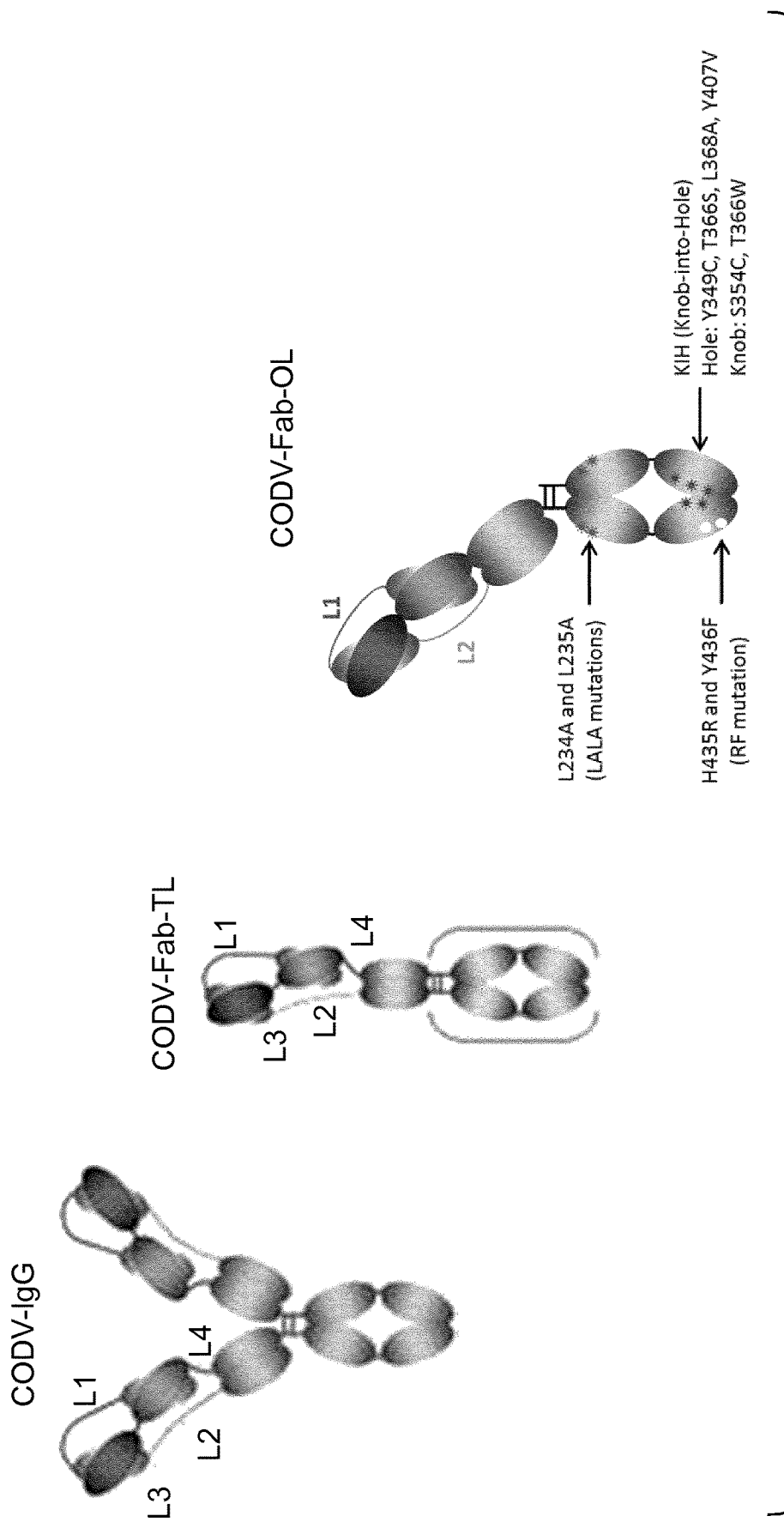

FIG. 17: Diagrammatic representation of the structure of the CODV-Ig, CODV-Fab-TL and CODV-Fab-OL (further showing LALA mutations (when Fc of IgG1 backbone is used) and Knob-into-Hole mutations).

EXAMPLES

Example 1: Antibody Generation 1.1 Construction of hCD3ε/δ-hFc Fusion Expression Plasmid (CD3ed-Fc)

Using cDNA containing plasmids as a template, human and *Macaca fascicularis* CD3ε and CDδ fusion proteins were generated, as described herein below in detail, in reading frame with heavy chain constant region including the hinge region, CH2 and CH3 domains of human immunoglobulin IgG additionally carrying a 8×His or Strep-II tag for optional tandem purification.

Using human genomic DNA as template, human CD3ε and human CDδ subunit extracellular domains were amplified, including the signal sequence. The resulting amplified cleaved and purified PCR products were combined by ligation PCR and ligated into mammalian expression vector pXL by InFusion method using NheI and HindIII site. Each subunit was cloned on one plasmid. The sequence of the resulting mature human CD3ε His-tagged Fc-fusion protein is herein disclosed under SEQ ID NO: 3. Amino acids 1 to 104 of SEQ ID NO: 3 correspond to amino acids 23 to 126 of the wild-type full-length human CD3ε (herein disclosed under SEQ ID NO: 1, available in Uniprot database under accession number P07766) protein and thus the extracellular domain of human CD3ε.

Using cynomolgus monkey genomic DNA as template, *Macaca fascicularis* CD3ε and CD3δ extracellular domains were amplified, including the signal sequence. The resulting amplified cleaved and purified PCR products were combined by ligation PCR and ligated into mammalian expression vector pXL by InFusion method using NheI and HindIII. Each subunit was cloned on one plasmid. The resulting sequences for mature *Macaca fascicularis* CD3ε Fc-fusion protein is disclosed under SEQ ID NO: 4. Amino acids 1 to 95 of SEQ ID NO: 3 correspond to amino acids 23 to 117 of the full-length *Macaca fascicularis* CD3ε protein and thus comprises the extracellular domain of wild-type full-length *Macaca fascicularis* CD3ε (herein disclosed under SEQ ID NO: 2, available in Uniprot database under accession number Q95LI5). The cloned fusion protein further contains one Alanine to Valine exchange at the amino acid position 35 in comparison to amino acid position 57 of the wild-type sequence.

1.2 Expression and Purification of Human and Cyno CD3ed-Fc

Freestyle HEK293 cells growing in F17 serum free suspension culture (Life) were transiently transfected with the expression plasmid. Co-transfection of both plasmids representing the CD3ε and CD3δ extracelullar domain (ECD) subunit were performed using Cellfectin transfection reagent (Life). The cells were cultured at 37° C. for 7 days. The culture supernatant containing recombinant protein was harvested by centrifugation and was clarified by filtration (0.22 μm).

For purification, the Fc-fusion protein variants were captured on protein A matrix (GE) and were eluted by pH shift. After polishing the protein by size exclusion chromatography (SEC) using a Superdex 200 (GE) and a final ultrafiltration concentration step the protein was used for further assays.

The human heterodimer was additionally applied on HisTrap collum (GE) after capture on protein A and desalted. The eluted protein was applied to a Strepavidin collumn (GE) and eluted with d-desthiobiotin before final polishing by SEC using a Superdex 200 (GE). This strategy was used to isolate heterodimers from homodimers.

1.3 Generation of Human/Cynomolgous Monkey Cross-Reactive Anti-CD3 Antibodies

Human and *Macaca fascicularis* CD3ε and CD3 δ cDNAs were cloned into Aldevron proprietary immunization vectors (pB8 and VV8) respectively, and used for genetic immunization of rats. Rats of immunization group MR12-266 ("CD3-cyno") were initially immunized with human CD3ε and CD3δcDNAs, followed by further two immunizations with a mixture of human and *Macaca fascicularis* CD3ε and CD3 δcDNAs. The immune serum was taken at day 24 of the immunization protocol, after 4 genetic applications (IS24d-4). Sera, diluted in PBS 1% BSA, were tested by flow cytometry using mammalian cells transiently transfected with the target cDNAs in co-transfection experiments to obtain human and *Macaca fascicularis* CD3ε and CD3δ TCR complexes. In addition the immune sera were tested on the following cell lines: Jurkat E6-1 (expressing human TCR), Jurkat-RT-T3.5 (negative for TCR) and cyno HSC-F (expressing cyno TCR); no negative cell line for the cyno TCR was available. A goat anti-rat IgG R-phycoerythrin conjugate (Southern Biotech, #3030-09) at 10 μg/ml was used as a secondary antibody.

Specific reactivity of the immune sera especially against cells transfected with combinations of CD3ε and CD3δcDNAs could be detected in the immunized animals when compared to cells transfected with an irrelevant cDNA. The same is valid for the test on the TCR-positive Jurkat cell line (E6-1), when compared to the TCR-negative cell line (RT-T3.5), much lesser signals but a still significant signals were detected on the cynomologues HSC-F cell line (see table 1).

TABLE 1

Detection of the specific reactivity of the immune sera against TCR-complex in each animal by flow cytometry. Data is presented as geometric means of the relative fluorescence intensities (rfu).

|  |  | pXL-CD3e-hum + pXL-CD3d-hum | pXL-CD3e-cyno + pXL-CD3d-cyno | pB1_irrelevant | Jurkat-E6-1 | Jurkat-RT-T3.5 | cyno HSC-F |
|---|---|---|---|---|---|---|---|
|  | w/o primary ab | 5 | 5 | 4 | 7 | 10 | 6 |
|  | OKT3 | — | — | — | 858 | 25 | — |
|  | FN18 | — | — | 4 | 7 | 10 | 1256 |
|  | Mouse-anti-HA | 6 | 6 | — | — | — | — |
|  | Rat-anti-myc | 9 | 7 | 1033 | 10 | 14 | 9 |
| rat #1 | 1:1000 | 290 | 273 | 5 | 186 | 36 | 55 |
|  | 1:5000 | 79 | 86 | 5 | 65 | 21 | 20 |
| rat #2 | 1:1000 | 499 | 401 | 5 | 390 | 55 | 75 |
|  | 1:5000 | 147 | 110 | 4 | 126 | 28 | 25 |
| rat #3 | 1:1000 | 239 | 247 | 5 | 108 | 30 | 31 |
|  | 1:5000 | 89 | 92 | 4 | 32 | 17 | 9 |
| rat #4 | 1:1000 | 280 | 283 | 5 | 176 | 37 | 73 |
|  | 1:5000 | 97 | 110 | 4 | 55 | 22 | 23 |
| rat #5 | 1:1000 | 208 | 137 | 4 | 99 | 31 | 11 |
|  | 1:5000 | 61 | 65 | 4 | 47 | 19 | 7 |

Rats of immunization group MR12-265 ("CD3-hum") were co-immunized with human CD3ε and CD3δ cDNAs cloned into the corresponding expression vectors. The immune serum was taken at day 24 of the immunization protocol, after 4 genetic applications (IS24d-4). Sera, diluted in PBS 1% BSA, were tested by flow cytometry using mammalian cells transiently transfected with the above mentioned target cDNAs in co-transfection experiments to obtain human and *Macaca fascicularis* CD3ε and CD3δ TCR complexes. A goat anti-rat IgG R-phycoerythrin conjugate (Southern Biotech, #3030-09) at 10 μg/ml was used as a secondary antibody. In addition the immune sera were tested on the following cell lines: Jurkat E6-1 (expressing human TCR), Jurkat-RT-T3.5 (negative for TCR) and cyno HSC-F (expressing cyno TCR); no negative cell line for the cyno TCR was available. A goat anti-rat IgG R-phycoerythrin conjugate (Southern Biotech, #3030-09) at 10 μg/ml was used as a secondary antibody.

Specific reactivity of the immune sera especially against cells transfected with combinations of CD3ε and CD3δ cDNAs could be detected in the immunized animals when compared to cells transfected with an irrelevant cDNA. The same is valid for the test on the TCR-positive Jurkat cell line (E6-1), when compared to the TCR-negative cell line (RT-T3.5), but much lesser signals (however in the positive rats still significant) were detected on the cyno HSC-F cell line (see table 2)

TABLE 2

Detection of the specific reactivity of the immune sera against TCR-complex in each animal by flow cytometry. Data is presented as geometric means of the relative fluorescence intensities (rfu).

|  |  | pXL-CD3e-hum + pXL-CD3d-hum | pXL-CD3e-cyno + pXL-CD3d-cyno | pB1_irrelevant | Jurkat-E6-1 | Jurkat-RT-T3.5 | cyno HSC-F |
|---|---|---|---|---|---|---|---|
|  | w/o primary ab | 5 | 5 | 4 | 7 | 10 | 6 |
|  | OKT3 | — | — | — | 858 | 25 | — |
|  | FN18 | — | — | 4 | 7 | 10 | 1256 |
|  | Mouse-anti-HA | 6 | 6 | — | — | — | — |
|  | Rat-anti-myc | 9 | 7 | 1033 | 10 | 14 | 9 |
| rat #1 | 1:1000 | 230 | 132 | 5 | 170 | 33 | 50 |
|  | 1:5000 | 78 | 40 | 4 | 54 | 19 | 15 |
| rat #2 | 1:1000 | 216 | 136 | 6 | 216 | 48 | 32 |
|  | 1:5000 | 75 | 40 | 4 | 66 | 24 | 11 |
| rat #3 | 1:1000 | 73 | 54 | 5 | 56 | 25 | 7 |
|  | 1:5000 | 25 | 20 | 4 | 23 | 15 | 6 |
| rat #4 | 1:1000 | 70 | 56 | 5 | 41 | 25 | 8 |
|  | 1:5000 | 25 | 18 | 4 | 15 | 15 | 6 |
| rat #5 | 1:1000 | 65 | 37 | 5 | 42 | 20 | 7 |
|  | 1:5000 | 24 | 17 | 4 | 17 | 14 | 6 |

Rats with positive sera were scarified and B cells were fused with mouse myeloma cells. The resulting hybridomas were screened on HEK293 cells transfected with human or cynomolgus CD3ε and CD3δ expression plasmids, on Jurkat E6.1 (CD3+) and Jurkat T3.5 (CD3-) by flow cytometry. Supernatant of Hybridoma clones was used to assess by surface plasmon resonance single point kinetic against human and *Macaca fascicularis* CD3ε/δ complex by fixing the analyte at 25 nM (data presented in table 3).

TABLE 3

Detection of the specific reactivity of different hybridoma clone supernatants by flow cytometry and Biacore analysis. Supernatants were tested on different cell lines (Jurkat E6-1, Jurkat-RT-T3.5 and cyno HSC-F). Biacore analysis was performed against CD3e/d complexes from human and cynomolgous monkey respectively.

| Sample-ID | Biacore human CD3ε/δ [RU] at 25 nM | Biacore cyno CD3ε/δ [RU] at 25 nM |
|---|---|---|
| 3G5-E10 | 27 | 3 |
| 18G9-H11 | 7 | −7 |
| 12D2-E5 | 27 | 5 |
| 6C9-C9 | 26 | 32 |
| 11F9-F8 | 11.5 | 16 |
| 8H2-F3 | 32.5 | 40 |
| 4B4-D7 | 11 | 14 |
| 4E7-C9 | 2.5 | 10 |
| 13C1-F6 | 17 | 15.5 |
| 11D7-C3 | 17 | 10 |
| 13H2-C3 | 16 | 7 |
| 10E6-G6 | 10.5 | 0 |
| 12G3-E8 | 24 | 17 |
| 11F3-B9 | 22 | 17 |
| 20E3-B5 | 11 | 5 |
| 10F4-C10 | 22 | 27 |
| 11H3-E5 | 7 | 9 |
| 18F5-H10 | n.a. | n.a. |
| 18H11-F10 | 35 | 55 |
| 20E5-F10 | 12 | 8 |
| 3H6-D2 | 9.5 | 7 |
| 8C2-F7 | 4.5 | 3 |
| 5B1-G2 | 1 | 0.5 |
| 7B7-F10 | 28 | 42 |
| 20B5-F10 | 1 | 9.5 |
| 16D3-E4 | −2 | −2 |
| 1E6-B8 | n.a. | n.a. |
| 16F8-A7 | 17.5 | 22.5 |
| 11A8-D6 | | |
| 3E8-G1 | | |
| 20G6-F3 | | |
| 9D7-B5 | n.a. | n.a. |
| 9G5-G10 | | |
| 17A11-D3 | | |

Positive clones were expanded and respective cDNAs for variable heavy and light chains were isolated by RT-PCR. VH and VL sequences were cloned into expression vectors in fusion with either the human $C_{H1}$, IGHG1-backbone or kappa chain in order to express Fab-fragments as well as full IgGs.

1.4 Expression of IgGs and Fab-Fragments

The expression plasmids encoding the heavy and light chain of the IgGs and Fab-fragments were propagated in E. Co/i NEB 10-beta (DH10B derivative). Plasmids used for transfection were prepared from E. Co/i using the QIAGEN Plasmid Plus Kit (Cat. No.: 12991).

HEK 293-FS cells growing in Freestyle Medium (Invitrogen) were transfected with indicated LC and HC plasmids encoding the heavy chains and light chains using 293fectin (Invitrogen) transfection reagent as described by the manufacturer. Cells were cultivated at 37° C. in a Kuhner ISF1-X shaking incubator at 110 rpm with 8% CO2. After 7 days of cultivation cells were removed by centrifugation, 10% Vol/Vol 1M Tris HCl pH 8.0 was added and the supernatant was filtered via a 0.2 µM bottle top filter to remove particles. CODV-IgG1 constructs were purified by affinity chromatography on Protein A columns (HiTrap Protein A HP Columns, GE Life Sciences). After elution from the column with 0.1M Citrat, pH 3.0, the CODV-IgG1 constructs were desalted using HiPrep 26/10 Desalting Columns, formulated in PBS (Gibco 14190-136).

Bispecific CODV-Fab constructs were purified by His-Trap High Performance columns (GE Healthcare, Cat. No.: 17-5248-02). After elution from the column (Elution buffer: 20 mM sodium phosphate, 0.5 M NaCl, 500 mM imidazole, pH 7.4), the protein containing fractions were pooled and desalted using HiPrep 26/10 Desalting Columns, formulated in PBS (Gibco 14190-136).

To separate monomers from aggregates a high resolution fractionation step in PBS (Gibco 14190-136) for both constructs, the CODV-IgG and the CODV-Fab fragment, was performed, using a HiLoad Superdex 200 26/60 320 ml column (GE Healthcare Cat. No.: 29-9893-36). Monomeric fractions were pooled and concentrated up to 1 mg/ml, using Vivaspin 20 centrifugation columns (VS2002 Sartorius Stedim biotech) and filtered using a 0.22 µm membrane (Millex® Syringe Filters SLGV033RS). Protein concentration was determined by measurement of absorbance at 280 nm. Each batch was analyzed by SDS-PAGE under reducing and non-reducing conditions to determine the purity and molecular weight of each subunit and of the monomer.

1.5 Assessment of Affinities of the Anti-CD3 Antibodies 1.5.1 Assessment of Affinities to Both Human and *Macaca fascicularis* CD3ε/δ

Binding affinities of anti-CD3 binding Fabs or CODV-Fabs were measured by surface plasmon resonance (SPR) using a Biacore3000 instrument (GE Healthcare). Assay buffer was HBS-EP (BR-1001-88, GE Healthcare). Capture of CD3ε/δ-Fc fusion proteins was achieved using the human antibody capture kit (GE Healthcare). The capture antibody was coupled to CM5 chips (BR-1001-88, GE Healthcare) to approx. 12.000 RU using the amine coupling kit (BR-100-50, GE Healthcare). The CD3ε6-Fc fusions proteins were captured at 10 µl/min to approx. 70 RU to yield Rmax values of 30 RU. Binding kinetics with the anti-CD3 Fabs or CODV-Fabs was measured at 30 µl/min for 240 sec. and 600 sec. for association and dissociation phase, respectively. Twofold dilutions of Fabs from 3 to 400 nM in assay buffer were used. All Fab concentrations were run in duplicate together with duplicate buffer blanks for double referencing. Regeneration of the capture surface was performed with a 1 min injection of 3M MgCl2 solution at 341/min. For data analysis the BIAevaluation software v.4.1 (GE Healthcare) was used. Data were fit globally using a 1:1 Langmuir model with mass transfer.

Measurement of binding affinities of anti-CD3 IgGs and CODV-Fc proteins was performed analogous to the binding assay for Fabs and CODV-Fabs with the exception of the capture antibody. In this case the His Capture Kit (28-9950-56, GE Healthcare) was used to capture human CD3-Fc protein via His-tag. For binding assay of with *Macaca fascicularis* CD3-Fc the Strep-MAB classic antibody (2-1507-001, IBA) was used as the capture antibody. In this case the regeneration solution was 10 mM Glycine buffer pH2.0.

TABLE 4

Affinities of selected CD3 antibodies against human and *Macaca fascicularis* CD3ε/δ complexes measured by Biacore.

| CD3εδ | Clone (Fab fragment) | ka (1/Ms) | kd (1/s) | Rmax (RU) | KD (M) | Chi2 | Ratio KD(cy)/KD(hu) |
|---|---|---|---|---|---|---|---|
| human | 12D2-E5 | 5.4E+06 | 6.2E-03 | 35 | 1.2E-09 | 0.34 | 4 |
| cyno | 12D2-E5 | steady state | steady state | 8 | 4.8E-09 | 0.129 | |
| human | 10E6-G6 | 1.4E+05 | 2.0E-03 | 37 | 1.4E-08 | 0.218 | 1 |
| cyno | 10E6-G6 | 1.9E+05 | 2.4E-03 | 18 | 1.3E-08 | 0.218 | |
| human | 4E7-C9 | 8.9E+04 | 1.6E-03 | 29 | 1.7E-08 | 0.244 | 1 |
| cyno | 4E7-C9 | 9.8E+04 | 1.5E-03 | 20 | 1.5E-08 | 0.232 | |
| human | 12G3-E8 | 1.1E+05 | 1.1E-03 | 30 | 9.3E-09 | 0.307 | 1 |
| cyno | 12G3-E8 | 1.7E+05 | 1.8E-03 | 15 | 1.0E-08 | 0.349 | |
| human | 5B1-G2 | 6.0E+04 | 3.9E-04 | 36 | 6.5E-09 | 0.218 | 1 |
| cyno | 5B1-G2 | 3.4E+04 | 1.5E-04 | 20 | 4.3E-09 | 2.1 | |
| human | 18F5-H10 | 2.0E+05 | 1.8E-04 | 28 | 8.9E-10 | 0.235 | 1 |
| cyno | 18F5-H10 | 1.4E+05 | 1.3E-04 | 15 | 8.9E-10 | 0.224 | |
| human | 18G9-H11 | 2.5E+05 | 1.1E-03 | 31 | 4.4E-09 | 0.975 | 6 |
| cyno | 18G9-H11 | 5.1E+04 | 1.2E-03 | 18 | 2.4E-08 | 0.617 | |
| human | 4B4-D7 | 1.1E+05 | 2.9E-03 | 22 | 2.7E-08 | 0.147 | 1 |
| cyno | 4B4-D7 | 1.1E+05 | 2.7E-03 | 12 | 2.4E-08 | 0.188 | |
| human | 1E6-B8 | 9.3E+04 | 3.9E-03 | 26 | 4.1E-08 | 0.157 | 1 |
| cyno | 1E6-B8 | 1.0E+05 | 4.2E-03 | 15 | 4.2E-08 | 0.122 | |
| human | 13H2-C3 | 1.7E+05 | 4.9E-03 | 20 | 2.9E-08 | 0.317 | 1 |
| cyno | 13H2-C3 | 1.8E+05 | 5.9E-03 | 12 | 3.2E-08 | 0.166 | |
| human | 20G6-F3 | 3.5E+04 | 2.7E-04 | 21 | 7.7E-09 | 0.208 | 1 |
| cyno | 20G6-F3 | 2.7E+04 | 2.2E-04 | 15 | 8.2E-09 | 0.184 | |
| human | 11F9-F8 | 7.7E+04 | 4.0E-04 | 22 | 5.2E-09 | 0.137 | 1 |
| cyno | 11F9-F8 | 8.3E+04 | 3.6E-04 | 13 | 4.4E-09 | 0.109 | |
| human | 20E5-F10 | 9.9E+04 | 4.3E-04 | 25 | 4.3E-09 | 0.125 | 1 |
| cyno | 20E5-F10 | 1.2E+05 | 3.4E-04 | 14 | 2.9E-09 | 0.104 | |
| human | SP-34 | 1.1E+06 | 3.0E-03 | 34 | 2.7E-09 | 2.3E-01 | 5 |
| cyno | SP-34 | 2.2E+05 | 2.8E-03 | 34 | 1.3E-08 | 4.7E-01 | |

SP-34 was used as IgG 1.5.2 Binding of Anti-CD3 Antibodies to huCD3ε, huCD3δ, and huCD3ε/δ Expressed on the Surface of HEK293F Cells by Flow Cytometry To analyze binding of antibodies to human CD3ε and human CD3δ expressed on the surface of cells, HEK293F cells were transfected with both constructs either alone or in co-transfection and signals were measured by flow cytometry. For transfection procedure FuGENE HD Transfection Reagent (Promega, # E2311) was used according to manufacturer's protocol.

HEK293F cells were seeded in Freestyle293 medium (Gibco) at 6E6 cells per tube in 50 ml Cellstar Cellreactor tubes with filter (Greiner bio-one). Transfections were done according to the FuGENE protocol. Complex preparation was done in OptiMEM without phenol red (Gibco) at ratio 3:1 (Protocol for transfection of 293F cells grown in 8,000 µl of medium in T-25 flasks using a FuGENE® HD:DNA ratio of 3.0:1, http://www.promega.com/techserv/tools/FugeneHdTool/default.aspx).

Cells were incubated on a shaker at 37° C. and 5% CO2. At day one to three after transfection cells were harvested and binding of antibodies was analyzed by flow cytometry.

Antibodies for staining were seeded at 1 µg in 50 µl per well Stain Buffer with FBS (BD Pharmingen) in 96-well U-bottom suspension culture plates (Greiner bio-one). Harvested transfected cells were resuspended in Stain Buffer with FBS and were added at 50 µl per well to the antibodies. Cells were incubated at 4° C. in the dark for 30 min and were washed twice. 0.5 µg secondary antibody Goat F(ab')2 Anti-Human IgG-FITC (Beckman Coulter, #732598) or Goat F(ab')2 Anti-Human kappa-PE (Southern Biotech, #206209), respectively, in combination with 0.5 µg 7-AAD per well was added in 100 µl Stain Buffer with FBS. Cells were incubated at 4° C. in the dark for 15 min and were washed twice. For measurement, cells were resuspended in 200 µl Stain Buffer with FBS. Cells were measured using the MACSQuant (Miltenyi Biotec) or LSRII (BD) flow cytometer, respectively. Further data analyses were performed using the FlowJo software (Tree Star, Inc.). Read out was percentage of 7-AAD negative single cells positive for antibody staining (data presented in table 5).

1.5.3 Binding of Anti-CD3 Fabs to huCD3ε/δ and huCD3ε/γ by SPR

Binding was tested by SPR using a BIAcore3000 instrument run with HBS-EP buffer. Recombinant huCD3 proteins (ε/δ (PB01226), ε/γ (PB01225)) were captured at 10 µl/min via Fc-tag by anti-human Fc capture antibody MAB1302 (Millipore) immobilized on a CM5 sensor chip. Anti-CD3 Fabs were used as analytes at 100 nM with association and dissociation times of 240 sec and 300 sec, respectively at 30 µl/min. After each cycle the surfaces were regenerated by a 2 min pulse of 10 mM glycine buffer pH2.5.

When only huCD3δ was expressed on the surface of HEK293F cells no signal could be detected by flow cytometry. In contrast, nearly all antibodies could bind to cells transfected with huCD3ε exclusively or in co-transfection with huCD3δ indicating that huCD3ε is necessary as epitope. In Biacore assays binding to huCD3ε was shown irrespective of whether the δ or the γ chain was used for the recombinant protein suggesting that huCD3ε is sufficient as antigen. The antibody 12D2 exceptionally bound only to huCD3ε when a co-chain was present. There may be an indirect effect of co-expression of the g or d chain regarding the conformational structure of the protein to display the epitope for this antibody. The same effect was shown for the published antibody OKT3. This antibody is described to interact with a conformational epitope formed after association of huCD3ε with huCD3δ or γ, respectively (Salmeron et al., 1991, The Journal of Immunology). It was also shown that it binds to the huCD3ε subunit exclusively (Kjer-Nielsen et al., 2004, PNAS). Because of the similar behavior of 12D2 and OKT3 an interaction with huCD3ε is supposable for 12D2. Taken all together, huCD3ε seems to be the antigenic structure for all analyzed antibodies (data presented in table 5).

performed using the FlowJo software (Tree Star, Inc.). Read out was percentage of cells positive for antibody binding. Cells treated only with the secondary but no primary antibody were used to set the gates. EC50 Curves were calculated by XLfit (Algorithm 205), EC50 values were calculated as inflection point of the slope (data are shown in table 6).

TABLE 5

Affinities of selected CD3 antibodies against huCD3δ, huCD3ε, huCD3ε/δ and huCD3ε/γ complexes measured by Flow cytometry and Biacore.

| | Flow cytometry % antibody positive transfected cells (n = 3-6) | | Biacore RU of Fab binding at 100 nM | |
|---|---|---|---|---|
| Clone | huCD3δ | huCD3ε (+/−SEM) | huCD3ε/δ (+/−SEM) | huCD3ε/δ | huCD3ε/γ |
| 10E6 | n.b. | 96.3 +/− 2.2 | 93.3 +/− 4.7 | 11 | 8 |
| 11F9 | n.b. | 97.0 +/− 1.5 | 96.0 +/− 2.5 | 10 | 7 |
| 12D2 | n.b. | n.b. | 96.3 +/− 2.2 | 11 | 5 |
| 12G3 | n.b. | 96.3 +/− 2.2 | 96.7 +/− 1.9 | 10 | 7 |
| 13H2 | n.b. | 93.3 +/− 3.3 | 93.0 +/− 4.2 | 9 | 6 |
| 18F5 | n.b. | 70.6 +/− 11.9 | 70.4 +/− 9.9 | 13 | 7 |
| 18G9 | n.b. | 95.0 +/− 2.5 | 97.0 +/− 1.5 | 10 | 3 |
| 1E6 | n.b. | 87.7 +/− 4.4 | 91.7 +/− 4.9 | 10 | 7 |
| 20E5 | n.b. | 96.7 +/− 1.9 | 95.3 +/− 3.2 | 11 | 8 |
| 20G6 | n.b. | 68.6 +/− 12.1 | 67.4 +/− 10.4 | 7 | 4 |
| 4B4 | n.b. | 71.5 +/− 10.8 | 69.5 +/− 8.7 | 11 | 3 |
| 4E7 | n.b. | 69.0 +/− 12.3 | 66.4 +/− 10.0 | 8 | 6 |
| 5B1 | n.b. | 97.0 +/− 1.5 | 97.0 +/− 1.5 | 10 | 7 |
| OKT3 | n.b. | n.b. | 70.2 +/− 9.6 | 4 | 3 | n.b. = no binding (<20% of binding of huCD3e + huCD3d)

1.6 Binding of CD3 Fab to Human T Cells

The binding capacity of the CD3-Fabs was determined by flow cytometry. Primary human T cells were used as target cells. Therefore, peripheral blood mononuclear cells (PBMCs) were isolated from 200 ml peripheral blood of healthy donors treated with EDTA by Ficoll density centrifugation. 15 ml Histopaque (Sigma-Aldrich) was pre-loaded on a 50 ml Leucosep-Tube (Greiner bio-one). Blood was diluted with autoMACS Rinsing Buffer+1% BSA (Miltenyi Biotec) and loaded on the membrane of a total of ten prepared tubes. Tubes were centrifuged without brake for 10 min at 1000×g. PBMCs were collected and washed with autoMACS Rinsing Buffer+1% BSA three times. Finally, PBMCs were resuspended in autoMACS Running Buffer (Miltenyi Biotec) for isolation of T lymphocytes by autoMACSpro technology using the Pan T Cell isolation Kit (Miltenyi Biotec) according to manufacturer's instructions. Purity of separated T cells was analyzed by MACSQuant flow cytometry using the human 7-Color Immunophenotyping Kit (Miltenyi Biotec). Isolated T cells were resuspended in Stain Buffer with FBS (BD Pharmingen) and 1E5 cells in 100 µl per well were seeded in 96-well U-bottom suspension culture plates (Greiner bio-one). Fab antibodies were diluted 1:3 in serial in PBS (Invitrogen) and 5 µl each were added to the cells at a final maximum concentration of 30000 ng/ml. The assay was incubated for 45 min at 4° C. Cells were washed twice with Stain Buffer with FBS and 1 µg secondary antibody Goat F(ab')2 Anti-Human kappa-FITC (Beckman Coulter, #732621) per well was added in 100 µl Stain Buffer with FBS per well. The assay was incubated for 20 min at 4° C. and washed twice afterwards. Cells were resuspended in 150 µl Stain Buffer with FBS per well and were measured using the MACSQuant (Miltenyi Biotec) or LSRII (BD) flow cytometer. Further data analyses were

TABLE 6

Affinities of CD3 Fab to human T cells measured by Flow cytometry. Presented are mean EC50 values calculated from curves.

| Antibody | Binding to human T cells EC50 [nM] mean +/− SEM | | |
|---|---|---|---|
| 12D2-E5-Fab | 3.8 | +/− | 0.2 |
| 4B4-D7-Fab | 15.3 | +/− | 3.0 |
| 1E6-C9-Fab | 18.7 | +/− | 3.5 |
| 10E6-G6-Fab | 4.7 | +/− | 0.9 |
| 4E7-C9-Fab | 6.2 | +/− | 0.8 |
| 12G3-E8-Fab | 4.4 | +/− | 0.3 |
| 5B1-G2-Fab | 11.1 | +/− | 3.6 |
| 18F5-H10-Fab | 4.1 | +/− | 0.0 |
| 18G9-H11-Fab | 1.7 | +/− | 0.5 |
| 13H2-C2-Fab | 14.3 | +/− | 0.9 |
| 20G6-F3-Fab | 14.0 | | (n = 1) |
| 11F9-F8-huFab | 11.6 | | (n = 1) |
| 20E5-F10-huFab | 8.2 | | (n = 1) |

1.7 Safety of CD3 Fab 1.7.1 Safety of CD3 Fab Measured by CD25+ and CD69+ Expression on Human T Cells The effect of CD3 Fab antibodies on activation status of T cells as safety read out was analyzed by flow cytometry based detection of the expression of activation marker CD25 and CD69 on the surface of primary human T cells.

Isolated primary human T lymphocytes were resuspended in RPMI+GlutaMAX I (Gibco)+10% FCS (Invitrogen) and 2.5E5 cells were seeded in 96-well U-bottom suspension culture plates (Greiner bio-one) in 100 µl per well.

5 µl Fab CD3 antibodies were added to the cells at a final concentration of 30 000 ng/ml. The assay was incubated for 20 h at 37° C. in 5% CO2.

After incubation time cells were spun down and stained for 15 min at 4° C. in 100 µl Stain Buffer with FBS (BD Pharmingen) per well with following labeled antibodies: CD25-V450, CD69-APC Cells were washed twice after staining, resuspended in 150 µl Stain Buffer with FBS, and 5000 cells were measured using the LSRII (BD) flow cytometer. Further data analyses were performed using the FlowJo software (Tree Star, Inc.). Read out was percentage of CD25pos and CD69pos T cells (table 7).

TABLE 7

Safety of CD3 Fab measured by CD25+ and CD69+ expression on human T cells

| Antibody | CD25+ % Activation of human T cells normalized to PBS C = 30000 ng/ml n = 1 | CD69+ % Activation of human T cells normalized to PBS C = 30000 ng/ml n = 1 |
|---|---|---|
| 11H3-E5-Fab | 0.7 | 0.5 |
| 12D2-E5-Fab - SEC | 3.2 | 11.1 |
| 4B4-D7-Fab | 2.5 | 5.4 |
| 1E6-B8/B9-C9-Fab | 1.8 | 3.2 |
| 10E6-G6-Fab | 0.8 | 2.6 |
| 4E7-C9-Fab | 0.4 | 0.1 |
| 12G3-E8-Fab | 0.0 | 1.5 |
| 5B1-G2-Fab | 0.4 | 4.2 |
| 6F4-D10-Fab | 2.1 | 6.4 |
| 18F5-H10-Fab | 0.0 | 0.1 |
| 18G9-H11-Fab | 0.7 | 2.2 |
| 13H2-C2-Fab | 0.5 | 0.4 |
| 13C1-F6-Fab | 0.4 | 0.2 |
| 1E6-B8/B9-C9-Fab | 0.6 | 1.7 |
| 20G6-F3-Fab | 0.2 | 3.2 |
| 1E6-B8/B9-C9-Fab | 2.5 | 7.8 |
| 1E6-B8/B9-C9-Fab | 0.1 | 1.0 |
| 11F9-F8-huFab | 1.0 | 0.8 |
| 20E5-F10-huFab | 1.5 | 1.3 |

1.7.2 Safety of CD3 Fab Measured by CD4+/CD69+, CD4+/CD25+, CD8+/CD69+ and CD8+/CD25+ Expression on Human T Cells The effect of CD3 Fab antibodies on activation status of T cells as safety read out was analyzed by flow cytometry based detection of the expression of activation marker CD25 and CD69 on the surface of primary human T cells. Isolated primary human T lymphocytes were resuspended in RPMI+GlutaMAX I (Gibco)+10% FCS (Invitrogen) and 2.5E5 cells were seeded in 96-well U-bottom suspension culture plates (Greiner bio-one) in 50 µl per well. Either T cells exclusively were tested and wells were filled-up with 50 µl RPMI+GlutaMAX I+10% FCS, or target cells (i.e. THP-1 cell line) were added at 2.5E4 cells per well in 50 µl RPMI+GlutaMAX I+10% FCS. Bispecific antibodies were diluted 1:3 in serial in PBS (Invitrogen) and 5 µl each were added to the cells at a final maximum concentration of 30 000 ng/ml. The assay was incubated for 20 h at 37° C. in 5% CO2. After incubation time cells were spun down and stained for 15 min at 4° C. in 100 µl Stain Buffer with FBS (BD Pharmingen) per well with following labeled antibodies: CD4-PE, CD8-APC-Cy7, CD25-APC, CD69-PE-Cy7. As Fluorescence Minus One (FMO) control activated T cells were stained as described above but CD25 was replaced by its isotype (Isotype APC-IG1k) in one tube and CD69 was replaced by its isotype (Isotype PE-Cy7-IG1k) in a second tube. Cells were washed twice after staining, resuspended in 150 µl Stain Buffer with FBS, and 5000 cells were measured using the LSRII (BD) flow cytometer. Further data analyses were performed using the FlowJo software (Tree Star, Inc.). Read out was percentage of CD4posCD25pos, CD4posCD69pos, CD8posCD25pos, and CD8posCD69pos T cells. Gates were set according to FMO controls (see table 8).

TABLE 8

Safety of CD3 Fab measured by CD4+/CD69+, CD4+/CD25+, CD8+/CD69+ and CD8+/CD25+ expression on human T cells

| Antibody | CD4+/CD69+ % Activation normalized to PBS C = 100 nM mean +/− SEM | CD8+/CD69+ % Activation normalized to PBS C = 100 nM mean +/− SEM | CD4+/CD25+ % Activation normalized to PBS C = 100 nM mean +/− SEM | CD8+/CD25+ % Activation normalized to PBS C = 100 nM mean +/− SEM |
|---|---|---|---|---|
| 20G6-F3-Fab | 0.1 +/− 0.1 | 0.0 +/− 0.0 | 0.4 +/− 0.1 | 0.0 +/− 0.1 |
| 4B4-D7-Fab | 3.2 +/− 1.1 | 0.3 +/− 0.3 | 1.3 +/− 0.6 | 0.0 +/− 0.0 |

Example 2: CD123 Sequences 2.1 Construction of CD123 (IL3RA)-hFc Fusion Expression Plasmids (CD123-Fc)

Using cDNA containing plasmids as a template, human and *Macaca fascicularis* CD123 fusion proteins were generated in reading frame with heavy chain constant region including a GS-linker (used in *Macaca* protein), the hinge region, CH2 and CH3 domains of human immunoglobulin IgG additionally carrying a Strep-II Tag (only in human protein version).

Using human genomic DNA as template, human CD123 (IL3RA) extracellular domain was amplified, including the signal sequence. The resulting amplified cleaved and purified PCR products were combined by ligation PCR and ligated into mammalian expression vector pXL by InFusion method using NheI and HindIII site. The sequence of the resulting mature human CD123 Strep-II tagged Fc-fusion protein is disclosed under SEQ ID NO: 196. Amino acids 1 to 284 correspond to the amino acids 22 to 305 of the full-length wild-type human CD123 protein (herein disclosed under SEQ ID NO: 194, available from the NCBI database under the accession number NP_002174.1) and thus the extracellular domain of human CD123.

To clone *Macaca fascicularis* CD123cDNA was made from blood of a *Macaca fascicularis* population. Using this isolated cDNA as template, *Macaca* CD123 (IL3ra) extracellular domain was amplified, including the signal sequence. The resulting amplified cleaved and purified PCR products were combined by ligation PCR and ligated into mammalian expression vector pXL by InFusion method using NheI and HindIII. The sequence of the resulting mature human CD123 Strep-II tagged Fc-fusion protein is disclosed under SEQ ID NO: 197. Amino acids 1 to 284 correspond to the amino acids 22 to 305 of the full-length wild-type *Macaca fascicularis* CD123 protein (herein disclosed under SEQ ID NO: 195, available from the NCBI database under the accession number NP_002174.1) and thus the extracellular domain of human CD123.

2.2 Expression and Purification of Human and *Macaca fascicularis* CD123-Fc

Freestyle HEK293 cells growing in F17 serum free suspension culture (Life) were transiently transfected with the expression plasmid. Transfection was performed using Cellfectin transfection reagent (Life) The cells were cultured at 37° C. for 7 days. The culture supernatant containing recombinant protein was harvested by centrifugation and was clarified by filtration (0.22 µm).

For purification the Fc-fusion protein variants were captured on protein A matrix (GE) and eluted by pH shift. After polishing the protein by SEC in PBS using a Superdex 200 (GE) and a final ultrafiltration concentration step, the protein was used for further assays.

2.3 Assessment of Affinities to Both Human and *Macaca fascicularis* CD123Rat IgGs from Hybridoma Screening of anti-CD123 rat IgGs for binding affinities to human CD123 and cross-reactivities to cyno CD123 was performed with hybridoma supernatants using a Proteon XPR36 (Biorad) in a one-shot kinetics approach. A capture assay was established using a goat anti-rat IgG (112-005-071, Jackson Immuno Research). The capture antibody was coated on GLC chips (176-5011, Biorad) to approx. 8000 RU in the vertical direction using the amine coupling kit (176-2410, Biorad). Capture of the rat IgGs to approx. 200 RU in vertical direction resulted in Rmax values of up to 100 RU for CD123-Fc. Binding kinetics with human and cyno CD123-Fc fusion protein was measured at 100 µl/min in the horizontal direction with 120 sec. and 600 sec. for association and dissociation, respectively. The CD123-Fc proteins were used in twofold dilutions from 6 nM to 100 nM. PBSET buffer (176-2730, Biorad) was used as assay buffer. Regeneration was achieved by injection of 10 mM Glycine buffer pH 1.5 for 18 sec at 30 µl/min. Data processing and analysis was performed using ProteonManager software v3.0. Fitting of the sensorgrams was done with a 1:1 Langmuir model. Clones were selected based on affinities for human CD123 with KD<1 nM and crossreactivity to cyno CD123.

Fabs and CODV-Fabs

Binding affinities of anti-CD123 binding Fabs or CODV-Fabs were measured using a Biacore3000 instrument (GE Healthcare). Assay buffer was HBS-EP (BR-1001-88, GE Healthcare). Capture of CD123-Fc fusion proteins was achieved using the human antibody capture kit (GE Healthcare). The capture antibody was coupled to CM5 chips (BR-1001-88, GE Healthcare) to approx. 12.000 RU using the amine coupling kit (BR-100-50, GE Healthcare). The CD123-Fc fusions proteins were captured at 10 µl/min to approx. 70 RU to yield Rmax values of 30 RU. Binding kinetics with the anti-CD123 Fabs or CODV-Fabs was measured at 30 µl/min for 240 sec. and 600 sec. for association and dissociation phase, respectively. Twofold dilutions of Fabs from 3 to 200 nM in assay buffer were used. All Fab concentrations were run in duplicate together with duplicate buffer blanks for double referencing. Regeneration of the capture surface was performed with a 1 min injection of 3M MgCl2 solution at 30 µl/min. For data analysis the BIAevaluation software v.4.1 (GE Healthcare) was used. Data were fit globally using a 1:1 Langmuir model with mass transfer.

IgGs and CODV-Fc Proteins

Measurement of binding affinities of anti-CD123 IgGs and CODV-Fc proteins was performed analogous to the binding assay for Fabs and CODV-Fabs with the exception of the capture antibody. In this case the Strep-MAB classic antibody (2-1507-001, IBA) was used to capture human CD123-Fc via its StrepII-tag. Here the regeneration solution was 10 mM Glycine buffer pH2.0.

2.4 Generation of Human and *Macaca fascicularis* Cross-Reactive Anti-CD123 Antibodies Human and *Macaca fascicularis* CD123 cDNAs were cloned into Aldevron proprietary immunization vectors (pB8 and VV8) respectively. Three rats of immunization group MR13-296 were immunized with the immunization vector IL3RA-hum.-ECD (aa19-305). The immune serum was taken at day 24 of the immunization protocol, after 4 genetic applications (IS24d-4). Sera, diluted in PBS 3% FBS, were tested by flow cytometry using mammalian cells transiently transfected with the human and cyno IL3RA cDNA variants IL3RA-hum.ECD and IL3RA-hum.D3.

Specific reactivity of the immune sera against cells transfected with pB1-IL3RA-hum.ECD, as well as with IL3RA-cyno (pFF1262) and the THP-1 cells could be detected in all immunised animals when compared to cells transfected with an irrelevant cDNA.

Rats with positive sera were sacrificed and B cells were fused with mouse myeloma cells. The resulting hybridomas were screened on HEK293 cells transfected with human or cynomolgus CD123 expression plasmids, on different cell lines expressing CD123 by flow cytometry (data shown in table 10).

Target cells were seeded at 5E4 cells in 50 µl Stain Buffer with FBS (BD Pharmingen) per well in 96-well U-bottom suspension culture plates (Greiner bio-one). Hybridoma supernatants were diluted 1:3 in serial in PBS (Invitrogen) and 50 µl each were added to the cells at a final maximum concentration of 1 µg/ml. The assay was incubated for 45 min at 4° C.

Cells were washed twice with Stain Buffer with FBS and 1 µg secondary antibody Goat Anti-Rat IgG (H+L)-Alexa Fluor 488 (Invitrogen-Life Technologies, # MH10520) was added in 100 µl Stain Buffer with FBS per well. The assay was incubated for 15 min at 4° C. and washed twice afterwards.

Cells were resuspended in 200 µl Stain Buffer with FBS per well and were measured using the MACSQuant (Miltenyi Biotec) or LSRII (BD) flow cytometer. Further data analyses were performed using the FlowJo software (Tree Star, Inc.). Read out was percentage of cells positive for antibody binding. Cells treated only with the secondary but no primary antibody were used to set the gates. Curves were calculated by XLfit (Algorithm 205).

Specific binding of clones to CD123 could be shown on the surface of transfected HEK293 in comparison to untransfected HEK293 cells where no signal could be detected (data not shown). Binding of antibodies was concentration dependent with an EC50 value ranging between 0.4 and 17.7 ng/ml (table 9).

TABLE 9

Specific CD123 binding of rat IgG clones in hybridoma supernatants detected by flow cytometry. Concentration dependent binding of antibodies was measured using CD123 transfected HEK293 as target cells and a goat anti-rat IgG (H + L)-Alexa Fluor 488 secondary antibody. Presented are calculated EC50 values of the curves.

| Antibody | EC50 [ng/ml] |
| --- | --- |
| BFX - 1A6 | 6.4 |
| BFX - 1E1 | 2.2 |
| BFX - 2B8 | 5.5 |
| BFX - 2F4 | 4.5 |
| BFX - 2F8 | 3.4 |
| BFX - 2H7 | 17.7 |
| BFX - 3B10 | 2.0 |
| BFX - 3E3 | 2.0 |
| BFX - 5A5 | 10.1 |
| BFX - 6B10 | 5.0 |
| BFX - 6C10 | 6.1 |
| BFX - 6D6 | 0.9 |
| BFX - 8B11 | 0.4 |
| BFX - 9B8 | 1.2 |
| BFX - 9D7 | 0.9 |
| BFX - 9F6 | 1.3 |
| BFX - 9H2 | 14.9 |

TABLE 10

Binding data of CD123 antibodies to recombinant CD123 and CD123 expressing cells. Binding data showing affinities of CD123 antibodies against recombinant CD123 protein from human and cynomolgous monkey. Binding on cell surface was detected by flow cytometry. SP2 refers to cell expressing N-terminal truncated (D1 region) variant of CD123. Antibodies were tested by Proteon XPR36 on their ability to compete with the IL3 binding to CD123.

| Clone | ka (1/Ms) | kd (1/s) | KD (nM) Human | KD (nM) Cyno | MoIm-13 | THP-1 | OCI-AML3 | SP2 | Basophils | IL3 Blocking |
| --- | --- | --- | --- | --- | --- | --- | --- | --- | --- | --- |
| 1E1 | 4.6E+05 | 1.1E−04 | 0.23 | 0.72 | + | + | + | + | + | − |
| 2B8 | 6.6E+05 | 1.2E−05 | 0.018 | 0.77 | + | + | + | + | + | − |
| 2F8 | 1.3E+05 | 6.6E−05 | 0.53 | 0.51 | + | + | + | − | + | + |
| 3B10 | 2.2E+05 | 0.5E−05 | 0.21 | 0.27 | + | + | + | − | + | + |
| 3E3 | 1.6E+05 | 6.4E−05 | 0.4 | 0.12 | + | + | + | − | + | + |
| 5A5 | 1.3E+05 | 1.2E−04 | 1.1 | 0.05 | + | + | + | + | + | − |
| 6B10 | 2.3E+05 | 1.5E−05 | 0.15 | 0.1 | + | + | + | + | + | − |
| 6C10 | 1.8E+05 | 1.4E−04 | 0.75 | 0.79 | + | + | + | + | + | − |
| 8B11 | 4.7E+05 | 6.2E−06 | 0.01 | 0.1 | + | + | + | + | + | − |
| 9B8 | 1.5E+06 | 2.8E−04 | 0.19 | 0.17 | + | + | + | + | + | + |
| 9D7 | 1.0E+06 | 3.2E−04 | 0.3 | 0.07 | + | + | + | + | + | + |
| 9F6 | 1.8E+05 | 6.7E−06 | 0.04 | 0.5 | + | + | + | + | + | − |

2.5 Humanization of Anti-CD123 Rat Antibody Sequences

Humanization of rat antibodies was performed by CDR-grafting or by the 4D method (US20110027266). For the rat-anti-CD3 antibody 3E3 the closest *Rattus* germline sequence identified was IGHV2S48*01 and IGHJ3*01 for the heavy chain variable region and IGLV3S2*01 and IGKJ3*01 for the light chain variable region. The calculated rat germinality index (frameworks sequences only) is 94.51% for the VH and 98.9% for the VL.

Potential exposed problematic residues were checked and one residue in CDRH2 was modified.

Using the grafting method, a variety of humanized variants were generated based on the closest human germline sequences identified: IGHV4-59*05 and IGHJ4*01 for the VH (germinality index on frameworks: 75.82%); IGLV6-57*01 and IGLJ3*01 for VL (germinality index on frameworks: 72.22%).

In addition to CDR grafting, the 4D humanization protocol (US20110027266) was used to humanize the Rat anti-CD123 3E3 variable light (VL) and heavy (VH) domains. A molecular dynamics (MD) simulation was performed on the minimized 3D homology model (done with MOE; PDB used: 1FLR) of Rat anti-CD123 3E3 and compared to the 49 Human models derived from the seven representative light chains (vk1, vk2, vk3, vk4, vlambda1, vlambda2, vlambda3) and the seven representative heavy chains (vh1a, vh1b, vh2, vh3, vh4, vh5, vh6) designed by LGCR/SDI and available within MOE.

Two Models have been selected for the "4D humanization": Vl3-vh4 with and VL3-VH2 with the best both hydrophobic and electrostatic components and sequence identity outside CDRs. For the pairwise association between the Rat anti-CD123 3E3 variable domain and the two selected models, the sequences were aligned based on the optimal 3D superposition of the alpha carbons of the corresponding homology models.

Example 3: Antibodies in the Bispecific CODV-Fab Format

3.1 Cloning of Selected CD3 Sequences in Combination with Anti-CD123 mAb 7G3 in the Bispecific CODV-Fab Format to Study their T-Cell Engagement Activity Selected CD3 antibody sequences, such as I2C, mAb2 (Macrogenics) and the so-called "20G6-F3", "4E7-C9", "4B4-D7" and "18F5-H10" were expressed as monospecific anti-CD3 Fabs, Said selected sequences were as well expressed as bispecific CD3xCD123 CODV-Fabs using sequences of the monoclonal antibody 7G3, resulting in the CODV-Fab constructs "I2Cx7G3" and the so-called "7G3x20G6", "7G3x4E7", "7G3x4B4" and "7G3x18F5", as further described in the section "antibody-like bin ding proteins" herein above. Purified proteins were used in a Biacore assay to compare the affinity against CD3ε/δ complexes (data presented in table 11). No changes in affinities could be detected by Biacore analysis when CD3 sequences were introduced into the bispecific CODV-Fab format.

TABLE 11

Comparison of affinities between Fab-fragments and CODV-Fabs against CD3ε/δ complexes from human and cynomolgous monkey

|  | Molecule | hu kon 1/Ms | hu koff 1/s | hu KD nM | cy KD nM |
|---|---|---|---|---|---|
| Fab-fragments | I2C | 1.1E+07 | 1.3E-03 | 0.13 | 0.5 |
|  | mAb2 | 3.1E+05 | 4.3E-03 | 13.7 | 16.3 |
|  | BDW-20G6-F3 | 3.5E+04 | 2.7E-04 | 8 | 8 |
|  | BDX-4E7-C9 | 8.9E+04 | 1.5E-03 | 17 | 15 |
|  | BDW-4B4-D7 | 1.1E+05 | 2.9E-03 | 27 | 24 |
|  | BDX-18F5-H10 | 2.0E+05 | 1.8E-04 | 1 | 1 |
| CODV-Fabs | 7G3 x I2C | 4.0E+06 | 2.0E-03 | 0.5 | 0.4 |
|  | 7G3 x 20G6 | 7.2E+04 | 5.1E-04 | 7 | 7 |
|  | 7G3 x 4E7 | 1.2E+05 | 1.9E-03 | 16 | 10 |
|  | 7G3 x 4B4 | 2.7E+05 | 4.4E-03 | 17 | 18 |

3.2 Bispecific CODV-Fabs Directed Against CD123 and CD3 Mediate Potent Redirected T-Cell Killing Such bispecific CODV-Fabs have the ability to localize a T-cell (by binding such T-cell to the CD3-binding portion of a CD3-binding CODV-Fab) to the location of a tumor cell (by binding such cancer cell to the CD123 portion of the CODV-Fab). The localized T-cell can then mediate the killing of the tumor cell in a process termed herein "redirected" killing. Bispecific CODV-Fab specific for CD123 and CD3 were constructed having the anti-CD123 variable domains of monoclonal antibody 7G3 and anti-CD3 variable domains of selected CD3 antibodies generated in example 1.

Therefore, peripheral blood mononuclear cells (PBMCs) were isolated from 200 ml peripheral blood of healthy donors treated with EDTA by Ficoll density centrifugation. 15 ml Histopaque (Sigma-Aldrich) was preloaded on a 50 ml Leucosep-Tube (Greiner bio-one). Blood was diluted with autoMACS Rinsing Buffer+1% BSA (Miltenyi Biotec) and loaded on the membrane of a total of ten prepared tubes. Tubes were centrifuged without brake for 10 min at 1000×g. PBMCs were collected and washed with autoMACS Rinsing Buffer+1% BSA three times. Finally, PBMCs were resuspended in autoMACS Running Buffer (Miltenyi Biotec) for isolation of T lymphocytes by autoMACSpro technology using the Pan T Cell isolation Kit (Miltenyi Biotec) according to manufacturer's instructions. Purity of separated T cells was analyzed by MACSQuant flow cytometry using the human 7-Color Immunophenotyping Kit (Miltenyi Biotec).

T-cell engaging effect of bispecific antibodies was analyzed by a flow cytometry based cytotoxic assay. Target cells (i.e. THP-1 cell line) were stained for 15 min at 37° C. with 1 µM CFSE in 1 ml RPMI+GlutaMAX I (Gibco) per 1E7 cells. Afterwards, cells were washed twice and resuspended in RPMI+GlutaMAX I+10% FCS (Invitrogen). 2.5E4 target cells were seeded in 96-well U-bottom suspension culture plates (Greiner bio-one) in 50 µl medium per well.

Isolated primary human T lymphocytes were resuspended in RPMI+GlutaMAX I+10% FCS and were added at indicated effector-to-target ratio in 50 µl per well to the target cells (in general E:T=10:1).

Bispecific antibodies were diluted 1:3 in serial in PBS (Invitrogen) and 5 µl each were added to the cells at a final maximum concentration of 3 000 ng/ml. The assay was incubated for 20 h at 37° C. in 5% CO2.

To detect dead target cells, all cells were stained with 7-AAD. Therefore, 5 µg/ml 7-AAD diluted in Stain Buffer with FBS (BD Pharmingen) were added to each well and were incubated for 15 min at 4° C. in the dark. Cells were measured using the MACSQuant (Miltenyi Biotec) or LSRII (BD) flow cytometer, respectively. Further data analyses were performed using the FlowJo software (Tree Star, Inc.). Read out was percentage of CFSE and 7-AAD double positive cells.

The results of these investigations shown for example in tables 20 to 22 demonstrate the ability of the CD123×CD3 CODV-Fabs to mediate redirected killing of tumor cells.

3.3 Safety Assessment of Redirected T-Cell Killing

The effect of bispecific antibodies on activation status of T cells as safety read out was analyzed by flow cytometry based detection of the expression of activation marker CD25 and CD69 on the surface of primary human T cells.

Isolated primary human T lymphocytes were resuspended in RPMI+GlutaMAX I (Gibco)+10% FCS (Invitrogen) and 2.5E5 cells were seeded in 96-well U-bottom suspension culture plates (Greiner bio-one) in 50 µl per well.

Either T cells exclusively were tested and wells were filled-up with 50 µl RPMI+GlutaMAX I+10% FCS, or target cells (i.e. THP-1 cell line) were added at 2.5E4 cells per well in 50 µl RPMI+GlutaMAX I+10% FCS.

Bispecific antibodies were diluted 1:3 in serial in PBS (Invitrogen) and 5 µl each were added to the cells at a final maximum concentration of 30 000 ng/ml. The assay was incubated for 20 h at 37° C. in 5% CO2.

After incubation time cells were spun down and stained for 15 min at 4° C. in 100 µl Stain Buffer with FBS (BD Pharmingen) per well with following labeled antibodies: CD4-PE, CD8-APC-Cy7, CD25-APC, CD69-PE-Cy7

As Fluorescence Minus One (FMO) control activated T cells were stained as described above but CD25 was replaced by its isotype (Isotype APC-IG1k) in one tube and CD69 was replaced by its isotype (Isotype PE-Cy7-IG1k) in a second tube.

Cells were washed twice after staining, resuspended in 150 µl Stain Buffer with FBS, and 5000 cells were measured using the LSRII (BD) flow cytometer. Further data analyses were performed using the FlowJo software (Tree Star, Inc.). Read out was percentage of CD4posCD25pos, CD4posCD69pos, CD8posCD25pos, and CD8posCD69pos T cells. Gates were set according to FMO controls (see table 12).

TABLE 12

Activity of CD123 × CD3 CODV-Fabs measured in a cytotoxic assay and safety measured by the expression of CD69

| Molecule | Activity EC50 [ng/ml] | Safety CD69 expression % cells/% max |
|---|---|---|
| 7G3 × I2C | 20 ± 9 | 25.8 ± 7.6 |
| 7G3 × OKT3 | 16 ± 5 | 25.5 ± 8.0 |
| 7G3 × 20G6 | 18 ± 5 | 8.7 ± 0.8 |
| 7G3 × 4E7 | 12 ± 3 | 12.3 ± 2.5 |
| 7G3 × 4B4 | 11 ± 2 | 11.6 ± 0.8 |
| 7G3 × 18F5 | 61 ± 15 | 9.8 ± 1.1 |

3.4 Humanization of Anti-CD3 Rat Antibody Sequences and Bispecific Antibodies

Humanization of rat antibodies was performed by CDR-grafting or by the 4D method (US20110027266).

For the rat-anti-CD3 antibody "20G6" the closest *Rattus* germline sequences was identified as IGHV6S17*01 and IGHJ2*01 (for the heavy chain variable region and IGKV1S21*01 and IGKJ4*01 for the light chain variable region). The calculated rat germinality index (frameworks sequences only) is 97.80% for the VH and 95.5% for the VL.

A variety of humanized variants using grafting method were generated based 1) on the closest human germline sequences identified IGHV3-30-01_IGHJ4-01 for the VH with a germinality index on framework of 77%; IGK2D-29-02_IGKJ4-01 for the VL with a germinality index on the framework of 80%), or
2) or based on the a closest germline sequence identified having a lower PI IGVH3-48*02-IGHJ4-01 for the VH with a germinality index on the framework of 75%; IGKV2-28*01-IGKJ4-01 for the VL with a geminality index on the framework of 77.5%, or
3) consisting on a more distant human germline sequence (change germline Glade) (IGVH1-46*01-IGHJ4*01 for the VH with a germinality index on the framework of 56%; IGKV4*01-IGKJ4*01 for the VL with a germinality index on the framework of 67.5%).

The Humanized sequences were then introduced into the CODV-Fab format of the so-called so-called CODV-Fab "7G3×20G6" in combination with the anti-CD123 sequence from antibody 7G3 as described before. Purified CD123× CD3 CODV-Fabs were used in a Biacore assay to assess the affinity to CDε/δ (see table 13).

TABLE 13

Affinty of selected humanized variants of the anti-CD3 antibody 20G6 to recombinant CD3ε/δ complex.

| Humanized sequence combinations used in the CODV-Fab "7G3 × 20G6" | ka (1/Ms) | kd (1/s) | Rmax (RU) | KD (M) |
|---|---|---|---|---|
| parental sequence | 2.17E+04 | 5.71E−04 | 46 | 2.63E−08 |
| VL1A_VH1A | 2.86E+04 | 4.34E−03 | 46 | 1.52E−07 |
| VL1B_VH1A | 2.99E+04 | 4.14E−03 | 45 | 1.38E−07 |
| VL1C_VH1D | 2.30E+04 | 1.01E−03 | 58 | 4.40E−08 |
| VL1D_VH1B | 1.86E+04 | 1.09E−03 | 62 | 5.87E−08 |
| VL1D_VH1C | 2.22E+04 | 7.13E−04 | 71 | 3.21E−08 |
| VL1D_VH1D | 2.40E+04 | 7.46E−04 | 59 | 3.10E−08 |

For the rat-anti-CD3 antibody 4B4-D7 the closest *Rattus* germline sequence was identified as IGHV6S17*01 (identity of 93%) and IGHJ2*01 (identity of 87.5%) for the heavy chain variable region and IGKV1S21*01 (identity of 93%) and IGKJ4*01 (identity of 100%) for the light chain variable region.

The calculated percentage of identity of the identified *Rattus* V-sequences to Human Germinality (frameworks sequences only) is 79% for the VH and 77.53% for the VL.

A variety of humanized variant pairs for VH and VL were generated by grafting with additional sequence engineering, using the closest human germline sequences (IGHV3-30*01_IGHJ6*02; IGKV2-30*02/IGKV2D-39*02_IGKJ2*01). The calculated percentages of Human Germinality (4 IMGT frameworks sequences only) for the humanized V-sequences are listed in table 14.

TABLE 14

Percentages of Human Germinality for humanized V-sequences obtained by grafting of the so-called "B4-D7" antibody. The percentages were calculated based on the 4 IMGT frameworks sequences only.

| Grafted "4B4-D7" variants | % Human germinality index |
|---|---|
| VL1Cmodif1 | 92.1 |
| VL1Cmodif2 | 91.0 |
| VL1Cmodif3 | 91.0 |
| VL1Amodif1 | 97.8 |
| VL1Amodif2 | 96.6 |
| VL1Amodif3 | 95.5 |

TABLE 14-continued

Percentages of Human Germinality for humanized V-sequences obtained by grafting of the so-called "B4-D7" antibody. The percentages were calculated based on the 4 IMGT frameworks sequences only.

| Grafted "4B4-D7" variants | % Human germinality index |
|---|---|
| VL2C | 95.5 |
| VL2D | 96.7 |
| VL2F | 96.7 |
| VH6Bmodif1 | 92.3 |
| VH6Bmodif2 | 90.1 |
| VH6Amodif1 | 94.5 |
| VH6Amodif2 | 92.3 |
| VH6Amodif3 | 91.2 |
| VH6C | 95.5 |
| VH6D | 93.5 |

In addition to CDR grafting, the 4D humanization protocol as described in the US patent application US20110027266 was used to humanize the Rat anti-CD3 4B4-D7 variable light (VL) and heavy (VH) domains. A molecular dynamics (MD) simulation was performed on the minimized 3D homology model (done with MOE; PDB used: 1FLR) of Rat anti-CD3 4B4-D7 and compared to the 49 Human models derived from the seven representative light chains (vk1, vk2, vk3, vk4, vlambda1, vlambda2, vlambda3) and the seven representative heavy chains (vh1a, vh1b, vh2, vh3, vh4, vh5, vh6) designed by LGCR/SDI and available within MOE Two Models were selected for the "4D humanization". vk1-vh6 with the highest 4D similarity, whit both hydrophobic and electrostatic components. vk2-vh3 with the highest sequence identity outside CDR. For the pairwise association between the Rat anti-CD3 4B4-D7 variable domain and the two selected models, the sequences were aligned based on the optimal 3D superposition of the alpha carbons of the corresponding homology models. A variety of other humanized variant pairs for VH and VL were further optimized.

The calculated percentages of Human Germinality (4 IMGT frameworks sequences only) for the humanized V-sequences are listed in Table 15:

TABLE 15

Percentages of Human Germinality for humanized V-sequences obtained by 4D humanization of the so-called "B4-D7" antibody. The percentages were calculated based on the 4 IMGT frameworks sequences only.

| 4D "4B4-D7" variants | % Human germinality index |
|---|---|
| VL1A | 75 |
| VL1B | 75 |
| VL2A | 83 |
| VL2B | 83 |
| VH1A | 80 |
| VH1B | 80 |
| VH2A | 80 |
| VH2B | 84.5 |

Humanized sequences were expressed as Fab-fragments and purified followed by a Biacore assay to assess the affinity to CD3ε/δ (data shown in table 16).

TABLE 16

Affinty of selected humanized variants of the anti-CD3 antibody 4B4-D7 to recombinant CD3ε/δ complex.

| Fab | VL | VH | Ligand | ka | kd | KD |
|---|---|---|---|---|---|---|
| 4B4 | | | huCD3 | 3.26E+05 | 2.85E−03 | 8.79E−09 |
| | | | cyCD3 | 1.90E+05 | 2.37E−03 | 1.26E−08 |
| 4B4_1 | VL1a 75% | VH1B 80% | huCD3 | 6.28E+05 | 1.74E−03 | 2.77E−09 |
| | | | cyCD3 | 5.06E+05 | 1.58E−03 | 3.13E−09 |
| 4B4_2 | VL1b 75% | VH1B 80% | huCD3 | 2.86E+05 | 2.14E−03 | 7.48E−09 |
| | | | cyCD3 | 2.77E+05 | 2.10E−03 | 7.57E−09 |
| 4B4_5 | VL2C 95.5% | VH6D 93.5% | huCD3 | 2.33E+05 | 4.23E−03 | 1.82E−08 |
| | | | cyCD3 | 2.53E+05 | 4.20E−03 | 1.66E−08 |
| 4B4_6 | VL1a 75% | VH1A 80% | huCD3 | 1.50E+06 | 1.85E−03 | 1.24E−09 |
| | | | cyCD3 | 1.49E+06 | 1.77E−03 | 1.19E−09 |
| 4B4_7 | VL1b 75% | VH1A 80% | huCD3 | 3.06E+05 | 2.48E−03 | 8.10E−09 |
| | | | cyCD3 | 3.01E+05 | 2.19E−03 | 7.28E−09 |
| 4B4_9 | VL2B 83% | VH2A 80% | huCD3 | 2.18E+05 | 2.91E−03 | 1.34E−08 |
| | | | cyCD3 | 2.85E+05 | 3.44E−03 | 1.21E−08 |
| 4B4_10 | VL1_CM2 91% | VH6_BM2 90% | huCD3 | 4.34E+05 | 3.99E−03 | 9.19E−09 |
| | | | cyCD3 | 4.30E+05 | 3.84E−03 | 8.94E−09 |
| 4B4_11 | VL1_CM3 91% | VH6_BM2 90% | huCD3 | 5.66E+05 | 7.74E−03 | 1.37E−08 |
| | | | cyCD3 | 2.38E+05 | 4.86E−03 | 2.04E−08 |
| 4B4_17 | VL2A 83% | VH2B 84.5% | huCD3 | 3.10E+05 | 2.76E−03 | 8.91E−09 |
| | | | cyCD3 | 2.98E+05 | 2.70E−03 | 9.07E−09 |
| 4B4_20 | VL2F 96.5% | VH6C 95.5% | huCD3 | 5.09E+04 | 1.71E−03 | 3.35E−08 |
| | | | cyCD3 | 4.56E+04 | 1.98E−03 | 4.34E−08 |

3.5 Binding CODV Hu-Fab CD123×CD3 to THP-1 and TF-1 Cells

Sequences of selected CD123 antibodies were cloned into the CODV-Fab format in combination with a CD3 binding sequence and proteins were expressed and purified.

Their binding capacity to cells naturally expressing CD123 was determined by flow cytometry. THP-1 cell line or TF-1 cell line were used as target cells.

Target cells were blocked with FcR-Blocker (Sigma). Therefore, target cells were resuspended in Stain Buffer with FBS (BD Pharmingen) and were blocked with 100 µl blocking reagent per ml for 1 h at 4° C. Cells were filled-up with Stain Buffer with FBS and 1E5 cells in 50 µl per well were seeded in 96-well U-bottom suspension culture plates (Greiner bio-one).
Antibodies were added at 3 µg in 50 µl Stain Buffer with FBS per well. The assay was incubated for 30 min at 4° C.

Cells were washed twice with Stain Buffer with FBS and 1 µg secondary antibody Goat F(ab')2 Anti-Human kappa-FITC (Beckman Coulter, #732621) per well was added in 100 µl Stain Buffer with FBS per well. The assay was incubated for 20 min at 4° C. and washed twice afterwards.

Cells were resuspended in 150 µl Stain Buffer with FBS per well and were measured using the MACSQuant (Miltenyi Biotec) or LSRII (BD) flow cytometer. Further data analyses were performed using the FlowJo software (Tree Star, Inc.). Read out was percentage of cells positive for antibody binding. Cells treated only with the secondary but no primary antibody were used to set the gates.

Binding of CD123×CD3 CODV-Fabs to CD123 was shown with two different cell lines expressing CD123 either with co-expression of CD131 on TF-1 cell line or on the surface of THP-1 cells lacking CD131 expression. Exemplarily shown are five different clones binding to target cells. As negative control (specificity control) a CD19×CD3 CODV-Fab was used as and a reference CD123×CD3 CODV-Fab as positive control (table 17).

TABLE 17

Specific binding of CD123 targeting sequences cloned into CODV-Fab backbone in combination with a CD3 binding sequence to THP-1 and TF-1 cell lines. Binding of antibodies was detected using CD123 expressing THP-1 and TF-1 as target cells. 3 µg antibody was added and detected by a secondary goat anti-human kappa-FITC antibody. Shown are percentages of antibody positive target cells.

| | % FITC positive Cells | |
|---|---|---|
| Antibody | THP-1 cells | TF-1 cells |
| medium control | 0.10 | 0.00 |
| sec. AB control | 0.00 | 0.20 |
| specificity control CD19 × CD3 | 0.10 | 0.20 |
| CODV-Fab CD123 × CD3 | 99.90 | 82.50 |
| CODV-Fab BFX-2F8-D6 × CD3 | 24.00 | 9.30 |
| CODV-Fab BFX-3E3-D3 × CD3 | 99.00 | 31.60 |
| CODV-Fab BFX-9B8-G6 × CD3 | 48.80 | 31.10 |
| CODV-Fab BFX-9D7-C8 × CD3 | 88.70 | 50.20 |
| CODV-Fab BFX-9F6-G3 × CD3 | 99.70 | 60.70 |

3.6 Cytotoxic Effect to THP-1 Cells Mediated by CODV-Fab CD123×CD3

T-cell engaging effects of bispecific antibodies consisting of new generated CD123 sequence and the same CD3 binding sequence was analyzed by a flow cytometry based cytotoxic assay. Effector cells were primary T cells isolated from whole blood of healthy donors. THP-1 cells were used as CD123 expressing target cells.

Peripheral blood mononuclear cells (PBMCs) were isolated from 200 ml peripheral blood of healthy donors treated with EDTA by Ficoll density centrifugation. 15 ml Histopaque (Sigma-Aldrich) was preloaded on a 50 ml Leucosep-Tube (Greiner bio-one). Blood was diluted with autoMACS Rinsing Buffer+1% BSA (Miltenyi Biotec) and loaded on the membrane of a total of ten prepared tubes. Tubes were centrifuged without brake for 10 min at 1000×g. PBMCs were collected and washed with autoMACS Rinsing Buffer+1% BSA three times. Finally, PBMCs were resuspended in autoMACS Running Buffer (Miltenyi Biotec) for isolation of T lymphocytes by autoMACSpro technology using the Pan T Cell isolation Kit (Miltenyi Biotec) according to manufacturer's instructions. Purity of separated T cells was analyzed by MACSQuant flow cytometry using the human 7-Color Immunophenotyping Kit (Miltenyi Biotec).

Target cells (i.e. THP-1 cell line) were stained for 15 min at 37° C. with 1 µM CFSE in 1 ml RPMI+GlutaMAX I+10% FCS (Invitrogen). 2.5E4 target cells were seeded in 96-well U-bottom suspension culture plates (Greiner bio-one) in 50 µl medium per well.

Isolated primary human T lymphocytes were resuspended in RPMI+GlutaMAX I+10% FCS and were added at indicated effector-to-target ratio in 50 µl per well to the target cells (in general E:T=10:1).

Bispecific antibodies were diluted 1:3 in serial in PBS (Invitrogen) and 5 µl each were added to the cells at a final maximum concentration of 3 000 ng/ml. The assay was incubated for 20 h at 37° C. in 5% CO2.

To detect dead target cells, all cells were stained with 7-AAD. Therefore, 5 µg/ml 7-AAD diluted in Stain Buffer with FBS (BD Pharmingen) were added to each well and were incubated for 15 min at 4° C. in the dark. Cells were measured using the MACSQuant (Miltenyi Biotec) or LSRII (BD) flow cytometer, respectively. Further data analyses were performed using the FlowJo software (Tree Star, Inc.). Read out was percentage of CFSE and 7-AAD double positive cells. Curves were calculated by XLfit (Algorithm 205).

As exemplarily shown in table 18 the bispecific antibodies were able to engage primary T cells and to lyse THP-1 target cells in vitro. An antibody concentration dependent increase in dead target cells could be detected after 20 h co-incubation. For the antibodies shown in here EC50 values were calculated ranging between 12.2 and 429.3 ng/ml.

TABLE 18

T-cell engaging effect of bispecific CODV-Fab CD123 × CD3 detected in flow cytometry based cytotoxic assays. Presented are mean EC50 values calculated from curves

| Antibody | EC50 [ng/ml] geomean +/− SEM (n = 4) | EC50 [nM] geomean +/− SEM (n = 4) | n |
|---|---|---|---|
| CODV-Fab BFX-2B8-F3 × CD3 | 106.9 +/− 33.9 | 1420.5 +/− 450.2 | 4 |
| CODV-Fab BFX-3E3-D3 × CD3 | 12.2 +/− 5.9 | 163.0 +/− 80.1 | 4 |
| CODV-Fab BFX-6B10-E4 × CD3 | 39.7 +/− 17.9 | 529.1 +/− 237.7 | 4 |
| CODV-Fab BFX-9B8-G6 × CD3 | 106.1 +/− 36.1 | 1410.2 +/− 479.8 | 4 |
| CODV-Fab BFX-9D7-C8 × CD3 | 86.3 +/− 29.3 | 1148.6 +/− 390.5 | 4 |
| CODV-Fab BFX-9F6-G3 × CD3 | 13.9 +/− 7.7 | 185.9 +/− 104.1 | 3 |
| CODV-Fab BFX-3B10-E6 × CD3 | 429.3 +/− 82.6 | 5709.3 +/− 1099.0 | 2 |

The CD123 clone 3E3 was combined with a humanized variant of anti-CD3 antibody 4B4 in the CODV-Fab format. Their T-cell engaging effect and their ability to activate T cells in vitro was analyzed.

Cytotoxic assays were performed as described above. The lytic effect of primary human T cells to THP-1 target cell mediated by these constructs is exemplarily shown in table 20 by CODV-Fab hz4B4(4D_A)×3E3. Cytotoxic activity could be induced reliably with a concentration dependent effect with T cells isolated from seven different healthy donors (table 19).

TABLE 19

T-cell engaging effect of bispecific CODV-Fab hz4B4(4D_A) × 3E3 detected in a flow cytometry based cytotoxic assay. Presented are mean EC50 values calculated from curves.

| CODV-Fab | Cytotoxicity (THP-1) geomean EC50 [pM] +/− SEM n = 7 | Cytotoxicity (THP-1) geomean EC50 [ng/ml] +/− SEM n = 7 |
|---|---|---|
| hz4B4(4D_A) × 3E3 CODV-Fab | 26.5 +/− 5.9 | 2.0 +/− 0.5 |

3.7 T-Cell Activating Effect of CD123×CD3 CODV-Fab or DART

The effect of bispecific antibodies on activation status of T cells as safety read out was analyzed by flow cytometry based detection of the expression of activation marker CD25 and CD69 on the surface of primary human T cells, as described before. The comparison included the single chain CD123×CD3 bi-specific diabody in DART format (herein called "MGD006") which was described in WO2015026892 as comprising a first polypeptide chain of sequence SEQ ID NO:386 (which is SEQ ID NO:1 as shown in WO2015026892) and a second polypeptide chain of sequence SEQ ID NO:387 (which is SEQ ID NO:3 as shown in WO2015026892) covalently bonded to one another by a disulfide bond.

When the CODV-Fabs were incubated with isolated T cells alone no significant increase in expression of late activation marker CD25 could be detected on the surface of CD4 positive and CD8 positive T cells (data not shown). Equally, there was no concentration dependent increase in expression level of early activation marker CD69 on both T-cell subsets (table 20). Therefore, the construct was evaluated as not active (NA). In contrast, a huge increase in expression level of both markers was measurable when THP-1 target cells were added (CD25 data not shown, CD69 data table 21).

TABLE 20

Effect of bispecific CD123 × CD3 CODV- Fab or DART on activation state of T cells detected by CD69 expression level in a flow cytometry based assay. Presented are mean percentages of activated CD8 and CD4 T cells at 100 nM antibody concentration and the Min-Effect-Concentration in assays with T cells exclusively.

| | Safety - T cell activation w/o target cells n = 3 | | | |
|---|---|---|---|---|
| CODV-Fab | CD4+/CD69+ % Activation normalized to PBS C = 100 nM mean +/− SEM | CD4+/CD69+ Min-Effect-Conc [pM] mean +/− SEM | CD8+/CD69+ % Activation normalized to PBS C = 100 nM mean +/− SEM | CD8+/CD69+ Min-Effect-Conc [pM] mean +/− SEM |
| hz4B4(4D_A) × 3E3 CODV-Fab | 14 +/− 2 | NA | 13 +/− 2 | NA |
| hz20G6 × hz7G3 CODV-Fab | 22 +/− 2 | | 22 +/− 2 | |
| hz20G6 × hz7G3 CODV-Fab-TL1 | 18 +/− 4 | | 15 +/− 2 | |
| hz20G6 × hz7G3 CODV-Fab-OL1 | 6 +/− 2 | | 9 +/− 2 | |
| Single chain antibody DART format MGD006 | 82 +/− 9 | | 83 +/− 4 | |

The results shown in Table 20 indicate that the single chain antibody (DART) causes significantly more T-cell activation in the absence of target cells under the conditions tested.

TABLE 21

Effect of bispecific CODV-Fab hz4B4(4D_A) × 3E3 on activation state of T cells detected by CD69 expression level in a flow cytometry based assay. Shown are mean percentages of activated CD8 and CD4 T cells at maximal antibody concentration (Cmax) and at the antibody concentration at EC50 in cytotoxic assay. Assays were performed with co-incubation of THP-1 target cells and T cells.

Safety - T cell activation with THP-1 target cells
n = 3

| CODV-Fab | CD4+/CD69+ % Activation normalized to PBS C = meanEC50 Cytotox mean +/− SEM | CD4+/CD69+ % Activation normalized to PBS Cmax mean +/− SEM | CD8+/CD69+ % Activation normalized to PBS C = meanEC50 Cytotox mean +/− SEM | CD8+/CD69+ % Activation normalized to PBS Cmax mean +/− SEM |
|---|---|---|---|---|
| hz4B4(4D_A) × 3E3 CODV-Fab | 71 +/− 4 | 84 +/− 2 | 69 +/− 6 | 82 +/− 4 |

TABLE 22

Effect of bispecific fully humanized 7G3 containing CODV molecules and single chain Dart on activation state of T cells detected by CD69 expression level in a flow cytometry based assay. Shown are EC50 values of representative tests of activated CD8 and CD4 T cells in cytotoxic assay. Assays were performed with co-incubation of THP-1 target cells and T cells.

Safety - T cell activation with THP-1 target cells

| CODV-Fab | CD4+ T cells (% CD69+ cells) EC50 (pM) n = 1-6 | CD8+ T cells (% CD69+ cells) EC50 (pM) n = 1-6 |
|---|---|---|
| hz20G6 × hz7G3 CODV-Fab | 1.4 | 3.1 |
| hz20G6 × hz7G3 CODV-Fab-TL1 | 3.2 | 9.9 |
| hz20G6 × hz7G3 CODV-OL1 | 1.0 | 3.3 |
| Single chain antibody DART format MGD006 | 1.0 | 3.5 |

In order to assess the cytotoxic effects of new CD123 antibodies with humanized CD3 parts, the CODV-Fabs "hz20G6×7G3", "7G3×hz4B4", "hz4B4×3E3" were generated containing different combinations of Fvs. One Fc containing variant was also generated, the CODV-Fab "hz20G6×7G3-TL4" being Fc tagged at the light chain to form Fc heterodimers with the corresponding heavy chain (TL4 variant). Affinities to the CD3ε/δ-complex and CD123 of the bispecific construct were measured by Biacore. Furthermore, a cytotoxic assay was performed as described above and CD4+ activation and CD8+ activation was measured.

TABLE 23

Affinities and activities of bispecific CD123 × CD3 CODV-molecules.

| Bispecific molecule | KD (CD3e/d) [nM] | KD (CD123) [nM] | Cytotoxic assay (THP cells) EC50 [pM] | CD69 expression @ EC50 cytotox % CD4+ activation | CD69 expression @ EC50 cytotox % CD8+ activation |
|---|---|---|---|---|---|
| hz20G6 × 7G3 CODV-Fab | 5.0 | 0.6 | 30.9 ± 3.6 | 73 | 66 |
| 7G3 × hz4B4 CODV-Fab | 5.4 | 0.1 | 26.7 ± 2.9 | 65 | 55 |
| hz4B4 × 3E3 CODV-Fab | 7.0 | 4.8 | 26.5 ± 5.9 | 71 | 69 |
| Fc-tagged variant TL4: hz20G6 × 7G3 CODV-Fab-TL4 | 13.9 | 1.7 | 16.7 ± 10.1 | 73 | 74 |

Cytotoxic effects of the CODV-Fab "hz20G6×hz7G3", CODV-Fab-TL1 "hz20G6×hz7G3", CODV-Fab-OL1 "hz20G6×hz7G3" and the single chain Dart MGD006 were also assessed. Affinities to the CD3ε/δ-complex and CD123 of each bispecific construct were measured by Biacore. Furthermore, a cytotoxic assay was performed as described above and CD4+ activation and CD8+ activation was measured.

TABLE 24

Affinities and activities of bispecific CD123 ×
CD3 CODV-molecules and DART (MGD006)

| Bispecific molecule | KD (CD3e/d) [nM] | KD (CD123) [nM] | Cytotoxic assay (THP cells) EC50 [pM] n = 3 |
|---|---|---|---|
| hz20G6 × hz7G3 CODV-Fab | 9 | 0.2 | 2.1 +/− 0.2 |
| hz20G6 × hz7G3 CODV-Fab-TL1 | 11 | 0.2 | 1.0 +/− 0.1 |
| hz20G6 × hz7G3 CODV-Fab-OL1 | 15 | 0.4 | 0.9 +/− 0.1 |
| Single chain antibody DART format MGD006 | 9 | 0.2 | 0.3 +/− 0.04 |

To assess the potential of the molecules to trigger T-cell activation in the presence (wanted) and absence (unwanted) of target cells, a new assay was implemented. NFAT-RE-luc2 Jurkat Cells (Promega # CS176403 cells) were incubated with freshly isolated human T-cells in an Effector target ration of 1:1 at 37° C. and 5% CO2 in RPMI 1640, with 2 g/L (11 mM) Glucose, with GlutaMAX, with 25 mM HEPES in 386 well plates. After 5 hrs the incubation was stopped and luminesce was measures using Bio-Glo Luciferase Assay System, Promega # G7940 in a Luminescence HTS Micro Plate Reader.

TABLE 25

T-cell activation as activation induced by
CD123 × CD3 CODV-molecules and MGD006
measured in Jurkat-NFAT-Luc-reporter cell line.

| Bispecific molecule | With THP1 cells EC50 (pM) n = 3 | No target cells Activation at Cmax in relation to max. activation in assay with target cells (%) n = 3 |
|---|---|---|
| hz20G6 × hz7G3 CODV-Fab | 561 ± 0.2 | 0.2 ± 0.1 |
| hz20G6 × hz7G3 CODV-Fab-TL1 | 444 ± 0.2 | 0.4 ± 0.3 |
| hz20G6 × hz7G3 CODV-Fab-OL1 | 320 ± 0.2 | 0.4 ± 0.3 |
| Single chain antibody DART format MGD006 | 370 ± 0.2 | 25.1 ± 9.9 |

Results shown in Table 25 indicate that all antibodies induce reporter cell activation with EC50 values below nM in the presence of target cells. For T-cell engagement approaches, T-cell activation should be restricted to the presence of target cells. This is seen for the CODV molecules as there is no significant luminescence signal in the absence of target cells. In contrast, the single chain DART molecule induces a higher reporter cell line activation in the absence of target cells. These results are in agreement with the results obtained with primary T-cells.

3.8 In Vivo Anti-Tumor Activity of CD123×CD3 Bispecific CODV-Fab-TL1 and CD123×CD3 Bispecific CODV-Fab Materials and Methods
Human PBMC and T Cell Isolation from Whole Blood
PBMCs were isolated from the whole blood of human healthy donors with a Ficoll gradient centrifugation. Whole blood was diluted 1:1 in sterile phosphate buffered saline (PBS). Then, two volumes of thirty-five mL of the diluted blood were put into two 50 mL Falcon Tubes in presence of 15 mL Ficoll-Paque. The tubes were centrifuged at 200 g for 40 minutes at room temperature without brake. The two buffy coat layers were recovered and put in six 50 mL Falcon tubes with 45 mL of sterile PBS and centrifuged three times (in between each centrifugation, the supernatant was discarded and 45 mL of PBS was added) at 100 g during ten minutes at room temperature without brake. After the last centrifugation, the two pellets were put together in a final volume of 50 mL completed by PBS in a 50 mL Falcon tube. The total viable PBMCs number was defined by Vicell counting. The pellet was then recovered in Automacs running buffer from Myltenyi Biotech (130-091-221) and T cells were isolated from PBMCs using the negative selection KIT from Miltenyi Biotech (130-091-156) and Automacs according to manufacturer instructions. The purified T cells were recovered and put in culture in Xvivo-15 5% HIS+ peni-strepto1× medium at a concentration of 2.5×10E+6 cells/mL.

Human T Cell Amplification
The human enriched T cell population was activated and expanded in vitro during 14 days using the T Cell Activation/Expansion kit from Miltenyi Biotech (130-091-441)

Human T Cell Preparation for In Vivo Administration
Cells and cell culture medium were centrifuged 10 minutes at 400 g. The pellet was recovered at a concentration of 2×10E+7 cells/ml in sterile PBS. Elimination of the activating beads from the amplified T cells was performed using the MACsiMAG separator from Myltenyi Biotech (130-092-168) according to manufacturer instructions. Enriched T cell populations were counted by Vicell counting and were recovered in 25 mL of sterile PBS in a 50 mL Falcon tube. After a step of centrifugation at 400 g during 10 minutes at room temperature, the cell pellet was recovered in an adequate volume of sterile PBS to obtain a final concentration of 5×10E+7 cells/mL.

Tumor Model
Molm-13 human Acute Myeloid Leukemia cells expressing CD123 were obtained from the Leibniz-institut DSMZ-German collection of microorganisms and cell cultures (DSMZ Braunshweig, Germany). Cells were grown in culture (37° C., 5% $CO_2$, 95% humidity) in RPM11640 Glutamax medium (completed with foetal cow serum 20%). Molm-13 cells were infected with a Luciferase vector (SV40-PGL4-Puro—i.e. Luciferase vector consisting in Simian Virus 40 promoterlinked to the Luciferase 2 and the Puromycin resistance cassete sequences) carried by a non-replicative lentivirus.

The Molm13-luc+ tumoral cells were injected intravenously (IV) in NOD.Cg-Prkdcscid Il2rgtm1Wjl/SzJ NSG mice (10E+6 cells per animal in 200 µl PBS suspension). Twenty-four hours later, 10E+7 human T-cells were administered intraperitoneally (IP) to the same mice under a volume of 0.2 mL of sterile PBS.

Baseline bioluminescence imaging at day three post tumor implantation was performed using the IVIS100 imager (PerkinElmer, Waltham, Mass., USA) with the Living Image 3.2 acquisition software (Perkin-Elmer, Waltham, M, USA). Animals were injected IP with Beetle luciferin potassium salt (batch 316019, Promega, Lyon, France) 120 mg/kg solution in PBS 15 minutes before image. Mice were anesthetized with Ketamine®/Xylazine® (120 mg/kg; 6 mg/kg IM, 5 ml/kg) 5 minutes before image.

CODV-Fab-TL1 "hz20G6×hz7G3", CODV-Fab "hz20G6×hz7G3", CD123×CD3 bispecific DART competitor (Single chain antibody DART format MGD006 or a close analog herein called "DART-tool") or PBS treatments by intravenous route (IV) or continuous intraperitoneal infusion (CIP) started at day four post tumor implantation on established tumors already detectable in bones, as outlined in table 26 (CODV-Fab-TL1 "hz20G6×hz7G3"), table 27 (CODV-Fab "hz20G6×hz7G3" IV) and table 28 (CODV-Fab "hz20G6×hz7G3" CIP).

TABLE 26

CD123 × CD3 Bispecific CODV-Fab-TL1 intravenous (IV) evaluation study design

| Treatment Group | Dose (nmol/Kg) | Volume/ inj | Route | Schedule | Animal number |
|---|---|---|---|---|---|
| Control | — | — | — | — | 7 |
| CODV-Fab-TL1 "hz20G6 × hz7G3" | 1.3 | 0.2 ml | IV | Q3d (4, 7, 10) | 7 |
| CODV-Fab-TL1 "hz20G6 × hz7G3" | 0.13 | 0.2 ml | IV | Q3d (4, 7, 10) | 8 |
| CODV-Fab-TL1 "hz20G6 × hz7G3" | 0.013 | 0.2 ml | IV | Q3d (4, 7, 10) | 6 |
| CODV-Fab "hz20G6 × hz7G3" | 1.3 | 0.2 ml | IV | Qd (4-13) | 8 |
| Single chain antibody DART format MGD006 | 1.3 | 0.2 ml | IV | Qd (4-13) | 7 |

TABLE 27

CD123 × CD3 Bispecific CODV-Fab intravenous (IV) evaluation study design

| Treatment Group | Dose (nmol/Kg) | Volume/ inj | Route | Schedule | Animal number |
|---|---|---|---|---|---|
| Control | — | — | — | — | 5 |
| CODV-Fab "hz20G6 × hz7G3" | 1.3 | 0.2 ml | IV | Qd (4-13) | 8 |
| CODV-Fab "hz20G6 × hz7G3" | 0.13 | 0.2 ml | IV | Qd (4-13) | 5 |
| Single chain antibody DART format DART tool | 1.3 | 0.2 ml | IV | Qd (4-13) | 8 |
| Single chain antibody DART format DART tool | 0.13 | 0.2 ml | IV | Qd (4-13) | 7 |
| CODV-Fab hz20G6 × 7G3 | 1.3 | 0.2 ml | IV | Qd (4-13) | 8 |

TABLE 28

CD123 × CD3 Bispecific CODV-Fab continuous intraperitoneal infusion (CIP) evaluation study design

| Treatment Group | Dose (nmol/ Kg/day) | Volume/ day | Route | Schedule | Animal number |
|---|---|---|---|---|---|
| Vehicle | — | 6 µl/day | ip Alzet 1002 | Continuous infusion (4-14) | 9 |
| CODV-Fab "hz20G6 × hz7G3" | 3.9 | 6 µl/day | ip Alzet 1002 | Continuous infusion (4-14) | 9 |
| CODV-Fab "hz20G6 × hz7G3" | 1.3 | 6 µl/day | ip Alzet 1002 | Continuous infusion (4-14) | 10 |
| Single chain antibody DART format MGD006 | 3.9 | 6 µl/day | ip Alzet 1002 | Continuous infusion (4-14) | 9 |
| Single chain antibody DART format MGD006 | 1.3 | 6 µl/day | ip Alzet 1002 | Continuous infusion (4-14) | 9 |
| CODV-Fab "hz20G6 × hz7G3 | 1.3 | 0.2 ml | IV | Qd (4-13) | 10 |
| Vehicle | — | 6 µl/day | ip Alzet 1002 | Continuous infusion (4-14) | 10 |
| CODV-Fab "hz20G6 × hz7G3 | 0.13 | 6 µl/day | ip Alzet 1002 | Continuous infusion (4-14) | 8 |
| CODV-Fab "hz20G6 × hz7G3 | 0.013 | 6 µl/day | ip Alzet 1002 | Continuous infusion (4-14) | 8 |
| Single chain antibody DART format MGD006 | 0.13 | 6 µl/day | ip Alzet 1002 | Continuous infusion (4-14) | 8 |
| Single chain antibody DART format MGD006 | 0.013 | 6 µl/day | ip Alzet 1002 | Continuous infusion (4-14) | 9 |
| CODV-Fab "hz20G6 × hz7G3 | 1.3 | 0.2 ml | IV | Qd (4-13) | 10 |

DATA Collection and Efficacy Criteria

Animal body weight was monitored from day 3 to the end of assay in order to follow impact of therapy. A dosage producing a 20% weight loss or 15% weight loss for 3 consecutive days or 10% or more drug related deaths, was considered an excessively toxic dosage. Animal body weights included the tumor weights.

Tumor load was followed by non-invasive bioluminescence imaging (BLI). Baseline BLI was performed at day three post tumor implantation, 24 hours before start of treatments. Animals were dispatched in different groups based on all body bioluminescence signal. Tumor growth was followed in all body and long bones in posteriors legs by BLI signal measurements at days 7, 10 and 14 after tumor implantation. Long bone signal was measured by segmentation and could be influenced by nearby loco-regional signal (eg residual signal in soft tissues in late time points). Treated groups were compared to control animals bearing Molm13-luc+ disseminated tumor and Human T cells.

The primary efficacy end points were the ratio of tumor signal changes from baseline between treated and control groups (dT/dC), the number of partial tumor regressions (PR) and the number of complete tumor regression (CR).

Tumor growth based on bioluminescence signal curves (expressed in Phot/sec) in time was monitored for each animal of each treatment group and represented as median curve±MAD, both for all body and bone segmented signals. Changes in tumor bioluminescence signal are calculated for each control (C) or treated (T) animal and for each day by subtracting the tumor signal on the day of first treatment (staging day) from the tumor signal on the specified observation day. The median T is calculated for the treated group and the median C is calculated for the control group. Then the ratio T/C is calculated and expressed as a percentage:

$$dT/dC = [(\text{median } T \text{ day obs} - \text{median } T \text{ day 3})/(\text{median } C \text{ day obs} - \text{median } C \text{ day 3})] \times 100$$

The dose is considered as therapeutically active when dT/dC at the end of the experiment (day 14) is lower than 42% and very active when dT/dC is lower than 10%.

Percent tumor regression is defined as the % of tumor signal decrease in the treated group at a specified observation day compared to its signal on the first day of treatment. At a specific time point and for each animal, % regression is calculated as:

$$\% \text{ regression (at } t) = \frac{\text{Signal}_{t0} - \text{Signal}_{t}}{\text{Signal}_{t0}} \times 100$$

Given the risk of signal variability due to luciferin kinetics and possible IP miss-injection, signal regression for an animal is considered as a true tumor regression only when observed at least at two consecutive time points.

Partial regression (PR): Regressions are defined as partial if the tumor signal decreases below the signal at the start of treatment for two consecutive time points, one remaining superior to 50% of baseline signal.

Complete regression (CR): Regressions are defined as complete if the tumor signal decreases more than 50% below the signal at the start of treatment for two consecutive time points.

Statistical Analysis

IV Route Compounds Evaluation

Individual bioluminescence signal of each group of treatment was compared to others using Bonferroni-Holm adjustment for multiplicity pairwise comparisons following Two way anova with repeated measures by day: $p>0.05$: NS, $0.05>p>0.01$: *, $p<0.01$: **. Statistical analysis is performed for both all body bioluminescence signals and long-bones bioluminescence signals CIP Route Compounds Evaluation The CODV-Fab "hz20G6×hz7G3" CIP route evaluation results in data aggregation of two independent studies ($1^{st}$ study concerning compounds at high dosages, $2^{nd}$ study for low dosages, both studies including a vehicle control group and CODV-Fab "hz20G6×hz7G3" 1.3 nmol/kg IV Qd positive control group). Statistical analysis of bioluminescence signal of each mouse at each day was performed after data normalization by the mean of the bioluminescence signal of the vehicle group at the same day of the same experiment (pooled vehicle controls n=19; pooled positive controls n=20). Individual normalized bioluminescence signal of each group of treatment was compared to other groups using Bonferroni-Holm adjustment for multiplicity pairwise comparisons following Two way anova with repeated measures by day: $p>0.05$: NS, $0.05>p>0.01$: *, $p<0.01$: **. Statistical analysis is performed for both all body bioluminescence signals and long-bones bioluminescence signals.

Results

CD123×CD3 Bispecific CODV-Fab-TL1 "hz20G6×hz7G3" IV

Fully human CODV-Fab-TL1 "hz20G6×hz7G3" IV Q3d in presence of human T cells inhibited Molm13 tumor growth at all tested doses (1.3, 0.13 and 0.013 nmol/Kg Q3d) with dT/dC of 20%, 14% and 38% respectively in whole body (FIGS. 5 and 7) and was associated with tumor regression in long bones at all tested doses with 4/7 CR, 6/8 CR and 2/6 CR respectively (FIGS. 6 and 8).

Fully human CODV-Fab-TL1 "hz20G6×hz7G3" maximal response was obtained in whole body and in bone at 0.13 nmol/kg Q3d. At this dose, the activity was not statistically different from DART 1.3 nmol/kg IV Qd (whole body dT/dC 29% with 1/7CR and 1/7PR in long bones), and equivalent to CODV-Fab "hz20G6×hz7G3" 1.3 nmol/kg IV Qd (whole body dT/dC 23% with 1/8CR and 1/8PR tumor regression in long bones). Data were confirmed by terminal histopathology analysis (not shown).

Differences observed between whole body and long bones are linked to residual tumor growth in ovaries and abdominal fat consecutive to extra-medullar tumor dissemination after IV injection.

CD123×CD3 Bispecific CODV-Fab "hz20G6×hz7G3" IV

Fully human CODV-Fab "hz20G6×hz7G3" IV in presence of human T cells inhibited tumor growth at all tested doses (1.3 and 0.13 nmol/Kg Qd4-13) with dT/dC of 14% and 39% respectively (FIGS. 9 and 11) associated with tumor regression at 1.3 nmol/kg in long bones with 5/8 CR (FIGS. 10 and 12).

DART 1.3 nmol/kg IV Qd4-13 inhibited tumor growth with whole body dT/dC 29% and 3/8 CR tumor regression in long bones, not significantly different from CODV-Fab "hz20G6×hz7G3" 1.3 nmol/Kg IV. DART was inactive at inhibiting whole body tumor signal at 0.13 nmol/Kg IV Qd4-13 (dT/dC 62%) despite 1/7PR tumor regression in long bones. No significant difference was observed with the same dosage of fully human CODV-Fab "hz20G6×hz7G3" at the end of study. No statistical differences could be seen between fully human CODV-Fab "hz20G6×hz7G3" and partly humanised CODV-Fab hz20G6×7G3 compound when given at the same dosage of 1.3 nmol/kg iv QD4-13: at this dose CODV-Fab hz20G6×7G3 inhibited whole body tumor growth with dT/dC of 34% associated with tumor regressions in long bones (1/8CR and 1/8PR).

Differences observed between whole body and long bones are linked to residual tumor growth in ovaries and abdominal fat consecutive to extra-medullar tumor dissemination after IV injection.

CD123×CD3 Bispecific CODV-Fab CIP

Fully human CODV-Fab "hz20G6×hz7G3" CIP, in presence of human T cells, inhibited whole body tumor growth at 3.9, 1.3 and 0.13 nmol/Kg/day CIP4-14 and was inactive at 0.013 nmol/kg/day with respective dT/dC of 2%, 3%, 21%, and 57% in whole body (FIGS. 13 and 15). It was associated with tumor regression at 3.9, 1.3, and 0.13 nmol/kg in long bones with 5/9CR 3/9PR, 6/10CR 1/10PR and 7/8CR respectively (FIGS. 14 and 16).

DART 3.9, 1.3, and 0.13 nmol/kg/day CIP4-14, but not 0.013 nmol/kg/day inhibited whole body tumor growth with dT/dC of 21%, 5%, 21% and 46% respectively (FIG. 13) inducing tumor regression in long bones at 3.9, 1.3, and 0.13 nmol/kg with 3/9 CR 3/9PR; 8/9CR; and 4/8CR 2/8PR respectively (FIG. 14).

Full human CODV-Fab "hz20G6×hz7G3" 1.3 nmol/kg IV Qd4-13 inhibited tumor growth in whole body with dT/dC of 4% and 5% ($1^{st}$ and $2^{nd}$ study resp.) associated with tumor regression in long bones (8/10CR 1/10PR vs 8/10 CR in $1^{st}$ and $2^{nd}$ study resp).

The invention claimed is:

1. An antibody-like binding protein that specifically binds to CD3ε and CD123 comprising two polypeptide chains that form two antigen-binding sites, wherein a first polypeptide chain comprises an amino acid sequence as set forth in SEQ ID NO: 388; and a second polypeptide chain comprises an amino acid sequence as set forth in SEQ ID NO: 390.

2. An antibody-like binding protein that specifically binds to CD3ε and CD123 comprising two polypeptide chains that form two antigen-binding sites, wherein a first polypeptide chain comprises an amino acid sequence as set forth in SEQ ID NO: 391; and a second polypeptide chain comprises an amino acid sequence as set forth in SEQ ID NO: 393.

3. An antibody-like binding protein that specifically binds to CD3ε and CD123 comprising two polypeptide chains that form two antigen-binding sites, wherein the first polypeptide chain comprises a structure represented by the formula [I]:

$$V_{D1}\text{-}L_1\text{-}V_{D2}\text{-}L_2\text{-}C_L \quad [I]$$

and the second polypeptide chain comprises a structure represented by the formula [II]:

$$V_{D3}\text{-}L_3\text{-}V_{D4}\text{-}L_4\text{-}C_{H1} \quad [II]$$

wherein:
$V_{D1}$ is a light chain variable domain of a first immunoglobulin;
$V_{D2}$ is a light chain variable domain of a second immunoglobulin;
$V_{D3}$ is a heavy chain variable domain of the second immunoglobulin;
$V_{D4}$ is a heavy chain variable domain of the first immunoglobulin;
$C_L$ is a light chain constant domain of an immunoglobulin;
$C_{H1}$ is a $C_{H1}$ heavy chain constant domain of an immunoglobulin; and
$L_1$, $L_2$, $L_3$, and $L_4$ are amino acid linkers;
wherein the first polypeptide chain and the second polypeptide chain form a cross-over light chain-heavy chain pair; and
wherein $V_{D1}$ comprises a CDR1-L comprising an amino acid sequence as set forth in SEQ ID NO: 378, a CDR2-L comprising an amino acid sequence of WAS, and a CDR3-L comprising an amino acid sequence as set forth in SEQ ID NO: 379;
$V_{D2}$ comprises a CDR4-L comprising an amino acid sequence as set forth in SEQ ID NO: 142, a CDR5-L comprising an amino acid sequence of KVS, and a CDR6-L comprising an amino acid sequence as set forth in SEQ ID NO: 11;
$V_{D3}$ comprises a CDR1-H comprising an amino acid sequence as set forth in SEQ ID NO: 6, a CDR2-H comprising an amino acid sequence as set forth in SEQ ID NO: 7, and a CDR3-H comprising an amino acid sequence as set forth in SEQ ID NO: 8; and
$V_{D4}$ comprises a CDR4-H comprising an amino acid sequence as set forth in SEQ ID NO: 381, a CDR5-H comprising an amino acid sequence as set forth in SEQ ID NO: 384, and a CDR6-H comprising an amino acid sequence as set forth in SEQ ID NO: 382.

4. The antibody-like binding protein of claim 3, wherein:
$L_1$ comprises an amino acid sequence as set forth in SEQ ID NO: 389;
$L_2$ comprises an amino acid sequence as set forth in SEQ ID NO: 389; and
$L_3$ and $L_4$ are 0 amino acids in length.

5. The antibody-like binding protein of claim 3, wherein:
$V_{D1}$ comprises an amino acid sequence as set forth in SEQ ID NO: 385;
$V_{D2}$ comprises an amino acid sequence as set forth in SEQ ID NO: 141;
$V_{D3}$ comprises an amino acid sequence as set forth in SEQ ID NO: 138;
$V_{D4}$ comprises an amino acid sequence as set forth in SEQ ID NO: 383;
$C_L$ comprises an amino acid sequence as set forth in SEQ ID NO: 310; and
$C_{H1}$ comprises an amino acid sequence as set forth in SEQ ID NO: 313.

6. The antibody-like binding protein of claim 3, wherein:
(a) the first polypeptide chain comprises an amino acid sequence as set forth in SEQ ID NO: 388, or
an amino acid sequence that is at least 85% identical to the amino acid sequence as set forth in SEQ ID NO: 388, which comprises a CDR1-L comprising an amino acid sequence as set forth in SEQ ID NO: 378, a CDR2-L comprising an amino acid sequence WAS, a CDR3-L comprising an amino acid sequence as set forth in SEQ ID NO: 379, a CDR4-L comprising an amino acid sequence as set forth in SEQ ID NO: 142, a CDR5-L comprising an amino acid sequence of KVS, and a CDR6-L comprising an amino acid sequence as set forth in SEQ ID NO: 11; and (b) the second polypeptide chain comprises an amino acid sequence as set forth in SEQ ID NO: 390, or an amino acid sequence that is at least 85% identical to the amino acid sequence as set forth in SEQ ID NO: 390, which comprises a CDR1-H comprising an amino acid sequence as set forth in SEQ ID NO: 6, a CDR2-H comprising an amino acid sequence as set forth in SEQ ID NO: 7, a CDR3-H comprising an amino acid sequence as set forth in SEQ ID NO: 8, a CDR4-H comprising an amino acid sequence as set forth in SEQ ID NO: 381, a CDR5-H comprising an amino acid sequence as set forth in SEQ ID NO: 384, and a CDR6-H comprising an amino acid sequence as set forth in SEQ ID NO: 382.

7. The antibody-like binding protein of claim 3, wherein the second polypeptide chain further comprises a Fc domain ("Fc").

8. The antibody-like binding protein of claim 3, wherein the first polypeptide chain further comprises a Fc domain ("Fc").

9. An antibody-like binding protein that specifically binds to CD3ε and CD123 comprising two polypeptide chains that form two antigen-binding sites, wherein the first polypeptide chain comprises a structure represented by the formula [IV]:

$$V_{D1}\text{-}L_1\text{-}V_{D2}\text{-}L_2\text{-}C_L\text{-}L_5\text{-}Fc_2 \qquad [IV]$$

and the second polypeptide chain comprises a structure represented by the formula [III]:

$$V_{D3}\text{-}L_3\text{-}V_{D4}\text{-}L_4\text{-}C_{H1}\text{-}Fc \qquad [III]$$

wherein:
$V_{D1}$ is a light chain variable domain of a first immunoglobulin;
$V_{D2}$ is a light chain variable domain of a second immunoglobulin;
$V_{D3}$ is a heavy chain variable domain of the second immunoglobulin;
$V_{D4}$ is a heavy chain variable domain of the first immunoglobulin;
$C_L$ is a light chain constant domain of an immunoglobulin;
$C_{H1}$ is a $C_{H1}$ heavy chain constant domain of an immunoglobulin;
Fc is the immunoglobulin hinge region and $CH_2$, $CH_3$ immunoglobulin heavy chain constant domains of a first immunoglobulin;
$Fc_2$ is the immunoglobulin hinge region and $CH_2$, $CH_3$ immunoglobulin heavy chain constant domains of a second immunoglobulin; and
$L_1$, $L_2$, $L_3$, $L_4$, and $L_5$ are amino acid linkers;
wherein the first polypeptide chain of formula [IV] and the second polypeptide chain of formula [III] form a cross-over light chain-heavy chain pair; and
wherein $V_{D1}$ comprises a CDR1-L comprising an amino acid sequence as set forth in SEQ ID NO: 378, a CDR2-L comprising an amino acid sequence of WAS, and a CDR3-L comprising an amino acid sequence as set forth in SEQ ID NO: 379;

$V_{D2}$ comprises a CDR4-L comprising an amino acid sequence as set forth in SEQ ID NO: 142, a CDR5-L comprising an amino acid sequence of KVS, and a CDR6-L comprising an amino acid sequence as set forth in SEQ ID NO: 11;

$V_{D3}$ comprises a CDR1-H comprising an amino acid sequence as set forth in SEQ ID NO: 6, a CDR2-H comprising an amino acid sequence as set forth in SEQ ID NO: 7, and a CDR3-H comprising an amino acid sequence as set forth in SEQ ID NO: 8; and $V_{D4}$ comprises a CDR4-H comprising an amino acid sequence as set forth in SEQ ID NO: 381, a CDR5-H comprising an amino acid sequence as set forth in SEQ ID NO: 384, and a CDR6-H comprising an amino acid sequence as set forth in SEQ ID NO: 382.

10. The antibody-like binding protein of claim 9, wherein:
$L_1$ comprises an amino acid sequence as set forth in SEQ ID NO: 389;
$L_2$ comprises an amino acid sequence as set forth in SEQ ID NO: 389; and
$L_3$, $L_4$, and $L_5$ are 0 amino acids in length.

11. The antibody-like binding protein of claim 9, wherein:
Fc comprises an amino acid sequence as set forth in SEQ ID NO: 394; and
$Fc_2$ comprises an amino acid sequence as set forth in SEQ ID NO: 392.

12. The antibody-like binding protein of claim 9, wherein:
$V_{D1}$ comprises an amino acid sequence as set forth in SEQ ID NO: 385;
$V_{D2}$ comprises an amino acid sequence as set forth in SEQ ID NO: 141;
$V_{D3}$ comprises an amino acid sequence as set forth in SEQ ID NO: 138;
$V_{D4}$ comprises an amino acid sequence as set forth in SEQ ID NO: 383;
$C_L$ comprises an amino acid sequence as set forth in SEQ ID NO: 310; and
$C_{H1}$ comprises an amino acid sequence as set forth in SEQ ID NO: 313.

13. The antibody-like binding protein of claim 9, wherein:
(a) the first polypeptide chain comprises an amino acid sequence as set forth in SEQ ID NO: 391, or an amino acid sequence that is at least 85% identical to the amino acid sequence as set forth in SEQ ID NO: 391, which comprises a CDR1-L comprising an amino acid sequence as set forth in SEQ ID NO: 378, a CDR2-L comprising an amino acid sequence WAS, a CDR3-L comprising an amino acid sequence as set forth in SEQ ID NO: 379, a CDR4-L comprising an amino acid sequence as set forth in SEQ ID NO: 142, a CDR5-L comprising an amino acid sequence of KVS, and a CDR6-L comprising an amino acid sequence as set forth in SEQ ID NO: 11; and (b) the second polypeptide chain comprises an amino acid sequence as set forth in SEQ ID NO: 393, or an amino acid sequence that is at least 85% identical to the amino acid sequence as set forth in SEQ ID NO: 393, which comprises a CDR1-H comprising an amino acid sequence as set forth in SEQ ID NO: 6, a CDR2-H comprising an amino acid sequence as set forth in SEQ ID NO: 7, a CDR3-H comprising an amino acid sequence as set forth in SEQ ID NO: 8, a CDR4-H comprising an amino acid sequence as set forth in SEQ ID NO: 381, a CDR5-H comprising an amino acid sequence as set forth in SEQ ID NO: 384, and a CDR6-H comprising an amino acid sequence as set forth in SEQ ID NO: 382.

14. An antibody-like binding protein that binds specifically to CD3ε and CD123 comprising two polypeptide chains that form two antigen-binding sites, wherein a first polypeptide has a structure represented by the formula [I]:

$$V_{D1}\text{-}L_1\text{-}V_{D2}\text{-}L_2\text{-}C_L \qquad [I]$$

and a second polypeptide has a structure represented by the formula [II]:

$$V_{D3}\text{-}L_3\text{-}V_{D4}\text{-}L_4\text{-}C_{H1} \qquad [II]$$

wherein:
- $V_{D1}$ is a light chain variable domain of a first immunoglobulin;
- $V_{D2}$ is a light chain variable domain of a second immunoglobulin;
- $V_{D3}$ is a heavy chain variable domain of the second immunoglobulin;
- $V_{D4}$ is a heavy chain variable domain of the first immunoglobulin;
- $C_L$ is a light chain constant domain of an immunoglobulin;
- $C_{H1}$ is a $C_{H1}$ heavy chain constant domain of an immunoglobulin;
- $L_1$, $L_2$, $L_3$, and $L_4$ are amino acid linkers; and wherein the first polypeptide and the second polypeptide form a cross-over light chain-heavy chain pair; and
wherein $V_{D1}$ consists of the amino acid sequence as set forth in SEQ ID NO: 385, or an amino acid sequence that is at least 85% identical to the amino acid sequence as set forth in SEQ ID NO: 385, which comprises a CDR1-L of sequence SEQ ID NO: 378, a CDR2-L of sequence WAS, and a CDR3-L of sequence SEQ ID NO: 379;

$V_{D2}$ consists of the amino acid sequence as set forth in SEQ ID NO: 141, or an amino acid sequence that is at least 85% identical to the amino acid sequence as set forth in SEQ ID NO: 141, which comprises a CDR1-L of sequence SEQ ID NO: 142, a CDR2-L of sequence KVS, and a CDR3-L of sequence SEQ ID NO: 11;

$V_{D3}$ consists of the amino acid sequence as set forth in SEQ ID NO: 138, or an amino acid sequence that is at least 85% identical to the amino acid sequence as set forth in SEQ ID NO: 138, which comprises a CDR1-H of sequence SEQ ID NO: 6, a CDR2-H of sequence SEQ ID NO: 7, and a CDR3-H of sequence SEQ ID NO: 8; and $V_{D4}$ consists of the amino acid sequence as set forth in SEQ ID NO: 383, or an amino acid sequence that is at least 85% identical to the amino acid sequence as set forth in SEQ ID NO: 383, which comprises a CDR1-H of sequence SEQ ID NO: 381, a CDR2-H of sequence SEQ ID NO: 384, and a CDR3-H of sequence SEQ ID NO: 382.

15. The antibody-like binding protein of claim 14, wherein:
(a) the first polypeptide consists of the amino acid sequence as set forth in SEQ ID NO: 388, which comprises $V_{D1}$ of amino acid sequence SEQ ID NO: 385, $L_1$ of amino acid sequence SEQ ID NO: 389, $V_{D2}$ of amino acid sequence SEQ ID NO: 141, $L_2$ of amino acid sequence SEQ ID NO: 389, and $C_L$ of amino acid sequence SEQ ID NO: 310; or
an amino acid sequence that is at least 85% identical to the amino acid sequence as set forth in SEQ ID NO: 388, wherein the three CDRs of amino acid sequences SEQ ID NO: 378, WAS, and SEQ ID NO: 379 of $V_{D1}$, and the three CDRs of amino acid sequences SEQ ID NO: 142, KVS, and SEQ ID NO: 11 of $V_{D2}$ are unaltered; and
(b) the second polypeptide consists of the amino acid sequence as set forth in SEQ ID NO: 390, which comprises $V_{D3}$ of amino acid sequence SEQ ID NO: 138, $L_3$ is 0 amino acids, $V_{D4}$ of amino acid sequence SEQ ID NO: 383, $L_4$ is 0 amino acids, and $C_{H1}$ of amino acid sequence SEQ ID NO: 313, or
an amino acid sequence that is at least 85% identical to the amino acid sequence as set forth in SEQ ID NO: 390, wherein the three CDRs of amino acid sequences SEQ ID NO: 381, SEQ ID NO: 384, and SEQ ID NO: 382 of $V_{D4}$, and the three CDRs of amino acid sequences SEQ ID NO: 6, SEQ ID NO: 7, and SEQ ID NO: 8 of $V_{D3}$ are unaltered.

16. The antibody-like binding protein according to claim 14, wherein the polypeptide of formula [II] further comprises a Fc domain and has a structure represented by formula [III]:

$$V_{D3}\text{-}L_3\text{-}V_{D4}\text{-}L_4\text{-}C_{H1}\text{-}Fc \qquad [III]$$

wherein the polypeptide of formula [I] further comprises a Fc domain ($Fc_2$) and has a structure represented by formula [IV]:

$$V_{D1}\text{-}L_1\text{-}V_{D2}\text{-}L_2\text{-}C_L\text{-}L_5\text{-}Fc_2 \qquad [IV]$$

wherein:
Fc is the immunoglobulin hinge region and $CH_2$, $CH_3$ immunoglobulin heavy chain constant domains of an immunoglobulin,
$Fc_2$ is the immunoglobulin hinge region and $CH_2$, $CH_3$ immunoglobulin heavy chain constant domains of an immunoglobulin, and
$L_5$ is an amino acid linker; and
wherein:
(a) the polypeptide according to formula [IV] consists of the amino acid sequence as set forth in SEQ ID NO: 391, which comprises $V_{D1}$ of amino acid sequence SEQ ID NO: 385, $L_1$ of amino acid sequence SEQ ID NO: 389, $V_{D2}$ of amino acid sequence SEQ ID NO: 141, $L_2$ of amino acid sequence SEQ ID NO: 389, $C_L$ of amino acid sequence SEQ ID NO: 310, $L_5$ which is 0 amino acids, and $Fc_2$ of amino acid sequence SEQ ID NO: 392; or
an amino acid sequence that is at least 85% identical to the amino acid sequence as set forth in SEQ ID NO: 391, wherein the three CDRs of amino acid sequences SEQ ID NO: 378, WAS, and SEQ ID NO: 379 of $V_{D1}$, and the three CDRs of amino acid sequences SEQ ID NO: 142, KVS, and SEQ ID NO: 11 of $V_{D2}$ are unaltered; and
(b) the polypeptide according to formula [III] consists of the amino acid sequence as set forth in SEQ ID NO: 393, which comprises $V_{D3}$ of amino acid sequence SEQ ID NO: 138, $L_3$ is 0 amino acids, $V_{D4}$ of amino acid sequence SEQ ID NO: 383, $L_4$ is 0 amino acids, $C_{H1}$ of amino acid sequence SEQ ID NO: 313, and Fc of amino acid sequence SEQ ID NO: 394; or
an amino acid sequence that is at least 85% identical to the amino acid sequence as set forth in SEQ ID NO: 393, wherein the three CDRs of amino acid sequences SEQ ID NO: 381, SEQ ID NO: 384, and SEQ ID NO: 382 of $V_{D4}$, and the three CDRs of amino acid sequences SEQ ID NO: 6, SEQ ID NO: 7, and SEQ ID NO: 8 of $V_{D3}$ are unaltered; and
wherein the polypeptide of formula [IV] and the polypeptide of formula [III] form a cross-over light chain-heavy chain pair.

17. An antibody-like binding protein comprising two polypeptide chains that form two antigen-binding sites, wherein:

a first polypeptide chain comprises:
  a CDR1-L comprising an amino acid sequence as set forth in SEQ ID NO: 378;
  a CDR2-L comprising an amino acid sequence WAS;
  a CDR3-L comprising an amino acid sequence as set forth in SEQ ID NO: 379;
  a CDR4-L comprising an amino acid sequence as set forth in SEQ ID NO: 142;
  a CDR5-L comprising an amino acid sequence of KVS; and
  a CDR6-L comprising an amino acid sequence as set forth in SEQ ID NO: 11;
and
wherein a second polypeptide chain comprises:
  a CDR1-H comprising an amino acid sequence as set forth in SEQ ID NO: 6;
  a CDR2-H comprising an amino acid sequence as set forth in SEQ ID NO: 7;
  a CDR3-H comprising an amino acid sequence as set forth in SEQ ID NO: 8;
  a CDR4-H comprising an amino acid sequence as set forth in SEQ ID NO: 381;
  a CDR5-H comprising an amino acid sequence as set forth in SEQ ID NO: 384; and
  a CDR6-H comprising an amino acid sequence as set forth in SEQ ID NO: 382.

18. A pharmaceutical composition comprising:
(a) the antibody-like binding protein of any one of claim 1, 2, 3, 9, 14, or 17; and
(b) a pharmaceutically acceptable carrier.

19. A method of treating a hematological cancer comprising administering to a subject in need thereof a therapeutically effective amount of the pharmaceutical composition of claim 18.

20. An isolated nucleic acid comprising a nucleotide sequence encoding the antibody-like binding protein of any one of claim 1, 2, 3, 9, 14, or 17.

21. A host cell which has been transformed by the nucleic acid of claim 20.

22. A kit comprising at least one antibody-like binding protein of any one of claim 1, 2, 3, 9, 14, or 17.

* * * * *

SEQUENCE LISTING

<160> NUMBER OF SEQ ID NOS: 400

<210> SEQ ID NO 1
<211> LENGTH: 207
<212> TYPE: PRT
<213> ORGANISM: Homo sapiens

<400> SEQUENCE: 1

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 2
<211> LENGTH: 198
<212> TYPE: PRT
<213> ORGANISM: Macaca fascicularis

<400> SEQUENCE: 2

Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110

Cys Met Glu Met Asp Val Met Ala Val Ala Thr Ile Val Ile Val Asp
        115                 120                 125

Ile Cys Ile Thr Leu Gly Leu Leu Leu Val Tyr Tyr Trp Ser Lys
    130                 135                 140

Asn Arg Lys Ala Lys Ala Lys Pro Val Thr Arg Gly Ala Gly Ala Gly
145                 150                 155                 160

```
Gly Arg Gln Arg Gly Gln Asn Lys Glu Arg Pro Pro Val Pro Asn
            165                 170                 175

Pro Asp Tyr Glu Pro Ile Arg Lys Gly Gln Gln Asp Leu Tyr Ser Gly
            180                 185                 190

Leu Asn Gln Arg Arg Ile
        195

<210> SEQ ID NO 3
<211> LENGTH: 340
<212> TYPE: PRT
<213> ORGANISM: Homo sapiens
<220> FEATURE:
<221> NAME/KEY: DOMAIN
<222> LOCATION: (1)..(104)
<223> OTHER INFORMATION: extracellular domain of human CD3 epsilon
<220> FEATURE:
<221> NAME/KEY: MISC_FEATURE
<222> LOCATION: (105)..(340)
<223> OTHER INFORMATION: His-tagged FC-Fusion

<400> SEQUENCE: 3

Asp Gly Asn Glu Glu Met Gly Gly Ile Thr Gln Thr Pro Tyr Lys Val
1               5                   10                  15

Ser Ile Ser Gly Thr Thr Val Ile Leu Thr Cys Pro Gln Tyr Pro Gly
            20                  25                  30

Ser Glu Ile Leu Trp Gln His Asn Asp Lys Asn Ile Gly Gly Asp Glu
        35                  40                  45

Asp Asp Lys Asn Ile Gly Ser Asp Glu Asp His Leu Ser Leu Lys Glu
    50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp Gly Ser Asp Lys Thr His Thr Cys
            100                 105                 110

Pro Pro Cys Pro Ala Pro Glu Leu Leu Gly Gly Pro Ser Val Phe Leu
        115                 120                 125

Phe Pro Pro Lys Pro Lys Asp Thr Leu Met Ile Ser Arg Thr Pro Glu
    130                 135                 140

Val Thr Cys Val Val Val Asp Val Ser His Glu Asp Pro Glu Val Lys
145                 150                 155                 160

Phe Asn Trp Tyr Val Asp Gly Val Glu Val His Asn Ala Lys Thr Lys
                165                 170                 175

Pro Arg Glu Glu Gln Tyr Asn Ser Thr Tyr Arg Val Val Ser Val Leu
            180                 185                 190

Thr Val Leu His Gln Asp Trp Leu Asn Gly Lys Glu Tyr Lys Cys Lys
        195                 200                 205

Val Ser Asn Lys Ala Leu Pro Ala Pro Ile Glu Lys Thr Ile Ser Lys
    210                 215                 220

Ala Lys Gly Gln Pro Arg Glu Pro Gln Val Tyr Thr Leu Pro Pro Ser
225                 230                 235                 240

Arg Asp Glu Leu Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
        275                 280                 285
```

```
Ser Phe Phe Leu Tyr Ser Lys Leu Thr Val Asp Lys Ser Arg Trp Gln
        290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly His His His
                325                 330                 335

His His His His
        340

<210> SEQ ID NO 4
<211> LENGTH: 333
<212> TYPE: PRT
<213> ORGANISM: Macaca fascicularis
<220> FEATURE:
<221> NAME/KEY: Domain
<222> LOCATION: (1)..(95)
<223> OTHER INFORMATION: extracellular domain of Macaca fascicularis
      CD3epsilon protein
<220> FEATURE:
<221> NAME/KEY: MISC_FEATURE
<222> LOCATION: (96)..(333)
<223> OTHER INFORMATION: Fc fusion

<400> SEQUENCE: 4

Asp Gly Asn Glu Glu Met Gly Ser Ile Thr Gln Thr Pro Tyr Gln Val
1               5                   10                  15

Ser Ile Ser Gly Thr Thr Val Ile Leu Thr Cys Ser Gln His Leu Gly
            20                  25                  30

Ser Glu Val Gln Trp Gln His Asn Gly Lys Asn Lys Glu Asp Ser Gly
        35                  40                  45

Asp Arg Leu Phe Leu Pro Glu Phe Ser Glu Met Glu Gln Ser Gly Tyr
    50                  55                  60

Tyr Val Cys Tyr Pro Arg Gly Ser Asn Pro Glu Asp Ala Ser His His
65                  70                  75                  80

Leu Tyr Leu Lys Ala Arg Val Cys Glu Asn Cys Met Glu Met Asp Gly
                85                  90                  95

Ser Asp Lys Thr His Thr Cys Pro Pro Cys Pro Ala Pro Glu Leu Leu
            100                 105                 110

Gly Gly Pro Ser Val Phe Leu Phe Pro Pro Lys Pro Lys Asp Thr Leu
        115                 120                 125

Met Ile Ser Arg Thr Pro Glu Val Thr Cys Val Val Val Asp Val Ser
    130                 135                 140

His Glu Asp Pro Glu Val Lys Phe Asn Trp Tyr Val Asp Gly Val Glu
145                 150                 155                 160

Val His Asn Ala Lys Thr Lys Pro Arg Glu Glu Gln Tyr Asn Ser Thr
                165                 170                 175

Tyr Arg Val Val Ser Val Leu Thr Val Leu His Gln Asp Trp Leu Asn
            180                 185                 190

Gly Lys Glu Tyr Lys Cys Lys Val Ser Asn Lys Ala Leu Pro Ala Pro
        195                 200                 205

Ile Glu Lys Thr Ile Ser Lys Ala Lys Gly Gln Pro Arg Glu Pro Gln
    210                 215                 220

Val Tyr Thr Leu Pro Pro Ser Arg Asp Glu Leu Thr Lys Asn Gln Val
225                 230                 235                 240

Ser Leu Thr Cys Leu Val Lys Gly Phe Tyr Pro Ser Asp Ile Ala Val
                245                 250                 255

Glu Trp Glu Ser Asn Gly Gln Pro Glu Asn Asn Tyr Lys Thr Thr Pro
```

```
                    260                 265                 270
Pro Val Leu Asp Ser Asp Gly Ser Phe Phe Leu Tyr Ser Lys Leu Thr
            275                 280                 285

Val Asp Lys Ser Arg Trp Gln Gln Gly Asn Val Phe Ser Cys Ser Val
        290                 295                 300

Met His Glu Ala Leu His Asn His Tyr Thr Gln Lys Ser Leu Ser Leu
305                 310                 315                 320

Ser Pro Gly Ser Ala Trp Ser His Pro Gln Phe Glu Lys
            325                 330

<210> SEQ ID NO 5
<211> LENGTH: 121
<212> TYPE: PRT
<213> ORGANISM: Artificial Sequence
<220> FEATURE:
<223> OTHER INFORMATION: VH of the so-called "20G6-F3" anti-CD3 antibody

<400> SEQUENCE: 5

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Thr Lys Ala
            20                  25                  30

Trp Met His Trp Val Arg Gln Ser Pro Glu Lys Gln Leu Glu Trp Val
        35                  40                  45

Ala Gln Ile Lys Asp Lys Ser Asn Ser Tyr Ala Thr Tyr Tyr Ala Glu
    50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Lys Glu Glu Asp Thr Ala Ile Tyr
                85                  90                  95

Tyr Cys Arg Gly Val Tyr Tyr Ala Leu Ser Pro Phe Asp Tyr Trp Gly
            100                 105                 110

Gln Gly Val Met Val Thr Val Ser Ser
        115                 120

<210> SEQ ID NO 6
<211> LENGTH: 8
<212> TYPE: PRT
<213> ORGANISM: Artificial Sequence
<220> FEATURE:
<223> OTHER INFORMATION: CDR1-H of the so-called "20G6-F3" anti-
      CD3antibody

<400> SEQUENCE: 6

Gly Phe Thr Phe Thr Lys Ala Trp
1               5

<210> SEQ ID NO 7
<211> LENGTH: 10
<212> TYPE: PRT
<213> ORGANISM: Artificial Sequence
<220> FEATURE:
<223> OTHER INFORMATION: CDR2-H of the so-called "20G6-F3" anti-
      CD3antibody

<400> SEQUENCE: 7

Ile Lys Asp Lys Ser Asn Ser Tyr Ala Thr
1               5                   10

<210> SEQ ID NO 8
<211> LENGTH: 12
```

```
<212> TYPE: PRT
<213> ORGANISM: Artificial Sequence
<220> FEATURE:
<223> OTHER INFORMATION: CDR3-H of the so-called "20G6-F3" anti-
      CD3antibody

<400> SEQUENCE: 8

Arg Gly Val Tyr Tyr Ala Leu Ser Pro Phe Asp Tyr
1               5                   10

<210> SEQ ID NO 9
<211> LENGTH: 112
<212> TYPE: PRT
<213> ORGANISM: Artificial Sequence
<220> FEATURE:
<223> OTHER INFORMATION: VL of the so-called "20G6-F3" anti-CD3 antibody

<400> SEQUENCE: 9

Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asn
                20                  25                  30

Asn Gly Asn Thr Tyr Leu Ser Trp Tyr Leu Gln Lys Pro Gly Gln Ser
            35                  40                  45

Pro Gln Ser Leu Ile Tyr Lys Val Ser Asn Arg Phe Ser Gly Phe Ser
        50                  55                  60

Asp Arg Phe Ser Gly Ser Gly Ser Gly Thr Asp Phe Thr Leu Lys Ile
65                  70                  75                  80

Ser Arg Val Asp Pro Asp Asp Leu Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110

<210> SEQ ID NO 10
<211> LENGTH: 11
<212> TYPE: PRT
<213> ORGANISM: Artificial Sequence
<220> FEATURE:
<223> OTHER INFORMATION: CDR1-L of the so-called called "20G6-F3",
      "11D7-C3" , "13H2-C2" , "13C1-F6", "1E6-C9, "10F4-C10", "18G9-
      H11", "12G3-E8", "5B1-G2", "16F8-A7", "11F9-F8", "8C2-F7", "20E5-
      F10" and "3H6-D2" anti-CD3 antibodies

<400> SEQUENCE: 10

Gln Ser Leu Val His Asn Asn Gly Asn Thr Tyr
1               5                   10

<210> SEQ ID NO 11
<211> LENGTH: 9
<212> TYPE: PRT
<213> ORGANISM: Artificial Sequence
<220> FEATURE:
<223> OTHER INFORMATION: CDR3-L of the so-called "20G6-F3", "4B4-D7" ,
      "11H3-E5" , "13H2-C2", "13C1-F6", "10F4-C10", "4E7-C9", "11F3-
      B9", "12G3-E8", "5B1-G2", "6F4-D10", "16F8-A7", "20E5-F10" and
      "3H6-D2" anti-CD3 antibodies

<400> SEQUENCE: 11

Gly Gln Gly Thr Gln Tyr Pro Phe Thr
1               5

<210> SEQ ID NO 12
<211> LENGTH: 121
<212> TYPE: PRT
<213> ORGANISM: Artificial Sequence
```

```
<220> FEATURE:
<223> OTHER INFORMATION: VH of the so-called "4B4-D7" anti-CD3 antibody.

<400> SEQUENCE: 12

Glu Val Gln Leu Val Glu Thr Gly Gly Arg Leu Val Gln Pro Gly Arg
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Arg Ser Asn Asn Tyr Ala Thr Tyr Tyr Ala Glu
    50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Lys Glu Glu Asp Thr Ala Ile Tyr
                85                  90                  95

Tyr Cys Arg Gly Thr Tyr Tyr Ala Ser Lys Pro Phe Asp Tyr Trp Gly
            100                 105                 110

Gln Gly Val Met Val Thr Val Ser Ser
        115                 120

<210> SEQ ID NO 13
<211> LENGTH: 8
<212> TYPE: PRT
<213> ORGANISM: Artificial Sequence
<220> FEATURE:
<223> OTHER INFORMATION: CDR3-L of the so-called "20G6-F3", "4B4-D7",
      "11H3-E5" , "13H2-C2", "13C1-F6", "10F4-C10", "4E7-C9", "11F3-
      B9", "12G3-E8", "5B1-G2", "16F8-A7", "20E5-F10" and "3H6-D2" anti-
      CD3 antibodies.

<400> SEQUENCE: 13

Gly Phe Thr Phe Ser Asn Ala Trp
1               5

<210> SEQ ID NO 14
<211> LENGTH: 10
<212> TYPE: PRT
<213> ORGANISM: Artificial Sequence
<220> FEATURE:
<223> OTHER INFORMATION: CDR2-H of the so-called "4B4-D7" anti-CD3
      antibody

<400> SEQUENCE: 14

Ile Lys Ala Arg Ser Asn Asn Tyr Ala Thr
1               5                   10

<210> SEQ ID NO 15
<211> LENGTH: 12
<212> TYPE: PRT
<213> ORGANISM: Artificial Sequence
<220> FEATURE:
<223> OTHER INFORMATION: CDR3-H of the so-called "4B4-D7" anti-CD3
      antibody.

<400> SEQUENCE: 15

Arg Gly Thr Tyr Tyr Ala Ser Lys Pro Phe Asp Tyr
1               5                   10

<210> SEQ ID NO 16
<211> LENGTH: 112
<212> TYPE: PRT
<213> ORGANISM: Artificial Sequence
<220> FEATURE:
```

-continued

<223> OTHER INFORMATION: VL of the so-called "4B4-D7" anti-CD3 antibody

<400> SEQUENCE: 16

Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asp
            20                  25                  30

Asn Gly Asn Thr Tyr Leu Ser Trp Ser Leu Gln Arg Pro Gly Gln Ser
        35                  40                  45

Pro Gln Val Leu Ile Tyr Lys Val Ser Asn Arg Phe Ser Gly Thr Ser
    50                  55                  60

Asp Arg Phe Thr Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110

<210> SEQ ID NO 17
<211> LENGTH: 11
<212> TYPE: PRT
<213> ORGANISM: Artificial Sequence
<220> FEATURE:
<223> OTHER INFORMATION: CDR1-L of the so-called "4B4-D7", "11H3-E5" and
      "11F3-B9" anti-CD3 antibodies.

<400> SEQUENCE: 17

Gln Ser Leu Val His Asp Asn Gly Asn Thr Tyr
1               5                   10

<210> SEQ ID NO 18
<211> LENGTH: 122
<212> TYPE: PRT
<213> ORGANISM: Artificial Sequence
<220> FEATURE:
<223> OTHER INFORMATION: VH of the so-called "4E7-C9" anti-CD3 antibody

<400> SEQUENCE: 18

Glu Val Gln Val Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Asp Lys Ser Asn Asn Tyr Ala Thr Tyr Tyr Ala Glu
    50                  55                  60

Ser Leu Lys Gly Arg Phe Thr Ile Ser Arg Asp Asp Pro Lys Arg Ser
65                  70                  75                  80

Ile Tyr Leu Gln Met Asn Ser Leu Arg Glu Glu Asp Thr Ala Ile Tyr
                85                  90                  95

Tyr Cys Arg Tyr Val His Tyr Gly Ile Gly Tyr Ala Met Asp Ala Trp
            100                 105                 110

Gly Gln Gly Thr Ser Val Thr Val Ser Ser
        115                 120

<210> SEQ ID NO 19
<211> LENGTH: 10
<212> TYPE: PRT
<213> ORGANISM: Artificial Sequence
<220> FEATURE:

<223> OTHER INFORMATION: CDR2-H of the so-called "4E7-C9", "18F5-H10",
      "20E5-F10" and "3H6-D2" anti-CD3 antibodies

<400> SEQUENCE: 19

Ile Lys Asp Lys Ser Asn Asn Tyr Ala Thr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: CDR3-H of the so-called "4E7-C9" anti-CD3
      antibody

<400> SEQUENCE: 20

Arg Tyr Val His Tyr Gly Ile Gly Tyr Ala Met Asp Ala
1               5                   10

<210> SEQ ID NO 21
<211> LENGTH: 112
<212> TYPE: PRT
<213> ORGANISM: Artificial Sequence
<220> FEATURE:
<223> OTHER INFORMATION: VL of the so-called "4E7-C9" anti-CD3 antibody

<400> SEQUENCE: 21

Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Glu His Asn
            20                  25                  30

Asn Gly Asn Thr Tyr Leu Ser Trp Tyr Leu Gln Lys Pro Gly Gln Ser
        35                  40                  45

Pro Gln Pro Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Tyr Pro Phe Thr Phe Gly Pro Gly Thr Lys Leu Glu Leu Lys
            100                 105                 110

<210> SEQ ID NO 22
<211> LENGTH: 11
<212> TYPE: PRT
<213> ORGANISM: Artificial Sequence
<220> FEATURE:
<223> OTHER INFORMATION: CDR1-H of the so-called "4E7-C9" anti-CD3
      antibody

<400> SEQUENCE: 22

Gln Ser Leu Glu His Asn Asn Gly Asn Thr Tyr
1               5                   10

<210> SEQ ID NO 23
<211> LENGTH: 122
<212> TYPE: PRT
<213> ORGANISM: Artificial Sequence
<220> FEATURE:
<223> OTHER INFORMATION: VH of the so-called "18F5-H10" anti-CD3
      antibody

<400> SEQUENCE: 23

Glu Val Gln Val Val Glu Thr Gly Gly Ser Leu Val Gln Pro Gly Lys

```
1               5                   10                  15
Ser Leu Lys Leu Thr Cys Ala Thr Ser Gly Phe Thr Phe Thr Asn Ala
            20                  25                  30

Trp Met His Trp Val Arg Arg Ser Pro Glu Lys Gln Leu Glu Trp Val
            35                  40                  45

Ala Gln Ile Lys Asp Lys Ser Asn Asn Tyr Ala Thr Tyr Tyr Ala Glu
        50                  55                  60

Ser Val Lys Gly Arg Phe Thr Ile Ser Arg Asp Asp Ser Lys Ser Ser
65                  70                  75                  80

Ile Tyr Leu Gln Met Asn Ser Leu Lys Glu Glu Asp Thr Ala Ile Tyr
                85                  90                  95

Tyr Cys Arg Tyr Val His Tyr Arg Phe Ala Tyr Ala Leu Asp Ala Trp
                100                 105                 110

Gly Arg Gly Thr Ser Val Ser Val Ser Ser
            115                 120
```

<210> SEQ ID NO 24
<211> LENGTH: 8
<212> TYPE: PRT
<213> ORGANISM: Artificial Sequence
<220> FEATURE:
<223> OTHER INFORMATION: CDR1-H of the so-called "18F5-H10" anti-CD3
      antibody

<400> SEQUENCE: 24

```
Gly Phe Thr Phe Thr Asn Ala Trp
1               5
```

<210> SEQ ID NO 25
<211> LENGTH: 13
<212> TYPE: PRT
<213> ORGANISM: Artificial Sequence
<220> FEATURE:
<223> OTHER INFORMATION: CDR3-H of the so-called "18F5-H10" anti-CD3
      antibody

<400> SEQUENCE: 25

```
Arg Tyr Val His Tyr Arg Phe Ala Tyr Ala Leu Asp Ala
1               5                   10
```

<210> SEQ ID NO 26
<211> LENGTH: 112
<212> TYPE: PRT
<213> ORGANISM: Artificial Sequence
<220> FEATURE:
<223> OTHER INFORMATION: VL of the so-called "18F5-H10" anti-CD3
      antibody

<400> SEQUENCE: 26

```
Asp Val Leu Met Thr Gln Thr Pro Val Ser Leu Ser Val Ser Leu Gly
1               5                   10                  15

Gly Gln Val Ser Ile Ser Cys Arg Ser Ser Gln Ser Leu Val His Thr
            20                  25                  30

Asn Gly Asn Thr Tyr Leu Ser Trp Tyr Leu Gln Lys Pro Gly Gln Ser
            35                  40                  45

Pro Gln Leu Leu Ile Tyr Lys Val Ser Asn Arg Leu Ser Gly Ile Ser
        50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95
```

Thr His Tyr Pro Phe Thr Phe Gly Ala Gly Thr Lys Leu Glu Leu Lys
            100                 105                 110

<210> SEQ ID NO 27
<211> LENGTH: 11
<212> TYPE: PRT
<213> ORGANISM: Artificial Sequence
<220> FEATURE:
<223> OTHER INFORMATION: CDR1-L of the so-called "18F5-H10" anti-CD3
      antibody

<400> SEQUENCE: 27

Gln Ser Leu Val His Thr Asn Gly Asn Thr Tyr
1               5                   10

<210> SEQ ID NO 28
<211> LENGTH: 9
<212> TYPE: PRT
<213> ORGANISM: Artificial Sequence
<220> FEATURE:
<223> OTHER INFORMATION: CDR3-L of the so-called "18F5-H10", "11D7-C3",
      "1E6-C9" and "10E6-G6" anti-CD3 antibodies

<400> SEQUENCE: 28

Gly Gln Gly Thr His Tyr Pro Phe Thr
1               5

<210> SEQ ID NO 29
<211> LENGTH: 118
<212> TYPE: PRT
<213> ORGANISM: Artificial Sequence
<220> FEATURE:
<223> OTHER INFORMATION: VH of the so-called "12D2-E5" anti-CD3 antibody

<400> SEQUENCE: 29

Glu Val Lys Leu Val Glu Ser Gly Gly Gly Leu Val Gln Pro Gly Arg
1               5                   10                  15

Ser Leu Arg Leu Ser Cys Ala Ala Ser Gly Phe Asn Phe Tyr Ala Tyr
            20                  25                  30

Trp Met Gly Trp Val Arg Gln Ala Pro Gly Lys Gly Leu Glu Trp Ile
        35                  40                  45

Gly Glu Ile Lys Lys Asp Gly Thr Thr Ile Asn Tyr Thr Pro Ser Leu
    50                  55                  60

Lys Asp Arg Phe Thr Ile Ser Arg Asp Asn Ala Gln Asn Thr Leu Tyr
65                  70                  75                  80

Leu Gln Met Thr Lys Leu Gly Ser Glu Asp Thr Ala Leu Tyr Tyr Cys
                85                  90                  95

Ala Arg Glu Glu Arg Asp Gly Tyr Phe Asp Tyr Trp Gly Gln Gly Val
            100                 105                 110

Met Val Thr Val Ser Ser
        115

<210> SEQ ID NO 30
<211> LENGTH: 8
<212> TYPE: PRT
<213> ORGANISM: Artificial Sequence
<220> FEATURE:
<223> OTHER INFORMATION: CDR1-H of the so-called "12D2-E5" anti-CD3
      antibody

<400> SEQUENCE: 30

Gly Phe Asn Phe Tyr Ala Tyr Trp
1               5

<210> SEQ ID NO 31
<211> LENGTH: 8
<212> TYPE: PRT
<213> ORGANISM: Artificial Sequence
<220> FEATURE:
<223> OTHER INFORMATION: CDR2-H of the so-called "12D2-E5" anti-CD3
      antibody

<400> SEQUENCE: 31

Ile Lys Lys Asp Gly Thr Thr Ile
1               5

<210> SEQ ID NO 32
<211> LENGTH: 11
<212> TYPE: PRT
<213> ORGANISM: Artificial Sequence
<220> FEATURE:
<223> OTHER INFORMATION: CDR3-H of the so-called "12D2-E5" and "3G5-E10"
      anti-CD3 antibody

<400> SEQUENCE: 32

Ala Arg Glu Glu Arg Asp Gly Tyr Phe Asp Tyr
1               5                   10

<210> SEQ ID NO 33
<211> LENGTH: 109
<212> TYPE: PRT
<213> ORGANISM: Artificial Sequence
<220> FEATURE:
<223> OTHER INFORMATION: VL of the so-called "12D2-E5" anti-CD3
      antibody.

<400> SEQUENCE: 33

Gln Phe Val Leu Thr Gln Pro Asn Ser Val Ser Thr Asn Leu Gly Ser
1               5                   10                  15

Thr Val Lys Leu Ser Cys Lys Arg Ser Thr Gly Asn Ile Gly Ser Asn
            20                  25                  30

Tyr Val Asn Trp Tyr Gln Gln His Glu Gly Arg Ser Pro Thr Thr Met
        35                  40                  45

Ile Tyr Arg Asp Asp Lys Arg Pro Asp Gly Val Pro Asp Arg Phe Ser
    50                  55                  60

Gly Ser Ile Asp Arg Ser Ser Asn Ser Ala Leu Leu Thr Ile Asn Asn
65                  70                  75                  80

Val Gln Thr Glu Asp Glu Ala Asp Tyr Phe Cys Gln Ser Tyr Ser Ser
                85                  90                  95

Gly Ile Val Phe Gly Gly Gly Thr Lys Leu Thr Val Leu
            100                 105

<210> SEQ ID NO 34
<211> LENGTH: 8
<212> TYPE: PRT
<213> ORGANISM: Artificial Sequence
<220> FEATURE:
<223> OTHER INFORMATION: CDR1-H of the so-called "12D2-E5" anti-CD3
      antibody

<400> SEQUENCE: 34

Thr Gly Asn Ile Gly Ser Asn Tyr
1               5

<210> SEQ ID NO 35
<211> LENGTH: 8
<212> TYPE: PRT

<213> ORGANISM: Artificial Sequence
<220> FEATURE:
<223> OTHER INFORMATION: CDR3-H of the so-called "12D2-E5" anti-CD3 antibody

<400> SEQUENCE: 35

Gln Ser Tyr Ser Ser Gly Ile Val
1               5

<210> SEQ ID NO 36
<211> LENGTH: 121
<212> TYPE: PRT
<213> ORGANISM: Artificial Sequence
<220> FEATURE:
<223> OTHER INFORMATION: VH of the so-called "11D7-C3" anti-CD3 antibody

<400> SEQUENCE: 36

Glu Val Gln Phe Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Lys Glu Glu Asp Thr Ala Thr Tyr
                85                  90                  95

Tyr Cys Arg Gly Leu Tyr Tyr Gly Leu Ser Pro Ser Asp Tyr Trp Gly
            100                 105                 110

Gln Gly Val Met Val Thr Val Ser Ser
        115                 120

<210> SEQ ID NO 37
<211> LENGTH: 10
<212> TYPE: PRT
<213> ORGANISM: Artificial Sequence
<220> FEATURE:
<223> OTHER INFORMATION: CDR2-H of the so-called "11D7-C3", "11H3-E5",
      "13H2-C2", "13C1-F6", "1E6-C9", "10F4-C10", "18G9-H11", "11F3-B9",
      "6F4-D10", "16F8-A7", "11F9-F8" and "20B5-F10" anti-CD3
      antibodies

<400> SEQUENCE: 37

Ile Lys Ala Lys Ser Asn Asn Tyr Ala Thr
1               5                   10

<210> SEQ ID NO 38
<211> LENGTH: 12
<212> TYPE: PRT
<213> ORGANISM: Artificial Sequence
<220> FEATURE:
<223> OTHER INFORMATION: CDR3-H of the so-called "11D7-C3" anti-CD3 antibody

<400> SEQUENCE: 38

Arg Gly Leu Tyr Tyr Gly Leu Ser Pro Ser Asp Tyr
1               5                   10

<210> SEQ ID NO 39
<211> LENGTH: 112
<212> TYPE: PRT
<213> ORGANISM: Artificial Sequence

```
<220> FEATURE:
<223> OTHER INFORMATION: VL of the so-called "11D7-C3" anti-CD3
      antibody.

<400> SEQUENCE: 39

Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Leu Ser Trp Tyr Leu Gln Lys Pro Gly Gln Ser
        35                  40                  45

Pro Gln Leu Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr His Tyr Pro Phe Thr Phe Gly Ser Gly Thr Lys Leu Glu Ile Lys
            100                 105                 110

<210> SEQ ID NO 40
<211> LENGTH: 121
<212> TYPE: PRT
<213> ORGANISM: Artificial Sequence
<220> FEATURE:
<223> OTHER INFORMATION: VH of the so-called "11H3-E5" anti-CD3 antibody

<400> SEQUENCE: 40

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Lys Glu Glu Asp Thr Ala Ile Tyr
                85                  90                  95

Tyr Cys Arg Gly Thr Tyr Tyr Ala Tyr Lys Pro Phe Asp Tyr Trp Gly
            100                 105                 110

Gln Gly Val Met Val Thr Val Ser Ser
            115                 120

<210> SEQ ID NO 41
<211> LENGTH: 12
<212> TYPE: PRT
<213> ORGANISM: Artificial Sequence
<220> FEATURE:
<223> OTHER INFORMATION: CDR3-H of the so-called called "11H3-E5" anti-
      CD3 antibody

<400> SEQUENCE: 41

Arg Gly Thr Tyr Tyr Ala Tyr Lys Pro Phe Asp Tyr
1               5                   10

<210> SEQ ID NO 42
<211> LENGTH: 112
<212> TYPE: PRT
```

<213> ORGANISM: Artificial Sequence
<220> FEATURE:
<223> OTHER INFORMATION: VL of the so-called "11H3-E5" anti-CD3 antibody

<400> SEQUENCE: 42

Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asp
            20                  25                  30

Asn Gly Asn Thr Tyr Leu Ser Trp Ser Leu Gln Lys Pro Gly Gln Ser
        35                  40                  45

Pro Gln Val Leu Ile Tyr Lys Val Ser Asn Arg Phe Ser Gly Thr Ser
50                  55                  60

Asp Arg Phe Thr Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110

<210> SEQ ID NO 43
<211> LENGTH: 121
<212> TYPE: PRT
<213> ORGANISM: Artificial Sequence
<220> FEATURE:
<223> OTHER INFORMATION: VH of the so-called "13H2-C2" anti-CD3
      antibody.

<400> SEQUENCE: 43

Glu Glu Glu Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Asp Lys Gln Leu Glu Trp Val
        35                  40                  45

Ala Gln Ile Lys Ala Lys Ser Asn Asn Tyr Ala Thr Tyr Tyr Ala Glu
50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Lys Glu Glu Asp Thr Ala Ile Tyr
                85                  90                  95

Tyr Cys Arg Tyr Val His Tyr Gly Leu Ala Pro Met Asp Ala Trp Gly
            100                 105                 110

Gln Gly Thr Ser Val Thr Val Ser Ser
        115                 120

<210> SEQ ID NO 44
<211> LENGTH: 12
<212> TYPE: PRT
<213> ORGANISM: Artificial Sequence
<220> FEATURE:
<223> OTHER INFORMATION: CDR3-H of the so-called "13H2-C2" anti-CD3
      antibody

<400> SEQUENCE: 44

Arg Tyr Val His Tyr Gly Leu Ala Pro Met Asp Ala
1               5                   10

<210> SEQ ID NO 45
<211> LENGTH: 112

```
<212> TYPE: PRT
<213> ORGANISM: Artificial Sequence
<220> FEATURE:
<223> OTHER INFORMATION: VL of the so-called "13H2-C2" anti-CD3 antibody

<400> SEQUENCE: 45

Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Leu Ser Trp Tyr Leu Gln Lys Ala Gly Gln Ser
        35                  40                  45

Pro Gln Leu Leu Ile Tyr Lys Val Ser Asn Arg Phe Ser Gly Ile Ser
    50                  55                  60

Asp Arg Phe Ser Gly Ser Gly Ser Gly Thr Asp Phe Ile Leu Lys Ile
65                  70                  75                  80

Ser Arg Val Glu Pro Asp Asp Leu Gly Val Phe Tyr Cys Gly Gln Gly
                85                  90                  95

Thr Gln Tyr Pro Phe Thr Phe Gly Ala Gly Thr Lys Leu Glu Leu Lys
            100                 105                 110

<210> SEQ ID NO 46
<211> LENGTH: 121
<212> TYPE: PRT
<213> ORGANISM: Artificial Sequence
<220> FEATURE:
<223> OTHER INFORMATION: VH of the so-called "13C1-F6" and "11F9-F8"
      anti-CD3 antibodies

<400> SEQUENCE: 46

Glu Val Gln Leu Val Glu Thr Gly Gly Thr Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Thr Ser
65                  70                  75                  80

Val Tyr Leu Gln Leu Asn Ser Leu Arg Glu Glu Asp Thr Ala Ile Tyr
                85                  90                  95

Tyr Cys Arg Gly Thr Gln Tyr Gly Tyr Asn Pro Phe Asp Tyr Trp Gly
            100                 105                 110

Gln Gly Val Met Val Thr Val Ser Ser
        115                 120

<210> SEQ ID NO 47
<211> LENGTH: 12
<212> TYPE: PRT
<213> ORGANISM: Artificial Sequence
<220> FEATURE:
<223> OTHER INFORMATION: CDR3-H of so-called "13C1-F6", "10E6-G6" and
      "11F9-F8" anti-CD3 antibodies

<400> SEQUENCE: 47

Arg Gly Thr Gln Tyr Gly Tyr Asn Pro Phe Asp Tyr
1               5                   10

<210> SEQ ID NO 48
```

```
<211> LENGTH: 112
<212> TYPE: PRT
<213> ORGANISM: Artificial Sequence
<220> FEATURE:
<223> OTHER INFORMATION: VL of the so-called "13H2-C2" anti-CD3 antibody

<400> SEQUENCE: 48

Asp Val Val Met Thr Gln Ser Pro Val Ser Leu Ser Val Ser Leu Gly
1               5                   10                  15

Gly Gln Val Ser Ile Ser Cys Arg Ser Ser Gln Ser Leu Val His Asn
                20                  25                  30

Asn Gly Asn Thr Tyr Leu Ser Trp Tyr Leu Gln Arg Ser Gly Gln Ser
            35                  40                  45

Pro Gln Leu Leu Ile Tyr Lys Val Ser Asn Arg Leu Ser Gly Ile Ser
        50                  55                  60

Asp Arg Phe Ser Gly Ser Gly Ser Gly Thr Asp Phe Thr Leu Lys Ile
65                  70                  75                  80

Ser Arg Ile Glu Pro Asp Asp Leu Gly Val Tyr Tyr Cys Gly Gln Gly
                85                  90                  95

Thr Gln Tyr Pro Phe Thr Phe Gly Ser Gly Thr Arg Leu Glu Ile Lys
            100                 105                 110

<210> SEQ ID NO 49
<211> LENGTH: 118
<212> TYPE: PRT
<213> ORGANISM: Artificial Sequence
<220> FEATURE:
<223> OTHER INFORMATION: VH of the so-called "18H11-F10" anti-CD3
      antibody

<400> SEQUENCE: 49

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Ile Phe Ser Asp Tyr
                20                  25                  30

Tyr Met Ala Trp Val Arg Gln Ala Pro Lys Lys Gly Leu Glu Trp Val
            35                  40                  45

Ala Thr Ile Ser Ile Ser Gly Ser Arg Thr Tyr Tyr Pro Asp Ser Val
        50                  55                  60

Lys Gly Arg Phe Thr Val Ser Arg Asp Asn Ala Lys Ser Ser Leu Tyr
65                  70                  75                  80

Leu Gln Met Asn Ser Leu Lys Ser Glu Asp Thr Ala Thr Tyr Tyr Cys
                85                  90                  95

Ala Thr Asn Asn Pro Gly Gly Trp Phe Val Tyr Trp Gly Gln Gly Thr
            100                 105                 110

Leu Val Thr Val Ser Ser
        115

<210> SEQ ID NO 50
<211> LENGTH: 8
<212> TYPE: PRT
<213> ORGANISM: Artificial Sequence
<220> FEATURE:
<223> OTHER INFORMATION: CDR1-H of the so-called "18H11-F10" anti-CD3
      antibody

<400> SEQUENCE: 50

Gly Phe Ile Phe Ser Asp Tyr Tyr
1               5
```

```
<210> SEQ ID NO 51
<211> LENGTH: 8
<212> TYPE: PRT
<213> ORGANISM: Artificial Sequence
<220> FEATURE:
<223> OTHER INFORMATION: CDR2-H of the so-called "18H11-F10" anti-CD3
      antibody

<400> SEQUENCE: 51

Ile Ser Ile Ser Gly Ser Arg Thr
1               5

<210> SEQ ID NO 52
<211> LENGTH: 11
<212> TYPE: PRT
<213> ORGANISM: Artificial Sequence
<220> FEATURE:
<223> OTHER INFORMATION: CDR3-H of the so-called "18H11-F10" anti-CD3
      antibody

<400> SEQUENCE: 52

Ala Thr Asn Asn Pro Gly Gly Trp Phe Val Tyr
1               5                   10

<210> SEQ ID NO 53
<211> LENGTH: 106
<212> TYPE: PRT
<213> ORGANISM: Artificial Sequence
<220> FEATURE:
<223> OTHER INFORMATION: VL of the so-called "18H11-F10" anti-CD3
      antibody

<400> SEQUENCE: 53

Asn Ile Gln Met Thr Gln Ser Pro Ser Leu Leu Ser Ala Ser Val Gly
1               5                   10                  15

Asp Arg Val Thr Leu Ser Cys Lys Ala Gly Gln Asn Ile Asn Asn Asp
            20                  25                  30

Leu Ala Trp Tyr Gln Gln Lys Leu Gly Glu Ala Pro Arg Leu Leu Ile
        35                  40                  45

Tyr Asn Ala Asn Ser Leu Gln Thr Gly Ile Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Val Ala Thr Tyr Phe Cys Gln Gln Tyr Ser Ser Gly Asp Thr
                85                  90                  95

Phe Gly Ala Gly Thr Lys Leu Glu Leu Lys
            100                 105

<210> SEQ ID NO 54
<211> LENGTH: 6
<212> TYPE: PRT
<213> ORGANISM: Artificial Sequence
<220> FEATURE:
<223> OTHER INFORMATION: CDR1-L of the so-called "18H11-F10" anti-CD3
      antibody

<400> SEQUENCE: 54

Gln Asn Ile Asn Asn Asp
1               5

<210> SEQ ID NO 55
<211> LENGTH: 8
<212> TYPE: PRT
<213> ORGANISM: Artificial Sequence
<220> FEATURE:
```

<223> OTHER INFORMATION: CDR3-L of the so-called "18H11-F10" anti-CD3
    antibody

<400> SEQUENCE: 55

Gln Gln Tyr Ser Ser Gly Asp Thr
1               5

<210> SEQ ID NO 56
<211> LENGTH: 121
<212> TYPE: PRT
<213> ORGANISM: Artificial Sequence
<220> FEATURE:
<223> OTHER INFORMATION: VH of the so-called "1E6-C9" anti-CD3 antibody

<400> SEQUENCE: 56

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Tyr Ala
            20                  25                  30

Trp Met His Trp Val Arg Gln Ser Pro Asp Lys Gln Leu Gln Trp Val
        35                  40                  45

Ala Gln Ile Lys Ala Lys Ser Asn Asn Tyr Ala Thr Tyr Tyr Ala Glu
    50                  55                  60

Ser Val Glu Gly Arg Phe Thr Ile Ser Arg Asp Asp Ser Lys Ser Ser
65                  70                  75                  80

Val Tyr Leu Gln Met Asn Ser Leu Lys Glu Glu Asp Thr Ala Ile Tyr
                85                  90                  95

Tyr Cys Arg Gly Val Tyr Tyr Gly Leu Leu Gly Leu Asp Ala Trp Gly
            100                 105                 110

Gln Gly Thr Ser Val Thr Val Ser Ser
        115                 120

<210> SEQ ID NO 57
<211> LENGTH: 8
<212> TYPE: PRT
<213> ORGANISM: Artificial Sequence
<220> FEATURE:
<223> OTHER INFORMATION: CDR1-H of the so-called "1E6-C9" anti-CD3
    antibody

<400> SEQUENCE: 57

Gly Phe Thr Phe Ser Tyr Ala Trp
1               5

<210> SEQ ID NO 58
<211> LENGTH: 12
<212> TYPE: PRT
<213> ORGANISM: Artificial Sequence
<220> FEATURE:
<223> OTHER INFORMATION: CDR3-H of the so-called "1E6-C9" anti-CD3
    antibody

<400> SEQUENCE: 58

Arg Gly Val Tyr Tyr Gly Leu Leu Gly Leu Asp Ala
1               5                   10

<210> SEQ ID NO 59
<211> LENGTH: 112
<212> TYPE: PRT
<213> ORGANISM: Artificial Sequence
<220> FEATURE:
<223> OTHER INFORMATION: VL of the so-called "1E6-C9" anti-CD3 antibody

<400> SEQUENCE: 59

```
Asp Val Val Met Thr Gln Thr Pro Val Ser Leu Ser Val Arg Leu Gly
1               5                   10                  15

Gly Gln Val Ser Ile Ser Cys Arg Ser Ser Gln Ser Leu Val His Asn
            20                  25                  30

Asn Gly Asn Thr Tyr Leu Ser Trp Phe Leu Gln Lys Pro Gly Gln Ser
            35                  40                  45

Pro Gln Leu Leu Ile Tyr Lys Val Ser Asn Arg Phe Ser Gly Ile Ser
        50                  55                  60

Asp Arg Phe Ser Gly Ser Ala Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr His Tyr Pro Phe Thr Phe Gly Ser Gly Thr Lys Leu Glu Ile Lys
                100                 105                 110
```

<210> SEQ ID NO 60
<211> LENGTH: 121
<212> TYPE: PRT
<213> ORGANISM: Artificial Sequence
<220> FEATURE:
<223> OTHER INFORMATION: VH of the so-called "10F4-C10" anti-CD3
      antibody

<400> SEQUENCE: 60

```
Glu Val Gln Leu Val Glu Thr Gly Gly Ser Leu Val Gln Pro Gly Lys
1               5                   10                  15

Ser Leu Lys Ile Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
            35                  40                  45

Ala Gln Ile Lys Ala Lys Ser Asn Asn Tyr Ala Thr Tyr Tyr Ala Glu
        50                  55                  60

Ser Val Lys Gly Arg Phe Thr Ile Ser Arg Asp Asp Ser Lys Ser Ser
65                  70                  75                  80

Ile Tyr Leu Gln Met Asn Ser Leu Lys Glu Glu Asp Thr Ala Ile Tyr
                85                  90                  95

Tyr Cys Arg Ala Val Asn Tyr Gly Asn Tyr Pro Leu Asp Tyr Trp Gly
                100                 105                 110

Gln Gly Val Met Val Thr Val Ser Ser
            115                 120
```

<210> SEQ ID NO 61
<211> LENGTH: 12
<212> TYPE: PRT
<213> ORGANISM: Artificial Sequence
<220> FEATURE:
<223> OTHER INFORMATION: CDR3-H of the so-called "10F4-C10" anti-CD3
      antibody

<400> SEQUENCE: 61

```
Arg Ala Val Asn Tyr Gly Asn Tyr Pro Leu Asp Tyr
1               5                   10
```

<210> SEQ ID NO 62
<211> LENGTH: 112
<212> TYPE: PRT
<213> ORGANISM: Artificial Sequence
<220> FEATURE:
<223> OTHER INFORMATION: VL of the so-called "10F4-C10" anti-CD3
      antibody

<400> SEQUENCE: 62

Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Leu Ser Trp Cys Leu Gln Lys Pro Gly Gln Ser
        35                  40                  45

Pro Gln Leu Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gln Gln Gly
                85                  90                  95

Thr Gln Tyr Pro Phe Thr Phe Gly Ala Gly Thr Lys Leu Glu Leu Lys
            100                 105                 110

<210> SEQ ID NO 63
<211> LENGTH: 121
<212> TYPE: PRT
<213> ORGANISM: Artificial Sequence
<220> FEATURE:
<223> OTHER INFORMATION: VH of the so-called "10E6-G6" anti-CD3 antibody

<400> SEQUENCE: 63

Glu Val Gln Leu Val Glu Thr Gly Gly Gly Leu Val Gln Ser Gly Lys
1               5                   10                  15

Ser Leu Lys Leu Thr Cys Ala Thr Ser Gly Phe Thr Val Thr Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Glu Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Lys Glu Glu Asp Thr Ala Ile Tyr
                85                  90                  95

Tyr Cys Arg Gly Thr Gln Tyr Gly Tyr Asn Pro Phe Asp Tyr Trp Gly
            100                 105                 110

Gln Gly Val Met Val Thr Val Ser Ser
        115                 120

<210> SEQ ID NO 64
<211> LENGTH: 8
<212> TYPE: PRT
<213> ORGANISM: Artificial Sequence
<220> FEATURE:
<223> OTHER INFORMATION: CDR1-H of the so-called "10E6-G6" anti-CD3
      antibody

<400> SEQUENCE: 64

Gly Phe Thr Val Thr Asn Ala Trp
1               5

<210> SEQ ID NO 65
<211> LENGTH: 10
<212> TYPE: PRT
<213> ORGANISM: Artificial Sequence
<220> FEATURE:
<223> OTHER INFORMATION: CDR3-H of the so-called "10E6-G6" anti-CD3 antibody

<400> SEQUENCE: 65

Ile Lys Ala Lys Ser Asn Asn Tyr Glu Thr
1               5                   10

<210> SEQ ID NO 66
<211> LENGTH: 112
<212> TYPE: PRT
<213> ORGANISM: Artificial Sequence
<220> FEATURE:
<223> OTHER INFORMATION: VL of the so-called "10E6-G6" anti-CD3 antibody

<400> SEQUENCE: 66

Asp Val Val Met Thr Gln Ser Pro Val Ser Leu Ser Val Ser Leu Gly
1               5                   10                  15

Gly Gln Val Ser Ile Ser Cys Arg Ser Ser Gln Ser Leu Val His Asn
            20                  25                  30

Asn Gly Tyr Thr Tyr Leu Ser Trp Tyr Leu Gln Lys Pro Gly Gln Ser
        35                  40                  45

Pro Gln Val Phe Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Ile Glu Pro Asp Asp Leu Gly Val Tyr Tyr Cys Gly Gln Gly
                85                  90                  95

Thr His Tyr Pro Phe Thr Phe Gly Ser Gly Thr Lys Leu Glu Ile Lys
            100                 105                 110

<210> SEQ ID NO 67
<211> LENGTH: 11
<212> TYPE: PRT
<213> ORGANISM: Artificial Sequence
<220> FEATURE:
<223> OTHER INFORMATION: CDR1-L of the so-called "10E6-G6" anti-CD3
      antibody

<400> SEQUENCE: 67

Gln Ser Leu Val His Asn Asn Gly Tyr Thr Tyr
1               5                   10

<210> SEQ ID NO 68
<211> LENGTH: 122
<212> TYPE: PRT
<213> ORGANISM: Artificial Sequence
<220> FEATURE:
<223> OTHER INFORMATION: VH of the so-called "18G9-H11" anti-CD3
      antibody

<400> SEQUENCE: 68

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Ile Gln Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Lys Glu Glu Asp Thr Ala Leu Tyr

-continued

```
                    85                  90                  95
Tyr Cys Thr Trp Arg His Tyr Tyr Ser Ser His Thr Met Asp Ala Trp
                100                 105                 110

Gly Gln Gly Thr Leu Val Thr Val Ser Ser
        115                 120

<210> SEQ ID NO 69
<211> LENGTH: 13
<212> TYPE: PRT
<213> ORGANISM: Artificial Sequence
<220> FEATURE:
<223> OTHER INFORMATION: CDR3-H of the so-called "18G9-H11" anti-CD3
      antibody

<400> SEQUENCE: 69

Thr Trp Arg His Tyr Tyr Ser Ser His Thr Met Asp Ala
1               5                   10

<210> SEQ ID NO 70
<211> LENGTH: 112
<212> TYPE: PRT
<213> ORGANISM: Artificial Sequence
<220> FEATURE:
<223> OTHER INFORMATION: VL of the so-called "18G9-H11" anti-CD3
      antibody

<400> SEQUENCE: 70

Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Leu Ser Trp Tyr Leu Gln Lys Pro Gly Gln Ser
        35                  40                  45

Pro Gln Leu Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Ala Pro Thr Asp Leu Gly Val Tyr Tyr Cys Gly Gln Gly
                85                  90                  95

Ser Gln Tyr Pro Phe Thr Phe Gly Ala Gly Thr Lys Leu Glu Leu Lys
            100                 105                 110

<210> SEQ ID NO 71
<211> LENGTH: 9
<212> TYPE: PRT
<213> ORGANISM: Artificial Sequence
<220> FEATURE:
<223> OTHER INFORMATION: CDR3-L of the so-called "18G9-H11" anti-CD3
      antibody

<400> SEQUENCE: 71

Gly Gln Gly Ser Gln Tyr Pro Phe Thr
1               5

<210> SEQ ID NO 72
<211> LENGTH: 121
<212> TYPE: PRT
<213> ORGANISM: Artificial Sequence
<220> FEATURE:
<223> OTHER INFORMATION: VH of the so-called "11F3-B9" anti-CD3 antibody

<400> SEQUENCE: 72

Glu Val Gln Leu Val Glu Thr Gly Gly Ser Leu Val Gln Pro Gly Lys
```

```
                1               5                   10                  15
            Ser Leu Thr Leu Thr Cys Ala Thr Ser Gly Phe Thr Phe Ser Asn Ala
                            20                  25                  30

Trp Met His Trp Val Arg Gln Ser Pro Glu Lys Gln Leu Glu Trp Val
                            35                  40                  45

Ala Gln Ile Lys Ala Lys Ser Asn Asn Tyr Ala Thr Tyr Tyr Ala Glu
                            50                  55                  60

Ser Val Lys Gly Arg Phe Thr Ile Ser Arg Asp Asp Ser Lys Arg Ser
            65                  70                  75                  80

Val Tyr Leu Gln Met Asn Ser Leu Lys Glu Glu Asp Thr Ala Ile Tyr
                            85                  90                  95

Tyr Cys Arg Tyr Val Asn Tyr Gly Leu Ala Pro Met Asp Val Trp Gly
                            100                 105                 110

Gln Gly Thr Ser Val Thr Val Ser Ser
                            115                 120
```

<210> SEQ ID NO 73
<211> LENGTH: 112
<212> TYPE: PRT
<213> ORGANISM: Artificial Sequence
<220> FEATURE:
<223> OTHER INFORMATION: VL of the so-called "11F3-B9" anti-CD3 antibody

<400> SEQUENCE: 73

```
            Asp Val Val Met Thr Gln Thr Pro Val Ser Leu Ser Val Ser Leu Gly
            1               5                   10                  15

Gly Gln Val Ser Ile Ser Cys Arg Ser Ser Gln Ser Leu Val His Asp
                            20                  25                  30

Asn Gly Asn Thr Tyr Leu Ser Trp Tyr Leu Gln Lys Pro Gly Gln Ser
                            35                  40                  45

Pro Gln Leu Leu Ile Tyr Lys Val Ser Asn Arg Phe Ser Gly Phe Ser
                            50                  55                  60

Asp Arg Phe Ser Gly Ser Gly Ser Gly Thr Asp Phe Thr Leu Lys Ile
            65                  70                  75                  80

Ser Arg Val Glu Pro Asp Asp Leu Gly Val Tyr Tyr Cys Gly Gln Gly
                            85                  90                  95

Thr Gln Tyr Pro Phe Thr Phe Gly Ala Gly Thr Lys Leu Glu Leu Lys
                            100                 105                 110
```

<210> SEQ ID NO 74
<211> LENGTH: 123
<212> TYPE: PRT
<213> ORGANISM: Artificial Sequence
<220> FEATURE:
<223> OTHER INFORMATION: VH of the so-called "12G3-E8" anti-CD3 antibody

<400> SEQUENCE: 74

```
            Glu Val Arg Val Val Glu Thr Gly Gly Ser Leu Val Gln Pro Gly Lys
            1               5                   10                  15

Ser Leu Lys Leu Thr Cys Ala Thr Ser Gly Phe Thr Phe Ser Leu Ala
                            20                  25                  30

Trp Met His Trp Val Arg Gln Ser Pro Glu Lys Lys Leu Glu Trp Val
                            35                  40                  45

Ala Gln Ile Lys Asp Lys Ala Asn Asn Tyr Ala Thr Tyr Tyr Ala Glu
                            50                  55                  60

Ser Val Lys Gly Arg Phe Thr Ile Ser Arg Asp Asp Ser Lys Arg Ser
            65                  70                  75                  80
```

Val Tyr Leu Gln Met Asn Arg Leu Lys Glu Glu Asp Thr Ala Ile Tyr
                85                  90                  95

Tyr Cys Arg Gly Val Tyr Tyr Gly Phe Ser Met Thr Pro Phe Asp Tyr
        100                 105                 110

Trp Gly Gln Gly Val Met Val Thr Val Ser Ser
        115                 120

<210> SEQ ID NO 75
<211> LENGTH: 8
<212> TYPE: PRT
<213> ORGANISM: Artificial Sequence
<220> FEATURE:
<223> OTHER INFORMATION: CDR1-H of the so-called "18G9-H11" anti-CD3
      antibody

<400> SEQUENCE: 75

Gly Phe Thr Phe Ser Leu Ala Trp
1               5

<210> SEQ ID NO 76
<211> LENGTH: 10
<212> TYPE: PRT
<213> ORGANISM: Artificial Sequence
<220> FEATURE:
<223> OTHER INFORMATION: CDR2-H of the so-called "18G9-H11" anti-CD3
      antibody

<400> SEQUENCE: 76

Ile Lys Asp Lys Ala Asn Asn Tyr Ala Thr
1               5                   10

<210> SEQ ID NO 77
<211> LENGTH: 14
<212> TYPE: PRT
<213> ORGANISM: Artificial Sequence
<220> FEATURE:
<223> OTHER INFORMATION: CDR3-H of the so-called "18G9-H11" anti-CD3
      antibody

<400> SEQUENCE: 77

Arg Gly Val Tyr Tyr Gly Phe Ser Met Thr Pro Phe Asp Tyr
1               5                   10

<210> SEQ ID NO 78
<211> LENGTH: 112
<212> TYPE: PRT
<213> ORGANISM: Artificial Sequence
<220> FEATURE:
<223> OTHER INFORMATION: VL of the so-called "12G3-E8" anti-CD3 antibody

<400> SEQUENCE: 78

Asp Val Ala Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Leu Ser Trp Tyr Leu Gln Lys Pro Gly Gln Ser
        35                  40                  45

Pro Gln Val Leu Ile Tyr Lys Val Ser Asn Arg Phe Ser Gly Ile Ser
    50                  55                  60

Asp Arg Phe Ser Gly Ser Gly Ser Gly Ala Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Tyr Pro Phe Thr Phe Gly Ala Gly Thr Lys Leu Glu Leu Lys
            100                 105                 110

<210> SEQ ID NO 79
<211> LENGTH: 121
<212> TYPE: PRT
<213> ORGANISM: Artificial Sequence
<220> FEATURE:
<223> OTHER INFORMATION: VH of the so-called "5B1-G2" anti-CD3 antibody

<400> SEQUENCE: 79

Glu Val Gln Val Val Glu Thr Gly Gly Ser Leu Val Gln Pro Gly Lys
1               5                   10                  15

Ser Leu Lys Leu Thr Cys Ala Thr Ser Gly Phe Ser Phe Ser Asn Ala
            20                  25                  30

Trp Met His Trp Val Arg Gln Ser Pro Glu Lys Gln Leu Glu Trp Val
        35                  40                  45

Ala Gln Ile Lys Asp Lys Ala Asn Asn Tyr Ala Thr Tyr Tyr Ala Glu
    50                  55                  60

Ser Val Lys Gly Arg Phe Thr Ile Ser Arg Asp Asp Ser Lys Gly Ser
65                  70                  75                  80

Ile Tyr Leu Gln Met Asn Ser Leu Lys Glu Glu Asp Thr Ala Val Tyr
                85                  90                  95

Tyr Cys Arg Gly Leu Tyr Tyr Gly Leu Phe Pro Ser Asp Tyr Trp Gly
            100                 105                 110

Gln Gly Val Met Val Thr Val Ser Ser
        115                 120

<210> SEQ ID NO 80
<211> LENGTH: 8
<212> TYPE: PRT
<213> ORGANISM: Artificial Sequence
<220> FEATURE:
<223> OTHER INFORMATION: CDR1-H of the so-called "5B1-G2" anti-CD3
      antibody

<400> SEQUENCE: 80

Gly Phe Ser Phe Ser Asn Ala Trp
1               5

<210> SEQ ID NO 81
<211> LENGTH: 12
<212> TYPE: PRT
<213> ORGANISM: Artificial Sequence
<220> FEATURE:
<223> OTHER INFORMATION: CDR3-H of the so-called "5B1-G2" anti-CD3
      antibody

<400> SEQUENCE: 81

Arg Gly Leu Tyr Tyr Gly Leu Phe Pro Ser Asp Tyr
1               5                   10

<210> SEQ ID NO 82
<211> LENGTH: 112
<212> TYPE: PRT
<213> ORGANISM: Artificial Sequence
<220> FEATURE:
<223> OTHER INFORMATION: VL of the so-called "5B1-G2" anti-CD3 antibody

<400> SEQUENCE: 82

Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asn

```
                20                  25                  30

Asn Gly Asn Thr Tyr Leu Ser Trp Tyr Leu Leu Lys Pro Gly Gln Ser
            35                  40                  45

Pro Gln Leu Leu Ile Tyr Lys Val Ser Asn Arg Phe Ser Gly Ile Ser
     50                  55                  60

Asp Arg Phe Ser Gly Gly Ser Gly Thr Asp Phe Thr Leu Lys Ile
65                  70                  75                  80

Ser Arg Leu Glu Pro Asp Asp Leu Gly Ile Tyr Tyr Cys Gln Gly
                85                  90                  95

Thr Gln Tyr Pro Phe Thr Phe Gly Ser Gly Thr Lys Leu Glu Ile Lys
            100                 105                 110

<210> SEQ ID NO 83
<211> LENGTH: 117
<212> TYPE: PRT
<213> ORGANISM: Artificial Sequence
<220> FEATURE:
<223> OTHER INFORMATION: part of VH of the so-called "16F8-A7" anti-CD3
      antibody

<400> SEQUENCE: 83

Val Glu Thr Gly Gly Asn Leu Val Gln Pro Lys Ser Leu Lys Leu
1               5                   10                  15

Thr Cys Ala Thr Ser Gly Phe Thr Phe Ser Asn Ala Trp Met His Trp
            20                  25                  30

Val Arg Gln Ser Pro Glu Lys Gln Leu Glu Trp Val Ala Gln Ile Lys
        35                  40                  45

Ala Lys Ser Asn Asn Tyr Ala Thr Tyr Tyr Ala Glu Ser Val Lys Gly
    50                  55                  60

Arg Phe Thr Ile Ser Arg Asp Asp Ser Lys Ser Ser Val Tyr Leu Gln
65                  70                  75                  80

Met Asn Ser Leu Lys Glu Glu Asp Thr Ala Ile Tyr Tyr Cys Arg Tyr
                85                  90                  95

Val Asn Tyr Gly Leu Ala Pro Met Asp Val Trp Gly Gln Gly Thr Ser
            100                 105                 110

Val Thr Val Ser Ser
        115

<210> SEQ ID NO 84
<211> LENGTH: 12
<212> TYPE: PRT
<213> ORGANISM: Artificial Sequence
<220> FEATURE:
<223> OTHER INFORMATION: CDR3-H of the so-called "16F8-A7" and "11F3-B9"
      anti-CD3 antibodies

<400> SEQUENCE: 84

Arg Tyr Val Asn Tyr Gly Leu Ala Pro Met Asp Val
1               5                   10

<210> SEQ ID NO 85
<211> LENGTH: 112
<212> TYPE: PRT
<213> ORGANISM: Artificial Sequence
<220> FEATURE:
<223> OTHER INFORMATION: VL of the so-called "16F8-A7" anti-CD3 antibody

<400> SEQUENCE: 85

Asp Val Val Met Thr Gln Thr Pro Val Ser Leu Ser Val Ser Leu Gly
1               5                   10                  15
```

Gly Gln Val Ser Ile Ser Cys Arg Ser Ser Gln Ser Leu Val His Asn
            20                  25                  30

Asn Gly Asn Thr Tyr Leu Ser Trp Tyr Leu Gln Lys Pro Gly Gln Ser
            35                  40                  45

Pro Gln Leu Leu Ile Tyr Lys Val Ser Asn Arg Phe Ser Gly Phe Ser
        50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Tyr Pro Phe Thr Phe Gly Ala Gly Thr Lys Leu Glu Leu Lys
            100                 105                 110

<210> SEQ ID NO 86
<211> LENGTH: 171
<212> TYPE: PRT
<213> ORGANISM: Homo sapiens

<400> SEQUENCE: 86

Met Glu His Ser Thr Phe Leu Ser Gly Leu Val Leu Ala Thr Leu Leu
1               5                   10                  15

Ser Gln Val Ser Pro Phe Lys Ile Pro Ile Glu Leu Glu Asp Arg
            20                  25                  30

Val Phe Val Asn Cys Asn Thr Ser Ile Thr Trp Val Glu Gly Thr Val
            35                  40                  45

Gly Thr Leu Leu Ser Asp Ile Thr Arg Leu Asp Leu Gly Lys Arg Ile
        50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
            115                 120                 125

Glu Thr Gly Arg Leu Ser Gly Ala Ala Asp Thr Gln Ala Leu Leu Arg
        130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 87
<211> LENGTH: 112
<212> TYPE: PRT
<213> ORGANISM: Artificial Sequence
<220> FEATURE:
<223> OTHER INFORMATION: VL of the so-called "11F9-F8" anti-CD3 antibody

<400> SEQUENCE: 87

Asp Val Val Leu Thr Gln Thr Pro Val Ser Leu Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Leu Ser Trp Ser Leu Gln Lys Pro Gly Gln Ser
            35                  40                  45

Pro Gln Val Leu Ile Tyr Lys Val Ser Asn Arg Phe Ser Gly Ile Ser

```
                50             55             60
Asn Arg Phe Ser Gly Ser Gly Ser Gly Thr Asp Phe Thr Leu Lys Ile
 65                 70                  75                  80

Ser Arg Val Glu Pro Asp Asp Leu Gly Val Tyr Tyr Cys Gly Gln Gly
                 85                  90                  95

Ala His Tyr Pro Phe Thr Phe Gly Ser Gly Thr Lys Leu Glu Ile Lys
                100                 105                 110
```

<210> SEQ ID NO 88
<211> LENGTH: 9
<212> TYPE: PRT
<213> ORGANISM: Artificial Sequence
<220> FEATURE:
<223> OTHER INFORMATION: CDR3-L of the so-called "11F9-F8" anti-CD3
      antibody

<400> SEQUENCE: 88

```
Gly Gln Gly Ala His Tyr Pro Phe Thr
 1               5
```

<210> SEQ ID NO 89
<211> LENGTH: 118
<212> TYPE: PRT
<213> ORGANISM: Artificial Sequence
<220> FEATURE:
<223> OTHER INFORMATION: VH of the so-called "3G5-E10" anti-CD3 antibody

<400> SEQUENCE: 89

```
Glu Val Lys Leu Val Glu Ser Gly Gly Gly Leu Val Gln Pro Gly Arg
 1               5                  10                  15

Ser Leu Lys Leu Ser Cys Ala Ala Ser Gly Phe Asn Phe Asn Val Tyr
                20                  25                  30

Trp Met Gly Trp Val Arg Gln Ala Pro Gly Lys Gly Leu Glu Trp Ile
            35                  40                  45

Gly Glu Ile Lys Lys Asp Ser Asn Ser Ile Asn Tyr Thr Pro Ser Leu
        50                  55                  60

Lys Glu Lys Phe Thr Ile Ser Arg Asp Asn Ala Gln Asn Thr Leu Tyr
 65                 70                  75                  80

Leu Gln Val Asn Lys Leu Gly Ser Glu Asp Thr Ala Ile Tyr Tyr Cys
                85                  90                  95

Ala Arg Glu Glu Arg Asp Gly Tyr Phe Asp Tyr Trp Gly Gln Gly Val
                100                 105                 110

Met Val Thr Val Ser Ser
            115
```

<210> SEQ ID NO 90
<211> LENGTH: 8
<212> TYPE: PRT
<213> ORGANISM: Artificial Sequence
<220> FEATURE:
<223> OTHER INFORMATION: CDR1-H of the so-called "3G5-E10" anti-CD3
      antibody

<400> SEQUENCE: 90

```
Gly Phe Asn Phe Asn Val Tyr Trp
 1               5
```

<210> SEQ ID NO 91
<211> LENGTH: 8
<212> TYPE: PRT
<213> ORGANISM: Artificial Sequence
<220> FEATURE:

<223> OTHER INFORMATION: CDR2-H of the so-called "3G5-E10" anti-CD3
    antibody

<400> SEQUENCE: 91

Ile Lys Lys Asp Ser Asn Ser Ile
1               5

<210> SEQ ID NO 92
<211> LENGTH: 107
<212> TYPE: PRT
<213> ORGANISM: Artificial Sequence
<220> FEATURE:
<223> OTHER INFORMATION: VL of the so-called "3G5-E10" anti-CD3 antibody

<400> SEQUENCE: 92

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 93
<211> LENGTH: 6
<212> TYPE: PRT
<213> ORGANISM: Artificial Sequence
<220> FEATURE:
<223> OTHER INFORMATION: CDR1-L of the so-called "3G5-E10" anti-CD3
    antibody

<400> SEQUENCE: 93

Glu Asn Val Val Thr Tyr
1               5

<210> SEQ ID NO 94
<211> LENGTH: 9
<212> TYPE: PRT
<213> ORGANISM: Artificial Sequence
<220> FEATURE:
<223> OTHER INFORMATION: CDR3-L of the so-called "3G5-E10" anti-CD3
    antibody

<400> SEQUENCE: 94

Gly Gln Gly Tyr Ser Tyr Pro Tyr Thr
1               5

<210> SEQ ID NO 95
<211> LENGTH: 119
<212> TYPE: PRT
<213> ORGANISM: Artificial Sequence
<220> FEATURE:
<223> OTHER INFORMATION: VH of the so-called "9D7-F3" anti-CD3 antibody

<400> SEQUENCE: 95

Ala Val Gln Leu Val Glu Ser Gly Gly Gly Leu Val Gln Pro Lys Glu
1               5                   10                  15

```
Ser Leu Lys Ile Ser Cys Ala Ala Ser Gly Phe Thr Phe Ser Asn Ala
            20                  25                  30

Ala Met Tyr Trp Val Arg Gln Ala Pro Gly Lys Gly Leu Glu Trp Val
        35                  40                  45

Ala Arg Ile Arg Thr Lys Pro Asn Asn Tyr Ala Thr Tyr Tyr Ala Asp
    50                  55                  60

Ser Val Thr Gly Arg Phe Ile Ile Ser Arg Asp Asp Ser Arg Ser Met
65                  70                  75                  80

Val Tyr Leu Gln Met Asp Asn Leu Gln Thr Glu Asp Thr Ala Met Tyr
                85                  90                  95

Tyr Cys Thr Ala Leu Ile Ser Thr Ala Met Ala Ala Trp Gly Gln Gly
            100                 105                 110

Thr Ser Val Thr Val Ser Ser
            115

<210> SEQ ID NO 96
<211> LENGTH: 8
<212> TYPE: PRT
<213> ORGANISM: Artificial Sequence
<220> FEATURE:
<223> OTHER INFORMATION: CDR1-H of the so-called "9D7-F3" anti-CD3
      antibody

<400> SEQUENCE: 96

Gly Phe Thr Phe Ser Asn Ala Ala
1               5

<210> SEQ ID NO 97
<211> LENGTH: 10
<212> TYPE: PRT
<213> ORGANISM: Artificial Sequence
<220> FEATURE:
<223> OTHER INFORMATION: CDR2-H of the so-called "9D7-F3" anti-CD3
      antibody

<400> SEQUENCE: 97

Ile Arg Thr Lys Pro Asn Asn Tyr Ala Thr
1               5                   10

<210> SEQ ID NO 98
<211> LENGTH: 10
<212> TYPE: PRT
<213> ORGANISM: Artificial Sequence
<220> FEATURE:
<223> OTHER INFORMATION: CDR3-H of the so-called "9D7-F3" anti-CD3
      antibody

<400> SEQUENCE: 98

Thr Ala Leu Ile Ser Thr Ala Met Ala Ala
1               5                   10

<210> SEQ ID NO 99
<211> LENGTH: 106
<212> TYPE: PRT
<213> ORGANISM: Artificial Sequence
<220> FEATURE:
<223> OTHER INFORMATION: VL of the so-called "9D7-F3" anti-CD3 antibody

<400> SEQUENCE: 99

Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asn Lys Tyr
            20                  25                  30
```

Leu Asn Trp Tyr His Gln Met Leu Gly Glu Ala Pro Lys Leu Val Ile
            35                  40                  45

Ser Asn Thr Asn Asn Leu Gln Ala Gly Ile Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Phe Cys Leu Gln His Arg Ser Gly Tyr Thr
                 85                  90                  95

Phe Gly Leu Gly Thr Lys Leu Glu Leu Lys
            100                 105

<210> SEQ ID NO 100
<211> LENGTH: 6
<212> TYPE: PRT
<213> ORGANISM: Artificial Sequence
<220> FEATURE:
<223> OTHER INFORMATION: CDR1-L of the so-called "9D7-F3" and "6C9-C9"
      anti-CD3 antibody

<400> SEQUENCE: 100

Gln Asn Ile Asn Lys Tyr
1               5

<210> SEQ ID NO 101
<211> LENGTH: 8
<212> TYPE: PRT
<213> ORGANISM: Artificial Sequence
<220> FEATURE:
<223> OTHER INFORMATION: CDR3-L of the so-called "9D7-F3" anti-CD3
      antibody

<400> SEQUENCE: 101

Leu Gln His Arg Ser Gly Tyr Thr
1               5

<210> SEQ ID NO 102
<211> LENGTH: 114
<212> TYPE: PRT
<213> ORGANISM: Artificial Sequence
<220> FEATURE:
<223> OTHER INFORMATION: VH of the so-called "8C2-F7" anti-CD3 antibody

<400> SEQUENCE: 102

Gln Ile Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Phe
                 20                  25                  30

Ala Met Asn Trp Val Lys Gln Ala Pro Gly Asn Gly Leu Lys Trp Met
            35                  40                  45

Gly Trp Ile Asn Thr Gln Thr Gly Lys Pro Thr Tyr Ala Asp Gly Phe
 50                  55                  60

Lys Gln Arg Phe Val Phe Ser Leu Glu Thr Ser Ala Ser Thr Ile Tyr
 65                  70                  75                  80

Leu Gln Ile Asn Asn Leu Asn Ile Glu Asp Thr Ala Thr Tyr Phe Cys
                 85                  90                  95

Thr Arg Gly Ala Leu Ala Ser Val Gly Gln Gly Val Leu Val Thr Val
            100                 105                 110

Ser Ser

<210> SEQ ID NO 103

```
<211> LENGTH: 8
<212> TYPE: PRT
<213> ORGANISM: Artificial Sequence
<220> FEATURE:
<223> OTHER INFORMATION: CDR1-H of the so-called "8C2-F7" anti-CD3
      antibody

<400> SEQUENCE: 103

Gly Tyr Thr Phe Thr Asp Phe Ala
1               5

<210> SEQ ID NO 104
<211> LENGTH: 8
<212> TYPE: PRT
<213> ORGANISM: Artificial Sequence
<220> FEATURE:
<223> OTHER INFORMATION: CDR2-H of the so-called "8C2-F7" anti-CD3
      antibody

<400> SEQUENCE: 104

Ile Asn Thr Gln Thr Gly Lys Pro
1               5

<210> SEQ ID NO 105
<211> LENGTH: 7
<212> TYPE: PRT
<213> ORGANISM: Artificial Sequence
<220> FEATURE:
<223> OTHER INFORMATION: CDR3-H of the so-called "8C2-F7" anti-CD3
      antibody

<400> SEQUENCE: 105

Thr Arg Gly Ala Leu Ala Ser
1               5

<210> SEQ ID NO 106
<211> LENGTH: 112
<212> TYPE: PRT
<213> ORGANISM: Artificial Sequence
<220> FEATURE:
<223> OTHER INFORMATION: VL of the so-called "8C2-F7" anti-CD3 antibody

<400> SEQUENCE: 106

Asp Val Val Met Thr Gln Thr Pro Val Ser Leu Ser Val Ser Leu Gly
1               5                   10                  15

Ser His Val Ser Ile Ser Cys Arg Ser Ser Gln Ser Leu Val His Asn
            20                  25                  30

Asn Gly Asn Thr Tyr Leu Ser Trp Tyr Leu Gln Lys Pro Gly Gln Ser
        35                  40                  45

Pro Gln Pro Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Glu Ile
65                  70                  75                  80

Asn Arg Val Glu Pro Asp Asp Leu Gly Val Tyr Tyr Cys Gly Gln Gly
                85                  90                  95

Ala Gln Tyr Pro Phe Thr Phe Gly Ser Gly Thr Lys Leu Glu Ile Lys
            100                 105                 110

<210> SEQ ID NO 107
<211> LENGTH: 124
<212> TYPE: PRT
<213> ORGANISM: Artificial Sequence
<220> FEATURE:
<223> OTHER INFORMATION: VH of the so-called "20E5-F10" anti-CD3
      antibody
```

<400> SEQUENCE: 107

Glu Val Gln Leu Val Glu Thr Gly Glu Asn Leu Val Gln Pro Gly Lys
1               5                   10                  15

Ser Leu Arg Leu Thr Cys Ala Thr Ser Gly Phe Ser Phe Ser Asn Ala
            20                  25                  30

Trp Met His Trp Ile Arg Gln Ser Pro Glu Lys Gln Leu Glu Trp Val
        35                  40                  45

Ala Gln Ile Lys Asp Lys Ser Asn Asn Tyr Ala Thr Tyr Tyr Ala Glu
    50                  55                  60

Ser Val Asn Gly Arg Phe Thr Ile Ser Arg Asp Asp Ser Lys Ser Ser
65                  70                  75                  80

Ile Tyr Leu His Met Asp Asn Leu Lys Glu Glu Asp Ser Ala Ile Tyr
                85                  90                  95

Tyr Cys Arg Tyr Val His Tyr Gly Val Arg Phe Phe Tyr Thr Met Asp
            100                 105                 110

Val Trp Gly Gln Gly Thr Ser Val Thr Val Ser Ser
            115                 120

<210> SEQ ID NO 108
<211> LENGTH: 15
<212> TYPE: PRT
<213> ORGANISM: Artificial Sequence
<220> FEATURE:
<223> OTHER INFORMATION: CDR3-H of the so-called "20E5-F10" anti-CD3
      antibody

<400> SEQUENCE: 108

Arg Tyr Val His Tyr Gly Val Arg Phe Phe Tyr Thr Met Asp Val
1               5                   10                  15

<210> SEQ ID NO 109
<211> LENGTH: 112
<212> TYPE: PRT
<213> ORGANISM: Artificial Sequence
<220> FEATURE:
<223> OTHER INFORMATION: VL of the so-called "20E5-F10" anti-CD3
      antibody

<400> SEQUENCE: 109

Asp Val Val Met Thr Gln Thr Pro Val Ser Leu Ser Val Ser Leu Gly
1               5                   10                  15

Asp Gln Val Ser Ile Ser Cys Arg Pro Ser Gln Ser Leu Val His Asn
            20                  25                  30

Asn Gly Asn Thr Tyr Leu Ser Trp Tyr Leu Gln Lys Pro Gly Gln Ser
        35                  40                  45

Pro His Pro Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110

<210> SEQ ID NO 110
<211> LENGTH: 121
<212> TYPE: PRT
<213> ORGANISM: Artificial Sequence
<220> FEATURE:

<223> OTHER INFORMATION: VH of the so-called "20B5-F10" anti-CD3
    antibody

<400> SEQUENCE: 110

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Ile Ser Ser
65                  70                  75                  80

Val Tyr Leu Gln Met Asn Asn Leu Lys Glu Glu Asp Thr Ala Ile Tyr
                85                  90                  95

Tyr Cys Arg Gly Val Tyr Tyr Gly Phe Leu Gly Met Asp Ala Trp Gly
            100                 105                 110

Gln Gly Thr Ser Val Thr Val Ser Ser
        115                 120

<210> SEQ ID NO 111
<211> LENGTH: 12
<212> TYPE: PRT
<213> ORGANISM: Artificial Sequence
<220> FEATURE:
<223> OTHER INFORMATION: CDR3-H of the so-called "20B5-F10" anti-CD3
    antibody

<400> SEQUENCE: 111

Arg Gly Val Tyr Tyr Gly Phe Leu Gly Met Asp Ala
1               5                   10

<210> SEQ ID NO 112
<211> LENGTH: 112
<212> TYPE: PRT
<213> ORGANISM: Artificial Sequence
<220> FEATURE:
<223> OTHER INFORMATION: VL of the so-called "20B5-F10" anti-CD3
    antibody

<400> SEQUENCE: 112

Asp Val Val Met Thr Gln Thr Pro Val Ser Leu Ser Val Ser Leu Gly
1               5                   10                  15

Gly Gln Val Ser Ile Ser Cys Arg Ser Ser Gln Arg Leu Val His Asn
            20                  25                  30

Asn Gly Asn Thr Tyr Leu Ser Trp Tyr Leu Gln Lys Pro Gly Gln Ser
        35                  40                  45

Pro Gln Leu Leu Val Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Glu Tyr Pro Phe Thr Phe Gly Ser Gly Thr Lys Leu Glu Ile Lys
            100                 105                 110

<210> SEQ ID NO 113
<211> LENGTH: 11
<212> TYPE: PRT

```
<213> ORGANISM: Artificial Sequence
<220> FEATURE:
<223> OTHER INFORMATION: CDR1-L of the so-called "20B5-F10" anti-CD3
      antibody

<400> SEQUENCE: 113

Gln Arg Leu Val His Asn Asn Gly Asn Thr Tyr
1               5                   10

<210> SEQ ID NO 114
<211> LENGTH: 9
<212> TYPE: PRT
<213> ORGANISM: Artificial Sequence
<220> FEATURE:
<223> OTHER INFORMATION: CDR3-L of the so-called "20B5-F10" anti-CD3
      antibody

<400> SEQUENCE: 114

Gly Gln Gly Thr Glu Tyr Pro Phe Thr
1               5

<210> SEQ ID NO 115
<211> LENGTH: 119
<212> TYPE: PRT
<213> ORGANISM: Artificial Sequence
<220> FEATURE:
<223> OTHER INFORMATION: VH of the so-called "6C9-C9" anti-CD3 antibody

<400> SEQUENCE: 115

Ala Val Gln Leu Val Glu Ser Gly Gly Gly Leu Val Arg Pro Lys Glu
1               5                   10                  15

Ser Leu Lys Ile Ser Cys Ala Ala Ser Gly Phe Thr Phe Arg Asn Ala
            20                  25                  30

Ala Met Tyr Trp Val Arg Gln Ala Pro Gly Lys Gly Leu Glu Trp Val
        35                  40                  45

Ala Arg Ile Arg Thr Gln Pro Asn Asn Tyr Ala Lys Tyr Tyr Ala Asp
    50                  55                  60

Ser Val Lys Asp Arg Phe Thr Ile Ser Arg Asp Asp Ser Lys Ser Met
65                  70                  75                  80

Val Tyr Leu Gln Met Asp Asn Leu Lys Thr Glu Asp Thr Ala Met Tyr
                85                  90                  95

Tyr Cys Thr Gly Leu Val Val Thr Ala Met Asp Ala Trp Gly Gln Gly
            100                 105                 110

Thr Ser Val Thr Val Ser Ser
        115

<210> SEQ ID NO 116
<211> LENGTH: 8
<212> TYPE: PRT
<213> ORGANISM: Artificial Sequence
<220> FEATURE:
<223> OTHER INFORMATION: CDR1-H of the so-called "6C9-C9" anti-CD3
      antibody

<400> SEQUENCE: 116

Gly Phe Thr Phe Arg Asn Ala Ala
1               5

<210> SEQ ID NO 117
<211> LENGTH: 10
<212> TYPE: PRT
<213> ORGANISM: Artificial Sequence
<220> FEATURE:
<223> OTHER INFORMATION: CDR2-H of the so-called "6C9-C9" anti-CD3
``` antibody

<400> SEQUENCE: 117

Ile Arg Thr Gln Pro Asn Asn Tyr Ala Lys
1               5                   10

<210> SEQ ID NO 118
<211> LENGTH: 10
<212> TYPE: PRT
<213> ORGANISM: Artificial Sequence
<220> FEATURE:
<223> OTHER INFORMATION: CDR3-H of the so-called "6C9-C9" anti-CD3
      antibody

<400> SEQUENCE: 118

Thr Gly Leu Val Val Thr Ala Met Asp Ala
1               5                   10

<210> SEQ ID NO 119
<211> LENGTH: 106
<212> TYPE: PRT
<213> ORGANISM: Artificial Sequence
<220> FEATURE:
<223> OTHER INFORMATION: VL of the so-called "6C9-C9" anti-CD3 antibody

<400> SEQUENCE: 119

Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asn Lys Tyr
                20                  25                  30

Leu Asn Trp Tyr Gln Gln Lys Leu Gly Glu Ala Pro Lys Leu Leu Ile
            35                  40                  45

Tyr Val Thr Asn Asn Leu Gln Thr Gly Ile Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Leu Gln His Arg Ser Met Tyr Thr
                85                  90                  95

Phe Gly Thr Gly Thr Lys Leu Glu Leu Lys
            100                 105

<210> SEQ ID NO 120
<211> LENGTH: 8
<212> TYPE: PRT
<213> ORGANISM: Artificial Sequence
<220> FEATURE:
<223> OTHER INFORMATION: CDR3-L of the so-called "6C9-C9" anti-CD3
      antibody

<400> SEQUENCE: 120

Leu Gln His Arg Ser Met Tyr Thr
1               5

<210> SEQ ID NO 121
<211> LENGTH: 118
<212> TYPE: PRT
<213> ORGANISM: Artificial Sequence
<220> FEATURE:
<223> OTHER INFORMATION: VH the so-called "3E8-G1" anti-CD3 antibody

<400> SEQUENCE: 121

Glu Val Gln Val Val Glu Ser Gly Gly Gly Leu Val Gln Pro Gly Arg
1               5                   10                  15

```
Ser Leu Lys Leu Ser Cys Ala Ala Ser Gly Phe Thr Phe Ser Asn Tyr
            20                  25                  30

Tyr Met Asp Trp Val Arg Gln Ala Pro Lys Lys Gly Leu Glu Trp Val
        35                  40                  45

Ala Thr Ile Thr Ala Ser Gly Ser Arg Ile Tyr Tyr Pro Asp Ser Val
50                  55                  60

Lys Gly Arg Phe Thr Ile Ser Arg Asp Asn Ala Lys Ser Ser Leu Tyr
65                  70                  75                  80

Leu Leu Met Asn Ser Leu Lys Ser Glu Asp Thr Ala Thr Tyr Tyr Cys
                85                  90                  95

Ala Arg Glu Arg Thr Asp Ala Tyr Phe Asp Tyr Trp Gly Gln Gly Val
            100                 105                 110

Met Val Thr Val Ser Ser
            115
```

<210> SEQ ID NO 122
<211> LENGTH: 8
<212> TYPE: PRT
<213> ORGANISM: Artificial Sequence
<220> FEATURE:
<223> OTHER INFORMATION: CDR1-H of the so-called "3E8-G1" anti-CD3
      antibody

<400> SEQUENCE: 122

```
Gly Phe Thr Phe Ser Asn Tyr Tyr
1               5
```

<210> SEQ ID NO 123
<211> LENGTH: 8
<212> TYPE: PRT
<213> ORGANISM: Artificial Sequence
<220> FEATURE:
<223> OTHER INFORMATION: CDR2-H of the so-called "3E8-G1" anti-CD3
      antibody

<400> SEQUENCE: 123

```
Ile Thr Ala Ser Gly Ser Arg Ile
1               5
```

<210> SEQ ID NO 124
<211> LENGTH: 11
<212> TYPE: PRT
<213> ORGANISM: Artificial Sequence
<220> FEATURE:
<223> OTHER INFORMATION: CDR3-H of the so-called "3E8-G1" anti-CD3
      antibody

<400> SEQUENCE: 124

```
Ala Arg Glu Arg Thr Asp Ala Tyr Phe Asp Tyr
1               5                   10
```

<210> SEQ ID NO 125
<211> LENGTH: 111
<212> TYPE: PRT
<213> ORGANISM: Artificial Sequence
<220> FEATURE:
<223> OTHER INFORMATION: VL of the so-called "3E8-G1" anti-CD3 antibody

<400> SEQUENCE: 125

```
Gln Phe Ile Leu Thr Gln Pro Asn Ser Val Ser Thr Ile Leu Gly Ser
1               5                   10                  15

Thr Val Lys Leu Ser Cys Lys Arg Ser Thr Gly Asn Ile Gly Thr Asn
            20                  25                  30
```

```
Tyr Val Ser Trp Tyr Gln His His Glu Gly Arg Ser Pro Thr Thr Met
            35                  40                  45

Ile Tyr Arg Asp Asp Lys Arg Pro Asp Gly Val Pro Asp Arg Phe Ser
 50                  55                  60

Gly Ser Ile Asp Arg Ser Ser Asn Ser Ala Leu Leu Thr Ile Asn Asn
 65                  70                  75                  80

Val Gln Thr Glu Asp Glu Ala Asp Tyr Phe Cys Gln Ser Tyr Ile Ser
                85                  90                  95

Gly Leu Asn Pro Val Phe Gly Gly Gly Ser Lys Leu Thr Val Leu
                100                 105                 110

<210> SEQ ID NO 126
<211> LENGTH: 8
<212> TYPE: PRT
<213> ORGANISM: Artificial Sequence
<220> FEATURE:
<223> OTHER INFORMATION: CDR1-L of the so-called "3E8-G1" anti-CD3
      antibody

<400> SEQUENCE: 126

Thr Gly Asn Ile Gly Thr Asn Tyr
 1               5

<210> SEQ ID NO 127
<211> LENGTH: 10
<212> TYPE: PRT
<213> ORGANISM: Artificial Sequence
<220> FEATURE:
<223> OTHER INFORMATION: CDR3-L of the so-called "3E8-G1" anti-CD3
      antibody

<400> SEQUENCE: 127

Gln Ser Tyr Ile Ser Gly Leu Asn Pro Val
 1               5                  10

<210> SEQ ID NO 128
<211> LENGTH: 124
<212> TYPE: PRT
<213> ORGANISM: Artificial Sequence
<220> FEATURE:
<223> OTHER INFORMATION: VH of the so-called "3H6-D2" anti-CD3 antibody.

<400> SEQUENCE: 128

Glu Val Gln Leu Val Glu Thr Gly Gly Arg Leu Val Gln Pro Gly Lys
 1               5                  10                  15

Ser Leu Lys Leu Thr Cys Ala Thr Ser Gly Phe Thr Phe Ser Asn Ala
                20                  25                  30

Trp Met His Trp Val Arg Gln Ser Pro Glu Lys Gln Leu Glu Trp Val
            35                  40                  45

Ala Gln Ile Lys Asp Lys Ser Asn Asn Tyr Ala Thr Tyr Tyr Ala Glu
 50                  55                  60

Ser Val Lys Gly Arg Phe Thr Ile Ser Arg Asp Asp Ser Lys Ser Ile
 65                  70                  75                  80

Ile Tyr Leu Gln Met Asn Ser Leu Lys Glu Glu Asp Thr Ala Ile Tyr
                85                  90                  95

Tyr Cys Arg Ala Leu Thr Tyr Tyr Gly Tyr Lys Arg Asp Ala Met Asp
                100                 105                 110

Gly Trp Gly His Gly Thr Ser Val Thr Val Ser Ser
            115                 120

<210> SEQ ID NO 129
```

```
<211> LENGTH: 15
<212> TYPE: PRT
<213> ORGANISM: Artificial Sequence
<220> FEATURE:
<223> OTHER INFORMATION: CDR3-H of the so-called "3H6-D2" anti-CD3
      antibody

<400> SEQUENCE: 129

Arg Ala Leu Thr Tyr Tyr Gly Tyr Lys Arg Asp Ala Met Asp Gly
1               5                   10                  15

<210> SEQ ID NO 130
<211> LENGTH: 112
<212> TYPE: PRT
<213> ORGANISM: Artificial Sequence
<220> FEATURE:
<223> OTHER INFORMATION: VL of the so-called "3H6-D2" anti-CD3 antibody.

<400> SEQUENCE: 130

Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asn
                20                  25                  30

Asn Gly Asn Thr Tyr Leu Ser Trp Tyr Leu Gln Lys Pro Gly Gln Ser
            35                  40                  45

Pro Gln Leu Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Tyr Pro Phe Thr Phe Gly Ala Gly Thr Lys Leu Glu Leu Lys
            100                 105                 110

<210> SEQ ID NO 131
<211> LENGTH: 114
<212> TYPE: PRT
<213> ORGANISM: Artificial Sequence
<220> FEATURE:
<223> OTHER INFORMATION: VH of the so-called "8H2" anti-CD3 antibody

<400> SEQUENCE: 131

Gln Ile Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Phe
                20                  25                  30

Ala Met Asn Trp Val Lys Gln Ala Pro Gly Asn Gly Leu Lys Trp Met
            35                  40                  45

Gly Trp Ile Asn Thr Gln Thr Gly Lys Pro Thr Tyr Ala Asp Gly Phe
    50                  55                  60

Lys Gln Arg Phe Val Phe Ser Leu Glu Thr Ser Ala Ser Thr Ile Tyr
65                  70                  75                  80

Leu Gln Ile Asn Asn Leu Asn Ile Glu Asp Thr Ala Thr Tyr Phe Cys
                85                  90                  95

Thr Arg Gly Ala Leu Ala Ser Val Gly Gln Gly Val Met Val Thr Val
            100                 105                 110

Ser Ser

<210> SEQ ID NO 132
<211> LENGTH: 112
```

```
<212> TYPE: PRT
<213> ORGANISM: Artificial Sequence
<220> FEATURE:
<223> OTHER INFORMATION: VL of the so-called "8H2" anti-CD3 antibody

<400> SEQUENCE: 132

Asp Val Val Met Thr Gln Thr Pro Val Ser Leu Ser Val Ala Ile Gly
1               5                   10                  15

Gln Pro Ala Ser Ile Ser Cys Lys Ser Ser Gln Ser Leu Val Gly Thr
            20                  25                  30

Ser Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Ile Pro
    50                  55                  60

Asp Arg Phe Ser Gly Ser Gly Ser Glu Thr Asp Phe Thr Leu Lys Ile
65                  70                  75                  80

Ser Arg Val Glu Thr Asp Asp Leu Gly Val Tyr Tyr Cys Leu Gln Gly
                85                  90                  95

Ser His Phe Pro Leu Thr Phe Gly Ser Gly Thr Lys Leu Glu Ile Lys
            100                 105                 110

<210> SEQ ID NO 133
<211> LENGTH: 11
<212> TYPE: PRT
<213> ORGANISM: Artificial Sequence
<220> FEATURE:
<223> OTHER INFORMATION: CDR1-L of the so-called "8H2" anti-CD3 antibody

<400> SEQUENCE: 133

Gln Ser Leu Val Gly Thr Ser Gly Lys Thr Tyr
1               5                   10

<210> SEQ ID NO 134
<211> LENGTH: 9
<212> TYPE: PRT
<213> ORGANISM: Artificial Sequence
<220> FEATURE:
<223> OTHER INFORMATION: CDR3-L of the so-called "8H2" anti-CD3 antibody

<400> SEQUENCE: 134

Leu Gln Gly Ser His Phe Pro Leu Thr
1               5

<210> SEQ ID NO 135
<211> LENGTH: 121
<212> TYPE: PRT
<213> ORGANISM: Artificial Sequence
<220> FEATURE:
<223> OTHER INFORMATION: VH1a of humanized "20G6" anti-CD3 antibody

<400> SEQUENCE: 135

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gly Leu Glu Trp Val
        35                  40                  45

Ala Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asn Ser Lys Asn Thr
65                  70                  75                  80
```

```
Leu Tyr Leu Gln Met Asn Ser Leu Arg Ala Glu Asp Thr Ala Val Tyr
                85                  90                  95

Tyr Cys Arg Gly Val Tyr Ala Leu Ser Pro Phe Asp Tyr Trp Gly
            100                 105                 110

Gln Gly Thr Leu Val Thr Val Ser Ser
        115                 120

<210> SEQ ID NO 136
<211> LENGTH: 121
<212> TYPE: PRT
<213> ORGANISM: Artificial Sequence
<220> FEATURE:
<223> OTHER INFORMATION: VH1b of humanized "20G6" anti-CD3 antibody.

<400> SEQUENCE: 136

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gln Leu Glu Trp Val
        35                  40                  45

Ala Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Arg Gly Val Tyr Ala Leu Ser Pro Phe Asp Tyr Trp Gly
            100                 105                 110

Gln Gly Thr Leu Val Thr Val Ser Ser
        115                 120

<210> SEQ ID NO 137
<211> LENGTH: 121
<212> TYPE: PRT
<213> ORGANISM: Artificial Sequence
<220> FEATURE:
<223> OTHER INFORMATION: VH1c of humanized "20G6" anti-CD3 antibody.

<400> SEQUENCE: 137

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gln Leu Glu Trp Val
        35                  40                  45

Ala Gln Ile Lys Asp Lys Ser Asn Ser Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Arg Gly Val Tyr Ala Leu Ser Pro Phe Asp Tyr Trp Gly
            100                 105                 110

Gln Gly Thr Leu Val Thr Val Ser Ser
        115                 120

<210> SEQ ID NO 138
```

```
<211> LENGTH: 121
<212> TYPE: PRT
<213> ORGANISM: Artificial Sequence
<220> FEATURE:
<223> OTHER INFORMATION: VH1d of humanized "20G6" anti-CD3 antibody

<400> SEQUENCE: 138

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gln Leu Glu Trp Val
        35                  40                  45

Ala Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Arg Gly Val Tyr Tyr Ala Leu Ser Pro Phe Asp Tyr Trp Gly
            100                 105                 110

Gln Gly Thr Leu Val Thr Val Ser Ser
        115                 120

<210> SEQ ID NO 139
<211> LENGTH: 112
<212> TYPE: PRT
<213> ORGANISM: Artificial Sequence
<220> FEATURE:
<223> OTHER INFORMATION: VL1a of humanized "20G6" anti-CD3 antibody

<400> SEQUENCE: 139

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Asn
            20                  25                  30

Asn Gly Asn Thr Tyr Leu Ser Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Gln Gly Thr Lys Leu Glu Ile Lys
            100                 105                 110

<210> SEQ ID NO 140
<211> LENGTH: 112
<212> TYPE: PRT
<213> ORGANISM: Artificial Sequence
<220> FEATURE:
<223> OTHER INFORMATION: VL1b of humanized "20G6" anti-CD3 antibody

<400> SEQUENCE: 140

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Asn
            20                  25                  30
```

Asn Gly Asn Thr Tyr Leu Ser Trp Tyr Leu Gln Lys Pro Gly Gln Ser
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Gly
                85                  90                  95

Thr Gln Tyr Pro Phe Thr Phe Gly Gly Gly Thr Lys Val Glu Ile Lys
            100                 105                 110

<210> SEQ ID NO 141
<211> LENGTH: 112
<212> TYPE: PRT
<213> ORGANISM: Artificial Sequence
<220> FEATURE:
<223> OTHER INFORMATION: VL1c of humanized "20G6" anti-CD3 antibody.

<400> SEQUENCE: 141

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Val His Asn
                20                  25                  30

Asn Ala Asn Thr Tyr Leu Ser Trp Tyr Leu Gln Lys Pro Gly Gln Ser
            35                  40                  45

Pro Gln Ser Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Gly
                85                  90                  95

Thr Gln Tyr Pro Phe Thr Phe Gly Ser Gly Thr Lys Val Glu Ile Lys
            100                 105                 110

<210> SEQ ID NO 142
<211> LENGTH: 11
<212> TYPE: PRT
<213> ORGANISM: Artificial Sequence
<220> FEATURE:
<223> OTHER INFORMATION: CDR1-L of the VL1c variant of the humanized
      "20G6" anti-CD3 antibody.

<400> SEQUENCE: 142

Gln Ser Leu Val His Asn Asn Ala Asn Thr Tyr
 1               5                  10

<210> SEQ ID NO 143
<211> LENGTH: 112
<212> TYPE: PRT
<213> ORGANISM: Artificial Sequence
<220> FEATURE:
<223> OTHER INFORMATION: VL1d of humanized "20G6" anti-CD3 antibody

<400> SEQUENCE: 143

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Val His Asn
                20                  25                  30

Asn Gly Asn Thr Tyr Leu Ser Trp Tyr Leu Gln Lys Pro Gly Gln Ser
            35                  40                  45

Pro Gln Ser Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Gly Gln Gly
                85                  90                  95
Thr Gln Tyr Pro Phe Thr Phe Gly Ser Gly Thr Lys Val Glu Ile Lys
            100                 105                 110

<210> SEQ ID NO 144
<211> LENGTH: 121
<212> TYPE: PRT
<213> ORGANISM: Artificial Sequence
<220> FEATURE:
<223> OTHER INFORMATION: VH2a of humanized "20G6" anti-CD3 antibody

<400> SEQUENCE: 144

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Thr Lys Ala
            20                  25                  30
Trp Met Asn Trp Val Arg Gln Ala Pro Gly Lys Gly Leu Glu Trp Val
        35                  40                  45
Ser Gln Ile Lys Asp Lys Ser Asn Ser Tyr Ala Thr Tyr Tyr Ala Asp
    50                  55                  60
Ser Val Lys Gly Arg Phe Thr Ile Ser Arg Asp Asn Ala Lys Asn Ser
65                  70                  75                  80
Leu Tyr Leu Gln Met Asn Ser Leu Arg Asp Glu Asp Thr Ala Val Tyr
                85                  90                  95
Tyr Cys Arg Gly Val Tyr Tyr Ala Leu Ser Pro Phe Asp Tyr Trp Gly
            100                 105                 110
Gln Gly Thr Leu Val Thr Val Ser Ser
        115                 120

<210> SEQ ID NO 145
<211> LENGTH: 121
<212> TYPE: PRT
<213> ORGANISM: Artificial Sequence
<220> FEATURE:
<223> OTHER INFORMATION: VH2b of humanized "20G6" anti-CD3 antibody.

<400> SEQUENCE: 145

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Thr Lys Ala
            20                  25                  30
Trp Met His Trp Val Arg Gln Ala Pro Gly Lys Gly Leu Glu Trp Val
        35                  40                  45
Ser Gln Ile Lys Asp Lys Ser Asn Ser Tyr Ala Thr Tyr Tyr Ala Asp
    50                  55                  60
Ser Val Lys Gly Arg Phe Thr Ile Ser Arg Asp Asn Ala Lys Asn Ser
65                  70                  75                  80
Leu Tyr Leu Gln Met Asn Ser Leu Arg Asp Glu Asp Thr Ala Val Tyr
                85                  90                  95
Tyr Cys Arg Gly Val Tyr Tyr Ala Leu Ser Pro Phe Asp Tyr Trp Gly
            100                 105                 110
Gln Gly Thr Leu Val Thr Val Ser Ser
        115                 120

```
<210> SEQ ID NO 146
<211> LENGTH: 121
<212> TYPE: PRT
<213> ORGANISM: Artificial Sequence
<220> FEATURE:
<223> OTHER INFORMATION: VH2c of humanized "20G6" anti-CD3 antibody

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gln Leu Glu Trp Val
        35                  40                  45

Ser Gln Ile Lys Asp Lys Ser Asn Ser Tyr Ala Thr Tyr Tyr Ala Ala
    50                  55                  60

Ser Val Lys Gly Arg Phe Thr Ile Ser Arg Asp Asp Ala Lys Asn Ser
65                  70                  75                  80

Leu Tyr Leu Gln Met Asn Ser Leu Arg Asp Glu Asp Thr Ala Val Tyr
                85                  90                  95

Tyr Cys Arg Gly Val Tyr Tyr Ala Leu Ser Pro Phe Asp Tyr Trp Gly
            100                 105                 110

Gln Gly Thr Leu Val Thr Val Ser Ser
        115                 120

<210> SEQ ID NO 147
<211> LENGTH: 121
<212> TYPE: PRT
<213> ORGANISM: Artificial Sequence
<220> FEATURE:
<223> OTHER INFORMATION: VH2d of humanized "20G6" anti-CD3 antibody

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gln Leu Glu Trp Val
        35                  40                  45

Ser Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asp Ala Lys Asn Ser
65                  70                  75                  80

Leu Tyr Leu Gln Met Asn Ser Leu Arg Asp Glu Asp Thr Ala Val Tyr
                85                  90                  95

Tyr Cys Arg Gly Val Tyr Tyr Ala Leu Ser Pro Phe Asp Tyr Trp Gly
            100                 105                 110

Gln Gly Thr Leu Val Thr Val Ser Ser
        115                 120

<210> SEQ ID NO 148
<211> LENGTH: 112
<212> TYPE: PRT
<213> ORGANISM: Artificial Sequence
<220> FEATURE:
<223> OTHER INFORMATION: VL2a of humanized "20G6" anti-CD3 antibody

<400> SEQUENCE: 148
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Asn
            20                  25                  30

Asn Gly Asn Thr Tyr Leu Asp Trp Tyr Leu Gln Lys Pro Gly Gln Ser
        35                  40                  45

Pro Gln Leu Leu Ile Tyr Lys Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Gly Gly Thr Lys Leu Glu Ile Lys
            100                 105                 110
```

<210> SEQ ID NO 149
<211> LENGTH: 112
<212> TYPE: PRT
<213> ORGANISM: Artificial Sequence
<220> FEATURE:
<223> OTHER INFORMATION: VL2b of humanized "20G6" anti-CD3 antibody

<400> SEQUENCE: 149

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Asn
            20                  25                  30

Asn Gly Asn Thr Tyr Leu Asp Trp Tyr Leu Gln Lys Pro Gly Gln Ser
        35                  40                  45

Pro Gln Leu Leu Ile Tyr Lys Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Gly Gly Thr Lys Val Glu Ile Lys
            100                 105                 110
```

<210> SEQ ID NO 150
<211> LENGTH: 112
<212> TYPE: PRT
<213> ORGANISM: Artificial Sequence
<220> FEATURE:
<223> OTHER INFORMATION: VL2c of humanized "20G6" anti-CD3 antibody

<400> SEQUENCE: 150

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Asn
            20                  25                  30

Asn Gly Asn Thr Tyr Leu Asp Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95
```

```
Thr Gln Tyr Pro Phe Thr Phe Gly Ser Gly Thr Lys Val Glu Ile Lys
            100                 105                 110
```

<210> SEQ ID NO 151
<211> LENGTH: 112
<212> TYPE: PRT
<213> ORGANISM: Artificial Sequence
<220> FEATURE:
<223> OTHER INFORMATION: VL2d of humanized "20G6" anti-CD3 antibody

<400> SEQUENCE: 151

```
Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Val His Asn
            20                  25                  30

Asn Gly Asn Thr Tyr Leu Ser Trp Tyr Leu Gln Lys Pro Gly Gln Ser
        35                  40                  45

Pro Gln Ser Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Ser Gly Thr Lys Val Glu Ile Lys
            100                 105                 110
```

<210> SEQ ID NO 152
<211> LENGTH: 121
<212> TYPE: PRT
<213> ORGANISM: Artificial Sequence
<220> FEATURE:
<223> OTHER INFORMATION: VH3a of humanized "20G6" anti-CD3 antibody

<400> SEQUENCE: 152

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Lys Ala
            20                  25                  30

Trp Met His Trp Val Arg Gln Ala Pro Gly Gln Gly Leu Glu Trp Met
        35                  40                  45

Gly Gln Ile Lys Asp Lys Ser Asn Ser Tyr Ala Thr Tyr Tyr Ala Gln
    50                  55                  60

Lys Phe Gln Gly Arg Val Thr Met Thr Arg Asp Thr Ser Thr Ser Thr
65                  70                  75                  80

Val Tyr Met Glu Leu Ser Ser Leu Arg Ser Glu Asp Thr Ala Val Tyr
                85                  90                  95

Tyr Cys Arg Gly Val Tyr Tyr Ala Leu Ser Pro Phe Asp Tyr Trp Gly
            100                 105                 110

Gln Gly Thr Leu Val Thr Val Ser Ser
        115                 120
```

<210> SEQ ID NO 153
<211> LENGTH: 121
<212> TYPE: PRT
<213> ORGANISM: Artificial Sequence
<220> FEATURE:
<223> OTHER INFORMATION: VH3b of humanized "20G6" anti-CD3 antibody

<400> SEQUENCE: 153

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Lys Ala
            20                  25                  30

Trp Met His Trp Val Arg Gln Ala Pro Gly Lys Gln Leu Glu Trp Met
        35                  40                  45

Gly Gln Ile Lys Asp Lys Ser Asn Ser Tyr Ala Thr Tyr Tyr Ala Gln
    50                  55                  60

Lys Phe Gln Gly Arg Val Thr Met Thr Arg Asp Thr Ser Thr Ser Thr
65                  70                  75                  80

Val Tyr Met Glu Leu Ser Ser Leu Arg Ser Glu Asp Thr Ala Val Tyr
                85                  90                  95

Tyr Cys Arg Gly Val Tyr Tyr Ala Leu Ser Pro Phe Asp Tyr Trp Gly
            100                 105                 110

Gln Gly Thr Leu Val Thr Val Ser Ser
        115                 120

<210> SEQ ID NO 154
<211> LENGTH: 112
<212> TYPE: PRT
<213> ORGANISM: Artificial Sequence
<220> FEATURE:
<223> OTHER INFORMATION: VL3a of humanized "20G6" anti-CD3 antibody

<400> SEQUENCE: 154

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Val His Asn
            20                  25                  30

Asn Gly Asn Thr Tyr Leu Ala Trp Tyr Gln Gln Lys Pro Gly Gln Ser
        35                  40                  45

Pro Lys Leu Leu Ile Tyr Lys Val Ser Asn Arg Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gly Gln Gly
                85                  90                  95

Thr Gln Tyr Pro Phe Thr Phe Gly Gly Gly Thr Lys Val Glu Ile Lys
            100                 105                 110

<210> SEQ ID NO 155
<211> LENGTH: 112
<212> TYPE: PRT
<213> ORGANISM: Artificial Sequence
<220> FEATURE:
<223> OTHER INFORMATION: VL3b of humanized "20G6" anti-CD3 antibody

<400> SEQUENCE: 155

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Val His Asn
            20                  25                  30

Asn Gly Asn Thr Tyr Leu Ala Trp Tyr Gln Gln Lys Pro Gly Gln Ser
        35                  40                  45

Pro Lys Leu Leu Ile Tyr Lys Val Ser Asn Arg Glu Ser Gly Val Pro
    50                  55                  60

Asp Arg Phe Ser Gly Ser Gly Ser Gly Thr Asp Phe Thr Leu Thr Ile
65                  70                  75                  80

```
Ser Ser Leu Gln Ala Glu Asp Val Ala Val Tyr Tyr Cys Gly Gln Gly
                85                  90                  95

Thr Gln Tyr Pro Phe Thr Phe Gly Gln Gly Thr Lys Leu Glu Ile Lys
            100                 105                 110
```

<210> SEQ ID NO 156
<211> LENGTH: 112
<212> TYPE: PRT
<213> ORGANISM: Artificial Sequence
<220> FEATURE:
<223> OTHER INFORMATION: VL3c of humanized "20G6" anti-CD3 antibody

<400> SEQUENCE: 156

```
Asp Ile Val Met Thr Gln Ser Pro Ser Ser Leu Ala Val Ser Leu Gly
1               5                   10                  15

Glu Arg Ala Thr Ile Asn Cys Lys Ser Ser Gln Ser Leu Val His Asn
            20                  25                  30

Asn Gly Asn Thr Tyr Leu Ala Trp Tyr Gln Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gly Gln Gly
                85                  90                  95

Thr Gln Tyr Pro Phe Thr Phe Gly Ser Gly Thr Lys Val Glu Ile Lys
            100                 105                 110
```

<210> SEQ ID NO 157
<211> LENGTH: 112
<212> TYPE: PRT
<213> ORGANISM: Artificial Sequence
<220> FEATURE:
<223> OTHER INFORMATION: VL3d of humanized "20G6" anti-CD3 antibody

<400> SEQUENCE: 157

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Val His Asn
            20                  25                  30

Asn Gly Asn Thr Tyr Leu Ser Trp Tyr Gln Gln Lys Pro Gly Gln Ser
        35                  40                  45

Pro Lys Ser Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gly Gln Gly
                85                  90                  95

Thr Gln Tyr Pro Phe Thr Phe Gly Ser Gly Thr Lys Val Glu Ile Lys
            100                 105                 110
```

<210> SEQ ID NO 158
<211> LENGTH: 112
<212> TYPE: PRT
<213> ORGANISM: Artificial Sequence
<220> FEATURE:
<223> OTHER INFORMATION: VL1A of humanized "4B4" anti-CD3 antibody

<400> SEQUENCE: 158

Asp Val Val Met Thr Gln Thr Pro Val Ser Leu Ser Val Ser Val Gly
1               5                   10                  15

Gly Arg Val Ser Ile Ser Cys Arg Ser Ser Gln Ser Leu Val His Asp
            20                  25                  30

Asn Gly Asn Thr Tyr Leu Ser Trp Ser Leu Gln Lys Pro Gly Lys Ser
        35                  40                  45

Pro Lys Val Leu Ile Tyr Lys Val Ser Asn Arg Phe Ser Gly Val Ser
    50                  55                  60

Ser Arg Phe Thr Gly Ser Gly Ser Gly Thr Asp Phe Thr Leu Lys Ile
65              70                  75                  80

Ser Ser Val Gln Pro Asp Asp Leu Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110

<210> SEQ ID NO 159
<211> LENGTH: 112
<212> TYPE: PRT
<213> ORGANISM: Artificial Sequence
<220> FEATURE:
<223> OTHER INFORMATION: VL1B of humanized "4B4" anti-CD3 antibody.

<400> SEQUENCE: 159

Asp Val Val Met Thr Gln Thr Pro Val Ser Leu Ser Val Ser Val Gly
1               5                   10                  15

Gly Arg Val Ser Ile Ser Cys Arg Ser Ser Gln Ser Leu Val His Asp
            20                  25                  30

Asn Ala Asn Thr Tyr Leu Ser Trp Ser Leu Gln Lys Pro Gly Lys Ser
        35                  40                  45

Pro Lys Val Leu Ile Tyr Lys Val Ser Asn Arg Phe Ser Gly Val Ser
    50                  55                  60

Ser Arg Phe Thr Gly Ser Gly Ser Gly Thr Asp Phe Thr Leu Lys Ile
65              70                  75                  80

Ser Ser Val Gln Pro Asp Asp Leu Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110

<210> SEQ ID NO 160
<211> LENGTH: 112
<212> TYPE: PRT
<213> ORGANISM: Artificial Sequence
<220> FEATURE:
<223> OTHER INFORMATION: VL2A of humanized "4B4" anti-CD3 antibody

<400> SEQUENCE: 160

Asp Val Val Met Thr Gln Thr Pro Val Ser Leu Ser Val Ser Pro Gly
1               5                   10                  15

Gly Pro Val Ser Ile Ser Cys Arg Ser Ser Gln Ser Leu Val His Asp
            20                  25                  30

Asn Gly Asn Thr Tyr Leu Ser Trp Ser Leu Gln Lys Pro Gly Gln Ser
        35                  40                  45

Pro Gln Val Leu Ile Tyr Lys Val Ser Asn Arg Phe Ser Gly Val Ser
    50                  55                  60

Asp Arg Phe Thr Gly Ser Gly Ser Gly Thr Asp Phe Thr Leu Lys Ile
65              70                  75                  80

Ser Arg Val Glu Pro Asp Asp Leu Gly Val Tyr Tyr Cys Gly Gln Gly
                85                  90                  95

```
Thr Gln Tyr Pro Phe Thr Phe Gly Ser Gly Thr Lys Leu Glu Ile Lys
            100                 105                 110
```

<210> SEQ ID NO 161
<211> LENGTH: 112
<212> TYPE: PRT
<213> ORGANISM: Artificial Sequence
<220> FEATURE:
<223> OTHER INFORMATION: VL2B of humanized "4B4" anti-CD3 antibody

<400> SEQUENCE: 161

```
Asp Val Val Met Thr Gln Thr Pro Val Ser Leu Ser Val Ser Pro Gly
1               5                   10                  15

Gly Pro Val Ser Ile Ser Cys Arg Ser Ser Gln Ser Leu Val His Asp
            20                  25                  30

Asn Ala Asn Thr Tyr Leu Ser Trp Ser Leu Gln Lys Pro Gly Gln Ser
        35                  40                  45

Pro Gln Val Leu Ile Tyr Lys Val Ser Asn Arg Phe Ser Gly Val Ser
    50                  55                  60

Asp Arg Phe Thr Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110
```

<210> SEQ ID NO 162
<211> LENGTH: 112
<212> TYPE: PRT
<213> ORGANISM: Artificial Sequence
<220> FEATURE:
<223> OTHER INFORMATION: VL1Cmodif1 of humanized "4B4" anti-CD3 antibody

<400> SEQUENCE: 162

```
Asp Val Val Met Thr Gln Ser Pro Leu Ser Leu Pro Val Thr Leu Gly
1               5                   10                  15

Gln Pro Val Ser Ile Ser Cys Arg Ser Ser Gln Ser Leu Val His Asp
            20                  25                  30

Asn Gly Asn Thr Tyr Leu Ser Trp Ser Leu Gln Arg Pro Gly Gln Ser
        35                  40                  45

Pro Arg Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110
```

<210> SEQ ID NO 163
<211> LENGTH: 112
<212> TYPE: PRT
<213> ORGANISM: Artificial Sequence
<220> FEATURE:
<223> OTHER INFORMATION: VL1Cmodif2 of humanized "4B4" anti-CD3 antibody

<400> SEQUENCE: 163

```
Asp Val Val Met Thr Gln Ser Pro Leu Ser Leu Ser Val Thr Leu Gly
1               5                   10                  15
```

```
Gln Pro Val Ser Ile Ser Cys Arg Ser Ser Gln Ser Leu Val His Asp
            20                  25                  30

Asn Gly Asn Thr Tyr Leu Ser Trp Ser Leu Gln Arg Pro Gly Gln Ser
        35                  40                  45

Pro Arg Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110
```

<210> SEQ ID NO 164
<211> LENGTH: 112
<212> TYPE: PRT
<213> ORGANISM: Artificial Sequence
<220> FEATURE:
<223> OTHER INFORMATION: VL1Cmodif3 of humanized "4B4" anti-CD3 antibody

<400> SEQUENCE: 164

```
Asp Val Val Met Thr Gln Ser Pro Leu Ser Leu Ser Val Thr Leu Gly
1               5                   10                  15

Gln Pro Val Ser Ile Ser Cys Arg Ser Ser Gln Ser Leu Val His Asp
            20                  25                  30

Asn Ala Asn Thr Tyr Leu Ser Trp Ser Leu Gln Arg Pro Gly Gln Ser
        35                  40                  45

Pro Arg Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110
```

<210> SEQ ID NO 165
<211> LENGTH: 112
<212> TYPE: PRT
<213> ORGANISM: Artificial Sequence
<220> FEATURE:
<223> OTHER INFORMATION: VL1Amodif1of humanized "4B4" anti-CD3 antibody

<400> SEQUENCE: 165

```
Asp Val Val Met Thr Gln Ser Pro Leu Ser Leu Pro Val Thr Leu Gly
1               5                   10                  15

Gln Pro Val Ser Ile Ser Cys Arg Ser Ser Gln Ser Leu Val His Asp
            20                  25                  30

Asn Gly Asn Thr Tyr Leu Asn Trp Phe Leu Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Gln Gly Thr Lys Leu Glu Ile Lys
            100                 105                 110
```

<210> SEQ ID NO 166
<211> LENGTH: 112
<212> TYPE: PRT
<213> ORGANISM: Artificial Sequence
<220> FEATURE:
<223> OTHER INFORMATION: VL1Amodif2of humanized "4B4" anti-CD3 antibody

<400> SEQUENCE: 166

```
Asp Val Val Met Thr Gln Ser Pro Leu Ser Leu Ser Val Thr Leu Gly
1               5                   10                  15

Gln Pro Val Ser Ile Ser Cys Arg Ser Gln Ser Leu Val His Asp
            20                  25                  30

Asn Gly Asn Thr Tyr Leu Asn Trp Phe Leu Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Gly
                85                  90                  95

Thr Gln Tyr Pro Phe Thr Phe Gly Gln Gly Thr Lys Leu Glu Ile Lys
            100                 105                 110
```

<210> SEQ ID NO 167
<211> LENGTH: 112
<212> TYPE: PRT
<213> ORGANISM: Artificial Sequence
<220> FEATURE:
<223> OTHER INFORMATION: VL1Amodif3 of humanized "4B4" anti-CD3 antibody

<400> SEQUENCE: 167

```
Asp Val Val Met Thr Gln Ser Pro Leu Ser Leu Ser Val Thr Leu Gly
1               5                   10                  15

Gln Pro Val Ser Ile Ser Cys Arg Ser Gln Ser Leu Val His Asp
            20                  25                  30

Asn Gly Asn Thr Tyr Leu Asn Trp Phe Leu Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110
```

<210> SEQ ID NO 168
<211> LENGTH: 112
<212> TYPE: PRT
<213> ORGANISM: Artificial Sequence
<220> FEATURE:
<223> OTHER INFORMATION: VL2C of humanized "4B4" anti-CD3 antibody

<400> SEQUENCE: 168

```
Asp Ile Val Met Thr Gln Thr Pro Leu Ser Leu Ser Val Thr Pro Gly
1               5                   10                  15

Gln Pro Ala Ser Ile Ser Cys Lys Ser Gln Ser Leu Val His Asp
            20                  25                  30
```

```
Asn Gly Asn Thr Tyr Leu Ser Trp Ser Leu Gln Lys Pro Gly Gln Ser
            35                  40                  45

Pro Gln Val Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gly Gln Gly
                 85                  90                  95

Thr Gln Tyr Pro Phe Thr Phe Gly Ser Gly Thr Lys Leu Glu Ile Lys
            100                 105                 110

<210> SEQ ID NO 169
<211> LENGTH: 112
<212> TYPE: PRT
<213> ORGANISM: Artificial Sequence
<220> FEATURE:
<223> OTHER INFORMATION: VL2D of humanized "4B4" anti-CD3 antibody

<400> SEQUENCE: 169

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Val His Asp
             20                  25                  30

Asn Gly Asn Thr Tyr Leu Ser Trp Tyr Leu Gln Lys Pro Gly Gln Ser
            35                  40                  45

Pro Gln Ser Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gly Gln Gly
                 85                  90                  95

Thr Gln Tyr Pro Phe Thr Phe Gly Ser Gly Thr Lys Val Glu Ile Lys
            100                 105                 110

<210> SEQ ID NO 170
<211> LENGTH: 112
<212> TYPE: PRT
<213> ORGANISM: Artificial Sequence
<220> FEATURE:
<223> OTHER INFORMATION: VL2F of humanized "4B4" anti-CD3 antibody

<400> SEQUENCE: 170

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Val His Asp
             20                  25                  30

Asn Ala Asn Thr Tyr Leu Ser Trp Tyr Leu Gln Lys Pro Gly Gln Ser
            35                  40                  45

Pro Gln Ser Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gly Gln Gly
                 85                  90                  95

Thr Gln Tyr Pro Phe Thr Phe Gly Ser Gly Thr Lys Val Glu Ile Lys
            100                 105                 110

<210> SEQ ID NO 171
```

```
<211> LENGTH: 121
<212> TYPE: PRT
<213> ORGANISM: Artificial Sequence
<220> FEATURE:
<223> OTHER INFORMATION: VH1A of humanized "4B4" anti-CD3 antibody

<400> SEQUENCE: 171

Gln Val Gln Leu Val Glu Thr Gly Gly Gly Leu Val Lys Pro Gly Gln
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gly Leu Glu Trp Val
        35                  40                  45

Ala Gln Ile Lys Ala Arg Ser Asn Asn Tyr Ala Thr Tyr Tyr Ala Glu
    50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Thr Pro Glu Asp Thr Ala Ile Tyr
                85                  90                  95

Tyr Cys Arg Gly Thr Tyr Tyr Ala Ser Lys Pro Phe Asp Tyr Trp Gly
            100                 105                 110

Gln Gly Val Met Val Thr Val Ser Ser
        115                 120

<210> SEQ ID NO 172
<211> LENGTH: 121
<212> TYPE: PRT
<213> ORGANISM: Artificial Sequence
<220> FEATURE:
<223> OTHER INFORMATION: VH1B of humanized "4B4" anti-CD3 antibody

<400> SEQUENCE: 172

Gln Val Gln Leu Val Glu Thr Gly Gly Gly Leu Val Lys Pro Gly Gln
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gly Leu Glu Trp Val
        35                  40                  45

Ala Gln Ile Lys Ala Arg Ser Asn Asn Tyr Ala Thr Tyr Tyr Ala Val
    50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Thr Pro Glu Asp Thr Ala Ile Tyr
                85                  90                  95

Tyr Cys Arg Gly Thr Tyr Tyr Ala Ser Lys Pro Phe Asp Tyr Trp Gly
            100                 105                 110

Gln Gly Val Met Val Thr Val Ser Ser
        115                 120

<210> SEQ ID NO 173
<211> LENGTH: 121
<212> TYPE: PRT
<213> ORGANISM: Artificial Sequence
<220> FEATURE:
<223> OTHER INFORMATION: VH2A of humanized "4B4" anti-CD3 antibody

<400> SEQUENCE: 173

Glu Val Gln Leu Val Glu Thr Gly Gly Gly Leu Val Gln Pro Gly Gly
1               5                   10                  15
```

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gly Leu Glu Trp Val
            35                  40                  45

Ala Gln Ile Lys Ala Arg Ser Asn Asn Tyr Ala Thr Tyr Tyr Ala Glu
        50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Arg Ala Glu Asp Thr Ala Ile Tyr
                85                  90                  95

Tyr Cys Arg Gly Thr Tyr Tyr Ala Ser Lys Pro Phe Asp Tyr Trp Gly
                100                 105                 110

Gln Gly Val Met Val Thr Val Ser Ser
            115                 120

<210> SEQ ID NO 174
<211> LENGTH: 121
<212> TYPE: PRT
<213> ORGANISM: Artificial Sequence
<220> FEATURE:
<223> OTHER INFORMATION: VH2B of humanized "4B4" anti-CD3 antibody

<400> SEQUENCE: 174

Glu Val Gln Leu Val Glu Thr Gly Gly Gly Leu Val Gln Pro Gly Gly
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gly Leu Glu Trp Val
            35                  40                  45

Ala Gln Ile Lys Ala Arg Ser Asn Asn Tyr Ala Thr Tyr Tyr Ala Asp
        50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Arg Ala Glu Asp Thr Ala Ile Tyr
                85                  90                  95

Tyr Cys Arg Gly Thr Tyr Tyr Ala Ser Lys Pro Phe Asp Tyr Trp Gly
                100                 105                 110

Gln Gly Val Met Val Thr Val Ser Ser
            115                 120

<210> SEQ ID NO 175
<211> LENGTH: 121
<212> TYPE: PRT
<213> ORGANISM: Artificial Sequence
<220> FEATURE:
<223> OTHER INFORMATION: VH6Bmodif1 of humanized "4B4" anti-CD3 antibody

<400> SEQUENCE: 175

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gln Leu Glu Trp Val
            35                  40                  45

Ala Gln Ile Lys Ala Arg Ser Asn Asn Tyr Ala Thr Tyr Tyr Ala Glu
        50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Arg Ala Glu Asp Thr Ala Val Tyr
                85                  90                  95

Tyr Cys Arg Gly Thr Tyr Tyr Ala Ser Lys Pro Phe Asp Tyr Trp Gly
            100                 105                 110

Gln Gly Thr Thr Val Thr Val Ser Ser
        115                 120

<210> SEQ ID NO 176
<211> LENGTH: 121
<212> TYPE: PRT
<213> ORGANISM: Artificial Sequence
<220> FEATURE:
<223> OTHER INFORMATION: VH6Bmodif2 of humanized "4B4" anti-CD3 antibody

<400> SEQUENCE: 176

Gln Val Gln Leu Val Glu Ser Gly Gly Arg Val Val Gln Pro Gly Arg
1               5                   10                  15

Ser Leu Arg Leu Thr Cys Ala Ala Ser Gly Phe Thr Phe Ser Asn Ala
            20                  25                  30

Trp Met His Trp Val Arg Gln Ala Pro Gly Lys Gln Leu Glu Trp Val
        35                  40                  45

Ala Gln Ile Lys Ala Arg Ser Asn Asn Tyr Ala Thr Tyr Tyr Ala Glu
    50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Arg Ala Glu Asp Thr Ala Val Tyr
                85                  90                  95

Tyr Cys Arg Gly Thr Tyr Tyr Ala Ser Lys Pro Phe Asp Tyr Trp Gly
            100                 105                 110

Gln Gly Thr Thr Val Thr Val Ser Ser
        115                 120

<210> SEQ ID NO 177
<211> LENGTH: 121
<212> TYPE: PRT
<213> ORGANISM: Artificial Sequence
<220> FEATURE:
<223> OTHER INFORMATION: VH6Amodif1 of humanized "4B4" anti-CD3 antibody

<400> SEQUENCE: 177

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Ala Arg Ser Asn Asn Tyr Ala Thr Tyr Tyr Ala Asp
    50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Arg Ala Glu Asp Thr Ala Val Tyr
                85                  90                  95

Tyr Cys Arg Gly Thr Tyr Tyr Ala Ser Lys Pro Phe Asp Tyr Trp Gly
            100                 105                 110

Gln Gly Thr Thr Val Thr Val Ser Ser
        115                 120

```
<210> SEQ ID NO 178
<211> LENGTH: 121
<212> TYPE: PRT
<213> ORGANISM: Artificial Sequence
<220> FEATURE:
<223> OTHER INFORMATION: VH6Amodif2 of humanized "4B4" anti-CD3 antibody

<400> SEQUENCE: 178

Gln Val Gln Leu Val Glu Ser Gly Gly Arg Val Val Gln Pro Gly Arg
1               5                   10                  15

Ser Leu Arg Leu Thr Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Ala Arg Ser Asn Asn Tyr Ala Thr Tyr Tyr Ala Asp
    50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Arg Ala Glu Asp Thr Ala Val Tyr
                85                  90                  95

Tyr Cys Arg Gly Thr Tyr Tyr Ala Ser Lys Pro Phe Asp Tyr Trp Gly
            100                 105                 110

Gln Gly Thr Thr Val Thr Val Ser Ser
        115                 120

<210> SEQ ID NO 179
<211> LENGTH: 121
<212> TYPE: PRT
<213> ORGANISM: Artificial Sequence
<220> FEATURE:
<223> OTHER INFORMATION: VH6Amodif3 of humanized "4B4" anti-CD3 antibody

<400> SEQUENCE: 179

Gln Val Gln Leu Val Glu Ser Gly Gly Arg Val Val Gln Pro Gly Arg
1               5                   10                  15

Ser Leu Arg Leu Thr Cys Ala Ala Ser Gly Phe Thr Phe Ser Asn Ala
            20                  25                  30

Trp Met His Trp Val Arg Gln Ala Pro Gly Lys Gln Leu Glu Trp Val
        35                  40                  45

Ala Gln Ile Lys Ala Arg Ser Asn Asn Tyr Ala Thr Tyr Tyr Ala Asp
    50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Arg Ala Glu Asp Thr Ala Val Tyr
                85                  90                  95

Tyr Cys Arg Gly Thr Tyr Tyr Ala Ser Lys Pro Phe Asp Tyr Trp Gly
            100                 105                 110

Gln Gly Thr Thr Val Thr Val Ser Ser
        115                 120

<210> SEQ ID NO 180
<211> LENGTH: 121
<212> TYPE: PRT
<213> ORGANISM: Artificial Sequence
<220> FEATURE:
<223> OTHER INFORMATION: VH6C of humanized "4B4" anti-CD3 antibody

<400> SEQUENCE: 180

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Asn Ala
        20                  25                  30

Trp Met His Trp Val Arg Gln Ala Pro Gly Lys Gln Leu Glu Trp Val
            35                  40                  45

Ala Gln Ile Lys Ala Arg Ser Asn Asn Tyr Ala Thr Tyr Tyr Ala Asp
    50                  55                  60

Ser Val Lys Gly Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Arg Gly Thr Tyr Tyr Ala Ser Lys Pro Phe Asp Tyr Trp Gly
            100                 105                 110

Gln Gly Thr Leu Val Thr Val Ser Ser
        115                 120
```

<210> SEQ ID NO 181
<211> LENGTH: 121
<212> TYPE: PRT
<213> ORGANISM: Artificial Sequence
<220> FEATURE:
<223> OTHER INFORMATION: VH6D of humanized "4B4" anti-CD3 antibody

<400> SEQUENCE: 181

```
Gln Val Gln Leu Val Glu Ser Gly Gly Gly Val Val Gln Pro Gly Arg
1               5                   10                  15

Ser Leu Arg Leu Ser Cys Ala Thr Ser Gly Phe Thr Phe Ser Asn Ala
            20                  25                  30

Trp Met His Trp Val Arg Gln Ala Pro Gly Lys Gln Leu Glu Trp Val
            35                  40                  45

Ala Gln Ile Lys Ala Arg Ser Asn Asn Tyr Ala Thr Tyr Tyr Ala Asp
    50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Arg Ala Glu Asp Thr Ala Val Tyr
                85                  90                  95

Tyr Cys Arg Gly Thr Tyr Tyr Ala Ser Lys Pro Phe Asp Tyr Trp Gly
            100                 105                 110

Gln Gly Thr Leu Val Thr Val Ser Ser
        115                 120
```

<210> SEQ ID NO 182
<211> LENGTH: 112
<212> TYPE: PRT
<213> ORGANISM: Artificial Sequence
<220> FEATURE:
<223> OTHER INFORMATION: VL "D7-VK3mut" of humanized "4B4" anti-CD3
      antibody

<400> SEQUENCE: 182

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Asp
            20                  25                  30

Asn Gly Asn Thr Tyr Leu Ser Trp Ser Gln Gln Arg Pro Gly Gln Ser
            35                  40                  45

Pro Arg Val Leu Ile Tyr Lys Val Ser Asn Arg Phe Ser Gly Val Pro
    50                  55                  60
```

-continued

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gly Gln Gly
                 85                  90                  95

Thr Gln Tyr Pro Phe Thr Phe Gly Gln Gly Thr Lys Val Glu Ile Lys
            100                 105                 110

<210> SEQ ID NO 183
<211> LENGTH: 121
<212> TYPE: PRT
<213> ORGANISM: Artificial Sequence
<220> FEATURE:
<223> OTHER INFORMATION: D7-VH1mut of humanized "4B4" anti-CD3 antibody

<400> SEQUENCE: 183

Glu Val Gln Leu Val Glu Ser Gly Gly Gly Leu Val Lys Pro Gly Gly
  1               5                  10                  15

Ser Leu Arg Leu Ser Cys Ala Thr Ser Gly Phe Thr Phe Ser Asn Ala
                 20                  25                  30

Trp Met His Trp Val Arg Gln Ala Pro Gly Lys Gly Leu Glu Trp Val
             35                  40                  45

Gly Gln Ile Lys Ala Arg Ser Asn Asn Tyr Ala Thr Tyr Tyr Ala Glu
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Arg Gly Thr Tyr Tyr Ala Ser Lys Pro Phe Asp Tyr Trp Gly
            100                 105                 110

Gln Gly Thr Leu Val Thr Val Ser Ser
        115                 120

<210> SEQ ID NO 184
<211> LENGTH: 11
<212> TYPE: PRT
<213> ORGANISM: Artificial Sequence
<220> FEATURE:
<223> OTHER INFORMATION: CDR1-L of the VL1B, VL2B, VL1Cmofif3 and VL2F
      variants of the humanized "4B4" anti-CD3 antibody

<400> SEQUENCE: 184

Gln Ser Leu Val His Asp Asn Ala Asn Thr Tyr
  1               5                  10

<210> SEQ ID NO 185
<211> LENGTH: 182
<212> TYPE: PRT
<213> ORGANISM: Homo sapiens

<400> SEQUENCE: 185

Met Glu Gln Gly Lys Gly Leu Ala Val Leu Ile Leu Ala Ile Ile Leu
  1               5                  10                  15

Leu Gln Gly Thr Leu Ala Gln Ser Ile Lys Gly Asn His Leu Val Lys
                 20                  25                  30

Val Tyr Asp Tyr Gln Glu Asp Gly Ser Val Leu Leu Thr Cys Asp Ala
             35                  40                  45

Glu Ala Lys Asn Ile Thr Trp Phe Lys Asp Gly Lys Met Ile Gly Phe
 50                  55                  60

Leu Thr Glu Asp Lys Lys Lys Trp Asn Leu Gly Ser Asn Ala Lys Asp
 65                  70                  75                  80
```

```
Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Gln Tyr Ser His Leu Gln Gly
                165                 170                 175

Asn Gln Leu Arg Arg Asn
            180

<210> SEQ ID NO 186
<211> LENGTH: 249
<212> TYPE: PRT
<213> ORGANISM: Artificial Sequence
<220> FEATURE:
<223> OTHER INFORMATION: heavy chain sequence of "20G6-F3" Fab

<400> SEQUENCE: 186

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Thr Lys Ala
            20                  25                  30

Trp Met His Trp Val Arg Gln Ser Pro Glu Lys Gln Leu Glu Trp Val
        35                  40                  45

Ala Gln Ile Lys Asp Lys Ser Asn Ser Tyr Ala Thr Tyr Tyr Ala Glu
    50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Lys Glu Glu Asp Thr Ala Ile Tyr
                85                  90                  95

Tyr Cys Arg Gly Val Tyr Tyr Ala Leu Ser Pro Phe Asp Tyr Trp Gly
            100                 105                 110

Gln Gly Val Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Glu Gln Lys Leu Ile Ser Glu Glu Asp Leu Asn
225                 230                 235                 240

Gly Ala Ala His His His His His His
            245
```

```
<210> SEQ ID NO 187
<211> LENGTH: 219
<212> TYPE: PRT
<213> ORGANISM: Artificial Sequence
<220> FEATURE:
<223> OTHER INFORMATION: light chain sequence of "20G6-F3" Fab

<400> SEQUENCE: 187

Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Leu Ser Trp Tyr Leu Gln Lys Pro Gly Gln Ser
        35                  40                  45

Pro Gln Ser Leu Ile Tyr Lys Val Ser Asn Arg Phe Ser Gly Phe Ser
    50                  55                  60

Asp Arg Phe Ser Gly Ser Gly Ser Gly Thr Asp Phe Thr Leu Lys Ile
65                  70                  75                  80

Ser Arg Val Asp Pro Asp Asp Leu Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 188
<211> LENGTH: 250
<212> TYPE: PRT
<213> ORGANISM: Artificial Sequence
<220> FEATURE:
<223> OTHER INFORMATION: heavy chain sequence of "4E7-C9" Fab

<400> SEQUENCE: 188

Glu Val Gln Val Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Asp Lys Ser Asn Asn Tyr Ala Thr Tyr Tyr Ala Glu
    50                  55                  60

Ser Leu Lys Gly Arg Phe Thr Ile Ser Arg Asp Asp Pro Lys Arg Ser
65                  70                  75                  80

Ile Tyr Leu Gln Met Asn Ser Leu Arg Glu Glu Asp Thr Ala Ile Tyr
```

```
            85                  90                  95
Tyr Cys Arg Tyr Val His Tyr Gly Ile Gly Tyr Ala Met Asp Ala Trp
            100                 105                 110
Gly Gln Gly Thr Ser Val Thr Val Ser Ser Ala Ser Thr Lys Gly Pro
            115                 120                 125
Ser Val Phe Pro Leu Ala Pro Ser Ser Lys Ser Thr Ser Gly Gly Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
            165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
            195                 200                 205
His Lys Pro Ser Asn Thr Lys Val Asp Lys Lys Val Glu Pro Lys Ser
            210                 215                 220
Cys Asp Lys Thr His Thr Glu Gln Lys Leu Ile Ser Glu Glu Asp Leu
225                 230                 235                 240
Asn Gly Ala Ala His His His His His
            245                 250

<210> SEQ ID NO 189
<211> LENGTH: 219
<212> TYPE: PRT
<213> ORGANISM: Artificial Sequence
<220> FEATURE:
<223> OTHER INFORMATION: light chain sequence of "4E7-C9" Fab

<400> SEQUENCE: 189

Asp Val Val Met Thr Gln Thr Pro Val Ser Leu Ser Val Ser Leu Gly
1               5                   10                  15
Gly Gln Val Ser Ile Ser Cys Arg Ser Ser Gln Ser Leu Glu His Asn
            20                  25                  30
Asn Gly Asn Thr Tyr Leu Ser Trp Tyr Leu Gln Lys Pro Gly Gln Ser
            35                  40                  45
Pro Gln Pro Leu Ile Tyr Lys Val Ser Asn Arg Phe Ser Gly Ile Ser
            50                  55                  60
Asp Arg Phe Ser Gly Ser Gly Ser Gly Thr Asp Phe Thr Leu Lys Ile
65                  70                  75                  80
Ser Arg Val Glu Pro Asp Asp Leu Gly Val Tyr Tyr Cys Gly Gln Gly
            85                  90                  95
Thr Gln Tyr Pro Phe Thr Phe Gly Pro Gly Thr Lys Leu Glu Leu Lys
            100                 105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
            130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
            165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
```

```
                195                 200                 205
Pro Val Thr Lys Ser Phe Asn Arg Gly Glu Cys
    210                 215
```

<210> SEQ ID NO 190
<211> LENGTH: 249
<212> TYPE: PRT
<213> ORGANISM: Artificial Sequence
<220> FEATURE:
<223> OTHER INFORMATION: heavy chain sequence of "4B4-D7" Fab

<400> SEQUENCE: 190

```
Glu Val Gln Leu Val Glu Thr Gly Gly Arg Leu Val Gln Pro Gly Arg
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Arg Ser Asn Asn Tyr Ala Thr Tyr Tyr Ala Glu
    50                  55                  60

Ser Val Lys Gly Arg Phe Thr Ile Ser Arg Asp Asp Ser Lys Ser Thr
65                  70                  75                  80

Ile Tyr Leu Gln Met Asn Ser Leu Lys Glu Glu Asp Thr Ala Ile Tyr
                85                  90                  95

Tyr Cys Arg Gly Thr Tyr Tyr Ala Ser Lys Pro Phe Asp Tyr Trp Gly
            100                 105                 110

Gln Gly Val Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Glu Gln Lys Leu Ile Ser Glu Glu Asp Leu Asn
225                 230                 235                 240

Gly Ala Ala His His His His His
                245
```

<210> SEQ ID NO 191
<211> LENGTH: 218
<212> TYPE: PRT
<213> ORGANISM: Artificial Sequence
<220> FEATURE:
<223> OTHER INFORMATION: light chain sequence of "4B4-D7" Fab

<400> SEQUENCE: 191

```
Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asp
            20                  25                  30
```

```
Asn Gly Asn Thr Tyr Leu Ser Trp Ser Leu Gln Arg Pro Gly Gln Ser
            35                  40                  45

Pro Gln Val Leu Ile Tyr Lys Val Ser Asn Arg Phe Ser Gly Thr Ser
        50                  55                  60

Asp Arg Phe Thr Gly Ser Gly Ser Gly Thr Asp Phe Thr Leu Lys Ile
 65                  70                  75                  80

Ser Arg Val Glu Pro Asp Asp Leu Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu
    210                 215

<210> SEQ ID NO 192
<211> LENGTH: 250
<212> TYPE: PRT
<213> ORGANISM: Artificial Sequence
<220> FEATURE:
<223> OTHER INFORMATION: heavy chain sequence of "18F5-H10" Fab

<400> SEQUENCE: 192

Glu Val Gln Val Val Glu Thr Gly Gly Ser Leu Val Gln Pro Gly Lys
 1               5                  10                  15

Ser Leu Lys Leu Thr Cys Ala Thr Ser Gly Phe Thr Phe Thr Asn Ala
            20                  25                  30

Trp Met His Trp Val Arg Arg Ser Pro Glu Lys Gln Leu Glu Trp Val
        35                  40                  45

Ala Gln Ile Lys Asp Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Ser
 65                  70                  75                  80

Ile Tyr Leu Gln Met Asn Ser Leu Lys Glu Glu Asp Thr Ala Ile Tyr
                85                  90                  95

Tyr Cys Arg Tyr Val His Tyr Arg Phe Ala Tyr Ala Leu Asp Ala Trp
            100                 105                 110

Gly Arg Gly Thr Ser Val Ser Val Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

-continued

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Glu Gln Lys Leu Ile Ser Glu Glu Asp Leu
225                 230                 235                 240

Asn Gly Ala Ala His His His His His His
                245                 250

<210> SEQ ID NO 193
<211> LENGTH: 219
<212> TYPE: PRT
<213> ORGANISM: Artificial Sequence
<220> FEATURE:
<223> OTHER INFORMATION: light chain sequence of "18F5-H10" Fab

<400> SEQUENCE: 193

Asp Val Leu Met Thr Gln Thr Pro Val Ser Leu Ser Val Ser Leu Gly
1               5                   10                  15

Gly Gln Val Ser Ile Ser Cys Arg Ser Ser Gln Ser Leu Val His Thr
            20                  25                  30

Asn Gly Asn Thr Tyr Leu Ser Trp Tyr Leu Gln Lys Pro Gly Gln Ser
        35                  40                  45

Pro Gln Leu Leu Ile Tyr Lys Val Ser Asn Arg Leu Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr His Tyr Pro Phe Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 194
<211> LENGTH: 378
<212> TYPE: PRT
<213> ORGANISM: Homo sapiens

<400> SEQUENCE: 194

Met Val Leu Leu Trp Leu Thr Leu Leu Leu Ile Ala Leu Pro Cys Leu
1               5                   10                  15

Leu Gln Thr Lys Glu Asp Pro Asn Pro Pro Ile Thr Asn Leu Arg Met

```
            20                  25                  30
Lys Ala Lys Ala Gln Gln Leu Thr Trp Asp Leu Asn Arg Asn Val Thr
        35                  40                  45

Asp Ile Glu Cys Val Lys Asp Ala Asp Tyr Ser Met Pro Ala Val Asn
 50                  55                  60

Asn Ser Tyr Cys Gln Phe Gly Ala Ile Ser Leu Cys Glu Val Thr Asn
 65                  70                  75                  80

Tyr Thr Val Arg Val Ala Asn Pro Pro Phe Ser Thr Trp Ile Leu Phe
                 85                  90                  95

Pro Glu Asn Ser Gly Lys Pro Trp Ala Gly Ala Glu Asn Leu Thr Cys
            100                 105                 110

Trp Ile His Asp Val Asp Phe Leu Ser Cys Ser Trp Ala Val Gly Pro
        115                 120                 125

Gly Ala Pro Ala Asp Val Gln Tyr Asp Leu Tyr Leu Asn Val Ala Asn
130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

Ile Pro Cys Thr Asp Lys Phe Val Val Phe Ser Gln Ile Glu Ile Leu
        195                 200                 205

Thr Pro Pro Asn Met Thr Ala Lys Cys Asn Lys Thr His Ser Phe Met
210                 215                 220

His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270

Arg Ala Arg Glu Arg Val Tyr Glu Phe Leu Ser Ala Trp Ser Thr Pro
        275                 280                 285

Gln Arg Phe Glu Cys Asp Gln Glu Gly Ala Asn Thr Arg Ala Trp
290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335

Arg Ile Pro His Met Lys Asp Pro Ile Gly Asp Ser Phe Gln Asn Asp
            340                 345                 350

Lys Leu Val Val Trp Glu Ala Gly Lys Ala Gly Leu Glu Glu Cys Leu
        355                 360                 365

Val Thr Glu Val Gln Val Gln Lys Thr
        370                 375

<210> SEQ ID NO 195
<211> LENGTH: 378
<212> TYPE: PRT
<213> ORGANISM: Macaca fascicularis

<400> SEQUENCE: 195

Met Thr Leu Leu Trp Leu Thr Leu Leu Val Ala Thr Pro Cys Leu
1               5                  10                  15
```

Leu Arg Thr Lys Glu Asp Pro Asn Ala Pro Ile Arg Asn Leu Arg Met
            20                  25                  30

Lys Glu Lys Ala Gln Gln Leu Met Trp Asp Leu Asn Arg Asn Val Thr
        35                  40                  45

Asp Val Glu Cys Ile Lys Gly Thr Asp Tyr Ser Met Pro Ala Met Asn
    50                  55                  60

Asn Ser Tyr Cys Gln Phe Gly Ala Ile Ser Leu Cys Glu Val Thr Asn
65                  70                  75                  80

Tyr Thr Val Arg Val Ala Ser Pro Pro Phe Ser Thr Trp Ile Leu Phe
                85                  90                  95

Pro Glu Asn Ser Gly Thr Pro Arg Ala Gly Ala Glu Asn Leu Thr Cys
            100                 105                 110

Trp Val His Asp Val Asp Phe Leu Ser Cys Ser Trp Val Val Gly Pro
        115                 120                 125

Ala Ala Pro Ala Asp Val Gln Tyr Asp Leu Tyr Leu Asn Asn Pro Asn
    130                 135                 140

Ser His Glu Gln Tyr Arg Cys Leu His Tyr Lys Thr Asp Ala Arg Gly
145                 150                 155                 160

Thr Gln Ile Gly Cys Arg Phe Asp Asp Ile Ala Pro Leu Ser Arg Gly
                165                 170                 175

Ser Gln Ser Ser His Ile Leu Val Arg Gly Arg Ser Ala Ala Val Ser
            180                 185                 190

Ile Pro Cys Thr Asp Lys Phe Val Phe Ser Gln Ile Glu Arg Leu
    195                 200                 205

Thr Pro Pro Asn Met Thr Gly Glu Cys Asn Glu Thr His Ser Phe Met
    210                 215                 220

His Trp Lys Met Lys Ser His Phe Asn Arg Lys Phe Arg Tyr Glu Leu
225                 230                 235                 240

Arg Ile Gln Lys Arg Met Gln Pro Val Arg Thr Glu Gln Val Arg Asp
                245                 250                 255

Thr Thr Ser Phe Gln Leu Pro Asn Pro Gly Thr Tyr Thr Val Gln Ile
            260                 265                 270

Arg Ala Arg Glu Thr Val Tyr Glu Phe Leu Ser Ala Trp Ser Thr Pro
    275                 280                 285

Gln Arg Phe Glu Cys Asp Gln Glu Glu Gly Ala Ser Ser Arg Ala Trp
    290                 295                 300

Arg Thr Ser Leu Leu Ile Ala Leu Gly Thr Leu Leu Ala Leu Leu Cys
305                 310                 315                 320

Val Phe Leu Ile Cys Arg Arg Tyr Leu Val Met Gln Arg Leu Phe Pro
                325                 330                 335

Arg Ile Pro His Met Lys Asp Pro Ile Gly Asp Thr Phe Gln Gln Asp
            340                 345                 350

Lys Leu Val Val Trp Glu Ala Gly Lys Ala Gly Leu Glu Glu Cys Leu
    355                 360                 365

Val Ser Glu Val Gln Val Val Glu Lys Thr
    370                 375

<210> SEQ ID NO 196
<211> LENGTH: 523
<212> TYPE: PRT
<213> ORGANISM: Homo sapiens
<220> FEATURE:
<221> NAME/KEY: DOMAIN
<222> LOCATION: (1)..(284)
<223> OTHER INFORMATION: extracellular domain of human CD123
<220> FEATURE:

<221> NAME/KEY: MISC_FEATURE
<222> LOCATION: (285)..(519)
<223> OTHER INFORMATION: Strep-II tagged Fc-Fusion

<400> SEQUENCE: 196

```
Thr Lys Glu Asp Pro Asn Pro Pro Ile Thr Asn Leu Arg Met Lys Ala
1               5                   10                  15

Lys Ala Gln Gln Leu Thr Trp Asp Leu Asn Arg Asn Val Thr Asp Ile
            20                  25                  30

Glu Cys Val Lys Asp Ala Asp Tyr Ser Met Pro Ala Val Asn Asn Ser
        35                  40                  45

Tyr Cys Gln Phe Gly Ala Ile Ser Leu Cys Glu Val Thr Asn Tyr Thr
    50                  55                  60

Val Arg Val Ala Asn Pro Pro Phe Ser Thr Trp Ile Leu Phe Pro Glu
65                  70                  75                  80

Asn Ser Gly Lys Pro Trp Ala Gly Ala Glu Asn Leu Thr Cys Trp Ile
                85                  90                  95

His Asp Val Asp Phe Leu Ser Cys Ser Trp Ala Val Gly Pro Gly Ala
            100                 105                 110

Pro Ala Asp Val Gln Tyr Asp Leu Tyr Leu Asn Val Ala Asn Arg Arg
        115                 120                 125

Gln Gln Tyr Glu Cys Leu His Tyr Lys Thr Asp Ala Gln Gly Thr Arg
    130                 135                 140

Ile Gly Cys Arg Phe Asp Asp Ile Ser Arg Leu Ser Ser Gly Ser Gln
145                 150                 155                 160

Ser Ser His Ile Leu Val Arg Gly Arg Ser Ala Ala Phe Gly Ile Pro
                165                 170                 175

Cys Thr Asp Lys Phe Val Val Phe Ser Gln Ile Glu Ile Leu Thr Pro
            180                 185                 190

Pro Asn Met Thr Ala Lys Cys Asn Lys Thr His Ser Phe Met His Trp
        195                 200                 205

Lys Met Arg Ser His Phe Asn Arg Lys Phe Arg Tyr Glu Leu Gln Ile
    210                 215                 220

Gln Lys Arg Met Gln Pro Val Ile Thr Glu Gln Val Arg Asp Arg Thr
225                 230                 235                 240

Ser Phe Gln Leu Leu Asn Pro Gly Thr Tyr Thr Val Gln Ile Arg Ala
                245                 250                 255

Arg Glu Arg Val Tyr Glu Phe Leu Ser Ala Trp Ser Thr Pro Gln Arg
            260                 265                 270

Phe Glu Cys Asp Gln Glu Glu Gly Ala Asn Thr Arg Ala Trp Arg Asp
        275                 280                 285

Lys Thr His Thr Cys Pro Pro Cys Pro Ala Pro Glu Leu Leu Gly Gly
    290                 295                 300

Pro Ser Val Phe Leu Phe Pro Pro Lys Pro Lys Asp Thr Leu Met Ile
305                 310                 315                 320

Ser Arg Thr Pro Glu Val Thr Cys Val Val Val Asp Val Ser His Glu
                325                 330                 335

Asp Pro Glu Val Lys Phe Asn Trp Tyr Val Asp Gly Val Glu Val His
            340                 345                 350

Asn Ala Lys Thr Lys Pro Arg Glu Glu Gln Tyr Asn Ser Thr Tyr Arg
        355                 360                 365

Val Val Ser Val Leu Thr Val Leu His Gln Asp Trp Leu Asn Gly Lys
    370                 375                 380

Glu Tyr Lys Cys Lys Val Ser Asn Lys Ala Leu Pro Ala Pro Ile Glu
```

```
            385                 390                 395                 400
Lys Thr Ile Ser Lys Ala Lys Gly Gln Pro Arg Glu Pro Gln Val Tyr
                405                 410                 415

Thr Leu Pro Pro Ser Arg Asp Glu Leu Thr Lys Asn Gln Val Ser Leu
                420                 425                 430

Thr Cys Leu Val Lys Gly Phe Tyr Pro Ser Asp Ile Ala Val Glu Trp
                435                 440                 445

Glu Ser Asn Gly Gln Pro Glu Asn Asn Tyr Lys Thr Thr Pro Pro Val
            450                 455                 460

Leu Asp Ser Asp Gly Ser Phe Phe Leu Tyr Ser Lys Leu Thr Val Asp
465                 470                 475                 480

Lys Ser Arg Trp Gln Gln Gly Asn Val Phe Ser Cys Ser Val Met His
                485                 490                 495

Glu Ala Leu His Asn His Tyr Thr Gln Lys Ser Leu Ser Leu Ser Pro
                500                 505                 510

Gly Ser Ala Trp Ser His Pro Gln Phe Glu Lys
                515                 520

<210> SEQ ID NO 197
<211> LENGTH: 519
<212> TYPE: PRT
<213> ORGANISM: Macaca fascicularis
<220> FEATURE:
<221> NAME/KEY: DOMAIN
<222> LOCATION: (1)..(284)
<223> OTHER INFORMATION: extracellular domain of Macaca fascicularis
      CD123
<220> FEATURE:
<221> NAME/KEY: MISC_FEATURE
<222> LOCATION: (285)..(516)
<223> OTHER INFORMATION: Strep-II tagged Fc-fusion

<400> SEQUENCE: 197

Thr Lys Glu Asp Pro Asn Ala Pro Ile Arg Asn Leu Arg Met Lys Glu
1               5                   10                  15

Lys Ala Gln Gln Leu Met Trp Asp Leu Asn Arg Asn Val Thr Asp Val
                20                  25                  30

Glu Cys Ile Lys Gly Thr Asp Tyr Ser Met Pro Ala Met Asn Asn Ser
            35                  40                  45

Tyr Cys Gln Phe Gly Ala Ile Ser Leu Cys Glu Val Thr Asn Tyr Thr
    50                  55                  60

Val Arg Val Ala Ser Pro Pro Phe Ser Thr Trp Ile Leu Phe Pro Glu
65                  70                  75                  80

Asn Thr Gly Thr Pro Arg Ala Gly Ala Glu Asn Leu Thr Cys Trp Val
                85                  90                  95

His Asp Val Asp Phe Leu Ser Cys Ser Trp Val Val Gly Pro Ala Ala
                100                 105                 110

Pro Ala Asp Val Gln Tyr Asp Leu Tyr Leu Asn Asn Pro Asn Ser His
            115                 120                 125

Glu Gln Tyr Arg Cys Leu His Tyr Lys Thr Asp Ala Arg Gly Thr Gln
    130                 135                 140

Ile Gly Cys Arg Phe Asp Asp Ile Ala Arg Leu Ser Arg Gly Ser Gln
145                 150                 155                 160

Ser Ser His Ile Leu Val Arg Gly Arg Ser Ala Ala Val Ser Ile Pro
                165                 170                 175

Cys Thr Asp Lys Phe Val Phe Phe Ser Gln Ile Glu Arg Leu Thr Pro
                180                 185                 190
```

```
Pro Asn Met Thr Gly Glu Cys Asn Glu Thr His Ser Phe Met His Trp
            195                 200                 205

Lys Met Lys Ser His Phe Asn Arg Lys Phe Arg Tyr Glu Leu Arg Ile
    210                 215                 220

Gln Lys Arg Met Gln Pro Val Arg Thr Glu Gln Val Arg Asp Thr Thr
225                 230                 235                 240

Ser Phe Gln Leu Pro Asn Pro Gly Thr Tyr Thr Val Gln Ile Arg Ala
                245                 250                 255

Arg Glu Thr Val Tyr Glu Phe Leu Ser Ala Trp Ser Thr Pro Gln Arg
                260                 265                 270

Phe Glu Cys Asp Gln Glu Glu Gly Ala Ser Ser Arg Ala Trp Arg Gly
            275                 280                 285

Ser Gly Gly Ser Gly Asp Lys Thr His Thr Cys Pro Pro Cys Pro Ala
        290                 295                 300

Pro Glu Leu Leu Gly Gly Pro Ser Val Phe Leu Phe Pro Pro Lys Pro
305                 310                 315                 320

Lys Asp Thr Leu Met Ile Ser Arg Thr Pro Glu Val Thr Cys Val Val
                325                 330                 335

Val Asp Val Ser His Glu Asp Pro Glu Val Lys Phe Asn Trp Tyr Val
                340                 345                 350

Asp Gly Val Glu Val His Asn Ala Lys Thr Lys Pro Arg Glu Glu Gln
            355                 360                 365

Tyr Asn Ser Thr Tyr Arg Val Val Ser Val Leu Thr Val Leu His Gln
    370                 375                 380

Asp Trp Leu Asn Gly Lys Glu Tyr Lys Cys Lys Val Ser Asn Lys Ala
385                 390                 395                 400

Leu Pro Ala Pro Ile Glu Lys Thr Ile Ser Lys Ala Lys Gly Gln Pro
                405                 410                 415

Arg Glu Pro Gln Val Tyr Thr Leu Pro Pro Ser Arg Asp Glu Leu Thr
            420                 425                 430

Lys Asn Gln Val Ser Leu Thr Cys Leu Val Lys Gly Phe Tyr Pro Ser
        435                 440                 445

Asp Ile Ala Val Glu Trp Glu Ser Asn Gly Gln Pro Glu Asn Asn Tyr
450                 455                 460

Lys Thr Thr Pro Pro Val Leu Asp Ser Asp Gly Ser Phe Phe Leu Tyr
465                 470                 475                 480

Ser Lys Leu Thr Val Asp Lys Ser Arg Trp Gln Gln Gly Asn Val Phe
                485                 490                 495

Ser Cys Ser Val Met His Glu Ala Leu His Asn His Tyr Thr Gln Lys
            500                 505                 510

Ser Leu Ser Leu Ser Pro Gly
        515

<210> SEQ ID NO 198
<211> LENGTH: 119
<212> TYPE: PRT
<213> ORGANISM: Artificial Sequence
<220> FEATURE:
<223> OTHER INFORMATION: VH of the so-called "1E1-G5" anti-CD123
      antibody

<400> SEQUENCE: 198

Gln Val Gln Leu Gln Glu Ser Gly Pro Thr Leu Val Lys Pro Gly Asp
1               5                   10                  15

Ser Val Lys Met Ser Cys Lys Ala Phe Gly Tyr Thr Phe Thr Asp His
                20                  25                  30
```

```
Ile Ile His Trp Val Lys Gln Ser His Gly Lys Ser Leu Glu Trp Ile
        35                  40                  45
Gly Tyr Ile Asn Pro Tyr Ser Gly Gly Thr Asn Tyr Asn Glu Lys Phe
    50                  55                  60
Lys Ser Lys Ala Thr Leu Thr Val Asp Lys Ser Ser Thr Ala Tyr
65                  70                  75                  80
Met Glu Phe Ser Arg Leu Thr Ser Glu Asp Ser Ala Ile Cys Tyr Cys
                85                  90                  95
Ala Leu Asn Tyr Gly Ser Tyr Tyr Ala Met Asp Ala Trp Gly Gln Gly
            100                 105                 110
Thr Ser Val Thr Val Ser Ser
        115

<210> SEQ ID NO 199
<211> LENGTH: 8
<212> TYPE: PRT
<213> ORGANISM: Artificial Sequence
<220> FEATURE:
<223> OTHER INFORMATION: CDR1-H of the so-called "1E1-G5" and "8B11-B7"
      anti-CD123 antibodies

<400> SEQUENCE: 199

Gly Tyr Thr Phe Thr Asp His Ile
1               5

<210> SEQ ID NO 200
<211> LENGTH: 8
<212> TYPE: PRT
<213> ORGANISM: Artificial Sequence
<220> FEATURE:
<223> OTHER INFORMATION: CDR2-H of the so-called "1E1-G5" and "6D6-B8"
      anti-CD123 antibodies

<400> SEQUENCE: 200

Ile Asn Pro Tyr Ser Gly Gly Thr
1               5

<210> SEQ ID NO 201
<211> LENGTH: 12
<212> TYPE: PRT
<213> ORGANISM: Artificial Sequence
<220> FEATURE:
<223> OTHER INFORMATION: CDR3-H of the so-called "1E1-G5", "6D6-B8",
      "8B11-B7" and "9F6-G3" anti-CD123 antibodies

<400> SEQUENCE: 201

Ala Leu Asn Tyr Gly Ser Tyr Tyr Ala Met Asp Ala
1               5                   10

<210> SEQ ID NO 202
<211> LENGTH: 107
<212> TYPE: PRT
<213> ORGANISM: Artificial Sequence
<220> FEATURE:
<223> OTHER INFORMATION: VL of the so-called "1E1-G5" anti-CD123
      antibody

<400> SEQUENCE: 202

Asp Ile Gln Met Thr Gln Ser Pro Ala Ser Leu Ser Ala Ser Leu Gly
1               5                   10                  15
Gln Thr Val Thr Ile Glu Cys Arg Pro Ser Glu Asp Ile Tyr Ser Asn
            20                  25                  30
Leu Ala Trp Phe Gln Gln Lys Pro Gly Ser Ser Pro Gln Leu Leu Ile
```

```
                35                  40                  45
Tyr Asp Ala Asn Asn Leu Ala Asp Gly Val Pro Ser Arg Phe Ser Gly
 50                  55                  60

Ser Gly Ser Gly Thr Gln Tyr Ser Leu Lys Ile Asn Ser Leu Gln Ser
65                  70                  75                  80

Glu Asp Val Ala Ser Tyr Phe Cys Gln Gln Tyr Asn Lys Tyr Pro Tyr
                85                  90                  95

Thr Phe Gly Thr Gly Thr Lys Leu Glu Leu Lys
            100                 105

<210> SEQ ID NO 203
<211> LENGTH: 6
<212> TYPE: PRT
<213> ORGANISM: Artificial Sequence
<220> FEATURE:
<223> OTHER INFORMATION: CDR1-L of the so-called "1E1-G5" anti-CD123
      antibody

<400> SEQUENCE: 203

Glu Asp Ile Tyr Ser Asn
1               5

<210> SEQ ID NO 204
<211> LENGTH: 9
<212> TYPE: PRT
<213> ORGANISM: Artificial Sequence
<220> FEATURE:
<223> OTHER INFORMATION: CDR1-L of the so-called "1E1-G5" anti-CD123
      antibody

<400> SEQUENCE: 204

Gln Gln Tyr Asn Lys Tyr Pro Tyr Thr
1               5

<210> SEQ ID NO 205
<211> LENGTH: 119
<212> TYPE: PRT
<213> ORGANISM: Artificial Sequence
<220> FEATURE:
<223> OTHER INFORMATION: VH of the so-called "2B8-F3" anti-CD123
      antibody

<400> SEQUENCE: 205

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asp Tyr
            20                  25                  30

Asn Met Ala Trp Val Arg Gln Ala Pro Lys Lys Gly Leu Glu Trp Val
        35                  40                  45

Ala Thr Ile Leu Tyr Asp Gly Arg Thr Tyr Tyr Arg Gly Ser Val
 50                  55                  60

Lys Gly Arg Phe Thr Ile Ser Arg Asp Asn Ala Lys Ser Thr Leu Tyr
65                  70                  75                  80

Leu Arg Met Asp Ser Leu Arg Ser Glu Asp Thr Ala Thr Tyr Tyr Cys
                85                  90                  95

Ala Thr His Ser Arg Gly Thr Tyr Phe Asp Tyr Trp Gly Gln Gly
            100                 105                 110

Val Met Val Thr Val Ser Ser
        115

<210> SEQ ID NO 206
```

```
<211> LENGTH: 8
<212> TYPE: PRT
<213> ORGANISM: Artificial Sequence
<220> FEATURE:
<223> OTHER INFORMATION: CDR1-H of the so-called "2B8-F3" anti-CD123
      antibody

<400> SEQUENCE: 206

Gly Phe Thr Phe Ser Asp Tyr Asn
1               5

<210> SEQ ID NO 207
<211> LENGTH: 8
<212> TYPE: PRT
<213> ORGANISM: Artificial Sequence
<220> FEATURE:
<223> OTHER INFORMATION: CDR2-H of the so-called "2B8-F3" anti-CD123
      antibody

<400> SEQUENCE: 207

Ile Leu Tyr Asp Gly Gly Arg Thr
1               5

<210> SEQ ID NO 208
<211> LENGTH: 12
<212> TYPE: PRT
<213> ORGANISM: Artificial Sequence
<220> FEATURE:
<223> OTHER INFORMATION: CDR3-H of the so-called "2B8-F3" anti-CD123
      antibody

<400> SEQUENCE: 208

Ala Thr His Ser Arg Gly Thr Asp Tyr Phe Asp Tyr
1               5                   10

<210> SEQ ID NO 209
<211> LENGTH: 106
<212> TYPE: PRT
<213> ORGANISM: Artificial Sequence
<220> FEATURE:
<223> OTHER INFORMATION: VL of the so-called "2B8-F3" anti-CD123
      antibody

<400> SEQUENCE: 209

Glu Ile Val Leu Thr Gln Ser Pro Thr Ser Met Thr Ala Ser Pro Gly
1               5                   10                  15

Glu Gln Val Thr Ile Thr Cys Arg Ala Ser Ser Ser Ile Asn Tyr Met
            20                  25                  30

His Trp Tyr Gln Gln Lys Pro Gly Ala Ser Pro Arg Pro Trp Ile Tyr
        35                  40                  45

Glu Thr Ser Lys Leu Ala Ser Gly Val Pro Asp Arg Phe Ser Gly Ser
    50                  55                  60

Ala Ser Gly Thr Ser Tyr Ser Leu Thr Ile Asn Asn Met Glu Ala Glu
65                  70                  75                  80

Asp Ala Ala Thr Tyr Tyr Cys Gln Gln Trp Asn Tyr Pro Ser Trp Thr
                85                  90                  95

Phe Gly Gly Gly Thr Lys Leu Glu Leu Lys
            100                 105

<210> SEQ ID NO 210
<211> LENGTH: 5
<212> TYPE: PRT
<213> ORGANISM: Artificial Sequence
<220> FEATURE:
<223> OTHER INFORMATION: CDR1-L of the so-called "2B8-F3" anti-CD123
``` antibody

<400> SEQUENCE: 210

Ser Ser Ile Asn Tyr
1               5

<210> SEQ ID NO 211
<211> LENGTH: 9
<212> TYPE: PRT
<213> ORGANISM: Artificial Sequence
<220> FEATURE:
<223> OTHER INFORMATION: CDR3-L of the so-called "2B8-F3" anti-CD123
      antibody

<400> SEQUENCE: 211

Gln Gln Trp Asn Tyr Pro Ser Trp Thr
1               5

<210> SEQ ID NO 212
<211> LENGTH: 123
<212> TYPE: PRT
<213> ORGANISM: Artificial Sequence
<220> FEATURE:
<223> OTHER INFORMATION: VH of the so-called "2F8-D6" anti-CD123
      antibody

<400> SEQUENCE: 212

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

Gly Val Ser Trp Val Arg Gln Pro Pro Gly Lys Gly Leu Glu Trp Ile
        35                  40                  45

Ala Thr Ile Ser Ser Ala Gly Ser Thr Tyr Tyr Asp Leu Val Leu Lys
    50                  55                  60

Ser Arg Leu Ser Ile Thr Arg Asp Thr Ser Lys Ser Gln Val Phe Leu
65                  70                  75                  80

Lys Val His Ser Leu Gln Thr Glu Asp Thr Ala Ile Tyr Leu Cys Ala
                85                  90                  95

Arg Asp Ala Pro Val Phe Asn Tyr Gly Ser Tyr Asn Ala Met Asp Ser
            100                 105                 110

Trp Gly Gln Gly Thr Ser Val Thr Val Ser Ser
        115                 120

<210> SEQ ID NO 213
<211> LENGTH: 8
<212> TYPE: PRT
<213> ORGANISM: Artificial Sequence
<220> FEATURE:
<223> OTHER INFORMATION: CDR1-H of the so-called "2F8-D6" anti-CD123
      antibody

<400> SEQUENCE: 213

Gly Phe Ser Leu Thr Ser Tyr Gly
1               5

<210> SEQ ID NO 214
<211> LENGTH: 7
<212> TYPE: PRT
<213> ORGANISM: Artificial Sequence
<220> FEATURE:
<223> OTHER INFORMATION: CDR2-H of the so-called "2F8-D6" anti-CD123
      antibody

```
<400> SEQUENCE: 214

Ile Ser Ser Ala Gly Ser Thr
1               5

<210> SEQ ID NO 215
<211> LENGTH: 17
<212> TYPE: PRT
<213> ORGANISM: Artificial Sequence
<220> FEATURE:
<223> OTHER INFORMATION: CDR3-H of the so-called "2F8-D6" anti-CD123
      antibody

<400> SEQUENCE: 215

Ala Arg Asp Ala Pro Val Phe Asn Tyr Gly Ser Tyr Asn Ala Met Asp
1               5                   10                  15

Ser

<210> SEQ ID NO 216
<211> LENGTH: 106
<212> TYPE: PRT
<213> ORGANISM: Artificial Sequence
<220> FEATURE:
<223> OTHER INFORMATION: VL of the so-called "2F8-D6" anti-CD123
      antibody

<400> SEQUENCE: 216

Asp Ile Gln Met Thr Gln Ser Pro Ser Phe Leu Ser Ala Thr Val Gly
1               5                   10                  15

Asp Arg Val Thr Ile Asn Cys Lys Ala Ser Gln Asn Ile Asn Lys Tyr
            20                  25                  30

Leu Asn Trp Tyr Gln Gln Lys Leu Gly Glu Ala Pro Lys Arg Leu Ile
        35                  40                  45

Tyr Asn Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Leu Gln His Lys Ser Gly Leu Thr
                85                  90                  95

Phe Gly Ser Gly Thr Lys Leu Glu Ile Lys
            100                 105

<210> SEQ ID NO 217
<211> LENGTH: 6
<212> TYPE: PRT
<213> ORGANISM: Artificial Sequence
<220> FEATURE:
<223> OTHER INFORMATION: CDR1-L of the so-called "2F8-D6" anti-CD123
      antibody

<400> SEQUENCE: 217

Gln Asn Ile Asn Lys Tyr
1               5

<210> SEQ ID NO 218
<211> LENGTH: 8
<212> TYPE: PRT
<213> ORGANISM: Artificial Sequence
<220> FEATURE:
<223> OTHER INFORMATION: CDR3-L of the so-called "2F8-D6" anti-CD123
      antibody

<400> SEQUENCE: 218

Leu Gln His Lys Ser Gly Leu Thr
```

```
<210> SEQ ID NO 219
<211> LENGTH: 125
<212> TYPE: PRT
<213> ORGANISM: Artificial Sequence
<220> FEATURE:
<223> OTHER INFORMATION: VH of the so-called "3B10-E6" anti-CD123
      antibody

<400> SEQUENCE: 219

Gln Val Gln Leu Gln Gln Ser Gly Pro Glu Leu Arg Arg Pro Gly Ser
1               5                   10                  15

Ser Val Arg Leu Ser Cys Lys Ala Ser Gly Tyr Arg Ile Lys Asp Phe
            20                  25                  30

Leu Ile His Trp Ile Lys Asn Arg Pro Glu His Gly Leu Glu Trp Ile
        35                  40                  45

Gly Trp Ile Asp Pro Glu Asp Gly Glu Thr Lys Tyr Ala Gln Lys Phe
    50                  55                  60

Gln Thr Lys Ala Thr Leu Thr Ala Asp Thr Ser Ser Asn Thr Ala Tyr
65                  70                  75                  80

Met Gln Leu Ser Ser Leu Thr Ser Glu Asp Thr Ala Thr Tyr Phe Cys
                85                  90                  95

Ala Arg Trp Gly Asp Val Tyr Tyr Gly Leu Met Arg Gly His Val Met
            100                 105                 110

Asp Ala Trp Gly Gln Gly Thr Ser Val Thr Val Ser Ser
        115                 120                 125

<210> SEQ ID NO 220
<211> LENGTH: 8
<212> TYPE: PRT
<213> ORGANISM: Artificial Sequence
<220> FEATURE:
<223> OTHER INFORMATION: CDR1-H of the so-called "3B10-E6" anti-CD123
      antibody

<400> SEQUENCE: 220

Gly Tyr Arg Ile Lys Asp Phe Leu
1               5

<210> SEQ ID NO 221
<211> LENGTH: 8
<212> TYPE: PRT
<213> ORGANISM: Artificial Sequence
<220> FEATURE:
<223> OTHER INFORMATION: CDR2-H of the so-called "3B10-E6" anti-CD123
      antibody

<400> SEQUENCE: 221

Ile Asp Pro Glu Asp Gly Glu Thr
1               5

<210> SEQ ID NO 222
<211> LENGTH: 18
<212> TYPE: PRT
<213> ORGANISM: Artificial Sequence
<220> FEATURE:
<223> OTHER INFORMATION: CDR3-H of the so-called "3B10-E6" anti-CD123
      antibody

<400> SEQUENCE: 222

Ala Arg Trp Gly Asp Val Tyr Tyr Gly Leu Met Arg Gly His Val Met
1               5                   10                  15
```

Asp Ala

<210> SEQ ID NO 223
<211> LENGTH: 113
<212> TYPE: PRT
<213> ORGANISM: Artificial Sequence
<220> FEATURE:
<223> OTHER INFORMATION: VL of the so-called "3B10-E6" anti-CD123
      antibody

<400> SEQUENCE: 223

```
Asp Val Leu Met Thr Gln Thr Pro Val Ser Leu Pro Val Ser Leu Gly
1               5                   10                  15

Gly Gln Val Ser Ile Ser Cys Arg Ser Ser Gln Ser Leu Val His Ser
            20                  25                  30

Asp Gly Asp Thr Tyr Leu His Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Pro Glu Asp Leu Gly Leu Tyr Tyr Cys Leu Gln Thr
                85                  90                  95

Thr His Phe Pro Pro Trp Thr Phe Gly Gly Gly Thr Lys Leu Glu Met
            100                 105                 110

Lys
```

<210> SEQ ID NO 224
<211> LENGTH: 11
<212> TYPE: PRT
<213> ORGANISM: Artificial Sequence
<220> FEATURE:
<223> OTHER INFORMATION: CDR1-L of the so-called "3B10-E6" anti-CD123
      antibody

<400> SEQUENCE: 224

```
Gln Ser Leu Val His Ser Asp Gly Asp Thr Tyr
1               5                   10
```

<210> SEQ ID NO 225
<211> LENGTH: 10
<212> TYPE: PRT
<213> ORGANISM: Artificial Sequence
<220> FEATURE:
<223> OTHER INFORMATION: CDR3-L of the so-called "3B10-E6" anti-CD123
      antibody

<400> SEQUENCE: 225

```
Leu Gln Thr Thr His Phe Pro Pro Trp Thr
1               5                   10
```

<210> SEQ ID NO 226
<211> LENGTH: 118
<212> TYPE: PRT
<213> ORGANISM: Artificial Sequence
<220> FEATURE:
<223> OTHER INFORMATION: VH of the so-called "3E3-D3" anti-CD123
      antibody

<400> SEQUENCE: 226

```
Gln Val Gln Leu Gln Glu Ser Gly Pro Gly Leu Val Gln Pro Ser Gln
1               5                   10                  15

Thr Leu Ser Leu Thr Cys Thr Val Ser Gly Phe Ser Leu Thr Thr Tyr
```

```
            20                  25                  30
Asp Val His Trp Val Arg Gln Pro Pro Gly Lys Gly Leu Glu Trp Met
        35                  40                  45

Gly Arg Ile Gln Asn Gly Gly Ile Thr Asp Tyr Asn Ser Ala Leu Lys
    50                  55                  60

Ser Arg Leu Ile Ile Ser Arg Asp Thr Ser Lys Ser Gln Val Phe Leu
65                  70                  75                  80

Lys Met Asn Ser Val Gln Thr Glu Asp Thr Ala Met Tyr Phe Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
        115

<210> SEQ ID NO 227
<211> LENGTH: 8
<212> TYPE: PRT
<213> ORGANISM: Artificial Sequence
<220> FEATURE:
<223> OTHER INFORMATION: CDR1-H of the so-called "3E3-D3" anti-CD123
      antibody

<400> SEQUENCE: 227

Gly Phe Ser Leu Thr Thr Tyr Asp
1               5

<210> SEQ ID NO 228
<211> LENGTH: 7
<212> TYPE: PRT
<213> ORGANISM: Artificial Sequence
<220> FEATURE:
<223> OTHER INFORMATION: CDR2-H of the so-called "3E3-D3" anti-CD123
      antibody

<400> SEQUENCE: 228

Ile Gln Asn Gly Gly Ile Thr
1               5

<210> SEQ ID NO 229
<211> LENGTH: 12
<212> TYPE: PRT
<213> ORGANISM: Artificial Sequence
<220> FEATURE:
<223> OTHER INFORMATION: CDR3-H of the so-called "3E3-D3" anti-CD123
      antibody

<400> SEQUENCE: 229

Ala Lys Thr Gly Ser Tyr Phe Tyr Ala Phe Asp His
1               5                   10

<210> SEQ ID NO 230
<211> LENGTH: 111
<212> TYPE: PRT
<213> ORGANISM: Artificial Sequence
<220> FEATURE:
<223> OTHER INFORMATION: VL of the so-called "3E3-D3" anti-CD123
      antibody

<400> SEQUENCE: 230

Gln Phe Val Leu Thr Gln Pro Asn Ser Val Ser Thr Asn Leu Gly Ser
1               5                   10                  15

Thr Val Lys Leu Ser Cys Lys Arg Asn Thr Gly Asn Ile Gly Ser Asn
            20                  25                  30
```

Tyr Val Asn Trp Tyr Gln Gln His Glu Gly Arg Ser Pro Thr Thr Met
            35                  40                  45

Ile Tyr Arg Asp Asp Lys Arg Pro Asp Gly Val Pro Asp Arg Phe Ser
 50                  55                  60

Gly Ser Ile Asp Arg Ser Ser Asn Ser Ala Leu Leu Thr Ile Asn Asn
 65                  70                  75                  80

Val Gln Thr Glu Asp Glu Ala Asp Tyr Phe Cys Gln Ser Tyr Ser Ser
                 85                  90                  95

Gly Ile Asn Ile Ile Phe Gly Gly Gly Thr Lys Leu Thr Val Leu
            100                 105                 110

<210> SEQ ID NO 231
<211> LENGTH: 8
<212> TYPE: PRT
<213> ORGANISM: Artificial Sequence
<220> FEATURE:
<223> OTHER INFORMATION: CDR1-L of the so-called "3E3-D3" anti-CD123
      antibody

<400> SEQUENCE: 231

Thr Gly Asn Ile Gly Ser Asn Tyr
1               5

<210> SEQ ID NO 232
<211> LENGTH: 10
<212> TYPE: PRT
<213> ORGANISM: Artificial Sequence
<220> FEATURE:
<223> OTHER INFORMATION: CDR3-L of the so-called "3E3-D3" anti-CD123
      antibody

<400> SEQUENCE: 232

Gln Ser Tyr Ser Ser Gly Ile Asn Ile Ile
1               5                   10

<210> SEQ ID NO 233
<211> LENGTH: 120
<212> TYPE: PRT
<213> ORGANISM: Artificial Sequence
<220> FEATURE:
<223> OTHER INFORMATION: VH of the so-called "5A5-B4" anti-CD123
      antibody

<400> SEQUENCE: 233

Gln Ile Gln Ile Val Gln Ser Gly Ser Asp Val Thr Ser Thr Cys Asn
1               5                   10                  15

Gly Cys Gly Thr Cys Tyr Phe Ser Gly Phe Ser Leu Ser Thr Thr Gly
            20                  25                  30

Ile Cys Val Ser Trp Ile Arg Gln Pro Ser Gly Lys Gly Gln Glu Trp
         35                  40                  45

Leu Ala Asp Phe Cys Trp Asp Gly Lys Gly Tyr Asn Pro Ser Leu
 50                  55                  60

Lys Asn Arg Leu Ser Ile Ser Lys Asp Thr Ser Asn Asn Gln Val Phe
 65                  70                  75                  80

Leu Lys Ile Thr Ser Val Asp Thr Ala Asp Thr Ala Thr Tyr Tyr Cys
                 85                  90                  95

Ala Arg Arg Arg Val Tyr Tyr Gly Ile Tyr Phe Asp Tyr Trp Gly Gln
            100                 105                 110

Gly Val Met Val Thr Val Ser Ser
            115                 120

```
<210> SEQ ID NO 234
<211> LENGTH: 10
<212> TYPE: PRT
<213> ORGANISM: Artificial Sequence
<220> FEATURE:
<223> OTHER INFORMATION: CDR1-H of the so-called "5A5-B4" anti-CD123
      antibody

<400> SEQUENCE: 234

Gly Phe Ser Leu Ser Thr Thr Gly Ile Cys
1               5                   10

<210> SEQ ID NO 235
<211> LENGTH: 7
<212> TYPE: PRT
<213> ORGANISM: Artificial Sequence
<220> FEATURE:
<223> OTHER INFORMATION: CDR2-H of the so-called "5A5-B4" anti-CD123
      antibody

<400> SEQUENCE: 235

Phe Cys Trp Asp Asp Gly Lys
1               5

<210> SEQ ID NO 236
<211> LENGTH: 13
<212> TYPE: PRT
<213> ORGANISM: Artificial Sequence
<220> FEATURE:
<223> OTHER INFORMATION: CDR3-H of the so-called "5A5-B4" anti-CD123
      antibody

<400> SEQUENCE: 236

Ala Arg Arg Arg Val Tyr Tyr Gly Ile Tyr Phe Asp Tyr
1               5                   10

<210> SEQ ID NO 237
<211> LENGTH: 106
<212> TYPE: PRT
<213> ORGANISM: Artificial Sequence
<220> FEATURE:
<223> OTHER INFORMATION: VL of the so-called "5A5-B4" anti-CD123
      antibody

<400> SEQUENCE: 237

Asp Ile Val Met Thr Gln Ser Pro Ala Leu Ala Val Ser Pro Gly Glu
1               5                   10                  15

Arg Val Ser Ile Ser Cys Arg Ala Ser Asn Ser Val Ser Thr Arg Met
            20                  25                  30

His Trp Tyr Gln Gln Lys Pro Gly Gln Gln Pro Lys Leu Leu Ile Tyr
        35                  40                  45

Gly Ala Ser Asn Leu Glu Ser Gly Val Pro Ala Arg Phe Ser Gly Ser
    50                  55                  60

Gly Ser Gly Thr Asp Phe Thr Leu Thr Ile Asp Pro Val Glu Ala Asp
65                  70                  75                  80

Asp Ile Ala Thr Tyr Phe Cys Gln Gln Ser Trp Asn Asp Pro Leu Thr
                85                  90                  95

Phe Gly Ser Gly Thr Lys Leu Glu Ile Lys
            100                 105

<210> SEQ ID NO 238
<211> LENGTH: 6
<212> TYPE: PRT
<213> ORGANISM: Artificial Sequence
<220> FEATURE:
```

<223> OTHER INFORMATION: CDR1-L of the so-called "5A5-B4" anti-CD123
     antibody

<400> SEQUENCE: 238

Asn Ser Val Ser Thr Arg
1               5

<210> SEQ ID NO 239
<211> LENGTH: 9
<212> TYPE: PRT
<213> ORGANISM: Artificial Sequence
<220> FEATURE:
<223> OTHER INFORMATION: CDR3-L of the so-called "5A5-B4" anti-CD123
     antibody

<400> SEQUENCE: 239

Gln Gln Ser Trp Asn Asp Pro Leu Thr
1               5

<210> SEQ ID NO 240
<211> LENGTH: 117
<212> TYPE: PRT
<213> ORGANISM: Artificial Sequence
<220> FEATURE:
<223> OTHER INFORMATION: VH of the so-called "6B10-E4" anti-CD123
     antibody

<400> SEQUENCE: 240

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser His Tyr
            20                  25                  30

Asn Met Ala Trp Val Arg Gln Ala Pro Lys Lys Gly Leu Glu Trp Val
        35                  40                  45

Ala Thr Ile Thr Tyr Asp Asp His Ser Thr Tyr Tyr Arg Asp Ser Val
    50                  55                  60

Lys Gly Arg Phe Thr Ile Ser Arg Asp Thr Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg Leu Val Asn Tyr Ala Phe Ala Tyr Trp Gly Gln Gly Thr Leu
            100                 105                 110

Val Thr Val Ser Ser
        115

<210> SEQ ID NO 241
<211> LENGTH: 8
<212> TYPE: PRT
<213> ORGANISM: Artificial Sequence
<220> FEATURE:
<223> OTHER INFORMATION: CDR1-H of the so-called "6B10-E4" anti-CD123
     antibody

<400> SEQUENCE: 241

Gly Phe Thr Phe Ser His Tyr Asn
1               5

<210> SEQ ID NO 242
<211> LENGTH: 8
<212> TYPE: PRT
<213> ORGANISM: Artificial Sequence
<220> FEATURE:
<223> OTHER INFORMATION: CDR2-H of the so-called "6B10-E4" anti-CD123
     antibody

<400> SEQUENCE: 242

Ile Thr Tyr Asp Asp His Ser Thr
1               5

<210> SEQ ID NO 243
<211> LENGTH: 10
<212> TYPE: PRT
<213> ORGANISM: Artificial Sequence
<220> FEATURE:
<223> OTHER INFORMATION: CDR3-H of the so-called "6B10-E4" anti-CD123
      antibody

<400> SEQUENCE: 243

Ala Arg Leu Val Asn Tyr Ala Phe Ala Tyr
1               5                   10

<210> SEQ ID NO 244
<211> LENGTH: 106
<212> TYPE: PRT
<213> ORGANISM: Artificial Sequence
<220> FEATURE:
<223> OTHER INFORMATION: VL of the so-called "6B10-E4" anti-CD123
      antibody

<400> SEQUENCE: 244

Asn Ile Val Met Thr Gln Ser Pro Lys Ser Met Ser Ile Ser Val Gly
1               5                   10                  15

Asp Arg Val Thr Met Asn Cys Lys Ala Ser Gln Thr Val Gly Asn Asn
            20                  25                  30

Ile Ala Trp Tyr Gln Gln Lys Pro Gly Leu Ser Pro Gln Leu Leu Ile
        35                  40                  45

Asp Tyr Ala Ser Asn Arg Tyr Thr Gly Val Pro Asn Arg Phe Thr Gly
    50                  55                  60

Gly Gly Tyr Gly Thr Asp Phe Ile Leu Thr Ile Asn Ser Val Gln Ala
65                  70                  75                  80

Glu Asp Ala Ala Phe Tyr Tyr Cys Gln Arg Met Tyr Asn Ser Pro Thr
                85                  90                  95

Phe Gly Gly Gly Thr Lys Leu Glu Leu Lys
            100                 105

<210> SEQ ID NO 245
<211> LENGTH: 6
<212> TYPE: PRT
<213> ORGANISM: Artificial Sequence
<220> FEATURE:
<223> OTHER INFORMATION: CDR1-L of the so-called "6B10-E4" anti-CD123
      antibody

<400> SEQUENCE: 245

Gln Thr Val Gly Asn Asn
1               5

<210> SEQ ID NO 246
<211> LENGTH: 8
<212> TYPE: PRT
<213> ORGANISM: Artificial Sequence
<220> FEATURE:
<223> OTHER INFORMATION: CDR3-L of the so-called "6B10-E4" anti-CD123
      antibody

<400> SEQUENCE: 246

Gln Arg Met Tyr Asn Ser Pro Thr
1               5

```
<210> SEQ ID NO 247
<211> LENGTH: 116
<212> TYPE: PRT
<213> ORGANISM: Artificial Sequence
<220> FEATURE:
<223> OTHER INFORMATION: VH of the so-called "6C10-C4" anti-CD123
      antibody

<400> SEQUENCE: 247

Glu Val Lys Leu Gln Glu Ser Gly Pro Ser Leu Val Gln Pro Ser Glu
1               5                   10                  15

Thr Leu Ser Leu Thr Cys Thr Val Ser Gly Phe Ser Leu Thr Ser Tyr
            20                  25                  30

Ser Val His Trp Val Arg Gln His Ser Gly Lys Ser Leu Glu Trp Met
        35                  40                  45

Gly Arg Met Trp Asn Asp Gly Asp Thr Ser Tyr Asn Ser Ala Phe Thr
    50                  55                  60

Ser Arg Leu Ser Ile Ser Arg Asp Thr Ser Lys Gly Gln Val Phe Leu
65                  70                  75                  80

Lys Met Asn Ser Leu Gln Thr Glu Asp Thr Gly Thr Tyr Tyr Cys Ala
                85                  90                  95

Arg Gly His Arg Thr Pro Phe Asp Tyr Trp Gly Gln Gly Val Met Val
            100                 105                 110

Thr Val Ser Ser
            115

<210> SEQ ID NO 248
<211> LENGTH: 8
<212> TYPE: PRT
<213> ORGANISM: Artificial Sequence
<220> FEATURE:
<223> OTHER INFORMATION: CDR1-H of the so-called "6C10-C4" anti-CD123
      antibody

<400> SEQUENCE: 248

Gly Phe Ser Leu Thr Ser Tyr Ser
1               5

<210> SEQ ID NO 249
<211> LENGTH: 7
<212> TYPE: PRT
<213> ORGANISM: Artificial Sequence
<220> FEATURE:
<223> OTHER INFORMATION: CDR2-H of the so-called "6C10-C4" anti-CD123
      antibody

<400> SEQUENCE: 249

Met Trp Asn Asp Gly Asp Thr
1               5

<210> SEQ ID NO 250
<211> LENGTH: 10
<212> TYPE: PRT
<213> ORGANISM: Artificial Sequence
<220> FEATURE:
<223> OTHER INFORMATION: CDR3-H of the so-called "6C10-C4" anti-CD123
      antibody

<400> SEQUENCE: 250

Ala Arg Gly His Arg Thr Pro Phe Asp Tyr
1               5                   10
```

```
<210> SEQ ID NO 251
<211> LENGTH: 113
<212> TYPE: PRT
<213> ORGANISM: Artificial Sequence
<220> FEATURE:
<223> OTHER INFORMATION: VL of the so-called "6C10-C4" and "9B8-G6"
      anti-CD123 antibodies

<400> SEQUENCE: 251

Asp Ile Val Met Thr Gln Ser Pro Ser Leu Ala Val Ser Ala Gly
1               5                   10                  15

Glu Thr Val Thr Ile Asn Cys Lys Ser Ser Gln Ser Phe Leu Ser Ser
                20                  25                  30

Gly Asp Glu Arg Asn Tyr Val Ala Trp Tyr Gln His Lys Pro Gly Gln
            35                  40                  45

Ser Pro Lys Leu Leu Ile Tyr Trp Ala Ser Thr Arg His Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Gln
                85                  90                  95

Tyr Tyr Asp Thr Pro Leu Thr Phe Gly Ser Gly Thr Lys Leu Glu Ile
            100                 105                 110

Lys

<210> SEQ ID NO 252
<211> LENGTH: 12
<212> TYPE: PRT
<213> ORGANISM: Artificial Sequence
<220> FEATURE:
<223> OTHER INFORMATION: CDR1-L of the so-called "6C10-C4" and "9B8-G6"
      anti-CD123 antibodies

<400> SEQUENCE: 252

Gln Ser Phe Leu Ser Ser Gly Asp Glu Arg Asn Tyr
1               5                   10

<210> SEQ ID NO 253
<211> LENGTH: 9
<212> TYPE: PRT
<213> ORGANISM: Artificial Sequence
<220> FEATURE:
<223> OTHER INFORMATION: CDR3-L of the so-called "6C10-C4", "9B8-G6" and
      "9D7-G3" anti-CD123 antibodies

<400> SEQUENCE: 253

Gln Gln Tyr Tyr Asp Thr Pro Leu Thr
1               5

<210> SEQ ID NO 254
<211> LENGTH: 119
<212> TYPE: PRT
<213> ORGANISM: Artificial Sequence
<220> FEATURE:
<223> OTHER INFORMATION: VH of the so-called "6D6-B8" anti-CD123
      antibody

<400> SEQUENCE: 254

Gln Val Gln Leu Gln Glu Ser Gly Pro Thr Leu Val Lys Pro Gly Asp
1               5                   10                  15

Ser Val Lys Met Ser Cys Lys Ala Ser Ala Tyr Thr Phe Thr Asp Asn
                20                  25                  30

Ile Ile His Trp Val Lys Gln Ser His Gly Lys Ser Leu Asp Trp Ile
```

```
                35                  40                  45
Gly Tyr Ile Asn Pro Tyr Ser Gly Gly Thr Asn Tyr Asn Gly Trp Phe
        50                  55                  60

Arg Ser Lys Ala Thr Leu Thr Val Asp Lys Ser Ser Thr Ala Tyr
 65                  70                  75                  80

Met Glu Phe Ser Arg Leu Thr Ser Asp Ser Ala Ile Tyr Tyr Cys
                85                  90                  95

Ala Leu Asn Tyr Gly Ser Tyr Tyr Ala Met Asp Ala Trp Gly Gln Gly
            100                 105                 110

Thr Ser Val Thr Val Ser Ser
        115

<210> SEQ ID NO 255
<211> LENGTH: 8
<212> TYPE: PRT
<213> ORGANISM: Artificial Sequence
<220> FEATURE:
<223> OTHER INFORMATION: CDR1-H of the so-called "6D6-B8" anti-CD123
      antibody

<400> SEQUENCE: 255

Ala Tyr Thr Phe Thr Asp Asn Ile
1               5

<210> SEQ ID NO 256
<211> LENGTH: 107
<212> TYPE: PRT
<213> ORGANISM: Artificial Sequence
<220> FEATURE:
<223> OTHER INFORMATION: VL of the so-called "6D6-B8" anti-CD123
      antibody

<400> SEQUENCE: 256

Asp Ile Gln Met Thr Gln Ser Pro Ala Ser Leu Ser Ala Ser Leu Gly
1               5                   10                  15

Glu Thr Val Thr Ile Asp Cys Arg Pro Ser Glu Asp Ile Phe Asn Asn
            20                  25                  30

Leu Ala Trp Tyr Gln Gln Lys Pro Gly Asn Ser Pro Gln Leu Leu Ile
        35                  40                  45

Tyr Asp Ala Asn Ser Leu Ala Asp Gly Val Pro Ser Arg Phe Ser Gly
    50                  55                  60

Ser Gly Ser Gly Thr Gln Tyr Ser Leu Met Ile Ile Arg Leu Gln Ser
65                  70                  75                  80

Glu Asp Val Ala Ser Tyr Phe Cys His Gln Tyr Asn Ile Tyr Pro Tyr
                85                  90                  95

Thr Phe Gly Ala Gly Thr Lys Leu Glu Leu Lys
            100                 105

<210> SEQ ID NO 257
<211> LENGTH: 6
<212> TYPE: PRT
<213> ORGANISM: Artificial Sequence
<220> FEATURE:
<223> OTHER INFORMATION: CDR1-L of the so-called "6D6-B8" anti-CD123
      antibody

<400> SEQUENCE: 257

Glu Asp Ile Phe Asn Asn
1               5

<210> SEQ ID NO 258
```

```
<211> LENGTH: 9
<212> TYPE: PRT
<213> ORGANISM: Artificial Sequence
<220> FEATURE:
<223> OTHER INFORMATION: CDR3-L of the so-called "6D6-B8" anti-CD123
      antibody

<400> SEQUENCE: 258

His Gln Tyr Asn Ile Tyr Pro Tyr Thr
1               5

<210> SEQ ID NO 259
<211> LENGTH: 119
<212> TYPE: PRT
<213> ORGANISM: Artificial Sequence
<220> FEATURE:
<223> OTHER INFORMATION: VH of the so-called "8B11-B7" anti-CD123
      antibody.

<400> SEQUENCE: 259

Gln Val Gln Leu Gln Glu Ser Gly Pro Thr Leu Val Asn Pro Gly Asp
1               5                   10                  15

Ser Val Lys Met Ser Cys Lys Ala Ser Gly Tyr Thr Phe Thr Asp His
                20                  25                  30

Ile Ile His Trp Val Lys Gln Ser His Gly Lys Ser Leu Glu Trp Ile
            35                  40                  45

Gly Tyr Ile Asn Pro Tyr Ser Gly Gly Ala Asn Tyr Asn Gly Lys Phe
    50                  55                  60

Lys Ser Lys Ala Thr Leu Thr Ile Asp Lys Ser Ser Thr Ala Tyr
65                  70                  75                  80

Met Glu Phe Ser Arg Leu Thr Ser Gly Asp Ser Ala Ile Tyr Tyr Cys
                85                  90                  95

Ala Leu Asn Tyr Gly Ser Tyr Tyr Ala Met Asp Ala Trp Gly Gln Gly
            100                 105                 110

Thr Ser Val Thr Val Ser Ser
        115

<210> SEQ ID NO 260
<211> LENGTH: 8
<212> TYPE: PRT
<213> ORGANISM: Artificial Sequence
<220> FEATURE:
<223> OTHER INFORMATION: CDR2-H of the so-called "8B11-B7" anti-CD123
      antibody

<400> SEQUENCE: 260

Ile Asn Pro Tyr Ser Gly Gly Ala
1               5

<210> SEQ ID NO 261
<211> LENGTH: 107
<212> TYPE: PRT
<213> ORGANISM: Artificial Sequence
<220> FEATURE:
<223> OTHER INFORMATION: VL of the so-called "8B11-B7" anti-CD123
      antibody

<400> SEQUENCE: 261

Asp Ile Gln Met Thr Gln Ser Pro Ala Ser Leu Ser Ala Ser Leu Gly
1               5                   10                  15

Glu Thr Val Thr Ile Glu Cys Arg Thr Ser Lys Asp Ile Tyr Ser Asn
                20                  25                  30

Leu Ala Trp Phe Gln Gln Glu Pro Gly Asn Ser Pro Gln Leu Leu Ile
```

```
            35                  40                  45
Tyr Asp Ala Ser Asn Leu Ala Asp Gly Val Pro Ser Arg Phe Ser Gly
 50                  55                  60

Ser Gly Ser Gly Thr Gln Tyr Ser Leu Gln Ile Asn Asn Leu Gln Ser
 65                  70                  75                  80

Glu Asp Val Ala Ser Tyr Phe Cys His Gln Tyr Asn Asn Tyr Pro Tyr
                 85                  90                  95

Thr Phe Gly Thr Gly Thr Lys Leu Glu Leu Lys
            100                 105
```

<210> SEQ ID NO 262
<211> LENGTH: 6
<212> TYPE: PRT
<213> ORGANISM: Artificial Sequence
<220> FEATURE:
<223> OTHER INFORMATION: CDR1-L of the so-called "8B11-B7" anti-CD123
      antibody

<400> SEQUENCE: 262

```
Lys Asp Ile Tyr Ser Asn
 1               5
```

<210> SEQ ID NO 263
<211> LENGTH: 9
<212> TYPE: PRT
<213> ORGANISM: Artificial Sequence
<220> FEATURE:
<223> OTHER INFORMATION: CDR3-L of the so-called "8B11-B7" anti-CD123
      antibody

<400> SEQUENCE: 263

```
His Gln Tyr Asn Asn Tyr Pro Tyr Thr
 1               5
```

<210> SEQ ID NO 264
<211> LENGTH: 121
<212> TYPE: PRT
<213> ORGANISM: Artificial Sequence
<220> FEATURE:
<223> OTHER INFORMATION: VH of the so-called "9B8-G6" anti-CD123
      antibody

<400> SEQUENCE: 264

```
Glu Val Lys Leu Gln Glu Ser Gly Pro Ser Leu Val Gln Ser Ser Gln
 1               5                  10                  15

Thr Leu Ser Leu Thr Cys Thr Val Ser Gly Phe Ser Leu Thr Ser Tyr
             20                  25                  30

His Ile His Trp Val Arg Gln Pro Pro Gly Lys Gly Leu Glu Trp Met
         35                  40                  45

Gly Val Met Trp Ser Asp Gly Asp Thr Ser Tyr Ser Ala Leu Lys
 50                  55                  60

Ser Arg Leu Ser Ile Ser Arg Asp Thr Ser Gln Ser Gln Val Phe Leu
 65                  70                  75                  80

Lys Met Asn Ser Leu Gln Thr Glu Asp Thr Ala Thr Tyr Tyr Cys Ala
                 85                  90                  95

Arg Gly Asp Tyr Ser Ser Tyr Ile Tyr Leu Trp Phe Ala Tyr Trp Gly
            100                 105                 110

Gln Gly Thr Leu Val Thr Val Ser Ser
        115                 120
```

<210> SEQ ID NO 265

```
<211> LENGTH: 8
<212> TYPE: PRT
<213> ORGANISM: Artificial Sequence
<220> FEATURE:
<223> OTHER INFORMATION: CDR1-H of the so-called "9B8-G6" and "9D7-C8"
      anti-CD123 antibodies

<400> SEQUENCE: 265

Gly Phe Ser Leu Thr Ser Tyr His
1               5

<210> SEQ ID NO 266
<211> LENGTH: 7
<212> TYPE: PRT
<213> ORGANISM: Artificial Sequence
<220> FEATURE:
<223> OTHER INFORMATION: CDR2-H of the so-called "9B8-G6" and "9D7-C8"
      anti-CD123 antibodies

<400> SEQUENCE: 266

Met Trp Ser Asp Gly Asp Thr
1               5

<210> SEQ ID NO 267
<211> LENGTH: 15
<212> TYPE: PRT
<213> ORGANISM: Artificial Sequence
<220> FEATURE:
<223> OTHER INFORMATION: CDR3-H of the so-called "9B8-G6" anti-CD123
      antibody

<400> SEQUENCE: 267

Ala Arg Gly Asp Tyr Ser Ser Tyr Ile Tyr Leu Trp Phe Ala Tyr
1               5                  10                  15

<210> SEQ ID NO 268
<211> LENGTH: 121
<212> TYPE: PRT
<213> ORGANISM: Artificial Sequence
<220> FEATURE:
<223> OTHER INFORMATION: VH of the so-called "9D7-C8" anti-CD123
      antibody

<400> SEQUENCE: 268

Glu Val Lys Leu Gln Glu Ser Gly Pro Ser Leu Val Gln Ser Gln
1               5                  10                  15

Thr Leu Ser Leu Thr Cys Thr Val Ser Gly Phe Ser Leu Thr Ser Tyr
                20                  25                  30

His Ile His Trp Val Arg Gln Thr Pro Gly Lys Gly Leu Glu Trp Met
            35                  40                  45

Gly Val Met Trp Ser Asp Gly Asp Thr Ser Tyr Asn Ser Ala Leu Lys
        50                  55                  60

Ser Arg Leu Ser Ile Ser Arg Asp Thr Ser Gln Ser Gln Val Phe Leu
65                  70                  75                  80

Lys Met Asn Ser Leu Gln Thr Glu Asp Thr Ala Thr Tyr Tyr Cys Ala
                85                  90                  95

Arg Gly Tyr Tyr Ser Ser Tyr Leu Tyr Leu Trp Phe Ala Tyr Trp Gly
            100                 105                 110

Gln Gly Thr Leu Val Thr Val Ser Ser
        115                 120

<210> SEQ ID NO 269
<211> LENGTH: 15
<212> TYPE: PRT
```

```
<213> ORGANISM: Artificial Sequence
<220> FEATURE:
<223> OTHER INFORMATION: CDR3-H of the so-called "9D7-C8" anti-CD123
      antibody

<400> SEQUENCE: 269

Ala Arg Gly Tyr Tyr Ser Ser Tyr Leu Tyr Leu Trp Phe Ala Tyr
1               5                   10                  15

<210> SEQ ID NO 270
<211> LENGTH: 113
<212> TYPE: PRT
<213> ORGANISM: Artificial Sequence
<220> FEATURE:
<223> OTHER INFORMATION: VL of the so-called "9D7-C8" anti-CD123
      antibody

<400> SEQUENCE: 270

Asp Ile Val Met Thr Gln Ser Pro Ser Ser Leu Ala Val Ser Glu Gly
1               5                   10                  15

Glu Thr Val Thr Ile Asn Cys Lys Ser Ser Gln Ser Phe Leu Ser Ser
                20                  25                  30

Gly Asp Gly Lys Asn Tyr Val Ala Trp Tyr Gln Tyr Lys Pro Gly Gln
            35                  40                  45

Ser Pro Lys Leu Leu Ile Tyr Trp Ala Ser Thr Arg Gln Ser Gly Val
        50                  55                  60

Pro Asp Arg Phe Ile Gly Ser Gly Ser Gly Thr Asp Phe Thr Leu Thr
65                  70                  75                  80

Ile Ser Thr Val Gln Ala Glu Asp Leu Ala Ile Tyr Tyr Cys Gln Gln
                85                  90                  95

Tyr Tyr Asp Thr Pro Leu Thr Phe Gly Ser Gly Thr Lys Leu Glu Ile
            100                 105                 110

Lys

<210> SEQ ID NO 271
<211> LENGTH: 12
<212> TYPE: PRT
<213> ORGANISM: Artificial Sequence
<220> FEATURE:
<223> OTHER INFORMATION: CDR1-L of the so-called "9D7-C8" anti-CD123
      antibody

<400> SEQUENCE: 271

Gln Ser Phe Leu Ser Ser Gly Asp Gly Lys Asn Tyr
1               5                   10

<210> SEQ ID NO 272
<211> LENGTH: 119
<212> TYPE: PRT
<213> ORGANISM: Artificial Sequence
<220> FEATURE:
<223> OTHER INFORMATION: VH of the so-called "9F6-G3" anti-CD123
      antibody

<400> SEQUENCE: 272

Gln Val Gln Leu Gln Glu Ser Gly Pro Thr Leu Val Lys Pro Gly Asp
1               5                   10                  15

Ser Val Lys Met Ser Cys Lys Ala Ser Gly Tyr Thr Phe Thr Asp Tyr
                20                  25                  30

Ile Ile His Trp Val Lys Gln Ser His Gly Lys Ser Leu Glu Trp Ile
            35                  40                  45

Gly Tyr Ile Asn Pro Tyr Ser Asp Gly Thr Asn Tyr Asn Glu Lys Phe
```

50                  55                  60

Lys Ser Lys Ala Thr Leu Thr Val Asp Lys Ser Thr Ser Thr Ala Tyr
 65                  70                  75                  80

Met Glu Phe Ser Arg Leu Thr Ser Glu Asp Ser Ala Ile Tyr Phe Cys
                 85                  90                  95

Ala Leu Asn Tyr Gly Ser Tyr Tyr Ala Met Asp Ala Trp Gly Gln Gly
            100                 105                 110

Thr Ser Val Thr Val Ser Ser
        115

<210> SEQ ID NO 273
<211> LENGTH: 8
<212> TYPE: PRT
<213> ORGANISM: Artificial Sequence
<220> FEATURE:
<223> OTHER INFORMATION: CDR1-H of the so-called "9F6-G3" anti-CD123
      antibody

<400> SEQUENCE: 273

Gly Tyr Thr Phe Thr Asp Tyr Ile
1               5

<210> SEQ ID NO 274
<211> LENGTH: 8
<212> TYPE: PRT
<213> ORGANISM: Artificial Sequence
<220> FEATURE:
<223> OTHER INFORMATION: CDR2-H of the so-called "9F6-G3" anti-CD123
      antibody

<400> SEQUENCE: 274

Ile Asn Pro Tyr Ser Asp Gly Thr
1               5

<210> SEQ ID NO 275
<211> LENGTH: 107
<212> TYPE: PRT
<213> ORGANISM: Artificial Sequence
<220> FEATURE:
<223> OTHER INFORMATION: VL of the so-called "9F6-G3" anti-CD123
      antibody

<400> SEQUENCE: 275

Asp Ile Gln Met Thr Gln Ser Pro Ala Ser Leu Ser Ala Ser Leu Gly
1               5                   10                  15

Glu Thr Val Thr Ile Glu Cys Arg Pro Ser Glu Asp Ile His Ser Asn
            20                  25                  30

Val Ala Trp Tyr Gln Gln Lys Pro Gly Asn Ser Pro Gln Leu Leu Ile
        35                  40                  45

Tyr Asp Ala Ser Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Ser Tyr Phe Cys His Gln Tyr Asn Ile Tyr Pro Tyr
                85                  90                  95

Thr Phe Gly Ser Gly Thr Lys Leu Glu Leu Lys
            100                 105

<210> SEQ ID NO 276
<211> LENGTH: 6
<212> TYPE: PRT
<213> ORGANISM: Artificial Sequence
<220> FEATURE:
<223> OTHER INFORMATION: CDR1-L of the so-called "9F6-G3" anti-CD123
      antibody

<400> SEQUENCE: 276

Glu Asp Ile His Ser Asn
1               5

<210> SEQ ID NO 277
<211> LENGTH: 118
<212> TYPE: PRT
<213> ORGANISM: Artificial Sequence
<220> FEATURE:
<223> OTHER INFORMATION: VH_G45A of humanized "3E3" anti-CD123 antibody

<400> SEQUENCE: 277

Gln Val Gln Leu Gln Glu Ser Gly Pro Gly Leu Val Gln Pro Ser Gln
1               5                   10                  15

Thr Leu Ser Leu Thr Cys Thr Val Ser Gly Phe Ser Leu Thr Thr Tyr
            20                  25                  30

Asp Val His Trp Val Arg Gln Pro Pro Gly Lys Gly Leu Glu Trp Met
        35                  40                  45

Gly Arg Ile Gln Asn Ala Gly Ile Thr Asp Tyr Asn Ser Ala Leu Lys
    50                  55                  60

Ser Arg Leu Ile Ile Ser Arg Asp Thr Ser Lys Ser Gln Val Phe Leu
65                  70                  75                  80

Lys Met Asn Ser Val Gln Thr Glu Asp Thr Ala Met Tyr Phe Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
        115

<210> SEQ ID NO 278
<211> LENGTH: 118
<212> TYPE: PRT
<213> ORGANISM: Artificial Sequence
<220> FEATURE:
<223> OTHER INFORMATION: VHmDG variant of "3E3" anti-CD123 antibody

<400> SEQUENCE: 278

Gln Val Gln Leu Gln Glu Ser Gly Pro Gly Leu Val Gln Pro Ser Gln
1               5                   10                  15

Thr Leu Ser Leu Thr Cys Thr Val Ser Gly Phe Ser Leu Thr Thr Tyr
            20                  25                  30

Asp Val His Trp Val Arg Gln Pro Pro Gly Lys Gly Leu Glu Trp Met
        35                  40                  45

Gly Arg Ile Gln Asp Gly Gly Ile Thr Asp Tyr Asn Ser Ala Leu Lys
    50                  55                  60

Ser Arg Leu Ile Ile Ser Arg Asp Thr Ser Lys Ser Gln Val Phe Leu
65                  70                  75                  80

Lys Met Asn Ser Val Gln Thr Glu Asp Thr Ala Met Tyr Phe Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
        115

<210> SEQ ID NO 279

```
<211> LENGTH: 6
<212> TYPE: PRT
<213> ORGANISM: Artificial Sequence
<220> FEATURE:
<223> OTHER INFORMATION: CDR2-H of VHmDG variant of "3E3" and CDR2H of
      humanized "3E3" anti-CD123 antibody

<400> SEQUENCE: 279

Gln Asp Gly Gly Ile Thr
1               5

<210> SEQ ID NO 280
<211> LENGTH: 118
<212> TYPE: PRT
<213> ORGANISM: Artificial Sequence
<220> FEATURE:
<223> OTHER INFORMATION: VH1A of humanized "3E3" anti-CD123 antibody

<400> SEQUENCE: 280

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Val His Trp Ile Arg Gln Pro Pro Gly Lys Gly Leu Glu Trp Ile
        35                  40                  45

Gly Arg Ile Gln Asn Ala Gly Ile Thr Asp Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
        115

<210> SEQ ID NO 281
<211> LENGTH: 118
<212> TYPE: PRT
<213> ORGANISM: Artificial Sequence
<220> FEATURE:
<223> OTHER INFORMATION: VH1B of humanized "3E3" anti-CD123 antibody

<400> SEQUENCE: 281

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Val His Trp Val Arg Gln Pro Pro Gly Lys Gly Leu Glu Trp Ile
        35                  40                  45

Gly Arg Ile Gln Asn Ala Gly Ile Thr Asp Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
        115
```

<210> SEQ ID NO 282
<211> LENGTH: 118
<212> TYPE: PRT
<213> ORGANISM: Artificial Sequence
<220> FEATURE:
<223> OTHER INFORMATION: VH1C of humanized "3E3" anti-CD123 antibody

<400> SEQUENCE: 282

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Val His Trp Ile Arg Gln Pro Pro Gly Lys Gly Leu Glu Trp Met
        35                  40                  45

Gly Arg Ile Gln Asn Ala Gly Ile Thr Asp Tyr Asn Pro Ser Leu Lys
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
        115

<210> SEQ ID NO 283
<211> LENGTH: 118
<212> TYPE: PRT
<213> ORGANISM: Artificial Sequence
<220> FEATURE:
<223> OTHER INFORMATION: VH1D of humanized "3E3" anti-CD123 antibody

<400> SEQUENCE: 283

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Val His Trp Val Arg Gln Pro Pro Gly Lys Gly Leu Glu Trp Met
        35                  40                  45

Gly Arg Ile Gln Asn Ala Gly Ile Thr Asp Tyr Asn Pro Ser Leu Lys
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
        115

<210> SEQ ID NO 284
<211> LENGTH: 118
<212> TYPE: PRT
<213> ORGANISM: Artificial Sequence
<220> FEATURE:
<223> OTHER INFORMATION: VH1E of humanized "3E3" anti-CD123 antibody

<400> SEQUENCE: 284

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Val His Trp Val Arg Gln Pro Pro Gly Lys Gly Leu Glu Trp Met
        35                  40                  45

Gly Arg Ile Gln Asn Ala Gly Ile Thr Asp Tyr Asn Pro Ser Leu Lys
    50                  55                  60

Ser Arg Leu Thr Ile Ser Arg Asp Thr Ser Lys Ser Gln Val Ser Leu
65                  70                  75                  80

Lys Leu Ser Ser Val Thr Ala Ala Asp Thr Ala Val Tyr Phe Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
            115

<210> SEQ ID NO 285
<211> LENGTH: 118
<212> TYPE: PRT
<213> ORGANISM: Artificial Sequence
<220> FEATURE:
<223> OTHER INFORMATION: VH1F of humanized "3E3" anti-CD123 antibody

<400> SEQUENCE: 285

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Val His Trp Ile Arg Gln Pro Pro Gly Lys Gly Leu Glu Trp Met
        35                  40                  45

Gly Arg Ile Gln Asn Ala Gly Ile Thr Asp Tyr Asn Pro Ala Leu Lys
    50                  55                  60

Ser Arg Leu Thr Ile Ser Arg Asp Thr Ser Lys Ser Gln Val Phe Leu
65                  70                  75                  80

Lys Leu Ser Ser Val Thr Ala Ala Asp Thr Ala Val Tyr Tyr Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
            115

<210> SEQ ID NO 286
<211> LENGTH: 118
<212> TYPE: PRT
<213> ORGANISM: Artificial Sequence
<220> FEATURE:
<223> OTHER INFORMATION: VH1G of humanized "3E3" anti-CD123 antibody

<400> SEQUENCE: 286

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Val His Trp Val Arg Gln Pro Pro Gly Lys Gly Leu Glu Trp Met
        35                  40                  45

Gly Arg Ile Gln Asn Ala Gly Ile Thr Asp Tyr Asn Pro Ala Leu Lys
    50                  55                  60
```

Ser Arg Leu Thr Ile Ser Arg Asp Thr Ser Lys Ser Gln Val Phe Leu
65                  70                  75                  80

Lys Leu Ser Ser Val Gln Ala Ala Asp Thr Ala Val Tyr Phe Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
        115

<210> SEQ ID NO 287
<211> LENGTH: 118
<212> TYPE: PRT
<213> ORGANISM: Artificial Sequence
<220> FEATURE:
<223> OTHER INFORMATION: VH1Fm1 of humanized "3E3" anti-CD123 antibody

<400> SEQUENCE: 287

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Val His Trp Ile Arg Gln Pro Pro Gly Lys Gly Leu Glu Trp Met
        35                  40                  45

Gly Arg Ile Gln Asn Ala Gly Ile Thr Asp Tyr Asn Pro Ala Leu Lys
    50                  55                  60

Ser Arg Leu Thr Ile Ser Arg Asp Thr Ser Lys Ser Gln Val Phe Leu
65                  70                  75                  80

Lys Met Ser Ser Val Thr Ala Ala Asp Thr Ala Val Tyr Tyr Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
        115

<210> SEQ ID NO 288
<211> LENGTH: 118
<212> TYPE: PRT
<213> ORGANISM: Artificial Sequence
<220> FEATURE:
<223> OTHER INFORMATION: VH1Fm2 of humanized "3E3" anti-CD123 antibody

<400> SEQUENCE: 288

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Val His Trp Ile Arg Gln Pro Pro Gly Lys Gly Leu Glu Trp Met
        35                  40                  45

Gly Arg Ile Gln Asn Ala Gly Ile Thr Asp Tyr Asn Pro Ser Leu Lys
    50                  55                  60

Ser Arg Leu Thr Ile Ser Arg Asp Thr Ser Lys Ser Gln Val Ser Leu
65                  70                  75                  80

Lys Met Ser Ser Val Thr Ala Ala Asp Thr Ala Val Tyr Tyr Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser

<210> SEQ ID NO 289
<211> LENGTH: 118
<212> TYPE: PRT
<213> ORGANISM: Artificial Sequence
<220> FEATURE:
<223> OTHER INFORMATION: VH1Fm2DG of humanized "3E3" anti-CD123 antibody

<400> SEQUENCE: 289

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Val His Trp Ile Arg Gln Pro Pro Gly Lys Gly Leu Glu Trp Met
        35                  40                  45

Gly Arg Ile Gln Asp Gly Gly Ile Thr Asp Tyr Asn Pro Ser Leu Lys
    50                  55                  60

Ser Arg Leu Thr Ile Ser Arg Asp Thr Ser Lys Ser Gln Val Ser Leu
65                  70                  75                  80

Lys Met Ser Ser Val Thr Ala Ala Asp Thr Ala Val Tyr Tyr Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
        115

<210> SEQ ID NO 290
<211> LENGTH: 118
<212> TYPE: PRT
<213> ORGANISM: Artificial Sequence
<220> FEATURE:
<223> OTHER INFORMATION: VH1Dm1 of humanized "3E3" anti-CD123 antibody

<400> SEQUENCE: 290

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Val His Trp Val Arg Gln Pro Pro Gly Lys Gly Leu Glu Trp Met
        35                  40                  45

Gly Arg Ile Gln Asn Ala Gly Ile Thr Asp Tyr Asn Pro Ser Leu Lys
    50                  55                  60

Ser Arg Leu Thr Ile Ser Arg Asp Thr Ser Lys Asn Gln Val Ser Leu
65                  70                  75                  80

Lys Met Ser Ser Val Thr Ala Ala Asp Thr Ala Val Tyr Phe Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
        115

<210> SEQ ID NO 291
<211> LENGTH: 118
<212> TYPE: PRT
<213> ORGANISM: Artificial Sequence
<220> FEATURE:
<223> OTHER INFORMATION: VH1Em1 of humanized "3E3" anti-CD123 antibody

<400> SEQUENCE: 291

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
                20                  25                  30

Asp Val His Trp Val Arg Gln Pro Pro Gly Lys Gly Leu Glu Trp Met
            35                  40                  45

Gly Arg Ile Gln Asn Ala Gly Ile Thr Asp Tyr Asn Pro Ala Leu Lys
50                  55                  60

Ser Arg Leu Thr Ile Ser Arg Asp Thr Ser Lys Ser Gln Val Ser Leu
65                  70                  75                  80

Lys Met Ser Ser Val Thr Ala Ala Asp Thr Ala Val Tyr Phe Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
            115

<210> SEQ ID NO 292
<211> LENGTH: 111
<212> TYPE: PRT
<213> ORGANISM: Artificial Sequence
<220> FEATURE:
<223> OTHER INFORMATION: VL1A of humanized "3E3" anti-CD123 antibody

<400> SEQUENCE: 292

Asn Phe Val Leu Thr Gln Pro His Ser Val Ser Glu Ser Pro Gly Lys
1               5                   10                  15

Thr Val Thr Ile Ser Cys Thr Arg Asn Thr Gly Asn Ile Gly Ser Asn
                20                  25                  30

Tyr Val Gln Trp Tyr Gln Gln Arg Pro Gly Ser Ser Pro Thr Thr Val
            35                  40                  45

Ile Tyr Arg Asp Asp Lys Arg Pro Ser Gly Val Pro Asp Arg Phe Ser
50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Ser Ser
                85                  90                  95

Gly Ile Asn Ile Ile Phe Gly Gly Gly Thr Lys Leu Thr Val Leu
            100                 105                 110

<210> SEQ ID NO 293
<211> LENGTH: 111
<212> TYPE: PRT
<213> ORGANISM: Artificial Sequence
<220> FEATURE:
<223> OTHER INFORMATION: VL1B of humanized "3E3" anti-CD123 antibody

<400> SEQUENCE: 293

Asn Phe Val Leu Thr Gln Pro His Ser Val Ser Glu Ser Pro Gly Lys
1               5                   10                  15

Thr Val Thr Ile Ser Cys Thr Arg Asn Thr Gly Asn Ile Gly Ser Asn
                20                  25                  30

Tyr Val Asn Trp Tyr Gln Gln Arg Pro Gly Ser Ser Pro Thr Thr Val
            35                  40                  45

Ile Tyr Arg Asp Asp Lys Arg Pro Ser Gly Val Pro Asp Arg Phe Ser
50                  55                  60

Gly Ser Ile Asp Ser Ser Ser Asn Ser Ala Ser Leu Thr Ile Ser Gly

```
                65                  70                  75                  80
Leu Lys Thr Glu Asp Glu Ala Asp Tyr Phe Cys Gln Ser Tyr Ser Ser
                    85                  90                  95
Gly Ile Asn Ile Ile Phe Gly Gly Gly Thr Lys Leu Thr Val Leu
                100                 105                 110
```

<210> SEQ ID NO 294
<211> LENGTH: 111
<212> TYPE: PRT
<213> ORGANISM: Artificial Sequence
<220> FEATURE:
<223> OTHER INFORMATION: VL1C of humanized "3E3" anti-CD123 antibody

<400> SEQUENCE: 294

```
Asn Phe Val Leu Thr Gln Pro His Ser Val Ser Glu Ser Pro Gly Lys
1               5                   10                  15
Thr Val Thr Ile Ser Cys Thr Arg Asn Thr Gly Asn Ile Gly Ser Asn
                20                  25                  30
Tyr Val Asn Trp Tyr Gln Gln Arg Pro Gly Ser Ser Pro Thr Thr Met
            35                  40                  45
Ile Tyr Arg Asp Asp Lys Arg Pro Ser Gly Val Pro Asp Arg Phe Ser
        50                  55                  60
Gly Ser Ile Asp Ser Ser Asn Ser Ala Ser Leu Thr Ile Ser Gly
65                  70                  75                  80
Leu Lys Thr Glu Asp Glu Ala Asp Tyr Phe Cys Gln Ser Tyr Ser Ser
                    85                  90                  95
Gly Ile Asn Ile Ile Phe Gly Gly Gly Thr Lys Leu Thr Val Leu
                100                 105                 110
```

<210> SEQ ID NO 295
<211> LENGTH: 111
<212> TYPE: PRT
<213> ORGANISM: Artificial Sequence
<220> FEATURE:
<223> OTHER INFORMATION: VL1D of humanized "3E3" anti-CD123 antibody

<400> SEQUENCE: 295

```
Asn Phe Val Leu Thr Gln Pro His Ser Val Ser Glu Ser Pro Gly Lys
1               5                   10                  15
Thr Val Thr Ile Ser Cys Thr Arg Asn Thr Gly Asn Ile Gly Ser Asn
                20                  25                  30
Tyr Val Asn Trp Tyr Gln Gln His Pro Gly Ser Ser Pro Thr Thr Met
            35                  40                  45
Ile Tyr Arg Asp Asp Lys Arg Pro Ser Gly Val Pro Asp Arg Phe Ser
        50                  55                  60
Gly Ser Ile Asp Ser Ser Asn Ser Ala Ser Leu Thr Ile Ser Gly
65                  70                  75                  80
Leu Lys Thr Glu Asp Glu Ala Asp Tyr Phe Cys Gln Ser Tyr Ser Ser
                    85                  90                  95
Gly Ile Asn Ile Ile Phe Gly Gly Gly Thr Lys Leu Thr Val Leu
                100                 105                 110
```

<210> SEQ ID NO 296
<211> LENGTH: 111
<212> TYPE: PRT
<213> ORGANISM: Artificial Sequence
<220> FEATURE:
<223> OTHER INFORMATION: VL1E of humanized "3E3" anti-CD123 antibody

<400> SEQUENCE: 296

```
Asn Phe Val Leu Thr Gln Pro His Ser Val Ser Thr Ser Pro Gly Ser
1               5                   10                  15

Thr Val Thr Ile Ser Cys Thr Arg Asn Thr Gly Asn Ile Gly Ser Asn
            20                  25                  30

Tyr Val Asn Trp Tyr Gln Gln Arg Pro Gly Ser Ser Pro Thr Thr Met
        35                  40                  45

Ile Tyr Arg Asp Asp Lys Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Phe Cys Gln Ser Tyr Ser Ser
                85                  90                  95

Gly Ile Asn Ile Ile Phe Gly Gly Gly Thr Lys Leu Thr Val Leu
            100                 105                 110
```

<210> SEQ ID NO 297
<211> LENGTH: 111
<212> TYPE: PRT
<213> ORGANISM: Artificial Sequence
<220> FEATURE:
<223> OTHER INFORMATION: VL1F of humanized "3E3" anti-CD123 antibody

<400> SEQUENCE: 297

```
Asn Phe Val Leu Thr Gln Pro His Ser Val Ser Thr Ser Pro Gly Ser
1               5                   10                  15

Thr Val Thr Ile Ser Cys Thr Arg Asn Thr Gly Asn Ile Gly Ser Asn
            20                  25                  30

Tyr Val Asn Trp Tyr Gln Gln Arg Pro Gly Ser Ser Pro Thr Thr Met
        35                  40                  45

Ile Tyr Arg Asp Asp Lys Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Val Lys Thr Glu Asp Glu Ala Asp Tyr Phe Cys Gln Ser Tyr Ser Ser
                85                  90                  95

Gly Ile Asn Ile Ile Phe Gly Gly Gly Thr Lys Leu Thr Val Leu
            100                 105                 110
```

<210> SEQ ID NO 298
<211> LENGTH: 111
<212> TYPE: PRT
<213> ORGANISM: Artificial Sequence
<220> FEATURE:
<223> OTHER INFORMATION: VL1G of humanized "3E3" anti-CD123 antibody

<400> SEQUENCE: 298

```
Asn Phe Val Leu Thr Gln Pro His Ser Val Ser Thr Ser Pro Gly Ser
1               5                   10                  15

Thr Val Thr Ile Ser Cys Thr Arg Asn Thr Gly Asn Ile Gly Ser Asn
            20                  25                  30

Tyr Val Asn Trp Tyr Gln Gln His Pro Gly Ser Ser Pro Thr Thr Met
        35                  40                  45

Ile Tyr Arg Asp Asp Lys Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Val Lys Thr Glu Asp Glu Ala Asp Tyr Phe Cys Gln Ser Tyr Ser Ser
```

```
                    85                  90                  95

Gly Ile Asn Ile Ile Phe Gly Gly Gly Thr Lys Leu Thr Val Leu
                100                 105                 110
```

<210> SEQ ID NO 299
<211> LENGTH: 111
<212> TYPE: PRT
<213> ORGANISM: Artificial Sequence
<220> FEATURE:
<223> OTHER INFORMATION: VL1Fm1 of humanized "3E3" anti-CD123 antibody

<400> SEQUENCE: 299

```
Asn Phe Val Leu Thr Gln Pro His Ser Val Ser Thr Ser Pro Gly Ser
1               5                   10                  15

Thr Val Thr Ile Ser Cys Thr Arg Asn Thr Gly Asn Ile Gly Ser Asn
                20                  25                  30

Tyr Val Asn Trp Tyr Gln Gln Arg Pro Gly Ser Ser Pro Thr Thr Met
            35                  40                  45

Ile Tyr Arg Asp Asp Lys Arg Pro Ser Gly Val Pro Asp Arg Phe Ser
        50                  55                  60

Gly Ser Ile Asp Arg Ser Ser Asn Ser Ala Ser Leu Thr Ile Ser Gly
65                  70                  75                  80

Val Lys Thr Glu Asp Glu Ala Asp Tyr Phe Cys Gln Ser Tyr Ser Ser
                85                  90                  95

Gly Ile Asn Ile Ile Phe Gly Gly Gly Thr Lys Leu Thr Val Leu
                100                 105                 110
```

<210> SEQ ID NO 300
<211> LENGTH: 111
<212> TYPE: PRT
<213> ORGANISM: Artificial Sequence
<220> FEATURE:
<223> OTHER INFORMATION: VL1Fm2 of humanized "3E3" anti-CD123 antibody

<400> SEQUENCE: 300

```
Asn Phe Val Leu Thr Gln Pro His Ser Val Ser Thr Ser Pro Gly Ser
1               5                   10                  15

Thr Val Thr Leu Ser Cys Thr Arg Asn Thr Gly Asn Ile Gly Ser Asn
                20                  25                  30

Tyr Val Asn Trp Tyr Gln Gln Arg Pro Gly Ser Ser Pro Thr Thr Met
            35                  40                  45

Ile Tyr Arg Asp Asp Lys Arg Pro Asp Gly Val Pro Asp Arg Phe Ser
        50                  55                  60

Gly Ser Ile Asp Arg Ser Ser Asn Ser Ala Ser Leu Thr Ile Ser Gly
65                  70                  75                  80

Val Lys Thr Glu Asp Glu Ala Asp Tyr Phe Cys Gln Ser Tyr Ser Ser
                85                  90                  95

Gly Ile Asn Ile Ile Phe Gly Gly Gly Thr Lys Leu Thr Val Leu
                100                 105                 110
```

<210> SEQ ID NO 301
<211> LENGTH: 118
<212> TYPE: PRT
<213> ORGANISM: Artificial Sequence
<220> FEATURE:
<223> OTHER INFORMATION: VH2A of humanized "3E3" anti-CD123 antibody

<400> SEQUENCE: 301

```
Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Phe Ser Leu Thr Thr Tyr
            20                  25                  30

Asp Val His Trp Val Arg Gln Pro Gly Lys Gly Leu Glu Trp Met
            35                  40                  45

Gly Arg Ile Gln Asn Ala Gly Ile Thr Asp Tyr Asn Ser Ala Leu Lys
        50                  55                  60

Ser Arg Leu Ile Ile Ser Arg Asp Thr Ser Lys Ser Gln Val Phe Leu
65                  70                  75                  80

Lys Met Asn Ser Val Thr Thr Ala Asp Thr Ala Met Tyr Phe Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
            115
```

<210> SEQ ID NO 302
<211> LENGTH: 118
<212> TYPE: PRT
<213> ORGANISM: Artificial Sequence
<220> FEATURE:
<223> OTHER INFORMATION: VH3A of humanized "3E3" anti-CD123 antibody

<400> SEQUENCE: 302

```
Gln Val Thr Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Thr Tyr
            20                  25                  30

Asp Val His Trp Val Arg Gln Pro Pro Gly Lys Gly Leu Glu Trp Met
            35                  40                  45

Gly Arg Ile Gln Asn Ala Gly Ile Thr Asp Tyr Asn Ser Ala Leu Lys
        50                  55                  60

Ser Arg Leu Ile Ile Ser Arg Asp Thr Ser Lys Ser Gln Val Phe Leu
65                  70                  75                  80

Lys Met Asn Ser Val Asp Thr Val Asp Thr Ala Met Tyr Phe Cys Ala
                85                  90                  95

Lys Thr Gly Ser Tyr Phe Tyr Ala Phe Asp His Trp Gly Gln Gly Thr
            100                 105                 110

Leu Val Thr Val Ser Ser
            115
```

<210> SEQ ID NO 303
<211> LENGTH: 111
<212> TYPE: PRT
<213> ORGANISM: Artificial Sequence
<220> FEATURE:
<223> OTHER INFORMATION: VL2A of humanized "3E3" anti-CD123 antibody.

<400> SEQUENCE: 303

```
Gln Phe Val Leu Thr Gln Pro Pro Ser Val Ser Thr Asn Pro Gly Ser
1               5                   10                  15

Thr Val Lys Leu Ser Cys Lys Arg Asn Thr Gly Asn Ile Gly Ser Asn
            20                  25                  30

Tyr Val Asn Trp Tyr Gln Gln Lys Pro Gly Gln Ser Pro Thr Thr Met
            35                  40                  45

Ile Tyr Arg Asp Asp Lys Arg Pro Asp Gly Val Pro Asp Arg Phe Ser
        50                  55                  60

Gly Ser Ile Asp Arg Ser Ser Asn Ser Ala Leu Leu Thr Ile Asn Asn
```

```
                65                  70                  75                  80
Val Gln Thr Glu Asp Glu Ala Asp Tyr Phe Cys Gln Ser Tyr Ser Ser
                    85                  90                  95

Gly Ile Asn Ile Ile Phe Gly Gly Gly Thr Lys Leu Thr Val Leu
                100                 105                 110

<210> SEQ ID NO 304
<211> LENGTH: 111
<212> TYPE: PRT
<213> ORGANISM: Artificial Sequence
<220> FEATURE:
<223> OTHER INFORMATION: VL2Am1 of humanized "3E3" anti-CD123 antibody

<400> SEQUENCE: 304

Gln Phe Val Leu Thr Gln Pro His Ser Val Ser Thr Asn Pro Gly Ser
1               5                   10                  15

Thr Val Lys Leu Ser Cys Lys Arg Asn Thr Gly Asn Ile Gly Ser Asn
                20                  25                  30

Tyr Val Asn Trp Tyr Gln Gln Lys Pro Gly Gln Ser Pro Thr Thr Met
            35                  40                  45

Ile Tyr Arg Asp Asp Lys Arg Pro Asp Gly Val Pro Asp Arg Phe Ser
        50                  55                  60

Gly Ser Ile Asp Arg Ser Ser Asn Ser Ala Leu Leu Thr Ile Asn Asn
65                  70                  75                  80

Val Gln Thr Glu Asp Glu Ala Asp Tyr Phe Cys Gln Ser Tyr Ser Ser
                    85                  90                  95

Gly Ile Asn Ile Ile Phe Gly Gly Gly Thr Lys Leu Thr Val Leu
                100                 105                 110

<210> SEQ ID NO 305
<211> LENGTH: 111
<212> TYPE: PRT
<213> ORGANISM: Artificial Sequence
<220> FEATURE:
<223> OTHER INFORMATION: VL2Am2 of humanized "3E3" anti-CD123 antibody.

<400> SEQUENCE: 305

Gln Phe Val Leu Thr Gln Pro His Ser Val Ser Thr Asn Pro Gly Ser
1               5                   10                  15

Thr Val Lys Leu Ser Cys Lys Arg Asn Thr Gly Asn Ile Gly Ser Asn
                20                  25                  30

Tyr Val Asn Trp Tyr Gln Gln Arg Pro Gly Ser Ser Pro Thr Thr Met
            35                  40                  45

Ile Tyr Arg Asp Asp Lys Arg Pro Asp Gly Val Pro Asp Arg Phe Ser
        50                  55                  60

Gly Ser Ile Asp Arg Ser Ser Asn Ser Ala Leu Leu Thr Ile Asn Asn
65                  70                  75                  80

Val Gln Thr Glu Asp Glu Ala Asp Tyr Phe Cys Gln Ser Tyr Ser Ser
                    85                  90                  95

Gly Ile Asn Ile Ile Phe Gly Gly Gly Thr Lys Leu Thr Val Leu
                100                 105                 110

<210> SEQ ID NO 306
<211> LENGTH: 344
<212> TYPE: PRT
<213> ORGANISM: Artificial Sequence
<220> FEATURE:
<223> OTHER INFORMATION: polypeptide I of the so-called CODV-Fab "7G3 x
      20G6" antibody-like binding protein
```

```
<400> SEQUENCE: 306

Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Leu Ser Trp Tyr Leu Gln Lys Pro Gly Gln Ser
        35                  40                  45

Pro Gln Ser Leu Ile Tyr Lys Val Ser Asn Arg Phe Ser Gly Phe Ser
    50                  55                  60

Asp Arg Phe Ser Gly Ser Gly Ser Gly Thr Phe Thr Leu Lys Ile
65                  70                  75                  80

Ser Arg Val Asp Pro Asp Asp Leu Gly Val Tyr Tyr Cys Gly Gln Gly
                85                  90                  95

Thr Gln Tyr Pro Phe Thr Phe Gly Ser Gly Thr Lys Leu Glu Ile Lys
                100                 105                 110

Gly Gln Pro Lys Ala Ala Pro Asp Phe Val Met Thr Gln Ser Pro Ser
            115                 120                 125

Ser Leu Thr Val Thr Ala Gly Glu Lys Val Thr Met Ser Cys Lys Ser
    130                 135                 140

Ser Gln Ser Leu Leu Asn Ser Gly Asn Gln Lys Asn Tyr Leu Thr Trp
145                 150                 155                 160

Tyr Leu Gln Lys Pro Gly Gln Pro Pro Lys Leu Leu Ile Tyr Trp Ala
                165                 170                 175

Ser Thr Arg Glu Ser Gly Val Pro Asp Arg Phe Thr Gly Ser Gly Ser
            180                 185                 190

Gly Thr Asp Phe Thr Leu Thr Ile Ser Ser Val Gln Ala Glu Asp Leu
        195                 200                 205

Ala Val Tyr Tyr Cys Gln Asn Asp Tyr Ser Tyr Pro Tyr Thr Phe Gly
    210                 215                 220

Gly Gly Thr Lys Leu Glu Ile Lys Thr Lys Gly Pro Ser Arg Thr Val
225                 230                 235                 240

Ala Ala Pro Ser Val Phe Ile Phe Pro Pro Ser Asp Glu Gln Leu Lys
                245                 250                 255

Ser Gly Thr Ala Ser Val Val Cys Leu Leu Asn Asn Phe Tyr Pro Arg
            260                 265                 270

Glu Ala Lys Val Gln Trp Lys Val Asp Asn Ala Leu Gln Ser Gly Asn
        275                 280                 285

Ser Gln Glu Ser Val Thr Glu Gln Asp Ser Lys Asp Ser Thr Tyr Ser
    290                 295                 300

Leu Ser Ser Thr Leu Thr Leu Ser Lys Ala Asp Tyr Glu Lys His Lys
305                 310                 315                 320

Val Tyr Ala Cys Glu Val Thr His Gln Gly Leu Ser Ser Pro Val Thr
                325                 330                 335

Lys Ser Phe Asn Arg Gly Glu Cys
            340

<210> SEQ ID NO 307
<211> LENGTH: 7
<212> TYPE: PRT
<213> ORGANISM: Artificial Sequence
<220> FEATURE:
<223> OTHER INFORMATION: L1 of the so-called CODV-Fab "7G3x20G6",
      "7G3x4E7", "7G3x4B4", "7G3x18F5", "hz20G6x7G3", "7G3xhz4B4",
      "hz4B4x3E3" and CODV-Fab "hz20G6x7G3-TL4" antibody-like binding
      proteins
```

```
<400> SEQUENCE: 307

Gly Gln Pro Lys Ala Ala Pro
1               5

<210> SEQ ID NO 308
<211> LENGTH: 113
<212> TYPE: PRT
<213> ORGANISM: Artificial Sequence
<220> FEATURE:
<223> OTHER INFORMATION: VL1 or VL2 domain of the so-called CODV-Fab
      "7G3x20G6", "7G3x4E7", "7G3x4B4", "7G3x18F5", "hz20G6x7G3",
      "7G3xhz4B4" and CODV-Fab "hz20G6x7G3-TL4" antibody-like binding
      proteins

<400> SEQUENCE: 308

Asp Phe Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gly Gly Thr Lys Leu Glu Ile
            100                 105                 110

Lys

<210> SEQ ID NO 309
<211> LENGTH: 5
<212> TYPE: PRT
<213> ORGANISM: Artificial Sequence
<220> FEATURE:
<223> OTHER INFORMATION: L2 of the so-called CODV-Fab "7G3x20G6",
      "7G3x4E7", "7G3x4B4", "7G3x18F5", "hz20G6x7G3", "7G3xhz4B4",
      "hz4B4x3E3" and CODV-Fab "hz20G6x7G3-TL4" antibody-like binding
      proteins

<400> SEQUENCE: 309

Thr Lys Gly Pro Ser
1               5

<210> SEQ ID NO 310
<211> LENGTH: 107
<212> TYPE: PRT
<213> ORGANISM: Artificial Sequence
<220> FEATURE:
<223> OTHER INFORMATION: CL of the so-called CODV-Fab "7G3x20G6",
      "7G3x4E7", "7G3x4B4", "7G3x18F5", "hz20G6x7G3", "7G3xhz4B4" and
      "hz4B4x3E3" antibody-like binding proteins

<400> SEQUENCE: 310

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
```

```
            50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 311
<211> LENGTH: 342
<212> TYPE: PRT
<213> ORGANISM: Artificial Sequence
<220> FEATURE:
<223> OTHER INFORMATION: polypeptide II of the so-called CODV-Fab "7G3 x
      20G6" antibody-like binding protein

<400> SEQUENCE: 311

```
Glu Val Gln Leu Gln Gln Ser Gly Pro Glu Leu Val Lys Pro Gly Ala
 1               5                  10                  15

Ser Val L

```
Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
            325                 330                 335

Lys Val Asp Lys Lys Val
            340
```

<210> SEQ ID NO 312
<211> LENGTH: 120
<212> TYPE: PRT
<213> ORGANISM: Artificial Sequence
<220> FEATURE:
<223> OTHER INFORMATION: VH1 or VH2 domain of the so-called CODV-Fab
    "7G3x20G6", "7G3x4E7", "7G3x4B4", "7G3x18F5", "hz20G6x7G3",
    "7G3xhz4B4" and CODV-Fab "hz20G6x7G3-TL4" antibody-like binding
    proteins

<400> SEQUENCE: 312

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ser Thr Ala Tyr
65                  70                  75                  80

Met His Leu Asn Ser Leu Thr Ser Glu Asp Ser Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ala
        115                 120
```

<210> SEQ ID NO 313
<211> LENGTH: 98
<212> TYPE: PRT
<213> ORGANISM: Artificial Sequence
<220> FEATURE:
<223> OTHER INFORMATION: CH1 of the so-called CODV-Fab "7G3x20G6",
    "7G3x4E7", "7G3x4B4", "7G3x18F5", "hz20G6x7G3", "7G3xhz4B4",
    "hz4B4x3E3" antibody-like binding proteins

<400> SEQUENCE: 313

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 314
<211> LENGTH: 344
<212> TYPE: PRT
<213> ORGANISM: Artificial Sequence
<220> FEATURE:
<223> OTHER INFORMATION: polypeptide I of the so-called CODV-Fab "7G3 x 4E7" antibody-like binding protein

<400> SEQUENCE: 314

```
Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Glu His Asn
            20                  25                  30

Asn Gly Asn Thr Tyr Leu Ser Trp Tyr Leu Gln Lys Pro Gly Gln Ser
        35                  40                  45

Pro Gln Pro Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Tyr Pro Phe Thr Phe Gly Pro Gly Thr Lys Leu Glu Leu Lys
            100                 105                 110

Gly Gln Pro Lys Ala Ala Pro Asp Phe Val Met Thr Gln Ser Pro Ser
        115                 120                 125

Ser Leu Thr Val Thr Ala Gly Glu Lys Val Thr Met Ser Cys Lys Ser
130                 135                 140

Ser Gln Ser Leu Leu Asn Ser Gly Asn Gln Lys Asn Tyr Leu Thr Trp
145                 150                 155                 160

Tyr Leu Gln Lys Pro Gly Gln Pro Pro Lys Leu Leu Ile Tyr Trp Ala
                165                 170                 175

Ser Thr Arg Glu Ser Gly Val Pro Asp Arg Phe Thr Gly Ser Gly Ser
            180                 185                 190

Gly Thr Asp Phe Thr Leu Thr Ile Ser Ser Val Gln Ala Glu Asp Leu
        195                 200                 205

Ala Val Tyr Tyr Cys Gln Asn Asp Tyr Ser Tyr Pro Tyr Thr Phe Gly
    210                 215                 220

Gly Gly Thr Lys Leu Glu Ile Lys Thr Lys Gly Pro Ser Arg Thr Val
225                 230                 235                 240

Ala Ala Pro Ser Val Phe Ile Phe Pro Pro Ser Asp Gl

```
<212> TYPE: PRT
<213> ORGANISM: Artificial Sequence
<220> FEATURE:
<223> OTHER INFORMATION: polypeptide II of the so-called CODV-Fab "7G3 x
      4E7" antibody-like binding protein

<400> SEQUENCE: 315

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ser Thr Ala Tyr
65                  70                  75                  80

Met His Leu Asn Ser Leu Thr Ser Glu Asp Ser Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ala Ser Glu Val Gln Val Val Glu Thr
        115                 120                 125

Gly Gly Ser Leu Val Gln Pro Gly Lys Ser Leu Lys Leu Thr Cys Ala
    130                 135                 140

Thr Ser Gly Phe Thr Phe Ser Asn Ala Trp Met His Trp Val Arg Gln
145                 150                 155                 160

Ser Pro Glu Lys Gln Leu Glu Trp Val Ala Gln Ile Lys Asp Lys Ser
                165                 170                 175

Asn Asn Tyr Ala Thr Tyr Tyr Ala Glu Ser Leu Lys Gly Arg Phe Thr
            180                 185                 190

Ile Ser Arg Asp Asp Pro Lys Arg Ser Ile Tyr Leu Gln Met Asn Ser
        195                 200                 205

Leu Arg Glu Glu Asp Thr Ala Ile Tyr Tyr Cys Arg Tyr Val His Tyr
    210                 215                 220

Gly Ile Gly Tyr Ala Met Asp Ala Trp Gly Gln Gly Thr Ser Val Thr
225                 230                 235                 240

Val Ser Ser Arg Thr Ala Ser Thr Lys Gly Pro Ser Val Phe Pro Leu
                245                 250                 255

Ala Pro Ser Ser Lys Ser Thr Ser Gly Gly Thr Ala Ala Leu Gly Cys
            260                 265                 270

Leu Val Lys Asp Tyr Phe Pro Glu Pro Val Thr Val Ser Trp Asn Ser
        275                 280                 285

Gly Ala Leu Thr Ser Gly Val His Thr Phe Pro Ala Val Leu Gln Ser
    290                 295                 300

Ser Gly Leu Tyr Ser Leu Ser Ser Val Val Thr Val Pro Ser Ser Ser
305                 310                 315                 320

Leu Gly Thr Gln Thr Tyr Ile Cys Asn Val Asn His Lys Pro Ser Asn
                325                 330                 335

Thr Lys Val Asp Lys Lys Val
            340

<210> SEQ ID NO 316
<211> LENGTH: 344
<212> TYPE: PRT
<213> ORGANISM: Artificial Sequence
```

<220> FEATURE:
<223> OTHER INFORMATION: polypeptide I of the so-called CODV-Fab "7G3 x
      4B4" antibody-like binding protein

<400> SEQUENCE: 316

```
Asp Val Val Met Thr Gln Thr Pro Val Ser Leu Ser Val Ser Leu Gly
1               5                   10                  15

Gly Gln Val Ser Ile Ser Cys Arg Ser Ser Gln Ser Leu Val His Asp
            20                  25                  30

Asn Gly Asn Thr Tyr Leu Ser Trp Ser Leu Gln Arg Pro Gly Gln Ser
        35                  40                  45

Pro Gln Val Leu Ile Tyr Lys Val Ser Asn Arg Phe Ser Gly Thr Ser
    50                  55                  60

Asp Arg Phe Thr Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110

Gly Gln Pro Lys Ala Ala Pro Asp Phe Val Met Thr Gln Ser Pro Ser
        115                 120                 125

Ser Leu Thr Val Thr Ala Gly Glu Lys Val Thr Met Ser Cys Lys Ser
130                 135                 140

Ser Gln Ser Leu Leu Asn Ser Gly Asn Gln Lys Asn Tyr Leu Thr Trp
145                 150                 155                 160

Tyr Leu Gln Lys Pro Gly Gln Pro Pro Lys Leu Leu Ile Tyr Trp Ala
                165                 170                 175

Ser Thr Arg Glu Ser Gly Val Pro Asp Arg Phe Thr Gly Ser Gly Ser
            180                 185                 190

Gly Thr Asp Phe Thr Leu Thr Ile Ser Ser Val Gln Ala Glu Asp Leu
        195                 200                 205

Ala Val Tyr Tyr Cys Gln Asn Asp Tyr Ser Tyr Pro Tyr Thr Phe Gly
    210                 215                 220

Gly Gly Thr Lys Leu Glu Ile Lys Thr Lys Gly Pro Ser Arg Thr Val
225                 230                 235                 240

Ala Ala Pro Ser Val Phe Ile Phe Pro Pro Ser Asp Glu Gln Leu Lys
                245                 250                 255

Ser Gly Thr Ala Ser Val Val Cys Leu Leu Asn Asn Phe Tyr Pro Arg
            260                 265                 270

Glu Ala Lys Val Gln Trp Lys Val Asp Asn Ala Leu Gln Ser Gly Asn
        275                 280                 285

Ser Gln Glu Ser Val Thr Glu Gln Asp Ser Lys Asp Ser Thr Tyr Ser
    290                 295                 300

Leu Ser Ser Thr Leu Thr Leu Ser Lys Ala Asp Tyr Glu Lys His Lys
305                 310                 315                 320

Val Tyr Ala Cys Glu Val Thr His Gln Gly Leu Ser Ser Pro Val Thr
                325                 330                 335

Lys Ser Phe Asn Arg Gly Glu Cys
            340
```

<210> SEQ ID NO 317
<211> LENGTH: 342
<212> TYPE: PRT
<213> ORGANISM: Artificial Sequence
<220> FEATURE:
<223> OTHER INFORMATION: polypeptide II of the so-called CODV-Fab "7G3 x 4B4" antibody-like binding protein

<400> SEQUENCE: 317

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ser Thr Ala Tyr
65                  70                  75                  80

Met His Leu Asn Ser Leu Thr Ser Glu Asp Ser Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ala Ser Glu Val Gln Leu Val Glu Thr
        115                 120                 125

Gly Gly Arg Leu Val Gln Pro Gly Arg Ser Leu Lys Leu Thr Cys Ala
    130                 135                 140

Thr Ser Gly Phe Thr Phe Ser Asn Ala Trp Met His Trp Val Arg Gln
145                 150                 155                 160

Ser Pro Glu Lys Gln Leu Glu Trp Val Ala Gln Ile Lys Ala Arg Ser
                165                 170                 175

Asn Asn Tyr Ala Thr Tyr Tyr Ala Glu Ser Val Lys Gly Arg Phe Thr
            180                 185                 190

Ile Ser Arg Asp Asp Ser Lys Ser Thr Ile Tyr Leu Gln Met Asn Ser
        195                 200                 205

Leu Lys Glu Glu Asp Thr Ala Ile Tyr Tyr Cys Arg Gly Thr Tyr Tyr
    210                 215                 220

Ala Ser Lys Pro Phe Asp Tyr Trp Gly Gln Gly Val Met Val Thr Val
225                 230                 235                 240

Ser Ser Arg Thr Ala Ser Thr Lys Gly Pro Ser Val Phe Pro Leu Ala
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Lys Val
            340
```

<210> SEQ ID NO 318
<211> LENGTH: 344
<212> TYPE: PRT
<213> ORGANISM: Artificial Sequence
<220> FEATURE:
<223> OTHER INFORMATION: polypeptide I of the so-called CODV-Fab
"7G3x18F5" antibody-like binding protein.

<400> SEQUENCE: 318

Asp Val Leu Met Thr Gln Thr Pro Val Ser Leu Ser Val Ser Leu Gly
1               5                   10                  15

Gly Gln Val Ser Ile Ser Cys Arg Ser Ser Gln Ser Leu Val His Thr
            20                  25                  30

Asn Gly Asn Thr Tyr Leu Ser Trp Tyr Leu Gln Lys Pro Gly Gln Ser
        35                  40                  45

Pro Gln Leu Leu Ile Tyr Lys Val Ser Asn Arg Leu Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr His Tyr Pro Phe Thr Phe Gly Ala Gly Thr Lys Leu Glu Leu Lys
            100                 105                 110

Gly Gln Pro Lys Ala Ala Pro Asp Phe Val Met Thr Gln Ser Pro Ser
        115                 120                 125

Ser Leu Thr Val Thr Ala Gly Glu Lys Val Thr Met Ser Cys Lys Ser
130                 135                 140

Ser Gln Ser Leu Leu Asn Ser Gly Asn Gln Lys Asn Tyr Leu Thr Trp
145                 150                 155                 160

Tyr Leu Gln Lys Pro Gly Gln Pro Pro Lys Leu Leu Ile Tyr Trp Ala
                165                 170                 175

Ser Thr Arg Glu Ser Gly Val Pro Asp Arg Phe Thr Gly Ser Gly Ser
            180                 185                 190

Gly Thr Asp Phe Thr Leu Thr Ile Ser Ser Val Gln Ala Glu Asp Leu
        195                 200                 205

Ala Val Tyr Tyr Cys Gln Asn Asp Tyr Ser Tyr Pro Tyr Thr Phe Gly
    210                 215                 220

Gly Gly Thr Lys Leu Glu Ile Lys Thr Lys Gly Pro Ser Arg Thr Val
225                 230                 235                 240

Ala Ala Pro Ser Val Phe Ile Phe Pro Pro Ser Asp Glu Gln Leu Lys
                245                 250                 255

Ser Gly Thr Ala Ser Val Val Cys Leu Leu Asn Asn Phe Tyr Pro Arg
            260                 265                 270

Glu Ala Lys Val Gln Trp Lys Val Asp Asn Ala Leu Gln Ser Gly Asn
        275                 280                 285

Ser Gln Glu Ser Val Thr Glu Gln Asp Ser Lys Asp Ser Thr Tyr Ser
290                 295                 300

Leu Ser Ser Thr Leu Thr Leu Ser Lys Ala Asp Tyr Glu Lys His Lys
305                 310                 315                 320

Val Tyr Ala Cys Glu Val Thr His Gln Gly Leu Ser Ser Pro Val Thr
                325                 330                 335

Lys Ser Phe Asn Arg Gly Glu Cys
            340

<210> SEQ ID NO 319
<211> LENGTH: 343
<212> TYPE: PRT
<213> ORGANISM: Artificial Sequence
<220> FEATURE:
<223> OTHER INFORMATION: polypeptide II of the so-called CODV-Fab
"7G3x18F5" antibody-like binding protein.

<400> SEQUENCE: 319

Glu Val Gln Leu Gln Gln Ser Gly Pro Glu Leu Val Lys Pro Gly Ala
1 5 10 15

Ser Val Lys Met Ser Cys Lys Ala Ser Gly Tyr Thr Phe Thr Asp Tyr
20 25 30

Tyr Met Lys Trp Val Lys Gln Ser His Gly Lys Ser Leu Glu Trp Ile
35 40 45

Gly Asp Ile Ile Pro Ser Asn Gly Ala Thr Phe Tyr Asn Gln Lys Phe
50 55 60

Lys Gly Lys Ala Thr Leu Thr Val Asp Arg Ser Ser Ser Thr Ala Tyr
65 70 75 80

Met His Leu Asn Ser Leu Thr Ser Glu Asp Ser Ala Val Tyr Tyr Cys
85 90 95

Thr Arg Ser His Leu Leu Arg Ala Ser Trp Phe Ala Tyr Trp Gly Gln
100 105 110

Gly Thr Leu Val Thr Val Ser Ala Ser Glu Val Gln Val Val Glu Thr
115 120 125

Gly Gly Ser Leu Val Gln Pro Gly Lys Ser Leu Lys Leu Thr Cys Ala
130 135 140

Thr Ser Gly Phe Thr Phe Thr Asn Ala Trp Met His Trp Val Arg Arg
145 150 155 160

Ser Pro Glu Lys Gln Leu Glu Trp Val Ala Gln Ile Lys Asp Lys Ser
165 170 175

Asn Asn Tyr Ala Thr Tyr Tyr Ala Glu Ser Val Lys Gly Arg Phe Thr
180 185 190

Ile Ser Arg Asp Asp Ser Lys Ser Ser Ile Tyr Leu Gln Met Asn Ser
195 200 205

Leu Lys Glu Glu Asp Thr Ala Ile Tyr Tyr Cys Arg Tyr Val His Tyr
210 215 220

Arg Phe Ala Tyr Ala Leu Asp Ala Trp Gly Arg Gly Thr Ser Val Ser
225 230 235 240

Val Ser Ser Arg Thr Ala Ser Thr Lys Gly Pro Ser Val Phe Pro Leu
245 250 255

Ala Pro Ser Ser Lys Ser Thr Ser Gly Gly Thr Ala Ala Leu Gly Cys
260 265 270

Leu Val Lys Asp Tyr Phe Pro Glu Pro Val Thr Val Ser Trp Asn Ser
275 280 285

Gly Ala Leu Thr Ser Gly Val His Thr Phe Pro Ala Val Leu Gln Ser
290 295 300

Ser Gly Leu Tyr Ser Leu Ser Ser Val Val Thr Val Pro Ser Ser Ser
305 310 315 320

Leu Gly Thr Gln Thr Tyr Ile Cys Asn Val Asn His Lys Pro Ser Asn
325 330 335

Thr Lys Val Asp Lys Lys Val
340

<210> SEQ ID NO 320
<211> LENGTH: 344
<212> TYPE: PRT
<213> ORGANISM: Artificial Sequence
<220> FEATURE:
<223> OTHER INFORMATION: polypeptide I of the so-called CODV-Fab
"hz20G6 x 7G3" antibody-like binding protein

<400> SEQUENCE: 320

Asp Phe Val Met Thr Gln Ser Pro Ser Ser Leu Thr Val Thr Ala Gly
1 5 10 15

```
Glu Lys Val Thr Met Ser Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gly Gly Thr Lys Leu Glu Ile
            100                 105                 110

Lys Gly Gln Pro Lys Ala Ala Pro Asp Ile Val Met Thr Gln Thr Pro
        115                 120                 125

Leu Ser Leu Ser Val Thr Pro Gly Gln Pro Ala Ser Ile Ser Cys Lys
    130                 135                 140

Ser Ser Gln Ser Leu Val His Asn Asn Gly Asn Thr Tyr Leu Ser Trp
145                 150                 155                 160

Tyr Leu Gln Lys Pro Gly Gln Ser Pro Gln Ser Leu Ile Tyr Lys Val
                165                 170                 175

Ser Asn Arg Phe Ser Gly Val Pro Asp Arg Phe Ser Gly Ser Gly Ser
            180                 185                 190

Gly Thr Asp Phe Thr Leu Lys Ile Ser Arg Val Glu Ala Glu Asp Val
        195                 200                 205

Gly Val Tyr Tyr Cys Gly Gln Gly Thr Gln Tyr Pro Phe Thr Phe Gly
    210                 215                 220

Ser Gly Thr Lys Val Glu Ile Lys Thr Lys Gly Pro Ser Arg Thr Val
225                 230                 235                 240

Ala Ala Pro Ser Val Phe Ile Phe Pro Pro Ser Asp Glu Gln Leu Lys
                245                 250                 255

Ser Gly Thr Ala Ser Val Val Cys Leu Leu Asn Asn Phe Tyr Pro Arg
            260                 265                 270

Glu Ala Lys Val Gln Trp Lys Val Asp Asn Ala Leu Gln Ser Gly Asn
        275                 280                 285

Ser Gln Glu Ser Val Thr Glu Gln Asp Ser Lys Asp Ser Thr Tyr Ser
    290                 295                 300

Leu Ser Ser Thr Leu Thr Leu Ser Lys Ala Asp Tyr Glu Lys His Lys
305                 310                 315                 320

Val Tyr Ala Cys Glu Val Thr His Gln Gly Leu Ser Ser Pro Val Thr
                325                 330                 335

Lys Ser Phe Asn Arg Gly Glu Cys
            340

<210> SEQ ID NO 321
<211> LENGTH: 342
<212> TYPE: PRT
<213> ORGANISM: Artificial Sequence
<220> FEATURE:
<223> OTHER INFORMATION: polypeptide II of the so-called CODV-Fab
      "hz20G6 x 7G3" antibody-like binding protein

<400> SEQUENCE: 321

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Lys Ala
```

-continued

```
            20                  25                  30

Trp Met His Trp Val Arg Gln Ala Pro Gly Lys Gln Leu Glu Trp Val
        35                  40                  45

Ala Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Arg Gly Val Tyr Tyr Ala Leu Ser Pro Phe Asp Tyr Trp Gly
            100                 105                 110

Gln Gly Thr Leu Val Thr Val Ser Ser Ser Glu Val Gln Leu Gln Gln
        115                 120                 125

Ser Gly Pro Glu Leu Val Lys Pro Gly Ala Ser Val Lys Met Ser Cys
    130                 135                 140

Lys Ala Ser Gly Tyr Thr Phe Thr Asp Tyr Tyr Met Lys Trp Val Lys
145                 150                 155                 160

Gln Ser His Gly Lys Ser Leu Glu Trp Ile Gly Asp Ile Ile Pro Ser
                165                 170                 175

Asn Gly Ala Thr Phe Tyr Asn Gln Lys Phe Lys Gly Lys Ala Thr Leu
            180                 185                 190

Thr Val Asp Arg Ser Ser Ser Thr Ala Tyr Met His Leu Asn Ser Leu
        195                 200                 205

Thr Ser Glu Asp Ser Ala Val Tyr Tyr Cys Thr Arg Ser His Leu Leu
    210                 215                 220

Arg Ala Ser Trp Phe Ala Tyr Trp Gly Gln Gly Thr Leu Val Thr Val
225                 230                 235                 240

Ser Ala Arg Thr Ala Ser Thr Lys Gly Pro Ser Val Phe Pro Leu Ala
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Lys Val
            340

<210> SEQ ID NO 322
<211> LENGTH: 344
<212> TYPE: PRT
<213> ORGANISM: Artificial Sequence
<220> FEATURE:
<223> OTHER INFORMATION: polypeptide I of the so-called CODV-Fab 7G3 x
      hz4B4" antibody-like binding protein

<400> SEQUENCE: 322

Asp Val Val Met Thr Gln Thr Pro Val Ser Leu Ser Val Ser Val Gly
1               5                   10                  15

Gly Arg Val Ser Ile Ser Cys Arg Ser Ser Gln Ser Leu Val His Asp
            20                  25                  30
```

```
Asn Gly Asn Thr Tyr Leu Ser Trp Ser Leu Gln Lys Pro Gly Lys Ser
        35                  40                  45

Pro Lys Val Leu Ile Tyr Lys Val Ser Asn Arg Phe Ser Gly Val Ser
    50                  55                  60

Ser Arg Phe Thr Gly Ser Gly Ser Gly Thr Asp Phe Thr Leu Lys Ile
65                  70                  75                  80

Ser Ser Val Gln Pro Asp Asp Leu Gly Val Tyr Tyr Cys Gly Gln Gly
                85                  90                  95

Thr Gln Tyr Pro Phe Thr Phe Gly Ser Gly Thr Lys Leu Glu Ile Lys
            100                 105                 110

Gly Gln Pro Lys Ala Ala Pro Asp Phe Val Met Thr Gln Ser Pro Ser
        115                 120                 125

Ser Leu Thr Val Thr Ala Gly Glu Lys Val Thr Met Ser Cys Lys Ser
    130                 135                 140

Ser Gln Ser Leu Leu Asn Ser Gly Asn Gln Lys Asn Tyr Leu Thr Trp
145                 150                 155                 160

Tyr Leu Gln Lys Pro Gly Gln Pro Pro Lys Leu Leu Ile Tyr Trp Ala
                165                 170                 175

Ser Thr Arg Glu Ser Gly Val Pro Asp Arg Phe Thr Gly Ser Gly Ser
            180                 185                 190

Gly Thr Asp Phe Thr Leu Thr Ile Ser Ser Val Gln Ala Glu Asp Leu
        195                 200                 205

Ala Val Tyr Tyr Cys Gln Asn Asp Tyr Ser Tyr Pro Tyr Thr Phe Gly
    210                 215                 220

Gly Gly Thr Lys Leu Glu Ile Lys Thr Lys Gly Pro Ser Arg Thr Val
225                 230                 235                 240

Ala Ala Pro Ser Val Phe Ile Phe Pro Pro Ser Asp Glu Gln Leu Lys
                245                 250                 255

Ser Gly Thr Ala Ser Val Val Cys Leu Leu Asn Asn Phe Tyr Pro Arg
            260                 265                 270

Glu Ala Lys Val Gln Trp Lys Val Asp Asn Ala Leu Gln Ser Gly Asn
        275                 280                 285

Ser Gln Glu Ser Val Thr Glu Gln Asp Ser Lys Asp Ser Thr Tyr Ser
    290                 295                 300

Leu Ser Ser Thr Leu Thr Leu Ser Lys Ala Asp Tyr Glu Lys His Lys
305                 310                 315                 320

Val Tyr Ala Cys Glu Val Thr His Gln Gly Leu Ser Ser Pro Val Thr
                325                 330                 335

Lys Ser Phe Asn Arg Gly Glu Cys
            340
```

<210> SEQ ID NO 323
<211> LENGTH: 342
<212> TYPE: PRT
<213> ORGANISM: Artificial Sequence
<220> FEATURE:
<223> OTHER INFORMATION: polypeptide II of the so-called CODV-Fab “7G3 x hz4B4” antibody-like binding protein

<400> SEQUENCE: 323

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45
```

```
Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ser Ser Thr Ala Tyr
65                  70                  75                  80

Met His Leu Asn Ser Leu Thr Ser Glu Asp Ser Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ala Ser Gln Val Gln Leu Val Glu Thr
        115                 120                 125

Gly Gly Gly Leu Val Lys Pro Gly Gln Ser Leu Lys Leu Thr Cys Ala
    130                 135                 140

Thr Ser Gly Phe Thr Phe Ser Asn Ala Trp Met His Trp Val Arg Gln
145                 150                 155                 160

Ser Pro Glu Lys Gly Leu Glu Trp Val Ala Gln Ile Lys Ala Arg Ser
                165                 170                 175

Asn Asn Tyr Ala Thr Tyr Tyr Ala Glu Ser Val Lys Gly Arg Phe Thr
            180                 185                 190

Ile Ser Arg Asp Asp Ser Lys Ser Thr Ile Tyr Leu Gln Met Asn Ser
        195                 200                 205

Leu Thr Pro Glu Asp Thr Ala Ile Tyr Tyr Cys Arg Gly Thr Tyr Tyr
    210                 215                 220

Ala Ser Lys Pro Phe Asp Tyr Trp Gly Gln Gly Val Met Val Thr Val
225                 230                 235                 240

Ser Ser Arg Thr Ala Ser Thr Lys Gly Pro Ser Val Phe Pro Leu Ala
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Lys Val
            340
```

<210> SEQ ID NO 324
<211> LENGTH: 342
<212> TYPE: PRT
<213> ORGANISM: Artificial Sequence
<220> FEATURE:
<223> OTHER INFORMATION: polypeptide I of the so-called CODV-Fab "hz4B4 x 3E3" antibody-like binding protein

<400> SEQUENCE: 324

```
Gln Phe Val Leu Thr Gln Pro Asn Ser Val Ser Thr Asn Leu Gly Ser
1               5                   10                  15

Thr Val Lys Leu Ser Cys Lys Arg Asn Thr Gly Asn Ile Gly Ser Asn
            20                  25                  30

Tyr Val Asn Trp Tyr Gln Gln His Glu Gly Arg Ser Pro Thr Thr Met
        35                  40                  45

Ile Tyr Arg Asp Asp Lys Arg Pro Asp Gly Val Pro Asp Arg Phe Ser
```

```
    50                  55                  60

Gly Ser Ile Asp Arg Ser Ser Asn Ser Ala Leu Leu Thr Ile Asn Asn
65                  70                  75                  80

Val Gln Thr Glu Asp Glu Ala Asp Tyr Phe Cys Gln Ser Tyr Ser Ser
                85                  90                  95

Gly Ile Asn Ile Ile Phe Gly Gly Gly Thr Lys Leu Thr Val Leu Gly
            100                 105                 110

Gln Pro Lys Ala Ala Pro Asp Val Val Met Thr Gln Thr Pro Val Ser
        115                 120                 125

Leu Ser Val Ser Val Gly Gly Arg Val Ser Ile Ser Cys Arg Ser Ser
    130                 135                 140

Gln Ser Leu Val His Asp Asn Gly Asn Thr Tyr Leu Ser Trp Ser Leu
145                 150                 155                 160

Gln Lys Pro Gly Lys Ser Pro Lys Val Leu Ile Tyr Lys Val Ser Asn
                165                 170                 175

Arg Phe Ser Gly Val Ser Ser Arg Phe Thr Gly Ser Gly Ser Gly Thr
            180                 185                 190

Asp Phe Thr Leu Lys Ile Ser Ser Val Gln Pro Asp Asp Leu Gly Val
        195                 200                 205

Tyr Tyr Cys Gly Gln Gly Thr Gln Tyr Pro Phe Thr Phe Gly Ser Gly
    210                 215                 220

Thr Lys Leu Glu Ile Lys Thr Lys Gly Pro Ser Arg Thr Val Ala Ala
225                 230                 235                 240

Pro Ser Val Phe Ile Phe Pro Pro Ser Asp Glu Gln Leu Lys Ser Gly
                245                 250                 255

Thr Ala Ser Val Val Cys Leu Leu Asn Asn Phe Tyr Pro Arg Glu Ala
            260                 265                 270

Lys Val Gln Trp Lys Val Asp Asn Ala Leu Gln Ser Gly Asn Ser Gln
        275                 280                 285

Glu Ser Val Thr Glu Gln Asp Ser Lys Asp Ser Thr Tyr Ser Leu Ser
    290                 295                 300

Ser Thr Leu Thr Leu Ser Lys Ala Asp Tyr Glu Lys His Lys Val Tyr
305                 310                 315                 320

Ala Cys Glu Val Thr His Gln Gly Leu Ser Ser Pro Val Thr Lys Ser
                325                 330                 335

Phe Asn Arg Gly Glu Cys
            340

<210> SEQ ID NO 325
<211> LENGTH: 340
<212> TYPE: PRT
<213> ORGANISM: Artificial Sequence
<220> FEATURE:
<223> OTHER INFORMATION: polypeptide II of the so-called CODV-Fab
      "hz4B4 x 3E3" antibody-like binding protein

<400> SEQUENCE: 325

Gln Val Gln Leu Val Glu Thr Gly Gly Gly Leu Val Lys Pro Gly Gln
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gly Leu Glu Trp Val
        35                  40                  45

Ala Gln Ile Lys Ala Arg Ser Asn Asn Tyr Ala Thr Tyr Tyr Ala Glu
    50                  55                  60
```

-continued

Ser Val Lys Gly Arg Phe Thr Ile Ser Arg Asp Asp Ser Lys Ser Thr
65 70 75 80

Ile Tyr Leu Gln Met Asn Ser Leu Thr Pro Glu Asp Thr Ala Ile Tyr
85 90 95

Tyr Cys Arg Gly Thr Tyr Tyr Ala Ser Lys Pro Phe Asp Tyr Trp Gly
100 105 110

Gln Gly Val Met Val Thr Val Ser Ser Ser Gln Val Gln Leu Gln Glu
115 120 125

Ser Gly Pro Gly Leu Val Gln Pro Ser Gln Thr Leu Ser Leu Thr Cys
130 135 140

Thr Val Ser Gly Phe Ser Leu Thr Thr Tyr Asp Val His Trp Val Arg
145 150 155 160

Gln Pro Pro Gly Lys Gly Leu Glu Trp Met Gly Arg Ile Gln Asn Gly
165 170 175

Gly Ile Thr Asp Tyr Asn Ser Ala Leu Lys Ser Arg Leu Ile Ile Ser
180 185 190

Arg Asp Thr Ser Lys Ser Gln Val Phe Leu Lys Met Asn Ser Val Gln
195 200 205

Thr Glu Asp Thr Ala Met Tyr Phe Cys Ala Lys Thr Gly Ser Tyr Phe
210 215 220

Tyr Ala Phe Asp His Trp Gly Gln Gly Thr Leu Val Thr Val Ser Ser
225 230 235 240

Arg Thr Ala Ser Thr Lys Gly Pro Ser Val Phe Pro Leu Ala Pro Ser
245 250 255

Ser Lys Ser Thr Ser Gly Gly Thr Ala Ala Leu Gly Cys Leu Val Lys
260 265 270

Asp Tyr Phe Pro Glu Pro Val Thr Val Ser Trp Asn Ser Gly Ala Leu
275 280 285

Thr Ser Gly Val His Thr Phe Pro Ala Val Leu Gln Ser Ser Gly Leu
290 295 300

Tyr Ser Leu Ser Ser Val Val Thr Val Pro Ser Ser Ser Leu Gly Thr
305 310 315 320

Gln Thr Tyr Ile Cys Asn Val Asn His Lys Pro Ser Asn Thr Lys Val
325 330 335

Asp Lys Lys Val
340

<210> SEQ ID NO 326
<211> LENGTH: 572
<212> TYPE: PRT
<213> ORGANISM: Artificial Sequence
<220> FEATURE:
<223> OTHER INFORMATION: polypeptide I of the so-called CODV-Fab
"hz20G6 x 7G3 TL4" antibody-like binding protein

<400> SEQUENCE: 326

Asp Phe Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asn Ser
20 25 30

Gly Asn Gln Lys Asn Tyr Leu Thr Trp Tyr Leu Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

```
Ile Ser Ser Val Gln Ala Glu Asp Leu Ala Val Tyr Tyr Cys Gln Asn
                85                  90                  95
Asp Tyr Ser Tyr Pro Tyr Thr Phe Gly Gly Thr Lys Leu Glu Ile
                100                 105                 110
Lys Gly Gln Pro Lys Ala Ala Pro Asp Ile Val Met Thr Gln Thr Pro
                115                 120                 125
Leu Ser Leu Ser Val Thr Pro Gly Gln Pro Ala Ser Ile Ser Cys Lys
                130                 135                 140
Ser Ser Gln Ser Leu Val His Asn Asn Gly Asn Thr Tyr Leu Ser Trp
145                 150                 155                 160
Tyr Leu Gln Lys Pro Gly Gln Ser Pro Gln Ser Leu Ile Tyr Lys Val
                165                 170                 175
Ser Asn Arg Phe Ser Gly Val Pro Asp Arg Phe Ser Gly Ser Gly Ser
                180                 185                 190
Gly Thr Asp Phe Thr Leu Lys Ile Ser Arg Val Glu Ala Glu Asp Val
                195                 200                 205
Gly Val Tyr Tyr Cys Gly Gln Gly Thr Gln Tyr Pro Phe Thr Phe Gly
                210                 215                 220
Ser Gly Thr Lys Val Glu Ile Lys Thr Lys Gly Pro Ser Arg Thr Val
225                 230                 235                 240
Ala Ala Pro Ser Val Phe Ile Phe Pro Pro Ser Asp Glu Gln Leu Lys
                245                 250                 255
Ser Gly Thr Ala Ser Val Val Cys Leu Leu Asn Asn Phe Tyr Pro Arg
                260                 265                 270
Glu Ala Lys Val Gln Trp Lys Val Asp Asn Ala Leu Gln Ser Gly Asn
                275                 280                 285
Ser Gln Glu Ser Val Thr Glu Gln Asp Ser Lys Asp Ser Thr Tyr Ser
                290                 295                 300
Leu Ser Ser Thr Leu Thr Leu Ser Lys Ala Asp Tyr Glu Lys His Lys
305                 310                 315                 320
Val Tyr Ala Cys Glu Val Thr His Gln Gly Leu Ser Ser Pro Val Thr
                325                 330                 335
Lys Ser Phe Asn Arg Gly Glu Cys Glu Ser Lys Tyr Gly Pro Pro Cys
                340                 345                 350
Pro Pro Cys Pro Ala Pro Glu Phe Glu Gly Gly Pro Ser Val Phe Leu
                355                 360                 365
Phe Pro Pro Lys Pro Lys Asp Thr Leu Met Ile Ser Arg Thr Pro Glu
                370                 375                 380
Val Thr Cys Val Val Val Asp Val Ser Gln Glu Asp Pro Glu Val Gln
385                 390                 395                 400
Phe Asn Trp Tyr Val Asp Gly Val Glu Val His Asn Ala Lys Thr Lys
                405                 410                 415
Pro Arg Glu Glu Gln Phe Asn Ser Thr Tyr Arg Val Val Ser Val Leu
                420                 425                 430
Thr Val Leu His Gln Asp Trp Leu Asn Gly Lys Glu Tyr Lys Cys Lys
                435                 440                 445
Val Ser Asn Lys Gly Leu Pro Ser Ser Ile Glu Lys Thr Ile Ser Lys
                450                 455                 460
Ala Lys Gly Gln Pro Arg Glu Pro Gln Val Tyr Thr Leu Pro Pro Ser
465                 470                 475                 480
Gln Glu Glu Met Thr Lys Asn Gln Val Ser Leu Thr Cys Leu Val Lys
                485                 490                 495
```

```
Gly Phe Tyr Pro Ser Asp Ile Ala Val Glu Trp Glu Ser Asn Gly Gln
            500                 505                 510
Pro Glu Asn Asn Tyr Lys Thr Thr Pro Pro Val Leu Asp Ser Asp Gly
        515                 520                 525
Ser Phe Phe Leu Tyr Ser Arg Leu Thr Val Asp Lys Ser Arg Trp Gln
    530                 535                 540
Glu Gly Asn Val Phe Ser Cys Ser Val Met His Glu Ala Leu His Asn
545                 550                 555                 560
Arg Phe Thr Gln Lys Ser Leu Ser Leu Ser Leu Gly
                565                 570
```

<210> SEQ ID NO 327
<211> LENGTH: 228
<212> TYPE: PRT
<213> ORGANISM: Artificial Sequence
<220> FEATURE:
<223> OTHER INFORMATION: amino acid sequence Fc2 of the so-called
    CODV-Fab "hz20G6x7G3-TL4" antibody-like binding protein

<400> SEQUENCE: 327

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn Arg Phe Thr Gln Lys Ser Leu Ser
    210                 215                 220

Leu Ser Leu Gly
225
```

<210> SEQ ID NO 328
<211> LENGTH: 570
<212> TYPE: PRT
<213> ORGANISM: Artificial Sequence
<220> FEATURE:
<223> OTHER INFORMATION: polypeptide III of the so-called CODV-Fab "hz20G6 x 7G3 TL4" antibody-like binding protein

<400> SEQUENCE: 328

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gln Leu Glu Trp Val
        35                  40                  45

Ala Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Arg Gly Val Tyr Tyr Ala Leu Ser Pro Phe Asp Tyr Trp Gly
            100                 105                 110

Gln Gly Thr Leu Val Thr Val Ser Ser Glu Val Gln Leu Gln Gln
        115                 120                 125

Ser Gly Pro Glu Leu Val Lys Pro Gly Ala Ser Val Lys Met Ser Cys
130                 135                 140

Lys Ala Ser Gly Tyr Thr Phe Thr Asp Tyr Tyr Met Lys Trp Val Lys
145                 150                 155                 160

Gln Ser His Gly Lys Ser Leu Glu Trp Ile Gly Asp Ile Ile Pro Ser
                165                 170                 175

Asn Gly Ala Thr Phe Tyr Asn Gln Lys Phe Lys Gly Lys Ala Thr Leu
            180                 185                 190

Thr Val Asp Arg Ser Ser Ser Thr Ala Tyr Met His Leu Asn Ser Leu
        195                 200                 205

Thr Ser Glu Asp Ser Ala Val Tyr Tyr Cys Thr Arg Ser His Leu Leu
    210                 215                 220

Arg Ala Ser Trp Phe Ala Tyr Trp Gly Gln Gly Thr Leu Val Thr Val
225                 230                 235                 240

Ser Ala Arg Thr Ala Ser Thr Lys Gly Pro Ser Val Phe Pro Leu Ala
                245                 250                 255

Pro Cys Ser Arg Ser Thr Ser Glu Ser Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Lys Thr Tyr Thr Cys Asn Val Asp His Lys Pro Ser Asn Thr
                325                 330                 335

Lys Val Asp Lys Arg Val Glu Ser Lys Tyr Gly Pro Pro Cys Pro Pro
            340                 345                 350

Cys Pro Ala Pro Glu Phe Glu Gly Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser Gln Glu Asp Pro Glu Val Gln Phe Asn
385                 390                 395                 400

Trp Tyr Val Asp Gly Val Glu Val His Asn Ala Lys Thr Lys Pro Arg
```

```
                405                 410                 415

Glu Glu Gln Phe Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Gly Leu Pro Ser Ser Ile Glu Lys Thr Ile Ser Lys Ala Lys
    450                 455                 460

Gly Gln Pro Arg Glu Pro Gln Val Tyr Thr Leu Pro Pro Ser Gln Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Arg Leu Thr Val Asp Lys Ser Arg Trp Gln Glu Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Leu Gly
                565                 570

<210> SEQ ID NO 329
<211> LENGTH: 97
<212> TYPE: PRT
<213> ORGANISM: Artificial Sequence
<220> FEATURE:
<223> OTHER INFORMATION: CH1 of the so-called CODV-Fab "hz20G6x7G3-
      TL4"antibody-like binding protein

<400> SEQUENCE: 329

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg

<210> SEQ ID NO 330
<211> LENGTH: 229
<212> TYPE: PRT
<213> ORGANISM: Artificial Sequence
<220> FEATURE:
<223> OTHER INFORMATION: Fc of the so-called CODV-Fab "hz20G6x7G3-
      TL4"antibody-like binding protein

<400> SEQUENCE: 330

Val Glu Ser Lys Tyr Gly Pro Pro Cys Pro Pro Cys Pro Ala Pro Glu
1               5                   10                  15

Phe Glu Gly Gly Pro Ser Val Phe Leu Phe Pro Pro Lys Pro Lys Asp
            20                  25                  30
```

```
Thr Leu Met Ile Ser Arg Thr Pro Glu Val Thr Cys Val Val Asp
         35                  40                  45

Val Ser Gln Glu Asp Pro Glu Val Gln Phe Asn Trp Tyr Val Asp Gly
     50                  55                  60

Val Glu Val His Asn Ala Lys Thr Lys Pro Arg Glu Glu Gln Phe Asn
 65                  70                  75                  80

Ser Thr Tyr Arg Val Val Ser Val Leu Thr Val Leu His Gln Asp Trp
                 85                  90                  95

Leu Asn Gly Lys Glu Tyr Lys Cys Lys Val Ser Asn Lys Gly Leu Pro
             100                 105                 110

Ser Ser Ile Glu Lys Thr Ile Ser Lys Ala Lys Gly Gln Pro Arg Glu
         115                 120                 125

Pro Gln Val Tyr Thr Leu Pro Pro Ser Gln Glu Glu Met Thr Lys Asn
     130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                 165                 170                 175

Thr Pro Pro Val Leu Asp Ser Asp Gly Ser Phe Phe Leu Tyr Ser Arg
             180                 185                 190

Leu Thr Val Asp Lys Ser Arg Trp Gln Glu Gly Asn Val Phe Ser Cys
         195                 200                 205

Ser Val Met His Glu Ala Leu His Asn His Tyr Thr Gln Lys Ser Leu
     210                 215                 220

Ser Leu Ser Leu Gly
225

<210> SEQ ID NO 331
<211> LENGTH: 8
<212> TYPE: PRT
<213> ORGANISM: Artificial Sequence
<220> FEATURE:
<223> OTHER INFORMATION: Consensus sequence  CDR1-H of anti-CD3
      antibodies
<220> FEATURE:
<221> NAME/KEY: MISC_FEATURE
<222> LOCATION: (3)..(3)
<223> OTHER INFORMATION: Xaa is T or S
<220> FEATURE:
<221> NAME/KEY: MISC_FEATURE
<222> LOCATION: (4)..(4)
<223> OTHER INFORMATION: Xaa is F or V
<220> FEATURE:
<221> NAME/KEY: MISC_FEATURE
<222> LOCATION: (5)..(5)
<223> OTHER INFORMATION: Xaa is S or T
<220> FEATURE:
<221> NAME/KEY: MISC_FEATURE
<222> LOCATION: (6)..(6)
<223> OTHER INFORMATION: Xaa is N, K, L or Y

<400> SEQUENCE: 331

Gly Phe Xaa Xaa Xaa Xaa Ala Trp
1               5

<210> SEQ ID NO 332
<211> LENGTH: 10
<212> TYPE: PRT
<213> ORGANISM: Artificial Sequence
<220> FEATURE:
<223> OTHER INFORMATION: Consensus sequence for CDR2-H of anti-CD3
      antibodies
<220> FEATURE:
```

```
<221> NAME/KEY: MISC_FEATURE
<222> LOCATION: (3)..(3)
<223> OTHER INFORMATION: Xaa is A or D
<220> FEATURE:
<221> NAME/KEY: MISC_FEATURE
<222> LOCATION: (4)..(4)
<223> OTHER INFORMATION: Xaa is K or R
<220> FEATURE:
<221> NAME/KEY: MISC_FEATURE
<222> LOCATION: (5)..(5)
<223> OTHER INFORMATION: Xaa is S or A
<220> FEATURE:
<221> NAME/KEY: MISC_FEATURE
<222> LOCATION: (7)..(7)
<223> OTHER INFORMATION: Xaa is N or S
<220> FEATURE:
<221> NAME/KEY: MISC_FEATURE
<222> LOCATION: (9)..(9)
<223> OTHER INFORMATION: Xaa is A or E

<400> SEQUENCE: 332

Ile Lys Xaa Xaa Xaa Asn Xaa Tyr Xaa Thr
1               5                   10

<210> SEQ ID NO 333
<211> LENGTH: 15
<212> TYPE: PRT
<213> ORGANISM: Artificial Sequence
<220> FEATURE:
<223> OTHER INFORMATION: Consensus sequence for CDRF-H of anti-CD3
      antibodies
<220> FEATURE:
<221> NAME/KEY: MISC_FEATURE
<222> LOCATION: (2)..(2)
<223> OTHER INFORMATION: Xaa is Y, G or A
<220> FEATURE:
<221> NAME/KEY: MISC_FEATURE
<222> LOCATION: (3)..(3)
<223> OTHER INFORMATION: Xaa is V, T or L
<220> FEATURE:
<221> NAME/KEY: MISC_FEATURE
<222> LOCATION: (4)..(4)
<223> OTHER INFORMATION: Xaa is H, N, Y or Q
<220> FEATURE:
<221> NAME/KEY: MISC_FEATURE
<222> LOCATION: (6)..(6)
<223> OTHER INFORMATION: Xaa is G, R or A
<220> FEATURE:
<221> NAME/KEY: MISC_FEATURE
<222> LOCATION: (7)..(7)
<223> OTHER INFORMATION: Xaa is F or V or no amino acid
<220> FEATURE:
<221> NAME/KEY: MISC_FEATURE
<222> LOCATION: (8)..(8)
<223> OTHER INFORMATION: Xaa is R or no amino acid
<220> FEATURE:
<221> NAME/KEY: MISC_FEATURE
<222> LOCATION: (9)..(9)
<223> OTHER INFORMATION: Xaa is F, S or I or no amino acid
<220> FEATURE:
<221> NAME/KEY: MISC_FEATURE
<222> LOCATION: (10)..(10)
<223> OTHER INFORMATION: Xaa is F, L, N, M, Y, S, A or G
<220> FEATURE:
<221> NAME/KEY: MISC_FEATURE
<222> LOCATION: (11)..(11)
<223> OTHER INFORMATION: Xaa is  Y, A, K, S, N, T, F or L
<220> FEATURE:
<221> NAME/KEY: MISC_FEATURE
<222> LOCATION: (12)..(12)
<223> OTHER INFORMATION: Xaa is  A, P, G or T
<220> FEATURE:
<221> NAME/KEY: MISC_FEATURE
<222> LOCATION: (13)..(13)
<223> OTHER INFORMATION: Xaa is  M, L, F or S
<220> FEATURE:
<221> NAME/KEY: MISC_FEATURE
```

```
<222> LOCATION: (15)..(15)
<223> OTHER INFORMATION: Xaa is A, V, Y or G

<400> SEQUENCE: 333

Arg Xaa Xaa Xaa Tyr Xaa Xaa Xaa Xaa Xaa Xaa Xaa Xaa Asp Xaa
1               5                   10                  15

<210> SEQ ID NO 334
<211> LENGTH: 11
<212> TYPE: PRT
<213> ORGANISM: Artificial Sequence
<220> FEATURE:
<223> OTHER INFORMATION: Consensus sequence for CDR1-L of anti-CD3
      antibodies
<220> FEATURE:
<221> NAME/KEY: MISC_FEATURE
<222> LOCATION: (2)..(2)
<223> OTHER INFORMATION: Xaa is R or S
<220> FEATURE:
<221> NAME/KEY: MISC_FEATURE
<222> LOCATION: (4)..(4)
<223> OTHER INFORMATION: Xaa is V or E
<220> FEATURE:
<221> NAME/KEY: MISC_FEATURE
<222> LOCATION: (6)..(6)
<223> OTHER INFORMATION: Xaa is N, D or T
<220> FEATURE:
<221> NAME/KEY: MISC_FEATURE
<222> LOCATION: (9)..(9)
<223> OTHER INFORMATION: Xaa is N or Y

<400> SEQUENCE: 334

Gln Xaa Leu Xaa His Xaa Asn Gly Xaa Thr Tyr
1               5                   10

<210> SEQ ID NO 335
<211> LENGTH: 9
<212> TYPE: PRT
<213> ORGANISM: Artificial Sequence
<220> FEATURE:
<223> OTHER INFORMATION: consensus sequence for CDR3-L of anti-CD3
      antibodies
<220> FEATURE:
<221> NAME/KEY: MISC_FEATURE
<222> LOCATION: (4)..(4)
<223> OTHER INFORMATION: Xaa is T, A or S
<220> FEATURE:
<221> NAME/KEY: MISC_FEATURE
<222> LOCATION: (5)..(5)
<223> OTHER INFORMATION: Xaa is H, E or Q

<400> SEQUENCE: 335

Gly Gln Gly Xaa Xaa Tyr Pro Phe Thr
1               5

<210> SEQ ID NO 336
<211> LENGTH: 8
<212> TYPE: PRT
<213> ORGANISM: Artificial Sequence
<220> FEATURE:
<223> OTHER INFORMATION: Consensus sequence for CDR1-H of the so-called
      "1E1-G5", "6D6-B8", "8B11-B7", "9F6-G3" anti-CD123 antibodies
<220> FEATURE:
<221> NAME/KEY: MISC_FEATURE
<222> LOCATION: (1)..(1)
<223> OTHER INFORMATION: Xaa is G or A
<220> FEATURE:
<221> NAME/KEY: MISC_FEATURE
<222> LOCATION: (7)..(7)
<223> OTHER INFORMATION: Xaa is H, Y or N

<400> SEQUENCE: 336
```

```
Xaa Tyr Thr Phe Thr Asp Xaa Ile
1               5

<210> SEQ ID NO 337
<211> LENGTH: 8
<212> TYPE: PRT
<213> ORGANISM: Artificial Sequence
<220> FEATURE:
<223> OTHER INFORMATION: consensus sequence for CDR2-H of the so-called
      "1E1-G5", "6D6-B8", "8B11-B7", "9F6-G3" anti-CD123 antibodies
<220> FEATURE:
<221> NAME/KEY: MISC_FEATURE
<222> LOCATION: (6)..(6)
<223> OTHER INFORMATION: Xaa is G or D
<220> FEATURE:
<221> NAME/KEY: MISC_FEATURE
<222> LOCATION: (8)..(8)
<223> OTHER INFORMATION: Xaa is T or A

<400> SEQUENCE: 337

Ile Asn Pro Tyr Ser Xaa Gly Xaa
1               5

<210> SEQ ID NO 338
<211> LENGTH: 6
<212> TYPE: PRT
<213> ORGANISM: Artificial Sequence
<220> FEATURE:
<223> OTHER INFORMATION: consensus sequence for CDR1-L of the so-called
      "1E1-G5", "6D6-B8", "8B11-B7", "9F6-G3" anti-CD123 antibodies
<220> FEATURE:
<221> NAME/KEY: MISC_FEATURE
<222> LOCATION: (1)..(1)
<223> OTHER INFORMATION: Xaa is E or K
<220> FEATURE:
<221> NAME/KEY: MISC_FEATURE
<222> LOCATION: (4)..(4)
<223> OTHER INFORMATION: Xaa is F, H or Y
<220> FEATURE:
<221> NAME/KEY: MISC_FEATURE
<222> LOCATION: (5)..(5)
<223> OTHER INFORMATION: Xaa is N or S

<400> SEQUENCE: 338

Xaa Asp Ile Xaa Xaa Asn
1               5

<210> SEQ ID NO 339
<211> LENGTH: 9
<212> TYPE: PRT
<213> ORGANISM: Artificial Sequence
<220> FEATURE:
<223> OTHER INFORMATION: consensus sequence for CDR3-L of the so-called
      "1E1-G5", "6D6-B8", "8B11-B7", "9F6-G3" anti-CD123 antibodies
<220> FEATURE:
<221> NAME/KEY: MISC_FEATURE
<222> LOCATION: (1)..(1)
<223> OTHER INFORMATION: Xaa is H or Q
<220> FEATURE:
<221> NAME/KEY: MISC_FEATURE
<222> LOCATION: (5)..(5)
<223> OTHER INFORMATION: Xaa is I, K or N

<400> SEQUENCE: 339

Xaa Gln Tyr Asn Xaa Tyr Pro Tyr Thr
1               5

<210> SEQ ID NO 340
<211> LENGTH: 8
<212> TYPE: PRT
<213> ORGANISM: Artificial Sequence
<220> FEATURE:
```

-continued

```
<223> OTHER INFORMATION: consensus sequence for CDR1-H of the so-called
      "6C10-C4", 9B8-G6", "9D7-C8" anti-CD123 antibodies
<220> FEATURE:
<221> NAME/KEY: MISC_FEATURE
<222> LOCATION: (8)..(8)
<223> OTHER INFORMATION: Xaa is H or S

<400> SEQUENCE: 340

Gly Phe Ser Leu Thr Ser Tyr Xaa
1               5

<210> SEQ ID NO 341
<211> LENGTH: 7
<212> TYPE: PRT
<213> ORGANISM: Artificial Sequence
<220> FEATURE:
<223> OTHER INFORMATION: Consensus sequence for CDR2-H of the so-called
      "1E1-G5", "6D6-B8", "8B11-B7", "9F6-G3" anti-CD123 antibodies
<220> FEATURE:
<221> NAME/KEY: misc_feature
<222> LOCATION: (3)..(3)
<223> OTHER INFORMATION: Xaa can be any naturally occurring amino acid

<400> SEQUENCE: 341

Met Trp Xaa Asp Gly Asp Thr
1               5

<210> SEQ ID NO 342
<211> LENGTH: 15
<212> TYPE: PRT
<213> ORGANISM: Artificial Sequence
<220> FEATURE:
<223> OTHER INFORMATION: consensus sequence for CDR3-H of the so-called
      "1E1-G5", "6D6-B8", "8B11-B7", "9F6-G3" anti-CD123 antibodies
<220> FEATURE:
<221> NAME/KEY: MISC_FEATURE
<222> LOCATION: (4)..(4)
<223> OTHER INFORMATION: Xaa is D, Y or H
<220> FEATURE:
<221> NAME/KEY: MISC_FEATURE
<222> LOCATION: (5)..(5)
<223> OTHER INFORMATION: Xaa is Y or R
<220> FEATURE:
<221> NAME/KEY: MISC_FEATURE
<222> LOCATION: (6)..(6)
<223> OTHER INFORMATION: Xaa is S or T
<220> FEATURE:
<221> NAME/KEY: MISC_FEATURE
<222> LOCATION: (7)..(7)
<223> OTHER INFORMATION: Xaa is S or P
<220> FEATURE:
<221> NAME/KEY: MISC_FEATURE
<222> LOCATION: (8)..(8)
<223> OTHER INFORMATION: Xaa is Y or no amino acid
<220> FEATURE:
<221> NAME/KEY: MISC_FEATURE
<222> LOCATION: (9)..(9)
<223> OTHER INFORMATION: Xaa is L, I or no amino acid
<220> FEATURE:
<221> NAME/KEY: MISC_FEATURE
<222> LOCATION: (10)..(10)
<223> OTHER INFORMATION: Xaa is Y or no amino acid
<220> FEATURE:
<221> NAME/KEY: MISC_FEATURE
<222> LOCATION: (11)..(11)
<223> OTHER INFORMATION: Xaa is L or no amino acid
<220> FEATURE:
<221> NAME/KEY: MISC_FEATURE
<222> LOCATION: (12)..(12)
<223> OTHER INFORMATION: Xaa s W or no amino acid
<220> FEATURE:
<221> NAME/KEY: MISC_FEATURE
<222> LOCATION: (14)..(14)
<223> OTHER INFORMATION: Xaa is A or D
```

<400> SEQUENCE: 342

Ala Arg Gly Xaa Xaa Xaa Xaa Xaa Xaa Xaa Xaa Phe Xaa Tyr
1               5                   10                  15

<210> SEQ ID NO 343
<211> LENGTH: 12
<212> TYPE: PRT
<213> ORGANISM: Artificial Sequence
<220> FEATURE:
<223> OTHER INFORMATION: Consensus sequence for CDR1-L of "1E1-G5",
      "6D6-B8", "8B11-B7","9F6-G3" anti-CD123 antibodies
<220> FEATURE:
<221> NAME/KEY: MISC_FEATURE
<222> LOCATION: (9)..(9)
<223> OTHER INFORMATION: Xaa is E or G
<220> FEATURE:
<221> NAME/KEY: MISC_FEATURE
<222> LOCATION: (10)..(10)
<223> OTHER INFORMATION: Xaa is R or K

<400> SEQUENCE: 343

Gln Ser Phe Leu Ser Ser Gly Asp Xaa Xaa Asn Tyr
1               5                   10

<210> SEQ ID NO 344
<211> LENGTH: 5
<212> TYPE: PRT
<213> ORGANISM: Artificial Sequence
<220> FEATURE:
<223> OTHER INFORMATION: amino acid sequence of a linker sequence

<400> SEQUENCE: 344

Gly Gly Gly Gly Ser
1               5

<210> SEQ ID NO 345
<211> LENGTH: 10
<212> TYPE: PRT
<213> ORGANISM: Artificial Sequence
<220> FEATURE:
<223> OTHER INFORMATION: amino acid sequence of a linker sequence

<400> SEQUENCE: 345

Gly Gly Gly Gly Ser Gly Gly Gly Gly Ser
1               5                   10

<210> SEQ ID NO 346
<211> LENGTH: 5
<212> TYPE: PRT
<213> ORGANISM: Artificial Sequence
<220> FEATURE:
<223> OTHER INFORMATION: amino acid sequence of a linker sequence

<400> SEQUENCE: 346

Thr Val Ala Ala Pro
1               5

<210> SEQ ID NO 347
<211> LENGTH: 5
<212> TYPE: PRT
<213> ORGANISM: Artificial Sequence
<220> FEATURE:
<223> OTHER INFORMATION: amino acid sequence of a linker sequence

<400> SEQUENCE: 347

Gln Pro Lys Ala Ala
1               5

<210> SEQ ID NO 348
<211> LENGTH: 5
<212> TYPE: PRT
<213> ORGANISM: Artificial Sequence
<220> FEATURE:
<223> OTHER INFORMATION: amino acid sequence of a linker sequence

<400> SEQUENCE: 348

Gln Arg Ile Glu Gly
1               5

<210> SEQ ID NO 349
<211> LENGTH: 7
<212> TYPE: PRT
<213> ORGANISM: Artificial Sequence
<220> FEATURE:
<223> OTHER INFORMATION: amino acid sequence of a linker sequence

<400> SEQUENCE: 349

Ala Ser Thr Lys Gly Pro Ser
1               5

<210> SEQ ID NO 350
<211> LENGTH: 7
<212> TYPE: PRT
<213> ORGANISM: Artificial Sequence
<220> FEATURE:
<223> OTHER INFORMATION: amino acid sequence of a linker sequence

<400> SEQUENCE: 350

Ala Ser Thr Lys Gly Pro Ser
1               5

<210> SEQ ID NO 351
<211> LENGTH: 7
<212> TYPE: PRT
<213> ORGANISM: Artificial Sequence
<220> FEATURE:
<223> OTHER INFORMATION: amino acid sequence of a linker sequence

<400> SEQUENCE: 351

His Ile Asp Ser Pro Asn Lys
1               5

<210> SEQ ID NO 352
<211> LENGTH: 16
<212> TYPE: PRT
<213> ORGANISM: Artificial Sequence
<220> FEATURE:
<223> OTHER INFORMATION: linker and Histag sequence

<400> SEQUENCE: 352

Glu Pro Lys Ser Cys Asp Lys Thr His Thr His His His His His His
1               5                   10                  15

<210> SEQ ID NO 353
<211> LENGTH: 7
<212> TYPE: PRT
<213> ORGANISM: Artificial Sequence
<220> FEATURE:
<223> OTHER INFORMATION: CDR2-H variant of the so-called "3E3" anti-
      CD123 antibody.

<400> SEQUENCE: 353

Ile Gln Asn Ala Gly Ile Thr
1               5

```
<210> SEQ ID NO 354
<211> LENGTH: 4
<212> TYPE: PRT
<213> ORGANISM: Artificial Sequence
<220> FEATURE:
<223> OTHER INFORMATION: amino acid sequence of a linker sequence

<400> SEQUENCE: 354

Gly Gly Gly Ser
1

<210> SEQ ID NO 355
<211> LENGTH: 5
<212> TYPE: PRT
<213> ORGANISM: Artificial Sequence
<220> FEATURE:
<223> OTHER INFORMATION: shows the amino acid sequence of a linker
      sequence

<400> SEQUENCE: 355

Ser Gly Gly Gly Ser
1               5

<210> SEQ ID NO 356
<211> LENGTH: 7
<212> TYPE: PRT
<213> ORGANISM: Artificial Sequence
<220> FEATURE:
<223> OTHER INFORMATION: amino acid sequence of a linker sequence

<400> SEQUENCE: 356

Gly Ser Gly Gly Gly Gly Ser
1               5

<210> SEQ ID NO 357
<211> LENGTH: 8
<212> TYPE: PRT
<213> ORGANISM: Artificial Sequence
<220> FEATURE:
<223> OTHER INFORMATION: amino acid sequence of a linker sequence

<400> SEQUENCE: 357

Gly Gly Ser Gly Gly Gly Gly Ser
1               5

<210> SEQ ID NO 358
<211> LENGTH: 9
<212> TYPE: PRT
<213> ORGANISM: Artificial Sequence
<220> FEATURE:
<223> OTHER INFORMATION: amino acid sequence of a linker sequence

<400> SEQUENCE: 358

Gly Gly Gly Ser Gly Gly Gly Gly Ser
1               5

<210> SEQ ID NO 359
<211> LENGTH: 4
<212> TYPE: PRT
<213> ORGANISM: Artificial Sequence
<220> FEATURE:
<223> OTHER INFORMATION: amino acid sequence of a linker sequence

<400> SEQUENCE: 359

Lys Thr His Thr
1
```

```
<210> SEQ ID NO 360
<211> LENGTH: 5
<212> TYPE: PRT
<213> ORGANISM: Artificial Sequence
<220> FEATURE:
<223> OTHER INFORMATION: amino acid sequence of a linker sequence

<400> SEQUENCE: 360

Lys Thr His Thr Ser
1               5

<210> SEQ ID NO 361
<211> LENGTH: 6
<212> TYPE: PRT
<213> ORGANISM: Artificial Sequence
<220> FEATURE:
<223> OTHER INFORMATION: amino acid sequence of a linker sequence

<400> SEQUENCE: 361

Asp Lys Thr His Thr Ser
1               5

<210> SEQ ID NO 362
<211> LENGTH: 7
<212> TYPE: PRT
<213> ORGANISM: Artificial Sequence
<220> FEATURE:
<223> OTHER INFORMATION: amino acid sequence of a linker sequence

<400> SEQUENCE: 362

Asp Lys Thr His Thr Ser Pro
1               5

<210> SEQ ID NO 363
<211> LENGTH: 8
<212> TYPE: PRT
<213> ORGANISM: Artificial Sequence
<220> FEATURE:
<223> OTHER INFORMATION: amino acid sequence of a linker sequence

<400> SEQUENCE: 363

Ser Asp Lys Thr His Thr Ser Pro
1               5

<210> SEQ ID NO 364
<211> LENGTH: 9
<212> TYPE: PRT
<213> ORGANISM: Artificial Sequence
<220> FEATURE:
<223> OTHER INFORMATION: amino acid sequence of a linker sequence

<400> SEQUENCE: 364

Ser Asp Lys Thr His Thr Ser Pro Pro
1               5

<210> SEQ ID NO 365
<211> LENGTH: 11
<212> TYPE: PRT
<213> ORGANISM: Artificial Sequence
<220> FEATURE:
<223> OTHER INFORMATION: amino acid sequence of a linker sequence

<400> SEQUENCE: 365

Lys Ser Asp Lys Thr His Thr Ser Pro Pro Ser
1               5                   10
```

```
<210> SEQ ID NO 366
<211> LENGTH: 12
<212> TYPE: PRT
<213> ORGANISM: Artificial Sequence
<220> FEATURE:
<223> OTHER INFORMATION: amino acid sequence of a linker sequence

<400> SEQUENCE: 366

Pro Lys Ser Asp Lys Thr His Thr Ser Pro Pro Ser
1               5                   10

<210> SEQ ID NO 367
<211> LENGTH: 13
<212> TYPE: PRT
<213> ORGANISM: Artificial Sequence
<220> FEATURE:
<223> OTHER INFORMATION: amino acid sequence of a linker sequence

<400> SEQUENCE: 367

Pro Lys Ser Asp Lys Thr His Thr Ser Pro Pro Ser Pro
1               5                   10

<210> SEQ ID NO 368
<211> LENGTH: 14
<212> TYPE: PRT
<213> ORGANISM: Artificial Sequence
<220> FEATURE:
<223> OTHER INFORMATION: amino acid sequence of a linker sequence

<400> SEQUENCE: 368

Glu Pro Lys Ser Asp Lys Thr His Thr Ser Pro Pro Ser Pro
1               5                   10

<210> SEQ ID NO 369
<211> LENGTH: 15
<212> TYPE: PRT
<213> ORGANISM: Artificial Sequence
<220> FEATURE:
<223> OTHER INFORMATION: the amino acid sequence of a linker sequence

<400> SEQUENCE: 369

Glu Pro Lys Ser Asp Lys Thr His Thr Ser Pro Pro Ser Pro Gly
1               5                   10                  15

<210> SEQ ID NO 370
<211> LENGTH: 16
<212> TYPE: PRT
<213> ORGANISM: Artificial Sequence
<220> FEATURE:
<223> OTHER INFORMATION: amino acid sequence of a linker sequence

<400> SEQUENCE: 370

Gly Glu Pro Lys Ser Asp Lys Thr His Thr Ser Pro Pro Ser Pro Gly
1               5                   10                  15

<210> SEQ ID NO 371
<211> LENGTH: 17
<212> TYPE: PRT
<213> ORGANISM: Artificial Sequence
<220> FEATURE:
<223> OTHER INFORMATION: amino acid sequence of a linker sequence

<400> SEQUENCE: 371

Gly Glu Pro Lys Ser Asp Lys Thr His Thr Ser Pro Pro Ser Pro Gly
1               5                   10                  15

Gly
```

<210> SEQ ID NO 372
<211> LENGTH: 18
<212> TYPE: PRT
<213> ORGANISM: Artificial Sequence
<220> FEATURE:
<223> OTHER INFORMATION: amino acid sequence of a linker sequence

<400> SEQUENCE: 372

Gly Gly Glu Pro Lys Ser Asp Lys Thr His Thr Ser Pro Pro Ser Pro
1               5                   10                  15

Gly Gly

<210> SEQ ID NO 373
<211> LENGTH: 19
<212> TYPE: PRT
<213> ORGANISM: Artificial Sequence
<220> FEATURE:
<223> OTHER INFORMATION: amino acid sequence of a linker sequence

<400> SEQUENCE: 373

Gly Gly Glu Pro Lys Ser Asp Lys Thr His Thr Ser Pro Pro Ser Pro
1               5                   10                  15

Gly Gly Gly

<210> SEQ ID NO 374
<211> LENGTH: 20
<212> TYPE: PRT
<213> ORGANISM: Artificial Sequence
<220> FEATURE:
<223> OTHER INFORMATION: amino acid sequence of a linker sequence

<400> SEQUENCE: 374

Gly Gly Gly Glu Pro Lys Ser Asp Lys Thr His Thr Ser Pro Pro Ser
1               5                   10                  15

Pro Gly Gly Gly
            20

<210> SEQ ID NO 375
<211> LENGTH: 8
<212> TYPE: PRT
<213> ORGANISM: Artificial Sequence
<220> FEATURE:
<223> OTHER INFORMATION: CDR1-H of the so-called "7G3" antibody.

<400> SEQUENCE: 375

Gly Tyr Thr Phe Thr Asp Tyr Tyr
1               5

<210> SEQ ID NO 376
<211> LENGTH: 8
<212> TYPE: PRT
<213> ORGANISM: Artificial Sequence
<220> FEATURE:
<223> OTHER INFORMATION: CDR2-H of the so-called "7G3" antibody.

<400> SEQUENCE: 376

Ile Ile Pro Ser Asn Gly Ala Thr
1               5

<210> SEQ ID NO 377
<211> LENGTH: 13
<212> TYPE: PRT
<213> ORGANISM: Artificial Sequence
<220> FEATURE:
<223> OTHER INFORMATION: CDR3-H of the so-called "7G3" antibody.

<400> SEQUENCE: 377

Thr Arg Ser His Leu Leu Arg Ala Ser Trp Phe Ala Tyr
1               5                   10

<210> SEQ ID NO 378
<211> LENGTH: 12
<212> TYPE: PRT
<213> ORGANISM: Artificial Sequence
<220> FEATURE:
<223> OTHER INFORMATION: CDR1-L of the so-called "7G3" antibody.

<400> SEQUENCE: 378

Gln Ser Leu Leu Asn Ser Gly Asn Gln Lys Asn Tyr
1               5                   10

<210> SEQ ID NO 379
<211> LENGTH: 9
<212> TYPE: PRT
<213> ORGANISM: Artificial Sequence
<220> FEATURE:
<223> OTHER INFORMATION: CDR3-L of the so-called "7G3" antibody.

<400> SEQUENCE: 379

Gln Asn Asp Tyr Ser Tyr Pro Tyr Thr
1               5

<210> SEQ ID NO 380
<211> LENGTH: 120
<212> TYPE: PRT
<213> ORGANISM: Artificial Sequence
<220> FEATURE:
<223> OTHER INFORMATION: VH variant amino acid sequence of the so-called
      humanized "7G3" antibody.

<400> SEQUENCE: 380

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

Tyr Met Lys Trp Ala Arg Gln Met Pro Gly Lys Gly Leu Glu Trp Met
            35                  40                  45

Gly Asp Ile Ile Pro Ser Asn Gly Ala Thr Phe Tyr Asn Gln Lys Phe
        50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
                100                 105                 110

Gly Thr Met Val Thr Val Ser Ser
            115                 120

<210> SEQ ID NO 381
<211> LENGTH: 8
<212> TYPE: PRT
<213> ORGANISM: Artificial Sequence
<220> FEATURE:
<223> OTHER INFORMATION: CDR1-H of the so-called humanized "7G3"
      antibody

<400> SEQUENCE: 381

Gly Tyr Ser Phe Thr Asp Tyr Tyr

<210> SEQ ID NO 382
<211> LENGTH: 13
<212> TYPE: PRT
<213> ORGANISM: Artificial Sequence
<220> FEATURE:
<223> OTHER INFORMATION: CDR3-H of the so-called humanized "7G3" antibody.

<400> SEQUENCE: 382

Ala Arg Ser His Leu Leu Arg Ala Ser Trp Phe Ala Tyr
1               5                   10

<210> SEQ ID NO 383
<211> LENGTH: 120
<212> TYPE: PRT
<213> ORGANISM: Artificial Sequence
<220> FEATURE:
<223> OTHER INFORMATION: VH varaint of the so-called humanized "7G3" antibody.

<400> SEQUENCE: 383

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

Tyr Met Lys Trp Ala Arg Gln Met Pro Gly Lys Gly Leu Glu Trp Met
            35                  40                  45

Gly Asp Ile Ile Pro Ser Ser Gly Ala Thr Phe Tyr Asn Gln Lys Phe
    50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
            100                 105                 110

Gly Thr Met Val Thr Val Ser Ser
        115                 120

<210> SEQ ID NO 384
<211> LENGTH: 8
<212> TYPE: PRT
<213> ORGANISM: Artificial Sequence
<220> FEATURE:
<223> OTHER INFORMATION: CDR2-H of one of the so-called humanized "7G3" antibody.

<400> SEQUENCE: 384

Ile Ile Pro Ser Ser Gly Ala Thr
1               5

<210> SEQ ID NO 385
<211> LENGTH: 113
<212> TYPE: PRT
<213> ORGANISM: Artificial Sequence
<220> FEATURE:
<223> OTHER INFORMATION: VL varaint of the so-called humanized "7G3" antibody.

<400> SEQUENCE: 385

Asp Ile Val Met Thr Gln Ser Pro Asp Ser Leu Ala Val Ser Leu Gly
1               5                   10                  15

```
Glu Arg Ala Thr Ile Asn Cys Glu Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Pro Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Ser Tyr Pro Tyr Thr Phe Gly Gln Gly Thr Lys Leu Glu Ile
            100                 105                 110

Lys

<210> SEQ ID NO 386
<211> LENGTH: 272
<212> TYPE: PRT
<213> ORGANISM: Artificial Sequence
<220> FEATURE:
<223> OTHER INFORMATION: SEQ ID NO:1 of WO2015/026892

<400> SEQUENCE: 386

Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
                 20                  25                  30

Asn Tyr Ala Asn Trp Val Gln Gln Lys Pro Gly Gln Ala Pro Arg Gly
             35                  40                  45

Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
            115                 120                 125

Leu Lys Lys Pro Gly Ala Ser Val Lys Val Ser Cys Lys Ala Ser Gly
            130                 135                 140

Tyr Thr Phe Thr Asp Tyr Tyr Met Lys Trp Val Arg Gln Ala Pro Gly
145                 150                 155                 160

Gln Gly Leu Glu Trp Ile Gly Asp Ile Ile Pro Ser Asn Gly Ala Thr
            165                 170                 175

Phe Tyr Asn Gln Lys Phe Lys Gly Arg Val Thr Ile Thr Val Asp Lys
            180                 185                 190

Ser Thr Ser Thr Ala Tyr Met Glu Leu Ser Ser Leu Arg Ser Glu Asp
            195                 200                 205

Thr Ala Val Tyr Tyr Cys Ala Arg Ser His Leu Leu Arg Ala Ser Trp
            210                 215                 220

Phe Ala Tyr Trp Gly Gln Gly Thr Leu Val Thr Val Ser Ser Gly Gly
225                 230                 235                 240

Cys Gly Gly Gly Glu Val Ala Ala Leu Glu Lys Glu Val Ala Ala Leu
            245                 250                 255

Glu Lys Glu Val Ala Ala Leu Glu Lys Glu Val Ala Ala Leu Glu Lys
```

-continued

```
                260                 265                 270

<210> SEQ ID NO 387
<211> LENGTH: 280
<212> TYPE: PRT
<213> ORGANISM: Artificial Sequence
<220> FEATURE:
<223> OTHER INFORMATION: SEQ ID NO:3 of WO2015/026892

<400> SEQUENCE: 387

Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Gly Gly Gly Ser Gly Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Thr Tyr Ala Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Asp Arg Phe Thr
            180                 185                 190

Ile Ser Arg Asp Asp Ser Lys Asn Ser Leu Tyr Leu Gln Met Asn Ser
        195                 200                 205

Leu Lys Thr Glu Asp Thr Ala Val Tyr Tyr Cys Val Arg His Gly Asn
    210                 215                 220

Phe Gly Asn Ser Tyr Val Ser Trp Phe Ala Tyr Trp Gly Gln Gly Thr
225                 230                 235                 240

Leu Val Thr Val Ser Ser Gly Cys Gly Gly Gly Lys Val Ala Ala
                245                 250                 255

Leu Lys Glu Lys Val Ala Ala Leu Lys Glu Lys Val Ala Ala Leu Lys
            260                 265                 270

Glu Lys Val Ala Ala Leu Lys Glu
        275                 280

<210> SEQ ID NO 388
<211> LENGTH: 352
<212> TYPE: PRT
<213> ORGANISM: Artificial Sequence
<220> FEATURE:
<223> OTHER INFORMATION: polypeptide I of the so-called CODV-Fab
      "hz20G6xhz7G3", CODV-Fab-OL1 "hz20G6 7G3" and CODV-Fab-OL1a
      "hz20G6xhz7G3" antibody-like binding proteins

<400> SEQUENCE: 388

Asp Ile Val Met Thr Gln Ser Pro Asp Ser Leu Ala Val Ser Leu Gly
```

```
            1               5                   10                  15
        Glu Arg Ala Thr Ile Asn Cys Glu Ser Ser Gln Ser Leu Leu Asn Ser
                        20                  25                  30
        Gly Asn Gln Lys Asn Tyr Leu Thr Trp Tyr Gln Gln Lys Pro Gly Gln
                        35                  40                  45
        Pro Pro Lys Pro Leu Ile Tyr Trp Ala Ser Thr Arg Glu Ser Gly Val
                    50                  55                  60
        Pro Asp Arg Phe Ser Gly Ser Gly Ser Gly Thr Asp Phe Thr Leu Thr
        65                  70                  75                  80
        Ile Ser Ser Leu Gln Ala Glu Asp Val Ala Val Tyr Tyr Cys Gln Asn
                        85                  90                  95
        Asp Tyr Ser Tyr Pro Tyr Thr Phe Gly Gln Gly Thr Lys Leu Glu Ile
                        100                 105                 110
        Lys Gly Gly Ser Gly Ser Ser Gly Ser Gly Gly Asp Ile Val Met Thr
                        115                 120                 125
        Gln Thr Pro Leu Ser Leu Ser Val Thr Pro Gly Gln Pro Ala Ser Ile
                    130                 135                 140
        Ser Cys Lys Ser Ser Gln Ser Leu Val His Asn Asn Ala Asn Thr Tyr
        145                 150                 155                 160
        Leu Ser Trp Tyr Leu Gln Lys Pro Gly Gln Ser Pro Gln Ser Leu Ile
                        165                 170                 175
        Tyr Lys Val Ser Asn Arg Phe Ser Gly Val Pro Asp Arg Phe Ser Gly
                        180                 185                 190
        Ser Gly Ser Gly Thr Asp Phe Thr Leu Lys Ile Ser Arg Val Glu Ala
                        195                 200                 205
        Glu Asp Val Gly Val Tyr Tyr Cys Gly Gln Gly Thr Gln Tyr Pro Phe
                    210                 215                 220
        Thr Phe Gly Ser Gly Thr Lys Val Glu Ile Lys Gly Gly Ser Gly Ser
        225                 230                 235                 240
        Ser Gly Ser Gly Gly Arg Thr Val Ala Ala Pro Ser Val Phe Ile Phe
                        245                 250                 255
        Pro Pro Ser Asp Glu Gln Leu Lys Ser Gly Thr Ala Ser Val Val Cys
                        260                 265                 270
        Leu Leu Asn Asn Phe Tyr Pro Arg Glu Ala Lys Val Gln Trp Lys Val
                        275                 280                 285
        Asp Asn Ala Leu Gln Ser Gly Asn Ser Gln Glu Ser Val Thr Glu Gln
                    290                 295                 300
        Asp Ser Lys Asp Ser Thr Tyr Ser Leu Ser Ser Thr Leu Thr Leu Ser
        305                 310                 315                 320
        Lys Ala Asp Tyr Glu Lys His Lys Val Tyr Ala Cys Glu Val Thr His
                        325                 330                 335
        Gln Gly Leu Ser Ser Pro Val Thr Lys Ser Phe Asn Arg Gly Glu Cys
                        340                 345                 350

<210> SEQ ID NO 389
<211> LENGTH: 10
<212> TYPE: PRT
<213> ORGANISM: Artificial Sequence
<220> FEATURE:
<223> OTHER INFORMATION: Linker

<400> SEQUENCE: 389

Gly Gly Ser Gly Ser Ser Gly Ser Gly Gly
1               5                   10
```

```
<210> SEQ ID NO 390
<211> LENGTH: 339
<212> TYPE: PRT
<213> ORGANISM: Artificial Sequence
<220> FEATURE:
<223> OTHER INFORMATION: polypeptide II of the so-called CODV-Fab
      "hz20G6xhz7G3" antibody-like binding protein

<400> SEQUENCE: 390

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gln Leu Glu Trp Val
        35                  40                  45

Ala Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Arg Gly Val Tyr Ala Leu Ser Pro Phe Asp Tyr Trp Gly
            100                 105                 110

Gln Gly Thr Leu Val Thr Val Ser Ser Glu Val Gln Leu Val Gln Ser
        115                 120                 125

Gly Ala Glu Val Lys Lys Pro Gly Glu Ser Leu Lys Ile Ser Cys Lys
    130                 135                 140

Gly Ser Gly Tyr Ser Phe Thr Asp Tyr Tyr Met Lys Trp Ala Arg Gln
145                 150                 155                 160

Met Pro Gly Lys Gly Leu Glu Trp Met Gly Asp Ile Ile Pro Ser Ser
                165                 170                 175

Gly Ala Thr Phe Tyr Asn Gln Lys Phe Lys Gly Gln Val Thr Ile Ser
            180                 185                 190

Ala Asp Lys Ser Ile Ser Thr Thr Tyr Leu Gln Trp Ser Ser Leu Lys
        195                 200                 205

Ala Ser Asp Thr Ala Met Tyr Tyr Cys Ala Arg Ser His Leu Leu Arg
    210                 215                 220

Ala Ser Trp Phe Ala Tyr Trp Gly Gln Gly Thr Met Val Thr Val Ser
225                 230                 235                 240

Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Lys Val

<210> SEQ ID NO 391
<211> LENGTH: 578
<212> TYPE: PRT
```

<213> ORGANISM: Artificial Sequence
<220> FEATURE:
<223> OTHER INFORMATION: polypeptide IV of the so-called CODV-Fab-TL1 "hz20G6xhz7G3" antibody-like binding protein

<400> SEQUENCE: 391

```
Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Gly Gly Ser Gly Ser Ser Gly Ser Gly Gly Asp Ile Val Met Thr
        115                 120                 125

Gln Thr Pro Leu Ser Leu Ser Val Thr Pro Gly Gln Pro Ala Ser Ile
    130                 135                 140

Ser Cys Lys Ser Ser Gln Ser Leu Val His Asn Asn Ala Asn Thr Tyr
145                 150                 155                 160

Leu Ser Trp Tyr Leu Gln Lys Pro Gly Gln Ser Pro Gln Ser Leu Ile
                165                 170                 175

Tyr Lys Val Ser Asn Arg Phe Ser Gly Val Pro Asp Arg Phe Ser Gly
            180                 185                 190

Ser Gly Ser Gly Thr Asp Phe Thr Leu Lys Ile Ser Arg Val Glu Ala
        195                 200                 205

Glu Asp Val Gly Val Tyr Tyr Cys Gly Gln Gly Thr Gln Tyr Pro Phe
    210                 215                 220

Thr Phe Gly Ser Gly Thr Lys Val Glu Ile Lys Gly Gly Ser Gly Ser
225                 230                 235                 240

Ser Gly Ser Gly Gly Arg Thr Val Ala Ala Pro Ser Val Phe Ile Phe
                245                 250                 255

Pro Pro Ser Asp Glu Gln Leu Lys Ser Gly Thr Ala Ser Val Val Cys
            260                 265                 270

Leu Leu Asn Asn Phe Tyr Pro Arg Glu Ala Lys Val Gln Trp Lys Val
        275                 280                 285

Asp Asn Ala Leu Gln Ser Gly Asn Ser Gln Glu Ser Val Thr Glu Gln
    290                 295                 300

Asp Ser Lys Asp Ser Thr Tyr Ser Leu Ser Ser Thr Leu Thr Leu Ser
305                 310                 315                 320

Lys Ala Asp Tyr Glu Lys His Lys Val Tyr Ala Cys Glu Val Thr His
                325                 330                 335

Gln Gly Leu Ser Ser Pro Val Thr Lys Ser Phe Asn Arg Gly Glu Cys
            340                 345                 350

Asp Lys Thr His Thr Cys Pro Pro Cys Pro Ala Pro Glu Ala Ala Gly
        355                 360                 365

Gly Pro Ser Val Phe Leu Phe Pro Pro Lys Pro Lys Asp Thr Leu Met
    370                 375                 380
```

```
Ile Ser Arg Thr Pro Glu Val Thr Cys Val Val Asp Val Ser His
385                 390                 395                 400

Glu Asp Pro Glu Val Lys Phe Asn Trp Tyr Val Asp Gly Val Glu Val
                405                 410                 415

His Asn Ala Lys Thr Lys Pro Arg Glu Glu Gln Tyr Asn Ser Thr Tyr
            420                 425                 430

Arg Val Val Ser Val Leu Thr Val Leu His Gln Asp Trp Leu Asn Gly
        435                 440                 445

Lys Glu Tyr Lys Cys Lys Val Ser Asn Lys Ala Leu Pro Ala Pro Ile
    450                 455                 460

Glu Lys Thr Ile Ser Lys Ala Lys Gly Gln Pro Arg Glu Pro Gln Val
465                 470                 475                 480

Tyr Thr Leu Pro Pro Ser Arg Asp Glu Leu Thr Lys Asn Gln Val Ser
                485                 490                 495

Leu Thr Cys Leu Val Lys Gly Phe Tyr Pro Ser Asp Ile Ala Val Glu
            500                 505                 510

Trp Glu Ser Asn Gly Gln Pro Glu Asn Tyr Lys Thr Thr Pro Pro
        515                 520                 525

Val Leu Asp Ser Asp Gly Ser Phe Phe Leu Tyr Ser Lys Leu Thr Val
    530                 535                 540

Asp Lys Ser Arg Trp Gln Gln Gly Asn Val Phe Ser Cys Ser Val Met
545                 550                 555                 560

His Glu Ala Leu His Asn Arg Phe Thr Gln Lys Ser Leu Ser Leu Ser
                565                 570                 575

Pro Gly

<210> SEQ ID NO 392
<211> LENGTH: 226
<212> TYPE: PRT
<213> ORGANISM: Artificial Sequence
<220> FEATURE:
<223> OTHER INFORMATION: Fc2 of the so-called CODV-Fab-TL1
      "hz20G6xhz7G3" antibody-like binding protein

<400> SEQUENCE: 392

Asp Lys Thr His Thr Cys Pro Pro Cys Pro Ala Pro Glu

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
        180                 185                 190

Asp Lys Ser Arg Trp Gln Gln Gly Asn Val Phe Ser Cys Ser Val Met
            195                 200                 205

His Glu Ala Leu His Asn Arg Phe Thr Gln Lys Ser Leu Ser Leu Ser
    210                 215                 220

Pro Gly
225

<210> SEQ ID NO 393
<211> LENGTH: 570
<212> TYPE: PRT
<213> ORGANISM: Artificial Sequence
<220> FEATURE:
<223> OTHER INFORMATION: polypeptide III of the so-called CODV-Fab-TL1
      "hz20G6xhz7G3" antibody-like binding protein

<400> SEQUENCE: 393

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gln Leu Glu Trp Val
        35                  40                  45

Ala Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Arg Gly Val Tyr Tyr Ala Leu Ser Pro Phe Asp Tyr Trp Gly
        100                 105                 110

Gln Gly Thr Leu Val Thr Val Ser Ser Glu Val Gln Leu Val Gln Ser
    115                 120                 125

Gly Ala Glu Val Lys Lys Pro Gly Glu Ser Leu Lys Ile Ser Cys Lys
130                 135                 140

Gly Ser Gly Tyr Ser Phe Thr Asp Tyr Tyr Met Lys Trp Ala Arg Gln
            150                 155                 160
145

Met Pro Gly Lys Gly Leu Glu Trp Met Gly Asp Ile Ile Pro Ser Ser
        165                 170                 175

Gly Ala Thr Phe Tyr Asn Gln Lys Phe Lys Gly Gln Val Thr Ile Ser
    180                 185                 190

Ala Asp Lys Ser Ile Ser Thr Thr Tyr Leu Gln Trp Ser Ser Leu Lys
        195                 200                 205

Ala Ser Asp Thr Ala Met Tyr Tyr Cys Ala Arg Ser His Leu Leu Arg
    210                 215                 220

Ala Ser Trp Phe Ala Tyr Trp Gly Gln Gly Thr Met Val Thr Val Ser
225                 230                 235                 240

Ser Ala Ser Thr Lys Gly Pro Ser Val Phe Pro Leu Ala Pro Ser Ser
            245                 250                 255

Lys Ser Thr Ser Gly Gly Thr Ala Ala Leu Gly Cys Leu Val Lys Asp
        260                 265                 270

Tyr Phe Pro Glu Pro Val Thr Val Ser Trp Asn Ser Gly Ala Leu Thr
    275                 280                 285

Ser Gly Val His Thr Phe Pro Ala Val Leu Gln Ser Ser Gly Leu Tyr
        290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
            325                 330                 335

Lys Lys Val Glu Pro Lys Ser Cys Asp Lys Thr His Thr Cys Pro Pro
        340                 345                 350

Cys Pro Ala Pro Glu Ala Ala Gly Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly
                565                 570

<210> SEQ ID NO 394
<211> LENGTH: 231
<212> TYPE: PRT
<213> ORGANISM: Artificial Sequence
<220> FEATURE:
<223> OTHER INFORMATION: Fc region of the so-called CODV-Fab-TL1
      "hz20G6xhz7G3" antibody-like binding protein

<400> SEQUENCE: 394

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln

```
                65                  70                  75                  80
Tyr Asn Ser Thr Tyr Arg Val Val Ser Val Leu Thr Val Leu His Gln
                    85                  90                  95
Asp Trp Leu Asn Gly Lys Glu Tyr Lys Cys Lys Val Ser Asn Lys Ala
                100                 105                 110
Leu Pro Ala Pro Ile Glu Lys Thr Ile Ser Lys Ala Lys Gly Gln Pro
            115                 120                 125
Arg Glu Pro Gln Val Tyr Thr Leu Pro Pro Ser Arg Asp Glu Leu Thr
        130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
                180                 185                 190
Ser Lys Leu Thr Val Asp Lys Ser Arg Trp Gln Gln Gly Asn Val Phe
            195                 200                 205
Ser Cys Ser Val Met His Glu Ala Leu His Asn His Tyr Thr Gln Lys
        210                 215                 220
Ser Leu Ser Leu Ser Pro Gly
225                 230

<210> SEQ ID NO 395
<211> LENGTH: 570
<212> TYPE: PRT
<213> ORGANISM: Artificial Sequence
<220> FEATURE:
<223> OTHER INFORMATION: polypeptide II of the so-called CODV-Fab-OL1
      "hz20G6xhz7G3" antibody-like binding protein

<400> SEQUENCE: 395

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Thr Lys Ala
                20                  25                  30
Trp Met His Trp Val Arg Gln Ala Pro Gly Lys Gln Leu Glu Trp Val
            35                  40                  45
Ala Gln Ile Lys Asp Lys Ser Asn Ser Tyr Ala Thr Tyr Tyr Ala Asp
        50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Arg Gly Val Tyr Tyr Ala Leu Ser Pro Phe Asp Tyr Trp Gly
                100                 105                 110
Gln Gly Thr Leu Val Thr Val Ser Ser Glu Val Gln Leu Val Gln Ser
            115                 120                 125
Gly Ala Glu Val Lys Lys Pro Gly Glu Ser Leu Lys Ile Ser Cys Lys
        130                 135                 140
Gly Ser Gly Tyr Ser Phe Thr Asp Tyr Tyr Met Lys Trp Ala Arg Gln
145                 150                 155                 160
Met Pro Gly Lys Gly Leu Glu Trp Met Gly Asp Ile Ile Pro Ser Ser
                165                 170                 175
Gly Ala Thr Phe Tyr Asn Gln Lys Phe Lys Gly Gln Val Thr Ile Ser
                180                 185                 190
```

```
Ala Asp Lys Ser Ile Ser Thr Thr Tyr Leu Gln Trp Ser Leu Lys
            195                 200                 205
Ala Ser Asp Thr Ala Met Tyr Tyr Cys Ala Arg Ser His Leu Leu Arg
210                 215                 220
Ala Ser Trp Phe Ala Tyr Trp Gly Gln Gly Thr Met Val Thr Val Ser
225                 230                 235                 240
Ser Ala Ser Thr Lys Gly Pro Ser Val Phe Pro Leu Ala Pro Ser Ser
                245                 250                 255
Lys Ser Thr Ser Gly Gly Thr Ala Ala Leu Gly Cys Leu Val Lys Asp
            260                 265                 270
Tyr Phe Pro Glu Pro Val Thr Val Ser Trp Asn Ser Gly Ala Leu Thr
        275                 280                 285
Ser Gly Val His Thr Phe Pro Ala Val Leu Gln Ser Ser Gly Leu Tyr
    290                 295                 300
Ser Leu Ser Ser Val Val Thr Val Pro Ser Ser Ser Leu Gly Thr Gln
305                 310                 315                 320
Thr Tyr Ile Cys Asn Val Asn His Lys Pro Ser Asn Thr Lys Val Asp
                325                 330                 335
Lys Lys Val Glu Pro Lys Ser Cys Asp Lys Thr His Thr Cys Pro Pro
            340                 345                 350
Cys Pro Ala Pro Glu Ala Ala Gly Gly Pro Ser Val Phe Leu Phe Pro
        355                 360                 365
Pro Lys Pro Lys Asp Thr Leu Met Ile Ser Arg Thr Pro Glu Val Thr
    370                 375                 380
Cys Val Val Val Asp Val Ser His Glu Asp Pro Glu Val Lys Phe Asn
385                 390                 395                 400
Trp Tyr Val Asp Gly Val Glu Val His Asn Ala Lys Thr Lys Pro Arg
                405                 410                 415
Glu Glu Gln Tyr Asn Ser Thr Tyr Arg Val Val Ser Val Leu Thr Val
            420                 425                 430
Leu His Gln Asp Trp Leu Asn Gly Lys Glu Tyr Lys Cys Lys Val Ser
        435                 440                 445
Asn Lys Ala Leu Pro Ala Pro Ile Glu Lys Thr Ile Ser Lys Ala Lys
450                 455                 460
Gly Gln Pro Arg Glu Pro Gln Val Tyr Thr Leu Pro Pro Cys Arg Asp
465                 470                 475                 480
Glu Leu Thr Lys Asn Gln Val Ser Leu Trp Cys Leu Val Lys Gly Phe
                485                 490                 495
Tyr Pro Ser Asp Ile Ala Val Glu Trp Glu Ser Asn Gly Gln Pro Glu
            500                 505                 510
Asn Asn Tyr Lys Thr Thr Pro Pro Val Leu Asp Ser Asp Gly Ser Phe
        515                 520                 525
Phe Leu Tyr Ser Lys Leu Thr Val Asp Lys Ser Arg Trp Gln Gln Gly
    530                 535                 540
Asn Val Phe Ser Cys Ser Val Met His Glu Ala Leu His Asn Arg Phe
545                 550                 555                 560
Thr Gln Lys Ser Leu Ser Leu Ser Pro Gly
                565                 570

<210> SEQ ID NO 396
<211> LENGTH: 231
<212> TYPE: PRT
<213> ORGANISM: Artificial Sequence
<220> FEATURE:
<223> OTHER INFORMATION: Fc region of the so-called CODV-Fab-OL1
```

"hz20G6xhz7G3" antibody-like binding protein

<400> SEQUENCE: 396

Glu Pro Lys Ser Cys Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Cys Arg Asp Glu Leu Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn Arg Phe Thr Gln Lys
210 215 220

Ser Leu Ser Leu Ser Pro Gly
225 230

<210> SEQ ID NO 397
<211> LENGTH: 228
<212> TYPE: PRT
<213> ORGANISM: Artificial Sequence
<220> FEATURE:
<223> OTHER INFORMATION: Fc3 of the so-called CODV-Fab-OL1
"hz20G6xhz7G3" antibody-like binding protein

<400> SEQUENCE: 397

Gly Ser Asp Lys Thr His Thr Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser His Glu Asp Pro Glu Val Lys Phe Asn Trp Tyr Val Asp Gly Val
50 55 60

Glu Val His Asn Ala Lys Thr Lys Pro Arg Glu Glu Gln Tyr Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Ala Leu Pro Ala

```
                100                 105                 110
Pro Ile Glu Lys Thr Ile Ser Lys Ala Lys Gly Gln Pro Arg Glu Pro
            115                 120                 125
Gln Val Cys Thr Leu Pro Pro Ser Arg Asp Glu Leu Thr Lys Asn Gln
            130                 135                 140
Val Ser Leu Ser Cys Ala Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Val Ser Lys Leu
            180                 185                 190
Thr Val Asp Lys Ser Arg Trp Gln Gln Gly Asn Val Phe Ser Cys Ser
            195                 200                 205
Val Met His Glu Ala Leu His Asn His Tyr Thr Gln Lys Ser Leu Ser
210                 215                 220
Leu Ser Pro Gly
225

<210> SEQ ID NO 398
<211> LENGTH: 228
<212> TYPE: PRT
<213> ORGANISM: Artificial Sequence
<220> FEATURE:
<223> OTHER INFORMATION: Fc3 of the so-called CODV-Fab-OL1a
      "hz20G6xhz7G3"

<400> SEQUENCE: 398

Gly Ser Asp Lys Thr His Thr Cys Pro Pro Cys Pro Ala P

Leu Ser Pro Gly
225

<210> SEQ ID NO 399
<211> LENGTH: 570
<212> TYPE: PRT
<213> ORGANISM: Artificial Sequence
<220> FEATURE:
<223> OTHER INFORMATION: polypeptide of formula II of the so-called
      CODV-Fab-OL1a "hz20G6xhz7G3"

<400> SEQUENCE: 399

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gln Leu Glu Trp Val
            35                  40                  45

Ala Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Arg Gly Val Tyr Ala Leu Ser Pro Phe Asp Tyr Trp Gly
            100                 105                 110

Gln Gly Thr Leu Val Thr Val Ser Ser Glu Val Gln Leu Val Gln Ser
        115                 120                 125

Gly Ala Glu Val Lys Lys Pro Gly Glu Ser Leu Lys Ile Ser Cys Lys
    130                 135                 140

Gly Ser Gly Tyr Ser Phe Thr Asp Tyr Tyr Met Lys Trp Ala Arg Gln
145                 150                 155                 160

Met Pro Gly Lys Gly Leu Glu Trp Met Gly Asp Ile Ile Pro Ser Ser
                165                 170                 175

Gly Ala Thr Phe Tyr Asn Gln Lys Phe Lys Gly Gln Val Thr Ile Ser
            180                 185                 190

Ala Asp Lys Ser Ile Ser Thr Thr Tyr Leu Gln Trp Ser Ser Leu Lys
        195                 200                 205

Ala Ser Asp Thr Ala Met Tyr Tyr Cys Ala Arg Ser His Leu Leu Arg
    210                 215                 220

Ala Ser Trp Phe Ala Tyr Trp Gly Gln Gly Thr Met Val Thr Val Ser
225                 230                 235                 240

Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Lys Val Glu Pro Lys Ser Cys Asp Lys Thr His Thr Cys Pro Pro
            340                 345                 350
```

Cys Pro Ala Pro Glu Ala Ala Gly Gly Pro Ser Val Phe Leu Phe Pro
            355                 360                 365

Pro Lys Pro Lys Asp Thr Leu Met Ile Ser Arg Thr Pro Glu Val Thr
        370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Cys Arg Asp
465                 470                 475                 480

Glu Leu Thr Lys Asn Gln Val Ser Leu Trp Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly
                565                 570

<210> SEQ ID NO 400
<211> LENGTH: 231
<212> TYPE: PRT
<213> ORGANISM: Artificial Sequence
<220> FEATURE:
<223> OTHER INFORMATION: Fc3 of the so-called CODV-Fab-OL1a
      "hz20G6xhz7G3" antibody-like binding protein

<400> SEQUENCE: 400

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Cys Arg Asp Glu Leu Thr

-continued

```
            130                 135                 140
Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly
225                 230
```